(12) United States Patent
Blondelet-Rouault et al.

US007579167B2

(10) Patent No.: US 7,579,167 B2
(45) Date of Patent: Aug. 25, 2009

(54) POLYPEPTIDES INVOLVED IN THE BIOSYNTHESIS OF SPIRAMYCINS, NUCLEOTIDE SEQUENCES ENCODING THESE POLYPEPTIDES AND APPLICATIONS THEREOF

(75) Inventors: Marie-Helene Blondelet-Rouault, Orsay (FR); Helene Dominguez, Avignon (FR); Emmanuelle Darbon-Rongere, Voisins le Bretonneux (FR); Claude Gerbaud, Gagny (FR); Anne Gondran, Paris (FR); Fatma Karray, Bures sur Yvette (FR); Patricia Lacroix, Le Perreux (FR); Nathalie Oestreicher-Mermet-Bouvier, Clamart (FR); Pernodet Jean-Luc, Cachan (FR); Karine Tuphile, Caluire (FR)

(73) Assignees: Aventis Pharma S., Antony (FR); Centre National de la Recherche Scientifique, Paris (FR)

( * ) Notice: Subject to any disclaimer, the term of this patent is extended or adjusted under 35 U.S.C. 154(b) by 291 days.

(21) Appl. No.: 10/680,860

(22) Filed: Oct. 7, 2003

(65) Prior Publication Data

US 2005/0202528 A1 Sep. 15, 2005

Related U.S. Application Data

(60) Provisional application No. 60/493,490, filed on Aug. 7, 2003.

(30) Foreign Application Priority Data

Oct. 8, 2002 (FR) .................................. 02 12489
Feb. 27, 2003 (FR) .................................. 03 02439

(51) Int. Cl.
*C12P 21/06* (2006.01)
(52) U.S. Cl. ....................... 435/69.1; 435/6; 435/320.1; 435/325; 435/252; 530/350
(58) Field of Classification Search ....................... None
See application file for complete search history.

(56) References Cited

U.S. PATENT DOCUMENTS

| 5,098,837 | A | 3/1992 | Beckmann et al. |
| 5,240,849 | A | 8/1993 | Arisawa et al. |
| 5,322,937 | A | 6/1994 | Arisawa et al. |

FOREIGN PATENT DOCUMENTS

| EP | 0 346 000 | 12/1989 |
| EP | 0 524 832 | 1/1993 |
| EP | 0 354 641 | 9/1994 |
| EP | 0 791 656 | 8/1997 |
| EP | 0 791 655 | 10/2000 |
| WO | WO99/05283 | 2/1999 |
| WO | WO 03/010193 | 2/2003 |

OTHER PUBLICATIONS

Hara et al. (Accession No. E06690, Sep. 29, 1997.*
Arisawa, Akira et al., Cloning and Nucleotide Sequences of Two Genes Involved in the 4'-O-Acylation of Macrolide Antibiotics from *Streptomyces thermotolerans*, Bioscience, Biotechnology, and Biochemistry, (1993), vol. 57, No. 12, pp. 2020-2025.
Arisawa, Akira et al., Cloning of the Macrolide Antibiotic Biosynthesis Gen acyA, Which Encodes 3-O-Acyltransferase, from *Streptomyces thermotolerans* and Its Use for Direct Fermentative Production of a Hybrid Macrolide Antibiotic, Applied and Environmental Microbiology, (1994), vol. 60, No. 7, pp. 2657-2660.
Arisawa, Akira et al., Nucleotide Sequence Analysis of the Carbomycin Biosynthetic Genes Including the 3-O-Acyltransferase Gene from *Streptomyces thermotolerans*, Biosci. Biotech. Biochem, (1995), vol. 59, No. 4, pp. 582-588.
Bate, Neil et al., Multiple regulatory genes in the tylosin biosynthetic cluster of *Streptomyces fradiae*, Chemistry & Biology, (1999), vol. 6, No. 9, pp. 617-624.
Bate, Neil et al., The mycarose-biosynthetic genes of *Streptomyces fradiae*, producer of tylosin, Microbiology, (2000), vol. 146. pp. 139-146.
Gandecha, Atul R. et al., Analysis of four tylosin biosynthetic genes from tylLM region of the *Streptomyces fradiae* genome, Gene, (1997), vol. 184, pp. 197-203.
Gourmelen, Anne et al., Characterization of Glycosyl Transferase Inactivating Macrolides, Encoded by gimA from *Streptomyces ambofaciens*, Antimicrobial Agents and Chemotherapy, (1998), vol. 42, No. 10, pp. 2612-2619.
Omura, Satoshi et al., Bioconversion and Biosynthesis of 16-Membered Macrolide Antibiotics. X. Final Steps in the Biosynthesis of Spiramycin, using Enzyme Inhibitor: Cerulenin, Chemical & Pharmaceutical Bulletin, (1979), vol. 27, No. 1, pp. 176-182.
Omura, Satoshi et al., Isolation and Properties of Spiramycin I 3-Hydroxyl, Journal of Biochemistry, (1979), vol. 86, pp. 1753-1758.
Pernodet, Jean-Luc et al., Dispensable ribosomal resistance to spiramycin conferred by smA in the spiramycin producer *Streptomyces ambofaciens*, Microbiology, (1999), vol. 145, pp. 2355-2364.

(Continued)

*Primary Examiner*—Hope A Robinson

(57) ABSTRACT

The present invention relates to the isolation and identification of novel genes of the biosynthetic pathway for spiramycins and to novel polypeptides involved in this biosynthesis. The invention also relates to a method for producing these polypeptides. It also relates to the use of these genes for the purpose of increasing the levels of production and the purity of the spiramycin produced. The invention relates in particular to a microorganism which produces spiramycin I but which does not produce spiramycin II and III, and to the use of such a microorganism. The invention also relates to the use of the genes of the biosynthetic pathway for spiramycins for constructing mutants which can lead to the synthesis of novel antibiotics or to derived forms of spiramycins. The invention also relates to the molecules produced through the expression of these genes and to pharmacologically active compositions of a molecule produced through the expression of such genes.

19 Claims, 41 Drawing Sheets

OTHER PUBLICATIONS

Figure 1:
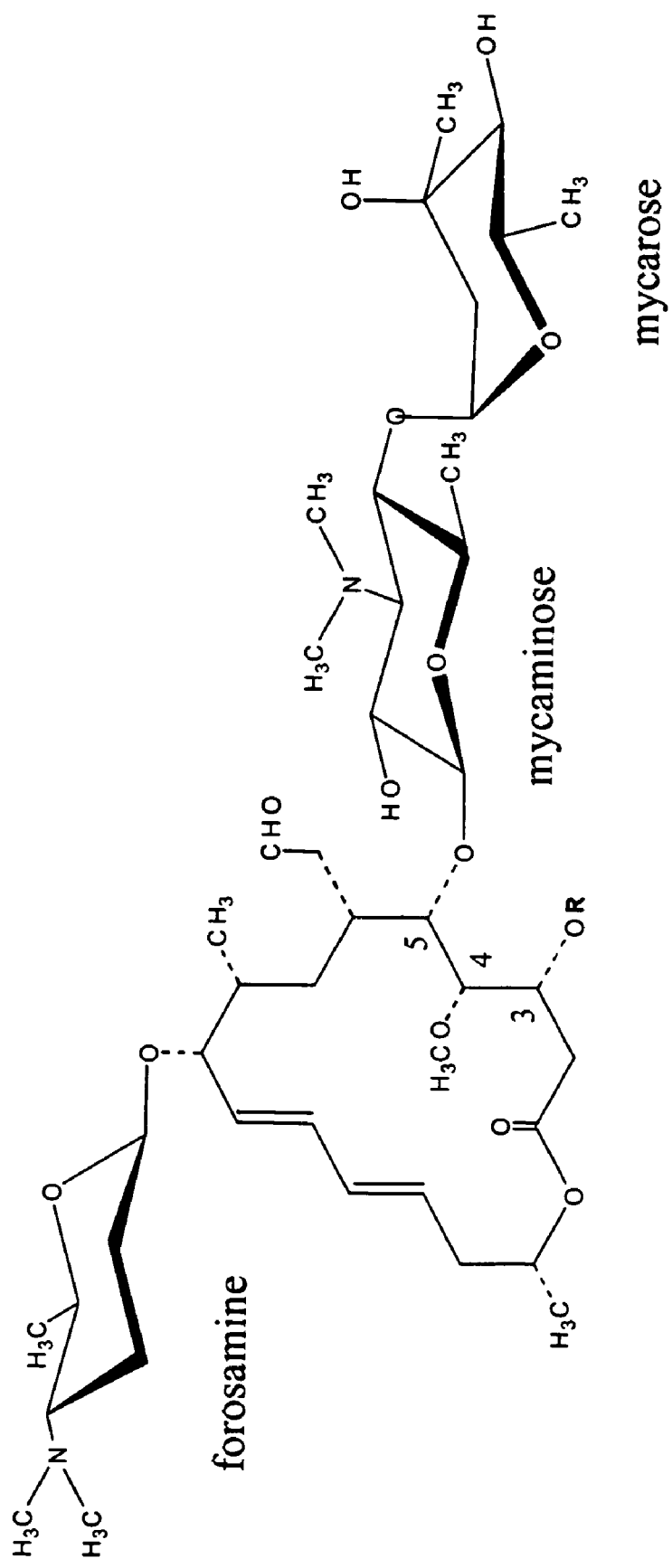

Pernodet, Jean-Luc et al., Resistance to spiramycin in *Streptomyces ambofaciens*, the producer organisms, involves at least two different mechanisms, Journal of General Microbiology, (1993), vol. 139, pp. 1003-1011.

Epp, Janet K. et al., Production of a hybrid macrolide antiobiotic in *Streptomyces ambofaciens* and *Streptomyces lividans* by introduction of a cloned carbomycin biosynthetic gene from Streptomyces thermotolerans, Gene, (1989), vol. 85, pp. 293-301.

Geistlich, Martin et al., Characterization of a novel regulatory gene governing the expression of a polyketide synthase gene in *Streptomyces ambofaciens*, Molecular Microbiology, (1992), vol. 6, No. 14, pp. 2019-2029.

Hara, Osamu et al., A Macrolide 3-O-Acyltransferase Gene from the Midecamycin-Producing Species *Streptomyces mycarofaciens*, Journal of Bacteriology, (1992), Vol. 174, No. 15, pp. 5141-5144.

Richardson, M. A. et al., Cloning of Spiramycin Biosynthetic Genes and Their Use in Constructing *Streptomyces ambofaciens* Mutants Defective in Spiramycin Biosynthesis, Journal of Bacteriology, (1990), vol. 172, No. 7, pp. 3790-3798.

* cited by examiner

R=H spiramycin I
R=COCH₃ spiramycin II
R=COCH₂CH₃ spiramycin III

```
FASTA (3.42 Sept 2001) function [optimized, BL50 matrix (15:-5)]
ktup: 2 join: 37, opt: 25, open/ext: -10/-2, width:  16

Smith-Waterman score: 1467;  63.130% identity (66.480% ungapped) in
377 aa overlap (3-367:11-380)

10        20        30        40
orf3       MTIPFLD-----AGAGYRELRAEIDAALQRVSASGRYLLDAELAAFEEEFAA
             .:: :    :..:   ....::  .:: ::.: :::::  ::::::::.::
tylB       MTGLPRPAVRVPFHDLRDVHAATG---VESEIGGALLRVAARGRYLLGAELAAFEERFAE
              10        20        30           40        50

50        60        70        80        90       100
orf3    YCDNDHCVAVGSGCDALELSLRALDIGPGDEVVVPAHTFIGTWLAVSATGARPVAV----
        ::  : :::::::: :   .:.: ::  .: :::::.::.::::..::::::  :: :
tylB    YCGNAHCVAVGSGLDDARLALWALGVGEGDEVIVPSHTFIASWLAVSATGATPVPVEPGD
           60        70        80        90       100       110

110       120       130       140       150       160
orf3    --DPTPDGLSLDPALVEAALTPRTRALMPVHLHGHPADLDPLLAIAGRHGLAVVEDAAQA
         .:  ..  :::   .:::::::::::::.::::.:::::.:..: . ..:  :::::::::
tylB    PGEPGPGAFLLDPDRLEAALTPRTRAVMPVHLYGHPVDLDPVGAFAEPHGLAVVEDAAQA
         120       130       140       150       160       170

170       180       190       200       210       220
orf3    HGARYRGRRIGSGHVVAFSFYPGKNLGAMGDGGAVVTGDSGVAERIRLLRNCGSREKYRH
        :::::::::::::::   .::::::::::::::::::.:::::.:  .:.:.:::: :.::::::
tylB    T-ARYRGRRIGSGHRTAFSFYPGKNLGALGDGGAVVTSDPELADRLRLLRNYGAREKYRH
         180       190       200       210       220       230

230       240       250       260       270       280
orf3    EVRSTHSRLDEFQAAVLRAKLPRLDAWNARRAGTAERYGRALGPVPQIAVPVTAPWADPV
        : :.:.::::::.:.:: .::: ::::::::.:  : :::::. .:  ...: .  : .::
tylB    EERGTNSRLDELQAAVLSVKLPYLDAWNTRRREIAARYGEALAGLPGVTVP-EGRVAEPV
         240       250       260       270       280       290

290       300       310       320       330       340
orf3    WHLYVIRCAERDELRRRLERAGVQTLIHYPVPPHRSPAYADDPAGA-PAGTHPLSERLAA
        :: ::.:  ::.::::::::.::::.:::: : ::: ::  ::: : .:::::.
tylB    WHQYVLRSPYRDRLRRRLAEAGVETLVHYPVAVHASGAYAG--AGPCPAGGLPRAERLAG
         300       310       320       330       340       350

350       360       370       380
orf3    QSLSLPLGPHLGEDEARAVVAAVRAASAGLAAYPTDGQRFPLVTEKR
        . :::::.:::: :::.::.:::.:::: :...:.
tylB    EVLSLPIGPHLPDEAVEVVIAAVQSAALDSWEEGP
         360       370       380
```

FIG. 25

Comparison of:
(A) SRMD=Query (B) MDMA=Sbjct

>gi|320536|pir||A60725 midecamycin-resistance protein mdmA - Streptomyces mycarofaciens
Length = 271

Score = 380 bits (975), Expect = e-104
Identities = 211/269 (78%), Positives = 232/269 (85%)

```
(A) Query:   7  LPPQSVSAPADSRSTARREWGQNFFRTAAAACRFSAQLDGSDTIPPDSPNDLMTVEIGAG  66
                 + P S SAPA SRSTARRE GQNFFR+AAAACRFS QLD      P S  D++TVEIGAG
(B) Sbjct:   1  MSPISASAPAASRSTARRELGQNFFRSAAAACRFSDQLDAFCADLPGSLADVLTVEIGAG  60

(A) Query:  67  SGRVTKVLASPGTPLLAVEIDPRWARRLAAESLPDVTVVNEDFLTLQLPGQPVRLIGNLP 126
                SGRVTK LAS G  LLAVEID  WARRL AESLPDVTVVNEDFL LQLP QP+RLIGNLP
(B) Sbjct:  61  SGRVTKALASAGRSLLAVEIDAYWARRLTAESLPDVTVVNEDFLNLQLPRQPIRLIGNLP 120

(A) Query: 127  FVTGTRMLRRCLDMGPARMRQGVFLLQREYVGKRTGAWGGNLFNAQWEPWYSFDRGLAFS 186
                FV+GT++LRRCL++GP RM Q VFLLQREYVGKRTGAWGGNLFNAQWEPWY+F+ GLAFS
(B) Sbjct: 121  FVSGTKILRRCLELGPNRMCQAVFLLQREYVGKRTGAWGGNLFNAQWEPWYTFEGGLAFS 180

(A) Query: 187  RQDFTPVPRADTQTLMVAPHRRPSVPWREKAAYQRFVQRFVDTGQMTVGDAARKVLRRGH 246
                R +F+PVPRADTQTL+V P RRPSVPWRE+    YQRF   Q++FDTGQMT+G+AARKVLRRGH
(B) Sbjct: 181  RNEFSPVPRADTQTLVVMPRRRPSVPWRERTDYQRFTQQIFDTGQMTIGEAARKVLRRGH 240

(A) Query: 247  AQFVRGAGVRPADRVKDLTVPEWTALFRA 275
                AQFVR AGVRPADRVKDLTV +W ALFRA
(B) Sbjct: 241  AQFVRSAGVRPADRVKDLTVRDWAALFRA 269
```

FIG. 26 phase 1 (att1): atcGCGGCGCTTCGTTCGGGACGAAGAGGTagat
phase 2 (att2): atcgGCGGCGCTTCGTTCGGGACGAAGAGGTagat
phase 3 (att3): atcgGCGGCGCTTCGTTCGGGACGAAGAGGTagat

FIG. 27

Probe I: PCR product ORF23c-ORF25c

Probe II: PCR product ORF1*c-ORF2*c

Probe III: DNA fragment covering orf1, orf2 and orf3

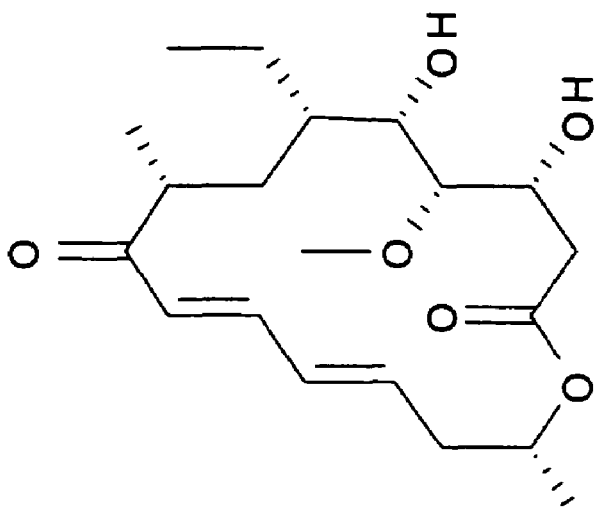
« Platenolide B » MM=368
Molecular mass =368
Molecular formula =C20H32O6
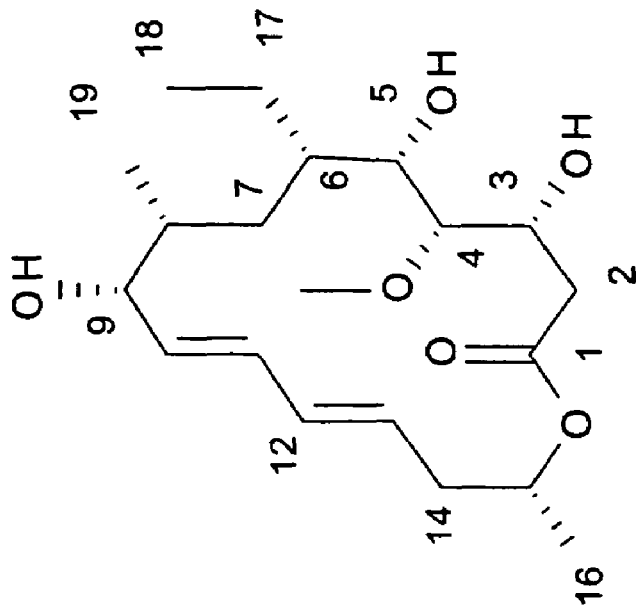
« Platenolide A » MM =370
Molecular mass =370
Molecular formula=C20H34O6
FIG. 36

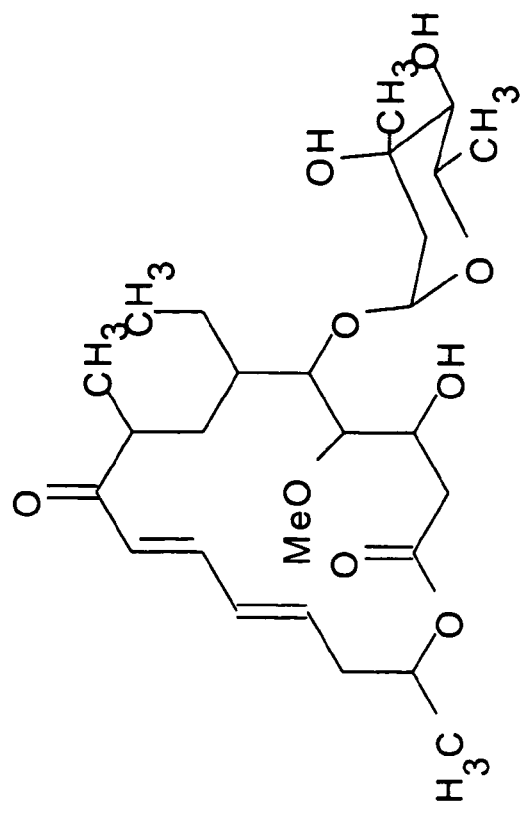
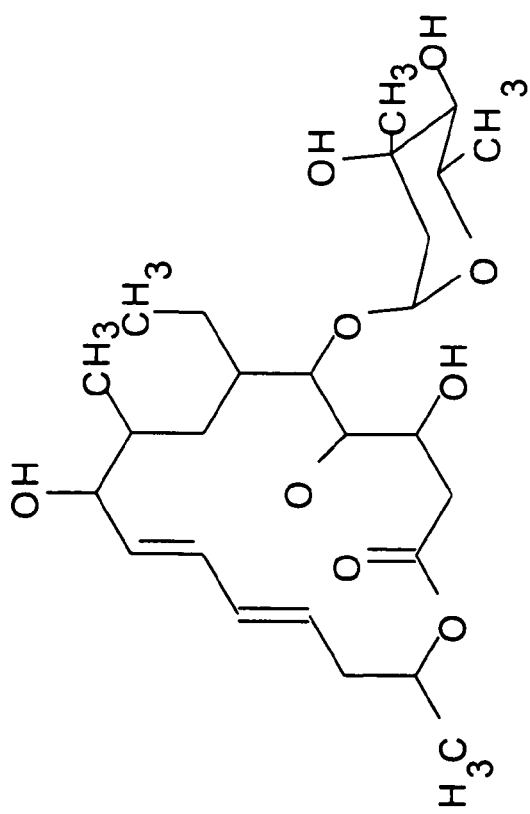
FIG. 40

POLYPEPTIDES INVOLVED IN THE BIOSYNTHESIS OF SPIRAMYCINS, NUCLEOTIDE SEQUENCES ENCODING THESE POLYPEPTIDES AND APPLICATIONS THEREOF

This is a Non-Provisional of U.S. application No. 60/493,490, filed Aug. 7, 2003.

The present invention relates to the isolation and identification of novel genes of the biosynthetic c pathway for spiramycins and to novel polypeptides involved in this biosynthesis. It also relates to the use of these genes for the purpose of increasing the levels of production and the purity of the spiramycin produced.

The invention also relates to the use of these genes for constructing mutants which can lead to the synthesis of novel antibiotics or to derived forms of spiramycins. The invention also relates to the molecules produced through the expression of these genes and, finally, to pharmacologically active compositions of a molecule produced through the expression of such genes.

*Streptomyces* are Gram-positive filamentous soil bacteria. They play an important role in the decomposition and mineralization of organic materials due to the great diversity of degrading enzymes that they secrete. They exhibit morphological differentiation phenomena which are unique in prokaryotes, accompanied by a metabolic differentiation characterized by the production of secondary metabolites having an extraordinary diversity of chemical structures and biological activities. Among these metabolites are the spiramycins produced naturally by the bacterium *Streptomyces ambofaciens*.

Spiramycin is an antibiotic of the macrolide family which is of use both in veterinary medicine and in human medicine. Macrolides are characterized by the presence of a lactone ring onto which are grafted one or more sugars. *Streptomyces ambofaciens* naturally produces spiramycin I, II and III (cf. FIG. 1); however, the antibiotic activity of spiramycin I is clearly greater than that of spiramycins II and III (Liu et al., 1999). The spiramycin I molecule consists of a lactone-based macrocycle, called platenolide, and three sugars: forosamine, mycaminose and mycarose (cf. FIG. 1). The antibiotic activity of spiramycins is due to inhibition of protein synthesis in prokaryotes via a mechanism involving binding of the antibiotic to the bacterial ribosome.

Certain compounds which are members of the macrolide family and which also possess a lactone ring have given rise to uses outside the field of antibiotics. Thus, the product FK506 has immunosuppressor effects and offers perspectives of therapeutic application in the field of organ transplantation, of rheumatoid arthritis and, more generally, in pathological conditions related to autoimmune reactions. Other macrolides, such as avermectin, have insecticidal and anti-helminth activity.

Many biosynthetic pathways, concerning antibiotics belonging to varied classes, and also other secondary metabolites (for a review, K, Chater, 1990), have to date already been studied in *Streptomycetes*. However, knowledge of the biosynthetic pathways for spiramycins is, to date, only very partial.

Spiramycin biosynthesis is a complex process comprising many steps and involving many enzymes (Omura et al., 1979a, Omura et al., 1979b). Spiramycins belong to the large class of polyketides which includes complex molecules which are particularly abundant in microorganisms found in the soil. These molecules are grouped together not through structural analogy, but through a certain similarity in the steps of their biosynthetic pathway. Specifically, polyketides are produced by a complex series of reactions, which have in common the fact that, in their biosynthetic pathway, there is a series of reactions catalyzed by one or more enzymes called "polyketide synthases" (PKS). In *Streptomyces ambofaciens*, the biosynthesis of the lactone-based macrocycle of spiramycins (platenolide) is carried out by a series of eight modules encoded by five PKS genes (S. Kuhstoss, 1996, U.S. Pat. No. 5,945,320). Spiramycins are obtained from this lactone ring. However, the various steps and enzymes involved in the synthesis of the sugars, and also their attachment to the lactone ring and the modification of this ring so as to obtain spiramycins still remain unknown to date.

U.S. Pat. No. 5,514,544 describes the cloning of a sequence called srmR in *Streptomyces ambofaciens*. In that patent, the hypothesis that the srmR gene encodes a protein which regulates the transcription of the genes involved in macrolide biosynthesis is put forward.

In 1987, Richardson and colleagues (Richardson et al., 1987) showed that the spiramycin resistance of *S. ambofaciens* is imparted by at least three genes; said genes were called srmA, srmB and srmC. U.S. Pat. No. 4,886,757 describes more particularly the characterization of a DNA fragment of *S. ambofaciens* containing the srmC gene. However, the sequence of this gene was not disclosed. In 1990, Richardson and colleagues (Richardson et al., 1990) put forward the hypothesis that there are three genes for spiramycin biosynthesis close to srmB. U.S. Pat. No. 5,098,837 reports the cloning of five genes potentially involved in spiramycin biosynthesis. These genes were named srmD, srmE, srmF, srmG and srmH.

One of the major difficulties in producing compounds such as spiramycins lies in the fact that very large fermentation volumes are necessary to produce a relatively small amount of product. It is therefore desirable to be able to increase the efficiency of production of such molecules in order to decrease the cost of production thereof.

The biosynthetic pathway for spiramycins is a complex process and it would be desirable to identify and to eliminate the parasitic reactions which might exist during this process. The aim of such a manipulation is to obtain a purer antibiotic and/or an improvement in productivity. In this respect, *Streptomyces ambofaciens* naturally produces spiramycin I, II and III (cf FIG. 1); however, the antibiotic activity of spiramycin I is clearly greater than that of spiramycins II and III (Liu et al., 1999). It would therefore be desirable to be able to have strains which produce only spiramycin I.

Due to the commercial value of macrolide antibiotics, the production of novel derivatives, in particular of analogs of spiramycins having advantageous properties, is intensely sought. It would be desirable to be able to generate, in sufficient amount, the biosynthetic intermediates of the biosynthetic pathway for spiramycins or spiramycin derivatives, in particular for the purpose of producing spiramycin-derived hybrid antibiotics.

GENERAL DESCRIPTION OF THE INVENTION

The present invention results from the cloning of genes the product of which is involved in spiramycin biosynthesis. The invention relates, first of all, to novel genes of the biosynthetic pathway for spiramycins and novel polypeptides involved in this biosynthesis.

The genes of the biosynthetic pathway and the associated coding sequences have been cloned and the DNA sequence of each one has been determined. The cloned coding sequences will hereafter be designated orf1*c, orf2*c, orf3*c, orf4*c, orf5*, orf6*, orf7*c, orf8*, orf9*, orf10*, orf1, orf2, orf3, orf4, orf5, orf6, orf7, orf8, orf9c, orf10, orf11c, orf12, orf13c, orf14, orf15c, orf16, orf17, orf18, orf19, orf20, orf21c, orf22c, orf23c, orf24c, orf25c, orf26, orf27, orf28c, orf29c, orf30c, orf31, orf32c, orf33 and orf34c. The function of the proteins encoded by these sequences in the biosynthetic pathway for spiramycins is developed in the discussion hereinafter, which is illustrated by FIGS. 4, 5, 6 and 8.

1) A first subject of the invention concerns a polynucleotide encoding a polypeptide involved in spiramycin biosynthesis, wherein the sequence of said polynucleotide is:
   (a) one of the sequences SEQ ID No. 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149,
   (b) one of the sequences consisting of the variants of the sequences (a),
   (c) one of the sequence derived from the sequences (a) and (b) due to the degeneracy of the genetic code.

2) A subject of the present invention is also a polynucleotide which hybridizes, under high stringency hybridization conditions, to at least one of the polynucleotides according to paragraph 1) above.

3) The invention also relates to a polynucleotide exhibiting at least 70%, 80%, 85%, 90%, 95% or 98% nucleotide identity with a polynucleotide comprising at least 10, 12, 15, 18, 20 to 25, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850 or 1900 consecutive nucleotides of a polynucleotide according to paragraph 1) above.

4) The invention also relates to a polynucleotide according to paragraph 2) or 3) above, which is isolated from a bacterium of the genus *Streptomyces*.

5) The invention also relates to a polynucleotide according to paragraph 2), 3) or 4) above, which encodes a protein involved in the biosynthesis of a macrolide.

6) The invention also relates to a polynucleotide according to paragraph 2), 3) or 4) above, which encodes a protein having an activity similar to the protein encoded by the polynucleotide with which it hybridizes or with which it exhibits the identity.

7) The invention also relates to a polypeptide resulting from the expression of a polynucleotide according to paragraph 1), 2), 3), 4), 5) or 6) above.

8) Another aspect of the invention concerns a polypeptide involved in a spiramycin biosynthesis, wherein the sequence of said polypeptide is:
   (a) one of the sequences SEQ ID No. 4, 6, 8, 10, 12, 14, 16, 18, 20, 22, 24, 26, 27, 29, 31, 32, 33, 35, 37, 38, 39, 41, 42, 44, 46, 48, 50, 51, 52, 54, 55, 56, 57, 58, 59, 61, 63, 65, 67, 69, 71, 73, 75, 77, 79, 81, 83, 85, 108, 110, 112, 114, 116, 117, 119, 121, 142, 144, 146, 148 and 150,
   (b) one of the sequences as defined in (a), except that throughout said sequence, one or more amino acids have been substituted, inserted or deleted without affecting the functional properties thereof,
   (c) one of the sequences consisting of the variants of the sequences (a) and (b).

9) Another subject of the invention concerns a polypeptide exhibiting at least 70%, 80%, 85%, 90%, 95% or 98% amino acid identity with a polypeptide comprising at least 10, 15, 20, 30 to 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620 or 640 consecutive amino acids of a polypeptide according to paragraph 8) above.

10) Another aspect of the invention concerns a polypeptide according to paragraph 9) above, which is isolated from a bacterium of the genus *Streptomyces*.

11) Another aspect of the invention concerns a polypeptide according to paragraph 9) or 10) above, which encodes a protein involved in the biosynthesis of a macrolide.

12) Another aspect of the invention concerns a polypeptide according to pargraph 9), 10) or 11) above, which has an activity similar to that of the polypeptide with which it shares the identity.

13) Another aspect of the invention concerns a recombinant DNA, which comprises at least one polynucleotide according to one of paragraphs 1), 2), 3), 4), 5) and 6) above.

14) Another aspect of the invention concerns a recombinant DNA according to paragraph 13) above, wherein said recombinant DNA is included in a vector.

15) Another aspect of the invention concerns a recombinant DNA according to paragraph 14) above, wherein said vector is chosen from bacteriophages, plasmids, phagemids, integrative vectors, fosmids, cosmids, shuttle vectors, BACs and PACs.

16) Another aspect of the invention concerns a recombinant DNA according to paragraph 15) above, which is chosen from pOS49.1, pOS49.11, pOSC49.12, pOS49.14, pOS49.16, pOS49.28, pOS44.1, pOS44.2, pOS44.4, pSPM5, pSPM7, pOS49.67, pOS49.88, pOS49.106, pOS49.120, pOS49.107, pOS49.32, pOS49.43, pOS49.44, pOS49.50, pOS49.99, pSPM17, pSPM21, pSPM502, pSPM504, pSPM507, pSPM508, pSPM509, pSPM1, pBXL1111, pBXL1112, pBXL1113, pSPM520, pSPM521, pSPM522, pSPM523, pSPM524, pSPM525, pSPM527, pSPM528, pSPM34, pSPM35, pSPM36, pSPM37, pSPM38, pSPM39, pSPM40, pSPM41, pSPM42, pSPM43, pSPM44, pSPM45, pSPM47, pSPM48, pSPM50, pSPM51, pSPM52, pSPM53, pSPM55, pSPM56, pSPM58, pSPM72, pSPM73, pSPM515, pSPM519, pSPM74, pSPM75, pSPM79, pSPM83, pSPM107, pSPM543 and pSPM106.

17) Another aspect of the invention concerns an expression vector, which comprises at least one nucleic acid sequence encoding a polypeptide according to paragraph 7), 8), 9), 10), 11) or 12) above.

18) The invention also relates to an expression system comprising a suitable expression vector and a host cell which allows the expression of one or more polypeptides according to paragraph 7), 8), 9), 10), 11) or 12) above.

19) The invention also relates to an expression system according to paragraph 18 above, which is chosen from prokaryotic expression systems and eukaryotic expression systems.

20) The invention also relates to an expression system according to paragraph 19) above, which is chosen from systems of expression in the bacterium *E. coli*, baculovirus expression systems which allow expression in insect cells, expression systems which allow expression in yeast cells and expression systems which allow expression in mammalian cells.

21) The invention also relates to a host cell into which at least one polypeptide and/or at least one recombinant DNA and/or at least one expression vector according to one of paragraphs 1), 2), 3), 4), 5), 6), 13), 14), 15), 16) and 17) above has been introduced.

22) The invention also relates to a method of producing a polypeptide according to paragraph 7), 8), 9), 10), 11) or 12) above, wherein said method comprises the following steps:

a) inserting at least one nucleic acid encoding said polypeptide into a suitable vector;
b) culturing, in a suitable culture medium, a host cell transformed or transfected beforehand with the vector of step a);
c) recovering the conditioned culture medium or a cell extract;
d) separating and purifying said polypeptide from said culture medium or else from the cell extract obtained in step c);
e) where appropriate, characterizing the recombinant polypeptide produced.

23) Another aspect of the invention concerns a microorganism blocked in a step of the biosynthetic pathway for at least one macrolide.

24) Another aspect of the invention concerns a microorganism according to paragraph 23) above, which is obtained by inactivating the function of at least one protein involved in the biosynthesis of this (these) macrolide(s) in a microorganism which produces this (these) macrolide(s).

25) Another aspect of the invention concerns a microorganism according to paragraph 24) above, wherein the inactivation of this (these) protein(s) is carried out by mutagenesis in the gene(s) encoding said protein(s) or by expression of one or more antisense RNAs complementary to the messenger RNA(s) encoding said protein(s).

26) Another aspect of the invention concerns a microorganism according to paragraph 25) above, wherein the inactivation of this (these) protein(s) is carried out by mutagenesis via irradiation, by action of a mutagenic chemical agent, by site-directed mutagenesis or by gene replacement.

27) Another aspect of the invention concerns a microorganism according to paragraph 25) or 26) above, wherein the mutagenesis or mutageneses is or are carried out in vitro or in situ, by suppression, substitution, deletion and/or addition of one or more bases in the gene(s) under consideration or by gene inactivation.

28) Another aspect of the invention concerns a microorganism according to paragraph 23), 24), 25), 26) or 27) above, wherein said microorganism is a bacterium of the genus *Streptomyces*.

29) Another aspect of the invention concerns a microorganism according to paragraph 23), 24), 25), 26), 27) or 28) above, wherein the macrolide is spiramycin.

30) Another aspect of the invention concerns a microorganism according to paragraph 23), 24), 25), 26), 27), 28) or 29) above, wherein said microorganism is a strain of *S. ambofaciens*.

31) Another aspect of the invention concerns a microorganism according to paragraph 23), 24), 25), 26), 27), 28), 29) or 30) above, wherein the mutagenesis is carried out in at least one gene comprising a sequence according to one of paragraphs 1), 2), 3), 4), 5) and 6) above.

32) Another aspect of the invention concerns a microorganism according to paragraph 25), 26), 27), 28), 29), 30) or 31) above, wherein the mutagenesis is carried out in one or more genes comprising one of the sequences corresponding to one or more of the sequences SEQ ID No. 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149.

33) Another aspect of the invention concerns a microorganism according to paragraph 25), 26), 27), 28), 29), 30), 31) or 32) above, wherein the mutagenesis consists of the gene inactivation of a gene comprising a sequence corresponding to the sequence SEQ ID No. 13.

34) Another aspect of the invention concerns a strain of *Streptomyces ambofaciens*, which is a strain chosen from one of the strains deposited with the Collection Nationale de Cultures de Microorganismes [National Collection of Cultures and Microorganisms] (CNCM) on Jul. 10, 2002, under the registration number I-2909, I-2911, I -2912, I-2913, I-2914, I-2915, I-2916 or I-2917.

35) Another aspect of the invention concerns a method of preparing a macrolide biosynthesis intermediate, which comprises the following steps:
a) culturing, in a suitable culture medium, a microorganism according to one of paragraphs 23), 24), 25), 26), 27), 28), 29), 30), 31), 32), 33) or 34) above,
b) recovering the conditioned culture medium or a cell extract,
c) separating and purifying said biosynthesis intermediate from said culture medium or else from the extract obtained in step b).

36) Another aspect of the invention concerns a method of preparing a molecule derived from a macrolide, wherein a biosynthesis intermediate is prepared according to the method of paragraph 35) above and the intermediate thus produced is modified.

37) Another aspect of the invention concerns a method of preparation according to paragraph 36) above, wherein said intermediate is modified chemically, biochemically, enzymatically and/or microbiologically.

38) Another aspect of the invention concerns a method of preparation according to paragraph 36) or 37) above, wherein one or more genes encoding proteins capable of modifying the intermediate by using it as substrate is (are) introduced into said microorganism.

39) Another aspect of the invention concerns a method of preparation according to paragraph 36), 37) or 38) above, wherein the macrolide is spiramycin.

40) Another aspect of the invention concerns a method of preparation according to paragraph 36), 37), 38) or 39) above, wherein the microorganism used is a strain of *S. ambofaciens*.

41) Another aspect of the invention concerns a microorganism which produces spiramycin I but which does not produce spiramycin II and III 42) Another aspect of the invention concerns a microorganism according to paragraph 41) above, which comprises all of the genes required for the biosynthesis of spiramycin I, but wherein the gene comprising the sequence SEQ ID No. 13 or one of its variants, or one of the sequences derived therefrom due to the degeneracy of the genetic code, and encoding a polypeptide of sequence SEQ ID No. 14 or one of its variants, is not expressed or has been made inactive.

43) Another aspect of the invention concerns a microorganism according to paragraph 42) above, wherein said inactivation is carried out by mutagenesis in the gene encoding said protein or by the expression of an antisense RNA complementary to the messenger RNA encoding said protein.

44) Another aspect of the invention concerns a microorganism according to paragraph 43) above, wherein said mutagenesis is carried out in the promoter of this gene, in the coding sequence or in a noncoding sequence so as to make the encoded protein inactive or to prevent its expression or its translation therefrom.

45) Another aspect of the invention concerns a microorganism according to paragraph 43) or 44) above, wherein the mutagenesis is carried out by irradiation, by action of a mutagenic chemical agent, by site-directed mutagenesis or by gene replacement.

46) Another aspect of the invention concerns a microorganism according to paragraph 43), 44) or 45) above, wherein the mutagenesis is carried out in vitro or in situ, by suppression, substitution, deletion and/or addition of one or more bases in the gene under consideration or by gene inactivation.

47) Another aspect of the invention concerns a microorganism according to paragraph 41) or 42) above, wherein said microorganism is obtained by expressing the genes of the biosynthetic pathway for spiramycin without these genes comprising the gene comprising the sequence corresponding to SEQ ID No. 13 or one of its variants, or one of the sequences derived therefrom due to the degeneracy of the genetic code, and encoding a polypeptide of sequence SEQ ID No. 14 or one of its variants.

48) Another aspect of the invention concerns a microorganism according to paragraph 41), 42), 43), 44), 45), 46) or 47) above, wherein said microorganism is a bacterium of the genus *Streptomyces*.

49) Another aspect of the invention concerns a microorganism according to paragraph 41), 42), 43), 44), 45), 46), 47) or 48) above, wherein said microorganism is obtained from a starting strain which produces spiramycins I, II and III.

50) Another aspect of the invention concerns a microorganism according to paragraph 41), 42), 43), 44), 45), 46), 47), 48) or 49) above, which is obtained by mutagenesis in a gene comprising the sequence corresponding to SEQ ID No. 13 or one of its variants, or one of the sequences derived therefrom due to the degeneracy of the genetic code, and encoding a polypeptide of sequence SEQ ID No. 14 or one of its variants having the same function.

51) Another aspect of the invention concerns a microorganism according to paragraph 41), 42), 43), 44), 45), 46), 47), 48), 49) or 50) above, wherein said microorganism is obtained from a strain of *S. ambofaciens* which produces spiramycins I, II and III, in which gene inactivation of the gene comprising the sequences corresponding to SEQ ID No. 13 or one of the sequences derived therefrom due to the degeneracy of the genetic code is carried out.

52) Another aspect of the invention concerns a strain of *S. ambofaciens*, which is the strain deposited with the Collection Nationale de Cultures de Microorganismes (CNCM) on Jul. 10, 2002, under the registration number I-2910.

53) Another aspect of the invention concerns a method of producing spiramycin I, which comprises the following steps:
 (a) culturing, in a suitable culture medium, a microorganism according to one of paragraphs 41), 42), 43), 44), 45), 46), 47), 48), 49), 50), 51) and 52) above,
 (b) recovering the conditioned culture medium or a cell extract,
 (c) separating and purifying the spiramycin I from said culture medium or else from the cell extract obtained in step b).

54) Another aspect of the invention concerns the use of a polynucleotide according to one of paragraphs 1), 2), 3), 4), 5) and 6) above, for improving the macrolide production of a microorganism.

55) Another aspect of the invention concerns a macrolide-producing mutant microorganism, which has a genetic modification in at least one gene comprising a sequence according to one of paragraphs 1), 2), 3), 4), 5) or 6) above and which overexpresses at least one gene comprising a sequence according to one of paragraphs 1), 2), 3), 4), 5) and 6) above.

56) Another aspect of the invention concerns a mutant microorganism according to paragraph 55) above, wherein the genetic modification consists of a suppression, a substitution, a deletion and/or an addition of one or more bases in the gene(s) under consideration, with the aim of expressing one or more proteins having greater activity or of expressing a higher level of this (these) protein(s).

57) Another aspect of the invention concerns a mutant microorganism according to paragraph 55) above, wherein the overexpression of the gene under consideration is obtained by increasing the copy number for the gene and/or introducing a promoter which is more active than the wild-type promoter.

58) Another aspect of the invention concerns a mutant microorganism according to paragraph 55) or 57) above, wherein the overexpression of the gene under consideration is obtained by transforming a macrolide-producing microorganism with a recombinant DNA construct according to paragraph 13, 14 or 17 above, allowing the overexpression of this gene.

59) Another aspect of the invention concerns a mutant microorganism according to paragraph 55), 56), 57) or 58) above, wherein the genetic modification is carried out in one or more genes comprising one of the sequences corresponding to one or more of the sequences SEQ ID No. 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or one of its variants, or one of the sequences derived therefrom due to the degeneracy of the genetic code.

60) Another aspect of the invention concerns a mutant microorganism according to paragraph 55), 56), 57), 58) or 59) above, wherein the microorganism overexpresses one or more genes comprising one of the sequences corresponding to one or more of the sequences SEQ ID No. 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or one of its variants, or one of the sequences derived therefrom due to the degeneracy of the genetic code.

61) Another aspect of the invention concerns a mutant microorganism according to paragraph 55), 56), 57), 58), 59) or 60) above, wherein said microorganism is a bacterium of the genus *Streptomyces*.

62) Another aspect of the invention concerns a mutant microorganism according to paragraph 55), 56), 57), 58), 59), 60) or 61) above, wherein the macrolide is spiramycin.

63) Another aspect of the invention concerns a mutant microorganism according to paragraph 55), 56), 57), 58), 59), 60), 61) or 62) above, wherein said microorganism is a strain of *S. ambofaciens*.

64) Another aspect of the invention concerns a method of producing macrolides, which comprises the following steps:
 (a) culturing, in a suitable culture medium, a microorganism according to one of paragraphs 55), 56), 57), 58), 59), 60), 61), 62), 63) and 64) above,
 (b) recovering the conditioned culture medium or a cell extract,
 (c) separating and purifying said macrolide(s) produced from said culture medium or else from the cell extract obtained in step b).

65) Another aspect of the invention concerns the use of a sequence and/or of a recombinant DNA and/or of a vector according to one of paragraphs 1), 2), 3), 4), 5), 6), 7), 8), 9), 10), 11), 12), 13), 14), 15), 16) and 17) above, for preparing hybrid antibiotics.

66) Another aspect of the invention concerns the use of at least one polynucleotide and/or at least one recombinant DNA and/or at least one expression vector and/or at least one polypeptide and/or at least one host cell according to one of paragraphs 1), 2), 3), 4), 5), 6), 7), 8), 9), 10), 11), 12), 13), 14), 15), 16), 17) and 21) above, for carrying out one or more bioconversions.

67) Another aspect of the invention concerns a polynucleotide which is a polynucleotide complementary to one of the polynucleotides according to paragraph 1), 2), 3), 4), 5) or 6) above.

68) Another aspect of the invention concerns a microorganism producing at least one spiramycin, which overexpresses:
a gene which can be obtained by polymerase chain reaction (PCR) using the following pair of sequence primers:

(SEQ ID No. 138)
    5' AAGCTTGTGTGCCCGGTGTACCTGGGGAGC 3'
    and
    (SEQ ID No. 139)
    5' GGATCCCGCGACGGACACGACCGCCGCGCA 3' and, as matrix, the cosmid pSPM36 or the total DNA of *Streptomyces ambofaciens*,
or a gene derived therefrom due to the degeneracy of the genetic code.

69) Another aspect of the invention concerns a microorganism according to paragraph 68 or 90, which is a bacterium of the genus *Streptomyces*.

70) Another aspect of the invention concerns a microorganism according to paragraph 68, 69 or 90, which is a bacterium of the species *Streptomyces ambofaciens*.

71) Another aspect of the invention concerns a microorganism according to paragraph 68, 69, 70 or 90, wherein the overexpression of said gene is obtained by transformation of said microorganism with an expression vector.

72) Another aspect of the invention concerns a strain of *Streptomyces ambofaciens*, which is the strain OSC2/pSPM75(1) or the strain OSC2/pSPM75(2) deposited with the Collection Nationale de Cultures de Microorganismes (CNCM) [National Collection of Cultures and Microorganisms] Pasteur Institute, 25, rue du Docteur Roux 75724 Paris Cedex 15, France, on Oct. 6, 2003, under the registration number I-3101.

73) Another aspect of the invention concerns a recombinant DNA which comprises:
a polynucleotide which can be obtained by polymerase chain reaction using the following pair of sequence primers:
5' AAGCTTGTGTGCCCGGTGTACCTGGGGAGC 3' (SEQ ID No. 138) and
5' GGATCCCGCGACGGACACGACCGCCGCGCA 3' (SEQ ID No. 139) and, as matrix, the cosmid pSPM36 or the total DNA of *Streptomyces ambofaciens*,
or a fragment of at least 10, 12, 15, 18, 20 to 25, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1460, 1470, 1480, 1490 or 1500 consecutive nucleotides of this polynucleotide.

74) Another aspect of the invention concerns a recombinant DNA according to paragraph 73 or 91, which is a vector.

75) Another aspect of the invention concerns a recombinant DNA according to paragraph 73, 74 or 91, which is an expression vector.

76) Another aspect of the invention concerns a host cell into which at least one recombinant DNA according to one of paragraphs 73, 74, 75 and 91 has been introduced.

77) Another aspect of the invention concerns a method of producing a polypeptide, wherein said method comprises the following steps:
a) transforming a host cell with at least one expression vector according to paragraph 75;
b) cultivating, in a suitable culture medium, said host cell;
c) recovering the conditioned culture medium or a cell extract;
d) separating and purifying said polypeptide from said culture medium or else from the cell extract obtained in step c);
e) where appropriate, characterizing the recombinant polypeptide produced.

78) Another aspect of the invention concerns a microorganism according to paragraph 51, wherein the gene inactivation is carried out by in-phase deletion of the gene or of a part of the gene comprising the sequence corresponding to SEQ ID No. 13 or one of the sequences derived therefrom due to the degeneracy of the genetic code.

79) Another aspect of the invention concerns a microorganism according to one of paragraphs 41, 42, 43, 44, 45, 46, 47, 48, 49, 50, 51 and 78, which also overexpresses:
a gene which can be obtained by polymerase chain reaction using the following pair of sequence primers:
5' AAGCTTGTGTGCCCGGTGTACCTGGGGAGC 3' (SEQ ID No. 138) and
5' GGATCCCGCGACGGACACGACCGCCGCGCA 3' (SEQ ID No. 139) and, as matrix, the cosmid pSPM36 or the total DNA of *Streptomyces ambofaciens*,
or a gene derived therefrom due to the degeneracy of the genetic code.

80) Another aspect of the invention concerns an expression vector, wherein the polynucleotide of sequence SEQ ID No. 47, or a polynucleotide derived therefrom due to the degeneracy of the genetic code, is placed under the control of a promoter which allows the expression of the protein encoded by said polynucleotide in *Streptomyces ambofaciens*.

81) Another aspect of the invention concerns an expression vector according to paragraph 80, which is the plasmid pSPM524 or pSPM525.

82) Another aspect of the invention concerns a strain of *Streptomyces ambofaciens* transformed with a vector according to paragraph 80 or 81.

83) Another aspect of the invention concerns a microorganism according to one of paragraphs 41, 42, 43, 44, 45, 46, 47, 48, 49, 50, 51, 78, 79 and 92, which also overexpresses the gene having coding sequence SEQ ID No. 47 or a coding sequence derived therefrom due to the degeneracy of the genetic code.

84) Another aspect of the invention concerns a microorganism according to paragraph 83, which is the strain SPM502 pSPM525 deposited with the Collection Nationale de Cultures de Microorganismes (CNCM) Pasteur Institute, 25 rue du Docteur Roux 75724 Paris Cedex 15, France, on Feb. 26, 2003, under the registration number I-2977.

85) Another aspect of the invention concerns a method of producing spiramycin(s), which comprises the following steps:
(a) culturing, in a suitable culture medium, a microorganism according to one of paragraphs 68, 69, 70, 71, 72, 78, 79, 82, 83, 84, 90 and 92,
(b) recovering the conditioned culture medium or a cell extract,
(c) separating and purifying the spiramycins from said culture medium or else from the cell extract obtained in step b).

86) Another aspect of the invention concerns a polypeptide, the sequence of which comprises the sequence SEQ ID No. 112 or the sequence SEQ ID No. 142.

87) Another aspect of the invention concerns a polypeptide, the sequence of which corresponds to the sequence translated from the coding sequence:
of a gene which can be obtained by polymerase chain reaction (PCR) using the following pair of sequence primers:
5' AAGCTTGTGTGCCCGGTGTACCTGGGGAGC 3' (SEQ ID No. 138) and
5' GGATCCCGCGACGGACACGACCGCCGCGCA 3' (SEQ ID No. 139) and, as matrix, the cosmid pSPM36 or the total DNA of *Streptomyces ambofaciens*,
or of a gene derived therefrom due to the degeneracy of the genetic code.

88) Another aspect of the invention concerns an expression vector which allows the expression of a polypeptide according to paragraph 86, 87 or 93 in *Streptomyces ambofaciens*.

89) Another aspect of the invention concerns an expression vector according to paragraph 88, which is the plasmid pSPM75.

90) Another aspect of the invention concerns a microorganism according to paragraph 68, wherein the gene which can be obtained by polymerase chain amplification is the gene of coding sequence SEQ ID No. 141, or a gene derived therefrom due to the degeneracy of the genetic code.

91) Another aspect of the invention concerns a recombinant DNA according to paragraph 73, wherein the polynucleotide which can be obtained by polymerase chain amplification is a polynucleotide of sequence SEQ ID No. 141.

92) Another aspect of the invention concerns a microorganism according to paragraph 79, wherein the gene which can be obtained by polymerase chain amplification is the gene of coding sequence SEQ ID No. 141, or a gene derived therefrom due to the degeneracy of the genetic code.

93) Another aspect of the invention concerns a polypeptide, the sequence of which is SEQ ID No. 142.

General Definitions

For the purpose of the present invention, the term "isolated" denotes a biological material (nucleic acid or protein) which has been removed from its original environment (the environment in which it is naturally located).

For example, a polynucleotide present in the natural state in a plant or an animal is not isolated. The same polynucleotide separated from the adjacent nucleic acids within which it is naturally inserted in the genome of the plant or the animal is considered to be "isolated".

Such a polynucleotide can be included in a vector and/or such a polynucleotide can be included in a composition, and can nevertheless remain in the isolated state due to the fact that the vector or the composition does not constitute its natural environment.

The term "purified" does not require the material to be present in a form of absolute purity, excluding the presence of other compounds. It is rather a relative definition.

A polynucleotide in the "purified" state after purification of the starting material or of the natural material by at least an order of magnitude, preferably 2 or 3, and preferentially 4 or 5, orders of magnitude.

For the purposes of the present invention, the term ORF ("Open Reading Frame") has been used to denote in particular the coding sequence of a gene.

For the purposes of the present invention, the expression "nucleotide sequence" can be used to denote equally a polynucleotide or a nucleic acid. The expression "nucleotide sequence" encompasses the genetic material itself and is not therefore restricted to the information concerning its sequence.

The terms "nucleic acid", "polynucleotide", "oligonucleotide" or alternatively "nucleotide sequence" encompass RNA, DNA or cDNA sequences or RNA/DNA hybrid sequences of more than one nucleotide, equally in the single-chain form or in the form of a duplex.

The term "nucleotide" denotes both the natural nucleotides (A, T, G, C) and also modified nucleotides which comprise at least one modification, such as (1) a purine analog, (2) a pyrimidine analog, or (3) a sugar analog, examples of such modified nucleotides being described, for example, in PCT application No. WO 95/04064.

For the purposes of the present invention, a first polynucleotide is considered to be "complementary" to a second polynucleotide when each base of the first polynucleotide is paired to the complementary base of the second polynucleotide, the orientation of which is reversed. The complementary bases are A and T (or A and U), or C and G.

The term "genes of the biosynthetic pathway for spiramycins" also comprises the regulatory genes and the genes imparting resistance to the producer microorganisms.

According to the invention, the term "fragment" of a reference nucleic acid will be intended to mean a nucleotide sequence which is shorter compared to the reference nucleic acid and comprises, on the common portion, a nucleotide sequence identical to the reference nucleic acid.

According to the invention, such a nucleic acid "fragment" may, where appropriate, be included in a larger polynucleotide of which it is a constituent.

Such fragments comprise, or alternatively consist of, polynucleotides of length ranging from 8, 10, 12, 15, 18, 20 to 25, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850 or 1900 consecutive nucleotides of a nucleic acid according to the invention.

According to the invention, the term "fragment" of a polypeptide will be intended to mean a polypeptide the amino acid sequence of which is shorter than that of the reference polypeptide and which comprises, over the entire portion common with these reference polypeptides, an identical amino acid sequence.

Such fragments may, where appropriate, be included in a larger polypeptide of which they are part.

Such fragments of a polypeptide according to the invention may be 10, 15, 20, 30 to 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620 or 640 amino acids in length.

For the purpose of the present invention, the expression "high stringency hybridization conditions" will be intended to mean hybridization conditions which are unfavorable to the hybridization of nonhomologous nucleic acid strands. High stringency hybridization conditions can, for example, be described as conditions of hybridization in the buffer described by Church & Gilbert (Church & Gilbert, 1984) at a temperature of between 55° C. and 65° C.; preferably the hybridization temperature is 55° C., even more preferably the hybridization temperature is 60° C., and most preferably the hybridization temperature is 65° C., followed by one or more washes carried out in 2×SSC buffer (1×SSC buffer corresponds to an aqueous solution of 0.15M NaCl, 15 mM of sodium citrate) at a temperature of between 55° C. and 65° C.; preferably this temperature is 55° C., even more preferably this temperature is 60° C., and most preferably this temperature is 65° C., followed by one or more washes in 0.5×SSC buffer at a temperature of between 55° C. and 65° C.; preferably this temperature is 55° C., even more preferably this temperature is 60° C., and most preferably this temperature is 65° C.

It goes without saying that the hybridization conditions described above can be adjusted as a function of the length of the nucleic acid the hybridization of which is sought, or of the type of labeling chosen, according to techniques known to those skilled in the art. The suitable hybridization conditions can, for example, be adjusted according to the work by F. Ausubel et al (2002).

The term "variant" of a nucleic acid according to the invention will be intended to mean a nucleic acid which differs by one or more bases compared to the reference polynucleotide. A variant nucleic acid may be of natural origin, such as a naturally found allelic variant, or may also be a non-natural variant obtained, for example, by mutagenesis techniques.

In general, the differences between the reference nucleic acid and the variant nucleic acid are small such that the nucleotide sequences of the reference nucleic acid and of the variant nucleic acid are very close and, in many regions, identical. The nucleotide modifications present in a variant nucleic acid may be silent, which means that they do not modify the amino acid sequences encoded by said variant nucleic acid.

However, the nucleotide changes in a variant nucleic acid may also result in substitutions, additions and/or deletions in the polypeptide encoded by the variant nucleic acid compared to the peptides encoded by the reference nucleic acid. In addition, nucleotide modifications in the coding regions may produce conservative or nonconservative substitutions in the amino acid sequence.

Preferably, the variant nucleic acids according to the invention encode polypeptides which conserve substantially the same function or biological activity as the polypeptide of the reference nucleic acid, or else the ability to be recognized by antibodies against the polypeptides encoded by the initial nucleic acid.

Some variant nucleic acids will thus encode mutated forms of the polypeptides, the systematic study of which will make it possible to deduce structure-activity relationships of the proteins in question.

The term "variant" of a polypeptide according to the invention will mainly be intended to mean a polypeptide the amino acid sequence of which contains one or more substitutions, additions or deletions of at least one amino acid residue, compared to the amino acid sequence of the reference polypeptide, it being understood that the amino acid substitutions can be indifferently conservative or nonconservative.

Preferably, the variant polypeptides according to the invention conserve substantially the same function or biological activity as the reference polypeptide, or else the ability to be recognized by antibodies against the initial polypeptide.

For the purpose of the invention, polypeptide having "an activity similar" to a reference polypeptide is intended to mean a polypeptide having a biological activity close, but not necessarily identical, to that of the reference polypeptide as measured in a biological assay suitable for measuring the biological activity of the reference polypeptide.

For the purpose of the invention, the term "hybrid antibiotic" is intended to mean a compound generated by constructing an artificial biosynthetic pathway using recombinant DNA technology.

DETAILED DESCRIPTION OF THE INVENTION

A subject of the present invention is more particularly novel genes of the biosynthetic pathway for spiramycins and novel polypeptides involved in this biosynthesis as presented in the detailed description below.

The genes of the biosynthetic pathway were cloned and the DNA sequence of these genes was determined. The sequences obtained were analyzed using the FramePlot program (J. Ishikawa & K. Hotta, 1999). Among the open reading frames, those exhibiting a codon usage typical of *Streptomyces* were identified. This analysis showed that this region comprises 44 ORFs located on either side of five genes encoding the enzyme "polyketide synthase" (PKS), and exhibiting a codon usage typical of *Streptomyces*. On either side of these five genes encoding PKSs, 10 and 34 ORFs, respectively, were identified downstream and upstream (downstream and upstream being defined by the orientation of the 5 PKS genes all oriented in the same direction) (cf. FIGS. 3 and 37). Thus, the 34 open reading frames of this type, occupying a region of approximately 41.7 kb (cf. SEQ ID No. 1 exhibiting a first region of 31 kb containing 25 ORFs and SEQ ID No. 140 exhibiting a region of approximately 12.1 kb, 1.4 kb of which overlap the preceding sequence (SEQ ID No. 1) and approximately 10.7 kb of which correspond to the subsequent sequence, the latter portion of approximately 10.7 kb containing 9 additional ORFs (including one ORF of partial sequence) cf. also FIGS. 3 and 37 below), were identified upstream of the 5 genes encoding the PKSs, and 10 occupying a region approximately 11.1 kb (SEQ ID No. 2 and FIG. 3) were identified downstream of the PKS genes. The 10 genes located downstream of the 5 PKS genes were thus named orf1*c, orf2*c, orf3*c, orf4*c, orf5*, orf6*, orf7*c, orf8*, orf9* and orf10* (SEQ ID No. 3, 5, 7, 9, 11, 13, 15, 17, 19 and 21). The "c" added in the name of the gene signifies, for the ORF in question, that the coding sequence is in the reverse orientation (the coding strand is therefore the strand complementary to the sequence given in SEQ ID No. 2 for these genes). Using the same nomenclature, the 34 ORFs upstream of the PKS genes were named orf1, orf2, orf3, orf4, orf5, orf6, orf7, orf8, orf9c, orf10, orf11c, orf12, orf13c, orf14, orf15c, orf16, orf17, orf18, orf19, orf20, orf21c, orf22c, orf23c, orf24c, orf25c, orf26, orf27, orf28c, orf29, orf30c, orf31, orf32c, orf33 and orf34c (SEQ ID Nos 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149) (cf. FIGS. 3 and 37).

The protein sequences deduced from these open reading frames were compared with those present in various databases using various programs: BLAST (Altschul et al., 1990) (Altschul et al., 1997), CD-search, COGs (Cluster of orthologous Groups) (these three programs are accessible in particular from the National Center for Biotechnology Information (NCBI) (Bethesda, Md., USA)), FASTA ((W. R. Pearson & D. J. Lipman, 1988) and (W. R. Pearson, 1990), BEAUTY (K. C. Worley et al., 1995)), (these two programs are accessible in particular from the INFOBIOGEN resource center, Evry, France). These comparisons made it possible to formulate hypotheses regarding the function of the products of these genes and to identify those liable to be involved in spiramycin biosynthesis.

Genes Located Downstream of the Genes Encoding the PKSs

Figure 3:
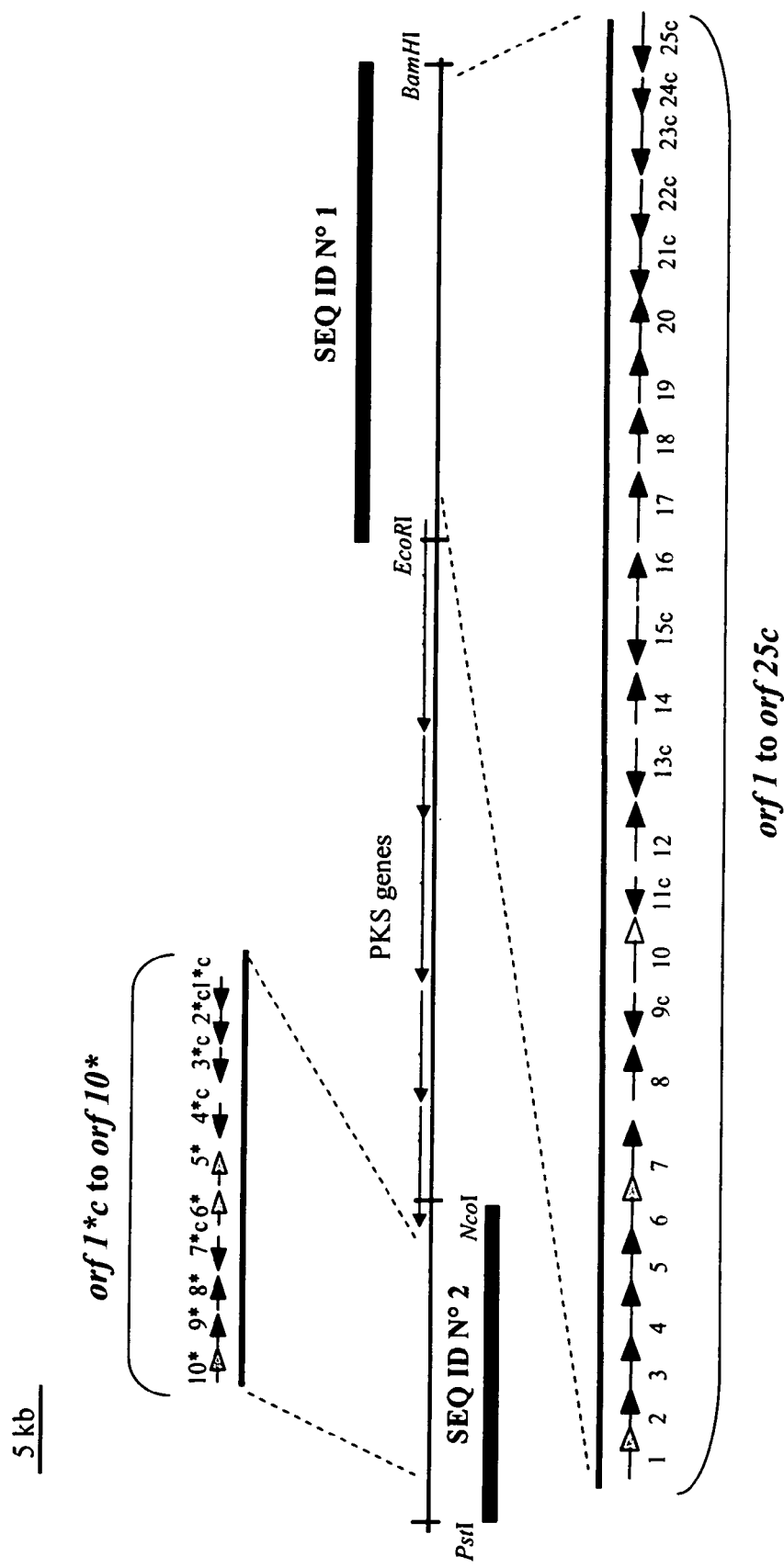

A diagrammatic representation of the organization of the region is given in FIG. 3. As will be demonstrated below, on the 10 genes identified downstream of the genes encoding the PKSs, 9 appear to be involved in the biosynthesis of or the resistance to spiramycins. They are the following 9 genes: orf1*c, orf2*c, orf3*c, orf4*c, orf5*, orf6*, orf7*c, orf8* and orf9*.

In table 1 below the references to the DNA sequence and the amino acid sequence of the 10 genes identified downstream of the 5 PKS genes are given.

TABLE 1

| Gene | Position in the sequence SEQ ID No. 2 | DNA sequence | Polypeptide sequences |
|---|---|---|---|
| orf1*c | 10882 to 10172 | SEQ ID No. 3 | SEQ ID No. 4 |
| orf2*c | 10052 to 8781 | SEQ ID No. 5 | SEQ ID No. 6 |
| orf3*c | 8741 to 7476 | SEQ ID No. 7 | SEQ ID No. 8 |
| orf4*c | 7459 to 6100 | SEQ ID No. 9 | SEQ ID No. 10 |
| orf5* | 5302 to 5976 | SEQ ID No. 11 | SEQ ID No. 12 |
| orf6* | 4061 to 5305 | SEQ ID No. 13 | SEQ ID No. 14 |
| orf7*c | 3665 to 2817 | SEQ ID No. 15 | SEQ ID No. 16 |
| orf8* | 1925 to 2755 | SEQ ID No. 17 | SEQ ID No. 18 |
| orf9* | 1007 to 1888 | SEQ ID No. 19 | SEQ ID No. 20 |
| orf10* | 710 to 937 | SEQ ID No. 21 | SEQ ID No. 22 |

The "c" added to the name of the gene indicates that the coding sequence is in the reverse orientation (the coding strand is therefore the strand complementary to the sequence given in SEQ ID No. 2 for these genes).

With the aim of determining the function of the polypeptides identified, three types of experiment were carried out: comparison of the identified sequences with sequences of known functions, gene inactivation experiments, leading to the construction of mutant strains, and analyses of the production of spiramycins and of spiramycin biosynthesis intermediates by these mutant strains.

The protein sequences deduced from these open reading frames were first of all compared with those present in various databases using various programs: BLAST (Altschul et al., 1990) (Altschul et al., 1997), CD-search, COGs (Cluster of Orthologous Groups), FASTA ((W. R. Pearson & D. J. Lipman, 1988) and (W. R. Pearson, 1990), BEAUTY (K. C. Worley et al., 1995)). These comparisons made it possible to formulate hypotheses regarding the function of the products of these genes and to identify those liable to be involved in spiramycin biosynthesis. Table 2 shows the proteins exhibiting strong similarity with the products of the 10 genes located downstream of the 5 PKS genes.

TABLE 2

| Gene product | Protein exhibiting significant similarity | GenBank accession number | BLAST* score | Reported function |
|---|---|---|---|---|
| orf1*c | TylMI(orf3*) (S. fradiae) | CAA57473 | 287 | N-methyltransferase |
| orf2*c | dnrQ gene product (Streptomyces) peucetius | AAD15266 | 153 | unknown |
| orf3*c | TylMII(orf2*) (S. fradiae) | CAA57472 | 448 | Glycosyltransferase |
| orf4*c | Crotonyl-CoA reductase (S. coelicolor) | NP_630556 | 772 | Crotonyl-CoA reductase |
| orf5* | MdmC (S. mycarofaciens) | B42719 | 355 | O-methyltransferase |
| orf6* | 3-O-acyltransferase (S. mycarofaciens) | Q00718 | 494 | Acyltransferase |
| orf7*c | MdmA (S. mycarofaciens) | A60725 | 380 | Protein involved in midecamycin resistance |
| orf8* | ABC-transporter (S. griseus) | CAC22119 | 191 | ABC-transporter |
| orf9* | ABC-transporter (S. griseus) | CAC22118 | 269 | ABC-transporter |
| orf10* | Putative small conserved hypothetical protein (S. coelicolor) | NP_627432 | 109 | unknown |

*a greater sequence similarity is associated with a higher BLAST score (Altschul et al., 1990).

Gene inactivation experiments were carried out in order to confirm these results. The methods used consist in performing a gene replacement. The target gene to be interrupted is replaced with a copy of this gene interrupted with a cassette imparting resistance to an antibiotic (for example apramycin, geneticin or hygromycin). The cassettes used are bordered on either side by translation termination codons in all the reading frames and by transcription terminators which are active in Streptomyces. Insertion of the cassette into the target gene may or may not be accompanied by a deletion in this target gene. The size of the regions flanking the cassette may range from a few hundred to several thousand base pairs. A second type of cassette can be used for the gene inactivation: cassettes termed "excisable cassettes". These cassettes have the advantage of being able to be excised in Streptomyces by a site-specific recombination event after having been introduced into the genome of S. ambofaciens. The aim is to inactivate certain genes in strains of Streptomyces without leaving, in the final strain, selection markers or large DNA sequences not belonging to the strain. After excision, only a short sequence of about 30 base pairs (called "cicatricial" site) remains in the genome of the strain (cf. FIG. 10). The use of this system consists, initially, in replacing the wild-type copy of the target gene (by virtue of two homologous recombination events, cf. FIG. 9) with a construct in which an excisable cassette has been inserted into this target gene. The insertion of this cassette is accompanied by a deletion in the target gene (cf. FIG. 9). Secondly, the excision of the excisable cassette from the genome of the strain is brought about. The excisable cassette functions by virtue of a system of site-specific recombination and has the advantage of making it possible to obtain Streptomyces mutants which do not in the end carry a resistance gene. Possible polar effects on the expression of the genes located downstream of the inactivated gene(s) are also avoided (cf. FIG. 10). The strains thus constructed were tested for their spiramycin production.

The orf1*c, orf2*c, orf3*c and orf4*c genes were not inactivated since the sequence comparison experiments made it possible to determine that these genes had a relatively high similarity with genes involved in the biosynthesis of a relatively close antibiotic. Thus, the orf1*c gene encodes a protein exhibiting 66% identity (determined using the BLAST program) with the protein encoded by the tylM1 gene which encodes an N-methyltransferase which is involved in the biosynthesis of tylosine and which catalyzes 3-N-methylation during the production of mycaminose in Streptomyces fradiae (A. R. Gandecha et al., 1997; GenBank accession number: CAA57473; BLAST score: 287). This similarity with a protein involved in the biosynthetic pathway for another antibiotic relatively close, and more particularly in the biosynthesis of mycaminose, suggests that the orf1*c gene encodes an N-methyltransferase responsible for an N-methylation during the biosynthesis of forosamine or of mycaminose (cf. FIGS. 5 and 6). This hypothesis is supported by the fact that the protein encoded by the orf1*c gene exhibits strong similarity with other proteins of similar function in other organisms (cf. table 3).

TABLE 3

| Protein exhibiting significant similarity | GenBank accession number | BLAST* score | Reported function |
|---|---|---|---|
| methyltransferase (S. antibioticus) | CAA05643 | 277 | methyltransferase |
| N,N-dimethyltransferase (S. venezuelae) | AAC68678 | 268 | N,N-dimethyltransferase |

TABLE 3-continued

| Protein exhibiting significant similarity | GenBank accession number | BLAST* score | Reported function |
|---|---|---|---|
| probable N-methylase snogX (S. nogalater) | T46679 | 243 | N-methyltransferase |

*a greater sequence similarity is associated with a higher BLAST score (Altschul et al., 1990).

The orf2*c gene encodes a protein exhibiting relatively strong similarity (35% identity) with a protein encoded by the tylMIII gene encoding an NDP hexose 3,4-isomerase involved in the biosynthesis of tylosine in Streptomyces fradiae (A. R. Gandecha et al., 1997; GenBank accession number: CAA57471; BLAST score: 130). This similarity with a protein involved in the biosynthetic pathway of another close antibiotic, and more particularly in the biosynthesis of mycaminose, strongly suggests that the orf*2c gene encodes an NDP hexose 3,4-isomerase responsible for isomerization during the biosynthesis of one of the sugars of spiramycin, possibly mycaminose (cf. FIGS. 5 and 6).

The orf3*c gene encodes a protein exhibiting relatively strong similarity (59% identity) with a protein encoded by the tylMII gene encoding a glycosyltransferase involved in tylosine biosynthesis in Streptomyces fradiae (A. R. Gandecha et al., 1997; GenBank accession number: CAA57472; BLAST score: 448). This similarity with a protein involved in the biosynthetic pathway for another close antibiotic strongly suggests that the orf*3c gene encodes a glycosyltransferase. This hypothesis is supported by the fact that the protein encoded by the orf3*c gene exhibits strong similarity with other proteins of similar function in other organisms (cf. table 4).

TABLE 4

| Protein exhibiting significant similarity | GenBank accession number | BLAST* score | Reported function |
|---|---|---|---|
| Glycosyltransferase (S. venezuelae) | AAC68677 | 426 | Glycosyltransferase |
| Glycosyltransferase (S. antibioticus) | CAA05642 | 425 | Glycosyltransferase |
| Glycosyltransferase (Saccharopolyspora erythraea) | CAA74710 | 395 | Glycosyltransferase |
| Glycosyltransferase (S. antibioticus) | CAA05641 | 394 | Glycosyltransferase |

*greater sequence similarity is associated with a higher BLAST score (Altschul et al., 1990).

The orf4*c gene encodes a protein exhibiting relatively strong similarity with several crotonyl-CoA reductases. In particular, the protein encoded by orf4*c has considerable similarity with a crotonyl-CoA reductase from Streptomyces coelicolor (M. Redenbach et al., 1996; GenBank accession number: NP_630556; BLAST score: 772). This similarity with a protein involved in the biosynthetic pathway for another close antibiotic strongly suggests that the orf4*c gene also encodes a crotonyl-CoA reductase. This hypothesis is supported by the fact that the protein encoded by the orf4*c gene exhibits strong similarity with other proteins of similar function in other organisms (cf table 5).

TABLE 5

| Protein exhibiting significant similarity | GenBank accession number | BLAST* score | Reported function |
|---|---|---|---|
| trans-2-enoyl-CoA reductase (EC1.3.1.38)(S. collinus) | S72400 | 764 | trans-2-enoyl-CoA reductase |
| Crotonyl-CoA reductase (S. fradiae) | CAA57474 | 757 | Crotonyl-CoA reductase |
| Crotonyl-CoA reductase (S. cinnamonensis) | AAD53915 | 747 | Crotonyl-CoA reductase |

*greater sequence similarity is associated with a higher BLAST score (Altschul et al., 1990).

The orf6* gene exhibits a certain similarity with the mdmB gene present in Streptomyces mycarofaciens (Hara and Hutchinson, 1992; GenBank accession number: A42719; BLAST score: 489) which produces macrolide antibiotic. In this producer, the gene is involved in the acylation of the lactone ring. The orf6* gene is therefore thought to encode an acyltransferase. This hypothesis is supported by the fact that the protein encoded by the orf6* gene exhibits strong similarity with other proteins of similar function in other organisms (cf. table 6).

TABLE 6

| Protein exhibiting significant similarity | GenBank accession number | BLAST* score | Reported function |
|---|---|---|---|
| AcyA (Streptomyces thermotolerans) | J4001 | 450 | macrolide 3-O-acyltransferase |
| Midecamycin 4"-O-propionyltransferase (S. mycarofaciens) | BAA09815 | 234 | Midecamycin 4"-O-propionyltransferase |
| Mycarose O-acyltransferase (Micromonospora megalomicea subsp. Nigra) | AAG13909 | 189 | Mycarose O-acyltransferase |

*greater sequence similarity is associated with a higher BLAST score (Altschul et al., 1990).

Inactivation of the orf6* gene was produced by an in-phase deletion/inversion and it showed that the resulting strain no longer produces spiramycin II and III but only spiramycin I (cf. FIG. 1). This confirms that the orf6* gene is indeed involved in the synthesis of spiramycin II and III. The enzyme encoded by this gene is responsible for the formation of spiramycin II and III by attachment of an acetyl or butyryl group to the carbon in the 3-position. The strains which no longer express the protein encoded by the orf6* gene are particularly advantageous since they no longer produce spiramycin II and III but only spiramycin I. As specified above, the antibiotic activity of spiramycin I is clearly greater than that of spiramycins II and III (Liu et al., 1999).

The orf5* gene encodes a protein exhibiting relatively strong similarity with several O-methyltransferases. In particular, the protein encoded by orf5* has considerable similarity with an O-methyltransferase (EC 2.1.1.-) MdmC from Streptomyces mycarofaciens (Hara & Hutchinson, 1992; GenBank accession number: B42719; BLAST score: 355). This similarity with a protein involved in the biosynthetic pathway for another antibiotic strongly suggests that the orf5* gene also encodes an O-methyltransferase. The orf5* gene is thought to be involved in the formation of precursors incorporated into the lactone ring. In fact, according to the sequence comparisons, the product of the orf5* gene is also relatively close to FkbG, which is responsible for the methylation of hydroxymalonyl-ACP according to (Wu et al., 2000; Hoffmeister et al., 2000; GenBank accession number: AAF86386; BLAST score: 247) (cf. FIG. 8). This hypothesis is supported by the fact that the protein encoded by the orf5* gene exhibits strong similarity with other proteins of similar function in other organisms (cf. table 7).

TABLE 7

| Protein exhibiting significant similarity | GenBank accession number | BLAST* score | Reported function |
|---|---|---|---|
| Probable O-methyltransferase (EC 2.1.1.-) safC (*Myxococcus xanthus*) | T18553 | 223 | O-methyltransferase |
| 4-O-methyltransferase (EC 2.1.1.-) - (*Streptomyces* sp.) | JC4004 | 222 | O-methyltransferase |

*greater sequence similarity is associated with a higher BLAST score (Altschul et al., 1990).

Due to the polar effect of the insertion of a nonexcised cassette into the orf 6* gene, it has been possible to determine that the orf 5* gene is essential to the biosynthetic pathway for spiramycins. Specifically, insertion of the excisable cassette into the coding portion of the orf 6* gene leads to a complete arrest of spiramycin production. However, once the inserted cassette has been excised (and therefore when only the orf6* gene is inactivated, cf. examples 14 and 15), production of spiramycin I is observed again. This shows that the orf 5* gene is essential to the biosynthetic pathway for spiramycins since its inactivation leads to a complete arrest of spiramycin production.

The orf5* gene encodes a protein exhibiting relatively strong similarity with several O-methyltransferases. The orf5* gene is thought to be an O-methyltransferase involved either directly in the synthesis of the platenolide, or in the synthesis of a methylated precursor (methoxymalonyl, see FIG. 8) incorporated into the platenolide by PKS. To verify this hypothesis, LC/SM and NMR analytical experiments were carried out on a strain of *S. ambofaciens* of genotype: orf6*:att1Ωhyg+. In this strain, the orf5* gene is not expressed, owing to the polar effect of the insertion, into the orf6* gene, of the cassette which contains transcription terminators (cf. example 27). It has been shown that this strain produces a molecule for which the UV spectrum has an appearance similar to that of spiramycin I, but the mass spectrum shows a molecular ion at 829. The difference in mass of 14 compared to the mass of spiramycin can be explained by the absence of methyl on the oxygen borne by carbon No. 4 of the lactone ring (the structure of this compound is given in FIG. 39). The results obtained by NMR are compatible with this hypothesis. The presence of a compound at 829 makes it possible to validate the hypothesis of the role of orf5* in spiramycin biosynthesis. In addition, the product corresponding to spiramycin without the methyl group exhibits very weak microbiological activity (10-fold weaker) compared with the unmodified spiramycin, when tested on the microorganism *Micrococcus luteus*.

The orf7*c gene encodes a protein exhibiting relatively strong similarity with a protein encoded by the mdmA of *Streptomyces mycarofaciens*, the latter gene encoding a protein involved in midecamycin resistance in the producer enzyme (Hara et al., 1990; GenBank accession number: A60725; BLAST score: 380). This similarity with the protein involved in the biosynthetic pathway for another antibiotic strongly suggests that the orf7*c gene also encodes a protein involved in spiramycin resistance. More particularly, the enzyme encoded by the orf7*c gene has methyltransferase activity and is involved in spiramycin resistance in *Streptomyces ambofaciens*. It has been demonstrated that this gene imparts resistance of the MLS I type, which resistance is known to be due to monomethylation, at position A2058 of 23S ribosomal RNA (Pemodet et al., 1996). This hypothesis is supported by the fact that the protein encoded by the orf7*c gene exhibits strong similarity with other proteins of similar function in other organisms (cf. table 8).

TABLE 8

| Protein exhibiting significant similarity | GenBank accession number | BLAST* score | Reported function |
|---|---|---|---|
| macrolide-lincosamide-streptogramin B resistance determinant (*S. fradiae*) | JC5319 | 238 | 23S rRNA methyltransferase |
| 23S ribosomal RNA methyltransferase ErmML (*Micrococcus luteus*) | AAL68827 | 119 | 23S rRNA methyltransferase |

*greater sequence similarity is associated with a higher BLAST score (Altschul et al., 1990).

The orf8* gene encodes a protein exhibiting relatively strong similarity with a protein of the ABC transporter type in *Streptomyces griseus* (Campelo, 2002, GenBank accession number: CAC22119; BLAST score: 191). This similarity with a protein of the ABC transporter type strongly suggests that the orf8* gene also encodes a protein of the ABC transporter type which may be involved in spiramycin resistance. This hypothesis is supported by the fact that the protein encoded by the orf8* gene exhibits strong similarity with other proteins of similar function in other organisms (cf. table 9).

TABLE 9

| Protein exhibiting significant similarity | GenBank accession number | BLAST* score | Reported function |
|---|---|---|---|
| AcrW (*Streptomyces galilaeus*) | BAB72060 | 94 | ABC transporter |
| Daunorubicin resistance transmembrane protein (*Streptomyces peucetius*) | P32011 | 89 | daunorubicin resistance |
| Probable ABC-transporter, transmembrane component. (*Streptomyces coelicolor*) | NP_626506 | 89 | ABC transporter |

*greater sequence similarity is associated with a higher BLAST score (Altschul et al., 1990).

The orf9* gene encodes a protein exhibiting relatively strong similarity with a protein of the ABC transporter type in *Streptomyces griseus* (Campelo, 2002, GenBank accession number: CAC22118; BLAST score: 269). This similarity with a protein of the ABC transporter type strongly suggests that the orf9* gene also encodes a protein of the ABC transporter type which may be involved in spiramycin resistance. This hypothesis is supported by the fact that the protein encoded by the orf9* gene exhibits strong similarity with other proteins of similar function in other organisms (cf. table 10).

TABLE 10

| Protein exhibiting significant similarity | GenBank accession number | BLAST* score | Reported function |
|---|---|---|---|
| Probable ABC-type transport protein, ATP-binding component (S. coelicolor) | NP_626505 | 231 | ABC transporter |
| Putative ABC transporter ATP-binding component (Streptomyces Coelicolor) | NP_627624 | 228 | ABC transporter |

*greater sequence similarity is associated with a higher BLAST score (Altschul et al., 1990).

The orf10* gene encodes a protein exhibiting relatively strong similarity with a protein of unknown function. However, genes similar to orf10* are found in the middle of several groups of genes involved in the biosynthesis of antibiotics. Thus, a gene close to orf10* is found in S. coelicolor (Redenbach et al., 1996, GenBank accession number: NP_627432, BLAST score: 109). A close gene (CouY) is also found in S. rishiriensis (Wang et al., 2000, GenBank accession number: AAG29779, BLAST score 97).

Genes Located Upstream of the Genes Encoding PKSs

In the DNA sequence located upstream of the genes encoding PKSs (downstream and upstream being defined by the orientation of the 5 PKS genes all oriented in the same direction) (cf. FIG. 3), 34 ORFs have been identified (cf. above). Thus, the 34 open reading frames of this type occupy a region of approximately 41.7 kb (cf. SEQ ID No. 1 exhibiting a first region of 31 kb containing 25 ORFs and SEQ ID No. 140 exhibiting a region of approximately 12.1 kb, 1.4 kb of which overlap the preceding sequence (SEQ ID No. 1) and approximately 10.7 kb of which correspond to the subsequent sequence), the latter portion of approximately 10.7 kb containing 9 additional ORFs (including an ORF partial sequence), cf. also FIGS. 3 and 37 below). A diagrammatic representation of the organization of the region is given in FIGS. 5 and 37. The 34 genes identified were named: orf1, orf2, orf3, orf4, orf5, orf6, orf7, orf8, orf9c, orf10, orf11c, orf12, orf13c, orf14, orf15c, orf16, orf17, orf18, orf19, orf20, orf21c, orf22c, orf23c, orf24c, orf25c, orf26, orf27, orf28c, orf29, orf30c, orf31, orf32c, orf33 and orf34c.

Given in table 11 below are the references to the DNA and amino acid sequence of the 34 genes identified upstream of the 5 PKS genes.

TABLE 11

| Gene[1] | Position in the sequence SEQ ID No. 1 | DNA sequence | Polypeptide sequence(s)[2] |
|---|---|---|---|
| orf1 | 658 to 1869 | SEQ ID No. 23 | SEQ ID No. 24 |
| orf2 | 1866 to 2405 | SEQ ID No. 25 | SEQ ID No. 26 and 27 |
| orf3 | 2402 to 3568 | SEQ ID No. 28 | SEQ ID No. 29 |
| orf4 | 3565 to 4473 | SEQ ID No. 30 | SEQ ID No. 31, 32 and 33 |
| orf5 | 4457 to 5494 | SEQ ID No. 34 | SEQ ID No. 35 |
| orf6 | 5491 to 6294 | SEQ ID No. 36 | SEQ ID No. 37, 38 and 39 |
| orf7 | 6296 to 7705 | SEQ ID No. 40 | SEQ ID No. 41 and 42 |
| orf8 | 8011 to 9258 | SEQ ID No. 43 | SEQ ID No. 44 |
| orf9c | 10081 to 9362 | SEQ ID No. 45 | SEQ ID No. 46 |
| orf10 | 10656 to 12623 | SEQ ID No. 47 | SEQ ID No. 48 |
| orf11c | 14482 to 12734 | SEQ ID No. 49 | SEQ ID No. 50, 51 and 52 |
| orf12 | 14601 to 16031 | SEQ ID No. 53 | SEQ ID No. 54, 55, 56, 57, 58 and 59 |
| orf13c | 17489 to 16092 | SEQ ID No. 60 | SEQ ID No. 61 |
| orf14 | 17809 to 18852 | SEQ ID No. 62 | SEQ ID No. 63 |
| orf15c | 20001 to 18961 | SEQ ID No. 64 | SEQ ID No. 65 |
| orf16 | 20314 to 21552 | SEQ ID No. 66 | SEQ ID No. 67 |
| orf17 | 21609 to 22879 | SEQ ID No. 68 | SEQ ID No. 69 |
| orf18 | 22997 to 24175 | SEQ ID No. 70 | SEQ ID No. 71 |
| orf19 | 24177 to 25169 | SEQ ID No. 72 | SEQ ID No. 73 |
| orf20 | 25166 to 26173 | SEQ ID No. 74 | SEQ ID No. 75 |
| orf21c | 27448 to 26216 | SEQ ID No. 76 | SEQ ID No. 77 |
| orf22c | 28560 to 27445 | SEQ ID No. 78 | SEQ ID No. 79 |
| orf23c | 29770 to 28649 | SEQ ID No. 80 | SEQ ID No. 81 |
| orf24c | 30074 to 29763 | SEQ ID No. 82 | SEQ ID No. 83 |
| orf25c | 30937 to 30071 | SEQ ID No. 84 | SEQ ID No. 85 |
| orf26 | 1647 to 2864 | SEQ ID No. 107 | SEQ ID No. 108 |
| orf27 | 2914 to 3534 | SEQ ID No. 109 | SEQ ID No. 110 |
| orf28c | 4967 to 3804 | SEQ ID No. 141 | SEQ ID No. 142 |
| orf29 | 5656 to 6663 | SEQ ID No. 113 | SEQ ID No. 114 |
| orf30c | 7723 to 6686 | SEQ ID No. 115 | SEQ ID No. 116 and 117 |
| | 7534 to 6686 | SEQ ID No. 143 | SEQ ID No. 144 |
| orf31 | 7754 to 8728 | SEQ ID No. 118 | SEQ ID No. 119 |
| orf32c | 10488 to 8977 | SEQ ID No. 145 | SEQ ID No. 146 |
| orf33 | 10562 to 10837 | SEQ ID No. 147 | SEQ ID No. 148 |
| orf34c | 12134 to 10899 | SEQ ID No. 149 | SEQ ID No. 150 |

[1]The "c" added to the name of the gene indicates that the coding sequence is in the reverse orientation (the coding strand is therefore the strand complementary to the sequence given in SEQ ID No. 1 or SEQ ID No. 140 for these genes).
[2]When several protein sequences are indicated for a single orf, the corresponding proteins are derived from several possible translation initiation sites.

Three types of experiment were carried out with the aim of determining the function of the polypeptides identified in table 11 above: comparison of the identity of the identified sequences with sequences of known functions, gene inactivation experiments, and analyses of spiramycin production by these mutant strains.

The protein sequences deduced from these open reading frames were all first of all compared with those present in various databases using various programs: BLAST (Altschul et al., 1990) (Altschul et al., 1997), CD-search, COGs (Cluster of Orthologous Groups), FASTA ((W. R. Pearson & D. J. Lipman, 1988) and (W. R. Pearson, 1990), BEAUTY (K. C. Worley et al., 1995)), (cf. above). These comparisons made it possible to formulate hypotheses regarding the function of the products of these genes and to identify those liable to be involved in spiramycin biosynthesis. Table 12 shows the proteins exhibiting strong similarity with the 34 genes located upstream of the 5 PKF genes.

TABLE 12

| Gene | Protein exhibiting significant similarity | GenBank accession number | BLAST* score | Reported function |
|---|---|---|---|---|
| orf1 | Cytochrome P450 tylI (Streptomyces fradiae) | S49051 | 530 | Cytochrome P450 |
| orf2 | ORF 15 × 4 (Listonella anguillarum) | AAB81630 | 113 | unknown |

TABLE 12-continued

| Gene | Protein exhibiting significant similarity | GenBank accession number | BLAST* score | Reported function |
|---|---|---|---|---|
| orf3 | aminotransferase-like protein (Streptomyces antibioticus) | AAF59939 | 431 | Amino-transferase |
| orf4 | alpha-D-glucose-1-phosphate thymidylyltransferase (Streptomyces venezuelae) | AAC68682 | 404 | alpha-D-glucose-1-phosphate thymidylyl-transferase |
| orf5 | AprE (Streptomyces tenebrarius) | AAG18457 | 476 | dTDP-glucose 4,6-dehydratase |
| orf6 | Thioesterase (Streptomyces avermitilis) | BAB69315 | 234 | Thioesterase |
| orf7 | TylCVI (Streptomyces fradiae) | AAF29379 | 461 | dNTP hexose 2,3-dehydratase |
| orf8 | probable aminotransferase (Saccharopolyspora spinosa) | AAG23279 | 465 | Amino-transferase |
| orf9c | SrmX (Streptomyces ambofaciens) | S25204 | 445 | Methyl-transferase |
| orf10 | SrmR (Streptomyces ambofaciens) | S25203 | 1074 | Regulatory protein |
| orf11c | SrmB (Streptomyces ambofaciens) | S25202 | 955 | Spiramycin resistance |
| orf12 | UrdQ (Streptomyces fradiae) | AAF72550 | 634 | NDP-hexose 3,4-dehydratase |
| orf13c | SC4H2.17 (Streptomyces coelicolor) | T35116 | 619 | Unknown |
| orf14 | putative reductase (Streptomyces coelicolor) | CAB90862 | 147 | Reductase |
| orf15c | Probable 3-keto reductase (Streptomyces antibioticus) | T51102 | 285 | 3-keto reductase |
| orf16 | Hypothetical NDP hexose 3,4-isomerase (Streptomyces fradiae) | CAA57471 | 209 | NDP hexose 3,4-isomerase |
| orf17 | Glycosyltransferase (Streptomyces venezuelae) | AAC68677 | 400 | Glycosyl-transferase |
| orf18 | Glycosyltransferase (Streptomyces rishiriensis) | AAG29785 | 185 | Glycosyl-transferase |
| orf19 | NDP-hexose 4-keto reductase TylCIV (Streptomyces fradiae) | AAD41822 | 266 | NDP-hexose 4-keto reductase |
| orf20 | EryBII (Saccharopolyspora erythraea) | AAB84068 | 491 | aldo-keto reductase |
| orf21c | TylCIII (Streptomyces fradiae) | AAD41823 | 669 | NDP-hexose 3-C-methyl-transferase |
| orf22c | FkbH (Streptomyces hygroscopicus) | AAF86387 | 463 | Involved in-methoxy-malonyl biosynthesis |
| orf23c | FkbI (Streptomyces hygroscopicus) | AAF86388 | 387 | Acyl-CoA dehydrogenase |
| orf24c | FkbJ (Streptomyces hygroscopicus) | AAF86389 | 87 | Involved in methoxy-malonyl biosynthesis |
| orf25c | FkbK (Streptomyces hygroscopicus) | AAF86390 | 268 | Acyl-CoA dehydrogenase |
| orf26 | TylCV (Streptomyces fradiae) | AAD41824 | 471 | Mycarosyl-transferase |
| orf27 | TylCVII (Streptomyces fradiae) | AAD41825 | 243 | NDP-hexose 3,5-(or 5-)epimerase |
| orf28c | AcyB2 (Streptomyces thermotolerans) | JC2032 | 329 | regulatory protein |
| orf29 | Beta-manannase (Sorangium cellulosum) | AAK19890 | 139 | Glycosyl-hydrolase |
| orf30c | Nucleoside-diphosphate-sugar epimerase (Corynebacterium glutamicum) | NP_600590 | 89 | Nucleoside-diphosphate-sugar epimerase |
| orf31 | Oxidoreductase (Streptomyces coelicolor) | NP_631148 | 261 | Oxidoreductase |
| orf32c | Regulatory protein of the GntR family (Streptomyces avermitilis) | NP_824604 | 282 | Regulatory protein |
| orf33 | Hypothetical protein (Xanthomonas campestris) | NP_635564 | 54 | Unknown |
| orf34c | Arabinofuranosidase (Streptomyces coelicolor) | NP_630049 | 654 | Arabino-furano-sidase |

*greater sequence similarity is associated with a higher BLAST score (Altschul et al., 1990).

Gene inactivation experiments were carried out in order to confirm these results. The methods used consist in performing a gene replacement. The target gene to be interrupted is replaced with a copy of this gene interrupted with a cassette imparting resistance to an antibiotic (for example apramycin or hygromycin). The cassettes used are bordered on either side by translation termination codons in all reading frames and by transcription terminators which are active in Streptomyces. Insertion of the cassette into the target gene may or may not be accompanied by deletion in this target gene. The size of the regions flanking the cassette may range from a few hundred to several thousand base pairs. A second type of cassette may be used for the gene inactivation: cassettes termed "excisable cassettes" (cf. above). The strains thus constructed were tested for their spiramycin production.

The orf1 gene encodes a protein exhibiting relatively strong similarity with several cytochrome P450s. In particular, the protein encoded by orf1 has considerable similarity with the protein encoded by the tyII gene involved in the biosynthesis of tylosine in Streptomyces fradiae (L. A. Merson-Davies et al., 1994; GenBank accession number: S49051; BLAST score: 530). This similarity with a protein involved in the biosynthetic pathway for another close antibiotic strongly suggests that the orf1 gene also encodes a cytochrome P450. This hypothesis is supported by the fact that the protein encoded by the orf1 gene exhibits strong similarity with other proteins of similar function in other organisms (cf. table 13).

TABLE 13

| Protein exhibiting significant similarity | GenBank accession number | BLAST* score | Reported function |
|---|---|---|---|
| Putative cytochrome P450 YJIB (*Bacillus subtilis*) | O34374 | 248 | Cytochrome P450 |
| Cytochrome P450 113A1 (*Saccharopolyspora erythraea*) | P48635 | 237 | Cytochrome P450 |
| Cytochrome P-450 hydroxylase homolog (*Streptomyces caelestis*) | AAC46023 | 208 | Cytochrome P450 hydroxylase |
| Cytochrome P450 monooxygenase (*Streptomyces venezuelae*) | AAC64105 | 206 | Cytochrome P450 monooxygenase |

*greater sequence similarity is associated with a higher BLAST score (Altschul et al., 1990).

The orf2 gene encodes a protein exhibiting relatively strong similarity with a dTDP-6-deoxy-3,4-ketohexulose isomerase of *Aneurinibacillus thermoaerophilus* (Pfoestl, A. et al., 2003, GenBank accession number: AA006351; BLAST score: 118). This similarity strongly suggests that the orf2 gene encodes an isomerase responsible for the isomerization reaction required for the biosynthesis of one of the sugars present in the spiramycin molecule, this sugar possibly being mycarose (cf. FIG. 5). Inactivation of the orf2 gene was performed. It could be shown that the resulting strain no longer produces spiramycins. This confirms that the orf2 gene is indeed involved in spiramycin biosynthesis.

The orf3 gene encodes a protein exhibiting relatively strong similarity with several aminotransferases. In particular, the protein encoded by orf3 has considerable similarity with an aminotransferase of *Streptomyces antibioticus* involved in oleandomycin biosynthesis (G. Draeger et al., 1999; GenBank accession number: AAF59939; BLAST score: 431). This similarity with a protein involved in the biosynthetic pathway for another close antibiotic strongly suggests that the orf3 gene encodes a 3-aminotransferase responsible for the transamination reaction necessary for the biosynthesis of one of the amino sugars of spiramycins (cf. FIG. 5). This hypothesis is supported by the fact that the protein encoded by the orf3 gene exhibits strong similarity with other proteins of similar function in other organisms (cf. table 15).

TABLE 15

| Protein exhibiting significant similarity | GenBank accession number | BLAST* score | Reported function |
|---|---|---|---|
| Aminotransferase (*Streptomyces antibioticus*) | T51111 | 429 | Aminotransferase |
| Transaminase (*Streptomyces venezuelae*) | AAC68680 | 419 | Transaminase |

*greater sequence similarity is associated with a higher BLAST score (Altschul et al., 1990).

The orf3 gene was inactivated. It was thus possible to show that the resulting strain no longer produces spiramycins. This confirms that the orf3 gene is indeed involved in spiramycin biosynthesis. The enzyme encoded by this gene is therefore clearly responsible for a bioconversion step essential to spiramycin biosynthesis. Spiramycin production can be complemented by the expression of the TylB protein of *S. fradiae* (cf. example 23). This demonstrates that the orf3 gene encodes a 3-aminotransferase responsible for the transamination reaction necessary for mycaminose biosynthesis (cf. FIG. 5). Since mycaminose is the first sugar to be attached to platenolide, the strain with the orf3 knockout (OS49.67) is expected to accumulate platenolide.

The biosynthesis intermediates of the strain with the orf3 gene knockout were studied (cf. example 20). These experiments made it possible to demonstrate that this strain produces two forms of platenolide: platenolide A and platenolide B, the deduced structure of these two molecules is given in FIG. 36. This strain also produces platenolide A+mycarose and platenolide B+mycarose (cf. example 20 and FIG. 40). These compounds comprise a sugar but do not comprise any mycaminose. In addition, if they are compared with spiramycin (cf. FIG. 1), these compounds comprise mycarose in place of mycaminose. These results are in agreement with the product of the orf3 gene being involved in mycaminose biosynthesis and it having a role as a 3 aminotransferase responsible for the transamination reaction required for mycaminose biosynthesis (cf. FIG. 5). It may be noted that the specificity of glycosylation does not appear to be absolute since molecules with mycarose attached at the position normally occupied by mycaminose are found (cf. FIG. 40).

The orf4 gene encodes a protein exhibiting relatively strong similarity with several NDP-glucose synthetases. In particular, the protein encoded by orf4 has considerable similarity with an alpha-D-glucose-1-phosphate thymidylyltransferase of *Streptomyces venezuelae* (Y. Xue et al., 1998; GenBank accession number: AAC68682; BLAST score: 404). This similarity with a protein involved in the biosynthetic pathway for another close antibiotic strongly suggests that the orf4 gene encodes an NDP-glucose synthetase responsible for the synthesis of NDP-glucose necessary for the biosynthesis of the three atypical sugars incorporated into the spiramycin molecule (cf. FIGS. 4, 5 and 6). This hypothesis is supported by the fact that the protein encoded by the orf4 gene exhibits strong similarity with other proteins of similar function in other organisms (cf. table 16).

TABLE 16

| Protein exhibiting significant similarity | GenBank accession number | BLAST* score | Reported function |
|---|---|---|---|
| Glucose-1-phosphate thymidyltransferase (*Streptomyces avermitilis*) | BAA84594 | 402 | Glucose-1-phosphate thymidyltransferase |
| AclY (*Streptomyces galilaeus*) | BAB72036 | 400 | dTDP-1-glucose synthetase |
| Putative glucose-1-phosphate thymidyltransferase (*Saccharopolyspora spinosa*) | AAK83289 | 399 | glucose-1-phosphate thymidyltransferase |

*greater sequence similarity is associated with a higher BLAST score (Altschul et al., 1990).

The orf53 gene encodes a protein exhibiting relatively strong similarity with several glucose dehydratases. In particular, the protein encoded by orf5 has considerable similarity with a dTDP-glucose 4,6-dehydratase of *Streptomyces tenebrarius* (T. B. Li et al., 2001; GenBank accession number: AAG18457, BLAST score: 476). This similarity with a protein involved in the biosynthetic pathway for another close antibiotic strongly suggests that the orf5 gene encodes an NDP-glucose dehydratase necessary for the biosynthesis of the three atypical sugars incorporated into the spiramycin molecule (cf. FIGS. 4, 5 and 6). This hypothesis is supported by the fact that the protein encoded by the orf5 gene exhibits strong similarity with other proteins of similar function in other organisms (cf. table 17).

TABLE 17

| Protein exhibiting significant similarity | GenBank accession number | BLAST* score | Reported function |
| --- | --- | --- | --- |
| dTDP-glucose 4,6-dehydratase (*Saccharopolyspora spinosa*) | AAK83290 | 464 | dTDP-glucose 4,6-dehydratase |
| thymidine diphospho-glucose 4,6-dehydratase (*Saccharopolyspora erythraea*) | AAA68211 | 445 | thymidine diphosphoglucose 4,6-dehydratase |
| dTDP-glucose 4,6-dehydratase (EC 4.2.1.46) - (*Streptomyces fradiae*) | S49054 | 443 | dTDP-glucose 4,6-dehydratase |
| TDP-glucose 4,6-dehydratase (*Streptomyces venezuelae*) | AAC68681 | 421 | TDP-glucose 4,6-dehydratase |
| SgcA (*Streptomyces globisporus*) | AAF13998 | 418 | dNDP-glucose 4,6-dehydratase |

*greater sequence similarity is associated with a higher BLAST score (Altschul et al., 1990).

The orf6 gene encodes a protein exhibiting relatively strong similarity with several thioesterases. In particular, the protein encoded by orf6 has considerable similarity with a thioesterase of *Streptomyces avermitilis* (S. Omura et al., 2001; GenBank accession number: BAB69315; BLAST score: 234). This similarity with a protein involved in the biosynthetic pathway for another close antibiotic strongly suggests that the orf6 gene encodes a thioesterase. This hypothesis is supported by the fact that the protein encoded by the orf6 gene exhibits strong similarity with other proteins of similar function in other organisms (cf. table 18).

TABLE 18

| Protein exhibiting significant similarity | GenBank accession number | BLAST* score | Reported function |
| --- | --- | --- | --- |
| RifR (*Amycolatopsis mediterranei*) | AAG52991 | 216 | Thioesterase |
| Thioesterase - (*Streptomyces fradiae*) | S49055 | 215 | Thioesterase |
| Thioesterase (*Streptomyces avermitilis*) | BAB69188 | 213 | Thioesterase |
| Thioesterase II (EC 3.1.2.-) - (*Streptomyces venezuelae*) | T17413 | 203 | Thioesterase |
| PimI protein (*Streptomyces natalensis*) | CAC20922 | 201 | Thioesterase |
| Thioesterase (*Streptomyces griseus*) | CAC22116 | 200 | Thioesterase |

*greater sequence similarity is associated with a higher BLAST score (Altschul et al., 1990).

The orf7 gene encodes a protein exhibiting relatively strong similarity with several hexose dehydratases. In particular, the protein encoded by orf7 has considerable similarity with a dNTP-hexose 2,3-dehydratase (encoded by the TylCVI gene) of *Streptomyces fradiae* involved in tylosine biosynthesis (L. A. Merson-Davies et al., 1994; GenBank accession number: AAF29379; BLAST score: 461). This similarity with a protein involved in the biosynthetic pathway for another close antibiotic strongly suggests that the orf7 gene also encodes a hexose 2-3-dehydratase necessary for the biosynthesis of two atypical sugars incorporated into the spiramycin molecule (cf. FIGS. 4 and 6). This hypothesis is supported by the fact that the protein encoded by the orf gene exhibits strong similarity with other proteins of similar function in other organisms (cf. table 19).

TABLE 19

| Protein exhibiting significant similarity | GenBank accession number | BLAST* score | Reported function |
| --- | --- | --- | --- |
| RifI8 (*Amycolatopsis mediterranei*) | AAG52988 | 459 | Hexose dehydratase |
| SimB3 (*Streptomyces antibioticus*) | AAK06810 | 444 | dNDP-4-keto-6-deoxyglucose 2,3-dehydratase |

*greater sequence similarity is associated with a higher BLAST score (Altschul et al., 1990).

The orf8 gene encodes a protein exhibiting relatively strong similarity with several aminotransferases. In particular, the protein encoded by orf8 has considerable similarity with an aminotransferase probably involved in forosamine biosynthesis in *Saccharopolyspora spinosa* (C. Waldron et al., 2001; GenBank accession number: AAG23279; BLAST score: 465). This similarity with a protein involved in the biosynthetic pathway for another close antibiotic strongly suggests that the orf8 gene encodes a 4-aminotransferase responsible for the transamination reaction necessary for forosamine biosynthesis (cf. FIG. 6). This hypothesis is supported by the fact that the protein encoded by the orf8 gene exhibits strong similarity with other proteins of similar function in other organisms (cf. table 20).

TABLE 20

| Protein exhibiting significant similarity | GenBank accession number | BLAST* score | Reported function |
| --- | --- | --- | --- |
| Putative amino sugar biosynthesis protein (*Bordetella bronchiseptica*) | CAA07666 | 213 | Protein involved in amino sugar biosynthesis |

*greater sequence similarity is associated with a higher BLAST score (Altschul et al., 1990).

The orf8 gene was inactivated. It was thus possible to show that the resulting strain no longer produces spiramycins. This confirms that the orf8 gene is indeed involved in spiramycin biosynthesis. The enzyme encoded by this gene is therefore clearly responsible for a bioconversion step essential to spiramycin biosynthesis. Validation of the hypothesis of the role played by the product of the orf8 gene in forosamine biosynthesis is provided by the fact that an inactivated mutant for the orf8 gene produces forocidin, this mutant is therefore blocked at the forocidin stage and does not produce any neo-spiramycin (cf. FIG. 7 and example 25). These results are in agreement with the product of the orf8 gene being involved in forosamine biosynthesis (cf. FIG. 6).

The orf9c gene has already been identified in *Streptomyces ambofaciens* and has been named srmX by Geistlich et al. (M. Geistlich et al., 1992). The similarity of the protein encoded by this gene with several methyltransferases involved in the biosynthetic pathway for other close antibiotics strongly suggests that the or9c gene encodes a methyltransferase responsible for the methylation reaction necessary for mycaminose or forosamine biosynthesis (cf. FIGS. 5 and 6). This hypothesis is supported by the fact that the protein encoded by the orf9c gene exhibits strong similarity with other proteins of similar function in other organisms (cf. table 21).

TABLE 21

| Protein exhibiting significant similarity | GenBank accession number | BLAST* score | Reported function |
| --- | --- | --- | --- |
| N,N-dimethyltransferase (*Streptomyces venezuelae*) | AAC68678 | 240 | N,N-dimethyltransferase |
| Methyltransferase (*Streptomyces antibioticus*) | CAA05643 | 232 | Methyltransferase |
| Putative aminomethylase (*Streptomyces nogalater*) | AAF01819 | 219 | Aminomethylase |

*greater sequence similarity is associated with a higher BLAST score (Altschul et al., 1990).

The orf10 gene has already been identified in *Streptomyces ambofaciens* and has been named srmR by Geistlich et al. (M. Geistlich et al., 1992). The protein encoded by this gene is involved in regulation of the biosynthetic pathway for spiramycins in *Streptomyces ambofaciens*. The orf10 gene was inactivated. It was thus possible to show that the resulting strain no longer produces spiramycins. This confirms that the orf10 gene is indeed involved in spiramycin bisynthesis. The protein encoded by this gene is therefore clearly essential for spiramycin biosynthesis.

In addition, the translation initiation point of orf10 was determined and it was possible to show that overexpression of this gene leads to an improvement in the production of spiramycins. The translation initiation site corresponds to an ATG located upstream of the ATG proposed by Geistlich et al. (M. Geistlich et al., 1992). It was also demonstrated that this 5' end is essential to the function of Orf10 since a 5'-truncated messenger is inactive (cf. example 17). To obtain the desired effect on the production of spiramycins, it is therefore essential for the overexpression of orf10 to be effected while taking care not to express a 5'-truncated messenger of orf10.

The orf11c gene has already been identified in *Streptomyces ambofaciens* and has been named srmB by Geistlich et al. (M. Geistlich et al., 1992) and Schoner et al. (B. Schoner et al., 1992). The protein encoded by this gene is involved in spiramycin resistance in *Streptomyces ambofaciens* and is an ABC-type transporter.

The orf12 gene encodes a protein exhibiting relatively strong similarity with several hexose dehydratases. In particular, the protein encoded by orf12 has considerable similarity with an NDP-hexose 3,4-dehydratase encoded by the UrdQ gene of *Streptomyces fradiae* and involved in urdamycin biosynthesis (D. Hoffmeister et al., 2000; GenBank accession number: AAF72550; BLAST score: 634). This similarity with a protein involved in the biosynthetic pathway for another close antibiotic strongly suggests that the orf12 gene encodes a 3,4 dehydratase responsible for the dehydration reaction necessary for forosamine biosynthesis (cf. FIG. 6). This hypothesis is supported by the fact that the protein encoded by the orf12 gene exhibits strong similarity with other proteins of similar function in other organisms (cf. table 22).

TABLE 22

| Protein exhibiting significant similarity | GenBank accession number | BLAST* score | Reported function |
| --- | --- | --- | --- |
| AknP (*Streptomyces galilaeus*) | AAF73452 | 625 | 3-dehydratase |
| NDP-hexose 3,4-dehydratase homolog (*Streptomyces cyanogenus*) | AAD13547 | 624 | NDP-hexose 3,4-dehydratase |
| RdmI (*Streptomyces purpurascens*) | AAL24451 | 608 | hexose-C-3-dehydratase |
| Probable CDP-4-keto-6-deoxyglucose 3-dehydratase (E1) (*Streptomyces violaceoruber*) | T46528 | 602 | CDP-4-keto-6-deoxyglucose 3-dehydratase |
| Probable NDP-hexose 3,4-dehydratase (*Saccharopolyspora spinosa*) | AAG23278 | 582 | NDP-hexose 3,4-dehydratase |
| dNTP-hexose dehydratase (*Amycolatopsis mediterranei*) | AAC01730 | 576 | dNTP-hexose dehydratase |

*greater sequence similarity is associated with a higher BLAST score (Altschul et al., 1990).

The orf12 gene was inactivated. It was possible to show that the resulting strain no longer produces spiramycins. This confirms that the orf12 gene is indeed involved in spiramycin biosynthesis. The enzyme encoded by this gene is therefore clearly responsible for a bioconversion step essential to spiramycin biosynthesis. Validation of the hypothesis of the role played by Orf12 in forosamine biosynthesis is provided by the fact that an inactivated mutant for the orf12 gene no longer produces forosamine. However, it produces a small amount of forocidin. This mutant is therefore blocked at the forocidin stage and does not produce any neo-spiramycin (cf. FIG. 7 and example 26). This mutant also produces a compound having the structure shown in FIG. 38. The latter compound contains two sugars, mycaminose and mycarose, but does not contain any forosamine. In addition, if it is compared with the structure of spiramycin (cf. FIG. 1), this compound contains the sugar mycarose in the expected place of forosamine. These results are in agreement with the product of the orf12 gene being involved in forosamine biosynthesis (cf. FIG. 6). It may be noted that the specificity of glycosylation is not absolute since molecules in which mycarose is attached at the position normally occupied by forosamine are observed (see FIG. 38).

The orf13c gene encodes a protein exhibiting relatively strong similarity with a protein of unknown function in *Streptomyces coelicolor*. This protein was named SC4H2.17 (GeneBank accession number: T35116; BLAST score: 619). The protein encoded by the orf13c gene also exhibits strong similarity with other proteins of other organisms (cf. table 23).

TABLE 23

| Protein exhibiting significant similarity | GenBank accession number | BLAST* score | Reported function |
| --- | --- | --- | --- |
| hflX protein (*Mycobacterium leprae*) | S72938 | 473 | unknown |

TABLE 23-continued

| Protein exhibiting significant similarity | GenBank accession number | BLAST* score | Reported function |
|---|---|---|---|
| Possible ATP/GTP-binding protein (*Mycobacterium leprae*) | NP_301739 | 470 | ATP/GTP-binding protein |
| GTP-binding protein (*Mycobacterium tuberculosis* CDC1551) | AAK47114 | 468 | GTP-binding protein |
| ATP/GTP-binding protein (*Streptomyces fradiae*) | T44592 | 388 | ATP/GTP-binding protein |

*greater sequence similarity is associated with a higher BLAST score (Altschul et al., 1990).

No precise function has been attributed to the proteins close to that encoded by orf13c. The orf13c gene was inactivated for the purpose of studying the function of this gene in the biosynthetic pathway for spiramycins in *Streptomyces ambofaciens*. It was possible to show that the resulting strain produces spiramycins. This indicates that the orf13c gene is not essential to spiramycin biosynthesis and that it is not essential to the survival of the bacterium. The enzyme encoded by this gene is not therefore responsible for a bioconversion step essential to spiramycin biosynthesis.

The orf14 gene encodes a protein exhibiting relatively strong similarity with a putative reductase (M. Redenbach et al., 1996; Bentley et al., 2002; GenBank accession number: CAB90862; BLAST score: 147).

The orf14 gene was inactivated. It was thus possible to show that the resulting strain no longer produces spiramycins. This confirms that the orf14 gene is indeed involved in spiramycin biosynthesis. The enzyme encoded by this gene is therefore clearly responsible for a bioconversion step essential to spiramycin biosynthesis. The biosynthesis intermediates of the strain with the orf14 gene knockout were studied (cf. example 20). These experiments made it possible to demonstrate that this strain produces platenolide A but does not produce platenolide B (cf. FIG. 36).

The orf15c gene encodes a protein exhibiting relatively strong similarity with several keto reductases. In particular, the protein encoded by orf15c has considerable similarity with a 3-keto reductase in *Streptomyces antibioticus* (GenBank accession number: T51102, BLAST score: 285). This similarity strongly suggests that the orf15c gene encodes a 3-keto reductase responsible for the reduction reaction necessary for forosamine biosynthesis (cf. FIG. 6). This hypothesis is supported by the fact that the protein encoded by the orf15c gene exhibits strong similarity with other proteins of similar function in other organisms (cf. table 24).

TABLE 24

| Protein exhibiting significant similarity | GenBank accession number | BLAST* score | Reported function |
|---|---|---|---|
| oxidoreductase homolog (*Streptomyces cyanogenus*) | AAD13550 | 272 | Oxidoreductase |
| D-oliose 4-keto reductase (*Streptomyces argillaceus*) | CAB96550 | 265 | D-oliose 4-keto reductase |
| AknQ (*Streptomyces galilaeus*) | AAF73453 | 263 | putative 3-keto reductase |

TABLE 24-continued

| Protein exhibiting significant similarity | GenBank accession number | BLAST* score | Reported function |
|---|---|---|---|
| Probable NDP-hexose 3-keto reductase (*Saccharopolyspora spinosa*) | AAG23275 | 253 | NDP-hexose 3-keto reductase |

*greater sequence similarity is associated with a higher BLAST score (Altschul et al., 1990).

The orf16 gene encodes a protein exhibiting relatively strong similarity with several isomerases. In particular, the protein encoded by orf16 has considerable similarity with an NDP-hexose 3,4-isomerase in *Streptomyces fradiae* (Gandecha et al., 1997; GenBank accession number: CAA57471, BLAST score: 209). This similarity strongly suggests that the orf16 gene encodes a protein involved in the biosynthesis of one of the sugars of spiramycin (cf. FIGS. 5 and 6). This hypothesis is supported by the fact that the protein encoded by the orf16 gene exhibits strong similarity with other proteins of similar function in other organisms (cf. table 25).

TABLE 25

| Protein exhibiting significant similarity | GenBank accession number | BLAST* score | Reported function |
|---|---|---|---|
| Putative tautomerase (*Streptomyces venezuelae*) | AAC68676 | 145 | Tautomerase |
| TDP-4-keto-6-deoxy-hexose 3,4-isomerase (*Micromonospora megalomicea* subsp. *nigra*) | AAG13907 | 112 | TDP-4-keto-6-deoxyhexose 3,4-isomerase |

*greater sequence similarity is associated with a higher BLAST score (Altschul et al., 1990).

The orf17 gene encodes a protein exhibiting relatively strong similarity with several glycosyltransferases. In particular, the protein encoded by orf17 has considerable similarity with a glycosyltransferase of *Streptomyces venezuelae* (Y. Xue et al., 1998; GenBank accession number: AAC68677; BLAST score: 400). The similarity of the protein encoded by the orf17 gene with several glycosyltransferases involved in the biosynthetic pathway for other close antibiotics strongly suggests that this gene also encodes a glycosyltransferase. This hypothesis is supported by the fact that the protein encoded by the orf17 gene exhibits some similarity with other proteins of similar function in other organisms (cf. table 26).

TABLE 26

| Protein exhibiting significant similarity | GenBank accession number | BLAST* score | Reported function |
|---|---|---|---|
| Glycosyltransferase (*Streptomyces fradiae*) | CAA57472 | 399 | Glycosyltransferase |
| Glycosyltransferase (*Streptomyces antibioticus*) | CAA05642 | 378 | Glycosyltransferase |
| Glycosyltransferase (*Streptomyces antibioticus*) | CAA05641 | 360 | Glycosyltransferase |

TABLE 26-continued

| Protein exhibiting significant similarity | GenBank accession number | BLAST* score | Reported function |
|---|---|---|---|
| Glycosyltransferase (*Saccharopolyspora erythraea*) | CAA74710 | 344 | Glycosyltransferase |

*greater sequence similarity is associated with a higher BLAST score (Altschul et al., 1990).

The orf18 gene encodes a protein exhibiting relatively strong similarity with several glycosyltransferases. In particular, the protein encoded by orf18 has considerable similarity with a glycosyltransferase of *Streptomyces rishiriensis* (Wang et al., 2000; GenBank accession number: AAG29785; BLAST score: 185). The similarity of the protein encoded by the orf18 gene with several glycosyltransferases involved in the biosynthetic pathway for other close antibiotics strongly suggests that this gene also encodes a glycosyltransferase. This hypothesis is supported by the fact that the protein encoded by the orf18 gene exhibits strong similarity with other proteins of similar function in other organisms (cf. table 27).

TABLE 27

| Protein exhibiting significant similarity | GenBank accession number | BLAST* score | Reported function |
|---|---|---|---|
| NovM (*Streptomyces spheroides*) | AAF67506 | 184 | Glycosyltransferase |
| probable glycosyltransferase (*Streptomyces violaceoruber*) | T46519 | 169 | Glycosyltransferase |
| Glycosyltransferase homolog (*Streptomyces cyanogenus*) | AAD13553 | 167 | Glycosyltransferase |
| Glycosyltransferase homolog (*Streptomyces cyanogenus*) | AAD13555 | 163 | Glycosyltransferase |
| dNTP-hexose glycosyltransferase (*Amycolatopsis mediterranei*) | AAC01731 | 160 | Glycosyltransferase |

*greater sequence similarity is associated with a higher BLAST score (Altschul et al., 1990).

The orf19 gene encodes a protein exhibiting relatively strong similarity with several keto reductases. In particular, the protein encoded by orf19 has considerable similarity with an NDP-hexose 4-keto reductase (TylCIV) *Streptomyces fradiae* (Bate et al., 2000; GenBank accession number: AAD41822; BLAST score: 266). The similarity of the protein encoded by the orf19 gene with this keto reductase involved in the biosynthetic pathway for a close antibiotic strongly suggests that this gene also encodes a 4-keto reductase responsible for the reduction reaction necessary for mycarose biosynthesis (cf. FIG. 4). This hypothesis is supported by the fact that the protein encoded by the orf19 gene exhibits strong similarity with other proteins of similar function in other organisms (cf. table 28).

TABLE 28

| Protein exhibiting significant similarity | GenBank accession number | BLAST* score | Reported function |
|---|---|---|---|
| NDP-4-keto-6-deoxyhexose 4-keto reductase | AAL14256 | 251 | NDP-4-keto-6-deoxyhexose |

TABLE 28-continued

| Protein exhibiting significant similarity | GenBank accession number | BLAST* score | Reported function |
|---|---|---|---|
| (*Streptomyces venezuelae*) | | | 4-keto reductase |
| EryBIV (*Saccharopolyspora erythraea*) | AAB84071 | 249 | oxidoreductase |
| TDP-4-keto-6-deoxyhexose 4-keto reductase (*Micromonospora megalomicea* subsp. *Nigra*) | AAG13916 | 218 | TDP-4-keto-6-deoxyhexose 4-keto reductase |
| dTDP-4-keto-6-deoxy-L-hexose 4-reductase (*Streptomyces avermitilis*) | BAA84595 | 212 | dTDP-4-keto-6-deoxy-L-hexose 4-reductase |

*greater sequence similarity is associated with a higher BLAST score (Altschul et al., 1990).

The orf20 gene encodes a protein exhibiting relatively strong similarity with several hexose reductases. In particular, the protein encoded by orf20 has considerable similarity with the EryBII of *Saccharopolyspora erythraea* which encodes a dTDP-4-keto-L-6-deoxyhexose 2,3-reductase (R. G. Summers et al., 1997), GenBank accession number: AAB84068; BLAST score: 491). The similarity of the protein encoded by the orf20c gene with several hexose reductases involved in the biosynthetic pathway for other close antibiotics strongly suggests that this gene encodes a 2,3-reductase responsible for the reduction necessary for mycarose biosynthesis (cf. FIG. 4). This hypothesis is supported by the fact that the protein encoded by the orf20c gene exhibits strong similarity with other proteins of similar function in other organisms (cf. table 29).

TABLE 29

| Protein exhibiting significant similarity | GenBank accession number | BLAST* score | Reported function |
|---|---|---|---|
| TylCII (*Streptomyces fradiae*) | AAD41821 | 464 | NDP-hexose 2,3-enoyl reductase |
| TDP-4-keto-6-deoxyhexose 2,3-reductase (*Micromonospora megalomicea* subsp. *Nigra*) | AAG13914 | 446 | TDP-4-keto-6-deoxyhexose 2,3-reductase |
| dTDP-4-keto-6-deoxy-L-hexose 2,3-reductase (*Streptomyces avermitilis*) | BAA84599 | 377 | dTDP-4-keto-6-deoxy-L-hexose 2,3-reductase |

*greater sequence similarity is associated with a higher BLAST score (Altschul et al., 1990).

The orf21c gene encodes a protein exhibiting relatively strong similarity with several hexose methyltransferases. In particular, the protein encoded by orf21c has considerable similarity with the TylCIII gene of *Streptomyces fradiae* which encodes an NDP-hexose 3-C-methyltransferase (N. Bate et al., 2000; GenBank accession number: AAD41823; BLAST score: 669). The similarity of the protein encoded by the orf21c gene with several hexose methyltransferases involved in the biosynthetic pathway for other close antibiotics strongly suggests that this gene encodes a hexose methyltransferase responsible for the methylation reaction necessary for mycarose biosynthesis (cf. FIG. 4). This hypothesis is supported by the fact that the protein encoded by the orf21c gene exhibits strong similarity with other proteins of similar function in other organisms (cf. table 30).

TABLE 30

| Protein exhibiting significant similarity | GenBank accession number | BLAST* score | Reported function |
|---|---|---|---|
| eryH (*Saccharopolyspora erythraea*) | 228448 | 592 | Erythromycin biosynthesis gene |
| S-adenosyl-dependent methyltransferase (*Coxiella burnetii*) | AAK71270 | 358 | Methyltransferase |
| NovU (*Streptomyces spheroides*) | AAF67514 | 184 | C-methyltransferase |

*greater sequence similarity is associated with a higher BLAST score (Altschul et al., 1990).

The orf22c gene encodes a protein exhibiting relatively strong similarity with the protein encoded by the fkbH gene of *Streptomyces hygroscopicus* var. *ascomyceticus* which encodes an enzyme involved in methoxymalonyl biosynthesis (K. Wu et al., 2000; GenBank accession number: AAF86387; BLAST score: 463). The similarity of the protein encoded by the orf22c gene with this protein involved in the biosynthetic pathway for another close macrolide strongly suggests that this gene also. encodes an enzyme involved in methoxymalonyl biosynthesis in *Streptomyces ambofaciens* (cf. FIG. 8).

The orf23c gene encodes a protein exhibiting relatively strong similarity with the protein encoded by the fkbH gene of *Streptomyces hygroscopicus* var. *ascomyceticus* which encodes an acyl-CoA dehydrogenase involved in methoxymalonyl (K. Wu, et al., 2000; GenBank accession number: AAF86388; BLAST score: 387). The similarity of the protein encoded by the orf23c gene with several acyl-CoA dehydrogenases involved in the biosynthetic pathway for other close antibiotics strongly suggests that this gene encodes an acyl-CoA dehydrogenase involved in methoxymalonyl biosynthesis (cf. FIG. 8). This hypothesis is supported by the fact that the protein encoded by the orf23c gene exhibits strong similarity with other proteins of similar function in other organisms (cf. table 31).

TABLE 31

| Protein exhibiting significant similarity | GenBank accession number | BLAST* score | Reported function |
|---|---|---|---|
| Acyl-CoA dehydrogenase (*Polyangium cellulosum*) | AAK19892 | 171 | Acyl-CoA dehydrogenase |
| Probable acyl-CoA dehydrogenase - (*Streptomyces coelicolor*) | T36802 | 160 | acyl-CoA dehydrogenase |

*greater sequence similarity is associated with a higher BLAST score (Altschul et al., 1990).

The orf24c gene encodes a protein exhibiting relatively strong similarity with the protein encoded by the fkbJ gene of *Streptomyces hygroscopicus* var. *ascomyceticus* which is thought to encode the acyl carrier protein (ACP) involved in methoxymalonyl biosynthesis (K. Wu et al., 2000; GenBank accession number: AAF86389; BLAST score: 87). The similarity of the protein encoded by the orf24c gene with this protein involved in the biosynthetic pathway for another close macrolide strongly suggests that this gene encodes a protein involved in methoxymalonyl biosynthesis in *Streptomyces ambofaciens* (cf. FIG. 8).

The orf25c gene encodes a protein exhibiting a relatively strong similarity with the protein encoded by the fkbK gene of *Streptomyces hygroscopicus* var. *ascomyceticus* which encodes an acyl-CoA dehydrogenase involved in methoxymalonyl biosynthesis (K. Wu et al., 2000; GenBank accession number: AAF86390; BLAST score: 268). The similarity of the protein encoded by the orf25c gene with several acyl-CoA dehydrogenases involved in the biosynthetic pathway for other close antibiotics strongly suggests that this gene encodes an acyl-CoA dehydrogenase involved in methoxyrnalonyl biosynthesis (cf FIG. 8). This hypothesis is supported by the fact that the protein encoded by the orf25c gene exhibits strong similarity with other proteins of similar function in other organisms (cf. table 32).

TABLE 32

| Protein exhibiting significant similarity | GenBank accession number | BLAST* score | Reported function |
|---|---|---|---|
| Probable 3-Hydroxy-butyryl-CoA dehydrogenase (*Bacillus subtilis*) | P45856 | 177 | 3-Hydroxybutyryl-CoA dehydrogenase |
| 3-hydroxybutyryl-CoA dehydrogenase protein (*Bacillus thuringiensis serovar kurstaki*) | AAL32270 | 174 | 3-hydroxybutyryl-CoA dehydrogenase |
| 3-hydroxybutyryl-CoA dehydrogenase (*Deinococcus radiodurans*) | NP_294792 | 167 | 3-hydroxybutyryl-CoA dehydrogenase |

*greater sequence similarity is associated with a higher BLAST score (Altschul et al., 1990).

The orf26 gene encodes a protein exhibiting 65% identity (determined using the BLAST program) with the protein encoded by the tylCV gene which encodes a mycarosyltransferase involved in tylosine biosynthesis in *Streptomyces fradiae* (N. Bate, et al., 2000; GenBank accession number: AAD41824, BLAST score: 471). More particularly, TylCV is a glycosyltransferase which binds the mycarose molecule during tylosine synthesis. This similarity with a protein involved in the biosynthetic pathway for another relatively close antibiotic, and more particularly in mycarose transfer, suggests that the orf26 gene is a glycosyltransferase. This hypothesis is supported by the fact that the protein encoded by the orf26 gene exhibits strong similarity with other proteins of similar function in other organisms (cf. table 33).

TABLE 33

| Protein exhibiting significant similarity | GenBank accession number | BLAST* score | Reported function |
|---|---|---|---|
| Glycosyltransferase (*Streptomyces avermitilis*) | BAA84592 | 218 | Glycosyltransferase |
| CalG4 (*Micromonospora echinospora*) | AAM70365 | 217 | Glycosyltransferase |
| CalG2 (*Micromonospora echinospora*) | AAM70348 | 197 | Glycosyltransferase |

*greater sequence similarity is associated with a higher BLAST score (Altschul et al., 1990).

The orf27 gene encodes a protein exhibiting a 70% identity (determined using the BLAST program) with the protein encoded by the tylCVII gene which encodes an NDP-hexose 3,5- (or 5-) epimerase involved in tylosine biosynthesis in *Streptomyces fradiae* (N. Bate et al., 2000; GenBank accession number: AAD41825, BLAST score: 243). More particularly, TylCVII is a hexose 3,5- (or 5-) epimerase involved in mycarose biosynthesis. This similarity with a protein involved in the biosynthetic pathway for another relatively close antibiotic, and more particularly in mycarose biosynthesis, suggests that the orf27 gene encodes an epimerase. This hypothesis is supported by the fact that the protein encoded by the orf27 gene exhibits strong similarity with other proteins of similar function in other organisms (cf. table 34). Analysis of the close sequences obtained using the BLAST program strongly suggests that the orf27 gene encodes a 5-epimerase responsible for the epimerization reaction necessary for mycarose biosynthesis (cf. FIG. 4).

TABLE 34

| Protein exhibiting significant similarity | GenBank accession number | BLAST* score | Reported function |
| --- | --- | --- | --- |
| LanZ1 (*Streptomyces cyanogenus*) | AAD13558 | 172 | NDP-hexose 3,5-epimerase |
| Epi (*Saccharopolyspora spinosa*) | AAK83288 | 169 | TDP-4-keto-6-deoxyglucose 3,5-epimerase |
| dNTP-hexose 3,5-epimerase (*Amycolatopsis mediterranei*) | AAC01732 | 166 | dNTP-hexose 3,5-epimerase |

*greater sequence similarity is associated with a higher BLAST score (Altschul et al., 1990).

The sequence of orf28c was initially determined partially, since the sequence of a region of approximately 450 base pairs was only determined after resequencing (this region is symbolized by "N" in the incomplete sequence SEQ ID No. 106). The partial sequence of this ORF (SEQ ID No. 111) was nevertheless used for the analysis with the various computer programs as explained above. It was thus possible to determine that the orf28c gene encodes a protein exhibiting 64% identity, over the determined sequence (SEQ ID No. 112, which is the partial sequence of the Orf28c protein) (determined using the BLAST program), with the protein encoded by the acyB2 gene which encodes a regulatory protein involved in carbomycin biosynthesis in *Streptomyces thermotolerans* (A. Arisawa et al., 1993; GenBank accession number: JC2032, BLAST score: 329). This similarity with a protein involved in the biosynthetic pathway for a relatively close antibiotic suggests that the orf28c gene encodes a regulatory protein involved in spiramycin biosynthesis. This hypothesis is supported by the fact that the protein encoded by the orf28c gene also exhibits strong similarity with the TylR protein, which is a regulatory protein involved in tylosine biosynthesis in *Streptomyces fradiae* (N. Bate et al., 1999; GenBank accession number: AAF29380, BLAST score: 167).

It was possible to amplify the orf28c gene using oligonucleotides located on either side of the undetermined sequence and to subclone it into an expression vector. It was thus possible to demonstrate that overexpression of the orf28c gene significantly increases spiramycin production in the OSC2 strain (cf. example 24). This demonstrates that overexpresion of orf28c leads to an increase in spiramycin production and confirms its role as a regulator of the biosynthetic pathway for spiramycins.

The partial sequence of orf28c was subsequently completed and the missing region of approximately 450 base pairs was determined (cf. SEQ ID No. 140 and SEQ ID No. 141). The complete sequence of this ORF (SEQ ID No. 141) was used for the analysis with the various computer programs as explained above. It was thus possible to determine that the orf28c gene encodes a protein exhibiting 69% identity over the sequence determined (SEQ ID No. 142, which is the complete sequence of the Orf28c protein) (determined using the BLAST program), with the protein encoded by the acyB2 gene which encodes a regulatory protein involved in carbomycin biosynthesis in *Streptomyces thermotolerans* (Arisawa, A., et al., 1993; GenBank accession number: JC2032, BLAST score: 451). This similarity with a protein involved in regulating the biosynthesis of a relatively close antibiotic suggests that the orf28c gene encodes a regulatory protein involved in spiramycin biosynthesis. This hypothesis is supported by the fact that the protein encoded by the orf28c gene also exhibits strong similarity with the TylR protein, which is a regulatory protein involved in regulating tylosine biosynthesis in *Streptomyces fradiae* (Bate, N. et al., 1999; GenBank accession number: AAF29380, BLAST score: 224). The results of overexpression of this gene (cf. example 24) confirm its role as a regulator of the spiramycin biosynthesis pathway.

The orf28c gene was inactivated. It was thus possible to show that the resulting strain no longer produces spiramycins. This confirms that the orf28c gene is clearly involved in spiramycin biosynthesis and is essential to spiramycin biosynthesis. These results, combined with the results of overexpression of this gene (cf. example 24), are in agreement with Orf28c having a role as an activator essential to spiramycin biosynthesis.

The orf29 gene encodes a protein exhibiting 31% identity (determined using the BLAST program) with a probable glycosyl hydrolase located in the gene group involved in the biosynthesis of soraphen A (an antifungal agent of the polyketide class) in *Sorangium cellulosum* (J. Ligon et al., 2002; GenBank accession number: AAK19890, BLAST score: 139). This similarity with a protein involved in the biosynthetic pathway for a relatively close molecule suggests that the orf29 gene encodes a protein having glycosyl hydrolase activity. This hypothesis is supported by the fact that the protein encoded by the orf29 gene exhibits strong similarity with other proteins of similar function in other organisms (cf. table 35). Analysis of the sequence of the protein encoded by orf29 using the CD-search program (cf. above) also suggests that the orf29 gene encodes a glycosyl hydrolase.

TABLE 35

| Protein exhibiting significant similarity | GenBank accession number | BLAST* score | Reported function |
| --- | --- | --- | --- |
| ManA (*Caldicellulosiruptor saccharolyticus*) | AAC44232 | 136 | beta-1,4-mannanase |
| ManA (*Dictyoglomus thermophilum*) | AAB82454 | 129 | beta-mannanase |

*greater sequence similarity is associated with a higher BLAST score (Altschul et al., 1990).

Analysis of the protein sequence deduced from orf29, using the SignalP program (www.cbs.dtu.dk/services/SignalP/) (Nielsen, H., et al., 1997), shows that this protein has a C-terminal signal sequence with a predicted cleavage site between positions 30 and 31 (QSA/QA). It may be predicted that this protein is extracellular. It might, as a glycosylhydrolase, have a role in the reactivation of spiramycin inactivated by glycosylation by the glycosyltransferases GimA and/or GimB (Gourmelen et al, 1998).

The orf30c gene encodes a protein exhibiting 31% identity (determined using the BLAST program) with an nucleoside-diphosphate sugar epimerase in Corynebacterium glutamicum (GenBank accession number: NP_600590, BLAST score: 89). This similarity suggests that the orf30c gene encodes an epimerase. This hypothesis is supported by the fact that analysis of the sequence using the CD-search program (cf. above) also suggests that the orf30c gene encodes an epimerase.

orf30c exhibits two possible initiation codons (cf. SEQ ID No. 115) which give two possible proteins of 345 and 282 amino acids respectively (SEQ ID No. 116 and 117). However, the codon usage is typical of Streptomyces only from the second ATG; in addition, the deduced protein sequence of the sequence between the first ATG and the second does not align with the identified close sequences, whereas the shortest protein sequence (from the 2nd ATG: SEQ ID No. 144) aligns correctly with the beginning of these proteins. It can therefore be deduced from this that the second ATG is the correct initiation codon and that the sequence of this orf is therefore that presented in SEQ ID No. 143, which, once translated; corresponds to the protein of sequence SEQ ID No. 144.

The orf31 gene encodes a protein exhibiting 52% identity (determined using the BLAST program) with an oxidoreductase in Streptomyces coelicolor (GenBank accession number: NP_631148, BLAST score: 261). This similarity suggests that the orf31 gene encodes a reductase. This hypothesis is supported by the fact that analysis of the sequence using the CD-search program (cf. above) also suggests that the orf31 gene encodes a reductase. This hypothesis is also supported by the fact that the protein encoded by the orf31 gene exhibits strong similarity with other proteins of similar function in other organisms (cf. table 36).

TABLE 36

| Protein exhibiting significant similarity | GenBank accession number | BLAST* score | Reported function |
|---|---|---|---|
| Putative oxidoreductase (Streptomyces griseus) | BAB79295 | 173 | Oxidoreductase |
| MocA (Xanthomonas axonopodis) | NP_640644 | 171 | Oxidoreductase |

*greater sequence similarity is associated with a higher BLAST score (Altschul et al., 1990).

The orf31 gene was inactivated. It was thus possible to show that the resulting strain no longer produces spiramycins. This confirms that the orf31 gene is indeed involved in spiramycin biosynthesis. The enzyme encoded by this gene is therefore clearly responsible for a bioconversion step essential to spiramycin biosynthesis.

The sequence of orf32c was first of all determined partially (cf. example 19), since the coding sequence in 5' position was only determined in a second step. The partial sequence of this orf (SEQ ID No. 120) was, however, used for the analysis with the various computer programs as explained above. It was thus possible to determine that the orf32c gene encodes a protein exhibiting 47% identity, over the determined sequence (SEQ ID No. 121, which is the partial sequence of the Orf32c protein) (determined using the BLAST program), with a regulatory protein of the GntR family in Streptomyces coelicolor (GenBank accession number: NP_625576, BLAST score: 229). This similarity suggests that the orf32c gene encodes a transcriptional regulator of the GntR family. This hypothesis is supported by the fact that the protein encoded by the orf32c gene exhibits strong similarity with other proteins of similar function in other organisms.

The partial sequence of orf32c was subsequently completed and the missing region was determined (cf. SEQ ID No. 140 and SEQ ID No. 145). The complete sequence of this orf encodes a protein exhibiting 44% identity (determined using the BLAST program) with a regulatory protein of the GntR family in Streptomyces avermitilis (GenBank accession number: NP_824604, BLAST score: 282). This similarity suggests that the orf32c gene encodes a transcriptional regulator of the GntR family. This hypothesis is supported by the fact that the protein encoded by the orf32c gene exhibits strong similarity with other proteins of similar function in other organisms (cf. table 37).

TABLE 37

| Protein exhibiting significant similarity | GenBank accession number | BLAST* score | Reported function |
|---|---|---|---|
| Regulatory protein of the GntR family (Streptomyces avermitilis) | NP_828241 | 270 | Regulatory protein of the GntR family |
| Regulatory protein of the GntR family (Streptomyces coelicolor) | NP_625576 | 266 | Regulatory protein of the GntR family |
| SC5G8.04 (Streptomyces coelicolor) | NP_628991 | 258 | Regulatory protein of the GntR family |
| Transcriptional regulator (Streptomyces venezuelae) | AAF01064 | 224 | Transcriptional regulator |
| Regulatory protein of the GntR family (Streptomyces avermitilis) | NP_827432 | 239 | Regulatory protein of the GntR family |

*greater sequence similarity is associated with a higher BLAST score (Altschul et al., 1990).

The orf32c gene was inactivated with the aim of studying the function of this gene in the spiramycin biosynthesis pathway in Streptomyces ambofaciens. It was possible to show that the resulting strain produces spiramycins. This indicates that the orf32c gene is not essential to spiramycin biosynthesis and that it is not essential to survival of the bacterium.

The orf33 gene encodes a protein exhibiting 49% identity (determined using the BLAST program) with a hypothetical protein of Xanthomonas campestris (GenBank accession number: NP_635564, BLAST score: 54).

The sequence of orf34c is partial. In fact, the comparisons carried out between the product of this orf and the databases suggest that the C-terminal portion of this protein is not in the product deduced from the nucleotide sequence and therefore that this orf is longer and continues beyond the region sequenced. The partial sequence of this ORF was, however, used for the analysis with the various computer programs as explained above. It was possible to determine that the orf34c gene encodes a protein exhibiting 91% identity, over the sequence determined (SEQ ID No. 150, which is the partial sequence of the Orf34c protein) (determined using the BLAST program), with an arabinofuranosidase from Streptomyces coelicolor (Bentley et al., 2002; GenBank accession number: NP_630049, BLAST score: 654). In S. coelicolor, the gene encoding this arabinofuranosidase does not appear to be involved in secondary metabolite biosynthesis. In S. ambofaciens, this gene is therefore probably not involved in spiramycin biosynthesis.

A subject of the present invention is also polynucleotides which hybridize, under high stringency hybridization conditions, to at least one of the polynucleotides of sequence SEQ ID Nos 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or one of its variants, or one of the sequences derived therefrom due to the degeneracy of the genetic code. Preferentially, these said polynucleotides are isolated from a bacterium of the genus *Streptomyces*, more preferentially these polynucleotides encode proteins involved in the biosynthesis of a macrolide, and even more preferentially these polynucleotides encode a protein having activity similar to the protein encoded by the polynucleotides with which they hybridize. The high stringency hybridization conditions can be defined as hybridization conditions which are not favorable to the hybridization of nonhomologous nucleic acid strands. High stringency hybridization conditions may, for example, be described as hybridization conditions in the buffer described by Church & Gilbert (Church & Gilbert, 1984) at a temperature of between 55° C. and 65° C.; the hybridization temperature is preferably 55° C., the hybridization temperature is even more preferably 60° C., and the hybridization temperature is most preferably 65° C., followed by one or more washings carried out in 2×SSC buffer at a temperature of between 55° C. and 65° C.; this temperature is preferably 55° C., this temperature is even more preferably 60° C. and this temperature is most preferably 65° C., followed by one or more washes in 0.5×SSC buffer at a temperature of between 55° C. and 65° C.; this temperature is preferably 55° C., this temperature is even more preferably 60° C. and this temperature is most preferably 65° C. The hybridization conditions described above can be adjusted as a function of the length of the nucleic acid the hybridization of which is sought, or of the type of labeling chosen, according to techniques known to those skilled in the art. Suitable hybridization conditions can, for example, be adjusted according to the work by F. Ausubel et al., 2002.

The invention also relates to a polynucleotide having at least 70%, more preferably 80%, more preferably 85%, even more preferably 90%, even more preferably 95%, and most preferably 98%, nucleotide identity with a polynucleotide comprising at least 10, 12, 15, 18, 20 to 25, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850 or 1900 consecutive nucleotides of a polynucleotide chosen from the group consisting of the nucleotide sequences SEQ ID Nos 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or one of its variants, or one of the sequences derived therefrom due to the degeneracy of the genetic code, or a polynucleotide of complementary sequence. Preferentially, these said polynucleotides are isolated from a bactrium of the genus *Streptomyces*, more preferentially these polynucleotides encode proteins involved in the biosynthesis of a macrolide, and even more preferentially these polynucleotides encode proteins having activity similar to the proteins encoded by the polynucleotides with which they exhibit the identity. Most preferably, a polynucleotide according to the invention is chosen from the group consisting of the nucleotide sequences SEQ ID Nos 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or a polynucleotide of complementary sequence.

The optimal alignment of the sequences for the comparison can be carried out on a computer using known algorithms, for example those of the FASTA package (W. R. Pearson & D. J. Lipman, 1988) and (W. R. Pearson, 1990), accessible in particular from the INFOBIOGEN resource center, Evry, France. By way of illustration, the percentage sequence identity may be determined using the LFASTA (K.-M. Chao et al, 1992) or LALIGN (X. Huang and W. Miller, 1991) software. The LFASTA and LALIGN programs are part of the FASTA package. LALIGN provides optimal local alignments; this program is more rigorous, but also slower than LFASTA.

Another aspect of the invention concerns a polypeptide resulting from the expression of a nucleic acid sequence as defined above. Preferentially, the polypeptides according to the invention exhibit at least 70%, more preferably 80%, more preferably 85%, even more preferably 90%, even more preferably 95% and most preferably 98%, amino acid identity with a polypeptide comprising at least 10, 15, 20, 30 to 40, 50, 60, 70, 80, 90, 100, 120, 140, 160, 180, 200, 220, 240, 260, 280, 300, 320, 340, 360, 380, 400, 420, 440, 460, 480, 500, 520, 540, 560, 580, 600, 620 or 640 consecutive amino acids of a polypeptide chosen from SEQ ID Nos 4, 6, 8, 10, 12, 14, 16, 18, 20, 22, 24, 26, 27, 29, 31, 32, 33, 35, 37, 38, 39, 41, 42, 44, 46, 48, 50, 51, 52, 54, 55, 56, 57, 58, 59, 61, 63, 65, 67, 69, 71, 73, 75, 77, 79, 81, 83, 85, 108, 110, 112, 114, 116, 117, 119, 121, 142, 144, 146, 148 and 150, or one of these sequences except that, all along said sequence, one or more amino acids have been substituted, inserted or deleted without affecting the functional properties thereof, or one of the variants of these sequences. Preferentially, the polypeptides according to the invention are expressed in a natural state by a bacterium of the genus *Streptomyces*, more preferentially these polypeptides are involved in the biosynthesis of a macrolide, and even more preferentially these polypeptides have activity similar to that of the polypeptide with which they share the identity. Preferably, a polypeptide according to the invention is chosen from the group consisting of the polypeptide sequences SEQ ID Nos 4, 6, 8, 10, 12, 14, 16, 18, 20, 22, 24, 26, 27, 29, 31, 32, 33, 35, 37, 38, 39, 41, 42, 44, 46, 48, 50, 51, 52, 54, 55, 56, 57, 58, 59, 61, 63, 65, 67, 69, 71, 73, 75, 77, 79, 81, 83, 85, 108, 110, 112, 114, 116, 117, 119, 121, 142, 144, 146, 148 and 150, or one of these sequences except that, all along said sequence, one or more amino acids have been substituted, inserted or deleted without affecting the functional properties thereof, or one of the variants of these sequences. Most preferably, a polypeptide according to the invention is chosen from the group consisting of the polypeptide sequences SEQ ID Nos 4, 6, 8, 10, 12, 14, 16, 18, 20, 22, 24, 26, 27, 29, 31, 32, 33, 35, 37, 38, 39, 41, 42, 44, 46, 48, 50, 51, 52, 54, 55, 56, 57, 58, 59, 61, 63, 65, 67, 69, 71, 73, 75, 77, 79, 81, 83, 85, 108, 110, 112, 114, 116, 117, 119, 121, 142, 144, 146, 148 and 150.

The optimal alignment of the sequences for the comparison can be carried out on a computer using known algorithms, for example those of the FASTA package (W. R. Pearson & D. J. Lipman, 1988) and (W. R. Pearson, 1990), accessible in particular from the INFOBIOGEN resource center, Evry, France. By way of illustration, the percentage sequence identity may be determined using the LFASTA (K.-M. Chao et al., 1992) or LALIGN (X. Huang and W. Miller, 1991) software using the default parameters as defined by the INFOBIOGEN resource center, Evry, France. The LFASTA and LALIGN programs are part of the FASTA package. LALIGN provides optimal local alignments; this program is more rigorous, but also slower than LFASTA.

Another aspect of the invention concerns a recombinant DNA comprising at least one polynucleotide as described above. Preferentially, this recombinant DNA is a vector. Even more preferentially, the vector is chosen from bacteriophages, plasmids, phagemids, integrative vectors, fosmids, cosmids, shuttle vectors, BACs (Bacterial Artificial Chromosomes) and PACs (P1-derived Artificial Chromosomes). By way of illustration, the lambda phage and the M13 phage may be mentioned as bacteriophages. As plasmids, mention may be made of plasmids which replicate in *E. coli*, for example pBR322 and its derivatives, pUC18 and its derivatives, pUC19 and its derivatives, pGB2 and its derivatives (G. Churchward et al., 1984), pACYC 177 (GenBank accession number: X06402) and its derivatives, and pACYC184 (GenBank accession number: X06403) and its derivatives. Mention may also be made of plasmids which replicate in *Streptomyces*, such as, for example, pIJ101 and its derivatives, pSG5 and its derivatives, SLP1 and its derivatives, and SCP2* and its derivatives (Kieser et al. 2000). As phagemids, mention may be made, by way of illustration, of pBluescript II and its derivatives (marketed in particular by the company Stratagene (LaJolla, Calif., USA)), pGEM-T and its derivatives (marketed by the company Promega (Madison, Wis., USA)), [lacuna] the IS117 integration system (Kieser et al., 2000). As fosmids, mention may be made, by way of illustration, of the fosmid pFOS I (marketed by the company New England Bioloabs Inc., Beverly, Mass., USA) and its derivatives. As cosmids, mention may be made, by way of illustration, of the cosmid SuperCos and its derivatives (marketed in particular by the company Stratagene (LaJolla, Calif., USA)) and the cosmid pWED15 (Wahl et al., 1987) and its derivatives. As shuttle vectors, mention may be made, by way of illustration, of *E. coli/Streptomyces* shuttle plasmids, such as, for example, pIJ903 and its derivatives, the series of plasmids pUWL, pCAO106, pWHM3 and pOJ446 and their derivatives (Kieser et al. 2000), and *E. coli/Streptomyces* shuttle BACs, such as, for example, those described in patent application WO 01/40497. As BACs (Bacterial Artificial Chromosomes), mention may be made, by way of illustration, of the BAC pBeloBAC11(GenBank accession number: U51113). As PACs (P1-derived Artificial Chromosomes), mention may be made, by way of illustration, of the vector pCYPAC6 (GenBank accession number: AF133437). Most preferably, a vector according to the invention is chosen from pOS49.1, pOS49.11, pOSC49.12, pOS49.14, pOS49.16, pOS49.28, pOS44.1, pOS44.2, pOS44.4, pSPM5, pSPM7, pOS49.67, pOS49.88, pOS49.106, pOS49.120, pOS49.107, pOS49.32, pOS49.43, pOS49.44, pOS49.50, pOS49.99, pSPM17, pSPM21, pSPM502, pSPM504, pSPM507, pSPM508, pSPM509, pSPM1, pBXL1111, pBXL1112, pBXL1113, pSPM520, pSPM521, pSPM522, pSPM523, pSPM524, pSPM525, pSPM527, pSPM528, pSPM34, pSPM35, pSPM36, pSPM37, pSPM38, pSPM39, pSPM40, pSPM41, pSPM42, pSPM43, pSPM44, pSPM45, pSPM47, pSPM48, pSPM50, pSPM51, pSPM52, pSPM53, pSPM55, pSPM56, pSPM58, pSPM72, pSPM73, pSPM515, pSPM519, pSPM74, pSPM75, pSPM79, pSPM83, pSPM107, pSPM543 and pSPM106.

Another aspect of the invention concerns an expression system comprising a suitable expression vector and a host cell allowing the expression of one or more polypeptides as described above in a biological system. The expression vectors according to the invention comprise a nucleic acid sequence encoding one or more polypeptides as described above, and may be intended for the expression of the various polypeptides according to the invention in diverse host cells well known to those skilled in the art. By way of example, mention may be made of prokaryotic expression systems, such as the expression system in the bacterium *E. coli*, and eukaryotic expression systems, such as the baculovirus expression system which allows expression in insect cells, and the expression systems which allow expression in yeast cells, or the expression systems which allow expression in mammalian cells, in particular human cells. The expression vectors which can be used in such systems are well known to those skilled in the art; as regards prokayrotic cells, mention may be made, by way of illustration, of the expression vectors in *E. coli*, for example of the pET marketed by the company Stratagene (LaJolla, Calif., USA), the vectors of the GATEWAY family marketed by the company Invitrogen (Carlsbad, Calif., USA), the vectors of the pBAD family marketed by the company Invitrogen (Carlsbad, Calif., USA), the vectors of the pMAL family marketed by the company New England Bioloabs Inc. (Beverly, Mass., USA), and the rhamnose-inducible expression vectors mentioned in the publication B. Wilms et al., 2001 and their derivatives; mention may also be made of the expression vectors in *Streptomyces*, such as, for example, the vectors pIJ4123, pIJ6021, pPM927, pANT849, pANT 850, pANT 851, pANT1200, pANT1201 and pANT1202 and their derivatives (Kieser et al., 2000). As regards yeast cells, mention may be made, by way of illustration, of the vector pESC marketed by the company Stratagene (LaJolla, Calif., USA). As regards the baculovirus expression system which allows expression in insect cells, mention may be made, by way of illustration, of the vector BacPAK6 marketed by the company BD Biosciences Clontech, (Palo Alto, Calif., USA). As regards mammalian cells, mention may be made, by way of illustration, of the vectors comprising the CMV (Cytomegalovirus) immediate early gene promoter (for example the vector pCMV and its derivatives marketed by the company Stratagene (LaJolla, Calif., USA)), or the SV40 early promoter of the vacuolating simian virus (for example the vector pSG5 marketed by the company Stratagene (LaJolla, Calif., USA).

The invention also relates to a method of producing a polypeptide as described above, said method comprising the following steps:

a) inserting a nucleic acid encoding said polypeptide into a suitable vector;
b) culturing, in a suitable culture medium, a host cell transformed or transfected beforehand with the vector step a);
c) recovering the conditioned culture medium or a cell extract, for example by sonication or by osmotic shock;
d) separating and purifying said polypeptide from said culture medium or else from the cell extract obtained in step c);
e) where appropriate, characterizing the recombinant polypeptide produced.

A recombinant polypeptide according to the invention can be purified by passage over an appropriate series of chromatography columns, according to the methods known to those skilled in the art and described, for example, in F. Ausubel et al., (2002). By way of illustration, mention may be made of the "Histidine-Tag" technique, which consists in adding a short polyhistidine sequence to the polypeptide to be produced, it being possible for this polypeptide to be purified on a nickel column. A polypeptide according to the invention may also be prepared by in vitro synthesis techniques. By way of illustration of such techniques, a polypeptide according to the invention may be prepared using the "rapid translation system (RTS)", marketed in particular by the company Roche Diagnostics France S.A., Meylan, France.

Another aspect of the invention concerns host cells into which has been introduced at least one polynucleotide and/or at least one recombinant DNA and/or at least one expression vector according to the invention.

Another aspect of the invention concerns microorganisms blocked in a step of the biosynthetic pathway for at least one macrolide. The advantage lies, firstly, in studying the function of the mutated proteins and, secondly, in producing microorganisms which produce biosynthesis intermediates. These intermediates can be modified, optionally after separation, either by adding particular components to the production media, or by introducing into the microorganisms thus mutated other genes encoding proteins capable of modifying the intermediate by using it as a substrate. These intermediates can thus be modified chemically, biochemically, enzymatically and/or microbiologically. The microorganisms blocked in a step of the biosynthetic pathway for macrolides can be obtained by inactivating the function of one or more proteins involved in the biosynthesis of this or these macrolide(s) in microorganisms which produce this or these macrolide(s). Depending on the protein(s) inactivated, microorganisms blocked in the various steps of the biosynthetic pathway for this or these macrolide(s) may thus be obtained. The inactivation of this or these protein(s) can be carried out by any method known to those skilled in the art, for example by mutagenesis in the gene(s) encoding said protein(s) or by the expression of one or more antisense RNA(s) complementary to the messenger RNA(s) encoding said protein(s). The mutagenesis can, for example, be carried out by irradiation, by action of a mutagenic chemical agent, by solid-directed mutagenesis, by gene replacement, or any other method known to those skilled in the art. The conditions suitable for such a mutagenesis can, for example, be adjusted according to the teaching contained in the works by T. Kieser et al., (2000) and Ausubel et al., (2002). The mutagenesis can be carried out in vitro or in situ, by suppression, substitution, deletion and/or addition of one or more bases in the gene under consideration, or by gene inactivation. This mutagenesis can be carried out in a gene comprising a sequence as described above.

Preferentially, the microorganisms blocked in a step of the biosynthetic pathway for macrolides are bacteria of the genus *Streptomyces*. More preferentially, the inactivation of the function of one or more proteins involved in the biosynthesis of the macrolide(s) in question is carried out by mutagenesis. Even more preferentially, the macrolide in question is spiramycin and the microorganisms in which the mutagenesis or mutageneses is (are) carried out are strains of *S. ambofaciens*. More preferentially, the mutagenesis is carried out in one or more genes comprising one of the sequences corresponding to one or more of the sequences SEQ ID Nos 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149. Preferably, the mutagenesis or mutageneses is (are) carried out by gene inactivation. Most preferably, the mutagenesis consists of gene inactivation of a gene comprising a sequence corresponding to the sequence SEQ ID No. 13.

By way of illustration, the following microorganisms may be mentioned as examples of such microorganisms: OS49.16 (orf3:Ωhyg, cf. example 2), OS49.67 (orf3 in-phase deletion, cf example 6), OS49.107 (orf8:Ωhyg, cf. example 7), OS49.50 (orf10:Ωhyg, cf. example 8), SPM21 (orf2: att3Ωaac−, cf. example 10), SPM22 (orf2:att3 in-phase deletion, cf. example 10), SPM501 (orf6*:att1Ωhyg+, cf. example 14), SPM502 (orf6*:att1 in-phase deletion, cf. example 14), SPM507 (orf12:att3Ωaac−, cf. example 11), SPM508 (orf13c:att3Ωaac−, cf. example 12), and SPM509 (orf14:att3Ωaac−, cf. example 13), SPM107 (orf28c: att3aac+, cf. example 29), SPM543 (orf31:att3aac+, cf example 30), SPM106 (orf32c:att3aac+, cf. example 31).

Another aspect of the invention concerns a method of preparing a macrolide biosynthesis intermediate, using the microorganisms blocked in a step of the biosynthetic pathway for macrolides, as described above. The method consists in culturing, in a suitable culture medium, a microorganism blocked in a step of the biosynthetic pathway for macrolides, as described above, recovering the conditioned culture medium or a cell extract, for example by sonification or by osmotic shock, and separating and purifying said biosynthesis intermediate from said culture medium or else from the cell extract obtained in the preceding step. The conditions for culturing such microorganisms may be determined according to techniques well known to those skilled in the art. The culture medium may, for example, be the MP5 medium or the SL11 medium for *Streptomyces*, and in particular for *Streptomyces ambofaciens* (Pernodet et al., 1993). Those skilled in the art may in particular refer to the work by Kieser et al., (2000) as regards the culturing of *Streptomyces*. The intermediate produced can be recovered by any technique known to those skilled in the art. Those skilled in the art may, for example, refer to the techniques taught in U.S. Pat. No. 3,000, 785, and more particularly to the methods for extracting spiramycins described in that patent.

Another subject of the invention concerns a method of preparing a molecule derived from a macrolide, using the microorganisms blocked in a step of the biosynthetic pathway for this macrolide, as described above. The method consists in obtaining a biosynthesis intermediate according to the method above and in modifying the intermediate thus produced, optionally after separation from the culture medium. The conditions for culturing such microorganisms may be determined according to techniques well known to those skilled in the art. The culture medium may, for example, be the MP5 medium or the SL11 medium for *Streptomyces*, and in particular for *Streptomyces ambofaciens* (Pernodet et al., 1993). Those skilled in the art may in particular refer to the work by Kieser et al., 2000 with regard to the culturing of *Streptomyces*. The intermediates produced may be modified, optionally after separation, either by adding suitable components to the production media, or by introducing into the microorganisms other genes encoding proteins capable of modifying the intermediate by using it as a substrate. These intermediates can thus be modified chemically, biochemically, enzymatically and/or microbiologically. More preferentially, the macrolide in question is spiramycin and the microorganisms in which the mutagenesis or mutageneses is (are) carried out are strains of *S. ambofaciens*.

The invention also relates to a microorganism which produces spiramycin I but which does not produce spiramycin II and III. This microorganism comprises all of the genes necessary for the biosynthesis of spiramycin I but does not produce spiramycin II and III since the gene comprising the sequence corresponding to SEQ ID No. 13, or one of its variants, or one of the sequences derived therefrom due to the degeneracy of the genetic code, and encoding a polypeptide of sequence SEQ ID No. 14, or one of its variants, is not expressed or has been made inactive. The inactivation of this protein can be carried out by any method known to those skilled in the art, for example by mutagenesis in the gene encoding said protein or by the expression of antisense RNA complementary to the messenger RNA encoding said protein, it being understood that, if the expression of orf5* is affected by this manipulation, it will be necessary to perform another modification so that the orf5* gene is correctly expressed. The mutagenesis may be carried out in the coding sequence or in a noncoding sequence so as to make the encoded protein inactive or to prevent its expression or its translation therefrom. The mutagenesis may be carried out by site-directed mutagenesis, by gene replacement or any other method known to those skilled in the art. The conditions suitable for such a mutagenesis may, for example, be adjusted according to the teaching contained in the works by T. Kieser et al., (2000) and Ausubel et al., 2002. The mutagenesis may be carried out in vitro or in situ, by suppression, substitution, deletion and/or addition of one or more bases in the gene under consideration or by gene inactivation. The microorganism may also be obtained by expressing the genes of the biosynthetic pathway for spiramycin without them comprising the gene comprising the sequence SEQ ID No. 13, or one of its variants, or one of the sequences derived therefrom due to the degeneracy of the genetic code, and encoding a polypeptide of sequence SEQ ID No. 14, or one of its variants. Preferentially, the microorganism is a bacterium of the genus Streptomyces. More preferentially, the microorganism which produces spiramycin I but which does not produce spiramycin II and III is obtained from a starting microorganism which produces spiramycins I, II and III. Even more preferentially, the microorganism is obtained by mutagenesis in a gene comprising the sequence corresponding to SEQ ID No. 13, or one of its variants, or one of the sequences derived therefrom due to the degeneracy of the genetic code, and encoding a polypeptide of sequence SEQ ID No. 14, or one of its variants having the same function. Even more preferentially, this mutagenesis is carried out by gene inactivation. Preferably, the microorganism is obtained from a strain of S. ambofaciens which produces spiramycins I, II and III, in which gene inactivation of the gene comprising the sequence corresponding to SEQ ID No. 13, or one of the sequences derived therefrom due to the degeneracy of the genetic code, is carried out. Most preferably, the gene inactivation is carried out by in-phase deletion of the gene or of a part of the gene comprising the sequence corresponding to SEQ ID No. 13, or one of the sequences derived therefrom due to the degeneracy of the genetic code. By way of illustration, the strain SPM502 (orf6*:att1, cf. example 14) may be mentioned as a microorganism which produces spiramycin I but which does not produce spiramycin II and III.

The invention also relates to a microorganism which produces spiramycin I but which does not produce spiramycin II and III, as described above, which also overexpresses:

a gene which can be obtained by polymerase chain reaction using the pair of primers of the following sequence: 5' AAGCTTGTGTGCCCGGTGTACCTGGGGAGC 3' (SEQ ID No. 138) and 5' GGATCCCGCGACGGA-CACGACCGCCGCGCA 3' (SEQ ID No. 139), and as matrix the cosmid pSPM36 or the total DNA of Streptomyces ambofaciens, more preferably it is the gene of coding sequence SEQ ID No. 141, or a gene derived therefrom due to the degeneracy of the genetic code.

An example of sequence of such a gene is given in SEQ ID No. 111 (DNA); however, this sequence is partial since it does not comprise the 3' portion of the corresponding coding sequence. The translation of this portion of coding sequence into protein is given in SEQ ID No. 112. Those skilled in the art will easily be able to complete it in particular using the teaching given in example 24. The sequence undetermined in SEQ ID No. 111 was determined in a second step, and the complete sequence of this orf (orf18c) is given in SEQ ID No. 141. The translation into protein of this coding sequence is given in SEQ ID No. 142. Example 24 gives a method for cloning the orf28c gene and for producing an expression vector which allows the expression of orf28c. This example also shows that overexpression of the orf28c gene in the strain OSC2 leads to the improvement of spiramycin production in this strain. The overexpression of the orf28c gene can be obtained by increasing the number of copies of this gene and/or by introducing a promoter which is more active than the wild-type promoter. Preferably, the overexpression of said gene is obtained by introducing into the microorganism a recombinant DNA construct which allows overexpression of this gene. Preferably, this recombinant DNA construct increases the number of copies of said gene and makes it possible to obtain overexpression of said gene. In this recombinant DNA construct, the coding sequence of the gene can be placed under the control of a promoter which is more active than the wild-type promoter. By way of illustration, mention may be made of the ptrc promoter which is active in Streptomyces ambofaciens (E. Amann et al., 1988) and also the ermE* promoter. Thus, preferably, the copy or copies of the orf28c gene introduced is (are) placed under the control of the ermE* promoter, as is the case in the construct pSPM75 (cf. example 24).

The invention also relates to a microorganism which produces spiramycin I but which does not produce spiramycin II and 111, as described above, which also overexpresses the gene having coding sequence SEQ ID No. 47 or having a coding sequence derived therefrom due to the degeneracy of the genetic code. Preferentially, this microorganism is the strain SPM502 pSPM525 deposited with the Collection Nationale de Cultures de Microorganismes [National Collection of Cultures and Microorganisms] (CNCM) Pasteur Institute, 25, rue du Docteur Roux 75724 Paris Cedex 15, France, on Feb. 26, 2003, under the registration number I-2977.

The invention also relates to a method of producing spiramycin I; the method consists in culturing, in a suitable culture medium, a microorganism which produces spiramycin I but which does not produce spiramycin II and III, as described above, recovering the conditioned culture medium or a cell extract, and separating and purifying the spiramycin I from said culture medium or else from the cell extract obtained in the preceding step. The conditions for culturing such a microorganism may be determined according to techniques well known to those skilled in the art. The culture medium may, for example, be the MP5 medium or the SL11 medium for Streptomyces, and in particular for Streptomyces ambofaciens (Pemodet et al., 1993). Those skilled in the art may in particular refer to the work by Kieser et al., 2000 regarding the culturing of Streptomyces. The spiramycin I produced can be recovered by any techniques known to those skilled in the art. Those skilled in the art may, for example, refer to the techniques taught in U.S. Pat. No. 3,000,785, and more particularly to the methods for extracting spiramycins described in that patent.

Another aspect of the invention concerns the use of a nucleotide sequence according to the invention, for improving the macrolide production of a microorganism. Thus, the invention relates to a macrolide-producing mutant microorganism which has a genetic modification in at least one gene comprising a sequence as defined above, and/or which overexpresses at least one gene comprising a sequence as defined above. The genetic modification may consist of a suppression, a substitution, a deletion and/or an addition of one or more bases in the gene(s) under consideration with the aim of expressing one or more proteins having greater activity or of expressing a higher level of this or these protein(s). The overexpression of the gene under consideration can be obtained by increasing the number of copies of this gene and/or by introducing a promoter which is more active than the wild-type promoter. By way of illustration, mention may be made of the ptrc promoter which is active in Streptomyces

*ambofaciens* (E. Amann et al., 1988) and also the ermE* promoter (Bibb et al., 1985), (Bibb et al., 1994). Thus, the overexpression of the gene under consideration can be obtained by introducing, into a macrolide-producing microorganism under consideration, a recombinant DNA construct according to the invention which allows overexpression of this gene. Specifically, certain steps of macrolide biosynthesis are limiting and, if one or more proteins which are more active or a higher expression level of the wild-type protein(s) involved in these limiting steps are expressed, it is possible to improve the production of the macrolide(s) concerned. An increase in the rate of production of tylosine has, for example, been obtained in *Streptomyces fradiae* by duplication of the gene encoding a limiting methyltransferase which converts macrocine to tylosine (R. Baltz, 1997). The production of expression of a protein which is more active can be obtained in particular by mutagenesis; those skilled in the art may, for example, refer in this respect to the work by F. Ausubel et al., (2002). Preferentially, these mutant microorganisms improved in terms of their macrolide production are bacteria of the genus *Streptomyces*. More preferentially, the macrolide in question is spiramycin and the microorganisms in which the mutagenesis or mutageneses is (are) carried out are strains of *S. ambofaciens*. More preferentially, the genetic modification is carried out in one or more genes comprising one of the sequences corresponding to one or more of the sequences SEQ ID Nos 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or one of its variants, or one of the sequences derived therefrom due to the degeneracy of the genetic code. Preferably, the microorganism overexpresses one or more genes comprising one of the sequences corresponding to one or more of the sequences SEQ ID Nos 3, 5, 7, 9, 11, 13, 15, 17, 19, 21, 23, 25, 28, 30, 34, 36, 40, 43, 45, 47, 49, 53, 60, 62, 64, 66, 68, 70, 72, 74, 76, 78, 80, 82, 84, 107, 109, 111, 113, 115, 118, 120, 141, 143, 145, 147 and 149, or one of its variants, or one of the sequences derived therefrom due to the degeneracy of the genetic code. Preferably, the microorganism overexpresses the gene comprising a sequence corresponding to SEQ ID No. 111 or 141, or one of its variants, or one of the sequences derived therefrom due to the degeneracy of the genetic code. The sequence given in SEQ ID No. 111 is partial; however, those skilled in the art will easily be able to complete it in particular using the teaching given in example 24. The sequence undetermined in SEQ ID No. 111 was determined in a second step, and the complete sequence of this orf (orf28c) is given in SEQ ID No. 141. The translation into protein of this coding sequence is given in SEQ ID No. 142. Example 24 gives a method for cloning the orf28c gene and for producing an expression vector which allows the expression of orf28c. This example also shows that overexpression of the orf28c gene in the strain OSC2 leads to the improvement of spiramycin production in this strain. The overexpression of the orf28c gene can be obtained by increasing the number of copies of this gene and/or by introducing a promoter which is more active than the wild-type promoter. Preferably, the overexpression of said gene is obtained by introducing into the microorganism a recombinant DNA construct which allows overexpression of this gene. Preferably, this recombinant DNA construct increases the number of copies of said gene and makes it possible to obtain overexpression of said gene. In this recombinant DNA construct, the coding sequence of the gene can be placed under the control of a promoter which is more active than the wild-type promoter. By way of illustration, mention may be made of the ptrc promoter which is active in *Streptomyces ambofaciens* (E. Amann et al., 1988) and also the ermE* promoter. Thus, preferably, the copy or copies of the orf28c gene introduced is (are) placed under the control of the ermE* promoter, as is the case in the construct pSPM75 (cf. example 24).

Another aspect of the invention concerns a method of producing macrolides, using the microorganisms described in the preceding paragraph. This method consists in culturing, in a suitable culture medium, a microorganism defined in the preceding paragraph, recovering the conditioned culture medium or a cell extract, and separating and purifying the macrolide(s) produced from said culture medium or else from the cell extract obtained in the preceding step. The conditions for culturing such microorganisms may be determined according to techniques well known to those skilled in the art. The culture medium may, for example, be the MP5 medium or the SL11 medium for *Streptomyces*, and in particular for *Streptomyces ambofaciens* (Pernodet et al., 1993). Those skilled in the art may in particular refer to the work by Kieser et al., 2000 regarding the culturing of *Streptomyces*. The macrolide(s) produced can be recovered by any techniques known to those skilled in the art. Those skilled in the art may, for example, refer to the techniques taught in U.S. Pat. No. 3,000,785, and more particularly to the methods for extracting spiramycins described in that patent. Preferentially, the microorganisms used in such a method are bacteria of the genus *Streptomyces*. More preferentially, the macrolide in question is spiramycin and the mutant microorganisms improved in terms of their spiramycin production are strains of *S. ambofaciens*.

Another aspect of the invention concerns the use of a sequence and/or of a vector according to the invention, for preparing hybrid antibiotics. Specifically, the polynucleotides according to the invention may be used to obtain microorganisms expressing one or more mutant proteins giving rise to a modification in the substrate specificity, or else may be expressed in many antibiotic-producing microorganisms with the aim of generating hybrid antibiotics. Thus, the polynucleotides according to the invention may make it possible, by gene transfer between producer microorganisms, to produce hybrid antibiotics having advantageous pharmacological properties (Hopwood et al., 1985a, Hopwood et al., 1985b, Hutchinson et al., 1989). The principle by which genetic engineering can bring about the production of hybrid antibiotics was first of all proposed by Hopwood (Hopwood 1981). It was thus proposed that the enzymes involved in the biosynthesis of antibiotics often accept substrates which are structurally related but which differ from their natural substrate. It is generally accepted (Hopwood 1981, Hutchinson 1988, Robinson 1988) that the enzymes encoded by the genes of the biosynthetic pathway for antibiotics have a less strict substrate specificity than the enzymes of primary metabolism. It has thus been possible to show that a large number of non-natural substrates are converted by antibiotic-producing microorganisms, their mutants or purified enzymes of the biosynthetic pathway for these antibiotics (Hutchinson 1988). Using this teaching, those skilled in the art may construct microorganisms expressing one or more mutant proteins giving rise to a modification in the substrate specificity with the aim of generating hybrid antibiotics.

The invention also relates to the use of at least one polynucleotide and/or at least one recombinant DNA and/or at least one expression vector and/or at least one polypeptide and/or at least one host cell according to the invention, for carrying out one or more bioconversions. Thus, the invention makes it possible to construct bacterial or fungal strains in which one or more proteins according to the invention are expressed under the control of suitable expression signals.

Such strains can then be used to carry out one or more bioconversions. These bioconversions may be carried out either using whole cells, or using acellular extracts of said cells. These bioconversions may make it possible to convert a molecule into a derived form, with an enzyme of a biosynthetic pathway. For example, Carreras et al. describe the use of a strain of *Saccharopolyspora erythraea* and of *Streptomyces coelicolor* for producing new erythromycin derivatives (Carreras et al., 2002). Walczak et al. describe the use of a *Streptomyces* P450 monooxygenase for the bioconversion of desacetyladriamycin (an anthracycline analog) to novel anthracyclines (Walczak et al., 2001). Olonao et al. describe the use of a modified strain of *Streptomyces lividans* for the bioconversion of epsilon-rhodomycinone to rhodomycin D (Olonao et al., 1999). Those skilled in the art may apply this principle to any biosynthesis intermediate.

The invention also relates to a recombinant DNA which comprises:
a polynucleotide which can be obtained by polymerase chain reaction using the pair of primers of the following sequence:
5' AAGCTTGTGTGCCCGGTGTACCTGGGGAGC 3' (SEQ ID No. 138) and
5' GGATCCCGCGACGGACACGACCGCCGCGCA 3' (SEQ ID No. 139) and as matrix the cosmid pSPM36 or the total DNA of *Streptomyces ambofaciens*, more preferably it is a polynucleotide of sequence SEQ ID No. 141,
or a fragment of at least 10, 12, 15, 18, 20 to 25, 30, 40, 50, 60, 70, 80, 90, 100, 150, 200, 250, 300, 350, 400, 450, .500, 550, 600, 650, 700, 750, 800, 850, 900, 950, 1000, 1050, 1100, 1150, 1200, 1250, 1300, 1350, 1400, 1450, 1460, 1470, 1480, 1490 or 1500 consecutive nucleotides of the polynucleotide.

Preferentially, this recombinant DNA is a vector. Even more preferentially, the vector is chosen from bacteriophages, plasmids, phagemids, integrative vectors, fosmids, cosmids, shuttle vectors, BACs (Bacterial Artificial Chromosomes) and PACs (P1-derived Artificial Chromosomes). By way of illustration, the lambda phage and the M13 phage may be mentioned as bacteriophages. As plasmids, mention may be made of plasmids which replicate in *E. coli*, for example pBR322 and its derivatives, pUC18 and its derivatives, pUC19 and its derivatives, pGB2 and its derivatives (G. Churchward et al., 1984), pACYC177 (GenBank accession number: X06402) and its derivatives, and pACYC 184 (GenBank accession number: X06403) and its derivatives. Mention may also be made of plasmids which replicate in *Streptomyces*, such as, for example, pIJ101 and its derivatives, pSG5 and its derivatives, SLP1 and its derivatives, and SCP2* and its derivatives (Kieser et al. 2000). As phagemids, mention may be made, by way of illustration, of pBluescript II and its derivatives (marketed in particular by the company Stratagene (LaJolla, Calif., USA)), pGEM-T and its derivatives (marketed by the company Promega (Madison, Wis., USA)), and λZAPII and its derivatives (marketed in particular by the company Stratagene (LaJolla, Calif., USA)). As integrative vectors, mention may be made, by way of illustration, of vectors which integrate in *Streptomyces*, such as, for example, those derived from SLP1 (Kieser et al, 2000), those derived from pSAM2 (Kieser et al, 2000), vectors which use PhiC31 phage integration systems (Kieser et al, 2000) (for example pSET152 (Bierman et al., 1992)) or VWB integration systems (L. van Mellaert et al. 1998), and also vectors which use the IS117 integration system (Kieser et al., 2000). As fosmids, mention may be made, by way of illustration, of the fosmid pFOS1 (marketed by the company New England Bioloabs Inc., Beverly, Mass., USA) and its derivatives. As cosmids, mention may be made, by way of illustration, of the cosmid SuperCos and its derivatives (marketed in particular by the company Stratagene (LaJolla, Calif., USA)) and the cosmid pWED15 (Wahl et al., 1987) and its derivatives. As shuttle vectors, mention may be made, by way of illustration, of *E. coli/Streptomyces* shuttle plasmids, such as, for example, pIJ903 and its derivatives, the series of plasmids pUWL, pCAO106, pWHM3 and pOJ446 and their derivatives (Kieser et al. 2000), and *E. coli/Streptomyces* shuttle BACs, such as, for example, those described in patent application WO 01/40497. As BACs (Bacterial Artificial Chromosomes), mention may be made, by way of illustration, of the BAC pBeloBAC11 (GenBank accession number: U51113). As PACs (P1-derived Artificial Chromosomes), mention may be made, by way of illustration, of the vector pCYPAC6 (GenBank accession number: AF133437). More preferentially, this recombinant DNA is an expression vector. The expression vectors which can be used in such systems are well known to those skilled in the art; as regards prokayrotic cells, mention may be made, by way of illustration, of the expression vectors in *E. coli*, for example of the pET marketed by the company Stratagene (LaJolla, Calif., USA), the vectors of the GATEWAY family marketed by the company Invitrogen (Carlsbad, Calif., USA), the vectors of the pBAD family marketed by the company Invitrogen (Carlsbad, Calif., USA), the vectors of the pMAL family marketed by the company New England Bioloabs Inc. (Beverly, Mass., USA), and the rhamnose-inducible expression vectors mentioned in the publication B. Wilms et al., 2001 and their derivatives; mention may also be made of the expression vectors in *Streptomyces*, such as, for example, the vectors pIJ4123, pIJ6021, pPM927, pANT849, pANT 850, pANT 851, pANT1200, pANT1201 and pANT1202 and their derivatives (Kieser et al., 2000). As regards yeast cells, mention may be made, by way of illustration, of the vector pESC marketed by the company Stratagene (LaJolla, Calif., USA). As regards the baculovirus expression system which allows expression in insect cells, mention may be made, by way of illustration, of the vector BacPAK6 marketed by the company BD Biosciences Clontech, (Palo Alto, Calif., USA). As regards mammalian cells, mention may be made, by way of illustration, of the vectors comprising the CMV (Cytomegalovirus) immediate early gene promoter (for example the vector pCMV and its derivatives marketed by the company Stratagene (LaJolla, Calif., USA)), or the SV40 early promoter of the vacuolating simian virus (for example the vector pSG5 marketed by the company Stratagene (LaJolla, Calif., USA)). Another aspect of the invention relates to host cells into which at least one recombinant DNA described in this paragraph has been introduced.

Another aspect of the invention concerns a method of producing a polypeptide, wherein said method comprises the following steps:
a) transforming a host cell with at least one expression vector as described in the paragraph above;
b) culturing, in a suitable culture medium, said host cell;
c) recovering the conditioned culture medium or a cell extract;
d) separating and purifying said polypeptide from said culture medium or else from the cell extract obtained in step c);
e) where appropriate, characterizing the recombinant polypeptide produced.

The recombinant polypeptide thus produced can be purified by passage over an appropriate series of chromatography columns, according to the methods known to those skilled in the art and described, for example, in F. Ausubel et al., (2002). By way of illustration, mention may be made of the "Histidine-Tag" technique, which consists in adding a short polyhistidine sequence to the polypeptide to be produced, it being possible for this polypeptide to be purified on a nickel column. This polypeptide may also be prepared by in vitro synthesis techniques. By way of illustration of such techniques, the polypeptide may be prepared using the "rapid translation system (RTS)", marketed in particular by the company Roche Diagnostics France S.A., Meylan, France.

Another aspect of the invention concerns a microorganism which produces at least one spiramycin, which overexpresses:
    a gene which can be obtained by polymerase chain reaction (PCR) using the pair of primers of the following sequence:
    5' AAGCTTGTGTGCCCGGTGTACCTGGGGAGC 3' (SEQ ID No. 138) and
    5' GGATCCCGCGACGGACACGACCGCCGCGCA 3' (SEQ ID No. 139), and as matrix the cosmid pSPM36 or the total DNA of Streptomyces ambofaciens, more preferably it is the gene of coding sequence SEQ ID No. 141,
    or a gene derived therefrom due to the degeneracy of the genetic code.

An example of sequence of such a gene is given in SEQ ID No. 111 (DNA); however, this sequence is partial since it does not comprise the 3' portion of the corresponding coding sequence. The translation of this portion of coding sequence into protein is given in SEQ ID No. 112. Those skilled in the art will easily be able to complete it in 25 particular using the teaching given in example 24. This example thus gives a method for cloning the orf28c gene and for producing an expression vector which allows the expression of orf28c. This example also shows that overexpression of the orf28c gene in the strain OSC2 leads to the improvement of spiramycin production in this strain. Preferably, the microorganism overexpressing
    a gene which can be obtained by polymerase chain reaction (PCR) using the pair of primers of the following sequence:
    5' AAGCTTGTGTGCCCGGTGTACCTGGGGAGC 3' (SEQ ID No. 138) and
    5' GGATCCCGCGACGGACACGACCGCCGCGCA 3' (SEQ ID No. 139), and as matrix the cosmid pSPM36 or the total DNA of Streptomyces ambofaciens, more preferably it is the gene of coding sequence SEQ ID No. 141,
    or a gene derived therefrom due to the degeneracy of the genetic code is a bacterium of the genus Streptomyces; even more preferably, it is a bacterium of the species Streptomyces ambofaciens. Preferably, the overexpression of said gene is obtained by transformation of said microorganism with an expression vector; most preferably, the strain of microorganism is the strain OSC2/pSPM75(1) or of the strain OSC2/pSPM75(2) deposited with the Collection Nationale de Cultures de Microorganismes (CNCM) [National Collection of Cultures and Microorganisms] Pasteur Institute, 25, rue du Docteur Roux 75724 Paris Cedex 15, France, on Oct. 6, 2003, under the registration number I-3101.

Another aspect of the invention concerns a method of producing spiramycin(s), using the microorganisms described in the preceding paragraph. This method consists in culturing, in a suitable culture medium, a microorganism defined in the preceding paragraph, recovering the conditioned culture medium or a cell extract, and separating and purifying the spiramycin(s) produced from said culture medium or else from the cell extract obtained in the preceding step. The conditions for culturing such microorganisms may be determined according to techniques well known to those skilled in the art. The culture medium may, for example, be the MP5 medium or the SL11 medium for Streptomyces and in particular for Streptomyces ambofaciens (Pemodet et al., 1993). Those skilled in the art may in particular refer to the work by Kieser et al., 2000 regarding the culturing of Streptomyces. The spiramycin(s) produced can be recovered using any techniques known to those skilled in the art. Those skilled in the art may, for example, refer to the techniques taught in U.S. Pat. No. 3,000,785, and more particularly to the methods for extracting spiramycins described in that patent. Preferentially, the microorganisms used in such a method are bacteria of the genus Streptomyces. More preferentially, the microorganisms are strains of S. ambofaciens.

Another aspect of the invention concerns an expression vector wherein the polynucleotide of sequence SEQ ID No. 47, or a polynucleotide derived therefrom due to the degeneracy of the genetic code, is placed under the control of a promoter which allows expression of the protein encoded by said polynucleotide in Streptomyces ambofaciens. Examples of expression vectors which can be used in Streptomyces have been given above. Preferentially, such an expression vector is the plasmid pSPM524 or pSPM525.

Another aspect of the invention concerns a strain of Streptomyces ambofaciens transformed with a vector defined in the preceding paragraph.

Another aspect of the invention concerns a polypeptide the sequence of which comprises the sequence SEQ ID No. 112. The invention also relates to a polypeptide the sequence of which corresponds to the sequence translated from the coding sequence:
    of a gene which can be obtained by a polymerase chain reaction (PCR) using the pair of primers of the following sequence:
    5' AAGCTTGTGTGCCCGGTGTACCTGGGGAGC 3' (SEQ ID No. 138) and
    5' GGATCCCGCGACGGACACGACCGCCGCGCA 3' (SEQ ID No. 139) and as matrix the cosmid pSPM36 or the total DNA of Streptomyces ambofaciens, more preferably it is the gene of coding sequence SEQ ID No. 141,
    or of a gene derived therefrom due to the degeneracy of the genetic code. Preferentially, these polypeptides are expressed in the natural state by a bacterium of the genus Streptomyces, more preferentially these polypeptides are involved in spiramycin biosynthesis.

Another aspect of the invention concerns an expression vector which allows expression of a polypeptide as defined in the preceding paragraph in Streptomyces ambofaciens. Examples of expression vectors which can be used in Streptomyces have been given above. Preferentially, the expression vector in question is the plasmid pSPM75.

LIST OF FIGURES

Figure 2:
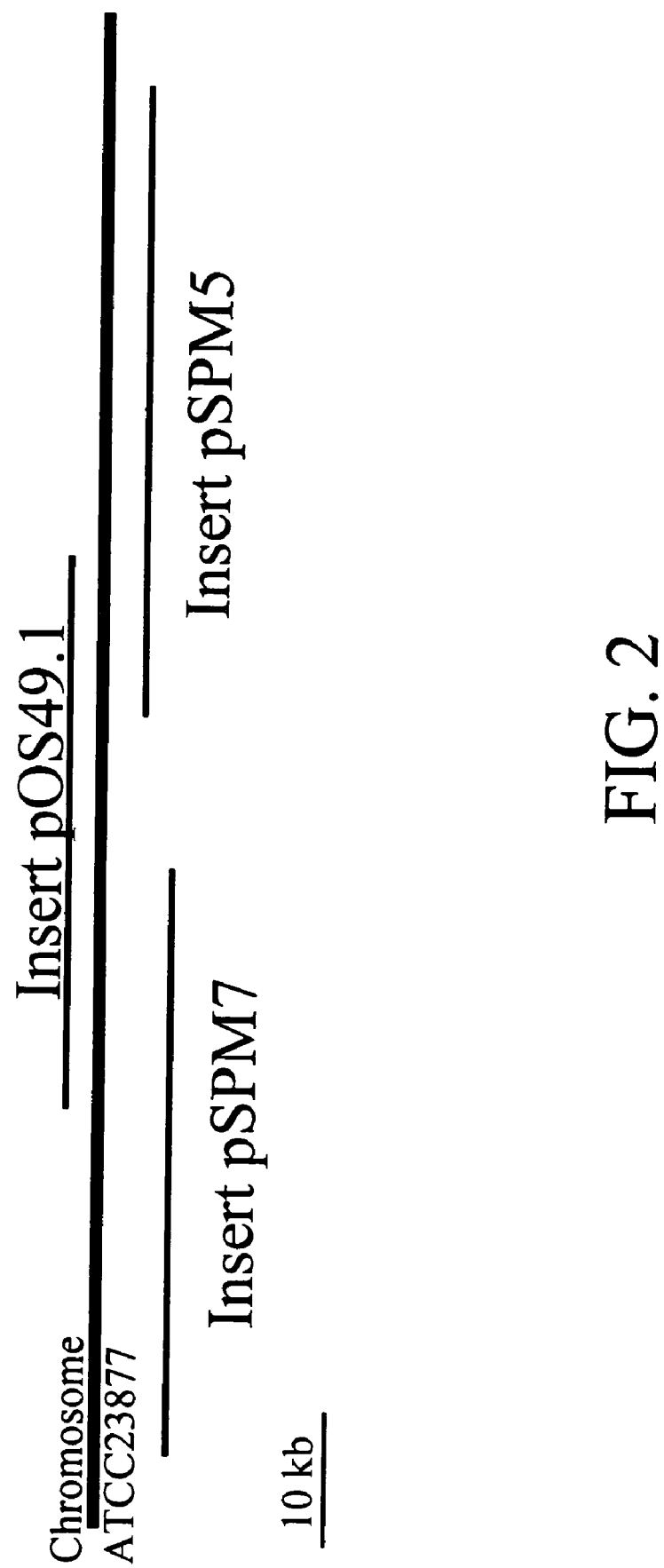
Figure 4:
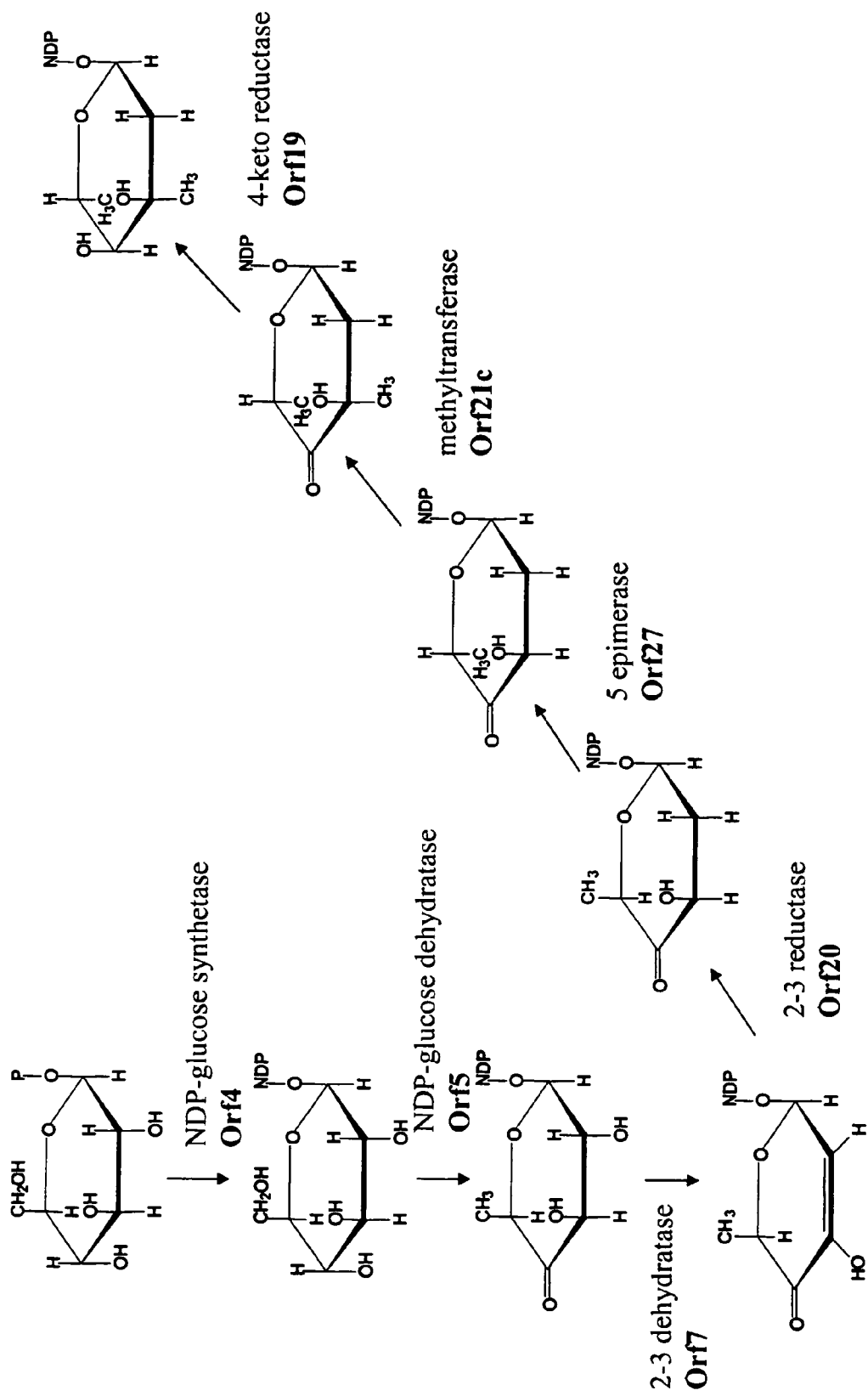
Figure 5:
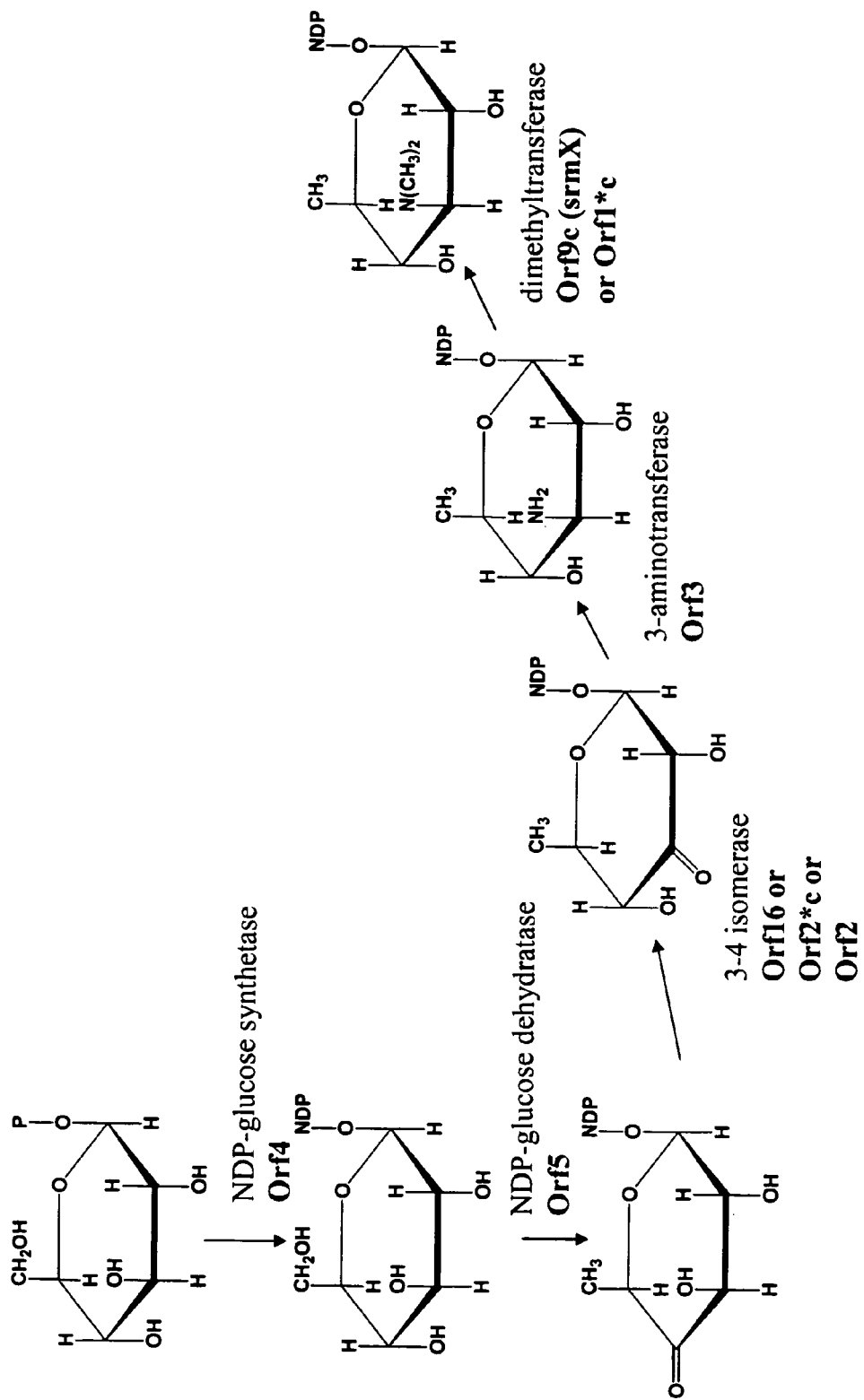
Figure 6:
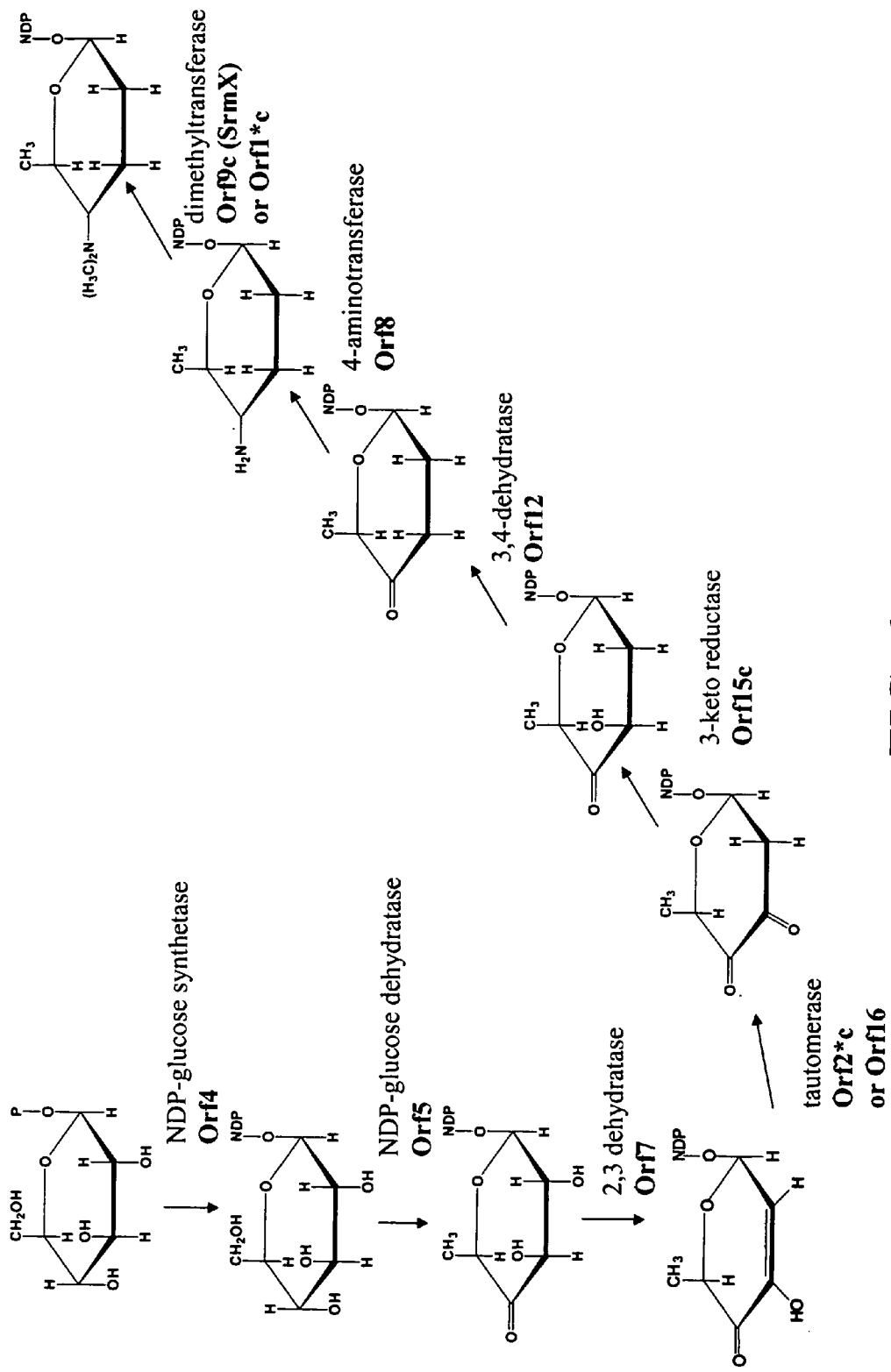
Figure 7:
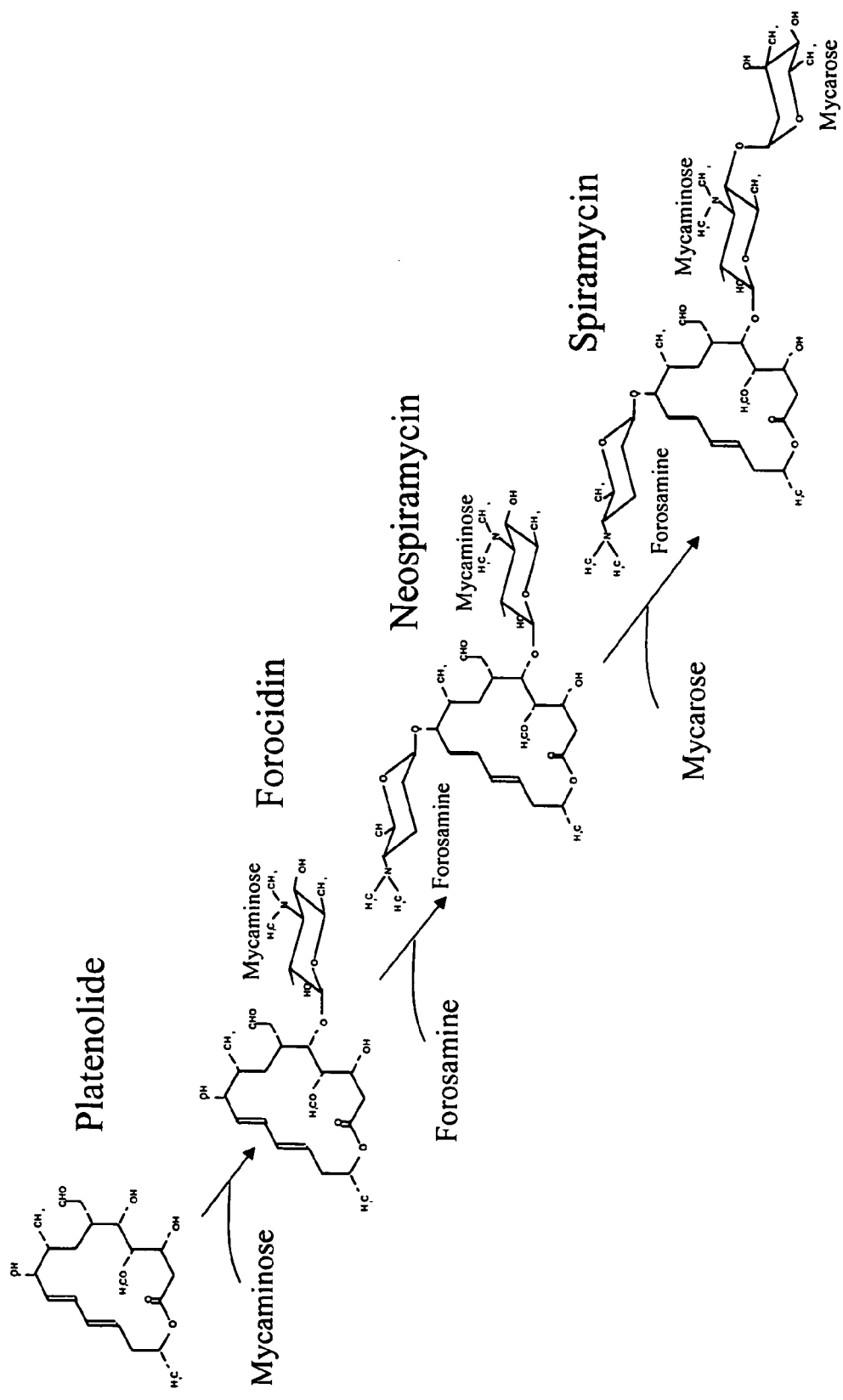
Figure 8:
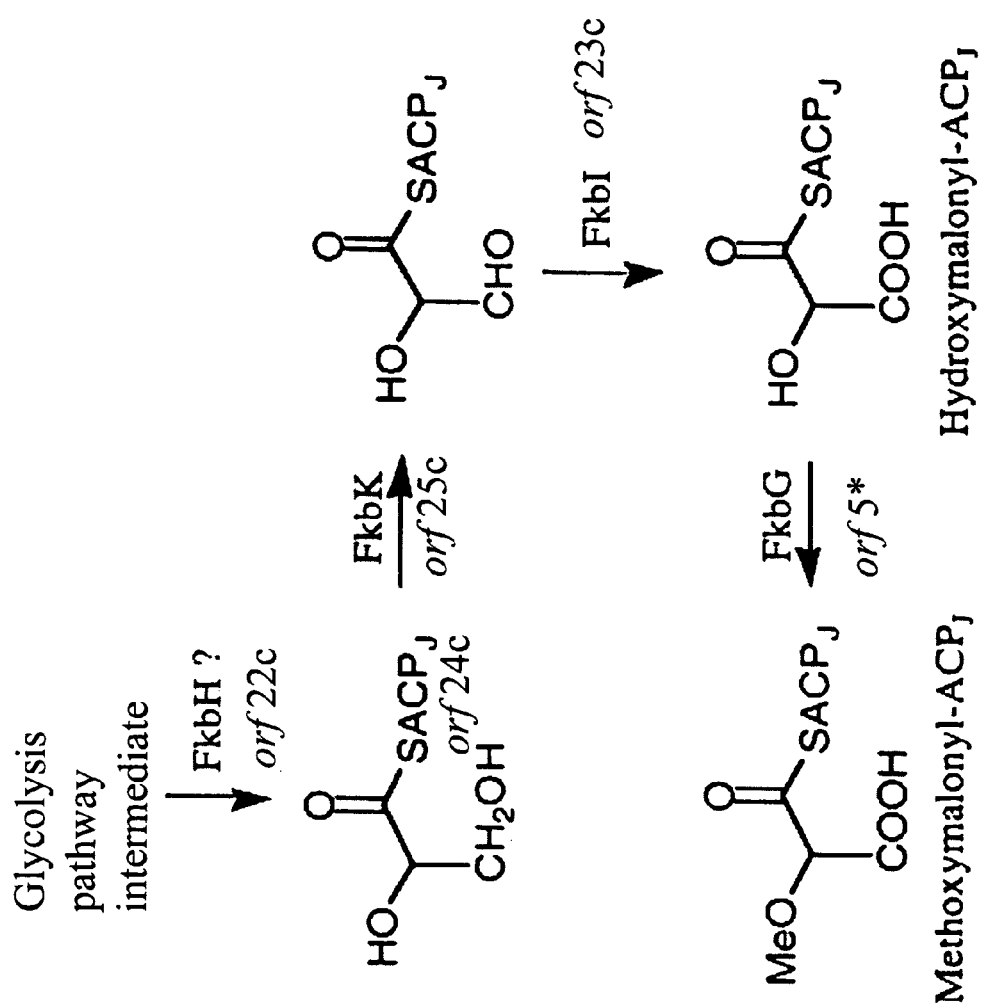

FIG. 1: Chemical structure of spiramycins I, II and III.
FIG. 2: Cosmids used for sequencing the region.
FIG. 3: Organization of a group of genes involved in the biosynthetic pathway for spiramycins.
FIG. 4: Proposed biosynthetic pathway for mycarose.
FIG. 5: Proposed biosynthetic pathway for mycaminose.
FIG. 6: Proposed biosynthetic pathway for forosamine.
FIG. 7: Preferential order of the addition of sugars to the spiramycin molecule and intermediates.
FIG. 8: Proposed biosynthetic pathway for methoxymalonyl in S. ambofaciens. This pathway is proposed by analogy with the biosynthesis of methoxymalonyl in *Streptomyces hygroscopicus* var. *ascomyceticus* (K. Wu et al., 2000).

Figure 9:
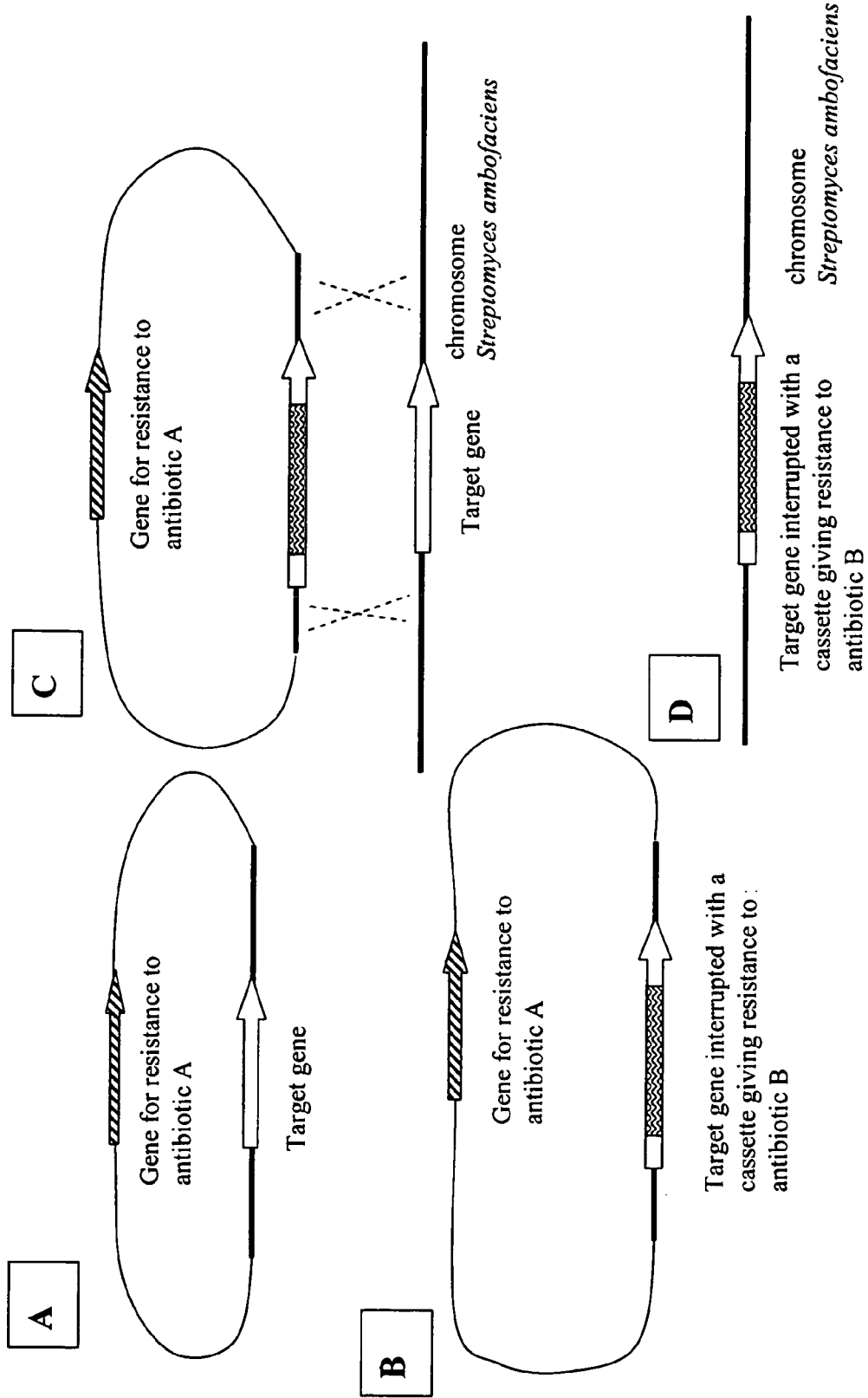

FIG. 9: Steps leading to the inactivation of a gene:
A) Cloning of the target gene into a vector which replicates *E. coli* but not in *Streptomyces*;
B) Insertion of the resistance cassette into the target gene (by cloning or recombination between short identical sequences);
C) Introduction of the plasmid into *Streptomyces ambofaciens* (by transformation or conjugation with *E. coli*) and selection of the clones having integrated the cassette then screening of clones having lost the vector portion so as to have a gene replacement;
D) Region of the chromosome of the mutant strain in which the target gene is inactivated by gene replacement.

Figure 10:
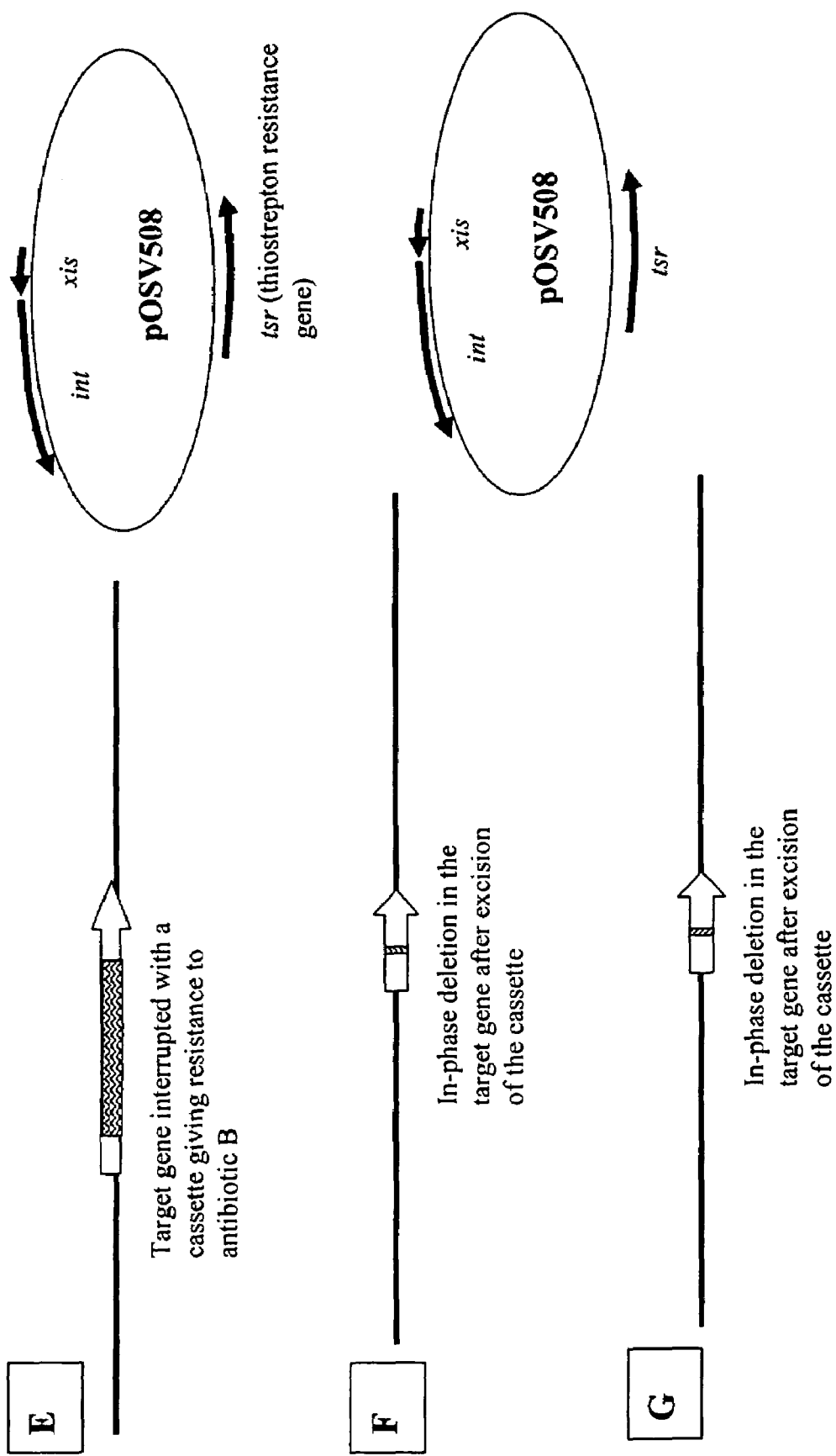

FIG. 10: Optional steps following the inactivation of a gene according to the method described in FIG. 9, which may be carried out if an excisable cassette has been used to interrupt the target gene;
E) Introduction into the mutant strain of the plasmid pOSV508 carrying the xis and int genes of pSAM2, the products of which will allow effective excision by site-specific recombination between the attL and attR sequences bordering the cassette;
F) Production of clones which have lost the excisable cassette and which are sensitive to the antibiotic against which the cassette provided resistance;
G) After growth and sporulation on solid medium without antibiotic, the plasmid pOSV508 is lost at high frequency. It is thus possible to obtain clones sensitive to thiostrepton in which the target gene contains an in-phase deletion. The sequence of the deleted target gene can be controlled by PCR amplification and sequencing of the PCR product.

Figure 11:
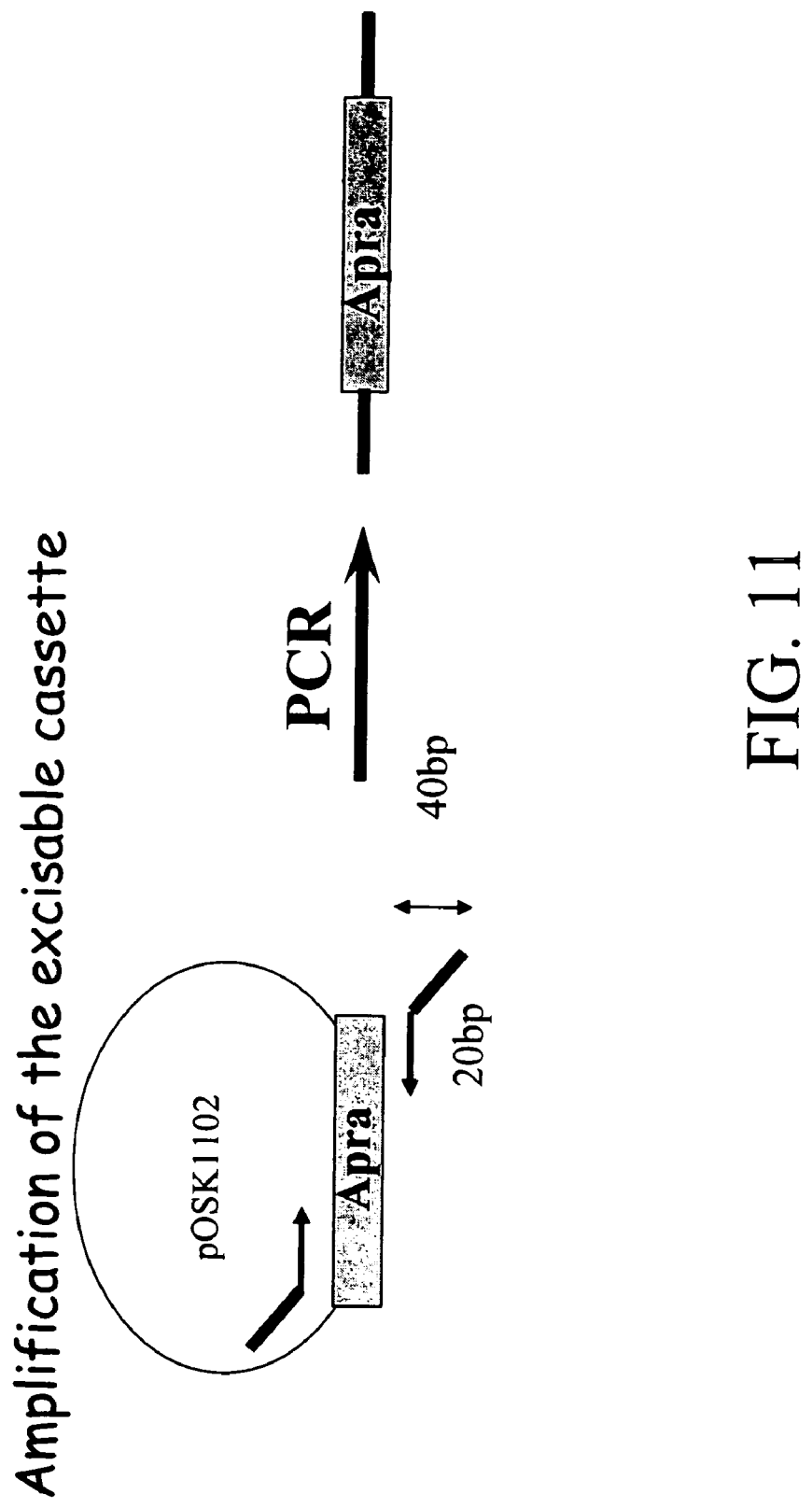

FIG. 11: Amplification of the excisable cassette with the aim of using it for a homologous recombination experiment. The technique of homologous recombination via short homologous sequences has been described by Chaveroche et al., 2000. The 39 or 40 deoxynucleotides located at the 5' end of these oligonucleotides comprise a sequence corresponding to a sequence of the gene to be inactivated, and the 20 deoxynucleotides located in the most 3' position correspond to the sequence of one of the ends of the excisable cassette.

Figure 12:
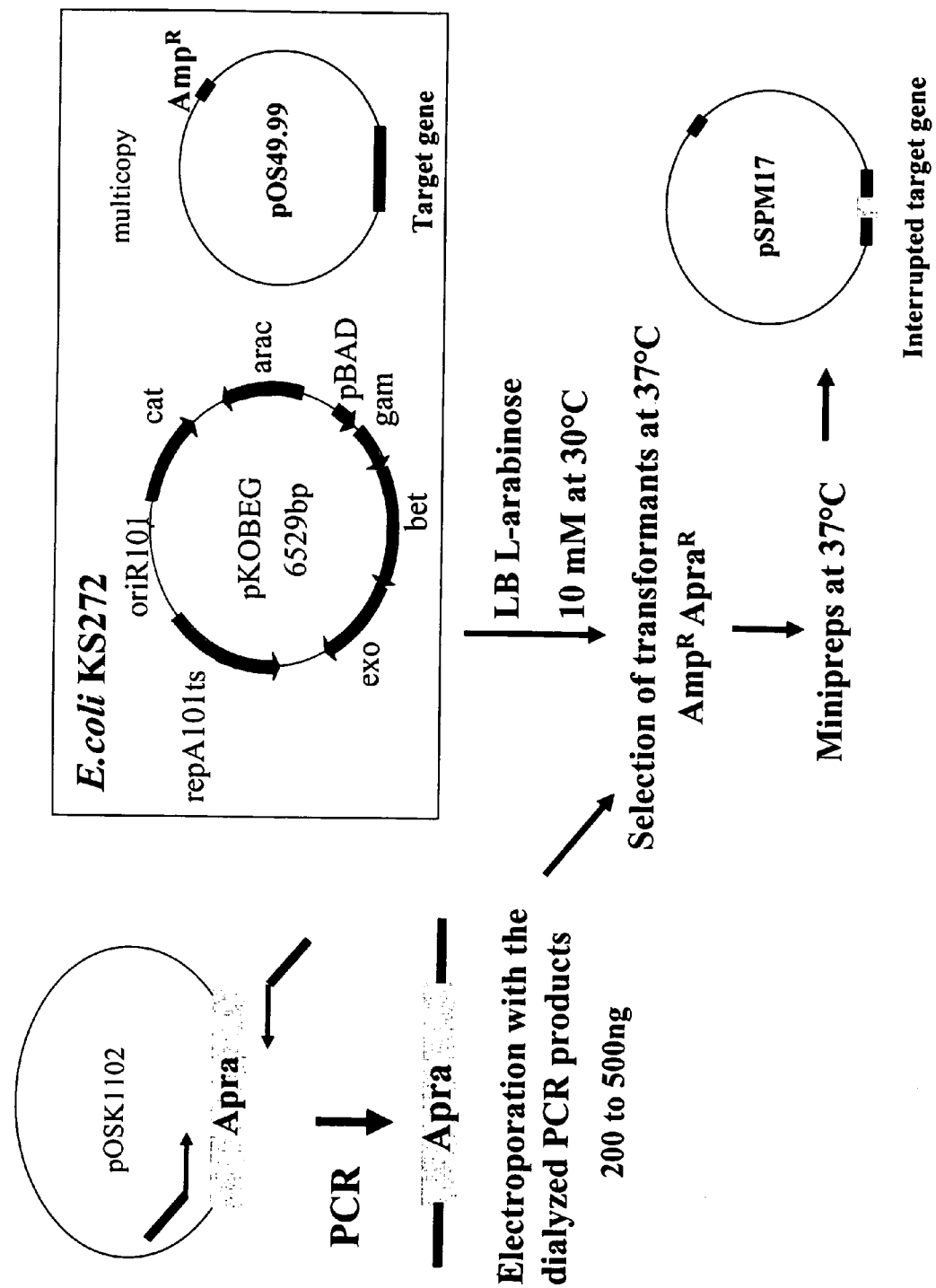

FIG. 12: Production of a construct for the inactivation of a target gene using the technique described by Chaveroche et al., 2000.

Figure 13:
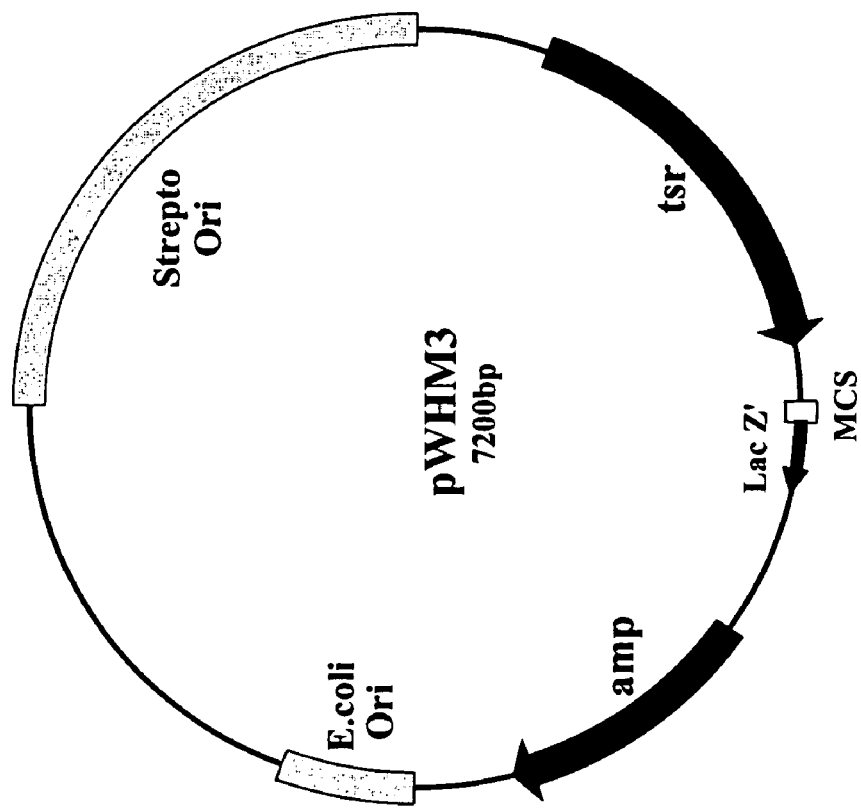

FIG. 13: Map of the plasmid pWHM3. Strepto ori: *Streptomyces* origin of replication.

Figure 14:
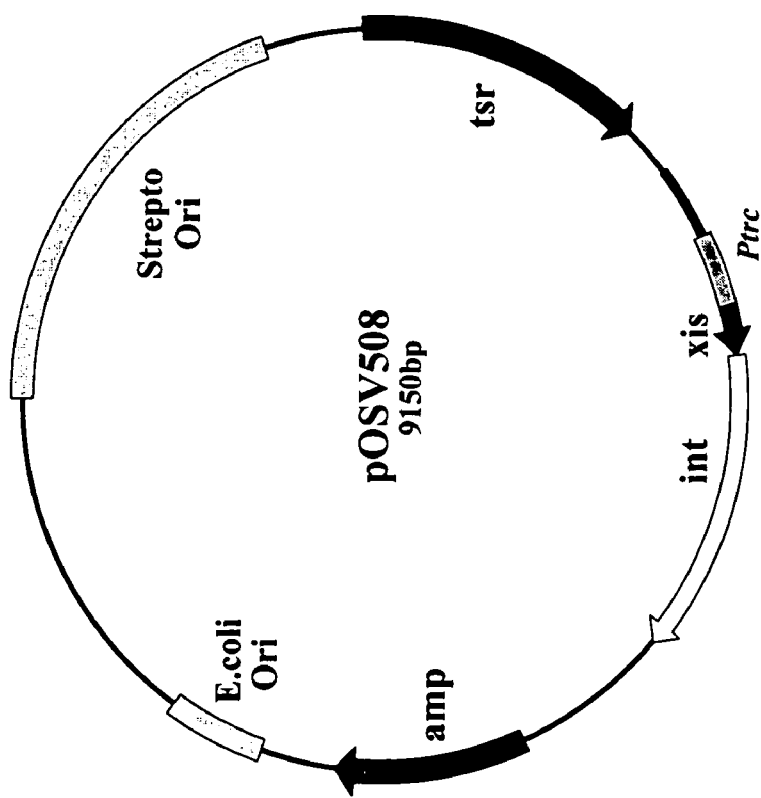

FIG. 14: Map of the plasmid pOSV508.

Figure 15:
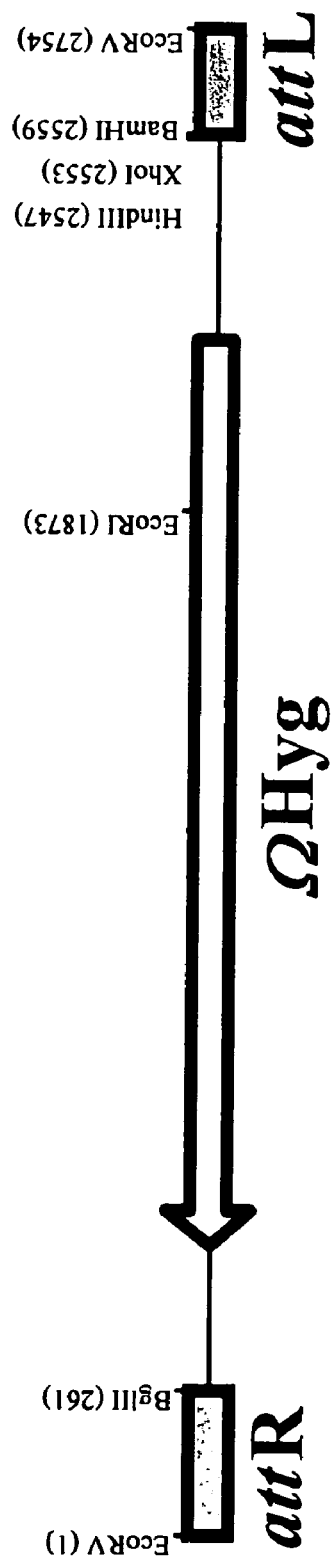

FIG. 15: Example of the structure of an excisable cassette. This consists of the Ωhyg cassette (Blondelet-Rouault et al., 1997) bordered by the attR and attL sites (Raynal et al., 1998), between which a recombination event will allow the excision of the cassette, by virtue of the expression of the xis and int genes.

Figure 16:
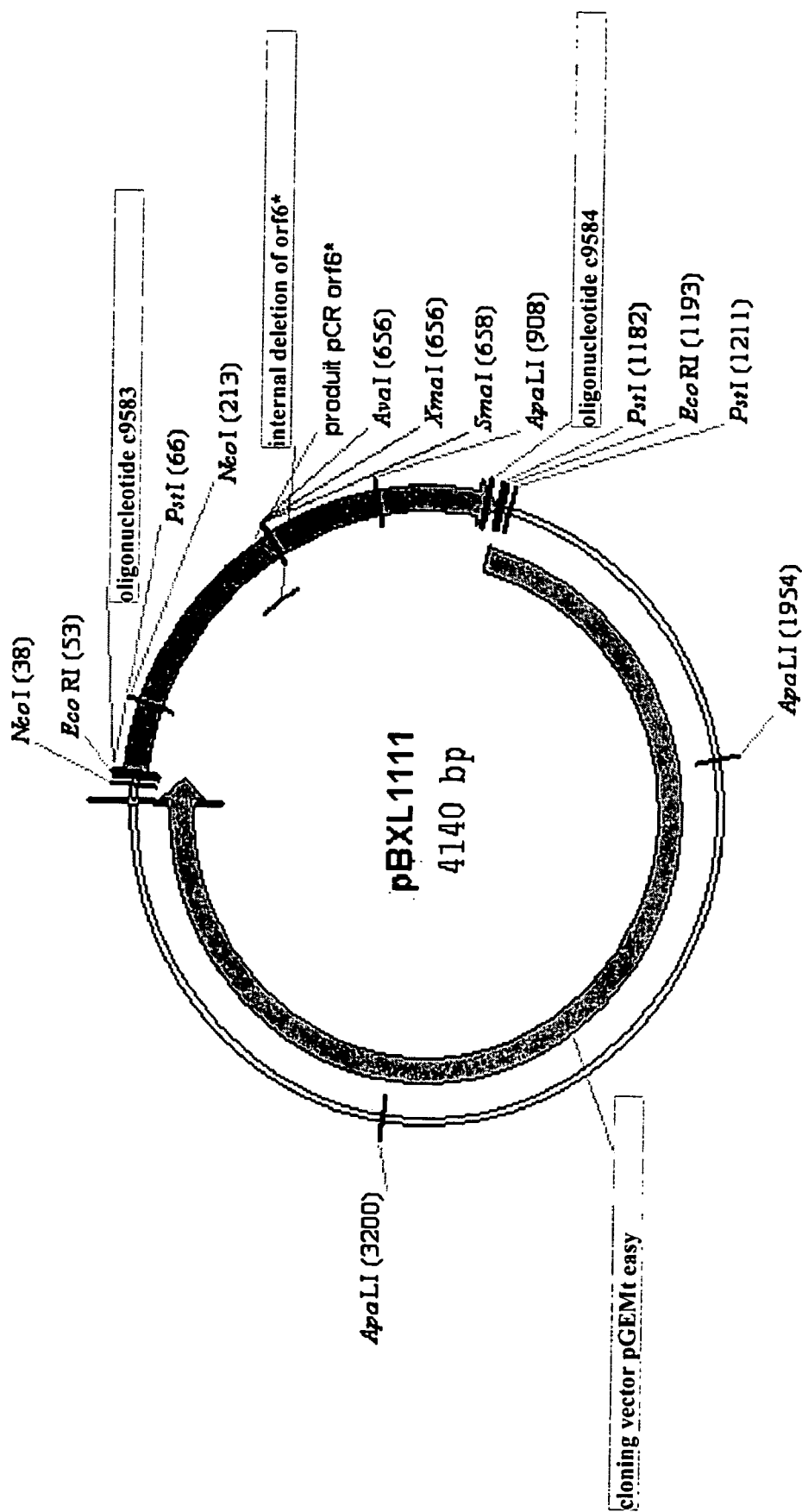

FIG. 16: Map of the plasmid pBXL1111.

Figure 17:
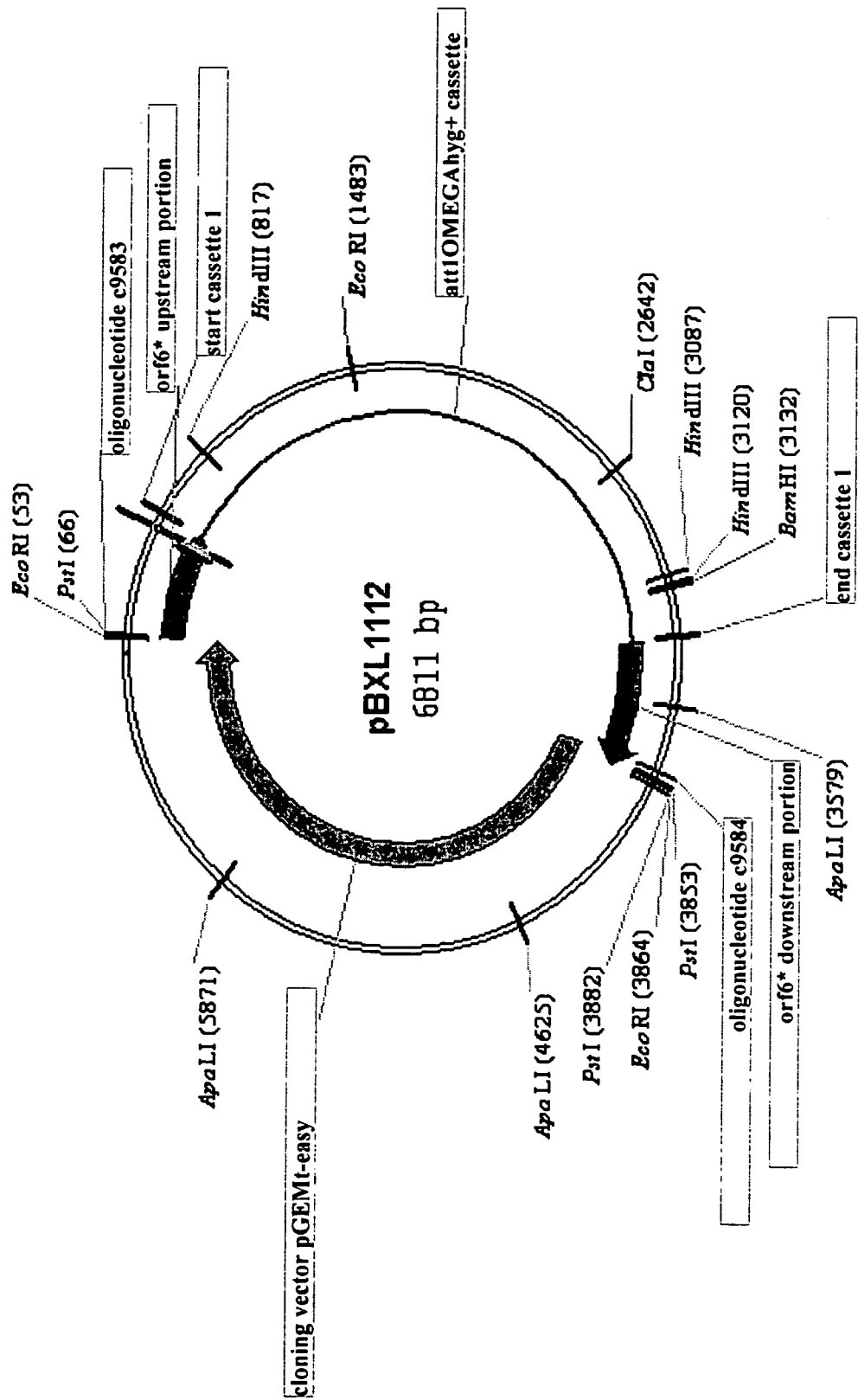

FIG. 17: Map of the plasmid pBXL1112.

Figure 18:
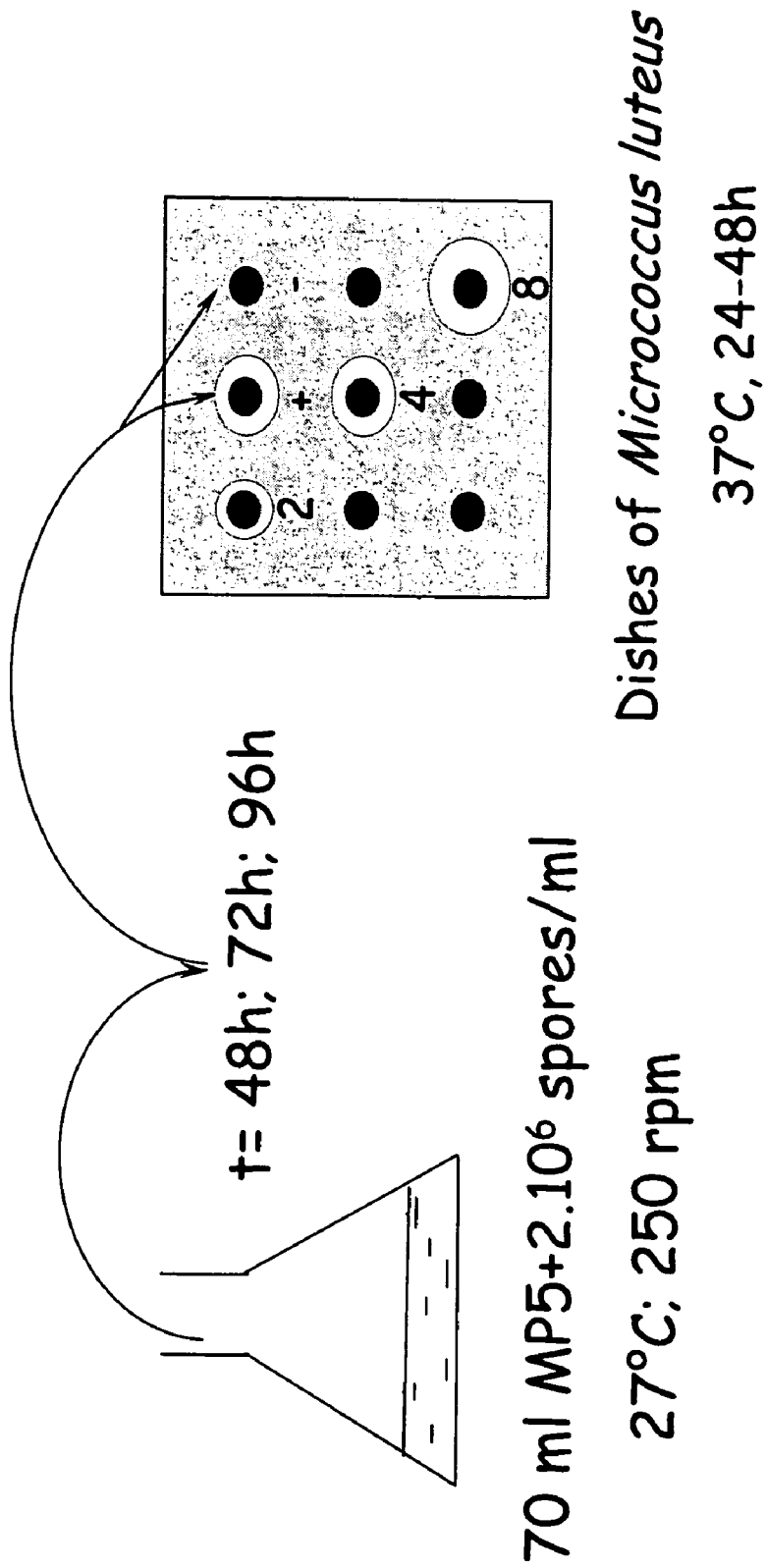

FIG. 18: Microbiological test for spiramycin production, based on the sensitivity of a strain of *Micrococcus luteus* to spiramycin. The strain of *Micrococcus luteus* used is a strain naturally sensitive to spiramycin but resistant to congocidine. The various strains of *Streptomyces* to be tested were cultured in 500 ml Erlenmeyer flasks containing 70 ml of MP5 medium, inoculated at an initial concentration of $2.5 \times 10^6$ spores/ml and grown at 27° C. with orbital shaking at 250 rpm. Samples of fermentation musts were taken after 48, 72 and 96 hours of culturing, and centrifuged. A ten-fold dilution of these supernatants in sterile culture medium is used for the test. The *Micrococcus luteus* indicator strain resistant to congocidine but sensitive to spiramycin (Gourmelen et al., 1998) was cultured in a square 12×12 cm dish. Disks of Whatman AA paper were soaked with 70 µl of the ten-fold dilution of each supernatant and placed on the surface of the dish. Disks soaked with a solution of spiramycin of various concentrations (2-4-8 µg/ml in MP5 culture medium) were diluted as a standard range. The dishes were incubated at 37° C. for 24 to 48 h. If the disk contains spiramycin, this diffuses into the agar and inhibits the growth of the *Micrococcus luteus* indicator strain. This inhibition creates a "halo" around the disk, this halo reflecting the area where the *Micrococcus luteus* strain has not grown. The presence of this halo is therefore an indication of the presence of spiramycin and makes it possible to determine whether the strain of *S. ambofaciens* in question is or is not a spiramycin producer. Comparison with the inhibition diameters obtained for the standard range makes it possible to obtain an indication of the amount of spiramycin produced by this strain.

Figure 19:
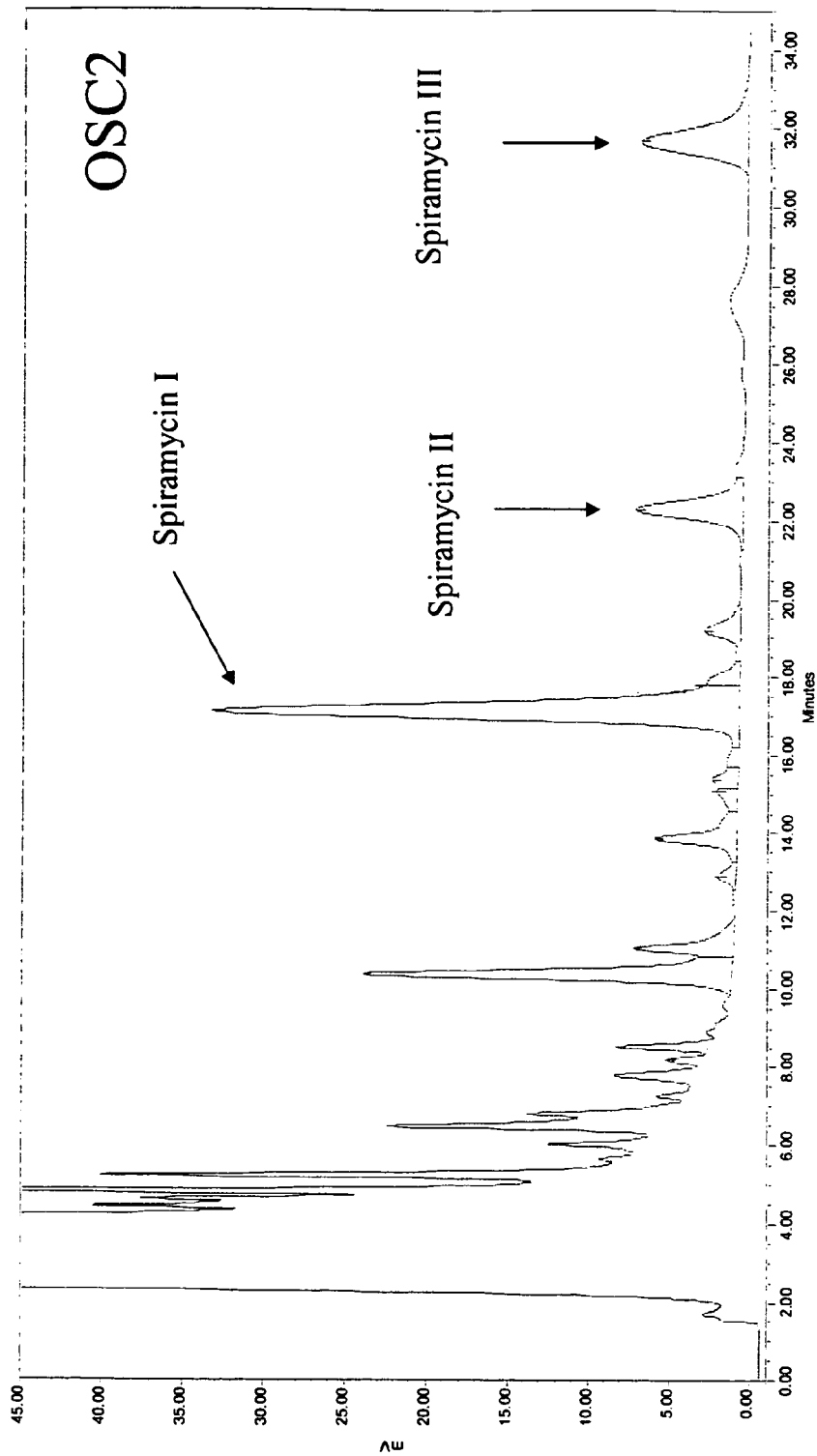

FIG. 19: HPLC chromatogram of the filtered culture medium supernatant of the strain OSC2.

Figure 20:
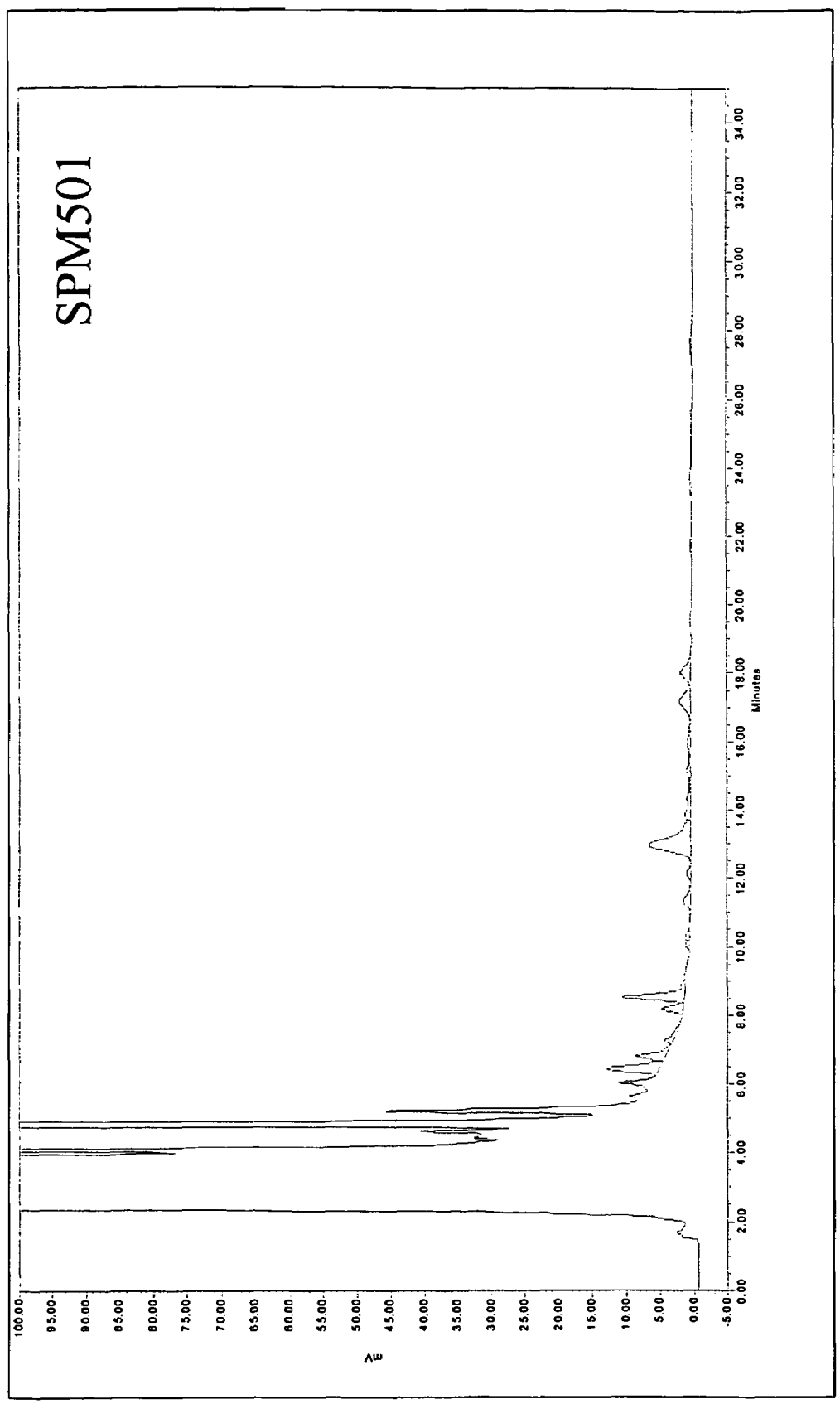

FIG. 20: HPLC chromatogram of the filtered culture medium supernatant of the strain SPM501.

Figure 21:
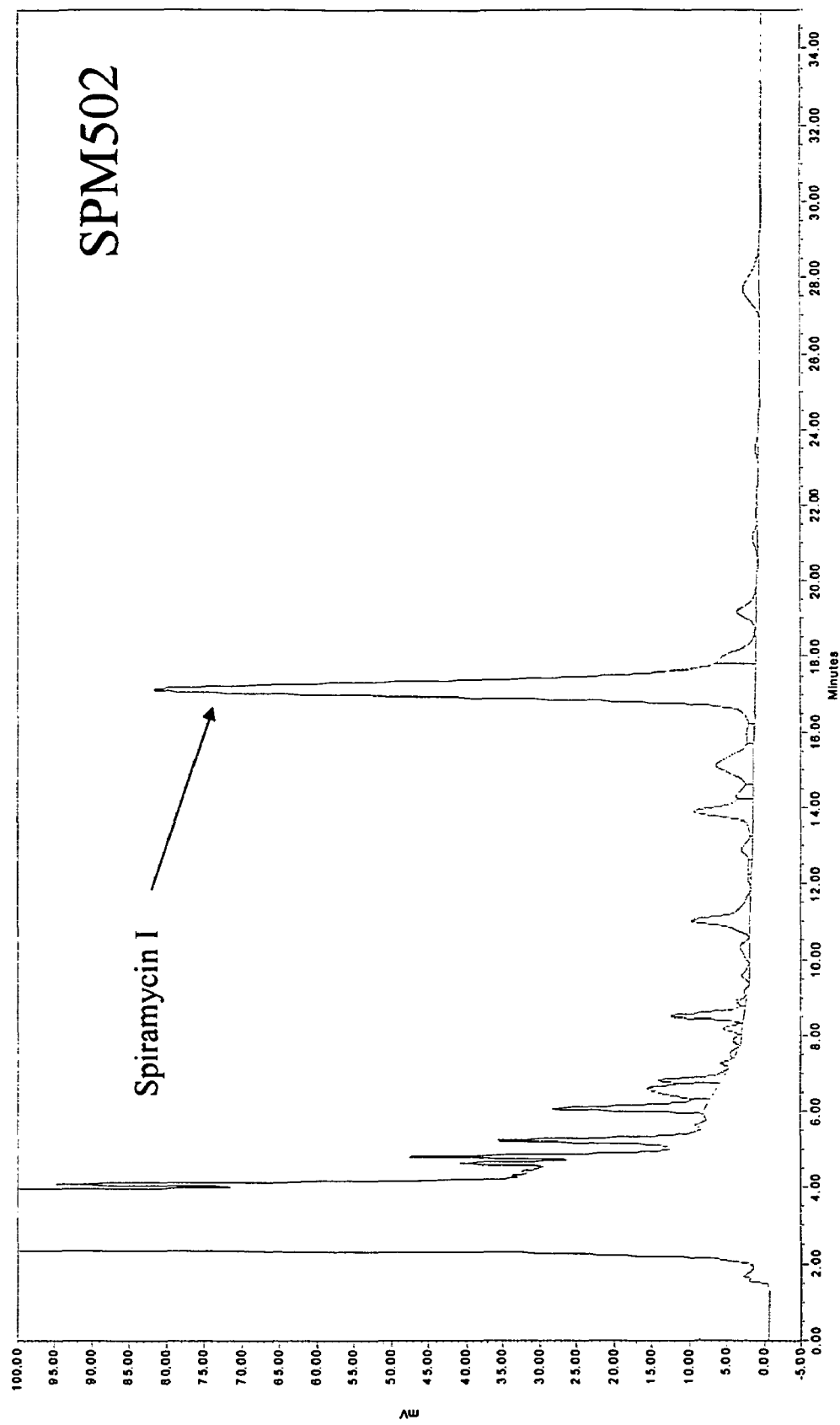

FIG. 21: HPLC chromatogram of the filtered culture medium supernatant of the strain SPM502.

Figure 22:
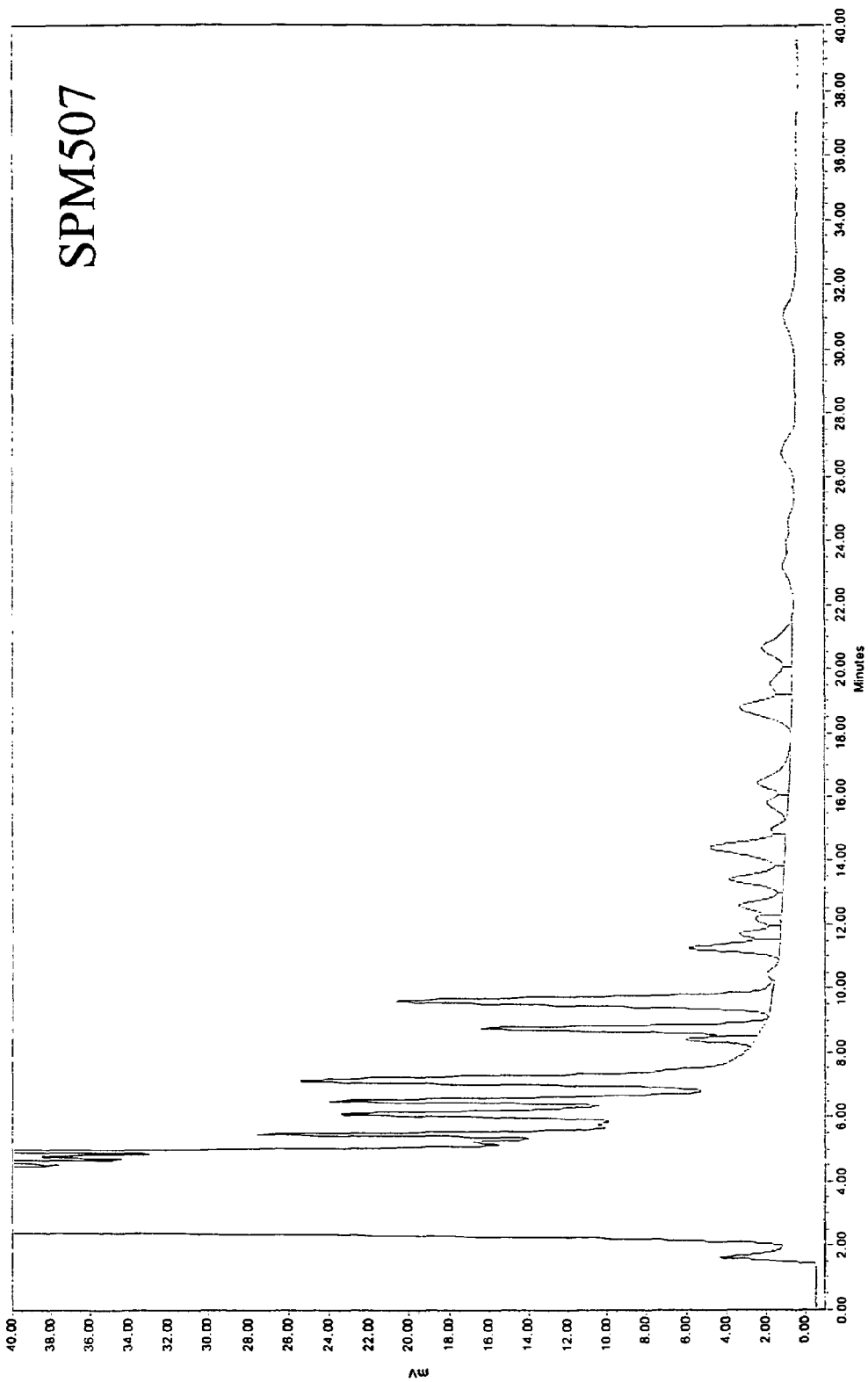

FIG. 22: HPLC chromatogram of the filtered culture medium supernatant of the strain SPM507.

Figure 23:
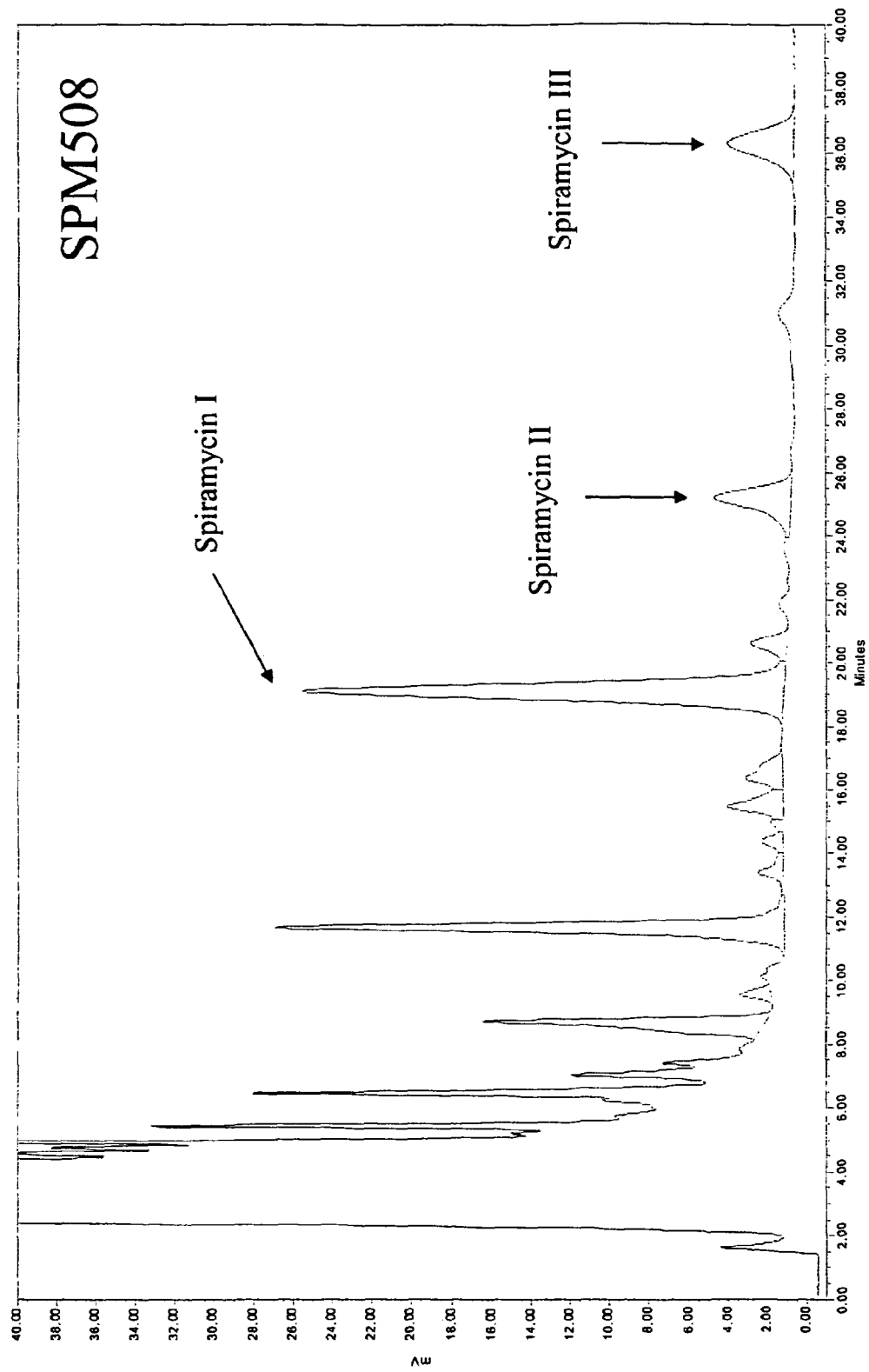

FIG. 23: HPLC chromatogram of the filtered culture medium supernatant of the strain SPM508.

Figure 24:
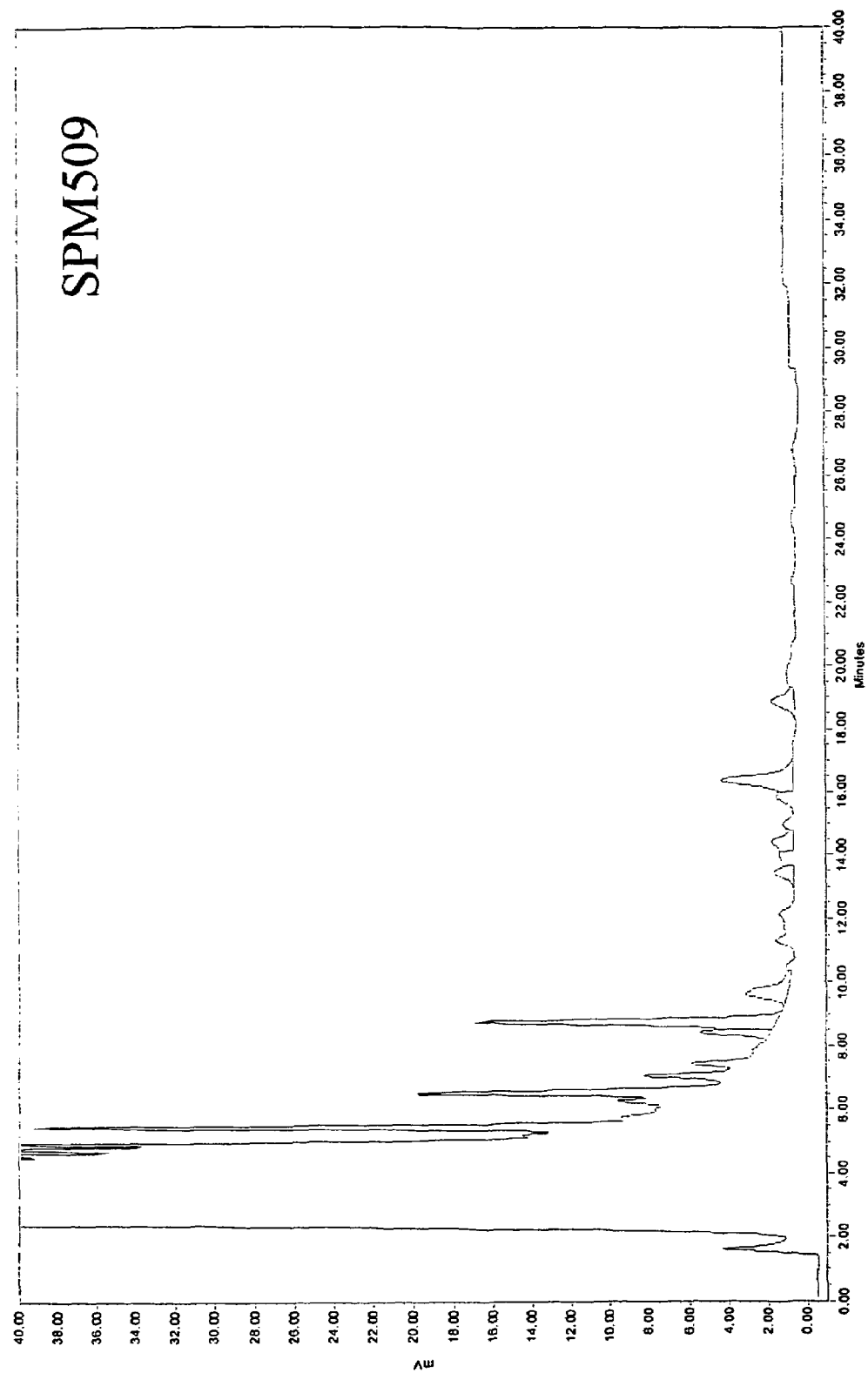

FIG. 24: HPLC chromatogram of the filtered culture medium supernatant of the strain SPM509.

FIG. 25: Alignment of the Orf3 protein (SEQ ID No. 29) with the TylB protein (SEQ ID No. 87) of *S. fradiae* produced using the FASTA program.

FIG. 26: Alignment of the MdmA protein of *S. mycarofaciens* (SEQ ID No. 88) with the SrmD protein (SEQ ID No. 16) produced using the FASTA program.

FIG. 27: Example of sequences of the residual sites after excision of the excisable cassette. Indicated in bold is the minimum att26 site as defined in Raynal et al., 1998. The sequence of phase 1 (att1) of 33 nucleotides is given in SEQ ID No. 104, the sequence of phase 2 (att2) of 34 nucleotides is given in SEQ ID No. 105, and the sequence of phase 3 (att3) of 35 nucleotides is given in SEQ ID No. 95.

Figure 28:
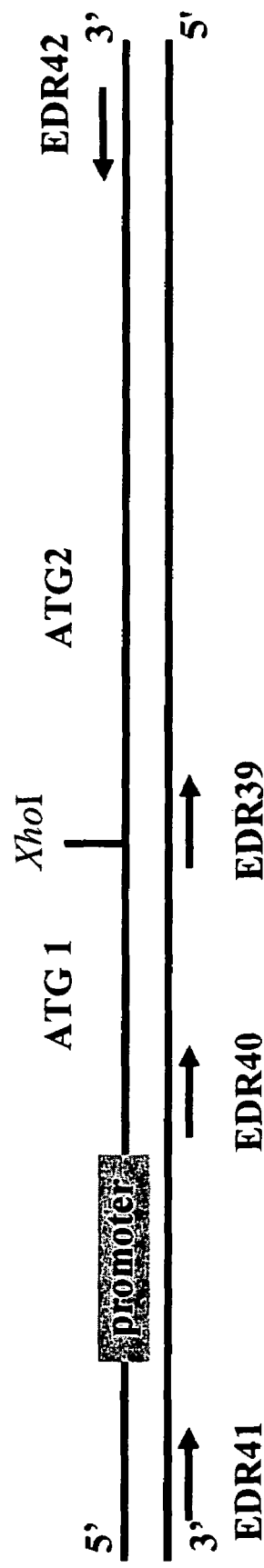

FIG. 28: Diagrammatic representation of the orf10 gene, location of the PCR primers used and construct obtained with each pair of primers.

Figure 29:

FIG. 29: Construction of the cassette pac-oritT.

Figure 30:
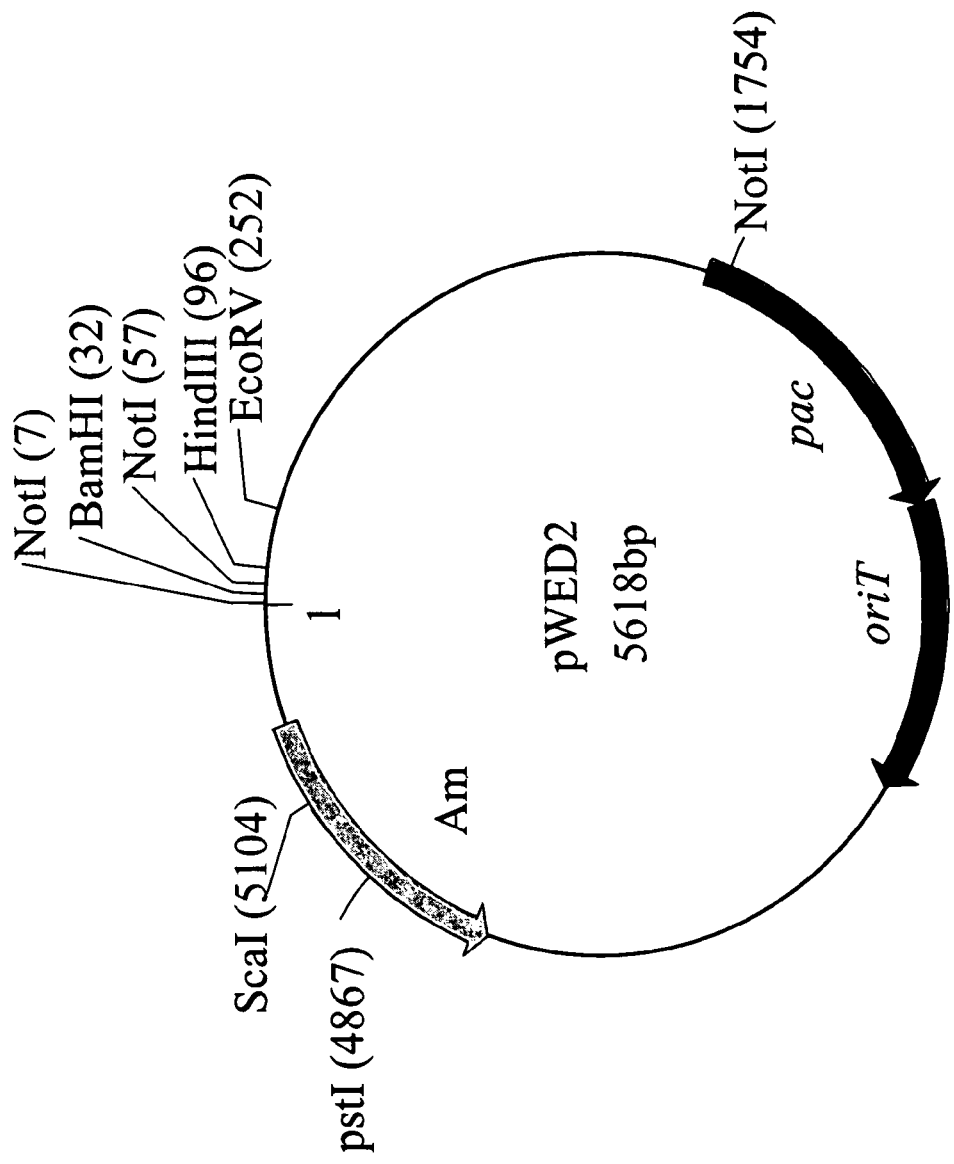

FIG. 30: Map of the cosmid pWED2.

Figure 31:
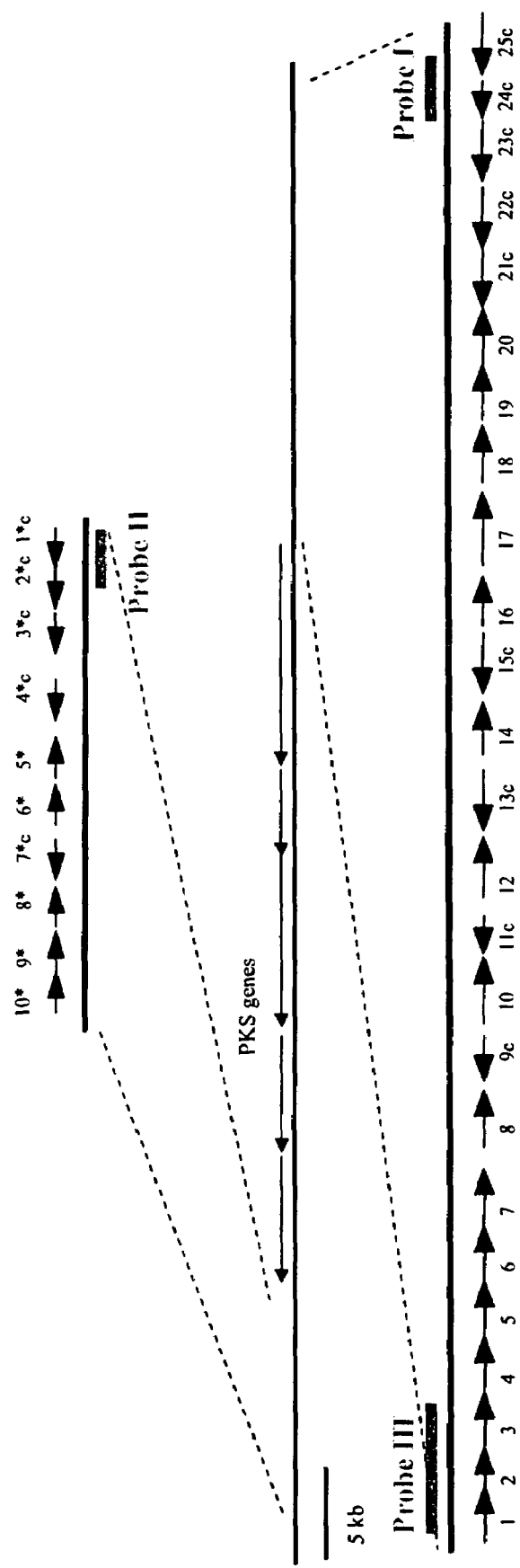

FIG. 31: Diagrammatic representation of the group of genes involved in the biosynthetic pathway for spiramycins and of the location of the three probes used to isolate the cosmids of the genomic DNA library of the *Streptomyces ambofaciens* strain OSC2 in *E. coli* (cf. example 19).

Figure 32:
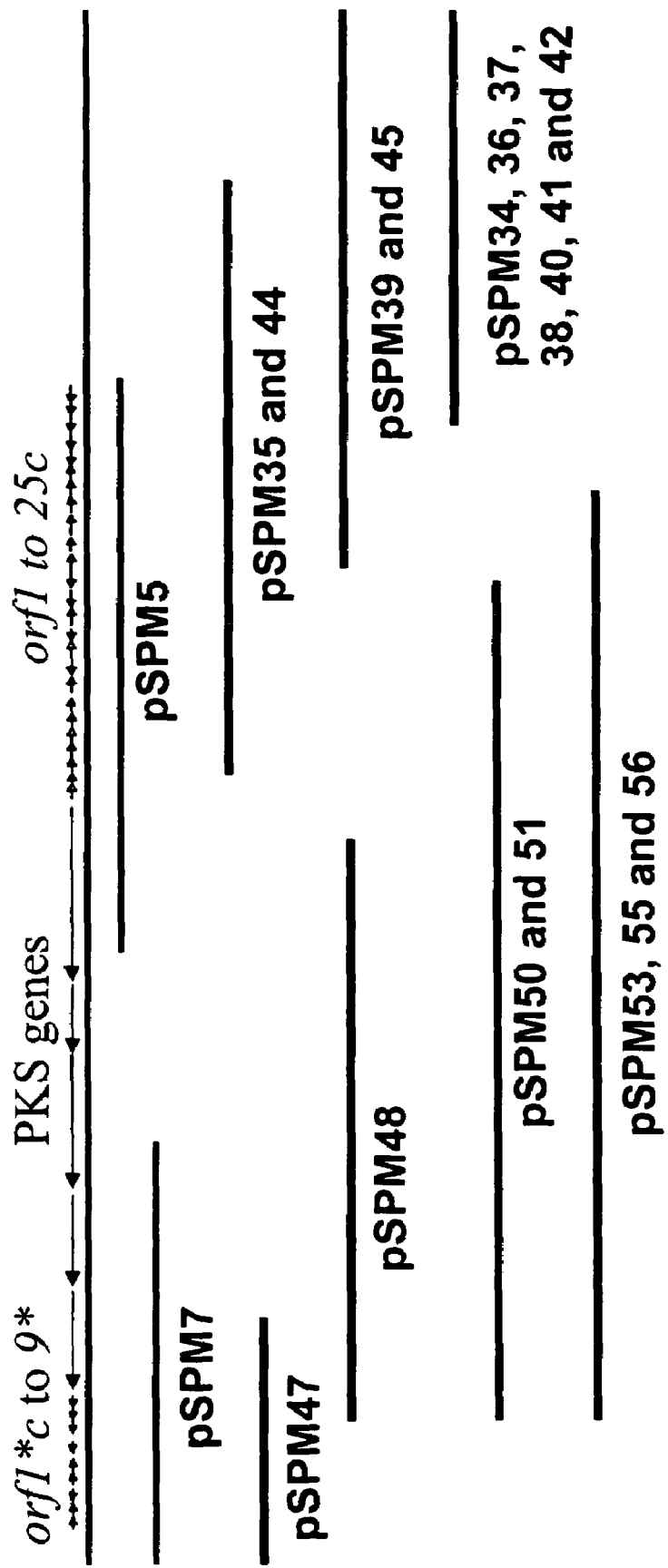

FIG. 32: Location of the inserts of the cosmids isolated from the genomic DNA library of the *Streptomyces ambofaciens* strain OCS2 in *E. coli* (cf. example 19). New cosmid DNA library.

Figure 33:
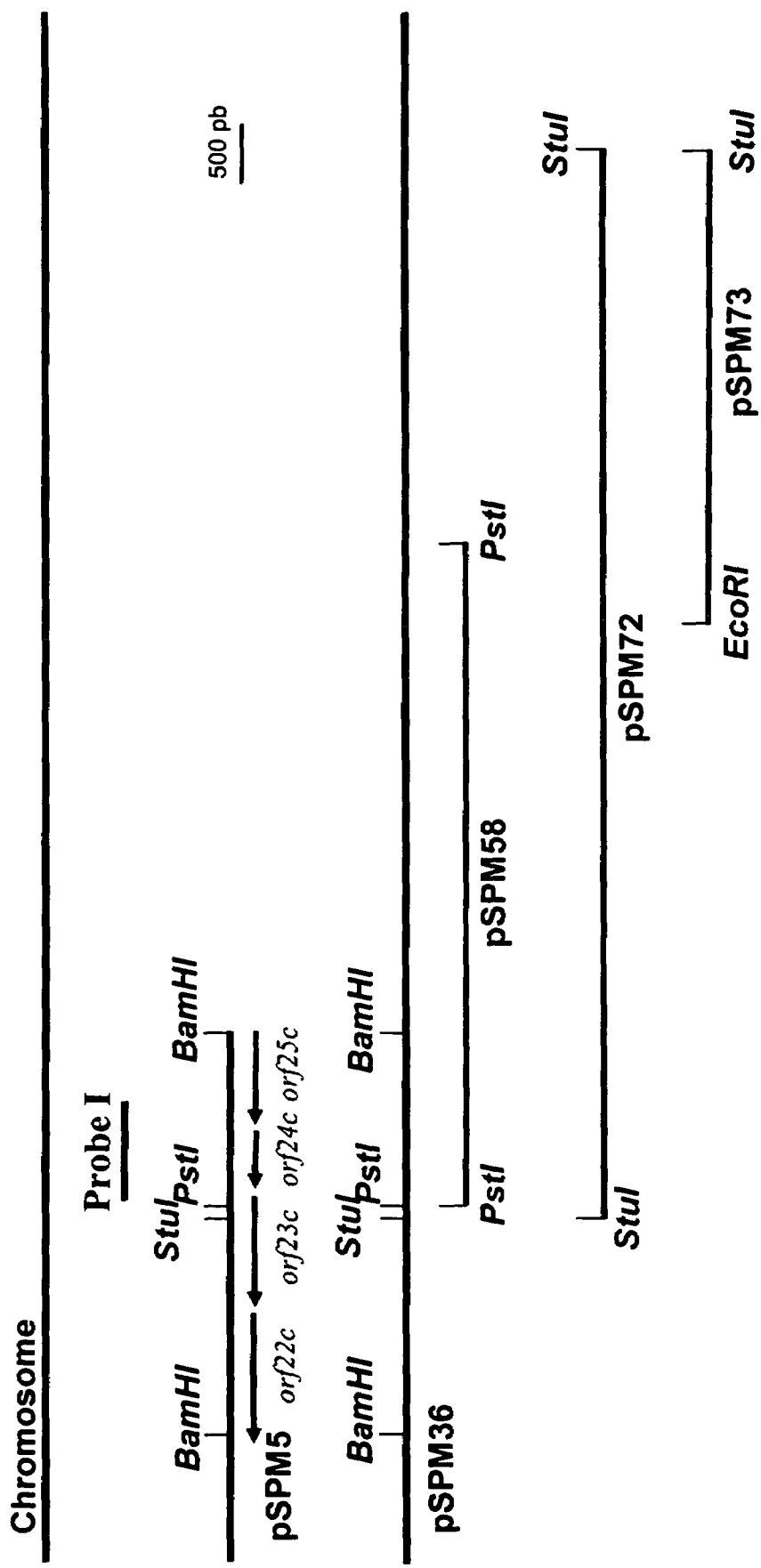

FIG. 33: Subcloning of the PstI-PstI fragment of the cosmid pSPM36 (insert of the plasmid pSPM58), subcloning of the StuI-StuI fragment of the cosmid pSPM36 (insert of the plasmid pSPM72) and subcloning of an EcoRI-StuI (insert of the plasmid pSPM73).

Figure 34:
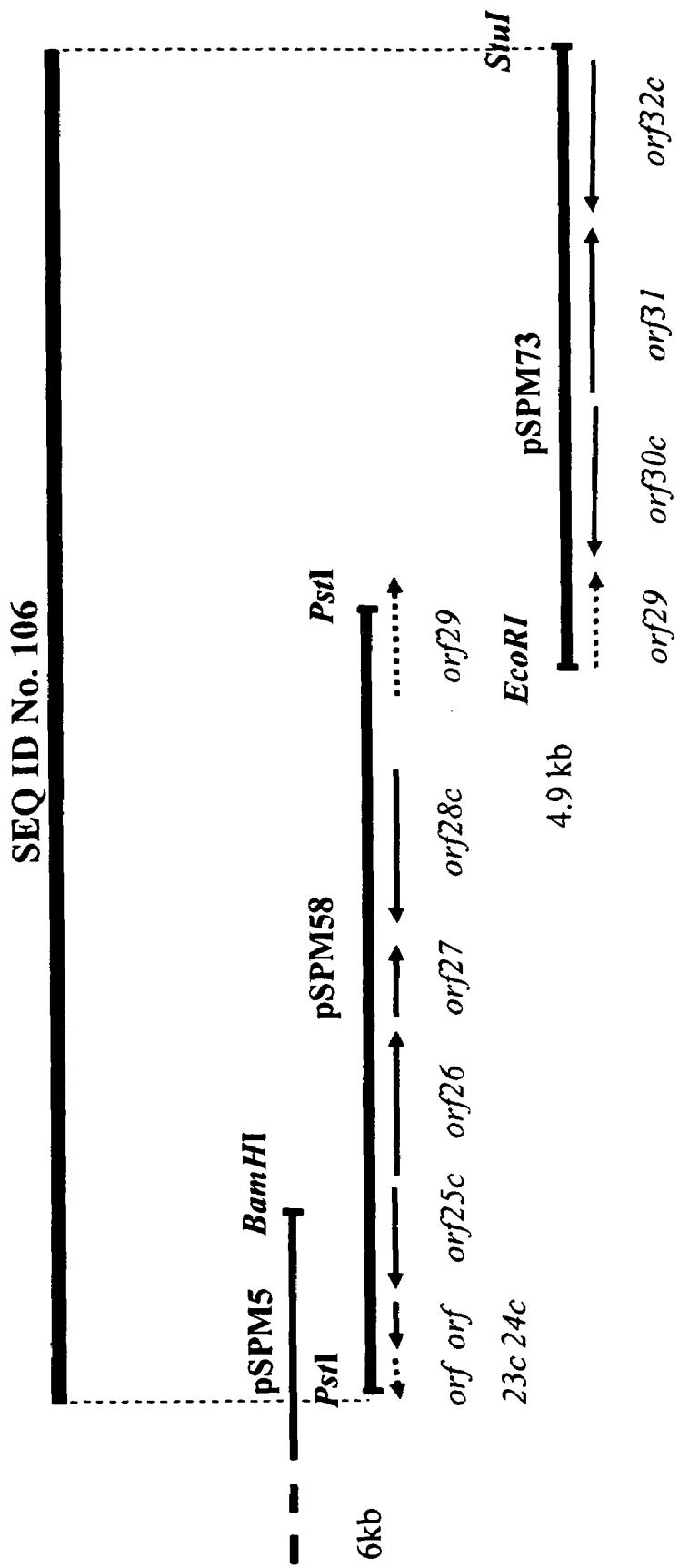

FIG. 34: Location of the open reading frames identified in the PstI-PstI insert of the plasmid pSPM58 and in the EcoRI-StuI insert of the plasmid pSPM73.

Figure 35:
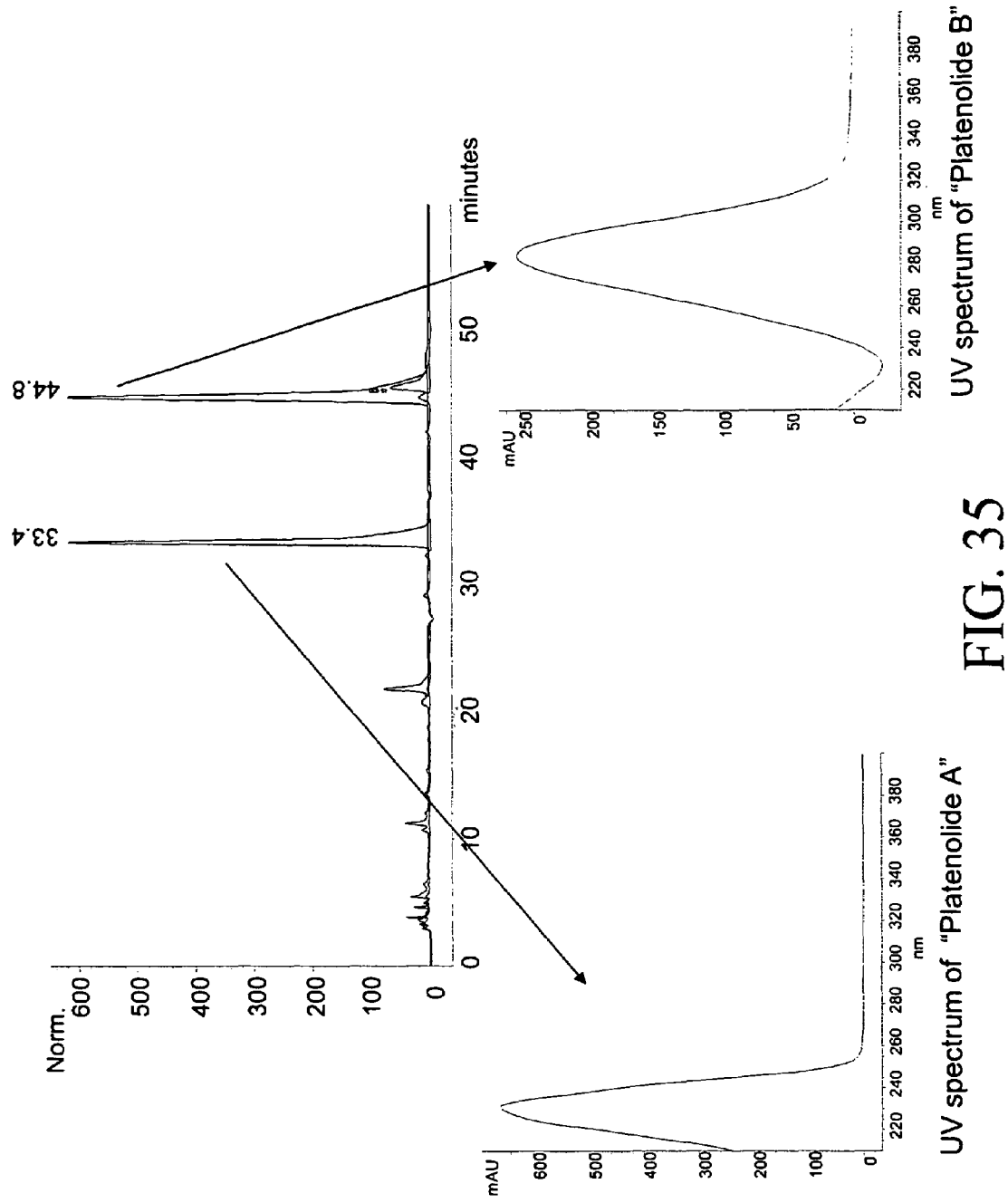

FIG. 35: Superposition of the HPLC chromatograms of the filtered culture medium supernatant of the strain OS49.67 produced at 238 and 280 nm (top) and UV spectra of the molecules eluted at 33.4 minutes and 44.8 minutes (bottom).

FIG. 36: Molecular structure of the platenolide A and platenolide B molecules.

Figure 37:
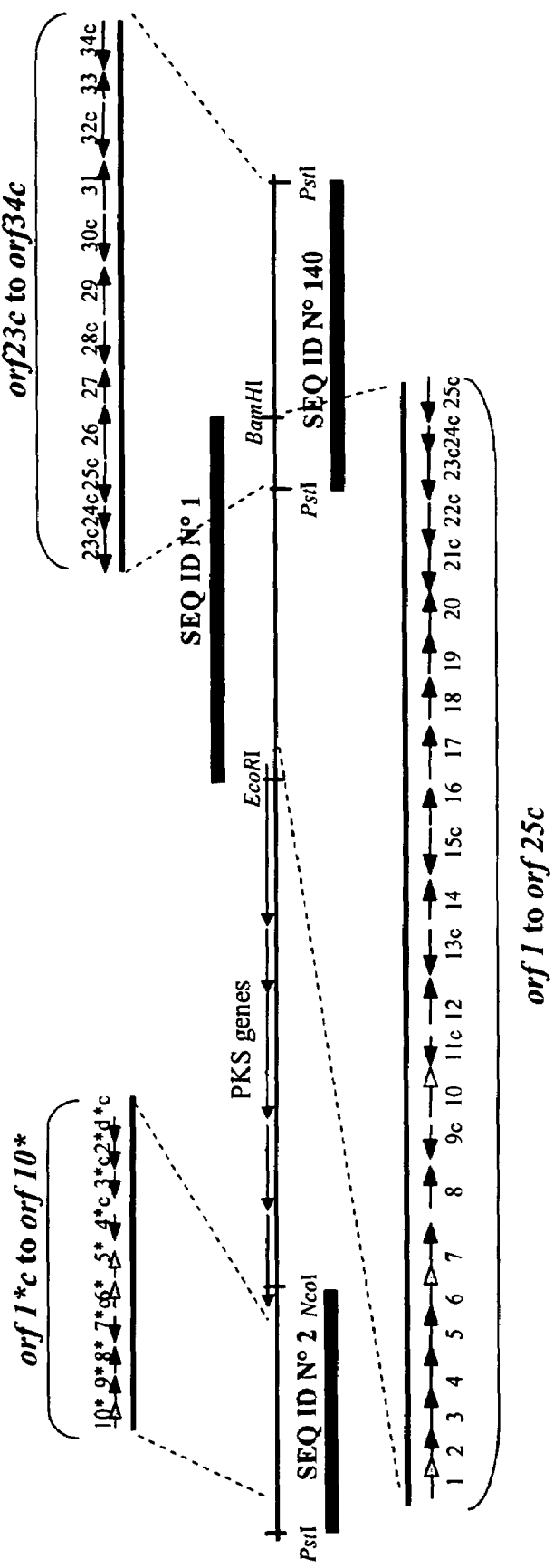

FIG. 37: Organization of the group of genes involved in the biosynthetic pathway for spiramycins.

Figure 38:
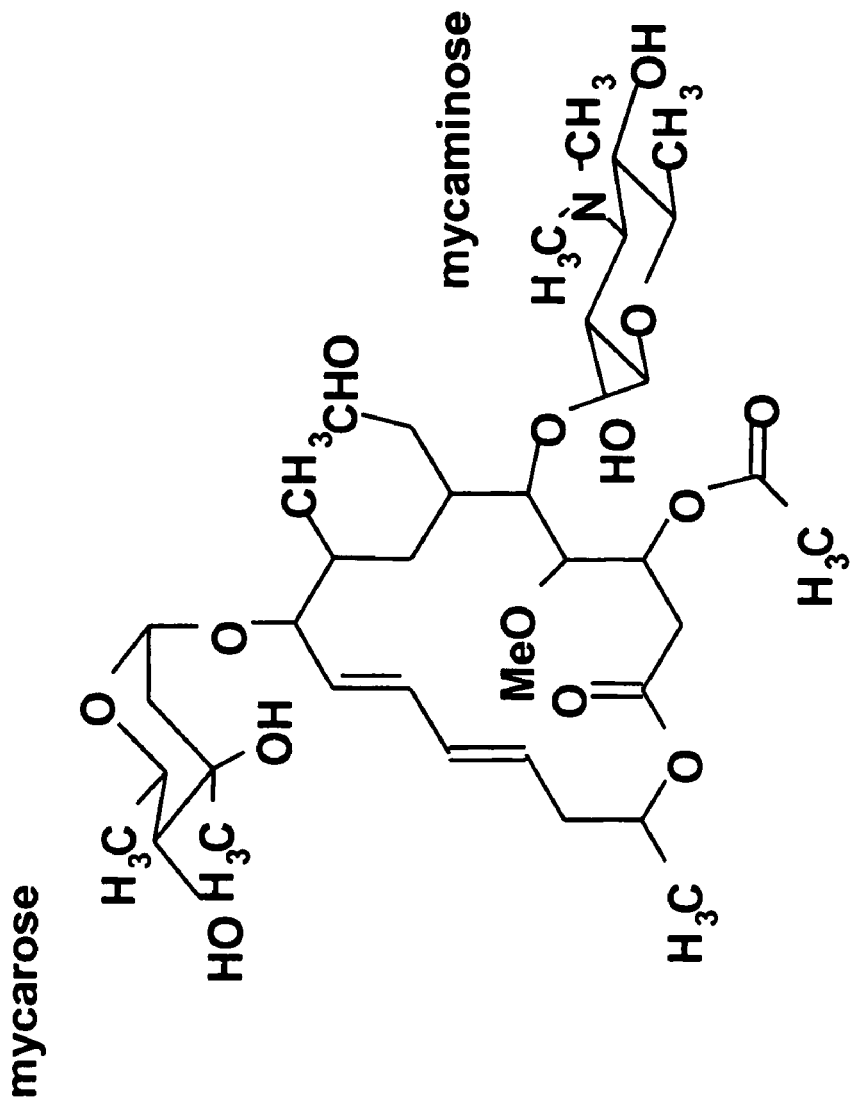

FIG. 38: Molecular structure of a biosynthesis intermediate produced by the strain SPM507.

Figure 39:
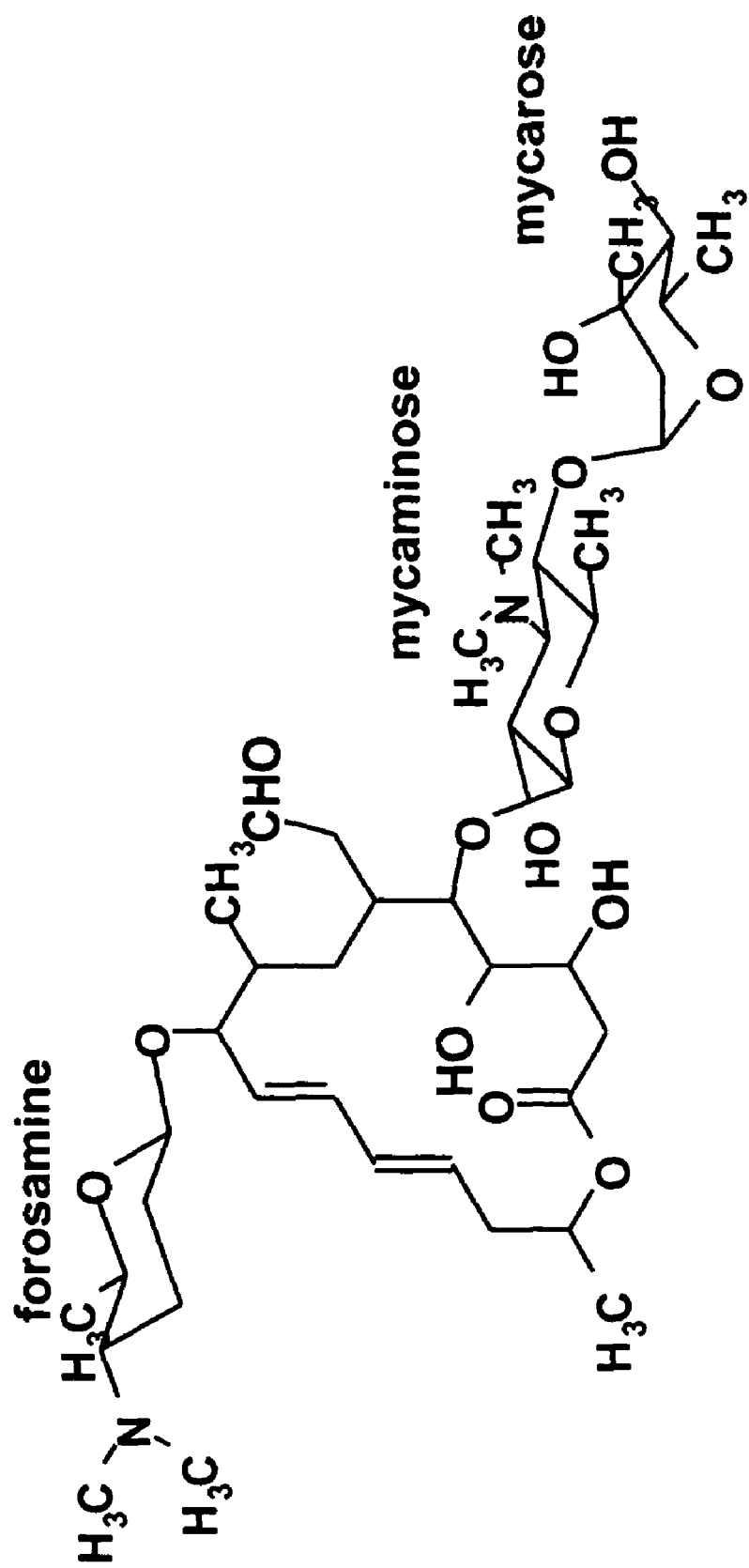

FIG. 39: Structure of a biosynthesis intermediate produced by a strain of S. ambofaciens of genotype orf6*:att1Ωhyg+ obtained from a strain which overproduces spiramycins. Insertion of the cassette att1Ωhyg+ into orf6* exerts a polar effect which prevents the expression of orf5*.

FIG. 40: Molecular structure of the platenolide A+mycarose and platenolide B+mycarose molecules produced by the strain OS49.67

Figure 41:
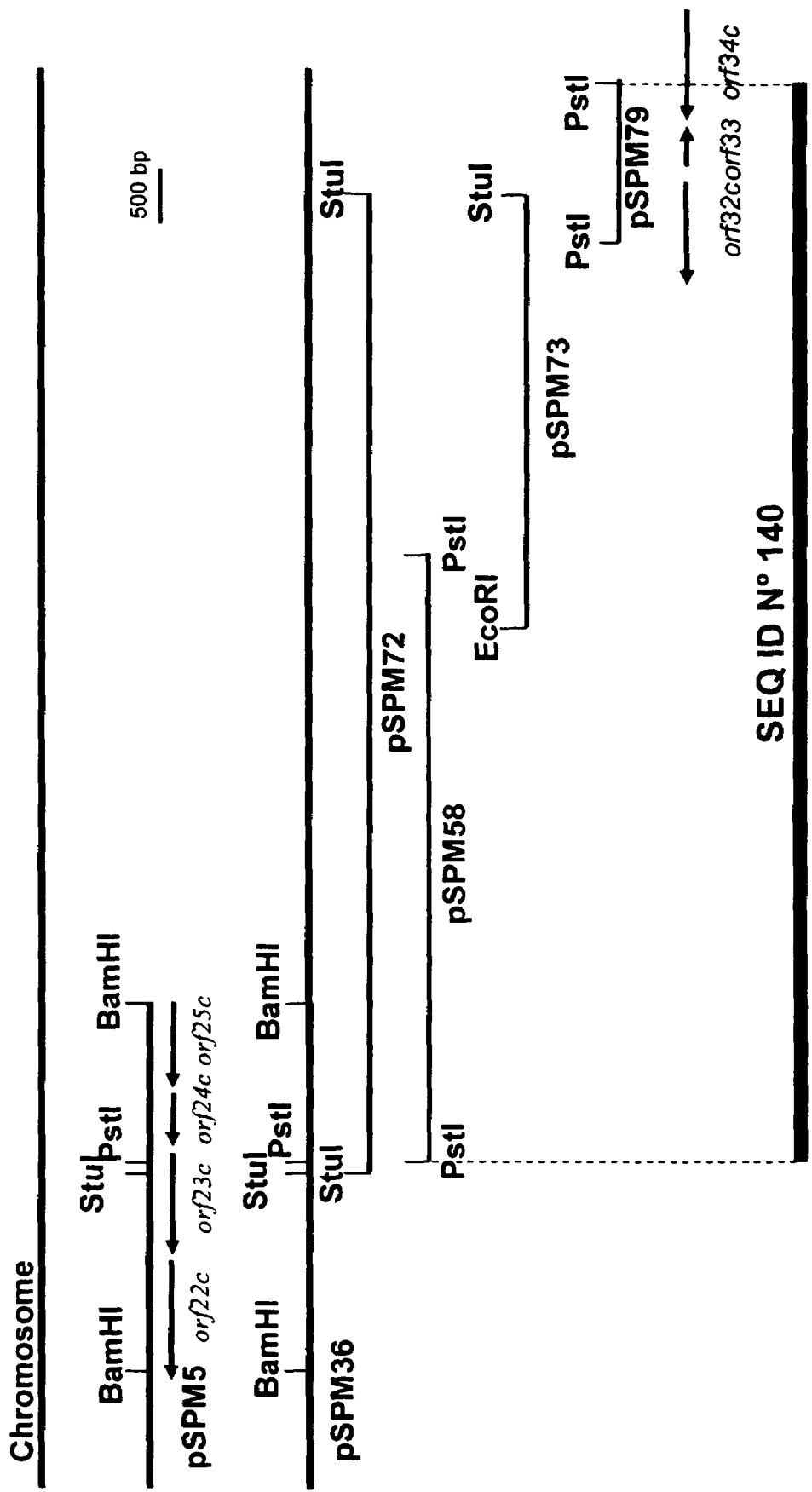

FIG. 41: Subcloning of a PstI-PstI fragment of the cosmid pSPM36 (insert of the plasmid (pSPM79)), localization of the open reading frames identified in the PstI-PstI insert of the plasmid pSPM79 and localization of the sequence SEQ ID No. 140.

The present invention is illustrated using the following examples, which should be considered as nonlimiting illustrations.

In summary, the genes of the biosynthetic pathway for spiramycins were isolated from a genomic DNA library of *Streptomyces ambofaciens*. This library was obtained by partial digestion of the genomic DNA of *Streptomyces ambofaciens*, with the BamHI restriction enzyme. Large DNA fragments, of 35 to 45 kb on average, were cloned into the cosmid pWED1 (Gourmelen et al., 1998) derived from the cosmid pWED15 (Wahl et al., 1987). These cosmids were introduced into *E. coli* using phage particles. The library thus obtained was hybridized with a probe (of sequence SEQ ID No. 86) corresponding to a portion of the tylB gene of *S. fradiae* (Merson-Davies & Cundliffe, 1994, GenBank accession number: U08223). After hybridization, one cosmid out of the 4 which hybridized with the probe was more particularly selected. This cosmid, named pOS49.1, was then digested with SacI and a 3.3 kb fragment containing the region which hybridized with the probe was subcloned into the vector pUC19 and sequenced. Four open reading frames were identified and one of them encodes a protein (SEQ ID No. 29) exhibiting strong sequence similarity with the TylB protein of *S. fradiae* (SEQ ID No. 87) (cf. FIG. 25). This gene was named orf 3 (SEQ ID No. 28) and was inactivated in *S. ambofaciens*. It was possible to demonstrate that the clones in which the orf3 gene was inactivated no longer produced spiramycins. This shows the involvement of the orf3 gene, or of genes located downstream, in spiramycin biosynthesis.

Once this confirmation had been obtained, a larger region of the cosmid pOS49.1 was sequenced, either side of the SacI fragment previously studied. Thus, it was possible to obtain, from the cosmid pOS49.1, the sequence of a region comprising seven whole open reading frames and two other incomplete open reading frames located on either side of these seven whole open reading frames. By virtue of a search in the databases, it was possible to show that one of the incomplete open reading frames corresponded to the srmG locus (a region encoding an enzyme called "polyketide synthase" (PKS)). The corresponding genes were subcloned by S. Burgett et al. in 1996 U.S. Pat. No. 5,945,320). Moreover, the other open reading frames, the seven whole ORFs named: orf1, orf2, orf3, orf4, orf5, orf6 and orf7 (SEQ ID No. 23, 25, 28, 30, 34, 36, 40) and the start of the eighth ORF named orf8 (sequence SEQ ID No. 43) were not found in the databases.

Subsequently, and with the aim of cloning other genes involved in spriramycin biosynthesis, other cosmids comprising fragments of the *S. ambofaciens* genome in this same region were isolated. For this, a further series of hybridizations on colonies was carried out using three probes. The first probe corresponds to a 3.7 kb DNA fragment containing orf1, orf2 and the start of orf3, subcloned from pOS49. 1. The second probe corresponds to a 2 kb DNA fragment containing a portion of orf7 and a portion of orf8, subcloned from pOS49.1. A third probe was also used. This latter probe corresponds to a 1.8 kb DNA fragment containing the srmD gene. The srmD gene is a gene isolated from *S. ambofaciens* capable of imparting spiramycin resistance. Specifically, prior studies had enabled the cloning of several resistance determinants of *S. ambofaciens*, imparting spiramycin resistance to a strain of *S. griseofuscus* (spiramycin-sensitive strain) (Pernodet et al., 1993) (Pernodet et al., 1999). To isolate resistance genes, a cosmid library of the genomic DNA of the strain *S. ambofaciens* had been produced in the cosmid pKC505 (Richardson M A et al., 1987). This pool of cosmids had been introduced into *S. griseofuscus*, naturally sensitive to spiramycin. Five cosmids capable of imparting apramycin resistance and spiramycin resistance in *S. griseofuscus* had thus been obtained. Among these 5 cosmids, a cosmid named pOS44. 1 contains, in its insert, the srmD gene which encodes a protein exhibiting a certain similarity with the protein encoded by the mdmA gene of *Streptomyces mycarofaciens* and involved in midecamycin resistance in this producer organism (Hara et al., 1990, GenBank accession number: A60725) (FIG. 26). The third probe used to locate the spiramycin biosynthesis genes was an insert of approximately 1.8 kb comprising the srmD gene.

These three probes were used to hybridize the genomic DNA library described above and made it possible to choose two cosmids (pSPM7 and pSPM5) liable to contain the longest inserts and having no common bands. The cosmid pSMP5 hybridized with the first and the second probe, but did not hybridize with the third probe, whereas the cosmid pSPM7 hybridized with the third probe only. These two cosmids were entirely sequenced using the "shotgut sequencing" technique. The sequences of the inserts of these two cosmids: pSPM7 and pSPM5, could be assembled since, although they did not overlap, each one of the inserts comprised a known sequence at one of its ends. Specifically, each one of these inserts comprised a fragment of the sequence of one of the genes encoding an enzyme called "polyketide synthase" (PKS). These 5 genes were cloned by S. Burgett et al. in 1996 (U.S. Pat. No. 5,945,320) (cf. FIG. 2). Thus, it was possible to determine a single *S. ambofaciens* genomic DNA sequence. A sequence of 30 943 nucleotides starting, in the 5' position, from an EcoRI site located in the first PKS gene and ranging up to a BamHI site in the 3' position is given in SEQ ID No. 1. This sequence corresponds to the region upstream of the PKS genes (cf. FIGS. 2 and 3). A second region of 11 171 nucleotides, starting from a PstI site in the 5' position and ranging up to a BstEII site in the 3' position, located in the fifth PKS gene, is given in SEQ ID No. 2. This region is the region downstream of the PKS genes (downstream and upstream being defined by the orientation of the 5 PKS genes or oriented in the same direction) (cf. FIGS. 2 and 3).

Next, and with the aim of cloning other genes involved in spiramycin biosynthesis, other cosmids comprising fragments of the *S. ambofaciens* genome in this same region were isolated (cf. example 18 and 19).

EXAMPLE 1

Construction of a Genomic DNA Library of the *Streptomyces ambofaciens* Strain ATCC23877 in *E. coli*

1.1. Extraction of the Genomic DNA of the *Streptomyces ambofaciens* Strain ATCC23877

The *Streptomyces ambofaciens* strain ATCC23877 (accessible in particular from the American Type Culture Collection (ATCC) (Manassas, Va., USA), under the number 23877) was cultured in YEME (Yeast Extract-Malt Extract) (Kieser, T, et al., 2000) and the genomic DNA of this strain was extracted and purified according to standard techniques of lysis and precipitation (Kieser T. et al., 2000).

1.2. Construction of the Genomic DNA Library

The genomic DNA of the *Streptomyces ambofaciens* strain ATCC23877 as isolated above was partially digested with the BamHI restriction enzyme so as to obtain DNA fragments having a size between approximately 35 and 45 kb. These fragments were cloned into the cosmid pWED1 (Gourmelen et al., 1998) digested beforehand with BamHI. The cosmid pWED1 is derived from the cosmid pWE15 (Wahl, et al., 1987) by deletion of the 4.1 kb HpaI-HpaI fragment containing the expression module which is active in mammals (Gourmelen et al., 1998). The ligation mixture was then encapsidated in vitro in lambda phage particles using the "Packagene® Lambda DNA packaging system" marketed by the company Promega, according to the manufacturer's recommendations. The phage particles obtained were used to infect the SURE® strain of *E. coli* marketed by the company Stratagene (LaJolla, Calif., USA). The clones were selected on LB medium+ampicillin (50 µg/ml) since the cosmid pWED1 imparts ampicillin resistance.

EXAMPLE 2

Isolation and Characterization of Genes Involved in Spiramycin Biosynthesis in *Streptomyces ambofaciens*

2.1 Colony Hybridization of the *E. coli* Clones of the Genomic Library of *Streptomyces ambofaciens* ATCC23877

Approximately 2 000 *E. coli* clones of the library obtained above were transferred onto a filter for colony hybridization. The probe used for the hybridization is an NaeI-NaeI DNA fragment (SEQ ID No. 86) comprising a portion of the tylB gene of *Streptomyces fradiae*. This fragment corresponds to nucleotides 2663 to 3702 of the DNA fragment described by L. A. Merson-Davies & E. Cundliffe (L. A. Merson-Davies & E. Cundliffe, 1994, GenBank accession number: U08223), in which the coding sequence of the tylB gene corresponds to nucleotides 2677 to 3843.

The NaeI-NaeI DNA fragment carrying a portion of the tylB gene of *Streptomyces fradiae* (SEQ ID No. 86) was labeled with $^{32}P$ using the random priming technique (Kit marketed by the company Roche) and used as a probe to hybridize the 2 000 clones of the library, transferred onto a filter. The membranes used are Hybond N nylon membranes marketed by the company Amersham (Amersham Biosciences, Orsay, France) and the hybridization was carried out at 55° C. in the buffer described by Church & Gilbert (Church & Gilbert, 1984). A wash was carried out in 2×SSC at 55° C. for a period of 15 minutes and two successive washes in 0.5×SSC were then carried out at 55° C., each for a period of 15 minutes. Under these hybridization and washing conditions, 4 clones out of the 2 000 hybridized exhibited a strong hybridization signal. These 4 clones were cultured in LB medium+ampicillin (50 µg/ml) and the corresponding 4 cosmids were extracted by standard alkaline lysis (Sambrook et al., 1989). It was then verified that the hybridization was indeed due to a DNA fragment present in the insert of these four cosmids. For this, the cosmids were digested independently with several enzymes (BamHI, PstI, and SacI). The digestion products were separated on agarose gel, transferred onto a nylon membrane and hybridized with the NaeI-NaeI DNA fragment comprising a portion of the tylB gene of *Streptomyces fradiae* (cf. above) under the same conditions as above. It was possible to validate the four cosmids and one of these cosmids was more particularly selected and named pOS49.1.

2.2 Verification of the Involvement of the Identified Region and Sequencing of the Insert of the Cosmid pOS49.1

Several fragments of the insert of the cosmid pOS49.1 were subcloned and their sequences were determined. The cosmid pOS49.1 was digested with the SacI enzyme and it was shown, by Southern blotting, under the conditions described above, that a 3.3 kb fragment contains the region which hybridizes with the tylB probe. This 3.3 kb fragment was isolated by electroelution from a 0.8% agarose gel, and then cloned into the vector pUC19 (GenBank accession number: M77789) and sequenced. The plasmid thus obtained was named pOS49.11. Four open reading frames exhibiting a codon use typical of *Streptomyces* could be identified in this fragment (two complete and two truncated open reading frames), using the FramePlot program (J. Ishikawa & K. Hotta, 1999). Sequence comparisons using the FASTA program (cf. (W. R. Pearson & D. J Lipman, 1988) and (W. R. Pearson, 1990), accessible in particular from the INFOBIOGEN resource center, Evry, France) made it possible to show that the protein deduced from one of these four open reading frames exhibits strong sequence similarities with the TylB protein (SEQ ID No. 87; GenBank accession number: U08223) of *S. fradiae* (cf. FIG. 25). This protein was named Orf3 (SEQ ID No. 29).

With the aim of testing whether the corresponding gene (the orf3 gene (SEQ ID No. 28)) was involved in spiramycin biosynthesis in *S. ambofaciens*, this gene was interrupted with an Ωhyg cassette (M-H. Blondelet-Rouault et al., 1997, GenBank accession number: X99315). For this, the plasmid pOS49.11 was digested with the XhoI enzyme and the fragment containing the four open reading frames (two complete and two truncated, including orf3 in its entirety) was subcloned into the XhoI site of the vector pBC SK+ marketed by the company Stratagene (LaJolla, Calif., USA). The plasmid thus obtained was named pOS49.12. For the purpose of inactivating orf3, a PmlI-BstEII fragment inside orf3 was replaced with the Ωhyg cassette by blunt-ended cloning into the latter plasmid. For this, the plasmid pOS49.12 was digested with the PmlI and BstEII enzymes, the unique site for which is in the coding sequence of the orf3 gene. The ends of the fragment corresponding to the vector were blunt-ended by treatment with the Klenow enzyme (DNA polymerase I large fragment). The Ωhyg cassette was obtained by digestion, with the BamHI enzyme, of the plasmid pHP45 Ωhyg (Blondelet-Rouault et al., 1997, GenBank accession number: X99315). The fragment corresponding to the Ωhyg cassette was recovered on agarose gel and its ends were blunt-ended by treatment with the Klenow enzyme. The two blunt-ended fragments thus obtained (the Ωhyg cassette and the plasmid pOS49.12) were ligated and the ligation product was used to transform *E. coli* bacteria. The plasmid thus obtained was named pOS49.14 and contains the orf3 gene interrupted with the Ωhyg cassette.

The insert of the plasmid pOS49.14, in the form of an XhoI-XhoI fragment the ends of which were made non-sticky by treatment with the Klenow enzyme, was cloned into the EcoRV site of the plasmid pOJ260 (the plasmid pOJ260 is a conjugative plasmid capable of replicating in *E. coli* but incapable of replicating in *S. ambofaciens* (M. Bierman et al., 1992). This plasmid imparts apramycin resistance in *E. coli* and *Streptomyces*). The plasmid obtained (insert of the plasmid pOS49.14 cloned into the plasmid pOJ260) was named pOS49.16. The latter was transferred into the *S. ambofaciens* strain ATCC23877 by conjugation using the conjugated *E. coli* strain S17-1, as described by Mazodier et al. (Mazodier et al., 1989). The *E. coli* strain S17-1 is derived from the *E. coli* strain 294 (Simon et al., 1983) (Simon, et al., 1986). It was possible to obtain transconjugant clones possessing the hygromycin resistance marker carried by the Ωhyg cassette and having lost the apramycin resistance marker carried by the vector pOJ260. For this, after conjugation, the clones were selected for their hygromycin resistance. The hygromycin-resistant clones were then subcultured respectively on medium with hygromycin (antibiotic B) and on medium with apramycin (antibiotic A) (cf. FIG. 9). The clones resistant to hygromycin (HygR) and sensitive to apramycin (ApraS) are, in principle, those in which a double recombination event has occurred and which therefore possess the orf3 gene interrupted with the Ωhyg cassette. Replacement of the wild-type copy of orf3 with the interrupted copy was verified by two successive hybridizations. Thus, the total DNA of the clones obtained was digested with various enzymes, separated on agarose gel, transferred onto a membrane and hybridized with a probe corresponding to the Ωhyg cassette (cf. above) in order to verify the presence of the cassette in the genomic DNA of the clones obtained. A second hybridization was carried out using, as probe, the XhoI-XhoI of the plasmid pOS49.11 containing the four open reading frames (two complete and two truncated, including orf3 in its entirety). The verification of the genotype can also be carried out by any method known to those skilled in the art, and in particular by PCR using the appropriate. oligonucleotides and sequencing of the PCR product. One of the orf3:: Ωhyg clones thus obtained, and the genotype of which was verified, was chosen and was called OS49.16.

The spiramycin production of the OS49.16 clone thus obtained was tested using the production test described below (cf. example 15). It was thus possible to demonstrate that this strain no longer produces spiramycin, confirming the involvement of orf3 and/or of the genes located downstream, such as, for example, orf4, in spiramycin biosynthesis.

Once this confirmation had been obtained, a larger region of the cosmid pOS49.1 was sequenced, on either side of the SacI fragment previously studied. Thus, it was possible to obtain, from the cosmid pOS49.1, the sequence of a region comprising seven whole open reading frames and two other incomplete open reading frames, located on either side of these seven open reading frames. By virtue of a search in the databases, it was possible to show that one of the incomplete open reading frames corresponded to the srmG locus (a region encoding an enzyme called "polyketide synthase" (PKS)). The corresponding genes were cloned by S. Burgett et al. in 1996 (U.S. Pat. No. 5,945,320). Moreover, the other open reading frames: the seven whole ORFs named: orf1, orf2, orf3, orf4, orf5, orf6 and orf7 (SEQ ID Nos 23, 25, 28, 30, 34, 36 and 40) and the start of the eighth ORF named orf8 (the whole sequence of this orf is given in SEQ ID No. 43), were not found in the databases.

EXAMPLE 3

Isolation and Characterization of Other Genes Involved in Spiramycin Biosynthesis in *Streptomyces ambofaciens*

Secondly, and with the aim of cloning other genes involved in spiramycin biosynthesis, other cosmids comprising fragments of the *S. ambofaciens* genome in this same region were isolated. For this, a further series of colony hybridizations was carried out using three probes:

The first probe used corresponds to a 3.7 kb BamHI-PstI DNA fragment containing a fragment of the PKS gene (the genes corresponding to PKS were cloned by S. Burgett et al. in 1996 (U.S. Pat. No. 5,945,320)), orf1, orf2 and the start of orf3, subcloned from pOS49.1 and ranging from a BamHI site located 1 300 base pairs upstream of the EcoRI site defining position 1 of SEQ ID No. 1 up to the PstI site located at 2472 (SEQ ID No. 1). This BamHI-PstI fragment was subcloned, from pOS49.1, into the plasmid pBC SK+, which made it possible to obtain the plasmid pOS49.28.

The second probe used corresponds to a PstI-BamHI DNA fragment of approximately 2 kb containing a fragment of orf7 and of orf8, subcloned from pOS49.1 and ranging from a PstI site located at position 6693 of SEQ ID No. 1 up to the BamHI site located at position 8714 of SEQ ID No. 1. This PstI-BamHI fragment was subcloned, from pOS49.1 into the plasmid pBC SK+, which made it possible to obtain the plasmid pOS49.76.

A third probe was also used. This corresponds to a 1.8 kb EcoRI-HindIII DNA fragment containing the srmD gene. The srmD gene is a gene isolated from *S. ambofaciens* capable of imparting spiramycin resistance. Specifically, prior studies had enabled the cloning of several resistance determinants of *S. ambofaciens*, imparting spiramycin resistance to a strain of *S. griseofuscus* (spiramycin-sensitive strain) (Pernodet et al., 1993) (Pernodet et al., 1999). To isolate resistant genes, a cosmid library of the genomic DNA of the *S. ambofaciens* strain ATCC23877 had been prepared in the cosmid pKC505 (M. A. Richardson et al., 1987). For this, the genomic DNA of the *S. ambofaciens* strain ATCC23877 had been partially digested with Sau3AI so as to obtain fragments having a size of between approximately 30 and 40 kb. The genomic DNA thus digested (3 μg) had been ligated with 1 μg of pKC505 digested beforehand with the BamHI enzyme (Pernodet et al., 1999). The ligation mixture had then been encapsidated in vitro in phage particles. The phage particles obtained had been used to infect the *E. coli* strain HB101 (accessible in particular from the American Type Culture Collection (ATCC) (Manassas, Va., USA), under the number 33694). Approximately 20 000 apramycin-resistant *E. coli* clones had been pooled and the cosmids of these clones had been extracted. This pool of cosmids had been introduced by protoplast transformation into the *S. griseofuscus* strain DSM 10191 (K. L. Cox & R. H. Baltz, 1984), naturally sensitive to spiramycin (R. N. Rao et al., 1987, this strain is available in particular from the German Collection of Microorganisms and Cell Cultures (Deutsche Sammlung von Mikro-organismen und Zellkulturen GmbH, DSMZ), (Braunschweig, Germany), under the number DSM 10191). The transformants had been selected on a medium containing apramycin. 1 300 of the clones growing on medium containing apramycin had been transferred onto medium containing 5 μg/ml of spiramycin. Several apramycin-resistant clones had also grown on medium containing spiramycin and the cosmids of these colonies had been extracted and used to transform *E. coli* and *S. griseofuscus* (Pernodet et al., 1999). Five cosmids capable of imparting apramycin resistance to *E. coli* and co-resistance to apramycin and spiramycin in *S. griseofuscus* have thus been obtained. Among these 5 cosmids, it was determined that a cosmid named pOS44.1 contains, in its insert, a gene (SEQ ID No. 15) which encodes a protein (SEQ ID No. 16) exhibiting a certain similarity with a protein encoded by the mdmA gene of *Streptomyces mycarofaciens* (SEQ ID No. 88); this gene was named srmD (cf. alignment shown in FIG. 26, carried out using the FASTA program (cf. (W. R. Pearson & D. J. Lipman, 1988) and (W. R. Pearson, 1990), accessible in particular from the INFO-BIOGEN resource center, Evry, France)).

To isolate the resistance determinant contained in the plasmid pOS44.1, the latter was partially digested with the Sau3AI restriction enzyme so as to obtain fragments having a size of approximately 1.5 to 3 kb, and these fragments were ligated into the vector pIJ486 linearized with the BamHI enzyme (Ward et al., 1986). A plasmid was selected for its ability to impart spiramycin resistance in the *S. griseofiscus* strain DSM 10191 (R. N. Rao et al., 1987), naturally sensitive to spiramycin (cf. above). For this, the pool of plasmids corresponding to the Sau3AI fragment of pOS44.1 ligated into the vector pIJ486 (cf. above) was introduced by protoplast transformation into the strain DSM 10191 and the transformants were selected for their thiostrepton resistance (due to the tsr gene carried by pIJ486). The clones growing on medium containing thiostrepton were transferred onto medium containing spiramycin. Several thiostrepton-resistant clones also grew on medium containing spiramycin and the plasmids of these colonies were extracted. A plasmid imparting resistance and containing an approximately 1.8 kb insert was selected and named pOS44.2. This 1.8 kb insert can be excised easily by virtue of a HindIII site and an EcoRI site present in the vector on either side of the insert. This 1.8 kb HindIII-EcoRI insert was sequenced and the resistance gene that it contains was named srmD. This fragment containing the srmD gene could thus be easily subcloned into the vector pUC19 (GenBank accession number: M77789) opened with EcoRI-HindIII, and the plasmid obtained was named pOS44.4. The 1.8 kb HindIII-EcoRI insert, containing the srmD gene, of this plasmid was used as a probe to locate the spiramycin biosynthesis genes (cf below).

A sample of an *Escherichia Coli* DH5α strain containing the plasmid pOS44.4 was deposited with the Collection Nationale de Cultures de Microorganismes [National Collection of Cultures and Microorganisms] (CNCM) Pasteur Institute, 25, rue du Docteur Roux 75724 Paris Cedex 15, France, on Jul. 10, 2002, under the registration number I-2918.

Approximately 2 000 clones of the library, obtained above (cf. example 1), were transferred onto a filter for colony hybridization according to conventional techniques (Sambrook et al., 1989).

The three probes described above were labeled with $^{32}P$ using the random priming technique (Kit marketed by Roche) and used to hybridize the 2 000 clones of the library, transferred onto the filter. The hybridization was carried out at 65° C. in the buffer described by Church & Gilbert (Church & Gilbert, 1984). A wash was carried out in 2×SSC at 65° C. for 15 minutes and two successive washes were then carried out in 0.5×SSC at 65° C., each for a period of 15 minutes. Under these hybridization and washing conditions, 16 clones out of the 2 000 hybridized exhibited a strong hybridization signal with at least one of the probes. However, no cosmid hybridized with the three probes. The 16 cosmids were extracted and digested with the BamHI restriction enzyme. Comparison of the restriction profiles of these various cosmids with one another led to two cosmids being chosen which were liable to contain the longest inserts of the region and which had no common bands. Thus, two cosmids, one named pSPM5 and the other pSPM7, were chosen. The cosmid pSPM5 hybridized with the probes orf1 to orf4 and the probe orf8, but did not hybridize with the probe srmD. pSPM7 hybridized only with the probe srmD and not with the other two probes.

These two cosmids were entirely sequenced using the "shotgun sequencing" technique. The sequences of the inserts of these two cosmids: pSPM7 and pSPM5, could be assembled since, although they did not overlap, each one of the inserts comprised a known sequence at one of its ends. Specifically, each one of these inserts comprised a fragment of the sequence of one of the genes encoding an enzyme called "polyketide synthase" (PKS). These 5 genes were cloned by S. Burgett et al. in 1996 (U.S. Pat. No. 5,945,320) (cf. FIG. 2). Thus, it was possible to determine a single *S. ambofaciens* genomic DNA sequence. A sequence of 30 943 nucleotides beginning, in the 5' position, from an EcoRI site located in the first PKS gene and ranging up to a BamHI site in the 3' position is given in SEQ ID No. 1. This sequence corresponds to the region upstream of the PKS genes (cf. FIGS. 2 and 3). A second region of 11 171 nucleotides, starting from a PstI, site in the 5' position and ranging up to an NcoI site in the 3' position located in the fifth PKS gene, is given in SEQ ID No. 2. This second region is the region downstream of the PKS genes (downstream and upstream being defined by the orientation of the 5 PKS genes all oriented in the same direction) (cf. FIGS. 2 and 3).

EXAMPLE 4

Analysis of the Nucleotide Sequences, Determination of the Open Reading Frames and Characterization of the Genes Involved in Spiramycin Biosynthesis The sequences obtained were analyzed using the FramePlot program (J. Ishikawa & K. Hotta 1999). This made it possible to identify, among the open reading frames, the open reading frames exhibiting a codon use typical of *Streptomyces*. This analysis made it possible to determine that this region comprises 35 ORFs located on either side of five genes encoding the enzyme "polyketide synthase" (PKS). 10 and 25 ORFs were identified respectively downstream and upstream of these genes (downstream and upstream being defined by the orientation of the 5 PKS genes all oriented in the same direction) (cf FIG. 3). Thus, the 25 open reading frames of this type, occupying a region of approximately 31 kb (SEQ ID No. 1 and FIG. 3), were identified upstream of the 5 PKS genes and 10 occupying a region of approximately 11.1 kb (SEQ ID No. 2 and FIG. 3) were identified downstream of the PKS genes. The genes of the upstream region were named orf1, orf2, orf3, orf4, orf5, orf6, orf7, orf8, orf9c, orf10, orf11c, orf12, orf13c, orf14, orf15c, orf16, orf17, orf18, orf19, orf20, orf21c, orf22c, orf23c, orf24c and orf25c (SEQ ID Nos 23, 25, 28, 30, 34, 36, 40, 43, 45, 47, 49, 53, 60, 62, 64, 66, 68, 70, 72, 74, 76, 78, 80, 82 and 84). The genes of the downstream region were named orf1*c, orf2*c, orf3*c, orf4*c, orf5*, orf6*, orf7*c, orf8*, orf9* and orf10* (SEQ ID Nos 3, 5, 7, 9, 11, 13, 15, 17, 19 and 21). The "c" added to the name of the gene means, for the ORF in question, that the coding sequence is in the reverse orientation (the coding strand is therefore the strand complementary to the sequence given in SEQ ID No. 1 or SEQ ID No. 2 for these genes) (cf. FIG. 3).

The protein sequences deduced from these open reading frames were compared with those present in various databases using various programs: BLAST (Altschul et al., 1990) (Altschul et al., 1997), CD-search, COGs (Cluster of Orthologous Groups) (these three programs are accessible in particular from the National Center for Biotechnology Information (NCBI) (Bethesda, Md., USA)), FASTA ((W. R. Pearson & D. J. Lipman, 1988) and (W. R. Pearson, 1990), BEAUTY (K. C. Worley et al., 1995)), (these two programs are accessible in particular from the INFOBIOGEN resource center, Evry, France). These comparisons made it possible to formulate hypotheses regarding the function of the products of these genes and to identify those which may be involved in spiramycin biosynthesis.

EXAMPLE 5

Gene Inactivation: Principle of the Construction of a Knocked-out Strain of *Streptomyces ambofaciens*

The methods used consist in carrying out a gene replacement. The target gene to be interrupted is replaced with a copy of this gene interrupted with a cassette imparting resistance to an antibiotic (for example apramycin or hygromycin), as illustrated in FIG. 9. The cassettes used are bordered on either side by translation termination codons in all the reading frames and by transcription terminators which are active in *Streptomyces*.

The insertion of the cassette into the target gene may or may not be accompanied by a deletion in this target gene. The size of the regions flanking the cassette can range from a few hundred to several thousand base pairs.

The constructs required for the inactivation of the gene with the cassette were obtained in *E. coli*, the reference organism for obtaining recombinant DNA constructs. The interrupted gene was obtained in a plasmid which replicates in *E. coli* but which cannot replicate in *Streptomyces*.

The constructs were then subcloned into vectors so as to allow the transformation and the inactivation of the desired gene in *S. ambofaciens*. For this, two plasmids were used:
  pOJ260 (M. Bierman et al., 1992) (cf. example 2) which imparts apramycin resistance in *E. coli* and *Streptomyces* and which was used when the target gene was interrupted with a cassette imparting hygromycin resistance.
  pOSK1205 (4726 bp). This plasmid derives from the plasmid pBK-CMV (marketed by the company Stratagene (LaJolla, Calif., USA)) in which an AvrII fragment containing the sequence encoding Neomycin/Kanamycin resistance has been replaced with a sequence encoding hygromycin resistance, while at the same time conserving the P SV40 promoter. For this, the plasmid pHP45-Ωhyg (Blondelet-Rouault et al., 1997) was digested with the NotI and PflmI enzymes and the fragment conferring hygromycin resistance was subcloned into the AvrII site of the vector pBK-CMV after all the ends had been blunt-ended by treatment with the Klenow enzyme. In pOSK1205, the cassette which confers hygromycin resistance is preceded by the pSV40 promoter. This plasmid confers hygromycin resistance in *E. coli* and *Streptomyces* and was used when the target gene was interrupted with a cassette conferring apramycin resistance.

The cassettes were introduced into the target gene either by cloning using restriction sites present in the target gene, or by recombination between short identical sequences as described, for example, by Chaveroche et al (M. K. Chaveroche et al., 2000).

The plasmid carrying the gene interrupted by the cassette can then be introduced into *Streptomyces ambofaciens*, for example by conjugation between *E. coli* and *Streptomyces* (P. Mazodier et al., 1989). This technique was used when the basic vector is the vector pOJ260. A second technique may be used: the technique of protoplast transformation after denaturation of the DNA by alkali treatment (T. Kieser et al., 2000), in order to increase the frequency of recombination as described, for example, by Oh & Chater (Oh & Chater, 1997). This technique was used when the basic vector is pOJ260 or pOSK1205 (cf. below). The transformants are then selected with the antibiotic corresponding to the cassette present in the target gene (cf. FIG. 9, antibiotic B). A mixture of clones, among which there has been integration by a single or by two recombination events, is thus selected. Next, the clones sensitive to the antibiotic for which the resistance gene is present in the vector (outside the recombination cassette) (cf. FIG. 9, antibiotic A) are sought. It is thus possible to select the clones for which there have, in principle, been two recombination events resulting in the replacement of the wild-type gene with the copy interrupted by the cassette. These steps are shown diagrammatically in FIG. 9.

Several cassettes can be used to interrupt the target genes. The Ωhyg cassette which confers hygromycin resistance (Blondelet-Rouault et al., 1997, GenBank accession number: X99315) can, for example, be used.

EXAMPLE 6

Construction of a Strain of *Streptomyces ambofaciens* with an In-phase Knockout in the orf3 Gene The orf 3 gene had been interrupted with the Ωhyg cassette (cf. example 2.2) and it was possible to demonstrate that an orf3::Ωhyg strain no longer produces spiramycin, confirming the involvement of one or more genes of the cloned region in spiramycin biosynthesis (cf. example 2.2). In view of their orientation, cotranscription of ORFs 1 to 7 is probable (cf. FIG. 3) and the phenotype observed (non-producer of spiramycins) may be due to the inactivation of one or more of the genes cotranscribed with orf3. To confirm the involvement of orf3 in spiramycin biosynthesis, a further inactivation of the orf3 gene was carried out, the latter inactivation being carried out in phase. For this, a DraIII fragment inside orf3 of 504 base pairs was deleted. A DNA fragment obtained from pOS49.1, ranging from the EcoRI site located at position I (SEQ ID No. 1) up to the SacI site located at position 5274 (SEQ ID No. 1), and which comprises a deletion between the two DraIII sites at positions 2563 and 3067 (504 nucleotides removed), was cloned into the plasmid pOJ260 (M. Bierman et al., 1992). The plasmid thus obtained was named pOS49.67.

The insert of pOS49.67 therefore consists of a DNA fragment of *S. ambofaciens* containing the orf1 gene, orf2 gene, orf3 gene with the in-phase deletion, orf4 gene and a portion of orf5. The vector in which this insert was subcloned is pOJ260, the plasmid pOS49.67 therefore imparts apramycin resistance and was introduced into the strain OS49.16 by protoplast transformation (cf. example 2). Since the strain OS49.16 is resistant to hygromycin, hygR and apraR transformants were obtained. After passaging such clones twice on nonselective medium, the clones sensitive to apramycin and to hygromycin (apraS and hygS) were sought. In some of these clones, a recombination event between homologous sequences is in fact expected to lead to the replacement of the copy of orf3 interrupted with the Ωhyg cassette (contained in the genome of the strain OS49.16) with the copy of orf3 with the in-phase deletion present on the vector. The clones resulting from this recombination are expected to be apraS and hygS after elimination of the vector sequences. The genotype of the strains thus obtained can be verified by hybridization or by PCR and sequencing of the PCR product (to verify that only one in-phase deleted copy of orf3 is present in the genome of the clones obtained). Clones having only the copy of orf3 with an in-phase deletion were thus obtained and their genotype was verified. A clone exhibiting the desired characteristics was more particularly selected and was named OS49.67.

A sample of the strain OS49.67 was deposited with the Collection Nationale de Cultures de Microorganismes (CNCM) Pasteur Institute, 25, rue du Docteur Roux 75724 Paris Cedex 15, France, on Jul. 10, 2002, under the registration number I-2916.

EXAMPLE 7

Construction of a Strain of *Streptomayces ambofaciens* with a Knockout in the orf8 Gene To carry out the inactivation of the orf8 gene, a construct in which the Ωhyg cassette was introduced into the coding sequence of orf8 was obtained. For this, the plasmid pOS49.88 was first of all constructed. The plasmid pOS49.88 is derived from the plasmid pUC19 (GenBank accession number: M77789) by insertion of a 3.7 kb fragment (PstI-EcoRI fragment obtained from the cosmid pSPM5) containing the end of orf7, orf8 and the beginning of orf9, cloned into the PstI-EcoRI sites of pUC19. The Ωhyg cassette (in the form of a BamHI fragment blunt-ended by treatment with the Klenow enzyme) was cloned into the unique SalI site of pOS49.88 located in orf8, after blunt-ending of all the ends by treatment with the Klenow enzyme.

Since the cloning was blunt-ended, two types of plasmid were obtained depending on the direction of insertion of the cassette: pOS49.106 in which the hyg and orf8 genes are in the same orientation, and pOS49.120 in which the hyg and orf8 genes are in opposite orientations. The insert of the plasmid pOS49.106 was then subcloned into the plasmid pOJ260, to give pOS49.107. For this, the plasmid pOS49.106 was digested with the Asp7181 enzyme and the ends were blunt-ended by treatment with the Klenow enzyme; this digestion product was redigested with the PstI enzyme and the fragment containing the orf8 gene into which the Ωhyg cassette was inserted was cloned into the vector pOJ260 (cf. above). For this, the vector pOJ260 was digested with the EcoRV and PstI enzymes and used for the ligation. This manipulation therefore makes it possible to obtain an oriented ligation since each one of the two fragments is blunt-ended on one side and PstI on the other. The plasmid obtained was named pOS49.107.

The plasmid pOS49.107 was intoduced into the *S. ambofaciens* strain ATCC23877 by protoplast transformation (T. Kieser, et al., 2000). After protoplast transformation, the clones are selected for their hygromycin resistance. The hygromycin-resistant clones are then subcultured respectively on medium with hygromycin (antibiotic B) and on medium with apramycin (antibiotic A) (cf. FIG. 9). The clones resistant to hygromycin (HygR) and sensitive to apramycin (ApraS) are in principle those in which a double crossing over event has occurred and which contain the orf8 gene interrupted with the Ωhyg cassette. The replacement of the wild-type copy of orf8 with the copy interrupted by the Ωhyg cassette was verified by Southern blotting. Thus, the total DNA of the clones obtained was digested with several enzymes, separated on agarose gel, transferred onto a membrane and hybridized with a probe corresponding to the Ωhyg cassette in order to verify the presence of the cassette in the genomic DNA of the clones obtained. A second hybridization was carried out using as probe the PstI-EcoRI insert containing the end of orf7, orf8 and the beginning of orf9, approximately 3.7 kb in size, of the plasmid pOS49.88. The verification of the genotype can be carried out by any method known to those skilled in the art, and in particular by PCR using the appropriate oligonucleotides and sequencing of the PCR product.

An orf8::Ωhyg clone was chosen and named OS49.107. A sample of the strain OS49.107 was deposited with the Collection Nationale de Cultures de Microorganismes (CNCM) Pasteur Institute, 25, rue du Docteur Roux 75724 Paris Cedex 15, France, on Jul. 10, 2002, under the registration number I-2917.

EXAMPLE 8

Construction of a Strain of *Streptomyces ambofaciens* with a Knockout in the orf10 Gene A 1.5 kb DNA fragment inside the orf10 gene was obtained by PCR using as matrix the genomic DNA of *S. ambofaciens* and the following primers:

```
SRMR1:
5' CTGCCAGTCCTCTCCCAGCAGTACG 3'    (SEQ ID No. 89)

SRMR2:
5' TGAAGCTGGACGTCTCCTACGTCGG 3'    (SEQ ID No. 90)
```

This PCR-derived DNA fragment was cloned into the vector pCR2.1 marketed by the company Invitrogen (Carlsbad, Calif., USA). The plasmid thus obtained was named pOS49.32. The Ωhyg cassette (in the form of a BamHI fragment, cf. above) was cloned into the unique BstEII site inside the fragment of the orf10 gene, after all the ends had been blunt-ended by treatment with the Klenow enzyme. Since the cloning was blunt-ended, two types of plasmid were obtained depending on the direction of insertion of the cassette: pOS49.43 in which the hyg and orf10 genes are in the same orientation and pOS49.44 in which the hyg and orf10 genes are in opposite orientations. The insert of the plasmid pOS49.43 was transferred (in the form of an Asp718I-XbaI fragment the ends of which were blunt-ended by treatment with the Klenow enzyme) into the EcoRV site of the plasmid pOJ260, which made it possible to obtain the plasmid pOS49.50. The plasmid pOS49.50 containing the fragment of the orf10 gene interrupted with the Ωhyg cassette was introduced into the *Streptomyces ambofaciens* strain ATCC23877. After transformation, the clones were selected for their hygromycin resistance. The hygromycin-resistant clones were then subcultured respectively on medium with hygromycin (antibiotic B) and on medium with apramycin (antibiotic A) (cf. FIG. 9). The clones resistant to hygromycin (HygR) and sensitive to apramycin (ApraS) are in principle those in which a double crossing over event has occurred and which contain the orf10 gene interruped with the Ωhyg cassette. Clones which contained the hygromycin resistance marker carried by the cassette and which had lost the apramycin resistance marker carried by the vector pOJ260 were thus obtained. The event consisting of replacement of the wild-type copy of orf10 with the orf10::Ωhyg interrupted copy was verified by Southern blotting. Thus, the total genomic DNA of the clones obtained was digested with several enzymes, separated on agarose gel, transferred onto a membrane and hybridized with a probe corresponding to the Ωhyg cassette in order to verify the presence of the cassette in the genomic DNA of the clones obtained. A second hybridization was carried out using as probe the 1.5 kb PCR product in the orf10 gene (cf. above).

A clone exhibiting the expected characteristics (orf10::Ωhyg) was more particularly selected and named OS49.50. It was in fact possible to verify, by virtue of two hybridizations, that the Ωhyg cassette was indeed present in the genome of this clone and that the expected digestion profile is indeed obtained in the case of replacement, subsequent to a double recombination event, of the wild-type gene with the copy interrupted with the Ωhyg cassette, in the genome of this clone. The verification of the genotype can also be carried out by any method known to those skilled in the art, and in particular by PCR using the appropriate oligonucleotides and sequencing of the PCR product.

EXAMPLE 9

Gene Inactivation: Principle of the Construction of a Strain of *Streptomyces ambofaciens* Knocked Out According to the "Excisable Cassette" Technique (cf. FIGS. 9 and 10)

A second type of cassette can be used for the gene inactivation: cassettes termed "excisable cassettes". These cassettes have the advantage of being able to be excised in *Streptomyces* by a site-specific recombination event after having been introduced into the genome of *S. ambofaciens*. The aim is to inactivate certain genes in strains of *Streptomyces* without leaving, in the final strain, selection markers or large DNA sequences not belonging to the strain. After excision, only a short sequence of approximately thirty or so base pairs (called "scar" site) remains in the genome of the strain (cf. FIG. 10).

The implementation of this system consists, firstly, in replacing the wild-type copy of the target gene (by virtue of two homologous recombination events, cf. FIG. 9) with a construct in which an excisable cassette has been inserted into this target gene. The insertion of this cassette is accompanied by a deletion in the target gene (cf. FIG. 9). Secondly, the excision of the excisable cassette from the genome of the strain is brought about. The excisable cassette functions by virtue of a site-specific recombination system and has the advantage of allowing *Streptomyces* mutants which do not ultimately carry a resistance gene to be obtained. Possible polar effects on the expression of the genes located downstream of the inactivated gene(s) are also avoided (cf. FIG. 10).

The employment of excisable cassettes has been described and used in many organisms including mammalian cells and yeast cells and in *E. coli* (Bayley et al., 1992; Brunelli and Pall, 1993; Camilli et al., 1994; Dale and Ow, 1991; Russell et al., 1992; Lakso et al., 1992). These excisable cassettes all use the Cre site-specific recombinase which acts on lox sites. This recombination system originates from the P1 bacteriophage.

To construct a system of the "excisable cassette" type in *Streptomyces*, the site-specific recombination system for the mobile genetic element pSAM2 of *Streptomyces* ambofaciens (Boccard et al., 1989a and b) is exploited. The system set up consists, initially, in constructing a recombinant vector comprising the gene to be interrupted, into which an excisable cassette is inserted. The insertion into the target gene of the excisable cassette is accompanied by a deletion in the target gene. It can be carried out by cloning using restriction sites present in the target gene or by recombination between short identical sequences as described, for example, by Chaveroche et al (Chaveroche M K et al., 2000). The excisable cassette can be constructed using, for example, the Ωhyg cassette (Blondelet Rouault et al., 1997). This cassette was bordered by attR and attL sequences which normally flank the integrated copy of pSAM2 (cf. FIG. 15). The attL and attR sequences contain all the sites required for the site-specific recombination allowing excision of pSAM2 or of any DNA fragment located between these two regions (Sezonov et al., 1997, Raynal et al., 1998). The construction of such a cassette is obviously not limited to the use of an Ωhyg cassette, but other resistance cassettes may be used as a basis to construct this cassette (for example the Ωaac or Ωvph cassette (Blondelet Rouault et al., 1997)).

After having obtained this construct, the strain of *Streptomyces* is transformed with the recombinant plasmid. The transformants are then selected with the antibiotic corresponding to the cassette present in the target gene (cf. FIG. 9, antibiotic B, this involves, for example, selection with hygromycin if the excisable cassette derives from the Ωhyg cassette). A mixture of clones among which there has been integration by a single or by two recombination events is thus selected. Subsequently, the clones sensitive to the antibiotic for which the resistance gene is present in the vector (outside the recombination cassette) (cf. FIG. 9, antibiotic A) are sought. It is thus possible to select the clones for which there have in principle been two recombination events resulting in the replacement of the wild-type gene with the copy interrupted with the cassette. These steps are shown diagrammatically in FIG. 9; the genotype of the clones thus obtained is verified by Southern blotting and a strain exhibiting the desired characteristics (replacement of the wild-type gene with the copy interrupted with the excisable cassette) is selected.

Next, the strain selected above is transformed with a plasmid which allows expression of the xis and int genes, which are both necessary for the site-specific recombination between the attR and attL sites. This recombination leads to the excisable cassette leaving the genome of the strain, by virtue of a recombination event (cf. FIG. 10) (Raynal et al., 1998). It is advantageous to choose the vector carrying the xis and int genes from the vectors which are relatively stable in *Streptomyces* (for example derived from the *Streptomyces* vector pWHM3, (Vara et al., 1989)), this makes it possible to obtain a strain which has lost the latter vector after a few sporulation cycles in the absence of selection pressure.

To excise the cassette, it is possible, for example, to use the plasmid pOSV508 (cf. FIG. 14), which is introduced by protoplast transformation into the strain of *S. ambofaciens* containing a gene interrupted with the excisable cassette. The plasmid pOSV508 is derived from the plasmid pWHM3 (J. Vara et al.,1989) (cf. FIG. 13) to which the xis and int genes of pSAM2 (F. Boccard et al., 1989b) have been added, placed under the control of the ptrc promoter (E. Amann et al., 1988). The xis and int genes placed under the control of the ptrc promoter were subcloned into the plasmid pWHM3 from the plasmid pOSint3 (Raynal et al., 1998) (cf. FIG. 14). Introduction of the plasmid pOSV508 carrying the xis and int genes of pSAM2, into the mutant strain, will allow effective excision, by site-specific recombination, of the excisable cassette between the attL and attR sites flanking this cassette (A. Raynal et al., 1998) (FIG. 10). Among the transformants, selected for their thiostrepton resistance due to the tsr gene carried by pOSV508, those which have become sensitive to the antibiotic to which the presence of the cassette imparts resistance are chosen (cf. FIG. 10). The excision is effective and it was observed that more than 90% of the transformants are of this type. After one or more cycles of growth and sporulation on a solid medium lacking thiostrepton, clones which have lost the plasmid pOSV508 are obtained. These clones can be detected by their sensitivity to thiostrepton. The sequence of the deleted target gene can be verified by PCR and sequencing of the PCR product.

Finally, the resulting strain carries, in the inactivated gene (internal deletion for example), a "scar" att site corresponding to the minimum attB site (Raynal et al., 1998), derived from the recombination between the attR and attL sites. This minimum attB site which remains is similar to that naturally present in strains of *Streptomyces ambofaciens, Streptomyces pristinaespiralis* and *Streptomyces lividans* (Sezonov et al., 1997).

The gene whose inactivation is desired can be cotranscribed with other genes located downstream. To avoid the inactivation of one of the genes having a polar effect on the expression of the genes downstream in the operon, it is important to obtain an in-phase deletion after excision of the cassette. The excisable cassette system as described above makes it possible to satisfy such a requirement. Those skilled in the art may, in fact, easily construct three different excisable cassettes, said cassettes leaving, after excision, a sequence of 33, 34 or 35 nucleotides respectively, without a stop codon whatever the reading frame. Knowing the sequence of the target gene and the size of the deletion associated with the insertion of the cassette, it is possible to choose between these three excisable cassettes so that the excision produces an in-phase deletion. Of the 33, 34 or 35 nucleotides added, 26 correspond to the minimum attB sequence (cf. FIG. 27).

In the case of the present application, two excisable cassettes were used. These two cassettes are as follows: att1Ωhyg+ (SEQ ID No. 91) and att3Ωaac− (SEQ ID No. 92); these cassettes leave respectively 33 and 35 nucleotides after excision. They comprise respectively the Ωhyg cassette or the Ωaac cassette, the + and − signs corresponding to the orientation of the resistance cassette. These two cassettes were constructed and cloned into the EcoRV site of the vector pBC SK+, the HindIII site of which was deleted beforehand. The plasmids obtained were named patt1Ωhyg+ and patt3Ωaac−, respectively. The excisable cassettes can be easily taken out by digestion of the plasmid with EcoRV.

EXAMPLE 10

Construction of a Strain of *Streptomyces ambofaciens* with a Knockout in the orf2 Gene The inactivation of the orf2 gene was carried out using the excisable cassette technique (cf. above). The starting strain used is the *Streptomyces ambofaciens* strain OSC2 which derives from the strain ATCC23877. However, the strain OSC2 differs from the strain ATCC23877 in that it has lost the mobile genetic element pSAM2 (Boccard et al., 1989a and b). This mobile element can be lost spontaneously during protoplastization (action of the lysozyme to digest the bacterial wall and fragment the mycelium (Kieser et al., 2000)) and regeneration of the protoplasts of the strain ATCC23877. To select the clones which had lost the pSAM2 element, a screen was set up, based on repression of the pra gene by the KorSA transcription repressor (Sezonov et al., 1995) (G. Sezonov et al., 2000). For this, a DNA fragment containing the promoter of the pra gene placed upstream of the aph gene (imparting kanamycin resistance and lacking its own promoter) was cloned into the unstable vector pWHM3Hyg, the latter deriving from the plasmid pWHM3 (Vara et al., 1989) in which the tsr gene has been replaced with the hyg gene (imparting hygromycin resistance). The plasmid thus obtained was named pOSV510. The strain ATCC23877 was transformed, after protoplastization, with the plasmid pOSV510. The Pra promoter is a promoter which is repressed by the KorSA repressor, the gene encoding the latter being located within the pSAM2 mobile element (Sezonov G. et al., 2000). After transformation with the plasmid pOSV510, the transformed bacteria are selected for their kanamycin resistance (due to the aph gene carried by pOSV510). The clones having lost the pSAM2 integrative element have lost the KorSA repressor and the Pra promoter is no longer repressed and allows expression of the aph kanamycin resistance gene. Selection with kanamycin after transformation with the plasmid pOSV510 therefore makes it possible to select the clones which have lost the pSAM2 integrative element (and therefore KorSA) and which contain the plasmid pOSV510. Since the plasmid pOSV510 is unstable, after a few cycles of sporulation without antibiotic, isolated clones are subcultured on medium with kanamycin, on medium with hygromycin and on medium without antibiotic. The clones sensitive to kanamycin and to hygromycin have lost pOSV510. The loss of the pSAM2 element was verified by hybridization and PCR. A clone exhibiting the desired characteristics was selected and was named OSC2.

A sample of the strain OSC2 was deposited with the Collection Nationale de Cultures de Microorganismes (CNCM) Pasteur Institute, 25, rue du Docteur Roux 75724 Paris Cedex 15, France, on Jul. 10, 2002, under the registration number I-2908.

The inactivation of the orf2 gene was carried out using the excisable cassette technique (cf. above and FIG. 10). For this, a 4.5 kb insert, the sequence of which starts from the EcoRI site located at position 1 up to the BamHI site located at position 4521 (SEQ ID No. 1), was subcloned into the EcoRI and BamHI sites of the plasmid pUC19 (GenBank accession number: M77789) from the cosmid pSPM5. The plasmid thus obtained was named pOS49.99.

This plasmid was introduced into the *E. coli* strain KS272, which already contained the plasmid pKOBEG (Chaveroche et al., 2000) (cf. FIG. 12).

In parallel, the att3Ωaac− excisable cassette (SEQ ID No. 92, cf. above) was amplified by PCR using as matrix the plasmid pOSK1102 (the plasmid pOSK1102 is a plasmid derived from the vector pGP704Not (Chaveroche et al., 2000) (V. L. Miller & J. J. Mekalanos, 1988) in which the att3Ωaac− cassette has been cloned, as an EcoRV fragment into the unique EcoRV site of pGP704Not) and using the following primers:

ORF2A (SEQ ID No. 93)
5' CCCGCGCGGCAGCCTCTCCGTGATCGAGTCCGGCGTGACCATCGCGC GCGCTTCGTTCGG-3'

ORF2B (SEQ ID No. 94)
5' GCTCCGTGCGTCATGCAGGAAGGTGTCGTAGTCGCGGTAGATCTGCC TCTTCGTCCCGAA-3'

The 40 deoxynucleotides located at the 5' end of these oligonucleotides comprise a sequence corresponding to a sequence in the target gene (orf2 in the present case) and the 20 deoxynucleotides located in the most 3' position (shown in bold above) correspond to the sequence of one of the ends of the att3Ωaac– excisable cassette (cf. FIG. 11).

The PCR product thus obtained was used to transform the *E. coli* strain containing the plasmids pKOBEG and pOS49.99 as described (Chaveroche et al., 2000) (cf. FIG. 12). Thus, the bacteria were transformed by electroporation and selected for their apramycin resistance. The plasmids of the clones obtained were extracted and digested with several restriction enzymes, for the purpose of verifying that the digestion profile obtained corresponds to the profile expected if there has been insertion of the cassette (att3Ωaac–) into the target gene (orf2), i.e. if there has indeed been homologous recombination between the ends of the PCR product and the target gene (Chaveroche et al., 2000). The verification of the construct can also be carried out by any method known to those skilled in the art, and in particular by PCR using the appropriate oligonucleotides and sequencing of the PCR product. A clone in which the plasmid has the expected profile was selected and the corresponding plasmid was named pSPM17.

This plasmid derives from pOS49.99 in which orf2 is interrupted with the apramycin cassette (cf. FIG. 12).

The insertion of the cassette is accompanied by a deletion in orf2, between the nucleotides 211 and 492 of the coding portion of orf2.

The plasmid pSPM17 was digested with the EcoRI enzyme and the ends were then blunt-ended by treatment with the Klenow enzyme; this digestion product was then digested with the XbaI enzyme and the insert containing the deleted orf2 gene was cloned into the vector pOSK1205 (cf. above). For this, the vector pOSK1205 was digested with the BamHI enzyme and the ends were then blunt-ended by treatment with the Klenow enzyme; this product was then digested with the XbaI enzyme and used for the ligation with the insert obtained from pSPM17 as above. This manipulation therefore makes it possible to obtain an oriented ligation since each one of the two fragments is blunt-ended on one side and XbaI on the other. The plasmid thus obtained was named pSPM21; it carries a hygromycin resistance gene (vector portion) and an insert in which the deleted orf2 gene is replaced with the att3Ωaac– cassette.

The vector pSPM21 was introduced into the *Streptomyces ambofaciens* strain OSC2 (cf. above) by protoplast transformation (T. Kieser et al, 2000). After transformation, the clones were selected for their apramycin resistance. The apramycin-resistant clones were then subcultured respectively on medium with apramycin (antibiotic B) and on medium with hygromycin (antibiotic A) (cf. FIG. 9). The clones resistant to apramycin (ApraR) and sensitive to hygromycin (HygS) are in principle those in which a double crossing over event has occurred and which contain the orf2 gene interrupted with the att3Ωaac– cassette. These clones were selected and the replacement of the wild-type copy of orf2 with the copy interrupted with the cassette was verified. The presence of the att3Ωaac– cassette was verified by colony PCR. A hybridization was also carried out. For this, the total DNA of the clones obtained was digested with several enzymes, separated on agarose gel, transferred onto a membrane and hybridized with a 3 kb probe corresponding to an EcoRI-BamHI fragment of the insert of the plasmid pOS49.99 (cf. above). The verification of the genotype can also be carried out by any method known to those skilled in the art, and in particular by PCR using the appropriate oligonucleotides and sequencing of the PCR product.

A clone exhibiting the expected characteristics was selected and named SPM21. It was possible to verify, using PCR and hybridization, that the att3Ωaac– cassette was indeed present in the genome of this clone and that the digestion profile expected in the case of replacement, subsequent to a double recombination event, of the wild-type gene with the copy interrupted with the att3Ωaac– cassette in the genome of this clone is indeed obtained. This clone therefore has the genotype: orf2::att3Ωaac–.

A sample of the strain SPM21 was deposited with the Collection Nationale de Cultures de Microorganismes (CNCM) Pasteur Institute, 25, rue du Docteur Roux 75724 Paris Cedex 15, France, on Jul. 10, 2002, under the registration number I-2914.

The strain SPM21 was transformed with the vector pOSV508 by protoplast transformation in order to bring about excision of the cassette (cf. FIG. 14). The plasmid pOSV508 is derived from the plasmid pWHM3 (J. Vara et al.,1989) (cf. FIG. 13) in which the xis and int genes of pSAM2 (F. Boccard et al., 1989b) have been added, placed under the control of the ptrc promoter (E. Amann et al., 1988) (cf. FIG. 14). The introduction, into the strain SPM21, of the plasmid pOSV508 carrying the xis and int genes of pSAM2 allows effective excision, by site-specific recombination, of the excisable cassette between the attL and attR sites flanking this cassette (A. Raynal et al., 1998) (FIG. 10). Among the transformants selected for their thiostrepton resistance due to the tsr gene carried by pOSV508, those which have become sensitive to apramycin, the resistance gene for which is carried by the att3Ωaac– cassette, are chosen; the excision in fact leads to the loss of this resistance gene (cf. FIG. 10). The plasmid pOSV508 is unstable and, after two successive passages on medium without antibiotic, isolated clones are subcultured on medium with thiostrepton and on medium without thiostrepton. The thiostrepton-sensitive clones have lost pOSV508. It was verified that the excision of this cassette indeed results in an in-phase deletion in the orf2 gene, by PCR and sequencing of the PCR product; the excision of the cassette in fact leaves a characteristic "scar" att3 sequence (which is similar to the attB site of origin after recombination between the attL and attR sites):

(SEQ ID No. 95)
5' ATCGCGCGCGCTTCGTTCGGGACGAAGAGGTAGAT 3'.

The strain thus obtained which has the desired genotype (orf2::att3) was named SPM22.

A sample of the strain SPM22 was deposited with the Collection Nationale de Cultures de Microorganismes (CNCM) Pasteur Institute, 25, rue du Docteur Roux 75724 Paris Cedex 15, France, Jul. 10, 2002, under the registration number I-2915.

EXAMPLE 11

Construction of a Strain of *Streptomyces ambofaciens* with a Knockout in the orf12 Gene For the inactivation of orf12, orf13c and orf14, the same starting plasmid (pSPM504) was used to introduce a cassette of the "excisable cassette" type, at various positions. This plasmid contains a 15.1 kb insert which corresponds to the region from orf7 to orf17. To construct this plasmid, a 15.1 kb BglII fragment originating from digestion of the cosmid pSPM7 (cf. above) was cloned into the plasmid pMBL18 (Nakano et al., 1995) digested with BamHI. Since BamHI and BglII ends are compatible, the plasmid pSPM502 is obtained after ligation. The entire insert of pSPM502 was then subcloned (in the form of a HindIII/NheI fragment) into the plasmid pOSK1205 (digested with HindIII/NheI), which made it possible to obtain the plasmid pSPM504.

This plasmid was introduced into the *E. coli* strain KS272 which already contained the plasmid pKOBEG (Chaveroche et al., 2000) (cf. FIG. 12).

In parallel, the att3Ωaac– excisable cassette was amplified by PCR using as matrix the plasmid pOSK1102 (the plasmid pOSK1102 is a plasmid derived from the vector pGP704Not (Chaveroche et al., 2000) (V. L. Miller & J. J. Mekalanos, 1988) in which the att3Ωaac– cassette has been cloned, as an EcoRV fragment, into the unique EcoRV site of pGP704Not); the primers used are as follows:

EDR8:
(SEQ ID No. 96)
5' CGGGATGATCGCTTGTCCGGCGGCCGGATGCCTAGCCTATCGCGCG CGCTTCGTTCGG 3'

EDR9:
(SEQ ID No. 97)
5' CCCGATCCAGAACGTCTGGTCGGTGATCAGGTCGCTGTTATCTGCC TCTTCGTCCCGAA 3'

The 40 (only 39 for EDR8) deoxynucleotides located at the 5' end of these oligonucleotides comprise a sequence corresponding to a sequence in the target gene (orf12 in the present case) and the 20 deoxynucleotides located in the most 3' position (shown in bold above) correspond to the sequence of one of the ends of the att3Ωaac– excisable cassette (cf. FIG. 11).

The PCR product thus obtained was used to transform the *E. coli* strain KS272 containing the plasmids pKOBEG and pSPM504 (cf. above), as described by Chaveroche et al. (Chaveroche et al., 2000) (cf. FIG. 12 for the principle, the plasmid pOS49.99 should be replaced by the plasmid pSPM504 and the plasmid obtained is no longer pSPM17 but pSPM507). Thus, the bacteria were transformed by electroporation with this PCR product and the clones were selected for their apramycin resistance. The plasmids of the clones obtained were extracted and digested with several restriction enzymes for the purpose of verifying that the digestion profile obtained corresponds to the profile expected if there has been insertion of the cassette (att3Ωaac–) into the target gene (orf12), i.e. if there has indeed been homologous recombination between the ends of the PCR product and the target gene (Chaveroche et al., 2000). The verification of the construct can also be carried out by any method known to those skilled in the art, and in particular by PCR using the appropriate oligonucleotides and sequencing of the PCR product. A clone in which the plasmid has the expected profile was selected and the corresponding plasmid was named pSPM507. This plasmid derives from pSPM504 in which orf12 is interrupted with the att3Ωaac– cassette (cf. FIG. 12). The insertion of the cassette is accompanied by a deletion in the orf12 gene, the interruption begins at the thirtieth codon of orf12. The last 46 codons of orf12 remain after the cassette. The vector pSPM507 was introduced into the *Streptomyces ambofaciens* strain OSC2 (cf. above) by protoplast transformation (T. Kieser et al., 2000). After transformation, the clones were selected for their apramycin resistance. The apramycin-resistant clones were then subcultured respectively on medium with apramycin (antibiotic B) and on medium with hygromycin (antibiotic A) (cf. FIG. 9). The clones resistant to apramycin (ApraR) and sensitive to hygromycin (HygS) are in principle those in which a double crossing over event has occurred and which contain the orf12 gene interrupted with the att3Ωaac– cassette. These clones were more particularly selected and the replacement of the wild-type copy of orf12 with the copy interrupted with the cassette was verified by hybridization. Thus, the total DNA of the clones obtained was digested with several enzymes, separated on agarose gel, transferred onto a membrane and hybridized with a probe corresponding to the att3Ωaac– cassette in order to verify the presence of the cassette in the genomic DNA of the clones obtained. A second hybridization was carried out using as probe a DNA fragment obtained by PCR and corresponding to a very large portion of the coding sequence of the orf12 gene.

The verification of the genotype can also be carried out by any method known to those skilled in the art, and in particular by PCR using the appropriate oligonucleotides and sequencing of the PCR product.

A clone exhibiting the expected characteristics (orf12:: att3Ωaac–) was more particularly selected and named SPM507. It was in fact possible to verify, by virtue of the two hybridizations, that the att3Ωaac– cassette was indeed present in the genome of this clone and that the digestion profile expected in the case of replacement, subsequent to a double recombination event, of the wild-type gene with the copy interrupted with the att3Ωaac– cassette in the genome of this clone is indeed obtained. This clone therefore has the genotype: orf12::att3Ωaac– and was named SPM507. Given the orientation of the genes (cf. FIG. 3), there is no need to excise the cassette to study the effect of the inactivation of orf12. Specifically, the fact that orf13c is oriented in the opposite direction to orf12 shows that these genes are not cotranscribed. The use of an excisable cassette makes it possible, on the other hand, to have the possibility of being rid of the selection marker at any moment, in particular by transformation of the plasmid pOSV508. A sample of the strain SPM507 was deposited with the Collection Nationale de Cultures de Microorganismes (CNCM) Pasteur Institute, 25, rue du Docteur Roux 75724 Paris Cedex 15, France, on Jul. 10, 2002 under the registration number I-2911.

EXAMPLE 12

Construction of a Strain of *Streptomyces ambofaciens* with a Knockout in the orf13c Gene The att3Ωaac– excisable cassette was amplified by PCR using as matrix the plasmid pOSK1102 (cf above), using the following primers:

EDR3:
(SEQ ID No. 98)
5' ACCGGGGCGGTCCTCCCCTCCGGGGCGTCACGGCCGCGGAATCTGCC TCTTCGTCCCGAA 3'

EDR4:
(SEQ ID No. 99)
5' CACGCAGCGAGCCGACGCACTGATGGACGACACGATGGCCATCGCGC GCGCTTCGTTCGG 3'

The 40 deoxynucleotides located at the 5' end of these oligonucleotides comprise a sequence corresponding to a sequence in the target gene (orf13c in the present case) and the 20 deoxynucleotides located in the most 3' position (shown in bold above) correspond to the sequence of one of the ends of the att3Ωaac– excisable cassette (cf. FIG. 11).

The PCR product thus obtained was used to transform the *E. coli* strain KS272 containing the plasmids pKOBEG and pSPM504 (cf. above), as described by Chaveroche et al.

(Chaveroche et al., 2000) (cf. FIG. 12 for the principle, the plasmid pOS49.99 should be replaced by the plasmid pSPM504 and the plasmid obtained is no longer pSPM17 but pSPM508). Thus, the bacteria were transformed by electroporation with this PCR product and the clones were selected for their apramycin resistance. The plasmids of the clones obtained were extracted and digested with several restriction enzymes for the purpose of verifying that the digestion profile obtained corresponds to the profile expected if there has been insertion of the cassette (att3Ωaac–) into the target gene (orf13c), i.e. if there has indeed been homologous recombination between the ends of the PCR product and the target gene (Chaveroche et al., 2000). The verification of the construct can also be carried out by any method known to those skilled in the art, and in particular by PCR using the appropriate oligonucleotides and sequencing of the PCR product. A clone in which the plasmid has the expected profile was selected and the corresponding plasmid was named pSPM508. This plasmid derives from pSPM504 in which orf13c is interrupted with the apramycin cassette (cf. FIG. 12). The insertion of the cassette is accompanied by a deletion in the orf13c gene, the interruption begins at the sixth codon of orf13c. The last 3 codons of orf13c remain after the cassette.

The vector pSPM508 was introduced into the *Streptomyces ambofaciens* strain OSC2 (cf. above) by protoplast transformation (T. Kieser et al., 2000). After transformation, the clones were selected for their apramycin resistance. The apramycin-resistant clones were then subcultured respectively on medium with apramycin (antibiotic B) and on medium with hygromycin (antibiotic A) (cf. FIG. 9). The clones resistant to apramycin (ApraR) and sensitive to hygromycin (HygS) are in principle those in which a double crossing over event has occurred and which contain the orf13c gene interrupted with att3Ωaac– cassette. These clones were more particularly selected and the replacement of the wild-type copy of orf13c with the copy interrupted with the cassette was verified by hybridization. Thus, the total DNA of the clones obtained was digested with several enzymes, separated on agarose gel, transferred onto a membrane and hybridized with a probe corresponding to the att3Ωaac– cassette in order to verify the presence of the cassette in the genomic DNA of the clones obtained. A second hybridization was carried out using as probe a PCR product corresponding to a sequence extending by about a hundred base pairs upstream and downstream of the coding sequence of orf13c. The verification of the genotype can also be carried out by any method known to those skilled in the art, and in particular by PCR using the appropriate oligonucleotides and sequencing of the PCT product.

A clone exhibiting the expected characteristics (orf13c:: att3Ωaac–) was more particularly selected and named SPM508. It was in fact possible to verify, by virtue of the two hybridizations, that the att3Ωaac– cassette was indeed present in the genome of this clone and that the digestion profile expected in the case of replacement, subsequent to a double recombination event, of the wild-type gene with the copy interrupted with the att3Ωaac– cassette in the genome of this clone is indeed obtained. This clone therefore has the genotype: orf13c::att3Ωaac– and was named SPM508. Given the orientation of the genes (cf. FIG. 3), there is no need to excise the cassette to study the effect of the inactivation of orf13c. The fact that orf14 is oriented in the opposite direction to orf13c shows that these genes are not cotranscribed. The use of an excisable cassette makes it possible, on the other hand, to add the possibility of being rid of the selection marker at any moment. A sample of the strain SPM508 was deposited with the Collection Nationale de Cultures de Microorganismes (CNCM) Pasteur Institute, 25, rue du Docteur Roux 75724 Paris Cedex 15, France, on Jul. 10, 2002 under the registration number I-2912.

EXAMPLE 13

Construction of a Strain of *Streptomyces ambofaciens* with a Knockout in the orf14 Gene The att3Ωaac– excisable cassette was amplified by PCR using as matrix the plasmid pOSK1102 (cf. above), using the following primers:

EDR5:
(SEQ ID No. 100)
5' GGGCGTGAAGCGGGCGAGTGTGGATGTCATGCGAGTACTCATCGCGC GCGCTTCGTTCGG 3'

EDR6:
(SEQ ID No. 101)
5' CGGGAAACGGCGTCGCACTCCTCGGGGCCGCGTCAGCCCATCTGCC TCTTCGTCCCGAA 3'

The 40 deoxynucleotides located at the 5' end of these oligonucleotides comprise a sequence corresponding to a sequence in the target gene (orf14 in the present case) and the 20 deoxynucleotides located in the most 3' position (shown in bold above) correspond to the sequence of one of the ends of the att3Ωaac– excisable cassette (cf. FIG. 11).

The PCR product thus obtained was used to transform the *E. coli* strain KS272 containing the plasmids pKOBEG and pSPM504 (cf. above), as described by Chaveroche et al. (Chaveroche et al., 2000) (cf. FIG. 12 for the principle, the plasmid pOS49.99 should be replaced by the plasmid pSPM504 and the plasmid obtained is no longer pSPM1 7 but pSPM509). Thus, the bacteria were transformed by electroporation with this PCR product and the clones were selected for their apramycin resistance. The plasmids of the clones obtained were extracted and digested with several restriction enzymes for the purpose of verifying that the digestion profile obtained corresponds to the profile expected if there has been insertion of the cassette (att3Ωaac–) into the target gene (orf14), i.e. if there has indeed been homologous recombination between the ends of the PCR product and the target gene (Chaveroche et al., 2000). The verification of the construct can also be carried out by any method known to those skilled in the art, and in particular by PCR using the appropriate oligonucleotides and sequencing of the PCR product. A clone in which the plasmid has the expected profile was selected and the corresponding plasmid was named pSPM509. This plasmid derives from pSPM504 in which orf14 is interrupted with the apramycin cassette (cf. FIG. 12). The insertion of the cassette is accompanied by a deletion in the orf14 gene, the interruption begins at the fourth codon of orf14. The final codon of orf14 remains after the cassette.

The vector pSPM509 was introduced into the *Streptomyces ambofaciens* strain OSC2 (cf. above) by protoplast transformation (T. Kieser et al., 2000). After transformation, the clones were selected for their apramycin resistance. The apramycin-resistant clones were then subcultured respectively on medium with apramycin (antibiotic B) and on medium with hygromycin (antibiotic A) (cf. FIG. 9). The clones resistant to apramycin (ApraR) and sensitive to hygromycin (HygS) are in principle those in which a double crossing over event has occurred and which contain the orf14 gene interrupted with att3Ωaac– cassette. These clones were more particularly selected and the replacement of the wild-type copy of orf14 with the copy interrupted with the cassette was verified by hybridization. Thus, the total DNA of the clones obtained was digested with several enzymes, separated on agarose gel, transferred onto a membrane and hybridized with a probe corresponding to the att3Ωaac– cassette in order to verify the presence of the cassette in the genomic DNA of the clones obtained. A second hybridization was carried out using as probe a PCR product corresponding to a sequence extending by about a hundred base pairs upstream and downstream of the coding sequence of orf14. The verification of the genotype can also be carried out by any method known to those skilled in the art, and in particular by PCR using the appropriate oligonucleotides and sequencing of the PCT product.

A clone exhibiting the expected characteristics (orf14:: att3Ωaac–) was more particularly selected and named SPM509. It was in fact possible to verify, by virtue of the two hybridizations, that the att3Ωaac– cassette was indeed present in the genome of this clone and that the digestion profile expected in the case of replacement, subsequent to a double recombination event, of the wild-type gene with the copy interrupted with the att3Ωaac– cassette in the genome of this clone is indeed obtained. This clone therefore has the genotype: orf14::att3Ωaac– and was named SPM509. Given the orientation of the genes (cf. FIG. 3), there is no need to excise the cassette to study the effect of the inactivation of orf14. The fact that orf15c is oriented in the opposite direction to orf14 shows that these genes are not cotranscribed. The use of an excisable cassette makes it possible, on the other hand, to add the possibility of being rid of the selection marker at any moment. A sample of the strain SPM509 was deposited with the Collection Nationale de Cultures de Microorganismes (CNCM) Pasteur Institute, 25, rue du Docteur Roux 75724 Paris Cedex 15, France, on Jul. 10, 2002 under the registration number I-2913.

EXAMPLE 14

Construction of a Strain of *Streptomyces ambofaciens* with a Knockout in the orf6* Gene The inactivation of the orf6* gene was carried out using the excisable cassette technique (cf. above and FIG. 10). For this, the cosmid pSPM7 was used as matrix to amplify a fragment of the orf6* gene using the following oligonucleotides:

C9583:
(SEQ ID No. 102)
5' CTGCAGGTGCTCCAGCGCGTCGATCT 3' (oligo sense)

C9584:
(SEQ ID No. 103)
5' CTGCAGACGGAGGCGGACCTGCGGCT 3' (oligo antisense)

The 20 deoxynucleotides located at the 3' end of these oligonucleotides correspond to a sequence located in the coding portion of the orf6* gene (SEQ ID No. 13) and the 6 deoxynucleotides located in the most 5' position correspond to the sequence of a PstI site which facilitates subsequent cloning. The amplified DNA fragment is approximately 1.1 1 kb in size. This PCR product was cloned into the vector pGEM-T Easy (marketed by the company Promega (Madison, Wis., USA)), which made it possible to obtain the plasmid named pBXL1111 (cf. FIG. 16).

The att1Ωhyg+ excisable cassette was then introduced into the coding sequence of the orf6* gene. For this, the plasmid pBXL1111 was digested with the SmaI and Asp718I restriction enzymes and the digestion product was treated with the Klenow enzyme. This manipulation makes it possible to produce an internal deletion of 120 bp in the coding sequence of the orf6* gene (cf. FIG. 15). In addition, on either side of the restriction sites, there remain respectively 511 bp and 485 bp of the sequence of orf6* which will allow the homologous recombination for the inactivation of the orf6* gene. The att1Ωhyg+ excisable cassette was prepared from the plasmid patt1Ωhyg+ (cf. above) by digestion of this plasmid with EcoRV. The latter was then subcloned into the vector pBXL11111 prepared beforehand as described above (SmaI and Asp718I digestion and then treatment with the Klenow enzyme). The plasmid obtained was named pBXL1112 (cf. FIG. 17). In this construct, the orf6* gene comprises a 120 bp deletion and is interrupted with the att1Ωhyg+ cassette.

The plasmid pBXL1112 was then digested with the PstI enzyme (site bordering the cassette since present in the PCR oligonucleotides) and the 3.7 kb PstI insert comprising a portion of orf6* interrupted with the att1Ωhyg+ cassette was then cloned into the PstI site of the plasmid pOJ260 (cf. above). The plasmid thus obtained was named pBXL1113.

The vector pBXL1113 was introduced into the *Streptomyces ambofaciens* strain OSC2 (cf. above) by protoplast transformation (T. Kieser et al., 2000). After transformation, the clones were selected for their hygromycin resistance. The hygromycin-resistant clones were then subcultured respectively on medium with hygromycin (antibiotic B) and on medium with apramycin (antibiotic A) (cf. FIG. 9). The clones resistant to hygromycin (HygR) and sensitive to apramycin (ApraS) are in principle those in which a double crossing over event has occurred and which contain the orf6* gene interrupted with the att1Ωhyg+ cassette. These clones were more particularly selected and the replacement of the wild-type copy of orf6* with the copy interrupted with the cassette was verified by the Southern blotting technique. Thus, the total DNA of the clones obtained was digested with several enzymes, separated on agarose gel, transferred onto a membrane and hybridized with a probe corresponding to the hyg gene (obtained by PCR) in order to verify the presence of the cassette in the genomic DNA of the clones obtained. A second hybridization was carried out using as probe the PstI-PstI, insert containing the orf6* gene, approximately 1.1 kb in size, and obtained from the plasmid pBXL1111 (cf. above and FIG. 16). The verification of the genotype can also be carried out by any method known to those skilled in the art, and in particular by PCR using the appropriate oligonucleotides and sequencing of the PCR product.

A clone exhibiting the expected characteristics (orf6*:: att1Ωhyg+) was more particularly selected and named SPM501. It was in fact possible to verify, using the two hybridizations, that the att1Ωhyg+ cassette was indeed present in the genome of this clone and that the digestion profile expected in the case of replacement, subsequent to a double recombination event, of the wild-type gene with the copy interrupted with the att1Ωhyg+ cassette in the genome of this clone is indeed obtained. This clone therefore has the genotype: orf6*::att1Ωhyg+ and was named SPM501. A sample of the strain SPM501 was deposited with the Collection Nationale de Cultures de Microorganismes (CNCM) Pasteur Institute, 25, rue du Docteur Roux 75724 Paris Cedex 15, France, on Jul. 10, 2002, under the registration number I-2909.

The strain SPM501 was transformed with the vector pOSV508 by protoplast transformation in order to bring about excision of the cassette (cf FIG. 14). The plasmid pOSV508 is derived from the plasmid pWHM3 (J. Vara et al., 1989) (cf. FIG. 13) in which the xis and int genes of pSAM2 (F. Boccard et al., 1989b), placed under the control of the ptrc promoter (E. Amann et al, 1988), have been added (cf. FIG.

14). The introduction, into the strain SPM501, of the plasmid pOSV508 carrying the xis and int genes of pSAM2 allows effective excision, by site-specific recombination, of the excisable cassette between the attL and attR sites flanking this cassette (A. Raynal et al., 1998) (FIG. 10). Among the transformants, selected for their thiostrepton resistance due to the tsr gene carried by pOSV508, those which have become sensitive to hygromycin, for which the resistance gene is carried by the att1Ωhyg+ cassette, are chosen; the excision in fact leads to the loss of this resistance gene (cf. FIG. 10). The plasmid pOSV508 is unstable and, after two successive passages on medium without antibiotic, isolated clones are subcultured on medium with thiostrepton and on medium without thiostrepton. The thiostrepton-sensitive clones have lost pOSV508. It was verified that the excision of the cassette had indeed occurred in phase in the orf6* gene, by PCR and sequencing of the PCR product. The interruption begins at the 158th codon, 40 codons are deleted (120 bp), and the excision of the cassette leaves a characteristic "scar" att1 sequence of 33 bp:

(SEQ ID No. 104)
5' ATCGCGCGCTTCGTTCGGGACGAAGAGGTAGAT 3'.

The strain thus obtained and having the desired genotype (orf6*::att1) was named SPM502.

A sample of the strain SPM502 was deposited with the Collection Nationale de Cultures de Microorganismes (CNCM) Pasteur Institute, 25, rue du Docteur Roux, 75724 Paris Cedex 15, France, on Jul. 10, 2002, under the registration number I-2910.

EXAMPLE 15

Analysis of the Strains of *Streptomyces ambofaciens* with a Knockout in the orf2, orf3, orf8, orf10, orf12, orf13c, orf14 or orf6* Gene In order to test the spiramycin production of the various strains obtained, a microbiological test based on the sensitivity of a strain of *Micrococcus luteus* was developed (cf. (A. Gourmelen et al., 1998)). The strain of *Micrococcus luteus* used is a strain derived from the strain DSM1790 naturally sensitive to spiramycin (this strain is available in particular from the German Collection of Microorganisms and Cell Cultures (Deutsche Sammlung von Mikro-organismen und Zellkulturen GmbH, DSMZ), (Braunschweig, Germany), under the number DSM 1790); the strain used in the present test differs from the strain DSM 1790 in that it is resistant to congocidine. This strain is a spontaneous mutant obtained by selection on medium containing increasing doses of congocidine. Such a strain was selected due to the fact that *Streptomyces ambofaciens* produces both spiramycin and congocidine. Since the aim is to assay the spiramycin production of the various strains obtained using a microbiological test based on the sensitivity of a strain of *Micrococcus luteus*, it is necessary to have a congocidine-resistant strain.

The various strains of *Streptomyces* to be tested were cultured in 500 ml Erlenmeyer flasks with baffles (baffled Erlenmeyers) containing 70 ml of MP5 medium (Pemodet et al., 1993). The baffled Erlenmeyers were inoculated at an initial concentration of $2.5 \times 10^6$ spores/ml of the various strains of *S. ambofaciens* and grown at 27° C. with orbital shaking at 250 rpm. 2 ml samples of suspensions were taken after 48, 72 and 96 hours of culturing, and centrifuged. The various supernatants were then frozen at −20° C. A ten-fold dilution of these supernatants in sterile culture medium is used for the test (cf. FIG. 18).

The *Micrococcus luteus* indicator strain resistant to congocidine but sensitive to spiramycin was cultured in 2TY medium (Sambrook et al., 1989) containing congocidine at 5 µg/ml, for 48 h at 37° C. The optical density (OD) of the culture is measured and this culture is diluted so as to adjust the optical density to 4. 0.4 ml of this preculture is diluted in 40 ml of DAM5 medium (Difco Antibiotic Medium 5, marketed by the company Difco), brought to a temperature of approximately 45° C. beforehand. This medium is then poured into a 12×12 cm square dish and left to stand at ambient temperature.

Once the medium had cooled and solidified, disks of Whatman AA paper (cf. A. Gourmelen et al., 1998), 12 mm in diameter, were soaked with 70 µl of the ten-fold dilution of each supernatant and placed on the surface of the dish. Disks soaked with a solution of spiramycin of various concentrations (2-4-8 µg/ml in MP5 culture medium) are used as a standard range. The dishes were left at 4° C. for 2 h so as to allow diffusion of the antibiotics into the agar, and were then incubated at 37° C. for 24 to 48 h.

If the disk contains spiramycin, this diffuses into the agar and inhibits the growth of the *Micrococcus luteus* indicator strain. This inhibition creates a "halo" around the disk, this halo reflecting the area in which the *Micrococcus luteus* strain has not grown. The presence of this halo is therefore an indication of the presence of spiramycin and makes it possible to determine whether the strain of *S. ambofaciens* corresponding to the disk in question is or is not a spiramycin producer. Comparison with the inhibition diameters obtained for the standard range makes it possible to obtain an indication of the amount of spiramycin produced by this strain.

The various strains described in the preceding examples were used in this test in order to detect their spiramycin production. The results obtained were grouped together in Table 38.

TABLE 38

| Strain | Inactivated gene | Example in which the strain is described | Phenotype: Producer (+) or nonproducer (−) of spiramycin |
|---|---|---|---|
| ATCC23877 | None | 1 | (+) |
| OS49.16 | orf3::Ωhyg | 2 | (−) |
| OS49.67 | In-phase deletion orf3 | 6 | (−) |
| OS49.107 | orf8::Ωhyg | 7 | (−) |
| OS49.50 | orf10:: Ωhyg | 8 | (−) |
| OSC2 | None | 10 | (+) |
| SPM21 | orf2::att3Ωaac− | 10 | (−) |
| SPM22 | In-phase deletion orf2::att3 | 10 | (−) |
| SPM501 | orf6*::att1Ωhyg+ | 14 | (−) |
| SPM502 | In-phase deletion orf6*::att1 | 14 | (+) |
| SPM507 | orf12::att3Ωaac− | 11 | (−) |
| SPM508 | orf13c::att3Ωaac− | 12 | (+) |
| SPM509 | orf14::att3Ωaac− | 13 | (−) |

These results make it possible to draw a certain number of conclusions regarding the function of the various genes involved in the spiramycin biosynthesis. Thus, the orf3 gene is essential to spiramycin biosynthesis. Specifically, an in-phase inactivation in this gene leads to a strain (OS49.67, (cf. example 6)) which no longer produces spiramycin. The in-phase inactivation makes it possible to discard the hypothesis of a possible influence of the cassette introduced on the expression of the genes located downstream of orf3.

Similarly, the orf8 and orf10 genes encode proteins essential to spiramycin biosynthesis since the strains OS49.107 and OS49.50 have a nonproducer phenotype. In addition, in these latter two strains, it is clearly the inactivation of the corresponding gene which is responsible for this nonproducer phenotype, since, in view of the orientation of the various orfs (cf. FIG. 3), the construct introduced cannot have a polar effect.

The study of the strains having an excisable cassette also makes it possible to draw a certain number of conclusions regarding the function of the interrupted gene. The strain SPM507 has the genotype: orf12::att3Ωaac−. In view of the orientation of the genes (cf. FIG. 3), there is no point in excising the cassette to study the effect of the inactivation of orf12. The fact that orf13c is oriented in the opposite direction to orf12 shows that these genes are not cotranscribed. The use of an excisable cassette makes it possible, on the other hand, to have the possibility of being rid of the selection marker at any moment. The phenotype of the strain SPM507 is nonproducer; it may therefore be concluded therefrom that the orf12 gene is a gene essential to spiramycin biosynthesis in *S. ambofaciens*.

The strain SPM508 has the genotype: orf13c::att3Ωaac−. In view of the orientation of the genes (cf. FIG. 3), there is no point in excising the cassette to study the effect of the inactivation of orf13c. The fact that orf14 is oriented in the opposite direction to orf13c shows that these genes are not cotranscribed. The use of an excisable cassette makes it possible, on the other hand, to have the possibility of being rid of the selection marker at any moment. The phenotype of the strain SPM508 is producer; it may therefore be concluded therefrom that the orf13c gene is not a gene essential to spiramycin biosynthesis in *S. ambofaciens*.

The strain SPM509 has the genotype: orf14::att3Ωaac−. In view of the orientation of the genes (cf. FIG. 3), there is no need to excise the cassette to study the effect of the inactivation of orf14; the fact that orf15c is oriented in the opposite direction to orf14 shows that these genes are not cotranscribed. The use of an excisable cassette makes it possible, on the other hand, to have the possibility of being rid of the selection marker at any moment. The phenotype of the strain SPM509 is nonproducer; it may therefore be concluded therefrom that the orf14 gene is a gene essential to spiramycin biosynthesis in *S. ambofaciens*.

The strain SPM21 has the genotype: orf2::att3Ωaac−. This strain has a spiramycin nonproducer phenotype. However, the orientation of the genes orf1 to orf8 (cf. FIG. 3) implies that these genes are cotranscribed. Thus, the phenotype observed may be due to a polar effect of the cassette introduced into orf2 on the expression of genes located downstream in the operon. The strain SPM22 has the genotype orf2::att3 and was obtained after in-phase excision of the cassette introduced. The excision of the cassette leaves only a characteristic "scar" sequence (cf. example 10). Since the strain SPM22 also has a nonproducer phenotype, it may be concluded therefrom that the orf2 gene is a gene essential to spiramycin biosynthesis in *S. ambofaciens*. Only the effect due to the inactivation of orf2 is observed here.

The strain SPM501 has the genotype: orf6*::att1 Ωhyg+. This strain has a spiramycin nonproducer phenotype. However, since the orf5* and orf6* genes (cf. FIG. 3) have the same orientation, the phenotype observed may be due to a polar effect of the cassette introduced into orf6* on the expression of orf5*. The arrangement of these genes implies that they may be cotranscribed. To reply to this question, the strain SPM502 was obtained after in-phase excision of the cassette introduced. In this strain, only the effect of the inactivation of orf6* is observed. This strain has the genotype orf6*::att1 (cf. example 14). Excision of the cassette leaves only an in-phase "scar" sequence (cf. example 14). The strain SPM502 has a producer phenotype (however, this strain produces only spiramycin I (cf*. example 16)). It may therefore be concluded that the orf5* gene is a gene essential to spiramycin biosynthesis in *S. ambofaciens*, since indirect inactivation thereof in the strain SPM501 leads to a nonproducer phenotype. On the other hand, the orf6* gene is not a gene essential to the biosynthesis of spiramycin I in *S. ambofaciens* (on the other hand, it is essential to the production of spiramycin II and III (cf. example 16)).

EXAMPLE 16

Assaying of the Production of Spiramycins I, II and III in the Mutant Strains Obtained The various strains to be tested were each cultured in seven 500 ml baffled Erlenmeyers containing 70 ml of MP5 medium (Pernodet et al., 1993). The Erlenmeyers were inoculated with $2.5 \times 10^6$ spores/ml of the various strains of *S. ambofaciens* and grown at 27° C. with orbital shaking at 250 rpm for 72 hours. The cultures corresponding to the same clone were pooled, optionally filtered through a pleated filter, and centrifuged for 15 min at 7000 rpm. The various supernatants were then stored at −30° C.

The assays were carried out by ion-pairing high performance liquid chromatography (HPLC). The HPLC analysis of the culture medium makes it possible to determine precisely the concentration of the three forms of spiramycin. The column used (Macherey-Nagel) is filled with a Nucleosil octyl grafted silica phase. The particle size is 5 μm and the pore size is 100 Å. The internal diameter of the column is 4.6 mm and it is 25 cm long. The mobile phase is a 70/30 (v/v) mixture of $H_3PO_4$ buffer (pH 2.2) and acetonitrile containing 6.25g /L of $NaClO_4$ perchlorate. The analysis is carried out in an isocratic system with a flow rate fixed at 1 ml/min. The column is thermocontrolled at 23° C. Detection is by UV spectrophotometry at 238 nm. The sample is refrigerated at +10° C. and the quantification is determined from the area of the peaks (by external calibration). Under these conditions, the retention times for spiramycin I, II and III are, respectively, approximately 17; 21 and 30 minutes, as could be verified using a commercial sample comprising the three forms of spiramycin.

The strain OSC2 has a spiramycin producer phenotype. It is the parental strain used to obtain the strains having an excisable cassette (cf. example 15). This strain was therefore used as a positive control for production of the three forms of spiramycin. This strain clearly produces the three forms of spiramycin, as was verified by HPLC (cf. FIG. 19).

The study of the strains having an excisable cassette makes it possible to draw a certain number of conclusions regarding the function of the interrupted genes. The strain SPM507 has the genotype: orf12::att3Ωaac−. The phenotype of the strain SPM507 is nonproducer (cf. example 15); it may therefore be concluded therefrom that the orf12 gene is a gene essential to spiramycin biosynthesis in *S. ambofaciens*. This strain no longer produces spiramycins, as was verified by HPLC (cf. FIG. 22). This result confirms the essential nature of the orf12 gene in spiramycin biosynthesis.

The strain SPM508 has the genotype: orf13c::att3Ωaac−. The strain SPM508 has a spiramycin producer phenotype (cf. example 15); it may therefore be concluded therefrom that the orf13c gene is not a gene essential to spiramycin biosynthesis in *S. ambofaciens*. This strain produces spiramycin I, II and III, as was verified by HPLC (cf. FIG. 23). This result confirms that the orf13c gene is not a gene essential to the biosynthesis of spiramycins I, II and III in *S. ambofaciens*.

The strain SPM509 has the genotype: orf14::att3Ωaac−. The phenotype of the strain SPM509 is nonproducer; it may therefore be concluded therefrom that the orf14 gene is a gene essential to spiramycin biosynthesis in *S. ambofaciens*. This strain no longer produces spiramycins, as was verified by HPLC (cf. FIG. 24). This result confirms the essential nature of the orf14 gene in spiramycin biosynthesis.

The strain SPM501 has the genotype: orf6*::att1Ωhyg+. This strain has a spiramycin nonproducer phenotype. This strain no longer produces spiramycins, as was verified by HPLC (cf. FIG. 20). However, since the orf5* and orf6* genes (cf. FIG. 3) have the same orientation, the phenotype observed may be due to a polar effect of the cassette introduced into orf6* on the expression of orf5* in the operon. This implies that these genes are contranscribed. To reply to this question, the strain SPM502 was obtained by excision of the cassette introduced, producing an in-phase deletion in the or6* gene and restoring the expression of orf5*. This strain has the genotype orf6*::att1 (cf. example 14 and 15). Excision of the cassette leaves only an in-phase "scar" att sequence (cf. example 14). The strain SPM502 has a spiramycin producer phenotype. However, as was proved by HPLC, this strain produces only spiramycin I and does not produce spiramycin II and III (cf. FIG. 21). It may therefore be concluded from these results that the orf5* gene is a gene essential to spiramycin biosynthesis in *S. ambofaciens*, since indirect inactivation thereof in the strain SPM501 leads to a spiramycin nonproducer phenotype .(cf. FIG. 20). On the other hand, the orf6* gene is not a gene essential to biosynthesis of spiramycin I in *S. ambofaciens*, since the inactivation of this gene leads to a spiramycin I producer phenotype (cf. FIG. 21). However, orf6* is essential to the production of spiramycin II and III (cf. example 16)). The orf6* gene therefore clearly encodes an acyltransferase responsible for the modification of the platenolide at position 3 (cf. FIG. 1).

EXAMPLE 17

Determination of the Translation Initiation Point of orf 10 and Improvement of Spiramycin Production 17.1 Construction of the Plasmids pSPM523, pSPM524 and pSPM525:

The orf10 gene was identified in *Streptomyces ambofaciens* and was named srmR by Geistlich et al. (M. Geistlich et al., 1992). Inactivation of the orf10 gene was carried out (cf. example 8). It was thus possible to show that the resulting strain no longer produces spiramycins (cf. example 15). This confirms that the orf10 gene is clearly involved in spiramycin biosynthesis. The protein encoded by this gene is therefore clearly essential to spiramycin biosynthesis. However, analysis of the sequence shows that two ATG codons located in the same reading frame may be used for the translation of orf10 (cf. FIG. 28). One of the two possible codons (the most upstream codon) begins at position 10656 of the sequence given in SEQ ID No. 1, whereas the other possible codon, located more downstream, begins at position 10809 (cf. SEQ ID No. 1). Before testing a possible effect of the overexpression of srmR on spiramycin production, it is important to first determine the translation initiation point.

With the aim of determining the translation iniation site, three constructs comprising three forms of orf10 were produced. These forms were obtained by PCR using oligonucleotides comprising either a HindIII restriction site or a BamHI restriction site.

The first pair used for the amplification corresponds to the following oligonucleotides:

EDR39:
(SEQ ID No. 122)
5'CCCAAGCTTGAGAAGGGAGCGGACATTCATGGCCCGCGCCGAACGC3'
(the HindIII site is shown in bold)

EDR42:
(SEQ ID No. 123)
5'CGGGATCCGGCTGACCATGGGAGACGGGCGCATCGCCGAGTTCAGC3'
(the BamHI site is shown in bold)

The pair of primers EDR39-EDR42 allows the amplification of an fragment of orf10 comprising the ATG located in the most 3' position (position 10809 in the sequence given in SEQ ID No. 1) (cf. FIG. 28). The fragment obtained is approximately 2 kb in size and will subsequently be referred to as "short orf10"; it does not contain the orf10 promoter. This 2kb fragment was cloned into the vector pGEM-T easy, to give the plasmid pSPM520.

The second pair used for the amplification corresponds to the following oligonucleotides:

EDR40:
(SEQ ID No. 124)
5'CCCAAGCTTGAGAAGGGAGCGGACATTCAATGCTTTGGTAAAGCAC3'
(the HindIII site is shown in bold)

EDR42:
(SEQ ID No. 123)
5'CGGGATCCGGCTGACCATGGGAGACGGGCGCATCGCCGAGTTCAGC3'
(the BamHI site is shown in bold)

The pair of primers EDR40-EDR42 allows the amplification of a fragment of orf10 comprising the ATG located in the most 5' position (position 10656 in the sequence given in SEQ ID No. 1) (cf. FIG. 28). This 2.2 kb fragment, subsequently referred to as "long orf10", was cloned into the vector pGEM-T easy, to give the plasmid pSPM521; this plasmid does not contain the orf10 promoter.

The third pair used for the amplification corresponds to the following oligonucleotides:

EDR41:
(SEQ ID No. 125)
5'-CCCAAGCTTTCAAGGAACGACGGGGTGGTCAGTCAAGT-3'
(the HindIII site is shown in bold)

EDR42:
(SEQ ID No. 123)
5'CGGGATCCGGCTGACCATGGGAGACGGGCGCATCGCCGAGTTCAGC3'
(the BamHI site is shown in bold)

The pair of primers EDR41-EDR42 allows the amplification of the orf10 gene with the two ATGs, and also its own promoter (cf. FIG. 28). This 2.8 kb fragment, subsequently referred to as "pro orf10", was cloned into the vector pGEM-T easy, to give the plasmid pSPM522.

The "pro orf10" fragment was obtained using as matrix the chromosomal DNA of the strain OSC2. The "short orf10" and "long orf10" fragments were, themselves, obtained using as matrix the DNA of the "pro orf10" fragment purified beforehand.

The HindIII-BamHI inserts of the plasmids pSPM520, pSPM521 and pSPM522 were then subcloned into the vector pUWL201 (plasmid derived from the plasmid pUWL199 (U. F. Wehmeier, 1995) in to which the KpnI-BamHI fragment of the region of the ermE promoter (cf. Bibb et al., 1985, in particular FIG. 2) carrying a mutation which increases the strength of the promoter (ermE* promoter) (Bibb et al., 1994) has been introduced (cf. Doumith et al., 2000)) predigested with the HindIII-BamHI enzymes. Thus, three plasmids were obtained: pSPM523 (derived from pUWL201 with the "short orf10" form as insert), pSPM524 (derived from pUWL201 with the "long orf10" for as insert) and pSPM525 (derived from pUWL201 with the "pro orf10" form) (FIG. 28).

17.2 Transformation of the Strain OS49.50 with the Constructs pSPM523, pSPM524 and pSPM525:

The strain OS49.50 (strain with a knockout in the orf10 gene, cf. example 8) was transformed independently by protoplast transformation (T. Kieser et al., 2000) with each of the plasmids pSPM523, pSPM524 and pSPM525. A negative control was also prepared by transforming the strain OS49.50 with the plasmid pUWL201 without insert. After protoplast transformation, the clones were selected for their thiostrepton resistance. The transformation of the clones with each of the plasmids was verified by extraction of these plasmids. Thus, four new strains were obtained: the strain OSC49.50 pUWL201, derived from the transformation with the plasmid pUWL201 without insert; the strain OSC49.50 pSPM523, derived from the transformation with the plasmid pSPM523; the strain OSC49.50 pSPM524, derived from the transformation with the plasmid pSPM524; and, finally, the strain OS49.50 pSPM525, derived from the transformation with the plasmid pSPM525.

The spiramycin production of each of these four strains was tested by HPLC. For this, the various strains of *Streptomyces* to be tested were cultured in 500 ml Erlenmeyers with baffles (baffled Erlenmeyers) containing 70 ml of MP5 medium (Pemodet et al., 1993). When the strain contains the plasmid pUWL201, or one of its derivatives, 5 µg/ml of thiostrepton are added. The baffled Erlenmeyers were inoculated at an initial concentration of $2.5 \times 10^6$ spores/ml of the various strains of *S. ambofaciens*, and the cultures were incubated at 27° C. with orbital shaking at 250 rpm for 96 hours. The cells were then separated from the medium by centrifugation and the supernatant was analyzed by HPLC (cf. example 16) in order to determine the amount of spiramycin produced. By virtue of a standard sample and measuring the area of the peaks, it was possible to determine the amount of each of the spiramycins produced by these strains. The results of this analysis are given in table 39, the data are expressed in mg per liter of supernatant. The results correspond to the total production of spiramycins (obtained by adding the production of spiramycin I, II and III).

TABLE 39

Spiramycin production of the strains derived from OS49.50, (results expressed in mg/l).

| Strain | Spiramycin production |
|---|---|
| OS49.50 pUWL201 | 0 |
| OS49.50 pSPM523 | 0 |
| OS49.50 pSPM524 | 93 |
| OS49.50 pSPM525 | 149 |

As shown by the results given in table 39, the negative control (strain OS49.50 transformed with the plasmid pUWL201) does not produce spiramycin. When the plasmid pSPM523 (which contains the "short orf10" form) is introduced into the strain OS49.50, no spiramycin production is observed. On the other hand, the presence of the plasmid pSPM524 (which contains the "long orf10" form) and of the plasmid pSPM525 (which contains the "pro orf10" form) restores the spiramycin production in the host strain OS49.50. Thus, only the orf10 fragments containing the most upstream ATG make it possible to restore spiramycin synthesis.

With the aim of confirming these results, the plasmid pSPM521 (plasmid pGEM-T easy containing the "long orf10" form) was digested with the XhoI restriction enzyme (this enzyme has a unique site in this plasmid, located between the two ATGs (cf. FIG. 28)). The XhoI ends were then blunt-ended by treatment with the Klenow enzyme. The plasmid was then closed back up on itself by the action of T4 DNA ligase, to give the plasmid pSPM527. If the most upstream ATG (position 10656 in the sequence given in SEQ ID No. 1) is indeed used as translation initiation site, this treatment will lead to a shift in the reading frame at the XhoI site and will have the effect of producing a protein exhibiting no activating acivity. On the other hand, if the translation initiation takes place at the most downstream ATG (position 10809 in the sequence given in SEQ ID No. 1), this treatment should have little or no effect on the expression of Orf10 (given the location of the transcription initiation point) and no effect on the protein produced.

The BamHI-HindII insert of pSPM527 was then subcloned into the vector pUWL201, to give the plasmid pSPM528. This plasmid was introduced into the strain OS49.50 and a clone having the desired plasmid was more particularly selected. The spiramycin production of the resulting strain was then tested by HPLC (cf. example 16 and above). Unlike what was observed with the plasmid pSPM524 (cf. table 39), the presence of the plasmid pSPM528 in the strain OS49.50 does not reestablish the spiramycin production. This confirms that the translation initiation of the orf10 gene is the ATG located in the most downstream position (ATG 1 cf. FIG. 28).

17.3 Improvement in Spiramycin Production of the *S. ambofaciens* Strain OSC2:

In order to test the effect of overexpression of the orf10 gene on spiramycin production, the plasmids pSPM523, pSPM524, pSPM525 and pSPM528 were introduced into the strain OSC2. For this, protoplasts of the strain OSC2 were transformed (T. Kieser et al., 2000) independently with each of the plasmids pSPM523, pSPM524, pSPM525 and pSPM528. A negative control was also produced by transforming the strain OSC2 with the plasmid pUWL201 without insert. After protoplast transformation, the clones were selected for their thiostrepton resistance. Thus, five new strains were obtained: the strain OSC2 pUWL201, derived from the transformation with the plasmid pUWL201 without insert, the strain OSC2 pSPM523, derived from the transformation with the plasmid pSPM523; the strain OSC2 pSPM524, derived from the transformation with the plasmid pSPM524; the strain OSC2 pSPM525, derived from the transformation with the plasmid pSPM525; and, finally, the strain OSC2 pSPM528, derived from the transformation with the plasmid pSPM528. The spiramycin production of these strains was then analyzed by HPLC (in the same way as in example 17.2). Analysis of the spiramycin production of the strain OSC2 was also carried out in parallel for comparison. The results of this analysis are given in table 40, the data are expressed in mg per liter of supernatant. The results correspond to the total production of spiramycins (obtained by adding the production of spiramycin I, II and III).

TABLE 40

Spiramycin production of the strains derived
from OSC2, (results expressed in mg/l).

| Strain | Spiramycin production |
|---|---|
| OSC2 | 69 |
| OSC2 pUWL201 | 103 |
| OSC2 pSPM523 | 19 |
| OSC2 pSPM524 | 135 |
| OSC2 pSPM525 | 278 |
| OSC2 pSPM528 | 68 |

Thus, it is observed that the presence of the plasmid pSPM524 or of the plasmid pSPM525 significantly increases the spiramycin production of the strain OSC2. This clearly demonstrates that overexpression of Orf10 has a positive effect on the spiramycin production. On the other hand, the plasmid pSPM528 has no effect on the spiramycin production.

In the same way, the plasmids pSPM525 and pUWL201 were introduced into the strain SPM502 (cf. example 14). Thus, two new strains were obtained: the strain SPM502 pUWL201, derived from the transformation with the plasmid pUWL201 without insert; and the strain SPM502 pSPM525, derived from the transformation with the plasmid pSPM525.

A sample of the strain SPM502 pSPM525 (this strain contains the plasmid pSPM525, cf. above) was deposited with the Collection Nationale de Cultures de Microorganismes (CNCM) Pasteur Institute, 25, rue du Docteur Roux 75724 Paris Cedex 15, France, on February 26, 2003 under the registration number I-2977.

The spiramycin production of the strains SPM502 pUWL201 and SPM502 pSPM525 was analyzed by HPLC (in the same way as in example 17.2). Analysis of the spiramycin production of the strain SPM502 was also carried out in parallel for comparison. The results of this analysis are given in table 41, the data are expressed in mg per liter of supernatant. The results correspond to the production of spiramycin I. In fact, none of these strains produces spiramycin II and III.

TABLE 41

Spiramycin I production of the strains derived
from SPM502, (results expressed in mg/l).

| Strain | Spiramycin I |
|---|---|
| SPM502 | 47 |
| SPM502 pUWL201 | 72 |
| SPM502 pSPM525 | 130 |

Thus, it was possible to observe that overexpression of the orf10 gene in the strain SPM502 considerably increases the production of spiramycin I.

EXAMPLE 18

Construction of a Genomic DNA Library of the
Streptomyces ambofaciens Strain OSC2 in E. coli in
the Cosmid pWED2

18.1 Construction of the Cosmid pWED2:

With the aim of facilitating the inactivation of genes in Streptomyces, a cosmid carrying the oriT sequence of the plasmid RK2 (which allows its introduction by conjugation into Streptomyces from a suitable strain of E. coli) and also carrying a gene for resistance to a an antibiotic imparting a detectable phenotype in Streptomyces was constructed. Such a cosmid containing large inserts of genomic DNA of Streptomyces ambofaciens can be used in gene inactivation experiments.

To construct this vector, a pac-oriT cassette (EcoRV fragment) was introduced into the cosmid pWED1 (Gourmelen et al., 1998), derived from the cosmid pWED15 (Wahl et al., 1987), at the unique HpaI site. The pac-oriT cassette was obtained by PCR. For this, the pac gene was amplified by PCR from the plasmid pVF 10.4 (Vara et al., 1985; Lacalle et al., 1989) using, as first primer, primer A (of sequence 5'-CCAGTA<u>GATATC</u>CCGCCAACCCGGAGCTGCAC-3' (SEQ ID No. 126), the EcoRV restriction site has been underlined and the 20 nucleotide sequence in bold corresponds to a region upstream of the promoter of the pac gene) and, as second primer, primer B (of sequence 5'-GAAAAGATCCGTCATGGGGTCGTGCGCTCCTT-3' (SEQ ID No. 127), which comprises, at its 5' end, a 12 nucleotide sequence corresponding to the start of the oriT sequence (double underlined) and a 20 nucleotides sequence (in bold) corresponding to the end of the pac gene (cf. FIG. 29, 1 st PCR).

As regards the oriT gene, it was amplified by PCR from the plasmid pPM803 (P. Mazodier et al., 1989) using, as first primer, primer C (of sequence 5'-CACGACCCCATG<u>ACGGATCTTTTCCGCTGCAT</u>-3' (SEQ ID No. 128)), which comprises, at its 5' end, a 12 nucleotide sequence corresponding to a sequence downstream of the coding sequence of the pac gene (in bold) and a 20 nucleotide sequence corresponding to the start of the oriT sequence and, as second primer, primer D (of sequence 5'-GAGCCG<u>GATATC</u>ATCGGTCTTGCCTTGCTCGT-3' (SEQ ID No. 129)), which comprises the EcoRV restriction site (single underlined) and a 20 nucleotide sequence corresponding to the end of the oriT sequence (double underlined) (cf. FIG. 29, 2nd PCR).

The amplification product obtained with the primers A and B and that obtained with primers C and D have, at one of their ends, a common sequence of 24 nucleotides. A third PCR was carried out by mixing the two amplification products previously obtained and using, as primers, primers A and D (cf. FIG. 29, 3rd PCR). This made it possible to obtain an amplification product corresponding to the combination pac+oriT. This pac-oriT fragment was then cloned into the vector pGEM-T Easy (marketed by the company Promega (Madison, Wis., USA)), which made it possible to obtain the plasmid pGEM-T-pac-oriT. The insert of this plasmid was then subcloned into the cosmid pWED1. For this, the plasmid pGEM-pac-oriT was digested with the EcoRV enzyme and the EcoRV insert containing the combination pac+oriT was inserted into the cosmid pWED1 opened beforehand with the HpaI enzyme. The cosmid thus obtained was named pWED2 (cf. FIG. 30).

This cosmid makes it possible to facilitate the inactivation of genes in Streptomyces. Specifically, it carries the oriT sequence, which allows its introduction by conjugation into Streptomyces from a suitable strain of E. coli, but also a gene for resistance to an antibiotic imparting a detectable phenotype in Streptomyces. Such a cosmid containing large inserts of genomic DNA of Streptomyces ambofaciens can be used in gene inactivation experiments.

Thus, a cosmid derived from pWED2 containing the target gene may, for example, be introduced into the E. coli strain KS272 containing the plasmid pKOBEG (cf. Chaveroche et al. 2000) and a cassette will be introduced into the target gene according to the technique described by Chaveroche et al. 2000. The cosmid obtained by this technique (cosmid in which the target gene is inactivated) may then be introduced into an E. coli strain such as the S17.1 strain or any other strain making it possible to transfer plasmids containing the oriT sequence to Streptomyces by conjugation.

After conjugation between E. coli and Streptomyces, clones of Streptomyces in which the wild-type copy of the target gene will have been replaced with the interrupted copy may be obtained as described in example 2.

The resistance gene expressed in *Streptomyces*, present on this new cosmid, is the pac gene of *Streptomyces* alboniger (J. Vara et al., 1985; Lacalle et al., 1989), which encodes puromycin N-acetyltransferase and which imparts puromycin resistance. In gene inactivation experiments, the clones in which a double recombination event has taken place will be sought. These clones will have eliminated the cosmid pWED2 and will therefore have become sensitive to puromycin again.

18.2 Construction of a Genomic DNA Library of the *Streptomyces ambofaciens* Strain OSC2 in *E. coli* in the Cosmid pWED2

The genomic DNA of the *Streptomyces ambofaciens* strain OSC2 was partially digested with the BamHI restriction enzyme so as to obtain DNA fragments of between approximately 35 and 45 kb in size. These fragments were then cloned into the cosmid pWED2, the latter having been digested beforehand with BamHI, and then treated with alkaline phosphatase. The ligation mixture was then encapsidated in vitro in lambda phage particles using the "Packagene® Lambda DNA packaging system" marketed by the company Promega (Madison, Wis., USA) according to the manufacturer's recommendations. The phage particles obtained were used to infect the *E. coli* strain SURE® marketed by the company Stratagene (LaJolla, Calif., USA). The clones were selected on LB medium+ampicillin (50 µg/ml), the cosmid pWED2 imparting ampicillin resistance.

EXAMPLE 19

Isolation of Cosmids of the New Library Covering the Region of the Biosynthetic Pathway for Spiramycins. Subcloning and Sequencing of Fragments of these Cosmids 19.1 Hybridization on Colonies of the Genomic Library of *Streptomyces ambofaciens* OSC2:

Cosmids of the new library of *Streptomyces ambofaciens* OSC2 (cf. example 18) covering orf1* to orf10 * or a part or all of orf1 to orf25c, or a region more upstream of orf25c, were isolated. For this, successive hybridizations on the colonies of *E. coli* obtained according to example 18 were performed using the following 3 probes (cf. FIG. 31):

The first probe used corresponds to a DNA fragment of approximately 0.8 kb amplified by PCR using as matrix the cosmid pSPM5, and the following primers:

```
ORF23c:
5'-ACGTGCGCGGTGAGTTCGCCGTTGC-3'    (SEQ ID No. 130)
and

ORF25c:
5'-CTGAACGACGCCATCGCGGTGGTGC-3'.   (SEQ ID No. 131)
```

The PCR product thus obtained contains a fragment of the start of orf23c, orf24c in its entirety and the end of orf25c (cf. FIG. 31, probe I).

The second probe used corresponds to a DNA fragment of approximately 0.7 kb amplified by PCR using as matrix the total DNA of the *S. ambofaciens* strain ATCC23877, and the following primers:

```
ORF1*c:
5'-GACCACCTCGAACCGTCCGGCGTCA-3'    (SEQ ID No. 132)
and

ORF2*c:
5'-GGCCCGGTCCAGCGTGCCGAAGC-3'.     (SEQ ID No. 133)
```

The PCR product thus obtained contains a fragment of the end of orf1*c and of the start of orf2*c (cf. FIG. 31, probe II).

The third probe used corresponds to an EcoRI-BamHI fragment of approximately 3 kb containing orf1, orf2 and orf3 and obtained by digestion of the plasmid pOS49.99 (cf. FIG. 31, probe III).

Approximately 2000 clones of the library obtained in example 18.2 were transferred onto a filter for colony hybridization according to conventional techniques (Sambrook et al., 1989).

The first probe (cf. FIG. 31, probe I) was labeled with $^{32}$P by the random priming technique (kit marketed by the company Roche) and used for the hybridization on 2000 clones of the library, after transfer onto a filter. The hybridization was carried out at 65° C. in the buffer described by Church & Gilbert (Church & Gilbert, 1984). Two washes were carried out in 2×SSC, 0,1% SDS at 65° C., the first for 10 minutes and the second for 20 minutes, and a third wash lasting 30 minutes was then carried out in 0.2×SSC, 0.1% SDS at 65° C. Under these hybridization and washing conditions, 20 clones out of the 2000 hybridized exhibited a strong hybridization signal with the first probe. These 20 clones were cultured in LB medium+ampicillin (50 µg/ml) and the corresponding 20 cosmids were extracted by alkaline lysis (Sambrook et al., 1989) and then digested with the BamHI restriction enzyme. The digestion products were then separated on agarose gel, transferred onto a nylon membrane and hybridized with the first probe (cf. above: the PCR product ORF23c-ORF25c, probe I) under the same conditions as above. Twelve cosmids contained a BamHI fragment which hybridized strongly with the probe used. These 12 cosmids were named pSPM34, pSPM35, pSPM36, pSPM37, pSPM38, pSPM39, pSPM40, pSPM41, pSPM42, pSPM43, pSPM44 and pSPM45. The profiles, after digestion with BamHI, of these 12 cosmids were compared with one another and with that of the cosmid pSPM5. In addition, PCR amplification experiments using various primers corresponding to various genes already identified in the orf1-orf25c region made it possible to position the insert of some of these cosmids with respect to one another and to also determine the location of these inserts in the already known orf1-orf25c region (cf. FIG. 32). The cosmid pSPM36 was more particularly chosen since it was liable to contain a large region upstream of orf25c (cf. FIGS. 31 and 32).

Next, using the same conditions as those described above, the 2000 clones of the library of *Streptomyces ambofaciens* OSC2 were hybridized with the second probe corresponding to the PCR product: ORF1*c-ORF2*c (cf. FIG. 31, probe II). This hybridization made it possible to isolate cosmids whose insert is located in the region from orf1*c to orf10*c. Under the hybridization conditions used, 16 clones out of the 2000 hybridized exhibited a strong hybridization signal with this second probe. These 16 clones were cultured in LB medium+ampicillin (50 µg/ml) and the corresponding 16 cosmids were extracted by alkaline lysis (Sambrook et al., 1989) and then digested with the BamHI restriction enzyme. The digestion profiles (after digestion with BamHI) of these 16 cosmids were compared with one another and with that of the cosmid pSPM7. PCR amplification experiments with the primers ORF1*c and ORF2*c made it possible to choose two cosmids which clearly contained the orf1*c and orf2*c genes and the profiles of which had common bands but also different bands. In addition, other PCR amplification experiments using various primers corresponding to various genes already identified in the region orf1*c to orf10*c made it possible to position the insert of these cosmids with respect to one another and to also determine the location of these inserts in the already known region orf1*c to orf10*c (cf. FIG. 32). The two cosmids more particularly selected were named pSPM47 and pSPM48 (cf. FIG. 32).

Using the same conditions as those described above, the 2000 clones of the library of Streptomyces ambofaciens OSC2 were also hybridized with the third probe corresponding to the EcoRI-BamHI DNA fragment of the plasmid pOS49.99 (cf. FIG. 31 probe III). This hybridization made it possible to isolate the cosmids containing the region from orf1 up to orf3 and liable to contain either a large part of the PKS genes or a large part of the genes orf1 to orf25c of the biosynthetic pathway for spiramycins. Under these hybridization conditions, 35 clones out of the 2000 hybridized exhibited a strong hybridization signal with the third probe. These 35 clones were cultured in LB medium+ampicillin (50 μg/ml) and the corresponding 35 cosmids were extracted by alkaline lysis (Sambrook et al., 1989) then digested with the BamHI restriction enzyme. The profiles, after digestion with BamHI, of these 35 cosmids were compared with one another and with that of the cosmid pSPM5. In addition, PCR amplification experiments using various primers corresponding to various genes already identified in the region orf1 to orf25c made it possible to verify that these cosmids clearly contained inserts originating from the region orf1 to orf25c and to position the inserts of these cosmids with respect to one another and with respect to the already known region orf1 to orf25c (cf. FIG. 32). Five cosmids were more particularly selected, they were named pSPM50, pSPM51, pSPM53, pSPM55 and pSPM56 (cf. FIG. 32).

19.2 Subcloning and Sequencing of a Part of the Insert of the Cosmid pSPM36

The probe of approximately 0.8 kb obtained by PCR with the primers ORF23c and ORF25c (cf. above and FIG. 31, probe I) was also used in Southern blotting experiments on the total DNA of S. ambofaciens OSC2 digested with the PstI, enzyme. Under the hybridization conditions described above, this probe reveals a single PstI fragment of approximately 6 kb when hybridized on the total DNA of S. ambofaciens OSC2 digested with the PstI enzyme. A PstI site exists in the region of orf23c (cf. SEQ ID No. 80), but no other PstI, site exists up to the end (BamHII site) of the known sequence (cf. SEQ ID No. 1). This PstI-BamHI fragment is approximately 1.4 kb in size. The 6 kb PstI, fragment hybridized on the total DNA of S. ambofaciens digested with the PstI, enzyme therefore contains a region of approximately 4.6 kb located upstream of orf25c. This region is liable to contain other genes the products of which are involved in the biosynthetic pathway for spiramycin. It was verified, by digestion, that the cosmid pSPM36 indeed contained this 6 kb PstI fragment. This fragment was isolated from pSPM36, with the aim of determining the sequence further upstream of orf25c. For this, the cosmid pSPM36 was digested with the PstI restriction enzyme. The PstI-PstI fragment, approximately 6 kb in size, was isolated by electroelution from a 0.8% agarose gel and then cloned into the vector pBK-CMV (4512 bp) (marketed by the company Stratagene (La Jolla, Calif., USA)). The plasmid thus obtained was named pSPM58 (cf. FIG. 33) and the sequence of its insert was determined. The sequence of this insert is given in SEQ ID No. 134. However, not all the sequence was determined and a gap of approximately 450 nucleotides remains, the part of the sequence undetermined was noted by a succession of "N"s in the corresponding sequence.

19.3 Analysis of the New Nucleotide Sequences Determination of the Open Reading Frames and Characterization of the Genes Involved in Spiramycin Biosynthesis The sequence of the insert of the cosmid pSPM58 obtained was analyzed using the FramePlot program (J. Ishikawa & K. Hotta 1999). This made it possible to identify, among the open reading frames, the open reading frames exhibiting a codon use typical of Streptomyces. This analysis made it possible to determine that this insert comprises 4 new ORFs upstream of orf25c (cf. FIG. 34). These genes were named orf26 (SEQ ID No. 107), orf27 (SEQ ID No. 109), orf28c (SEQ ID No. 111, the sequence of this orf was not completely determined since a gap of approximately 450 nucleotides remains in the sequencing of the insert of pSPM58, these 450 nucleotides appearing in the form of a series of "N"s in the sequence SEQ ID No. 111) and orf29 (the sequence of the latter orf was incomplete in this insert). The "c" added to the name of the gene means, for the ORF in question, that the coding sequence is in the reverse orientation (cf. FIG. 34).

The protein sequences deduced from these open reading frames were compared with those present in various databases using various programs: BLAST (Altschul et al., 1990) (Altschul et al., 1997), CD-search, (these two programs are accessible in particular from the National Center for Biotechnology Information (NCBI) (Bethesda, Md., USA)), FASTA ((W. R. Pearson & D. J. Lipman, 1988) and (W. R. Pearson, 1990) (this program is accessible in particular from the INFOBIOGEN resource center, Evry, France). These comparisons made it possible to formulate hypotheses regarding the function of the products of these genes and to identify those liable to be involved in spiramycin biosynthesis.

19.4 Subcloning and Sequencing of Another Part of the Insert of the Cosmid pSPM36.

The probe of approximately 0.8 kb obtained by PCR with the primers ORF23c and ORF25c (cf. above and FIG. 31, probe I) was also used in Southern blotting experiments on the total DNA of the strain OSC2 digested with the StuI enzyme. Under the hybridization conditions described above for this probe, this probe reveals a single StuI fragment of approximately 10 kb when hybridized on the total DNA of the strain OSC2 digested with the StuI enzyme. Given the presence of an StuI site in orf23c (cf. SEQ ID No. 80) and the location of this site relative to the PstI site, this 10 kb fragment includes all of the PstI fragment previously studied (insert of pSPM58) and makes it possible to have access to an approximately 4 kb region not yet studied (cf. FIG. 33). It was verified, by digestion, that the cosmid pSPM36 indeed contained this 10 kb StuI fragment. This fragment was isolated from the cosmid pSPM36, with the aim of determining the sequence of the end of orf29 and of other genes further upstream of orf29. For this, the cosmid pSPM36 was digested with the StuI restriction enzyme. The StuI-StuI fragment, approximately 10 kb in size, was isolated by electroelution from a 0.8% agarose gel and then cloned into the vector pBK-CMV (4512 bp) (marketed by the company Stratagene (La Jolla, Calif., USA)). The plasmid thus obtained was named pSPM72 (cf. FIG. 33). The latter was then digested with EcoRI (EcoRI site in the insert of pSPM58) and HindIII (HindII site in the multiple cloning site of the vector, immediately after the StuI site of end of the insert) (cf. FIG. 33). The EcoRI-HindIII DNA fragment thus obtained corresponds to a fragment of the insert of the plasmid pSPM72 (cf. FIG. 33) and was subcloned into the vector pBC-SK+(marketed by the company Stratagene (La Jolla, Calif., USA)) digested beforehand with EcoRI and HindIII. The plasmid thus obtained was named pSPM73 and the sequence of its insert was determined. The sequence of this insert is given in SEQ ID No.135.

An assembly of the sequences of the inserts of pSPM58 and pSPM73 is given in SEQ ID No. 106. This sequence starts from the PstI, site in orf23c (cf. SEQ ID No. 80) and continues to the StuI site in orf32c (cf. FIG. 34). Since the sequence of orf28c (SEQ ID No. 111) is not complete (cf. example 19.3), a region of approximately 450 nucleotides is not sequenced, these 450 nucleotides appear in the form of a series of "N"s in the sequence SEQ ID No. 106.

19.5 Analysis of the New Nucleotide Sequences, Determination of the Open Reading Frames and Characterization of the Genes Involved in Spiramycin Biosynthesis The partial sequence of the insert of the cosmid pSPM73 obtained was analyzed using the FramePlot program (J. Ishikawa & K. Hotta, 1999). This made it possible to identify, among the open reading frames, the open reading frames exhibiting a codon use typical of *Streptomyces*. This analysis made it possible to determine that this insert comprises 4 ORFs, one incomplete and three complete (cf. FIG. 34). The incomplete ORF corresponds to the 3' portion of the coding sequence of orf29, which made it possible to complete the sequence of this gene by virtue of the partial sequence of this same orf obtained during the sequencing of the insert of the plasmid pSPM58 (cf. examples 19.2 and 19.3); the combination of the two sequences thus made it possible to obtain the complete sequence of orf29. The 4 genes were thus named orf29 (SEQ ID No. 113), orf30c (SEQ ID No. 115), orf31 (SEQ ID No. 118) and orf32c (SEQ ID No. 120). The "c" added to the name of the gene means, for the ORF in question, that the coding sequence is in the reverse orientation (cf. FIG. 34).

The protein sequences deduced from these open reading frames (SEQ ID No. 114 for orf29, SEQ ID No. 116 and 117 for orf30c, SEQ ID No. 119 for orf31 and SEQ ID No. 121 for orf32c) were compared with those present in various databases using various programs: BLAST (Altschul et al., 1990) (Altschul et al., 1997), CD-search, (these two programs are accessible in particular from the National Center for Biotechnology Information (NCBI) (Bethesda, Md., USA)), FASTA ((W. R. Pearson & D. J. Lipman, 1988) and (W. R. Pearson, 1990) (this program is accessible in particular from the INFOBIOGEN resource center, Evry, France). These comparisons made it possible to formulate hypotheses regarding the function of the products of these genes and to identify those liable to be involved in spiramycin biosynthesis.

19.6 Subcloning and Sequencing of a Third Portion of the Insert of the Cosmid pSPM36.

A probe (0.8 kb DNA fragment) corresponding to a sequence internal to orf32c was obtained by PCR using, as matrix, the total DNA of the *Streptomyces ambofaciens* strain and the following primers

```
KF36:
5'- TTGCCGTAGCCGAGGACCAGCG-3'     (SEQ ID No. 151)
and

KF37:
5'- CACATGGCCCTGGAGGACCCTG-3'.    (SEQ ID No. 152)
```

The PCR product thus obtained represents an internal sequence of orf32c. This probe was used in Southern blotting experiments on the chromosomal DNA of the strain OSC2 and on the DNA of the cosmid pSPM36, digested with the PstI enzyme. Using the same hybridization conditions as those described above (cf. example 19.1), this probe reveals two PstI, fragments of approximately 3.4 kb and 2.5 kb when hybridized on the total DNA of the strain OSC2 and on the DNA of the cosmid pSPM36, digested with the PstI enzyme. Given the presence of a PstI site in the probe used, these results can be explained. The first DNA fragment, which has a size of approximately 3.4 kb, is a fragment the sequence of which is already entirely known. The sequence of the 2.5 kb fragment is only partially known, over a region of 700 bp. This fragment was isolated from the cosmid pSPM36 with the aim of determining the sequence of the end of orf32c and other genes upstream of the latter. For this, the cosmid pSPM36 was digested with the PstI restriction enzyme. The PstI-PstI fragment, approximately 2.5 kb in size, was isolated by purification from a 0.8% agarose gel and then cloned into the vector pBK-CMV (4518 bp) (marketed by the company Stratagene (La Jolla, Calif., USA)). The plasmid thus obtained was called pSPM79 (cf. FIG. 41) and the sequence of its insert was determined.

The sequence of orf28c (SEQ ID No. 111) was not complete (cf. example 19.3). Specifically, it had not been possible to determine a region of approximately 450 nucleotides, these 450 nucleotides appear in the form of a series of "N"s in the sequence SEQ ID No. 106. The sequence of the entire missing region was determined by resequencing this region. The sequence of the inserts of pSPM58 and pSPM73 was therefore determined in its entirety. The complete sequence of the coding portion of orf28c is given in SEQ ID No. 141 and the protein deduced from this sequence in SEQ ID No. 142. The sequence of the insert of the plasmid pSPM79 is given in SEQ ID No. 161.

An assembly of the sequences of the inserts of pSPM58, pSPM73 and pSPM79 is given in SEQ ID No. 140 (cf. FIG. 41). This sequence starts from the PstI site in orf23c (cf. SEQ ID No. 80) and continues up to the PstI site in orf34c (cf. FIG. 41).

19.7 Analysis of the New Nucleotide Sequences Determination of the Open Reading Frames and Characterization of the Genes which may be Involved in Spiramycin Biosynthesis.

The sequence of the insert of the plasmid pSPM79 obtained was analyzed using the FramePlot program (Ishikawa J & Hotta K. 1999). This made it possible to identify, among the open reading frames, the open reading frames exhibiting a codon usage typical of *Streptomyces*. This analysis made it possible to determine that this insert contains 3 ORFs, two incomplete (orf32c and orf34c) and one complete (orf33) (cf. FIG. 41).

The first incomplete ORF corresponds to the 5' portion of the coding sequence of orf32c. This made it possible to complete the sequence of this gene by virtue of the partial sequence of this same orf obtained during the sequencing of the insert of the plasmid pSPM73 (cf. examples 19.4 and 19.5), the combination of the two sequences thus made it possible to obtain the complete sequence of orf32c. (SEQ ID No. 145). The "c" added to the name of the gene means, for the ORF in question, that the coding sequence is in the reverse orientation (cf. FIG. 41). The complete orf was called orf33 (SEQ ID No. 147). The third ORF was called orf34c (SEQ ID No. 149). The "c" added to the name of the gene means, for the ORF in question, that the coding sequence is in the reverse orientation (cf. FIG. 37). The comparisons performed between the product of this orf and the databanks suggest that the C-terminal portion of this protein is not in the product deduced from the nucleotide sequence and therefore that this orf is longer and continues beyond the region sequenced.

The protein sequences deduced from these open reading frames were compared with those present in various databases using various programs: BLAST (Altschul et al., 1990) (Altschul et al., 1997), CD-search (these two programs are accessible in particular from the National Center for Biotechnology Information (NCBI) (Bethesda, Md., USA)), FASTA ((Pearson W. R. & D. J. Lipman, 1988) and (Pearson W. R., 1990) (this program is accessible in particular from the INFOBIOGEN resource center, Evry, France). These comparisons made it possible to formulate hypotheses regarding the function of the products of these genes and to identify those which may be involved in spiramycin biosynthesis.

EXAMPLE 20

Analysis of the Production of Spiramycin Biosynthesis Intermediates 20.1 Sample Preparation:

The various strains to be tested were each cultured in seven 500 ml baffled Erlenmeyers containing 70 ml of MP5 medium (Pemodet et al., 1993). The Erlenmeyers were inoculated with $2.5 \times 10^6$ spores/ml of the various strains of *S. ambofaciens* and grown at 27° C. with orbital shaking at 250 rpm for 96 hours. The cultures corresponding to the same clone were pooled, optionally filtered through a pleated filter, and centrifuged for 15 min at 7000 rpm.

The pH of the must was then adjusted to 9 with sodium hydroxide and the supernatant was extracted with methyl isobutyryl ketone (MIBK). The organic phase (MIBK) was then recovered and evaporated. The dry extract was then taken up in 1 ml of acetonitrile, then diluted to 1/10 (100 μl qs 1 ml with water) before being used for the liquid chromatography/mass spectrometry (LC/MS) analyses.

20.2 Analysis of the Samples by LC/MS:

The samples were analyzed by LC/MS with the aim of determining the mass of the various products synthesized by the strains to be tested.

The high performance liquid chromatography column used is a Kromasil C8 150*4.6 mmm, 5 mmm, 100 Å column.

The mobile phase is a gradient consisting of a mixture of acetonitrile and an aqueous 0.05% trifluoroacetic acid solution, the flow rate is fixed at 1 ml/min. The temperature of the column oven is maintained at 30° C.

The UV detection at the column outlet was carried out at two different wavelengths: 238 nm and 280 nm.

The mass spectrometer coupled to the chromatography column is a Single Quadripole device marketed by the company Agilent, with cone voltages at 30 and at 70 V.

20.3 Analysis of the Biosynthesis Intermediates Produced by the Strain OS49.67:

The strain OS49.67 in which the orf3 gene is inactivated by an in-phase deletion does not produce spiramycins (cf. examples 6 and 15).

A sample was prepared according to the method described above (cf. paragraph 20.1) and was analyzed by LC/MS as described above (cf. paragraph 20.2).

More particularly, the analysis by chromatography was carried out in a solvent gradient with, as mobile phase: 20% of acetonitrile from time T=0 to 5min, then linear increase to 30% at T=35 minutes, followed by a plateau up to T=50 minutes.

Under these conditions, two products were more particularly observed: an absorbent at 238 nm (retention time of 33.4 min) and an absorbent at 280 nm (retention time of 44.8 min) (cf. FIG. 35). FIG. 35 shows the superposition of the HPLC chromatograms produced at 238 and 280 nm (top) and also the UV spectra of the molecules eluted at 33.4 minutes and 44.8 minutes (bottom).

The coupled mass spectrometry analysis conditions were as follows: the scanning is carried out in scan mode, covering a mass range of between 100 and 1000 Da. The gain of the electromultiplier was 1 V. As regards the electrospray source, the pressure of the nebulizing gas was 35 psig, the flow rate of the drying gas was 12.0 l. min$^{-1}$, the temperature of the drying gas was 350° C., and the capillary voltage was brought to +/− 3000 V. These experiments made it possible to determine the mass of the two products separated. These masses are, respectively, 370 g/mol for the product eluted first ([M−H$_2$O]$^+$=353 major product) and 368 g/mol for the second product ([M−H$_2$O]$^+$=351 major product).

In order to obtain the structure, the products mentioned above were isolated and purified under the following conditions: the mobile phase is a 70/30 (v/v) mixture of an aqueous 0.05% trifluoroacetic acid solution and acetonitrile. The chromatography is carried out in an isocratic system with a fixed flow rate of 1 ml/min. Under these conditions, the retention times of the 2 products are, respectively, 8 and 13.3 minutes. In addition, in this case, the sample prepared (cf. paragraph 20.1) is not diluted in water before injection of 10 μl.

The 2 products are recovered at the chromatographic column outlet and isolated under the following conditions: an Oasis HLB 1 cc 30 mg cartridge (Waters) is conditioned sequentially with 1 ml of acetonitrile, then 1 ml of water/acetonitrile (20 v/80 v) and 1 ml of 80/20 water/acetonitrile. The sample is then introduced and the cartridge washed successively with 1 ml of water/acetonitrile (95/5) and 1 ml of water/deuterated acetonitrile (95/5), then eluted with 600 μl of 40/60 water/deuterated acetonitrile. The solution recovered is then directly analyzed by NMR.

The NMR spectra obtained for these two compounds are as follows:

First product eluted: Platenolide A: (spectrum 9646V)

1H spectrum in CD3CN (chemical shifts in ppm): 0.90 (3H, t, J=6 Hz), 0.93 (3H, d, J=5 Hz), 1.27 (3H, d, J=5 Hz), between 1.27 and 1.40 (3H, m), 1.51 (1H, m), 1.95 (1H, m), 2.12 (1H, m), 2.30 (1H, d, J=12 Hz), 2.50 (1H, d, J=11 Hz), 2.58 (1H, dd, J=9 and 12 Hz), 2.96 (1H, d, J=7 Hz), 3.43 (3H, s), 3.70 (1H, d, J=9 Hz), 3.86 (1H, d, J=7 Hz), 4.10 (1H, m), 5.08 (1H, m), 5.58 (1H, dt, J=3 and 12 Hz), 5.70 (1H, dd, J=8 and 12 Hz), 6.05 (1H, dd, J=9 and 12 Hz), 6.24 (1H, dd, J=9 and 12 Hz).

Second product eluted: Platenolide B: (spectrum 9647V)

1H spectrum in CD3CN (chemical shifts in ppm): 0.81 (3H, t, J=6 Hz), 0.89 (1H, m), 1.17 (3H, d, J=5 Hz), 1.30 (4H, m), 1.47 (2H, m), 1.61 (1H, t, J=10 Hz), 2.20 (1H, m), 2.38 (1H, d, J=13 Hz), 2.52 (1H, m), 2.58 (1H, m), 2.68 (1H, dd, J=8 and 13 Hz), 3.10 (1H, d, J=7 Hz), 3.50 (3H, s), 3.61 (1H, d, J=8 Hz), 3.82 (1H, d, J=7 Hz), 5.09 (1H, m), 6,20 (1H, m), 6.25 (1H, dd, J=9 and 12 Hz), 6.58 (1H, d, J=12 Hz), 7.19 (1H, dd, J=9 and 12 Hz).

These experiments thus made it possible to determine the structure of the these two compounds. The first product eluted is platenolide A and the second is platenolide B; the deduced structure of these two molecules is given in FIG. 36.

It was also possible to determine, using the LC/MS technique combined with NMR, under conditions slightly different from those described above, but the setting up of which is well known to those skilled in the art, that the strain OS49.67 produces, in addition to platenolide A and B, a derivative of these two compounds. They are platenolide A+mycarose and platenolide B+mycarose (the structure of these two compounds is given in FIG. 40). The results of analysis of the must of the strain OS49.67 are given in table 42.

TABLE 42

Results of the LC/MS analysis of the must of the strain OS49.67

| Identity | [ ] (mg/l) | Ion masses | Max absorption |
|---|---|---|---|
| Platenolide A Exact mass = 370 | 16.1 | [M + Na]$^+$ 393.0 | 231 nm |

TABLE 42-continued

Results of the LC/MS analysis of the must of the strain OS49.67

| Identity | [ ] (mg/l) | Ion masses | Max absorption |
|---|---|---|---|
| Molecular formula = $C_{20}H_{34}O_6$ | | $[M + K]^+$ 408.9 $[M - H_2O + H]^+$ 353.0 $[2M + Na]^+$ 763.2 | |
| Platenolide B Exact mass = 368 Molecular formula = $C_{20}H_{32}O_6$ | 1.4 | $[M - H_2O + H]^+$ 351.0 $[M + Na]^+$ 391.0 $[M + K]^+$ 406.9 $[2M + Na]^+$ 759.1 | 283 nm |
| Platenolide A + 'mycarose' Exact mass = 514 Molecular formula = $C_{27}H_{46}O_9$ | 4.27 | $[M + Na]^+$ 537.0 $[M + K]^+$ 553.0 | 230 nm |
| Platenolide B + 'mycarose' Exact mass = 512 Molecular formula = $C_{27}H_{44}O_9$ | ND | $[M + Na]^+$ 535.0 $[M + K]^+$ 550.9 $[PlatB - H_2O + H]^+$ 350.9 | 284 nm |

20.4 Analysis of the Biosynthesis Intermediates Produced by the Strain SPM509:

The strain SPM509 in which the orf14 gene is inactivated (orf14::att3Ωaac−) does not produce spiramycins (cf. examples 13, 15 and 16). A sample was prepared according to the method described above (cf. paragraph 20.1) and was analyzed by LC/MS as described above (cf. paragraphs 20.2 and 20.3). Analysis of the biosynthesis intermediates present in the culture supernatant of the strain SPM509 cultured in MP5 medium showed that this strain produced only form B of platenolide ("platenolide B", cf. FIG. 36) and not form A ("platenolide A", cf. FIG. 36).

EXAMPLE 21

Interruption of the orf14 Gene in a Strain with a Knockout in the orf3 Gene (OS49.67)

The product of the orf14 gene is essential to spiramycin biosynthesis (cf. examples 13, 15 and 16: the strain SPM509 in which this gene is interrupted no longer produces spiramycins). Analysis of the biosynthesis intermediates present in the culture supernatant of the strain SPM509 cultured in MP5 medium showed that this strain produced only the form B of platenolide and not form A (cf. example 20). One of the hypotheses which may explain this observation is that the product of orf14 is involved in the conversion of form B of platenolide to form A via an enzymatic reduction step. To test this hypothesis, the orf14 gene was inactivated in a mutant no longer producing spiramycin, but producing forms A and B of platenolide. This is the case of the strain OS49.67 (cf. examples 6 and 20) in which the orf3 gene is inactivated by an in-phase deletion (Δorf3). To inactivate the orf14 gene in this strain, the plasmid pSPM509 was introduced by protoplast transformation of the strain OS49.67 (T. Kieser et al., 2000). The inactivation of the orf14 gene has already been described in the case of the strain OSC2 (cf. example 13) and the same procedure was carried out for the inactivation of the orf14 gene in the strain OS49.67. After transformation with the plasmid pSPM509, the clones were selected for their apramycin resistance. The apramycin-resistant clones were then subcultured respectively on medium with apramycin and on medium with hygromycin. The clones resistant to apramycin (ApraR) and sensitive to hygromycin (HygS) are in principle those in which a double crossing over event has occurred and in which the orf14 gene has been replaced with a copy of orf14 interrupted with the att3Ωaac− cassette. These clones were more particularly selected and the replacement of the wild-type copy of orf14 with the copy interrupted with the cassette was verified by hybridization. Thus, the total DNA of the clones obtained was digested with several enzymes, separated on agarose gel, transferred onto a membrane and hybridized with a probe corresponding to the att3Ωaac− cassette in order to verify that the gene replacement had indeed taken place. The verification of the genotype can also be carried out by any method known to those skilled in the art, and in particular by PCR using the appropriate oligonucleotides and sequencing of the PCR product.

A clone exhibiting the expected characteristics (Δorf3, orf14::att3Ωaac−) was more particularly selected and named SPM510. It was in fact possible to verify, by virtue of the two hybridizations, that the att3Ωaac− cassette was indeed present in the genome of this clone and that the digestion profile expected in the case of a replacement, subsequent to a double recombination event, of the wild-type orf14 gene with the copy interrupted with the att3Ωaac− cassette in the genome of this clone is indeed obtained.

EXAMPLE 22

Functional Complementation of the Interruption of the orf14 gene 22.1 Construction of the Plasmid pSPM519:

The orf14 gene was amplified by PCR using the following pair of oligonucleotides: EDR31: 5' CCCAAGCTTCT-GCGCCCGCGGGCGTGAA 3' (SEQ ID No. 136) and EDR37: 5' GCTCTAGAACCGTGTAGCCGCGCCCCGG 3' (SEQ ID No. 137) and, as matrix, the chromosomal DNA of the strain OSC2. The oligonucleotides EDR31 and EDR37 carry, respectively, the HindIII and XbaI restriction site (sequence in bold). The 1.2 kb fragment thus obtained was cloned into the vector pGEM-T easy (marketed by the company Promega (Madison, Wis., USA)), to give the plasmid pSPM515. This plasmid was then digested with the HindIII and XbaI restriction enzymes. The 1.2 kb HindIII/XbaI insert obtained was cloned into the vector pUWL201 (cf. example 17.1) digested beforehand with the same enzymes. The plasmid thus obtained was named pSPM519.

22.1 Transformation of the Strains SPM509 and SPM510 with Plasmid pSPM519:

The plasmid pSPM519 was introduced into the strains SPM509 (cf. example 13) and SPM510 (cf. example 17) by protoplast transformation (T. Kieser et al., 2000). After transformation, the clones were selected for their thiostrepton resistance. The clones were then subcultured on a medium containing thiostrepton.

The strain SPM509 is a spiramycin nonproducer strain (cf. examples 13, 15 and 16 and FIG. 24). The spiramycin production of the strain SPM509 transformed with the vector pSPM519 (strain named SPM509 pSPM519) was analyzed by culturing this strain in MP5 medium in the presence of thiostrepton. The culture supernatants were then analyzed by HPLC (cf examples 16. and 17). The results of this analysis are given in table 43, the data are expressed in mg per liter of supernatant. The results correspond to the total production of spiramycins (obtained by adding the production of spiramycin I, II and III). It was observed that the presence of the vector pSPM519 in the strain SPM509 restores the spiramycin production (cf. table 43).

TABLE 43

Spiramycin production of the strain SPM509 transformed with the vector pSPM519, (results expressed in mg/l of supernatant).

| Strain | Spiramycin production |
|---|---|
| SPM509 pSPM519 | 58 |

The strain SPM510 transformed with the plasmid pSPM519 was named SPM510 pSPM509.

EXAMPLE 23

Functional Complementation of the Interruption of the orf3 Gene by the tylB gene of S. fradiae 23.1 Construction of the Plasmid pOS49.52:

The plasmid pOS49.52 corresponds to a plasmid which allows expression of the TylB protein in S. ambofaciens. In order to construct it, the coding sequence of the tylB gene of S. fradiae (Merson-Davies & Cundliffe, 1994, GenBank accession number: U08223 (sequence of the region), SFU08223 (DNA sequence) and AAA21342 (protein sequence)) was introduced in the plasmid pKC1218 (Bierman et al., 1992, Kieser et al., 2000, a strain of E. coli containing this plasmid is accessible in particular from the ARS (NRRL) Agricultural Research Service Culture Collection) (Peoria, Ill., USA), under the number B-14790). In addition, this coding sequence was placed under the control of the ermE* promoter (cf. above, in particular example 17.1, Bibb et al., 1985, Bibb et al., 1994).

23.1 Transformation of the Strain OS49.67 with the Plasmid pOS49.52:

The strain OS49.67 in which the orf3 gene is inactivated by an in-phase deletion does not produce spiramycins (cf. examples 6 and 15). The plasmid pOS49.52 was introduced into the strain OS49.67 by protoplast transformation (T. Kieser et al., 2000). After transformation, the clones were selected for their apramycin resistance. The clones were then subcultured on a medium containing apramycin. A clone was more particularly selected and was named OS49.67 pOS49.52.

As was demonstrated above, the strain OS49.67 does not produce spiramycins (cf. examples 6 and 15). The spiramycin production of the strain OS49.67 transformed with the vector pOS49.52 was analyzed by the technique described in example 15. It was thus possible to demonstrate that this strain has a spiramycin producer phenotype. Thus, the TylB protein allows functional complementation of the interruption of the orf3 gene.

EXAMPLE 24

Improvement of Spiramycin Production by Overexpression of the orf28c Gene 24.1 Construction of the Plasmid pSPM75:

The orf28c gene was amplified by PCR using a pair of oligonucleotides comprising a HindIII restriction site or a BamHI restriction site. These primers have the following sequence:

KF30:
(SEQ ID No. 138)
5' AAGCTTGTGTGCCCGGTGTACCTGGGGAGC 3'
with a HindIII restriction site
(which is shown in bold)

KF31:
(SEQ ID No. 139)
5' GGATCCCGCGACGGACACGACCGCCGCGCA 3'
with the BamHI restriction site
(which is shown in bold)

The primers KF30 and KF31 carry, respectively, the HindIII and BamHI restriction sites (sequence in bold). The pair of primers KF30 and KF31 makes it possible to amplify a DNA fragment approximately 1.5 kb in size containing the orf28c gene, using as matrix the cosmid pSPM36 (cf. above). The 1.5 kb fragment thus obtained was cloned into the vector pGEM-T easy (marketed by the company Promega (Madison, Wis., USA)) to give the plasmid pSPM74. The plasmid pSPM74 was then digested with the HindIII and BamHI restriction enzymes and the approximately 1.5 kb HindIII/BamHI insert obtained was subcloned into the vector pUWL201 (cf. example 17.1) digested beforehand with the same enzymes. The plasmid thus obtained was named pSPM75; it contains all the coding sequence of orf28c placed under the control of the ermE* promoter.

24.2 Transformation of the Strain OSC2 with the Plasmid pSPM75:

The plasmid pSPM75 was introduced into the strains OSC2 by protoplast transformation (T. Kieser et al., 2000). After protoplast transformation, the clones were selected for their thiostrepton resistance. The clones were then subcultured on a medium containing thiostrepton and the transformation with the plasmid was verified by plasmid extraction. Two clones were more particularly selected and named OSC2/pSPM75(1) and OSC2/pSPM75(2).

A sample of the strain OSC2/pSPM75(2) was deposited with the Collection Nationale de Cultures de Microorganismes (CNCM) [National Collection of Cultures and Microorganisms] Pasteur Institute, 25, rue du Docteur Roux 75724 Paris Cedex 15, France, on Oct. 6, 2003 under the registration number I-3101.

In order to test the effect of overexpression of the orf28c gene on spiramycin production, the spiramycin production of the OSC2/pSPM75(1) and OSC2/pSPM75(2) clones was tested by the technique described in example 15. Analysis of the spiramycin production of the strain OSC2 was also carried out in parallel for comparison. It was thus possible to observe that the presence of the plasmid pSPM75 significantly increases the spiramycin production of the strain OSC2. This demonstrates than overexpression of orf28c leads to an increase in spiramycin production and confirms its role as a regulator.

The spiramycin production of the OSC2/pSPM75(1) and OSC2/pSPM75(2) clones was also analyzed by HPLC (in the same way as in example 17.2). Analysis of the spiramycin production of the strain OSC2 was also carried out in parallel for comparison. The results of this analysis are given in table 44, the data are expressed in mg per liter of supernatant. The results correspond to the total production of spiramycins (obtained by adding the production of spiramycin I, II and III).

TABLE 44

Spiramycin production of the strains derived from OSC2 transformed with pSPM75, (results expressed in mg/l).

| Strain | Spiramycins |
|---|---|
| OSC2 | 50 |
| OSC2/pSPM75(1) | 120 |
| OSC2/pSPM75(2) | 155 |

Thus, it is observed that the presence of the plasmid pSPM75 significantly increases the spiramycin production of the strain OSC2. This clearly demonstrates that overexpression of orf28c has a positive effect on the spiramycin production.

EXAMPLE 25

Analysis of the Production of Spiramycin Biosynthesis Intermediates by a Strain which has been Inactivated in the orf8 Gene:

The strain OS49.107, in which the orf8 gene is inactivated by insertion of the Ωhyg cassette, does not produce spiramycins (cf. examples 7 and 15). The orf8 gene encodes a protein exhibiting relatively strong similarity with several aminotransferases and strongly suggests that the orf8 gene encodes a 4-aminotransferase responsible for the transamination reaction required for forosamine biosynthesis (cf. FIG. 6). It is therefore expected that spiramycin biosynthesis will be blocked at the forocidin stage (cf. FIG. 7). The strain OS49.107, which is a spiramycin non-producer, should therefore produce forocidin.

A sample of supernatant of the strain OS49.107 was prepared according to the method described above (cf. example 16, without MIBK extraction) and was analyzed by LC/MS as described above (cf. paragraph 20.2 and 20.3). In SIM mode, the mass 558 relating to the molecular ion of forocidin was selected and several peaks were detected. The presence of compounds of mass 558 is compatible with the hypothesis of orf8 having a role in forosamine synthesis.

EXAMPLE 26

Analysis of the Production of Spiramycin Biosynthesis Intermediates by a Strain which has been Inactivated in the orf12 Gene The strain SPM507, in which the orf12 gene is inactivated, does not produce spiramycins (cf. examples 11 and 15). The orf12 gene is thought to encode a 3,4-dehydratase responsible for the dehydration reaction required for forosamine biosynthesis (cf. FIG. 6). It is therefore expected that spiramycin biosynthesis will be blocked at the forocidin stage (cf. FIG. 7). The strain SPM507, which is a spiramycin non-producing strain, should therefore produce forocidin.

A sample of supernatant of the strain SPM507 was prepared according to the method described above (cf. example 16, without MIBK extraction) and was analyzed by LC/MS as described above (cf. paragraphs 20.2 and 20.3). Under these conditions, the forocidin retention time is approximately 12.9 minutes. In SIM mode, the mass 558 relating to the molecular ion $[M+H]^+$ of forocidin was selected and a peak was detected.

The presence of a compound at 558 makes it possible to validate the hypothesis that the product of orf12 has a role in spiramycin biosynthesis.

However, the forocidin is present in a relatively low amount and, under these conditions, a product which absorbs at 238 nm was more particularly observed (retention time of 17.1 min). The LC/MS analysis made it possible to determine the mass of this compound, which is 744.3 g/mol ($[M+H]^+$= 744.3 major product).

In order to obtain the structure, the products mentioned above were isolated and purified under the conditions described above (cf. paragraph 20.1). The organic phase (MIBK) is then recovered and evaporated. The dry extract is taken up with water and extracted with heptane. The aqueous solution is then extracted by binding to an Oasis HLB 1 g cartridge (Waters SAS, St-Quentin en-Yvelines, France). The compound is recovered by elution with a 30/70 water/acetonitrile mixture. This solution is then injected (100 µl) onto the analytical column and the fractions are recovered on an Oasis HLB 1 cc 30 mg cartridge (Waters). Before use, the Oasis HLB 1 cc 30 mg cartridges (Waters) are conditioned sequentially with acetonitrile, and then a water/acetonitrile mixture (20 v/80 v) and an 80/20 water/acetonitrile mixture.

The Oasis HLB 1 cc 30 mg cartridge (Waters) is then washed successively with 1 ml of water/acetonitrile (95/5) and 1 ml of water/deuterated acetonitrile (95/5), and then eluted with 600 µl of 40/60 water/deuterated acetonitrile. The recovered solution is then directly analyzed by NMR.

The NMR spectrum obtained for this compound is as follows (19312V NMR spectrum):

1H spectrum in CD3CN/D2O (chemical shifts in ppm): 0.92 (3H, d, J=6 Hz), 1.10 (1H, unresolved peak), 1.14 (3H, s), 1.17 (3H, d, J=6 Hz), 1.22 (3H, d, J=6 Hz), 1.25 (3H, d, J=6 Hz), 1.40 (1H, unresolved peak), 1.75 (1H, dd, J=12 and 2 Hz), 1.81 (1H, unresolved peak), 1.90 (1H, d, J=12 Hz), 2.05 (1H, unresolved peak), 2.12 (3H, s), 2.15 (1H, unresolved peak), 2.35 (2H, unresolved peak), 2.45 (6H, broad s), 2.53 (1H, unresolved peak), 2.64 (1H, dd, J=12 and 9 Hz), 2.80 (1H, dd, J=9 and 16 Hz), 2.95 (1H, d, J=8 Hz), 3.23 (2H, unresolved peak), 3.34 (1H, d, J=7 Hz), 3.45 (3H, s), 3.49 (1H, unresolved peak), 3.93 (1H, dd, J=7 and 3 Hz), 4.08 (1H, unresolved peak), 4.37 (1H, d, J=6 Hz), 4.88 (1H, unresolved peak), 5.05 (2H, unresolved peak), 5.65 (2H, unresolved peak), 6.08 (1H, dd, J=8 and 12 Hz), 6.40 (1H, dd, J=12 and 9 Hz), 9.60 (1H, s).

These experiments thus made it possible to determine the structure of this compound, this structure is given in FIG. 38.

EXAMPLE 27

Analysis of the Production of Spiramycin Biosynthesis Intermediates by a Strain which has been Inactivated in the orf5* Gene The strain SPM501 has the genotype orf6*::att1Ωhyg+. By virtue of the polar effect of the insertion of the att1Ωhyg+ cassette into the orf 6* gene, it was possible to determine that the orf5* gene is essential to the spiramycin biosynthesis pathway. Specifically, insertion of the excisable cassette into the coding portion of the orf6* gene leads to complete arrest of spiramycin production by virtue of a polar effect on the expression of the orf5* gene. However, once the inserted cassette has been excised (and therefore when only the orf6* gene is inactivated, cf. examples 14 and 15), production of spiramycin I is restored. This demonstrates that the orf5* gene is essential to spiramycin biosynthesis since its inactivation leads to a complete arrest of spiramycin production.

The orf5* gene encodes a protein exhibiting relatively strong similarity with several O-methyltransferases. The orf5* gene is thought to be an O-methyltransferase involved in platenolide biosynthesis. To verify this hypothesis, LC/MS and NMR analytical experiments were carried out on a strain of *S. ambofaciens* of genotype orf6*::att1Ωhyg+, obtained from a strain which overproduces spiramycins.

A sample of the supernatant of this strain was prepared according to the method described above (cf. example 16, without MIBK extraction) and was analyzed by LC/MS as described above (cf. paragraph 20.2 and 20.3). However, the column used is an X-Terra column (Waters SAS, St-Quentin en-Yvelines, France), and the cone voltage of the spectrometer is set at 380V so as to obtain fermentation of the compound analyzed. Under these conditions, a product for which the retention time is approximately 13.1 minutes is observed. The mass spectrum of this compound has an appearance similar to that of spiramycin I, but the molecular ion is 829. The difference in mass of 14 compared with the mass of spiramycin can be explained by the absence of methyl group on the oxygen borne by carbon No. 4 of the lactone ring (the structure of this compound is given in FIG. 39). The presence of a compound at 829 makes it possible to validate the hypothesis that orf5* has a role in spiramycin biosynthesis. Using a microbiological test carried out on a sensitive strain of *M. luteus* (cf. example 15 and FIG. 18), it was demonstrated that the intermediate molecule (spiramycin minus methyl group, the structure of which is given in FIG. 39) produced by the strain orf6*::Ωhyg+ is much less active (by a factor of 10) than the spiramycin of origin with the methyl group at position 4.

EXAMPLE 28

Construction of New "Excisable Cassettes"

New excisable cassettes were constructed. These cassettes are very similar to the excisable cassettes already described in example 9. The main difference between the former cassettes and the new cassettes is the absence, in the latter, of the sequences corresonding to the ends of the Ω interposon, which sequences contain a transcription terminator originating from the T4 phage.

In the cassettes without terminator, the gene which confers the resistance to an antibiotic is flanked by the attR and attL sequences which allow the excision. The resistance gene is the aac(3)IV gene which encodes an acetyltransferase which confers apramycin resistance. This gene is present in the Ωaac cassette (GenBank accession number: X99313, Blondelet-Rouault, M. H. et al., 1997) and was amplified by PCR using, as matrix, the plasmid pOSK1102 (cf. above) and, as primers, the oligonucleotides KF42 and KF43 each containing the HindIII restriction site (in bold) (AAGCTT) in the 5' position.

```
KF42:
                                        (SEQ ID No. 153)
5'-AAGCTTGTACGGCCCACAGAATGATGTCAC-3'
and KF43:
                                        (SEQ ID No. 154)
5'-AAGCTTCGACTACCTTGGTGATCTCGCCTT-3'.
```

The PCR product obtained, of approximately 1 kb, was cloned into the *E. coli* vector pGEMT Easy, producing the plasmid pSPM83.

The vector pSPM83 was digested with the HindIII restriction enzyme. The HindIII-HindIII fragment of the insert was isolated by purification from a 0.8% agarose gel, and then cloned into the HindIII site located between the attL and attR sequences of the various plasmids carrying the various possible excisable cassettes (cf. example 9 and FIG. 27) so as to replace the HindIII fragment corresponding to Ωacc with the HindII fragment corresponding to the aac gene alone. This made it possible to obtain the att1acc, att2aac and att3aac cassettes (depending on the desired phase, cf. example 9). Depending on the orientation of the aac gene relative to the attL and attR sequences, att1acc+, att1acc−, att2aac+, att2aac−, att3aac+ and att3aac− are distinguished (according to the same conventions as those adopted in example 9).

EXAMPLE 29

Construction of a Strain of *S. ambofaciens* with a Knockout in the orf28c Gene:

The orf28c gene was inactivated using the excisable cassette technique. The excisable cassette att3aac+ (cf. example 28) was amplified by PCR using, as matrix, the plasmid pSPM101 (the plasmid pSPM101 is a plasmid derived from the vector pGP704Not (Chaveroche et al., 2000) (Miller V L & Mekalanos J J, 1988) in which the att3aac+ cassette has been cloned as an EcoRV fragment into the unique EcoRV site of pGP704Not) and using the following primers:

```
KF32:
                                        (SEQ ID No. 155)
5' CAACCGCTTGAGCTGCTCCATCAACTGCTGGGCCGAGGTATCGCGCG
CGCTTCGTTCGGGACGAA 3'
and KF33:
                                        (SEQ ID No. 156)
5' TGGGTCCCGCCGCGCGGCACGACTTCGACTCGCTCGTCTATCTGCCT
CTTCGTCCCGAAGCAACT 3'
```

The 39 nucleotides located at the 5' end of these oligonucleotides contain a sequence corresponding to a sequence in the orf28c gene and the 26 nucleotides located in the most 3' position (shown in bold and underlined above) correspond to the sequence of one of the ends of the excisable cassette att3aac+ The PCR product thus obtained was used to transform the hyper-recombinant *E. coli* strain DY330 (Yu et al., 2000) (this strain contains the exo, bet and gam genes of the lambda phage, integrated into its chromosome, these genes are expressed at 42° C., it was used in place of the *E. coli* strain KS272 (Chaveroche et al., 2000)) containing the cosmid pSPM36. Thus, the bacteria were transformed by electroporation with this PCR product and the clones were selected for their resistance to apramycin. The cosmids of the clones obtained were extracted and digested with the BamHI restriction enzyme with the aim of verifying that the digestion profile obtained corresponded to the profile expected if insertion of the cassette (att3aac+) into the orf28c gene had taken place, i.e. if there had indeed been homologous recombination between the ends of the PCR product and the target gene. The construct can also be verified by any method known to those skilled in the art, and in particular by PCR using the appropriate oligonucleotides and sequencing of the PCR product. A clone for which the cosmid has the expected profile was selected and the corresponding cosmid was called pSPM107. This cosmid is a derivative of pSPM36, in which orf28c is interrupted by the att3aac+ cassette. Insertion of the cassette is accompanied by a deletion in the orf28c gene, the interruption begins at the 28th codon of orf28c. After the cassette, there remains the last 137 codons of orf28c.

The cosmid pSPM107 was, in a first step, introduced into the *E. coli* strain DH5α, and then into the *Streptomyces ambofaciens* strain OSC2 by protoplast transformation. After transformation, the clones were selected for their resistance to apramycin. The apramycin-resistant clones were then subcultured respectively on medium with apramycin (antibiotic B) and on medium with puromycin (antibiotic A) (cf. FIG. 9). The clones resistant to apramycin (ApraR) and sensitive to puromycin (PuroS) are, in principle, those in which a double crossing over event has occurred and which possess the orf28c gene interrupted by the att3aac+ cassette. These clones were more particularly selected and the replacement of the wild-type copy of orf28c with the copy interrupted by the cassette was verified by hybridization. Thus, the total DNA of the clones obtained was digested with several enzymes, separated on agarose gel, transferred onto a membrane and hybridized with a probe corresponding to the att3aac+ cassette so as to verify the presence of the cassette at the expected locus in the genomic DNA of the clones obtained. The genotype can also be verified by any method known to those skilled in the art, and in particular by PCR using the appropriate oligonucleotides and sequencing of the PCR product.

A clone exhibiting the expected characteristics (orf28c::att3aac+) was more particularly selected and called SPM107. This clone therefore has the genotype: orf28c::att3aac+ and was called SPM107. In view of the orientation of the genes (cf. FIG. 3), it is pointless to excise the cassette to study the effect of the inactivation of orf28c. The fact that orf29 is oriented in the opposite direction to orf28c shows that these genes are not cotranscribed. The use of an excisable cassette makes it possible, on the other hand, to have the possibility of being rid of the selection marker at any time, in particular by transformation with the plasmid pOSV508.

In order to test the effect of turning off the orf28c gene on spiramycin production, the spiramycin production of the strain SPM107 was tested by the technique described in example 15. It was thus possible to demonstrate that this strain has a spiramycin non-producing phenotype. This demonstrates that the orf28c gene is a gene essential to spiramycin biosynthesis in *S. ambofaciens*.

EXAMPLE 30

Construction of a Strain of *S. ambofaciens* with Knockout in the orf31 gene:

The orf31 gene was inactivated using the excisable cassette technique. The excisable cassette att3aac+ was amplified by PCR using, as matrix, the plasmid pSPM101, and the oligonucleotides EDR71 and EDR72.

EDR71:
(SEQ ID No. 157)
5' CGTCATCGACGTGCGGGGAAGACAGAGGTGATACCGATGATCGCGCG CGCTTCGTTCGGGACGAA 3'

EDR72:
(SEQ ID No. 158)
5' GCCAGCACCTCGTCCAGCTGCTCGACGGAACTCACCCCCATCTGCCT CTTCGTCCCGAAGCAACT 3'

The 39 nucleotides located at the 5' end of these oligonucleotides contain a sequence corresponding to a sequence in the orf31 gene and the 26 nucleotides located in the most 3' position (shown in bold and underlined above) correspond to the sequence of one of the ends of the excisable cassette att3aac+.

The PCR product thus obtained was used to transform the *E. coli* strain KS272 containing the plasmid pKOBEG and the cosmid pSPM36, as described by Chaveroche et al. (Chaveroche et al., 2000) (cf. FIG. 12 for the principle, the plasmid pOS49.99 should be replaced with the cosmid pSPM36 and the plasmid obtained is no longer pSPM17 but pSPM543). Thus, the bacteria were transformed with this PCR product by electroporation and the clones were selected for their resistance to apramycin. The cosmids of the clones obtained were extracted and digested with several restriction enzymes with the aim of verifying that the digestion profile obtained corresponds to the profile expected if insertion of the cassette (att3aac+) into the orf31 gene has taken place, i.e. if there has indeed been homologous recombination between the ends of the PCR product and the target gene. The construct can also be verified by any method known to those skilled in the art, and in particular by PCR using the appropriate oligonucleotides and sequencing of the PCR product. A clone for which the cosmid has the expected profile was selected and the corresponding cosmid was called pSPM543.

This cosmid is a derivative of pSPM36, in which orf31 is interrupted by the att3aac+ cassette (cf. FIG. 12). The insertion of the cassette is accompanied by a deletion in the orf31 gene, the interruption begins at the thirty-sixth codon of orf31. After the cassette, there remain the last 33 codons of orf31.

The cosmid pSPM543 was introduced into the *Streptomyces ambofaciens* strain OSC2 (cf. above) by protoplast transformation (Kieser, T et al., 2000). After transformation, the clones were selected for their resistance to apramycin. The apramycin-resistant clones were then subcultured respectively on medium with apramycin (antibiotic B) and on medium with puromycin (antibiotic A) (cf. FIG. 9). The clones resistant to apramycin (ApraR) and sensitive to puromycin (PuroS) are, in principle, those in which a double crossing over event has occurred and which possess the orf31 gene interrupted by the att3aac+ cassette. These clones were more particularly selected and the replacement of the wild-type copy of orf31 with the copy interrupted by the cassette was verified by hybridization. Thus, the total DNA of the clones obtained was digested with several enzymes, separated on agarose gel, transferred onto membrane and hybridized with a probe corresponding to the att3aac+ cassette so as to verify the presence of the cassette at the expected locus in the genomic DNA of the clones obtained. A second hybridization was carried out using, as probe, a DNA fragment obtained by PCR and corresponding to a very large portion of the coding sequence of the orf31 gene.

The genotype can also be verified by any method known to those skilled in the art, and in particular by PCR using the appropriate oligonucleotides and sequencing of the PCR product.

A clone exhibiting the expected characteristics (orf31::att3aac+) was more particularly selected and called SPM543. It was in fact possible to verify, by virtue of the two hybridizations, that the att3aac+ cassette was indeed present in the genome of this clone and that the digestion profile expected in the case of a replacement, subsequent to a double recombination event, of the wild-type gene with the copy interrupted by the att3aac+ cassette in the genome of this clone was indeed obtained. This clone therefore has the genotype: orf31::att3aac+ and was called SPM543. In view of the orientation of the genes (cf. FIG. 3), it is pointless to excise the cassette to study the effect of the inactivation of orf31. The fact that orf32c is oriented in the opposite direction to orf31 shows that these genes are not cotranscribed. The use of an excisable cassette makes it possible on the other hand, to have the possibility of being rid of the selection marker at any time, in particular by transformation with the plasmid pOSV508.

In order to test the effect of turning off the orf31 gene on spiramycin production, the spiramycin production of the strain SPM543 was tested by the technique described in example 15. It was thus possible to demonstrate that this strain has a spiramycin non-producing phenotype. This demonstrates that the orf31 gene is a gene essential to spiramycin biosynthesis in *S. ambofaciens*.

EXAMPLE 31

Construction of a Strain of *S. amibofaciens* with a Knockout in the orf32c Gene:

The orf32c gene was inactivated using the excisable cassette technique. The excisable cassette att3aac+ was amplified by PCR using, as matrix, the plasmid pSPM101 and using the following primers:

KF52:
(SEQ ID No. 159)
5' GATCCGCCAGCCTCACGTCACGCCGCGCCGCCTCCCTGACATCGCGC GCGCTTCGTTCGGGACGAA 3'.
and KF53:
(SEQ ID No. 160)
5' GAGGCGGACGTCGGTACGCGGTGGGAGCCGGAGTTCGACAATCTGCC TCTTCGTCCCGAAGCAACT 3'.

The 40 nucleotides located at the 5' end of these oligonucleotides contain a sequence corresponding to a sequence in the orf32c gene and the 26 nucleotides located in the most 3' position (shown in bold and underlined above) correspond to the sequence of one of the ends of the excisable cassette att3aac+.

The PCR product thus obtained was used to transform the hyper-recombinant *E. coli* strain DY330 (Yu et al., 2000) containing the cosmid pSPM36. Thus, the bacteria were transformed with this PCR product by electroporation and the clones were selected for their resistance to apramycin. The cosmids of the clones obtained were extracted and digested with the BamHI restriction enzymes with the aim of verifying that the digestion profile obtained corresponds to the expected profile if insertion of the cassette (att3aac+) into the orf32c gene has occurred, i.e. if there has indeed been homologous recombination between the ends of the PCR product and the target gene. The construct can also be verified by any method known to those skilled in the art, and in particular by PCR using the appropriate oligonucleotides and sequencing of the PCR product. A clone for which the cosmid has the expected profile was selected and the corresponding cosmid was called pSPM106. This cosmid is a derivative of pSPM36, in which orf32c is interrupted by the att3aac+ cassette. The insertion of the cassette is accompanied by deletion in the orf32c gene, the interruption begins at the 112th codon of orf32c. After the cassette, there remains the last 91 codons of orf32c.

The cosmid pSPM106 was, in a first step, introduced into the *E. coli* strain DH5α, and then into the *Streptomyces ambofaciens* strain OSC2 by transformation. After transformation, the clones are selected for their resistance to apramycin. The apramycin-resistant clones are then subcultured respectively on medium with apramycin (antibiotic B) and on medium with puromycin (antibiotic A) (cf. FIG. 9). The clones resistant to apramycin (ApraR) and sensitive to puromycin (PuroS) are, in principle, those in which a double crossing over event has occurred and which possess the orf32c gene interrupted by the att3aac+ cassette. These clones were more particularly selected and the replacement of the wild-type copy of orf32c with the copy interrupted by the cassette was verified by hybridization. Thus, the total DNA of the clones obtained was digested with several enzymes, separated on agarose gel, transferred onto membrane and hybridized with a probe corresponding to the att3aac+ cassette so as to verify the presence of the cassette in the genomic DNA of the clones obtained. The genotype can also be verified by any method known to those skilled in the art, and in particular by PCR using the appropriate oligonucleotides and sequencing of the PCR product.

A clone exhibiting the expected characteristics (orf32c::att3aac+) was more particularly selected. This clone therefore has the genotype: orf32c::att3aac+ and was called SPM106. In view of the orientation of the genes (cf. FIG. 3), it is pointless to excise the cassette to study the effect of the inactivation of the orf32c. The fact that orf33 is oriented in the opposite direction to orf32c shows that these genes are not cotranscribed. The use of an excisable cassette makes it possible, on the other hand, to have the possibility of being rid of the selection marker at any time, in particular by transformation with the plasmid pOSV508.

In order to test the effect of turning off the orf32c gene on spiramycin production, the spiramycin production of the strain SPM106 was tested by the technique described in example 15. It was thus possible to demonstrate that this strain has a spiramycin-producing phenotype. This demonstrates that the orf32c gene is not a gene essential to spiramycin biosynthesis in *S. ambofaciens*.

List of the Constructs Described in the Present Application

List of abbreviations: Am: Ampicillin; Hyg: Hygromycin; Sp: Spiramycin;

Ts: Thiostrepton; Cm: Chloramphenicol. Kn: Kanamycin, Apra: apramycin.

| Construct name | Selection marker | Main characteristics | Reference |
| --- | --- | --- | --- |
| pWE15 | Am | | (Wahl, et al., 1987) |
| pWED1 | Am | pWE15 in which a 4.1 kb HpaI—HpaI fragment has been deleted | (Gourmelen et al., 1998) |
| pOJ260 | Apra | Conjugative, nonreplicative in *Streptomyces* | (Bierman et al., 1992) |
| pHP45 Ωhyg | Hyg | Ωhyg cassette in pHP45. | (Blondelet-Rouault et al., 1997) |
| pKC505 | Apra | Cosmid | (Richardson MA et al., 1987) |
| pIJ486 | Ts | *Streptomyces* multicopy replicative plasmid | (Ward et al., 1986) |
| pOSint3 | Am | ptrc-xis-int in pTrc99A | (Raynal et al., 1998) |
| pWHM3 | Am, Ts | *E. coli*/*Streptomyces* replicative shuttle vector | (Vara et al., 1989) |

-continued

| Construct name | Selection marker | Main characteristics | Reference |
|---|---|---|---|
| pKOBEG | Cm | | (Chaveroche et al., 2000) |
| pGP704Not | Am | | (Chaveroche et al., 2000) |
| pMBL18 | Am | | (Nakano et al., 1995) |
| pGEM-T Easy | Am | E. coli vector for cloning PCR products | Mezei et al., 1994 |
| pOS49.1 | Am | pWED1 with insert at the BamHI site | Example 2 |
| pOS49.11 | Am | SacI fragment of pOS49.1 in pUC19. | Example 2 |
| pOSC49.12 | Ch | XhoI fragment of pOS49.11 in pBC SK+ | Example 2 |
| pOS49.14 | Cm, Hyg | pOSC49.12 with the orf3 gene interrupted wit the Ωhyg cassette | Example 2 |
| pOS49.16 | Apra, Hyg | Insert of pOS49.14 in pOJ260 | Example 2 |
| pOS49.28 | Cm | 3.7 kb BamHI-PstI fragment of pOS49.1 in pBC SK+ | Example 3 |
| pOS44.1 | Apra, Sp | pKC505 containing in insert imparting spiramycin resistance in S. griseofuscus | (Pernodet et al., 1999) |
| pOS44.2 | Ts, Sp | 1.8 kb Sau3AI fragment of pOS44.1 in pIJ486 | Example 3 |
| pOS44.4. | Am | Insert of pOS44.2 in pUC19 | Example 3 |
| pSPM5 | Am | pWED1 with S. ambofaciens DNA insert at the BamHI site | Example 3 |
| pSPM7 | Am | pWED1 with S. ambofaciens DNA insert at the BamHI site | Example 3 |
| pOSK1205 | Hyg | pBK-CMV in which hyg replaces neo | Example 5 |
| pOS49.67 | Apra | EcoRI-SacI fragment of pOS49.1, comprising an internal deletion of 504 nucleotides, in pOJ260 | Example 6 |
| pOS49.88 | Am | 3.7 kb PstI-EcoRI fragment of pOS49.1 in pUC19 | Example 7 |
| pOS49.106 | Am | pO49.88 with hyg in orf8 (hyg and orf8 in the same orientation) | Example 7 |
| pOS49.120 | Am | pOS49.88 with hyg in orf8 (hyg and orf8 in opposite orientations) | Example 7 |
| pOS49.107 | Apra, Hyg | Insert of pOS49.106 in pOJ260 | Example 7 |
| pOS49.32 | Am, Kn | 1.5 kb fragment within orf10, in pCR2.1-TOPO | Example 8 |
| pOS49.43 | Am, Kn | pOS49.32 with hyg in orf10 (hyg and orf10 in the same orientation) | Example 8 |
| pOS49.44 | Am, Kn | pOS49.32 with hyg in orf10 (hyg and orf10 in opposite orientations) | Example 8 |
| pOS49.50 | Apra, Hyg | Insert of pOS49.43 in pOJ260 | Example 8 |
| pWHM3Hyg | Am, Hyg | pWHM3 in which tsr is replaced with hyg | Example 10 |
| pOSV508 | Am, Ts | ptrc-xis-int in pWHM3 | Example 9 |
| patt1Ωhyg+ | Cm, Hyg | att1Ωhyg+ cassette in pBC SK+ in which the HindIII site has been deleted | Example 9 |
| patt3Ωaac− | Cm, Gn | att3Ωaac− cassette in pBC SK+ in which the HindIII site has been deleted | Example 9 |
| pOSV510 | Am, Hyg | pro pra-Amh in pWHM3Hyg | Example 10 |
| pOS49.99 | Am | 4.5 kb EcoRI-BamHI fragment of pSPM5 in pUC19 | Example 10 |
| pOSK1102 | Am, Apra | pGP704 Not containing the att3Ωaac− cassette | Example 10 |
| pSPM17 | Am, Apra | pOS49.99 in which orf2 is interrupted with the att3Ωaac− cassette | Example 10 |
| pSPM21 | Hyg, Apra | pOSK1205 containing the EcoRI-XbaI insert of pSPM17 (in which orf2 is interrupted with the att3Ωaac− cassette) | Example 10 |
| pSPM502 | Am | 15.1 kb BglII fragment of pSPM7 in pMBL18 | Example 11 |
| pSPM504 | Hyg | Insert of pSPM502 in pOSK1205 | Example 11 |
| pSPM507 | Hyg, Apra | pSPM504 in which orf12 is interrupted with the att3Ωaac− cassette | Example 11 |
| pSPM508 | Hyg, Apra | pSPM504 in which orf13c is interrupted with the att3Ωaac− cassette | Example 12 |
| pSPM509 | Hyg, Apra | pSPM504 in which orf14 is interrupted with the att3Ωaac− cassette | Example 13 |
| pBXL1111 | Am | 1.11 kb fragment containing orf6* amplified by PCR from pSPM7, in the vector pGEM-T Easy | Example 14 |
| pBXL1112 | Am, Hyg | pBXL1111 into which the att1Ωhyg+ cassette has been introduced after deletion of 120 bp in the coding sequence of the orf6* gene | Example 14 |
| pBXL1113 | Apra, Hyg | 3.7 kb PstI insert of pBXL1112 in pOJ260 | Example 14 |
| pSPM520 | Am | PCR fragment amplified by the oligonucleotides EDR39-EDR42 in pGEM-T Easy | Example 17 |
| pSPM521 | Am | PCR fragment amplified by the oligonucleotides EDR40-EDR42 in pGEM-T Easy | Example 17 |
| pSPM522 | Am | PCR fragment amplified by the oligonucleotides EDR41-EDR42 in pGEM-T Easy | Example 17 |
| pUWL201 | Am, Ts | | (Doumith et al., 2000) |
| pSPM523 | Am, Ts | HindIII-BamHI fragment of the insert of the plasmid pSPM520 in the vector pUWL201 | Example 17 |
| pSPM524 | Am, Ts | HindIII-BamHI fragment of the insert of the plasmid pSPM521 in the vector pUWL201 | Example 17 |
| pSPM525 | Am, Ts | HindIII-BamHI fragment of the insert of the plasmid pSPM522 in the vector pUWL201 | Example 17 |

| Construct name | Selection marker | Main characteristics | Reference |
|---|---|---|---|
| pSPM527 | Am | pSPM521 with reading frame shift at the XhoI site | Example 17 |
| pSPM528 | Am, Ts | HindIII-BamHI fragment of the insert of the plasmid pSPM527 in the vector pUWL201 | Example 17 |
| pVF 10.4 | | | (Vara et al., 1985; Lacalle et al., 1989) |
| pPM803 | Ts | | (Mazodier, P. et al., 1989) |
| pGEM-T-pac-oriT | Am | pac-oriT cassette (amplified by PCR from pVF 10.4 and pPM803) in pGEM-T Easy | Example 18 |
| pWED2 | Am | pac-oriT cassette obtained from pGEM-T-pac-oriT inserted into pWED1 | Example 18 |
| pSPM34 | Am | pWED2 with insert at the BamHI site | Example 19 |
| pSPM35 | Am | pWED2 with insert at the BamHI site | Example 19 |
| pSPM36 | Am | pWED2 with insert at the BamHI site | Example 19 |
| pSPM37 | Am | pWED2 with insert at the BamHI site | Example 19 |
| pSPM38 | Am | pWED2 with insert at the BamHI site | Example 19 |
| pSPM39 | Am | pWED2 with insert at the BamHI site | Example 19 |
| pSPM40 | Am | pWED2 with insert at the BamHI site | Example 19 |
| pSPM41 | Am | pWED2 with insert at the BamHI site | Example 19 |
| pSPM42 | Am | pWED2 with insert at the BamHI site | Example 19 |
| pSPM43 | Am | pWED2 with insert at the BamHI site | Example 19 |
| pSPM44 | Am | pWED2 with insert at the BamHI site | Example 19 |
| pSPM45 | Am | pWED2 with insert at the BamHI site | Example 19 |
| pSPM47 | Am | pWED2 with insert at the BamHI site | Example 19 |
| pSPM48 | Am | pWED2 with insert at the BamHI site | Example 19 |
| pSPM50 | Am | pWED2 with insert at the BamHI site | Example 19 |
| pSPM51 | Am | pWED2 with insert at the BamHI site | Example 19 |
| pSPM52 | Am | pWED2 with insert at the BamHI site | Example 19 |
| pSPM53 | Am | pWED2 with insert at the BamHI site | Example 19 |
| pSPM55 | Am | pWED2 with insert at the BamHI site | Example 19 |
| pSPM56 | Am | pWED2 with insert at the BamHI site | Example 19 |
| pSPM58 | Kn | Approximately 6 kb PstI—PstI fragment of the insert of pSPM36 in pBK-CMV | Example 19 |
| pSPM72 | Kn | Approximately 10 kb StuI—StuI fragment of the insert of pSPM36 cloned into pBK-CMV | Example 19 |
| pSPM73 | Cm | EcoRI-HindIII fragment of the insert of pSPM72 in pBC-SK+ | Example 19 |
| pSPM515 | Am | PCR fragment amplified by EDR31-EDR37 in pGEM-T easy | Example 22 |
| pSPM519 | Am, Ts | HindIII/XbaI insert of pSPM515 in pUWL201 | Example 22 |
| pOS49.52 | Apra | Coding sequence of tylB under the control of the ermE* promoter in the plasmid pKC1218 | Example 23 |
| pSPM74 | Am | PCR fragment amplified by KF30-KF31 in pGEM-T easy | Example 24 |
| pSPM75 | Am, Ts | HindIII/BamHI insert of pSPM74 in pUWL201 | Example 24 |
| pSPM79 | Kn | Approximately 2.5 kb PstI—PstI fragment of the insert of pSPM36 in pBK-CMV | Example 19 |
| pSPM83 | Am | PCR fragment amplified by KF42-KF43 in pGEM-T easy | Example 28 |
| pSPM107 | Am, Apra | pSPM36 in which orf28c is interrupted with the att3aac+ cassette | Example 29 |
| pSPM543 | Am, Apra | pSPM36 in which orf31 is interrupted with the att3aac+ cassette | Example 30 |
| pSPM106 | Am, Apra | pSPM36 in which orf32c is interrupted with the att3aac+ cassette | Example 31 |

Depositing of Biological Material

The following organisms were deposited with the Collection Nationale de Cultures de Microorganismes [National Collection of Cultures and Microorganisms] (CNCM), 25 rue du Docteur Roux, 75724 Paris Cedex 15, France, on Jul. 10, 2002, according to the provisions of the Treaty of Budapest.

Strain OSC2 under the registration number I-2908.
Strain SPM501 under the registration number I-2909.
Strain SPM502 under the registration number I-2910.
Strain SPM507 under the registration number I-2911.
Strain SPM508 under the registration number I-2912.
Strain SPM509 under the registration number I-2913.
Strain SPM21 under the registration number I-2914.
Strain SPM22 under the registration number I-2915.
Strain OS49.67 under the registration number I-2916.
Strain OS49.107 under the registration number I-2917.
*Escherichia Coli* strain DH5α containing the plasmid pOS44.4, under the registration number I-2918.

The following organisms were deposited with the Collection Nationale de Cultures de Microorganismes (CNCM), 25 rue du Docteur Roux, 75724 Paris Cedex 15, France, on Feb. 26, 2003, according to the provisions of the Treaty of Budapest.

Strain SPM502 pSPM525 under the registration number I-2977.

The following organisms were deposited with the Collection Nationale de Cultures de Microorganismes (CNCM), Pasteur Institute, 25 rue du Docteur Roux, 75724 Paris Cedex 15, France, on Oct. 6, 2003, according to the provisions of the Treaty of Budapest.

Strain OSC2/pSPM75(2) under the registration number I-3101.

All the publications and patents cited are incorporated into the present application by way of reference.

Bibliography:

Altschul S F, Gish W, Miller W, Myers E W, Lipman D J. Basic local alignment search tool. *J Mol Biol.* (1990). 215 (3):403-410.

Altschul S F, Madden T L, Schaffer A A, Zhang J, Zhang Z, Miller W, Lipman D J. Gapped BLAST and PSI-BLAST: a new generation of protein database search programs. *Nucleic Acids Res.* (1997). 25 (17):3389-402.

Amann, E., Ochs, B. and Abel, K. J. Tightly regulated tac promoter vectors useful for the expression of unfused and fused proteins in *Escherichia coli Gene* (1988) 69 (2), 301-315.

Arisawa, A., Kawamura, N., Tsunekawa, H., Okamura, K., Tone, H. and Okamoto, R. Cloning and nucleotide sequences of two genes involved in the 4"-O-acylation of macrolide antibiotics from *Streptomyces thermotolerans. Biosci. Biotechnol. Biochem.* (1993). 57 (12): 2020-2025.

Arisawa A, Kawamura N, Takeda K, Tsunekawa H, Okamura K, Okamoto R. Cloning of the macrolide antibiotic biosynthesis gene acyA, which encodes 3-O-acyltransferase, from *Streptomyces thermotolerans* and its use for direct fermentative production of a hybrid macrolide antibiotic. *Appl Environ Microbiol.* (1994). 60 (7):2657-2660.

August, P. R., Tang, L., Yoon, Y. J., Ning, Streptomyces, Mueller, R., Yu, T. W., Taylor, M., Hoffinann, D., Kim, C. G., Zhang, X., Hutchinson, C. R. and Floss, H. G. Biosynthesis of the ansamycin antibiotic rifamycin: deductions from the molecular analysis of the rif biosynthetic gene cluster of *Amycolatopsis mediterranei* S699. *Chem. Biol.* (1998) 5 (2), 69-79.

Ausubel Fred M., Brent Roger, Kingston Robert E., Moore David D., Seidman J. G., Smith John A., Struhl Kevin (Editeurs). Current Protocols in Molecular Biology, published by John Wiley & Sons Inc. Current Protocols Customer Service, 605 Third Avenue, 9th Floor New York, N.Y. 10158 USA (updated edition, March 2002).

Baltz R H, McHenney M A, Cantwell C A, Queener S W, Solenberg P J. Applications of transposition mutagenesis in antibiotic producing streptomycetes. *Antonie Van Leeuwenhoek.* (1997). 71 (1-2): 179-187.

Bate N, Butler A R, Gandecha A R, Cundliffe E. Multiple regulatory genes in the tylosin biosynthetic cluster of *Streptomyces fradiae. Chem Biol.* (1999). 6 (9): 617-624.

Bate, N., Butler, A. R., Smith, I. P. and Cundliffe, E. The mycarose-biosynthetic genes of *Streptomyces fradiae*, producer of tylosin. *Microbiology* (2000). 146 (Pt 1), 139-146.

Bayley C., Morgan, Dale E. C., Ow D. W. Exchange of gene activity in transgenic plants catalysed by the Cre-lox site specific system. *Plant Mol. Biol* (1992). 18: 353-361.

Bentley, S. D., Chater, K. F., Cerdeno-Tarraga, A. M., Challis, G. L., Thomson, N. R., James, K. D., Harris, D. E., Quail, M. A., Kieser, H., Harper, D., Bateman, A., Brown, S., Chandra, G., Chen, C. W., Collins, M., Cronin, A., Fraser, A., Goble, A., Hidalgo, J., Hornsby, T., Howarth, S., Huang, C. H., Kieser, T., Larke, L., Murphy, L., Oliver, K., O'Neil, S., Rabbinowitsch, E., Rajandream, M. A., Rutherford, K., Rutter, S., Seeger, K., Saunders, D., Sharp, S., Squares, R., Squares, S., Taylor, K., Warren, T., Wietzorrek, A., Woodward, J., Barrell, B. G., Parkhill, J. and Hopwood, D. A. Complete genome sequence of the model actinomycete *Streptomyces coelicolor* A3(2). *Nature* (2002). 417 (6885), 141-147.

Bibb M J, Findlay P R, Johnson M W. The relationship between base composition and codon usage in bacterial genes and its use for the simple and reliable identification of protein-coding sequences. *Gene.* (1984) 30 (1-3): 157-166.

Bibb M J, Janssen G R, Ward J M. Cloning and analysis of the promoter region of the erythromycin resistance gene (ermE) of *Streptomyces erythraeus. Gene.* (1985). 38 (1-3): 215-26.

Bibb M J, White J, Ward J M, Janssen G R. The mRNA for the 23S rRNA methylase encoded by the ermE gene of *Saccharopolyspora erythraea* is translated in the absence of a conventional ribosome-binding site. *Mol Microbiol.* (1994). 14 (3): 533-45.

Bierman M, Logan R, O'Brien K, Seno E T, Rao R N, Schoner B E. Plasmid cloning vectors for the conjugal transfer of DNA from *Escherichia coli* to *Streptomyces* spp. *Gene.* 1992;116(1):43-9.

Blondelet-Rouault M-H., Weiser J., Lebrihi A., Branny P. and Pemodet J-L. Antibiotic resistance gene cassettes derived from the Ω interposon for use in *E. coli* and *Streptomyces. Gene* (1997) 190:315-317.

Boccard F., Smokvina T., J.-L., Pernodet Fridmann A., and Guerineau M., Structural analysis of loci involved in pSAM2 site-specific integration in *Streptomyces. Plasmid,* (1989a). 21: 59-70.

Boccard F., Smokvina T., J.-L., Pemodet Fridmann A., and Guérineau M.. The integrated conjugative plasmid pSAM2 of *Streptomyces ambofaciens* is related to temperate bacteriophages. *EMBO J.* (1989b) 8: 973-980.

Brunelli J. P., Pall M. L., A series of Yeast/*E. coli* lambda expression vectors designed for directional cloning of cDNA and cre/lox mediated plasmid excision. Yeast. (1993) 9: 1309-1318.

Camilli A., Beattie D. T. and Mekalanos J. J. Use of genetic recombination as a reporter of gene expression. *Proc. Natl. Acad. Sci. USA* (1994) 91(7), 2634-2638.

Campelo, A. B. and Gil, J. A. The candicidin gene cluster from *Streptomyces griseus* IMRU 3570. *Microbiology* (2002) 148 (Pt 1), 51-59.

Carreras C, Frykman S, Ou S, Cadapan L, Zavala S, Woo E, Leaf T, Carney J, Burlingame M, Patel S, Ashley G, Licari P. *Saccharopolyspora erythraea*-catalyzed bioconversion of 6-deoxyerythronolide B analogs for production of novel erythromycins. *J Biotechnol.* (2002). 92(3): 217-28.

Chao K.-M., Pearson W. R., Miller W. Aligning two sequences within a specified diagonal band. *Comput. Appl. Biosci.* (1992) 8: 481-487.

Chater K. F. The improving prospects for yield increase by genetic engineering in antibiotic-producing *Streptomycetes. Biotechnology.* (1990). 8 (2): 115-121.

Chaveroche M K, Ghigo J M, d'Enfert C. A rapid method for efficient gene replacement in the filamentous fungus *Aspergillus nidulans. Nucleic Acids Res.* 2000; 28(22): E97.

Church G M, Gilbert W. Genomic sequencing. *Proc Natl Acad Sci USA.* (1984) 81 (7):1991-5.

Churchward G, Belin D, Nagamine Y. A pSC101-derived plasmid which shows no sequence homology to other commonly used cloning vectors. *Gene.* (1984) 31 (1-3): 165-71.

Comstock, L. E., Coyne, M. J., Tzianabos, A. O. and Kasper, D. L. Interstrain variation of the polysaccharide B biosynthesis locus of *Bacteroides fragilis:* characterization of the region from strain 638R *J. Bacteriol.* (1999). 181 (19): 6192-6196.

Cox K L, Baltz R H. Restriction of bacteriophage plaque formation in *Streptomyces* spp. *J. Bacteriol.* (1984) 159 (2): 499-504.

Dale E. C., Ow D. W., Gene transfer with subsequent removal of the selection gene from the host genome. *Proc. Natl. Acad. Sci. USA* (1991). 88: 10558-10562.

Doumith M, Weingarten P, Wehmeier U F, Salah-Bey K, Benhamou B, Capdevila C, Michel J M, Piepersberg W, Raynal M C. Analysis of genes involved in 6-deoxyhexose biosynthesis and transfer in *Saccharopolyspora erythraea*. *Mol Gen Genet.* (2000) 264(4): 477-485.

Draeger, G., Park,*Streptomyces*-H. H. and Floss, H. G. Mechanism of the 2-deoxygenation step in the biosynthesis of the deoxyhexose moieties of the antibiotics granaticin and oleandomycin *J. Am. Chem. Soc.* (1999) 121: 2611-2612.

Gandecha, A. R., Large, S. L. and Cundliffe, E. Analysis of four tylosin biosynthetic genes from the tylLM region of the *Streptomyces fradiae* genome. *Gene.* (1997). 184 (2) :197-203.

Geistlich, M., Losick, R., Tumer, J. R. and Rao, R. N. Characterization of a novel regulatory gene governing the expression of a polyketide synthase gene in *Streptomyces ambofaciens*. *Mol. Miciobiol.* (1992). 6 (14): 2019-2029.

Gourmelen A, Blondelet-Rouault M H, Pernodet J L. Characterization of a glycosyl transferase inactivating macrolides, encoded by gimA from *Streptomyces ambofaciens*. *Antimicrob Agents Chemother.* (1998). 42(10): 2612-9.

Huang X. and Miller W. A time-efficient, linear-space local similarity algorithm. *Adv. Appl. Math.* (1991). 12: 337-357.

Hara O and Hutchinson C R. Cloning of midecamycin (MLS)-resistance genes from *Streptomyces mycarofaciens, Streptomyces lividans* and *Streptomyces coelicolor* A3(2). *J Antibiot (Tokyo)*. (1990). 43 (8):977-991.

Hara O and Hutchinson C R. A macrolide 3-O-acyltransferase gene from the midecamycin-producing species *Streptomyces mycarofaciens*. *J Bacteriol*. (1992). 174 (15):5141-5144.

Hoffmeister D, Ichinose K, Domann S, Faust B, Trefzer A, Drager G, Kirschning A, Fischer C, Kunzel E, Bearden D, Rohr J and Bechthold A. The NDP-sugar co-substrate concentration and the enzyme expression level influence the substrate specificity of glycosyltransferases: cloning and characterization of deoxysugar biosynthetic genes of the urdamycin biosynthetic gene cluster. *Chem Biol.* (2000). 7 (11):821-831.

Hopwood, D. A. Future possibilities for the diskovery of new antibiotics by genetic engineering. In Beta-lactam antibiotics. Edited by M. R. J. Salton and G. D. Shockman. New York: Academic Press. (1981). 585-598.

Hopwood D. A., Malpartida F., Kieser H. M., Ikeda H., Duncan J., Fujii I., Rudd A. M., Floss H. G. and Omura S. Production of 'hybrid' antibiotics by genetic engineering. *Nature.* (1985a). 314 (6012): 642-644.

Hopwood D. A., Malpartida F., Kieser H. M., Ikeda H. and Omura S. (1985b) In *Microbiology* (ed S. Silver). *American Society for Microbiology,* Washington D.C., 409-413.

Houben Weyl, 1974, in Methode der Organischen Chemie [Methods in Organic Chemistry], E. Wunsch Ed., Volume 15-I and 15-II, Hutchinson, C. R. Prospects for the diskovery of new (hybrid) antibiotics by genetic engineering of antibiotic-producing bacteria. *Med Res Rev.* (1988). 8 (4): 557-567.

Hutchinson C. R., Borell C. W., Otten S. L., Stutzman-Engwall K. J. and Wang Y. Drug diskovery and development through the genetic engineering of antibiotic-producing microorganisms *J. Med. Chem.* (1989) 32 (5): 929-937.

Ishikawa J, Hotta K. FramePlot: a new implementation of the frame analysis for predicting protein-coding regions in bacterial DNA with a high G+C content. *FEMS Microbiol Lett.* (1999) 174(2):251-3.

Kieser, T, Bibb, M J, Buttner M J, Chater K F, Hopwood D A. Practical *Streptomyces* Genetics. 2000. The John Innes Foundation, Norwich UK.

Kuhstoss and al. Production of a novel polyketide through the construction of a hybrid polyketide synthase. *Gene.* (1996). 183(1-2): 231-236.

Lacalle R A, Pulido D, Vara J, Zalacain M, Jimenez A. Molecular analysis of the pac gene encoding a puromycin N-acetyl transferase from *Streptomyces alboniger. Gene.* (1989). 79(2):375-380.

Lakso M, Sauer B, Mosinger B Jr, Lee E J, Manning R W, Yu SH, Mulder K L, Westphal H. Targeted oncogene activation by site-specific recombination in transgenic mice. *Proc Natl Acad Sci USA.* (1992) 89 (14):6232-6.

Li, T. B., Shang, G. D., Xia, H. Z. and Wang, Y. G. Cloning of the sugar related biosynthesis gene cluster from *Streptomyces tenebrarius* H6. *Sheng Wu Gong Cheng Xue Bao* (2001). 17 (3): 329-331.

Ligon, J., Hill, S., Beck, J., Zirkle, R., Molnar, I., Zawodny, J., Money, S. and Schupp, T. Characterization of the biosynthetic gene cluster for the antifungal polyketide soraphen A from *Sorangium cellulosum* So ce26. *Gene* (2002). 285 (1-2), 257-267.

Liu L, Saevels J, Louis P, Nelis H, Rico S, Dierick K, Guyomard S, Roets E, Hoogmartens J. Interlaboratory study comparing the microbiological potency of spiramycins 1, II and III. *J Pharm Biomed Anal.* (1999). 20 (1-2):217-24.

Mazodier P, Petter R, Thompson C. Intergeneric conjugation between *Escherichia coli* and *Streptomyces* species. *J Bacteriol.* (1989). 171 (6):3583-5.

Merrifield R B, 1965a, *Nature,* 207(996): 522-523.

Merrifield R B., 1965b, *Science,* 150(693): 178-185.

Merson-Davies, L. A. and Cundliffe, E. Analysis of five tylosin biosynthetic genes from the tyllBA region of the *Streptomyces fradiae* genome, *Molecular microbiology.* (1994). 13 (2): 349-355.

Miller V L, Mekalanos J J. A novel suicide vector and its use in construction of insertion mutations: osmoregulation of outer membrane proteins and virulence determinants in *Vibrio cholerae* requires toxR. *J Bacteriol.* (1988) 170(6):2575-83.

Nakano, Y., Yoshida, Y., Yamashita, Y. & Koga, T. Construction of a series of pACYC-derived plasmid vectors. *Gene* (1995). 162: 157-8.

Nielsen H., Engelbrecht J., Brunak S. et von Heijne G. Identification of prokaryotic and eukaryotic signal peptides and prediction of their cleavage sites. *Protein Engineering.* (1997). 10: 1-6.

Oh S H, Chater K F. Denaturation of circular or linear DNA facilitates targeted integrative transformation of *Streptomyces coelicolor* A3(2): possible relevance to other organisms. *J Bacteriol.* 1997; 179 (1):122-7.

Olano C, Lomovskaya N, Fonstein L, Roll J T, Hutchinson C R. A two-plasmid system for the glycosylation of polyketide antibiotics: bioconversion of epsilon-rhodomycinone to rhodomycin D. *Chem Biol.* (1999). 6 (12): 845-55.

Omura S, Kitao C, Hamada H, Ikeda H. Bioconversion and biosynthesis of 16-membered macrolide antibiotics. X.

Final steps in the biosynthesis of spiramycin, using enzyme inhibitor: cerulenin. *Chem Pharm Bull (Tokyo)*. (1979a). 27(1): 176-82.

Omura S, Ikeda H, Kitao C. Isolation and properties of spiramycin I 3-hydroxyl acylase from *Streptomyces* and ambofaciens. *J Biochem (Tokyo)*. (1979b). 86(6): 1753-8.

Omura, S., Ikeda, H., Ishikawa, J., Hanamoto, A., Takahashi, C., Shinose, M., Takahashi, Y., Horikawa, H., Nakazawa, H., Osonoe, T., Kikuchi, H., Shiba, T., Sakaki, Y. and Hattori, M. Genome sequence of an industrial microorganism *Streptomyces avermitilis*: Deducing the ability of producing secondary metabolites. *Proc. Natl. Acad. Sci. U.S.A.* (2001). 98 (21), 12215-12220.

Pearson W. R. and D. J. Lipman. Improved Tools for Biological Sequence Analysis. *Proc. Natl. Acad. Sci. USA* 1988, 85: 2444-2448.

Pearson W. R. Rapid and Sensitive Sequence Comparison with FASTP and FASTA. *Methods in Enzymology*. 1990, 183: 63-98.

Pernodet J L, Simonet J M, Guerineau M. Plasmids in different strains of *Streptomyces ambofaciens*: free and integrated form of plasmid pSAM2. *Mol Gen Genet.* (1984);198 (1):35-41.

Pernodet J L, Alegre M T, Blondelet-Rouault M H, Guerineau M. Resistance to spiramycin in *Streptomyces ambofaciens*, the producer organism, involves at least two different mechanisms. *J Gen Microbiol.* (1993); 139 ( Pt 5):1003-11.

Pernodet J L, Fish S, Blondelet-Rouault M H, Cundliffe E. The macrolide-lincosamide-streptogramin B resistance phenotypes characterized by using a specifically deleted, antibiotic-sensitive strain of *Streptomyces lividans*. *Antimicrob Agents Chemother.* (1996), 40 (3): 581-5.

Pernodet J L, Gourmelen A, Blondelet-Rouault M H, Cundliffe E. Dispensable ribosomal resistance to spiramycin conferred by srmA in the spiramycin producer *Streptomyces ambofaciens*. *Microbiology*. (1999), 145 (Pt 9):2355-64.

Pfoestl, A., Hofinger, A., Kosma, P. and Messner, P. Biosynthesis of dTDP-3-acetamido-3,6-dideoxy-alpha-D-galactose in *Aneurinibacillus thermoaerophilus* L420-91T. *J. Biol. Chem.* (2003), 278 (29): 26410-26417.

Rao R N, Richardson M A, Kuhstoss S. Cosmid shuttle vectors for cloning and analysis of *Streptomyces* DNA. *Methods Enzymol.* (1987); 153: 166-98.

Raynal A, Tuphile K, Gerbaud C, Luther T, Guerineau M, and Pernodet J L. Structure of the chromosomal insertion site for pSAM2: functional analysis in *Escherichia coli*. *Molecular Microbiology* (1998) 28 (2) 333-342.

Redenbach, M., Kieser, H. M., Denapaite, D., Eichner, A., Cullum, J., Kinashi, H. and Hopwood, D. A. A set of ordered cosmids and a detailed genetic and physical map for the 8 Mb *Streptomyces coelicolor* A3(2) chromosome *Mol. Microbiol.* (1996). 21 (1): 77-96.

Richardson M A, Kuhstoss S, Solenberg P, Schaus N A, Rao R N. A new shuttle cosmid vector, pKC505, for streptomycetes: its use in the cloning of three different spiramycin-resistance genes from a *Streptomyces ambofaciens* library. *Gene.* (1987); 61 (3):231-41.

Robinson, J. A. Enzymes of Secondary Metabolism in Microorganisms. *Chem Soc Rev.* (1988). 17 :383-452.

Russell S H, Hoopes J L, Odell J T. Directed excision of a transgene from the plant genome. *Mol Gen Genet.* (1992). 234 (1): 49-59.

Sambrook J, Frisch E F, Maniatis T . Molecular Cloning: a laboratory manual $2^{nd}$ ed. Cold Spring Harbor Laboratory Press, Cold Spring Harbor, N.Y. USA (1989).

Schoner B, Geistlich M, Rosteck P Jr, Rao R N, Seno E, Reynolds P, Cox K, Burgett S and Hershberger C. Sequence similarity between macrolide-resistance determinants and ATP-binding transport proteins. *Gene.* (1992). 115 (1-2), 93-96.

Sezonov G, Hagege J, Pernodet J L, Friedmann A and Guerineau M. Characterization of pra, a gene for replication control in pSAM2, the integrating element of *Streptomyces ambofaciens*. *Mol Microbiol.* (1995). 17(3): 533-44.

Sezonov G., Blanc V., Bamas-Jacques N., Friedmann A., Pernodet J. L. and M. Guerineau, Complete conversion of antibiotic precursor to pristinamycin IIA by over expression of *Streptomyces pristinaespiralis* biosynthetic genes, *Nature Biotechnology.* (1997) 15: 349-353.

Sezonov G, Possoz C, Friedmann A, Pernodet J L, Guerineau M. KorSA from the *Streptomyces* integrative element pSAM2 is a central transcriptional repressor: target genes and binding sites. *J Bacteriol.* (2000). 182 (5):1243-50.

Simon R., Priefer U and Pühler. A broad host range mobilisation system for in vivo genetic engeneering: transposon mutagenesis in gram negative bacteria. *Bio/Technology* (1 983). 1: 784-791.

Simon, and al., Plasmid vectors for the genetic analysis and manipulation of rhizobia and other gram-negative bacteria, p. 640-659. In A. Weissbach, and H. Weissbach (eds.), Methods in enzymology, vol 118, Academic Press, Inc., Orlando, 1986

Summers, R. G., Donadio,*Streptomyces*, Staver, M. J., Wendt-Pienkowski, E., Hutchinson, C. R. and Katz, L. Sequencing and mutagenesis of genes from the erythromycin biosynthetic gene cluster of *Saccharopolyspora erythraea* that are involved in L-mycarose and D-desosamine production. *Microbiology* (1997). 143 (Pt 10): 3251-3262.

Van Mellaert L, Mei L, Lammertyn E, Schacht S, Anne J. Site-specific integration of bacteriophage VWB genome into *Streptomyces venezuelae* and construction of a VWB-based integrative vector. *Microbiology.* (1998). 144 ( Pt 12): 3351-8.

Vara J, Lewandowska-Skarbek M, Wang Y G, Donadio S, Hutchinson C R. Cloning of genes governing the deoxysugar portion of the erythromycin biosynthesis pathway in *Saccharopolyspora erythraea* (*Streptomyces erythreus*). *J Bacteriol.* (1989). 171(11): 5872-81.

Vara J, Malpartida F, Hopwood D A, Jimenez A. Cloning and expression of a puromycin N-acetyl transferase gene from *Streptomyces alboniger* in *Streptomyces lividans* and *Escherichia coli*. *Gene.* (1985). 33(2): 197-206.

Wahl, G. M., K. A. Lewis, J. C. Ruiz, B. Rothenberg, J. Zhao, and G. A. Evans. Cosmid vectors for rapid genomic walking, restriction mapping, and gene transfer. *Proc. Natl. Acad. Sci. USA* (1987). 84: 2160-2164.

Waldron, C., Matsushima, P., Rosteck, P. R., Broughton, M. C., Turner, J., Madduri, K., Crawford, K. P., Merlo, D. J. and Baltz, R. H. Cloning and analysis of the spinosad biosynthetic gene cluster of *Saccharopolyspora spinosa*(1) *Chem. Biol.* (2001) 8 (5): 487-499.

Walczak R J, Hines J V, Strohl W R, Priestley ND. Bioconversion of the anthracycline analogue desacetyladriamycin by recombinant DoxA, a P450-monooxygenase from *Streptomyces* sp. strain C5. *Org Lett.* (2001). 3 (15):2277-9.

Wang, Z. X., Li, S. M. and Heide, L. Identification of the coumermycin A(1) biosynthetic gene cluster of *Streptomyces rishiriensis* DSM 40489. *Antimicrob. Agents Chemother.* (2000) 44 (11), 3040-3048.

Ward, J. M., Janssen, G. R., Kieser, T, Bibb, M. J., Buttner, M. J. & Bibb, M. J. Construction and characterization of a series of multi-copy promoter-probe plasmid vectors for *Streptomyces* using the aminoglycoside phosphotransferase from Tn5 as indicator. *Mol Gen Genet* (1986). 203: 468-478.

Wehmeier U F. New multifunctional *Escherichia coli-Streptomyces* shuttle vectors allowing blue-white screening on XGal plates. *Gene.* (1995). 165(1): 149-150.

Wilms B, Hauck A, Reuss M, Syldatk C, Mattes R, Siemann M, Altenbuchner J. High-cell-density fermentation for production of L-N-carbamoylase using an expression system based on the *Escherichia coli* rhaBAD promoter. *Biotechnol Bioeng.* (2001). 73(2) :95-103.

Worley K. C., Wiese B. A., and Smith R. F. BEAUTY: An enhanced BLAST-based search tool that integrates multiple biological information resources into sequence similarity search results. *Genome Research* (1995). 5: 173-184.

Wu K, Chung L, Revill W P, Katz L and Reeves C D. The FK520 gene cluster of *Streptomyces hygroscopicus* var. *ascomyceticus* (ATCC 14891) contains genes for biosynthesis of unusual polyketide extender units. *Gene.* (2000). 251 (1): 81-90.

Xue Y, Zhao L, Liu H W and Sherman D H. A gene cluster for macrolide antibiotic biosynthesis in *Streptomyces venezuelae*: architecture of metabolic diversity. *Proc Natl Acad Sci USA.* (1998). 95 (21): 12111-12116.

Yu D, Ellis H M, Lee E C, Jenkins N A, Copeland N G et Court D L. An efficient recombination system for chromosome engineering in *Escherichia coli. Proc Natl Acad Sci USA.* (2000). 97(11): 5978-83.

We claim:

1. An isolated polynucleotide that encodes a polypeptide of the spiramycin biosynthesis pathway, wherein said polypeptide comprises the amino acid sequence SEQ ID NO:112 or 142.

2. A recombinant host cell transformed with the isolated polynucleotide of claim 1.

3. An isolated polynucleotide which is the full complement of one the polynucleotide of claim 1.

4. A recombinant DNA which comprises:
the isolated polynucleotide of claim 1 that can be obtained by polymerase chain reaction using the following pair of sequence primers:
5' AAGCTTGTGTGCCCGGTGTA.CCTGGGGGAGC 3' (SEQ ID NO: 138) and
5' GGATCCCGCGACGGACACGACCGCCGCGCA 3' (SEQ ID: 139).

5. A vector comprising the recombinant DNA of claim 4.

6. The vector of claim 5, which is an expression vector.

7. A method of producing a polypeptide comprising:
a) transforming a host cell with the expression vector of claim 6;
b) cultivating, in a suitable culture medium, said host cell;
c) recovering the conditioned culture medium or a cell extract; and
d) separating and purifying said polypeptide from said culture medium or from the cell extract obtained in step c).

8. A recombinant host cell into which the vector of claim 6 has been introduced.

9. An isolated polynucleotide that encodes a polypeptide of the spiramycin biosynthesis pathway, said polynucleotide comprises the nucleotide sequence of SEQ ID NO: 111.

10. A vector comprising the polynucleotide of claim 9.

11. A recombinant host cell into which the vector of claim 10 has been introduced.

12. The vector of claim 10, wherein said vector is selected from the group consisting of bacteriophage, plasmid, phagemid, integrative vector, fosmid, cosmid, shuttle vector, Bacterial Artificial Chromosome (BAC) and P1 Artificial Chromosome (PAC).

13. The vector of claim 12, wherein said vector is selected from the group consisting of pSPM36, pSPM58, pSPM74, pSPM75 and pSPM 107.

14. An isolated polynucleotide that encodes a polypeptide of the spiramycin biosynthesis pathway, wherein said polynucleotide comprises the nucleotide sequence of SEQ ID NO: 141.

15. A vector comprising the polynucleotide of claim 14.

16. A recombinant host cell into which the vector of claim 15 has been introduced.

17. The vector of claim 15, wherein said vector is selected from the group consisting of bacteriophage, plasmid, phagemid, integrative vector, fosmid, cosmid, shuttle vector, Bacterial Artificial Chromosome (BAC) and P1 Artificial Chromosome (PAC).

18. The vector of claim 17, wherein said vector is selected from the group consisting of pSPM36, pSPM58, pSPM74, pSPM75 and pSPM 107.

19. A strain of *Streptomyces ambofaciens*, which is the strain OSC2/pSPM75 or OSC2/pSPM75 deposited with the Collection Nationale de Cultures de Microorganismes under the accession number CNCM 1-3101.

* * * * *

UNITED STATES PATENT AND TRADEMARK OFFICE
CERTIFICATE OF CORRECTION

| | | |
|---|---|---|
| PATENT NO. | : 7,579,167 B2 | Page 1 of 3 |
| APPLICATION NO. | : 10/680860 | |
| DATED | : August 25, 2009 | |
| INVENTOR(S) | : Blondelet-Rouault et al. | |

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 291 days Delete the phrase "by 291 days" and insert -- by 623 days --.

In column 1, line 10, after "biosynthetic" delete "c".

In column 14, line 45-46, delete "orthologous" and insert -- Orthologous --, therefor.

In column 16, line 43, delete "tyIM1" and insert -- tyIMI --, therefor.

In column 20, line 8, delete "(Pemodet" and insert -- (Pernodet --, therefor.

In column 26, line 65, delete "orf53" and insert -- orf5 --, therefor.

In column 28, line 9, delete "orf" and insert -- orf7 --, therefor.

In column 35, line 24, delete "also." and insert -- also --, therefor.

In column 35, line 28, delete "fkbH" and insert -- fkbI --, therefor.

In column 36, line 7-8, delete "methoxyrnalonyl" and insert -- methoxymalonyl --, therefor.

In column 46, line 16, delete "(Pemodet" and insert -- (Pernodet --, therefor.

In column 46, line 35, delete "(Pemodet" and insert -- (Pernodet --, therefor.

In column 48, line 23, delete "111," and insert -- III, --, therefor.

Signed and Sealed this

Twenty-fourth Day of August, 2010

David J. Kappos
*Director of the United States Patent and Trademark Office*

CERTIFICATE OF CORRECTION (continued)
U.S. Pat. No. 7,579,167 B2

In column 48, line 43-44, delete "(Pemodet" and insert -- (Pernodet --, therefor.

In column 51, line 30, delete ".500," and insert -- 500, --, therefor.

In column 53, line 31, after "in" delete "25".

In column 54, line 6, delete "(Pemodet" and insert -- (Pernodet --, therefor.

In column 58, line 20, delete "(Pemodet" and insert -- (Pernodet --, therefor.

In column 62, line 41, delete "(Pemodet" and insert -- (Pernodet --, therefor.

In column 62, line 41-42, delete "(Pemodet" and insert -- (Pernodet --, therefor.

In column 81, line 62, delete "(Pemodet" and insert -- (Pernodet --, therefor.

In column 87, line 12, delete "for" and insert -- form --, therefor.

In column 87, line 38, delete "(Pemodet" and insert -- (Pernodet --, therefor.

In column 88, line 29, delete "HindII" and insert -- HindIII --, therefor.

In column 93, line 32, delete "PstI," and insert -- PstI --, therefor.

In column 93, line 37, delete "PstI," and insert -- PstI --, therefor.

In column 93, line 40, delete "PstI," and insert -- PstI --, therefor.

In column 93, line 41, delete "PstI," and insert -- PstI --, therefor.

In column 93, line 61, after "Sequences" insert -- , --.

In column 94, line 52, delete "(HindII" and insert -- (HindIII --, therefor.

In column 94, line 64, delete "PstI," and insert -- PstI --, therefor.

In column 95, line 59, delete "PstI," and insert -- PstI --, therefor.

In column 96, line 27, after "Sequences" insert -- , --.

In column 97, line 12, delete "(Pemodet" and insert -- (Pernodet --, therefor.

In column 106, line 8, delete "HindII" and insert -- HindIII --, therefor.

In column 115, line 22, delete "Hoffinann," and insert -- Hoffmann, --, therefor.

In column 116, line 15, delete "Pemodet" and insert -- Pernodet --, therefor.

In column 116, line 22, delete "Pemodet" and insert -- Pernodet --, therefor.

In column 117, line 18, delete "Tumer," and insert -- Turner, --, therefor.

In column 119, line 22, delete "Pemodet" and insert -- Pernodet --, therefor.

In column 119, line 26, delete "Pemodet" and insert -- Pernodet --, therefor.

In column 119, line 31, delete "Pemodet" and insert -- Pernodet --, therefor.

In column 119, line 50, delete "Pemodet" and insert -- Pernodet --, therefor.

In column 120, line 9, delete "Pemodet" and insert -- Pernodet --, therefor.

In column 120, line 16, delete "Pemodet" and insert -- Pernodet --, therefor.

In column 120, line 62, delete "Tumer," and insert -- Turner, --, therefor.

In column 449, line 25, in Claim 1, after "sequence" insert -- of --.

In column 449, line 25, in Claim 1, delete "NO:112" and insert -- NO: 112 --, therefor.

In column 449, line 30, in Claim 3, before "the" delete "one".

In column 449, line 35, in Claim 4, delete "A.C" and insert -- AC --, therefor.

In column 449, line 38, in Claim 4, delete "ID:" and insert -- ID NO: --, therefor.

In column 450, line 32, in Claim 13, delete "pSPM 107." and insert -- pSPM107. --, therefor.

In column 450, line 48, in Claim 18, delete "pSPM 107." and insert -- pSPM107. --, therefor.

In column 450, line 52, in Claim 19, delete "1-3101." and insert -- I-3101. --, therefor.

SEQUENCE LISTING

<160> NUMBER OF SEQ ID NOS: 161

<210> SEQ ID NO 1
<211> LENGTH: 30943
<212> TYPE: DNA
<213> ORGANISM: Streptomyces ambofaciens

<400> SEQUENCE: 1

```
gaattcggca attcccgggg cgccgggaaa ccggcacgcc attccgacca cggcaacggc      60
gtcggaccgg tcgtcactgc gggaaatcgc gagttctcca gacacctgca tccctcatat     120
gttcgccgta ccacgccgtg gcttttctgc cttttcttga tcttcccgag cgtacagcgg     180
gcgaactgcc gggcgacagg aacggccggt gaacgacaat caattgtgtc aagttcggag     240
attgtccacc gattctcgtc accggagacg gcgcgggatc atgcgggacc acacggcatc     300
gcaccaggtc cgcagggtcg gcgctccgac gtcccggccg gtcgcgcact ccggtgacct     360
gcacgcggag tcctgggcga gcggagaaga tttcagtacc tcgcggcgcg ggacaaccac     420
ttcgcgacga atatgtcagg tctccccgag cggtccgtgc cgccccgccc tgacccgtcc     480
gcgcccgtcc cgctccgccc cggtcgtcat ctcggccgga atttcagtcg gcagctcatt     540
gtgtcaggtt cgccttgccg acattctccg gagattccta agctctgccg gtaaccggga     600 ccgaaccac cgtgccgcgc gttcggtcca cacaccgctt ttcgaggagt ccgactgatg     660
ggtgaggccg tgacgggacc gatggagctg agcaaggacg cggacgcccg ggggctgctt     720
gagtggttcg cgtacaacag gacgcgtcat ccggtgttct gggacgagac ccgacaggcg     780
tggcaggtct tcggctacga cgactacgtg acggtgtcga caacccgca gttcttctcc     840 tcggacttca acatggtgat gccgacgccg cccgaactgg agatgatcat cggtccgggc     900
acgatcggcg cgctggaccc gcccgcgcac ggaccgatgc gcaagctggt gagccaggcg     960 ttcaccccc gacggatcgc ccggctggag cccagggtgc gcgcgatcac cgaggagctc    1020
ctggacaagg tggggcagca ggacgtcgtc gacgccgtgg gtgacctgtc ctacgcgctg    1080
ccggtcatcg tgatcgccga actgctgggc atacccgccg gcgaccgtga cctgttccgg    1140
gagtgggtcg acaccctgct gacgaacgag ggcctggagt acccgaacct cccggacaac    1200
```

```
ttcaccgaga cgatcgcgcc cgcgctcaag gagatgaccg actacctcct gaagcagatc   1260
cacgccaagc gggacgcgcc cgccgacgac ctggtcagcg ggctggtcca ggcggagcag   1320
gacggccgcc ggctgaccga cgtcgagatc gtcaacatcg tcgcgctgct cctgacggcg   1380
gggcacgtct cctccagcac cctgctcagc aacctgttcc tggtcctgga ggagaacccg   1440
caggcgctgg aggacctgcg ggccgatcgc tccctggtgc ccggcgcgat cgaggagacg   1500
ctgcgctacc gcagccccct caacaacatc ttccggttcg tcaaggagga caccaccgtc   1560
ctcggtccgc tcatggagaa gggccagatg gtgatcgcct ggagccagtc cgccaaccgg   1620
gacccccggc acttccccgga cccggacacc ttcgacatcc gccgctcgga cggcacccgg   1680
cacatggcct cgggcacgg catccaccac tgcctgggtg ccgccctcgc ccgcctggag   1740
ggcaaggtca tgctcgaact cctcctggac cgggtccaag gcttccgcat cgaccacgag   1800
cacaccgtgt tctacgaggc cgaccagctc actccgaagt acctgcccgt ccgggtcgac   1860
tggaactgaa cccgagggtc tcgtcccgga gtccagggcc gtcccgagcc ggccctggac   1920
ctcacgaccg cccgataagg agcgccgcca tcgccgagaa cacagccgag ctccctgccc   1980
ggcgggtcgg caggatcaag ccgtgccggc tgatcaggct cgagcagcac atcgacccgc   2040
gcggcagcct ctccgtgatc gagtccggcg tgaccgtgga cttccccgtc cgacgcgtct   2100
actacatgca tggccagacc cagtcctctc ccccgcgcgg cctgcacgcg caccgcaccc   2160
tggaacaact cgtcatcgcc gtccacggcg ccttctccat caccctcgac gacggcttcc   2220
agcacgccac ctaccgtctg gacgaacccg gagccggact ctgcatcggc ccatggtct   2280 ggcgcgtcct gaaggacttc gaccccgaca ccgtggccct ggtcctcgcc tcgcagcact   2340
acgaggagtc cgactactac cgcgactacg acaccttcct gcatgacgca cggagcctca   2400
catgaccatc cccttcctcg acgcgggcgc cggctaccgg gagttgcgag ccgagatcga   2460
cgcggccctg cagcgggtgt ccgcctccgg ccgctatctg ctcgacgcgg aactcgcggc   2520
cttcgaggag gagttcgccg cgtactgcga caacgaccac tgtgtggcgg tgggcagtgg   2580
ctgcgacgcg ctggagctgt ccctgcgggc gctggacatc ggtcccgggg acgaggtggt   2640
ggtgcccgcg cacaccttca tcgggacctg gctggccgtg tccgctaccg gggcacggcc   2700
ggtggccgtc gacccgacgc cggacgggct ctccctcgac ccggcgctgg tggaggcggc   2760 gctcaccct cggaccagag ccctgatgcc ggtgcacctg cacgggcacc cggccgacct   2820
cgacccgcta ctggcgatcg ccggacggca cggcctggcc gtggtcgagg acgccgcgca   2880
ggcccacggc gcccgttacc ggggccgcag gatcggctcg ggccacgtgg tcgcgttcag   2940
cttctacccc ggcaagaacc tcggcgccat ggggacggc ggcgcggtgg tcacgggtga   3000
ctccggtgtg gccgagcgga tccggttgct gcgcaactgc ggctcgcggg agaagtaccg   3060
gcacgaggtg cgctcgaccc actcccggct cgacgagttc caggcggccg tgctgcgggc   3120
caaactgccg cggctcgacg cgtggaacgc ccgccgggcc ggcacggccg aacggtacgg   3180
gcgggccctg ggtccggtac cgcagatcgc cgtcccggtc accgctccct gggccgaccc   3240
ggtgtggcac ctgtacgtga tccgctcgcg ggagcgcgac gagctgcgcc gccggctgga   3300
acgagccggg gtccagaccc tgatccacta ccccgtgccc ccgcaccggt cccggcctaa   3360
cgccgacgac ccggccggcg caccggcggg gaccacccg ctcagtgagc gcctggcggc   3420
gcagagcctc agccttcccc tgggaccgca cctcggggag gacgaggccc gcgccgtcgt   3480
ggcggcggtc cgggcggcgt ccgcagggct ggcggcgtac ccgacgccgg acggccagcg   3540
ttttcctcta gtgacggaga aacgatgacc gaggtcatgt cagggcgtcc cggaatgaaa   3600
```

```
gggatcatcc tcgcaggcgg cggagggacc cgcctacgcc ccttgaccgg cacgctgtcc    3660
aagcaactgc tgcccgtcta cgacaagccg atgatctact acccgctgtc cgtcctgatg    3720
ctgggcggca tccgcgagat cctcgtcgtc tcctccaccc agcacatcga gctgttccag    3780
cggctgctgg gcgacggctc ccgcctcggc ctcgacatca cctacgccga acaggccgag    3840
cccgagggca tagcgcaggc catcaccatc ggcaccgacc acatcggcga ctcaccggtc    3900
gcgctcatcc tgggcgacaa catcttccac ggccccggct tctcggccgt gctccagggc    3960
agcatccgcc acctcgacgg ctgtgtgctg ttcggctacc cggtcagcga cccgaagcgc    4020
tacggcgtcg gcgagatcga cgaccagggc gtactgctgt ccctggagga gaaaccggcc    4080
cggccccgct ccaacctcgc cgtcaccggc ctctacctct acgacaacga cgtggtcgac    4140
atcgccaaga acatccggcc ctcggcgcgc ggcgaactcg agatcacgga cgtcaacagg    4200
acctacctgg agcagaaacg cgcccggctc atcgaactgg ccacggctt cgcctggctc    4260
gacatgggca cccacgactc cctcctccag ggcggccagt acgtccagct catcgagcag    4320
cgccagggag tgcggatcgc ctgcatcgag gagatcgccc tgcgcatggg cttcatcgac    4380
gccgacaccc tccaccggct cggccgcgaa ctgggcacct ccggatacgg cgcgtacctg    4440
atggaggtgg ccacccgtgc aggcaccgaa tgagacgccg cgccggcccg cccgctccgc    4500
cggccgacgg ccgccggccc ggatcctcgt caccggggc gccggcttca tcggctcgcg    4560
cttcgtgaac gcgctgctgg acggctccct gccggagttc ggcaaacccg aggtgagggt    4620
gctcgacgcg ctcacctacg cgggcaacct ggccaatctg gccccggtgg gcgactgtcc    4680
ccggctgcgg atcttcccgg gggacatccg cgaccgcggc gcggtcaccc aggcgatggc    4740
gggggtcgac ctggtggtgc acttcgcggc cgagtcgcac gtggaccgct cgatcgacga    4800
cgccgacgcc ttcgtgcgca ccaacgtgct gggcacccag gtcctcctcc aggaggcact    4860
ggccgtacgc cccgggctgt tcgtgcacgt ctcgacggac gaggtgtacg gctccatcga    4920
ggaggggtcc tggcccgagg agcacccgct gaaccccaac tcgccctacg ccgcctcgaa    4980
ggcgtcctcc gacctgctgg cgctggccca ccaccgcacg cacggactgc cggtgtgcgt    5040
cacccgctgc tccaacaact acgggcccta ccagtacccg gagaagatca tcccgctgtt    5100
caccagcagc ctcctcgacg gcgggaccgt ccgctctac ggggacggcg gcaaccggcg    5160
cgactggctg cacgtggacg accactgccg gggcatcgcc ctggtggccc ggggcggccg    5220
gcccggcgag gtctacaaca tcggcggcgg caccgagctg agcaacgtcg agctcacgga    5280
gcgtctgctg aaactgtgcg gagccgactg gtcggcggtg cggcgggtgc ccgaccgcaa    5340
gggccacgac cggcgctact ccgtcgacta ccaagatc gcggacgagc tgggttacgc    5400
gccgcggatc accatcgacg aagggctgga gcggaccgtg cactggtacc gggagaaccg    5460
cgcgtggtgg gcgcccgcga agaggggcg atgacggtga cgaccgcatc cgtggacccg    5520
ctcgacctgt ggctccgccg gtaccagccg tccgcgtcac ccgccgtccg gctggtgtgc    5580
ttcccgcacg cgggcggctc ggcgagttcg ttcctgccgt tcaccggca gctgccggac    5640
cggatcgagg tcgtggccgt ccagtacccc gggcgccagg accgcaggag cgaaccgctg    5700
gtcgacacca tcgagggact ggccgagccc ctggccggcc tgctgaggc gcaggccggc    5760
cccccggtgg tgctgttcgg gcacagcatg ggcgcgctgt ggcctacga ggtcgcccgc    5820
gcgctccagc ggcggggagc ggctccggtg cgcctggtgg tctccgggcg ccgggccccc    5880
gccgtcgacc ggccgatgac cgtgcacctc tacgacgacg accggctggt cgaggaactc    5940
```

```
cgcaagctcg acggcaccga cagccaggtg ttcgccgatc cggagctgct ccggctggtg    6000
ctgcccgtga tccgcaacga ctaccgggcc gtggcggcct acgccaccg cccggggcg     6060 ccgctggact gccccctcac cgtgttcacc ggcgccgacg accccaccgt gaccgcggcc    6120
gaggcggcgg cctggcacga ggcggcgcg tccgacgtcg agacgcgcac cttccccggt    6180
ggccacttct tcccgtacca gcggaccgcg gaggtgtgcg gggccctggt cgacacgctc    6240
gagccgctgc tgtcggccgg gacgcgcggt gtccggcggg tccgcccggg gtgacgtggg    6300
cacggtcgag tacgccgtcc accggcgtac cgcggaacgg gtgagggtct ccgccgacac    6360
cctggacagc ccggtcaccg cgctggcgga ggtgccccgc tggctggagg aataccaccg    6420
ggcgcaccgc ttccacgtcg agccgatccc cttcgaccgg ctccggcggt ggtccttcga    6480
gccgggcacc ggcgacctgc ggcacgagac gggccgcttc ttctccgtgg aggggctgcg    6540
caccagctcg acgccgatc cggtcgcccg tgtccagccg atcatcgtgc agcccgaggt    6600
ggggctgctc ggcatcctgg cccgggagtt cgacggggtg ctgcacttcc tgatgcaggc    6660
caaacccgag cccggcaacg tcaacgggct gcagatctcc cccacggtgc aggccacgcg    6720
cagcaacttc gacgaggtgc accacggccg gtccaccccg ttcctcgacc acttcatcca    6780
ccgccccggc cgccgggtcc tgatcgacag catccagtcc gaacagggcg actggttcct    6840
gcacaagcgc aaccgcaaca tggtcgtcga gatcgacacc gacatcgagg ccgacgccgc    6900
gttccgctgg ctgaccctcg gcagatccg ccggctgatg ctccaggacg acctcgtcaa    6960
catggacacc cgcagtgtgc tggcctgtct gcccaccgcg cacggcacgc ccgacgacgg    7020
tgacgactcc ttcccggcgg cgctgcgccg ctccctctac ggggagaccg cgccgttgca    7080
cgatctgcac gccatcacca gctgcctcac cgacgtccgg gcgctgcggg tgctgcgcca    7140
gcagagcgtg ccgctcgacg acgcccggcg ggacggctgg gagcggaccg ggagcgcgat    7200
ccggcatcgc agcggcaggc atttcgagat catggcggtg gaggtgaccg cggagcgccg    7260
tgaagtggcc tcgtggaccc agccgttgct gcgcccgtgc tcgcagggac tggcggccct    7320
gatcacccgg cggatcaacg gggtgctgca cgccctggtg gcggcgcggt cggaggtcgg    7380
cacgctcaac gtcgccgagt tcggaccgac cgtccagtgc cggcccgacg aggcggacgg    7440
ccagtcgccc ccgtacctgg accgggtgct gacggccgga gccgaccgcg tccgctacga    7500
cgtggtgcag tcggaggagg gcgggcgctt ctaccacgcg cgcaaccgct atctggtggt    7560
cgaggcgggg ccggagctcg acacgggctg cccgcccggc ttctgctggg ctaccttcgg    7620
ccagctcacc gaactgctcg cgcacggcaa ctatctcaac gtcgaactcc gcaccctcat    7680
ggcgtgcgca cacgcctcct actgaatggt cacgaaagct gcaccgcgcg ggagaatcgg    7740
cagcgcgcca ccggccggcc ggcacccgga aggtaaagcg ccgttctccc gcatcggcgc    7800
cctgcgggaa acggcggaac ggccggcccg gaccgcgcgc aattcccggc gggacacggt    7860
gggagcccgc acgaggaacc gctttccccg ccttcggtgc cccggccgc gggaccaccc    7920 ccgcctcccg gccgggccgc ggaatacgac ggggcggcc gaggacattc ctttcccgcc    7980
tccggaaaag cgcgccccga gggcccccga atgccgggcg ggacggacgg cgactgcgcg    8040
cggacggcgg cccggcgtcg aacgcacctg cccgagtccg gacgagacag cgcgacgcga    8100
gaggcgaaaa tgatcaatct cttccagccc cagatggggg ccgaggaact ggcggcggtg    8160
tccgaggtct tcgacgacca atggctcggt cacggacccc ggaccgcggc gttcgagtcc    8220
gcgttcgccg agcacctcgg ggtcggcccc gagcacgtcg tcttcctcaa ctcgggcacc    8280
gccggcctct tcctggccct ggagtcgctc ggcctgcggc ccggcgacga ggtcgtgctc    8340
```

```
ccctcgccca gcttcctcgc cgcggcgaac gccgtacagc tctcgggagc gcgcccggtg   8400
ttctgcgaca ccgacccgcg gacgctgaac cccgccctgg agcacatcga ggcggccgtc   8460
accccgcgca ccaggccgt catcgcgctc cactacggcg ccacccccgg cgacatcgtg   8520
cgcatcgccg agcgctgccg ggagcggggc atcaccctga tcgaggacgc cgcgtgctcc   8580
gtggcctccc gcgtcgacgg ccgaccggtc ggcaccttcg cgacctcgc catgtggagc   8640 ttcgacgcca tgaaggtcct ggtcaccggc gacggaggga tgatctacgt caaggacccc   8700
ggggcggccg cccggatccg cgcctcgcc taccacggcc tcacgcggtc cagcggcctg   8760
ggatacgcca gggtctcggc gcgctggtgg gagatggacg tccccgaacc gggccgccgc   8820
gtcatcggga acgacctcac cgcggccatc ggcgcggtcc agttgcgccg gcttcccggc   8880
ttcgtggccc gccgcaggga gatcgtcgcc ctgtacgaca gcgaactgag ctcgctggag   8940
ggcgtgctga caccgcccgc gccacccgcg gggcacgagt ccacgcacta cttctactgg   9000
atccagctgg ccccggcgt ccgggaccgg gtggcacgcg acctgctcac cgacggcatc   9060
tacaccacct tccgctacgc acctctgcac aaggtgcccg cctacggcca caccggaggc   9120
gaactgcccg gcgtggagcg ggcgtccgaa cggaccctgt gcctgcccct gcaccccggc   9180
ctgtcggacg ccgacgtccg caccgtcgtg tcctccctgc gcagagccct gagcgccgcg   9240
gatccggccc ccgcctgacg cgcgcacgcg ccacggcccc tgtcccggcg gtgaccgccg   9300 ggacagggc cgtggcgcgt cctgcggacg gtccgggcca ccccgccgtc ccgtcggtgc   9360
gtcagcgacg cgtgccgagg aagaagcccg gtgagccctc gcccgtcacg acgtactcga   9420
cgtccaggcc ggccttgcgg tacgcggcct cgtactccgc acgcgagaac agcgtgaggt   9480
agtccacctc gctgcggtgc cggatgccct ccgcggtgtg cgccgatcagg tagtggatct   9540 ccatccgggt ccgcccgccc tcccgggtcg agtgggagac acgggcgacg ccctggtcgc   9600
ccggtgccgt ccgcagggcg tgggtggaga cgtggccgtc caggaaggtg tcggggaagt   9660
accacggttc gacggccagg acaccgtccg cggtcaggtg ccgcgccatg cggcgacgg   9720 cgtcctccag gtcggccgtg gtctccaggt acccgatcga gctgaacatg cagaccacgg   9780
cgtcgaacgt ctcgccgagg tcgaacgccc gcatgtcacc gcggtggagg gtgacgccgg   9840
ggagccgctc ctcggcgcgg gccgccatcc actcggacag ctccaggccg ctcacgcggt   9900
cgtagagctt ggcgaaggcc tccaggtggg taccggtgcc gcacgcgatg tcgagcaggc   9960
tggccgcgtc cggcgtacgt tcccggatca ggtcggtgac ccgggcggcc tcacccgcgt   10020
agtccttgcg gtcctggtag agcaggtcgt agacctcggc ggcactgtcg ttctcgtaca   10080
tgggaatcct ccgggccgtg aaggggaac cgtgggtctg tcgaagagga gtgcgccgtg   10140
cgctcggggc ggggcggcc tgccgccggc ccctcgcgat gatctccgta cggacaccca   10200
acagttcacg ccgagccggg gtcaaggaac gacggggtgg tcagtcaagt cgggcgctcc   10260
gcccccgggg cggggcgcgc cggcgacgcg cacggattcg gccaaccggt tgctcgttcc   10320 gccgaaatc acggtgtggc ccccgggcca ccgggtagct tatgcctcgt tcaccgcagc   10380
ggttgaagag gcagccttca accccggccc ggcctttatg gaattcattt ccaccgtgcc   10440
gcaacaccca ctgaaggacg gccggatatc ggccatgaag ccccggcctt tcagccaggc   10500
accctctctt gtcgaataga gtatgtcctc cgctgaagcc gccgaagacg gacgaagggg   10560
acgaacggtc acctcggtcg atctagacgg aatccttgaa agcgtaatag cctgtcaatg   10620
ctttggtaaa gcacagggat gggggtgcct gcgggatgag tgacctgggt tctggtgaag   10680
```

```
aagggtccga agaagacgag tcggacgacg cactcgcctt cctcgagttc atcgcccggt    10740
cggcaccacg gagcgaatac gaccggctca tggcccgcgc cgaacgctcg ggcgccgacg    10800
aggaccggat gcgccgactg gagcgcttca accggctcgc cctcaccgcg cagtcgatga    10860
tcgagtaccg ccgcgaccgg gaggcggagc tcgcggcccg ggtcgacgcc gcgcacgagt    10920
tcgtcgccgc ccggcggggc aaggacctgc tggagtccat cgcccgcaga gcacggctgc    10980
tgctgaagct ggacgtctcc tacgtcggcc tgcacgagga ggaccggccc ggcacggtgg    11040
tgctgagcgc cgacggcaac gcggtcaagg tcgccgagag ctaccggctg ccggccgacg    11100
gcggactggg cgccatggtg cgcacctgcc gcgctcccct ctggaccccg gactacctcg    11160
gggacaacag cttcacgcac gtcgaggccg tcgacgacat cgtccgcgcc gaaggcctgc    11220
gcgcggtcct ggccgtcccg ctgtgcgccg ggggcgaacc gatgggggtc ctctacgtcg    11280
ccgaccgtca ggtgcggcat ctgaccccca acgaggtcac cctgctgtgc tcgctcgccg    11340
atctggccgc ggtggcgatc gagcgcaacc ggctggtcga ggagctccac gacaccatcg    11400
ggcaactgcg ccaggacatc ggcgaggccc gcaccgccct cgcgcgcacc cgcaggtccg    11460
ccgacctcca gtcgcacctg gtcacgcagg tgatggacag gcgcggcgcc gactcgttac    11520
tcgcgacggc cgccgaggcg ctcggcggcg gagccggcct gtgcagcccg ctcgggcgcc    11580
cgctcgccga gtacgggacc ctgcgccccg tcgcccccac ggaactgcgc gcggcgtgcc    11640
gccgggccgc cgagaccggc cggcccacct ccgtggcccc ggggtctgg acggtgcccc    11700
tgcttcccgg gggcaacgcc ggcttcctgc tgaccgacct cggtccggac gcggaccaca    11760
ccgccgtccc cctgctcccg atggtcgccc gcaccctcgc gctgcacctg cgcgtccagc    11820
acgacgactc ccccaaggcg cagagccacc aggagttctt cgacgacctg atcggggcgc    11880
cccgctcacc cacgctcctc agggaacgcg ccctgatgtt ctccctcagc ttccgccgcc    11940
cgcacgtggt gctggtggcg gacgacccc gcgggacctc gccgcggctg gaggcctccg    12000
gcgccgacta cgcgaaggag ctcggcgggc tgtgcagcgt gcgggacggc gccgtcgtcc    12060
tgctgctgcc cggcgacgac cccgtcgccg tggcgcagac cgccgccccg gagctgaccg    12120
accgcgccgg gcaccccgtc accgtggggg tcgcgggccc cgcctcgacc gtcgacggca    12180
tcgccgacgc gcaccgtgag gccgcgaagt gtctggagac cctccgcgcg ctcggcggcg    12240
acggcggcac cgcgtgcgcc tccgacctgg gtttcctcgg catgctcctc gccgaggaga    12300
acgacgtccc cggttacatc aggacgacga tcggccccgt ggtcgactac gacacccacc    12360
gcttcacgga tctggttccc actctgaggg tgtacctgga gtcgggcagg agccccacgc    12420
gtgccgcaga gacactgcgc gtgcacccga acaccgtctc acggcggctg gagcgcatcg    12480
gcgtactgct gggagaggac tggcagtcac cggagcgggt gctggacata caactggccc    12540
tgcggctcta tcaggtgcgc tcggcgctct cctcgcaacc ggcgtccgag acccgggccg    12600
tgctcggatc gctgcgcgag tgacctctcc ggcacgggcg gcgccccgcc cgtcggcgcg    12660
gatcgcgccg acaggcgggc gttgaccacc ggccaccggt ccccgtacg acgaggtccc    12720
gggcccgcgt ggttcagccg gcgctgaact cggcgatgcg cccgtctccc atggtcagcc    12780
gggcgccggt gaaccgggac cgcatccgac ggtcgtgggt gacgaccacg acggcgccgc    12840
ggtagtccgc gagtgcctgc tccaactcct ccaccagcac cggggtgagg tggttggtgg    12900
gctcgtccag cagcagcagg tccatcgggt cgctcaccag ccgggcgatc tcgatccggc    12960
ggcgctgccc gtaggacaga tccttcacgc gtcgccgcag gtcggacggg ctgaacaggc    13020
cgagcgacag cagtttctcc gcgtggtcct ccaggtagcc ctcccggccc tgggcgaagg    13080
```

```
cccgcagcac ggtcagtccg ggcgcccagg gcgtctcgtc ctgccgcaga tgaccgaccc   13140
ggcagccgac gcgcaccgag ccgccgtccg gctccagttc cccggacagc acccgcaaca   13200
aggtggactt gcccgcaccg ttgggacctg tgacgagcag ccgttcgccg ggccggatcg   13260
tcagggagtc cacggcgagc cgacccgcga cgcgcacgtc ggtgagttcg gccaccgcct   13320
cctccgcctc cgggcccgcg gtgtcgatgc gggcggcgaa ggacaacggg tcggcgggag   13380
cgtggaccgg gttctcggtc agctgcgcca cgcgttgctt cgcgttgcgg atccgcacca   13440
tcgcgccgtg gtcgcgccct cgcctgcggt aggcgccgtg gccgaacacg gagagggaca   13500
tcttgcgcgg gatgccgtcc atccgcgcca cgttggaggt gatcagcccg cggttgcggt   13560
cgagttcggc acgccactcc tcgtactccc gcagccgccg ctcgcgttcc acggccttgg   13620
ccgtcaggta gccctcgtag ccgttgccgt agcgggtgac gctgccggag tcgacctcca   13680
ggatcgtggt ggtgagccgg tcgaggaaga cccggtcgtg ggtgaccgcg atcaccgtgc   13740
cgcggtggcc ggccaggtgg tcctccagcc attccatcgc ccggtcgtcg aggtcgttgg   13800
tcggttcgtc caggagcagc agctccggcg acgaggcgag ggtcgcggcg agcgcgaggc   13860
gggagcgttc gccaccggag agggttccga gcttgcggtc gcggtccagg ctcggcagtc   13920
cgaggccgtg cagcgcgacc tccacgcgca cgtcggcctc gtagccgcca cgcgcctggt   13980
actgctcgac cagagcggcg tagcgctgga ggccggcgga cagctcgcgc tcggagccgt   14040
tctcgtcgct ctcgcccagc tccgcctcgg cctcgcgcat cgccgcttcg agctcgcgca   14100
ggtcggacag ggccaggtcg acggcgtcct ggacggtggc gtcgaggggc agttccagtg   14160
tctgcgccag gtagccgacg ccgccgggag cgaccacggt gagcgcgccg ttgtcgggct   14220
ccacgcggcc ggcgaggatc ttgagcagcg tggacttgcc ggaaccgttg tcgccgatca   14280
cgccgacctt ctcgcccggc ttgatgctga aaccgacccg gtcgagcacg acacagtcgt   14340
ggtagcgctt cgtgatgtcg tgtagggcgt attgcgcaat cgacacgcgt aagtctcctg   14400
tttccacgat gaggatgagt ggatgcgtga gcgcgctcgc agaaagaacg gaaagcagaa   14460
gggacgccac cactgcggac atggccggtc aggggtgtc acgagcacgc tgctggatgc   14520
ggcaggcgga gtcagctcaa cgccgggcat cctcatctat cacagagatc ccatgcgaag   14580
aactatagcc gtgctacccg gtgccgcgca acggtatgcg tgtcgcaccg gccgacgtga   14640
tgcagtcgga ccgggatgat cgcttgtccg gcggccggat gcctagcctc gggagcaacc   14700
acagcggtct ttcacgagag gggtcgacca tgggcgatct caggaaccgc atcaccgagc   14760
tggtccgcgc gtaccaccgg gaacaggcgc ccggggcctt cgttcccggg acgacgcacg   14820
taccggtctc cggcgcggtg ctgagcgagg aggaccggct ggcgctggtg gagacggcgc   14880
tggagatgcg gatcgcggcc ggcccggcct cccggggctt cgagcggcag ttcgcccggt   14940
acctcgggct ccggaaggcg cacctgacca actccggttc ctccgccaac ctcctcgccc   15000
tcggcgcgct cacctcgccg cagctggagg agagacggct gcgtccgggg gacgaggtcg   15060
tcacggtcgc cgccgggttc cccacgacgg tcaacccgat cttccacaac gggctggtgc   15120
ccgtcttcgt ggacgtcgag ctcggcacgt acaaacgac gcccgagcgc atcgagcggg   15180
ccatcggccc ccggaccagg gcgatcatga tcgcgcacgc cctgggcaac cccttcgagg   15240
ccgaagaggt ggcccgcctc gcggacgagc gggagctgtt cctcatcgag acaactgcg   15300 acgcggtggg gtcccgctac cggggcaggc tcaccggctc cttcggcgac ctgtcgaccg   15360
tcagcttcta tcccgcgcac cacatcgcga tgggtgaggg gggctgcgtg ctcaccgaca   15420
```

```
acctggccct ggcgcggatc gtggaatcac tgcgcgactg ggggcgcgac tgctggtgcg    15480
agccgggtga ggacaaccgc tgcctcaagc ggttcgacca gaagatgggt gacctgccgc    15540
ccgggtacga ccacaagtac atcttctcgc acgtcggtta caacctgaag tcgaccgacc    15600
tgcaggcggc cctcgggctg tcccagctga cccggatcga ggagttcacc gaggccaggc    15660
gcgccaactg gcggcatctg cgcgccgcgt tggacgggct gcccggtctg ctgctgcctc    15720
atgccacacc gggcagcgat ccgagctggt tcgggttcct catcaccgtg gacccggacg    15780
ccgcgtacag cagggcggcc ctggtcgacc acctggaatc gcgccggatc agcacccgcc    15840
gcctgttcgg gggcaacctc gtgcggcacc ccgcctacac cgaccgtcgg taccgggtgt    15900
ccggctccct ggagaacagc gacctgatca ccgaccagac gttctggatc ggggtcttcc    15960
ccggcatcac cccggagatg atcgcctacg tcggcgacac gatcccggag tgcgtgctca    16020
agcactcctg aggggcggcg gtacgggggt gcgcgtggag gggaggaccg gggcggtcct    16080
cctccggggc gtcacggccg cggaagcgtc cgaagctccg aggcgaggtc ggggtggacc    16140
cgcgcggtga gcagggtgcc ctccggcgtg tgctcggtgc tgagcacctc gccctcgtcg    16200
tgcacccgcg ccaccaggct cccctcgtcg taggggatca cgacctccac ctccacctcg    16260
gggtgcggca gcaggcggtc gatcagttcc cgcagctcgt cgatgccccg acccgaacgg    16320
gcggacacga cgatcgcgtc cggctcctgc tccagcagac gggcgaggac gtccgggtcc    16380
gcgacatcgg ccttgttgac gaccacgacc tcggtggact cgccggcgcc cacgtcccgc    16440
agcacctcgc gcaccgaggc cagctgcgcg ccggggtccg ggtgcgaacc gtcgaccacg    16500
tgcagcacca gatgcgcgtc cgcgacctct tcgatcgtgg aacggaacgc ctccaccagg    16560
tggtgcggga ggtggcgtac gaagcccacg gtgtcggcga tggtgtaggg gcgcccgctc    16620
ggcgtcgtcg cccgccgcac ggtcgtgtcc agggtggcga acagggcgtt ctccaccagc    16680
acgccggctc cggtgaggcg gttgagcagc gatgacttgc cggcgttggt gtagccggcg    16740
agggcgaccg acagcacctt gttgcgccgt cgctcctccc ggttcacgtc ccggccggtc    16800
ttcagctgct ccagctcccg gcggagcctg ccatcttgt cgttgatccg ccgccggtcc    16860
gtctcgatct tcgtctcacc gggaccgcgc gtggccatgc caccgccgcc accgccgccc    16920
atctgccggg acagcgactg gccccagccg cgcagccgcg gcagcatgta ctgcatctgc    16980
gccagcgcca cctgcgcctt gccctcccgg gactgggcgt gctgcgcgaa gatgtccagg    17040
atcagggccg tgcggtccac gaccttgacc ccgacgacct cctccaggtg catcagctga    17100
ctggggctca gttccccgtc gcacaccacg gtgtcggcgc cggtctcctc gacgatgtcg    17160
cgcagctgcg acgccttgcc cgagccgatg tacgtcgccg gtccggcttc tgccggcgc    17220 tgcacgacgc cgtccagcac gagggcgccc gcggtctcgg cgagcgccgc cagctcggcg    17280
agcgaactgt cggcctccgc ggccgttccc gaggtccaga tgccgacgag caccacccgc    17340
tcgagtcgca gctggcggta tcgacctcg gagacgtcgg tcagttcggt ggagagcccc    17400
gcgacgcggc ggagggaggc ccggtcctcg cggtctaact gatcgccgtc ccattcctcg    17460
gcgtcggcgc cggccatcgt gtcgtccatc agtgcgtcgg ctcgctgcgt gccggcgaag    17520
tcctcgggat gcgtcaaagt acttccaatc tgggggttc gagagcgttc cggggcgggg    17580
cgcgtccggc ctgcggggcc gggcgcgggg ccggggggtc ggggccgacg tgtccgcacc    17640
tcgccgtcgg gggccggtgc cgtggaggtc gctgccggaa ctcacatgcc gtccacccta    17700
gccatgtcgc cggggtgtgc aaggacgtat cggcgatcac ctccccagct gacagagtgt    17760
gcaccgggta ctgcgcccgc gggcgtgaag cgggcgagtg tggatgtcat gcgagtactc    17820
```

```
attatcgggg gttcacagtt cgtgggccgg gccttcgccg ccgaggcact ggccgcgggg  17880
caccgggtca ccacgttcaa ccggggtgtc agcggcaccg acctgcccgg cgtcgaggcg  17940
gtcaggggcg accgcgaggt ggccggcgac ctggagcggc tggtgtccgg aaggcactgg  18000
gacgcggtcg tggacacctg cggttacgtg ccccgcacgg tgggggcctc ggccgcggcg  18060
ctgtccgggc acgcggacac ctacctctac gtctccagca tcgcctgcct gcccgactgg  18120
gcgcaggcgg tccgtccggt ggacgacgac tcacctgccc acgactgccc gccggacgcc  18180
ggaccggacc acgccgacgg tgactacggc gtcctgaagg ccggctgcga gcgcgccgtg  18240
gaccggcact tcgcgggccg gaccctgcac ctgcgggccg gtgtcatcct cgggccgcac  18300
gacaccatgc gcatgctcga cgcctggctg tggcgcatgc gcgtcgccga gggggagcac  18360
cgccgggtgc tcgccccggg caaccccgag gtgggcatgc gcctgatcga cgtacgcgat  18420
gtcgccgtct tcggcctcga ctgcctcgcg gacggccgta ccggcgcctt catcgtcaac  18480
ccgccggaga agaacaccac cttcggggag ttgctcacga agtgcgtcaa ggccaccggt  18540
tcggccgcgg agccggtgtg ggtcgacgag gggttcctcg ccgagcacgg cgtgagtccg  18600
tggacggacc tgccgatgtg ggtgcccgac accgcgcggg acaccctcgt gtgggcggcc  18660
ggagcaccgc gcgcccgggc cgcgggtctg gcctgccggc ccttctccga caccgtgcgg  18720
gacgcctggg aggtcgtccg ggaccggccc gtccggaaac tgccgctcgc ggccggctgc  18780
ggcctgtccc tgagccggga aaggagctg ctcgccgcct gggacgctcg cggcggtgcg  18840
gcggcgggct gacgcggccc ccgaggagtg cgacgccgtt tcccgctcgc ggggagcggc  18900
gctcgcgtgt ccgccccgcg gcccggcggc gcgtcctgtg tcccggcgcc cggggcgcgg  18960
ctacacggtg aaggtctcgg cgcgggccac gatctcgtcg accagccccg cctggcgcag  19020
cgcggcgtac gactcggcgg agacgtcctc ggcccggatc accgcacggc ggaagaccga  19080
caggatgttc acgaagtgcc ggtccacggg caggacgcgc tcctcccggt ggtcctggcg  19140
ggacagccgc agtacggggt ggtggctgtc cggggtcgtg aagacgtggc tcagggcgag  19200
cgagccggtc ctgccgtgca gctcgtacgc cgagcggtag ccgtgttcca tgccgaaggc  19260
gaggtgggcg gccacgccct gggggcggc gagcaggacg ctgccggaga ccacgacgcc  19320
ccggcggcgg tcacgcgca gcacggcgcc ggtcaggcgc agttcgggtc cgaggaagtg  19380
cagcgcggcc cgcagcgggt agacgccgtt gtcgagcagt gcgccgccgc cgatgtcggg  19440
tcggtagcgc atgtcgtcgt cggcgcgcgg cgggatggtg aaggcggcgg agaaggtgcg  19500
cagctctccg atggcaccgg cctccaacag ggctttgacg gtggcgtgtt gagagtggtg  19560
gaggaacatg aagttctcca tcagtaccag tccgcgctcc cgggccatgg cgaacaggcg  19620
ggccgcgtcg gcgtggttgg cggcggcggg cttctccacg aggacgtgtt tgcccgcccg  19680
cagcgccgcc gcgccccatt cggcgtgcag catgctgggc accgcgatgt agacggcgtc  19740
cacgtcgggg cgttccagca gggcctcgta gggcgcgacc gcctcgcagt cgaagtgcct  19800
gcccagggcc ttggcccggt ccgcgtcgcg gctgccgacg caggtcagca cggtgccggg  19860
ggtggagagc agggcgggca gggtgcgacg gcccgcgatg tcgccgcagc cgatcgctcc  19920
gaagcgcagc accggggacg cttccggccg cggcgggccg ggtgcggcga acggttcagc  19980
agaagtaccc agggcggtca tggatggttc cgtcaatcgg tccggatggt cacggcacag  20040
cgtggtgaac ggccggcgca cacccacgag tcgcttccgg caatgggcgg ccctgaagct  20100
acccggcggc ccgacgcgac ggcaaggccg atctgacaca gtgccgcgcc gagggaccgt  20160
```

```
cggtgcccccg cgtacccgct gacctgacac tacgccgacc aatctgtgga cgggcggtg      20220
gccgccgggg ttaggtgagc gcggcgcccg cggtgaccgc gacgccggtc cgaagcggcc      20280
ctcggggcac gccgttggag agaggagacg cgggtgacgg acgcgatcac gaccgagctg      20340
gccgaccgcg aactggggcg cagactgcac cggatacgcg gcgtccactg gtatttcggc      20400
aaccacggtg acccgtacgc cctcatcctg cgcggtcaga ccgacgaccc gtcggtgtac      20460
gaggagcggg tccgcgaggg cgggccgctg ttccgcagcc gtaccgggac ctgggtgacc      20520
gcggacccgg aggtggccgc ggccgtgctg ggcgactcgc gcttcggtgc gctggaccgc      20580
gccggacggc gcccggagga gtacctccag ccgtcgcccg ccacgtacct ggggctggac      20640
cgcgccgcgt acgcgcgtct gcggcgggtg gccgagcccg tgctgggcgc ggacgccgcc      20700
gccgcgtggc gccggctcgg cgaggacgtc gggcgccggc tgctcgccgg ccgcggttcc      20760
ggcctcgacc tgacggcgga cttcgcccgc cggctgccgg cattggtcct ggccgcgtgg      20820
ctcggggtgc cgggcgaacg gtgcgacgag tgggaggagt cgctgcgggc ggcggggccg      20880
ctgctggacg gtctgctgtg tccgcagacg ctggcggcca cccgtgcggc ggactcggcc      20940
gccgagggggc tgcgcgcgct gttggacgag gtggtcgccg cgcgtcccgg cgggtccggc      21000
gagggtgcgg tggcccgcat ggtcggcgcc ggagccgccc ccgacgacgc ggtggccgcc      21060
gccgtgtgcc tggcgctctc ggccgtcgaa ccgacgacga ccctggtgtg cgaagcggtc      21120
cggctgctgc tcgaccgacc cgagtggtgg cggcggttgt gcgactcccc cgctctggcg      21180
ccggccgcgt tccggcacac cctgcggcac gcgcccccgg tgcggctgga gagccgggtg      21240
gcccacgagg acgtgacggt ggcggatcgt ccgctgcccg ccgggagcca cgtggtggtg      21300
ctcgtgggcg cggcacggcg cgcgggcgcc ccggccgcgg agccggcgga cctggcgggc      21360
gcaccggcgg cggagctgcc ggacgacctg tggttcgcgc tgtccgggga gttcgtcggc      21420
cgtgccgccg agaccgcgct gggcgtgctg gccgaggccg ccccgggact gcggcgggac      21480
ggcgacatcg tccggcggcg ccgttccccg gtcctcggca ggtacgcgcg gttccccgtc      21540
gcgtactcct gacgggcccg cggccggcgt cccctcagtc ccccacgacg tttcatgaaa      21600
ggagtgccgt gcgcgtcctg gtgacctcca tcccgcacca cacgcactac taccacctgg      21660
taccgctgat ctgggctctg cgtgcctcgg ggcacgaggt ggtggcggcc ggccagccgt      21720
cgctggtcga cgccatcacc gccagcggca tcccggcgtt cgccctggcc gaggaggagt      21780
cgctggcgca gatcttcgag gaggtcgagg gcgatctcca gccgtatcag cacggcatcg      21840
acgagttcga cttcttcggc accctgaagg acagactgga ctgggagaag ctgctcgccc      21900
agcaggtgat cctgtccggc ctgtggctgg aaccgctcaa cggcgccacg accctcgaca      21960
gcatcgtcga cttcgcccgg gcctggaagc ccgacctggt gctgtgggag ccgttcacct      22020
atgcggggcc ggtggcggcc cgggcgtgcg gggccgcgca cgcccgcgtc ctgtggggggc      22080
cggacacgat cgggctgctg cggacgaagt tccttcaggc ccaggcgcgt cagcccgagg      22140
agcaccggga cgacccggtc gcggagtgga tgacctgggc cctggcgcgc tacgggtgcg      22200
acttccggga ggaggacgtg ctcggtcagt ggagcgtgga cccgatggcg gagggcgtca      22260
gtctgggcct cgacctgccg accgtcccga tgcgctacac cccgtacaac gggtcggcgg      22320
tgatccccga ctggctgacc gaggaaccga aacggcctcg ggtctgcctg accctggggg      22380
tgtcctcgcg ggagcacagt gaggacgagg tcccggtgca gaggtttatc gaggcgctgg      22440
ccgatctcga catcgagctg gtggcgaccc tggacgacgc ccagcgggac ctgctgccga      22500
ggatcccgga caacacgcgc atcgtcgact tcgtgcccat ggacgcgttg ctgccgacgt      22560
```

```
gctcggcgat catcaaccac agcggttcgg gcacgtgcaa caccgccgcg ctgcacgggg    22620
tgccgcagat catcctcggc ggcatcctgg acgccgccgt acggcagcac atgttcgcgc    22680
agaactccgc cgccctcacc ttcgctccgg aggaggtgac cggcgcgtcg ctgaggagcg    22740
cgctggtgcg cctgctcgag gagccgcggt tccgcgacgg cgcgcggcgg ctgaaggagc    22800
ggatgcgggc catgcccagc ccggccggga tcgtgccgac cctggagcgc ctcacggccc    22860
agcaccgccg ggcgtgttga accggcgcgc gggcccgtgc cggcggtgac cgcccgaccc    22920
gactctcgcg tgtgatcgat ctcgtcgact cagccgtgga ccggttcgcc tgtccgcgcc    22980
cgacactgga gtgctgatgc gggccctctt cacgaccgcg ccgctcgcgg gccacctgct    23040
tccgctggtg cccatcgcgt gggccctgcg ggcggccggc cacgaggtac tggtggcgac    23100
ccgggaggac ttcgtgccgg tcgccctgcg gtcggggctg ccgtccgcct cgtgcgggcc    23160
gcccgccgcg gacctggcgg gcgcggccga ggcgggggcg ctcgcgcggc cccgcggagc    23220
ggcggaggct cgggggtcc tgagcggggc gctggcgcgc gtcgcccggg gcagtctggc    23280
gggggtgcgg cggctggcgg acgcctggcg gccggatctg atcgtcagcg aacgggccga    23340
gttcgccggg ccgctggtcg cggcggccct cggggtcccg tgggtccgct accactggtc    23400
ggtctcgtcc ctggaggagt accggcgagc ggccgaggcc gagttcgcgc ccgagctggc    23460
ggcgctcggc ctcgaccggt tcccggaggc ggcgcgcgtg ctcgatccgt ggccggtgtc    23520
gctgcgccgg ccgacgcgg tcgcccacga cggggtccgg cacgtaccgg cccacgggga    23580
cgcccccgtc cccgactggg cgttcacgcg cggtcgcggg ccgcggatct gcgtgacgct    23640
cggcaccatg ctgccccggt acggcgccgc cgggatggcc gacttcctga cggagctggt    23700
ggcggagacc cgcggagggg actgcgaact gctcgtggcg gtcgacgacg acgtcgtcgc    23760
gcggtggccg tcgctgccct ccgcggtgcg gtacgccggc cggctgccgc tggcggaggt    23820
gctgcccgcg tgcgacgcgg tggtgcacca cggcgggcag ggcacgtccc tgaccgcgct    23880
ggccgcgggt cggccgcagg tcgtcatggc gcggctcgac gaccagttcg acaacgcgcg    23940
ggcactggcg gcggcggggg cggccctgct cgtaccgccg tcccgggcca ctcccgcggc    24000
cgtggccgcg gggtgcgccg aagtgctgga gaacgccctg tatgccaagg cggcagccgg    24060
gctcgccgag gagatggcgc tgctgccgtc gccgtcggcg gcggtcggac tcctggaaca    24120
cccggggccc gggccggaca tgccgcggag ttacccgaac gaggatgcgg tgtgacgtga    24180
atctggaagt actcaaccgt tcgaacgatc cgcgcgggcc ggtgatcacg gtggtcggcg    24240
cgtccggctt catcgggtcc gccctggtcg ccgagctggc gcgcatgccg gtgcggctgc    24300
gggcggtggc ccggcgcgag accccgttc cgcgggggc acgggccgcc gtcgaggtcc    24360
gccgggcgga cctcgcccgg ccggacgagg tcggggccgc cgtcgagggg cggacgccg    24420 tcgtgcacct cgccgcccac atcgcgcgcg cgcggtcgtg gcgcgcggcc gacgagcggt    24480
cgctgcgggt gaacgtcggt ctgctgcgcg acgtggccga cgcgttccgg gaccgctcgg    24540
ggcccgcccc ggccgtggtc ctggccagta ccctccaggc cggcgtcgag ctgtcccggc    24600
agggcccgta cgcccggcag aagtcggcgg ccgaggaggt cctgctgcgg gccgcctccg    24660
aggaggtggt ccgcgcgtc gtgctgcggc tgccgaccgt ctacgggcgc agcccgctga    24720
ccgggtggac gggccgcggg gtggtcgcgt cggtggcacg gcaggccgtc tcgggcgagc    24780
cggtcacgat gtggcacgac ggcacggtcg ggcgcgatct gctccacgtg gaggacgcgg    24840
cccgcgcctt cgcggcggcg ctcggtcacg tggagcggct ggacgcggc acgtggtccg    24900
```

```
tcggtacggg ccggctggag cccttgggag aggtgttctc ggccctcgcc gggctggtgg   24960
ccgagcggac ggggaggccc cccgtaccgg tggtctccac ggagccgccc gaccatgccg   25020
aggcgggcga cttcgagagc gcggtctgtg acccctccgc gttccgcgcg gtgaccgggt   25080
ggtctcccct cgttccgttg cgggcggggc tcggcgccgt ggtggagacg atggtggccg   25140
acggagcgag gggtgggatc cgaacgtgag cacggaccgg gagcaggccg cgcacacgcg   25200
gctcggtcgc agcgcgaccc tggtgagccg gctctggctg ggcaccgtga acttcagcgg   25260
ccgggtcgag gacggtgacg cgatgcagct gatggaggcg gcggtcgacc gcggcatcaa   25320
ctgcatcgac accgcggaca tctacggctg gcggatccac aagggccaca ccgaggaact   25380
ggtgggccgg tggctggcca agagcgccgc gcggcgggag gacgtcctgc tggccaccaa   25440
ggtcggcggg gacatgagcg aacgctcaa cgacggcggc ctgtcggcgc ggcacatcgt   25500
cacggcctgc gagcagtcgc tgcggcgcct gggcgtggac cacatcgacc tgtaccagat   25560
gcaccgcgtc gaccacgccg cgccgtggga cgagatctgg caggcgatgg accgtctggt   25620
ggcgagcggc aaggtgacct acgtgggtc gtcgaacttc gccggctgga acgtcgccgc   25680
cgcgcaggac gcggcccggc ggcgccagtc cctcggtctg gtgtccgagc agtgcctgta   25740
caacctggcg gtgcgccacg ccgagctgga actgctgccg gccgcccagg cgtacggact   25800
gggcgtgttc gcctggtcgc cgctgcacgg cgggctgctc agcggggtgc tgcgcaagct   25860
cgcggcgggc gtcgcggtga agtcggcaca ggggcgggcc cagctgctgc tgcccgagct   25920
gcgcgcgacg atcgaggcgt acgaggggtt ctgcggccgg atcggcgcgg atccggccga   25980
ggtcggtctg gcctgggtgc tgtcccggcc ggggatcagc ggcgcggtga tcggtccgcg   26040
cacggtggac cagctggact cggcgctgcg gtccctggac ctggtcctcg ggaggccga   26100 actggccgag ctgacgccca tcttcccgcc cctgggcaag ggcggccggg cgccggacgc   26160
gtggatcagc tgaaggggt gcatcggccg acgtcacgcc ggccgatgcc gccggtcaca   26220
cgacgtcgag cgcgggcagc gggaagacca gtcggccgcc gccgtcgagg aactcccgct   26280
cccgttcgac gaacccgtcc cggtagatcc agggcaggac cagcaactgg tccggcttct   26340
gcgccttcgc gtcctcctcg gacacgatgg ggatgcccgt cccgggggtg aaacgccccg   26400
ccttctcctc gctcacctcg ccgatgcacg gcaggtcccg ttcggtgatc ccgcagtact   26460
ggaggatgac gttgcccttg gtggaggcgc cgtacccgag ggtcagcagg ccctcttggc   26520
gggagcggtc caggaagccg cgcagggcgt cccgctggtc ggcgacgcgg cgggcgaagg   26580
cctcgaacgg tgccatgccg tccagtcccg cggcggcctc ggcggcccgg atgcgggcca   26640
ggcccgcctc gtccctcggg tgccgggaac cggtcctggc gagcgtgacg cacaggctgc   26700
cgccgtacac ctcggtgagc tcggcccgga tgacggtgag gccgacgcgt tccgccatcc   26760
actcgatctg gcgcagcgcg tagtactcca ggtgctcgtg gcagacgatg tcgtacgcgt   26820
cggcttcgag catggcgggc aggtagctct gctccatcat ccagacgccg tcctcggcga   26880
ggacgtcgcg gacgtcgctc atgaagcgca gcgggtccgg caggtcgtag aacatcgcga   26940
tggaggtgac ggccttcgcc cgccgcgccc cgaagcggtt ctcgaaggtc gcgcgggtga   27000
agtagtccac gaccaactcg gcgttcggcg ggtacaggtc gcggaacttg ccgccggtcg   27060
ggtcgatgcc gaccagtcgc gggccgtcgg cggggtagcc cttgaggagc gtggcgtcgt   27120
tgctgccgat gtcgaggacc aggtcgtccg ggccgaggtc caccagccgg cggacggcgg   27180
cgaccttgcc atgcaggtgg tcgaccatga agggccggat gcccgagcgg tagccgtagc   27240
cctcgccgta catgaggtcc gggtcggggg tgtggcgcag ttgcacgagg ccgcatccgg   27300
```

```
ccggggaaca cgcgacgagt tccagcggga ccgacggcac gacctcgtcg cggtcggccg    27360
ggaacacccc ggtgagcgcc tgttcgccca ggtcgagtac ggagagcagc tccttgttgc    27420
cgcagacgcg gcacgcggtg gcaatcatgg ggtcctttcg ggatcctggc cggggcgccg    27480
ccggcccgtg gccaggtcgg gagcttccag acggagggtg tcggggcgg  gccgggggga    27540 cggcaccagg tgcaggcggc cgatcgcgcc ggtggcggcg gaggcgtcct ggcacgggca    27600
gggatcgtcg gtgaatccgg cgaagcggta ggccacttcc atcatccggt tgcgttcggt    27660
ggcccggaag tcggctccga ggtgcacccc ggcccggtgc gcctggtccg tcagccagcg    27720
caggatcacc gtgccggccc ccagcgacac cacccggcac gaggtggcca gcagcttgat    27780
ccgccaggcc tcggggccgc gccgcagcag cacgacgccg accgcgccgt agggaccgaa    27840
gcgatcggtg acggtggtga ccagcacctc gtggtcgggg tcgtcgatga gggcgcgcag    27900
ctcgtcctcg gagtagtgca ctccggtggc gttcatctgg ctggtgcgca gggtcagttc    27960
ctcgacccgc gacagctcca ggggcgtggc gcggctgatc cgcatccgga tgtccagcga    28020
gcgcaggaag tccgcgtcgg gtccggtgaa gtcggaccgc tcggcgtccc ggcggaagga    28080
cgcctggtac atggagcggc ggcgggtcga gtcgacggtg acggtgcccg ggctgaactc    28140
cgggaggccg gtcagcccgg gtcgcctgctc ggcggcgtag gtgcggacct ccggcagttc    28200
gtgggtgacc tcggcccgtt cgaagggctg gtcgtcgatg aaggcgaggg tgctcggcgc    28260
gaagttcagc cggtcggcga tctcgcggac cgacttcgac ttcgggcccc agccgatcct    28320
cgggagcacg aagtactcgg cgacgccgag ctgttcgagc ttcgcccagg cgtgatcgtg    28380
gtcgttcttg ctggccaccg cctgcaggat gccgcgcgcg tccagctcgg tgatggtccg    28440
caggacgtcc ggggcgagcc ggacctcgtc ctcctcgagg agggtgccct gccagagggt    28500
gttgtccagg tcccagacca ggcatttgac caacggctcg gcggcgttgt cccggtgcac    28560
gtcgttccct tctctcgata cggcggttgc gaccgcgact cctcgacagg gcgtacgcgg    28620
cccgcggccg gcggggacac gggccggttc acccggccgc ggacatcacg tgccgggcca    28680
ggaccagttc gcagatctcg ttgctgccct cgatgatctc catgagcttg gcgtcgcggt    28740
gcgcccgtgc gacgacgtgt ccctcccgcg ccccggccga cgccagcacc tgcacggccc    28800
gttcggcccc gcgtgcggcg ccggtggccg cgacgtgctt ggccaggacg gcggcgacca    28860
ccatgtcggg gctgcccctcg tcccactggg cgctggcgtg ctcgcacgcc cgggcggcgt    28920
gctgttcggc gacgaacagt tcggcgaggt gccgggcgac gagctggtgg tccgagagcc    28980
gcgtgccgaa ctgctcccgt ccgccggcgt gacgtgcggc ggcggccagg caggcgcgca    29040
ggatgcccag ggagcccag  gccaccgaca tccggccgta gctcagcgcg gtggtgacca    29100
gcagggcggg ggtgcggtcg tggccctgga gcagggcgtc tgccggcagc cggacccccgt   29160 ccaggtggat gtcggcgtgt ccggccgcgc ggcagccgtg cgcgtcggtg atgcgctcga    29220
cgcgtacgcc gggggccgag gcgggcacca cgacggcgcc cgcgccctgc tccgtgcggc    29280
cgaagaccac cagcaggtcc gcgtacgcgg cgttggtcgc ccacaccttg acgccgtcga    29340
cgacgacttc gtcgccgtcg gaggtgatgc gggtgcgcag ggcggacagg tcgctgccgg    29400
cgccggcctc ggtgaacgcc acggcggcca gttcgccgcc ggtcaaccgg ggcaccaggg    29460
aggcctgctg gtccgctccg gcgagccggc gcagcgtcca ggcggccatg ccctgcgagg    29520
tcatgacgct ccgcaacgag ctgcagaggg cgccgacgtg cgcggtgagt cgccgttgc    29580 gccggctggt ccagccgagg ccgccgtgga ccgcgggcgc ctgtgcgcac agcaggcccc    29640
```

```
gggagccgag gtcgtgcagc aggccgaggg gcagctcgcc cgtccggtcc cactcggccg   29700
cccggtcgcc gaccagcgcg gtgaacagct cctcggcctc ggtgccgtcg gcgtgggagg   29760
tgtcagccac ctgcgtgccc ggtcgcctcg ccgggcgcgg ccagccgtcc gaccagccgg   29820
accatcgcgt cgacggtgcg gaagttgtcg agcatcaggt cggcgccgct gatgacgatg   29880
ccgtaggtct tctccaggtg cacgacgagc tgcatggcga acagcgagga catcccgccg   29940
acggcgaaca ggtcctggtc gcgctcccag gtggtcttgg tgcggtcctc gaggaacccg   30000
agcagttccc cggcgacctc gtcggcggtg ggggtcgtgc cggtggggtc gggccgaccg   30060
gacgtcgtgg tcatcgcgtg gcctcctggt agtcgtagaa tccccggccg ctcttgcggc   30120
cgagcaggcc ctggcggacc ttgtccagca gcagctcgct cgggcggagc gccggatcgc   30180
cggtccgttc gtgcatcacc cgcagcgagt cggccaggtt gtccagtccg atcaggtcgg   30240
ccgtggccag gggtccggtg cggtggccga tgcagtcgcg catcagcgcg tccacggtct   30300
ccggggtggc ccgccctcg tgcaccaccg cgatggcgtc gttcagcatc cggtgcagca   30360
ggcggctggt cacgaagccg gcgccgtcgc cgacgacgat gccccggcgg cccaggccgg   30420
acagcaggtc ccgggtggcc cgggcggccg cctctccgct gcgcggtccg aggaccacct   30480
cgaccgtggg gatcacgtac gcggggttca tgaagtgcac gccgacgagg tcctcggggc   30540
gggggacggg tcggccagc tcgtcgatgg ggacgcccga ggtgttgctg acgagcagcg   30600
tccccgggcg cgccacggac gccaggtccg ccagcacctc ggccttccgc tcggggtcct   30660
cggtgacggc ctcgatcacg gcggtcgcgg tggcgacggc ggccggcgcc tcctcgacgg   30720
tcagctcccc gggcgggcgg tcgtggggca gcgcgcccat cagccgggcc gtccgcagat   30780
gcagcgcgac cgcgtcgggg gcggccgcgc gcgcccggc ggaggtgtcg accagtgtga   30840
ccgggtgccc gtgtccgacg gcgagtgccg cgatggccgt gcccatgacg cccgcgccga   30900
gcacgacgag cggagaattt tccttggaat cgggcacgga tcc                     30943

<210> SEQ ID NO 2
<211> LENGTH: 11171
<212> TYPE: DNA
<213> ORGANISM: Streptomyces ambofaciens

<400> SEQUENCE: 2
ctgcaggcgc gcgggctgct cgggcaggag gcgcccgccg agagcctcga cgcgatgatc    60
gacgactact gcgcgcagat ccgcgaggtc cagcccgagg gcccgtaccg gctgctcggc   120
tggtccatgg gcgggctgct cgcgcaccgg gtcgccaccc gcctcagcg ggcggggcag   180 cgcgtcgacc tgctcgcgat cgtcgacgcc tatccgcccg cctcggtgcg ggccgactgg   240 gacgcggcg agatggtggc gcggatcggt gaggaactgg gcttcgacgt ggaccgggtc   300
ggccccggcc aggaggaggc gctgctcgcg gatctgcggg cgaaggggca tcccctgggg   360
catctgccgg gcggtgacat cggcgcggcg gtccgcgtgt acgtcaacag ctcgcgcctg   420
acgaggaacc tgcggcccga ggcgttcgac ggggacgtcc tcttcttcgc ctccgggacc   480
tcgttcgccc aggacgacca ggttcacgac gtcgccgcct ggcggccgta cgtcaccggg   540
cagatcaccg agcacgtgat cgaccacctc cacgaggacc tcttgatcga accggccgcg   600
gtcacggcca tctccgacgt gctcgtcggg catctgcccg cggacgacac accccgcgcg   660
tccggcgcac ccgcgcacc tgcgcatcc cgatgaggaa ggaaacatca tgagcaaccc   720
gttcgaggac acggaagcca cctacgtcgt gctggtcaac gacgagggc agcactcgct   780 gtggccgtcg ttcgcggagg tcccggcggg ctggtccgtc gtggtgccgg agacggaccg   840
```

-continued

```
gcagtcgtgc ctggactaca tcaacgagaa ctggaccgac atgcgcccca agagcctcgt    900
cgaggcgatg gcgacggccg ggcaggacgc cccttgagcc aggacgccat gatccgggcg    960
gtcggcgtcc gcaagagctt gcggcgacgt ccacgccctc gacggcgtgg acatcgaggt   1020
cgaacggggc cgggtgctcg ggctgctggg tcacaacggg gccggcaaga cgaccttggt   1080
gaacatcctt gccacggtct ccccggcgtc cgcgggcacg gtgaccgtcg ccggtttcga   1140
cgtcgcgacg cagggcgccg agatccgcgc gcgcatcggg gtgaccggcc agttcgcgtc   1200
ggtgacgag tacctgagcg gattccgcaa cctcgtcctg atcggccgcc tcctcggggc    1260
gggacggcgt gaggcggcgg cccgggccac cgagctcctg gagctgttcg agctgaccgg   1320
ggcggcccac cagccctccc gcacctactc gggcgggatg cgccgacggc tcgacctcgc   1380
cgccagcctg gtcggccggc cggacgtgct gttcctcgac gagccgacga ccgggctgga   1440
cccggcgacc cggatcgccc tgtgggagac ggtggagaag ctggtggcgg gcggcacgac   1500
cgtcctgctg accacccagt acctggacga ggcggaccgg ctggccgact ggatcaccgt   1560
cctgtcgaag ggccgggtgg tggcctcgga caccaccgac cggctcaagg ccgacctggg   1620
ccaccggtcg gtgcgggtgg tccttccgcc cgccgccgac ctgacggccg ccgccgccgc   1680
gctcaccgcc ggcgggttcc gtccgcggtc cgacgccggg gagcacgcgc tgaccacgcc   1740
cgtggacacc tcggccggta tcgcgggcgt catccgcgcg ctggacaccg tcggaacgca   1800
ggccgtcgag ctgaccgtca aggagccgtc cctggacgac gtctacctgg cgctcaccca   1860
tccctcaccc gccgccgacg cggcctgatc cccaggagtt ccgttggcca tccaggagcg   1920
cgccgtgaag gaggtggcgg tcgacaccgg tacccccggcc ggccccgtgt ggcgtggtgc   1980
cggcctcggc acccagctgt gggtactgac cgcgcggcag atccgttcca tgtacgcgca   2040
ccgccgcctg gcgctgttca gcctgatgca accggtgatc atgctgttgc tgctgagcga   2100
gatcttcggc agcatggccg acccggacga cttcccgcag ggcgtgcgct acatcgacta   2160
cgtggtgccc gcgctgctgg tcaccaccgg catcggctcg gcccagggcg cggggggtgg   2220
cctggtcagg gacatggaca acgggatggt ggcgcgcttc cgcgtcctgc cggcccggct   2280
gttcctggtg ctggtcgccc ggtcgctggc cgatctggtc cgtgtgttca ccgagttggt   2340
cgtcctcgtg gccgtcggtg tgatcctgct gggcttccgt ccggccgggg gtttgtgggg   2400
cacgtccgcc gccctgttgc tcaccctgtt cgtcatctgg tcgctgatct gggggttcat   2460
cgccctcgcg gcgtggctgc gcagcgtgga ggtgatgtcc agcctcgcgg ttctggtgat   2520
gttcccgctc atgttcgcct ccagtgcgtt cgtcccgctg gacgccctcc ggagtggct    2580
gcgctcggtg gcgcacctca accccgtgac gtacgcggtc gacagcgccc gccgcctggc   2640
gctggactgg gacccggggt ggagcgtgcc cggcgcgctg ctgaccagca ccgcgctcat   2700
ggcggtgggg atgtacgtcg ccgggcgttc cttcaagagg cccccgaacg aatgattccg   2760
gcgaacgggt ccgtcgcctg cccctccggg ctcgcccggg ggaggcgggc gcggtctcag   2820
cggtcggccg tccgcccgta ggcgcggaag agtgcggtcc actccgggac cgtgaggtcc   2880
ttgacccggt cggccggcct cacgcccgcc ccgcgcacga actgggcgtg tccgcggcgc   2940
agcaccttcc gcgcggcgtc gcccaccgtc atctggccgg tgtcgaagac ccgttggacg   3000
aaccgctggt aggcggcctt ctcacgccag ggcacggacg gcctgcggtg cggggcgacc   3060
atcagggtct gggtgtccgc gcgcggtacg ggggtgaagt cctggcgtga aaggccagg    3120
ccccggtcga acgagtacca cggctcccac tgggcgttga agaggtttcc gccccaggct   3180
```

```
ccggtccgct ttcccacgta ctcccgctgc aacaggaaca cgccctgccg catgcgcgcc   3240
ggacccatgt cgaggcagcg cctcagcatt ctggtgccgg tgacgaaggg aagattcccg   3300
atgagtctga ccggctgccc gggcagttgc agggtcagga aatcctcgtt caccaccgtg   3360
acgtccggca gcgattcggc ggccagccgc cgagcccagc ggggatctat ttccaccgcg   3420
agtaaaggcg tcccgggtga ggcgagcact ttggtcaccc gccctgatcc cgcgcctatt   3480
tcgacggtca tcaggtcatt cggagaatcg ggcggaatgg tgtccgaacc gtccagctga   3540
gcggagaaac gacaggccgc ggcggctgta cgaaagaagt tctgaccccca ttctctccgc   3600
gcggtgctgc gtgaatcagc gggtgcggag acggattgcg gtggcagtgg ggatttcaat   3660
gtcacctcgg cgacattacc aagtcttgac ccaacggtcc atcaaccacc ggtataccccc   3720
atgcaattca gccaccgtcc ggcccgatcc cgacgttcgg ccgcgggcct ttcgggcccg   3780
accggtgacc agcgcgcgaa ccggagttcc cggcgatatt tccggctcct ggcgactcgc   3840
cacagtctcg tcggggcgg ccggcgccat gactccgacg ggggcgattc ccggccgact   3900
tcgtcaggtc cggagggtcc cccgggcggc gcgggccgat ggccgctgac tgtgtcatct   3960
gcgggttgtc ggccgaacac accgcgcccc aggatgactc agccgttcct gcggtcgtcc   4020
cgaccccggt cccacccccg aaaagaggag cgagaatcca gtgctccagc gcgtcgatct   4080
gtcgtcactc accggcctcc gctggtatgc ggcgctgacg gtattcgcct gtcacatcgc   4140
ccagcagggc ttcttcgccg accagcaggt gggcagcgca ctgctgcaca tcaccccgct   4200
cggttccatg gcgtctcga tcttcttcat actgagtgga ttcgtcctcg cctggtcggc   4260
ccgcgacgag gactccgtgc cgactttctg gcggcgccgc atcgcgaaga tctatccgct   4320
gcatctcgcg acgttcggca tcgcggctct catcatttttc tccctgtcgg agccggtact   4380
tcccggcggt tccgtatggg acgggctggt gcccaatgtt ctgctcgtgc agtcctggct   4440
tcccgacgcg accctcacgg ccagtttcaa cacgcccagc tggtcgctct cctgtgagat   4500
cgccttctat ctgtcgttcc cgctgtggta ccggctggtg cgcaggattc ccgcacggcg   4560
gctgtggtgg tgcgccgcgg ggatcgccgt ggccgtgacg tgtgtgccccc tgctggcggg   4620
cctgctcccg gcgagcgagg aggtggcccc cgggatgtcg ctcaacgagg tctggttcgc   4680
gtactggctt ccgccggtgc gcatgctgga gttcgtcctc ggcatcgtga tggcgctgat   4740
cctgcgcgcg gggatctgga agggccccgg tccggcggtc tgcacggcgc tcctcgccgc   4800
gagttacggc ctcacccaga tggtgccccc gatcttcacc ctcgtcgcct gctccgtcgt   4860
accggccgcg ctgctgatca cggcgctggc cgacgccgac gtgcacggcc ggcgcacggg   4920
gctgcgttcg gcgacgctgg tgcggctggg ccagtggtcc ttcgccttct acctggtcca   4980
cttcctgatc atccgctacg acaccggct gatgggcggc gatctgggct acgagcggca   5040
gtggagcacc ccggccgcga tcgcgctgtc cctggggatg ctgggggtgg cggtcctggc   5100
cggcggtctg ctgcacaccg tcgtcgaaca gccctgcatg cgcctgttcg gcagccgcag   5160
gtccgcctcc cgtccgaagc ccggcgccac cgcggctccc cggaactcac ccgcggccga   5220
cgcggccggc gtgcccctgc tcccgggcgt accgggcccc gcgcacaccc ccgcagcgac   5280
gaacgaaccc accccgagag gatgatgagc gtggcagacc agacggctct cagccccgcg   5340
ctgctggagt acgcccggag cgtcgcgctg cggacgacg gcctgctgcg cgaactgcac   5400
gaggtgaccg ccgggctccc cggcggccgg gccatgcaga tcatgcccga ggaggcgcag   5460
ttcctcgccc tgctgatccg gctcgtcggt gcccggcggg tgctggagat cggcaccttc   5520
acggggtaca gcacgctgtg catggcgcgg gcactgcccg ccgacggcac cgtcgtcacc   5580
```

```
tgcgacatca gcgacaggtg gcccggcgtc ggcgcaccgt actggcgccg ggccggggtg    5640
gagtcccgga tcgacctgcg cgtcggcgac gccgtccgga ccctcgccga gctccgcgag    5700
cacgaggggg acggctcgtt cgacctggtc ttcgtcgacg ccgacaagac cgggtacccg    5760
cactactacg agcaggcgct ggccctggta cgccccggcg gactggtggc ggtcgacaac    5820
accctgttct tcggccgggt ggccgacccg gccgtcgagg acgccgacac cgtcgccgtg    5880
cgcgcgctca acgagctgct gcgcgacgac gaacgcgtgg acatcgccct gctgacggtc    5940
gccgacggga tcactctggc ccgccggcgg gagtgagtcc gcacggggtg cggagcacct    6000
ggtgccgtca ccggcccgca cacgtccgcc gccgacctgc ccgggcaggt cgccgagctg    6060
ctgccctggc gtggccggcc ctcgtcgagg ccgcgcggt cagcggaacc ggttgatcgc    6120
gtcgatgtgc cgcgcccgct tctcctcgtc gcgcacgccc agcccctccg tgggcgccag    6180
gcagagcacg ccgaccttgc cctggtgctg gttgccgtgc acgtcgtgca cggcaaccgc    6240
cgtgtcggcc agcgggtagg tgcgcgagag ggtgggtgg atcctcccct tggcgacgag    6300
ccggttcgcc tcccacgcct cgcggtagtt ggcgaagtgg gtgccgacga tacgcttgag    6360
gtgcatccag aggtagcggt tgtcgaactc gtggcggaag cccgaggtgg aggcgcaggt    6420
gacgatcgtg ccgcccctgc gggtgacgta gacggacgcc ccgaaggtct cccggccggg    6480
gtgctcgaag acgatgtcga cgtcctcgcc cccggtgacc tcgcggatgc gcttgccgaa    6540
gcgcttccac tcccgcgggt cctgggtgtc ctcgtcgctc cagaagcggt agtcctcggc    6600
ggagcggtcg atgatggcct ccgcgcccat ggcccggcac acctcggcct tgcgcgcgct    6660
ggagaccacg cagacggggt gggccccgcc ggcgagggcc agctgggtgg cgtacgagcc    6720
caggccgccg ctggcgcccc agatcagcac gttgtcgccc tgcttcatgc cggcgccgtt    6780
gcgggagacc agctggcggt aggcggtgga gttgaccaga ccgggcgcgg cggcctcctc    6840
ccaggtcaga tgggccgcct tgggcatcag ctggttggac ttgacgaggg ccacctcggc    6900
caggcccccg aagttggtct cgaagcccca gatgcgctgg gccgggtcga gcatggtgtc    6960
gtcgtgcccc tcggggctct ccagctccac cgacagacag tgcgcgacga cctcgtcacc    7020
gggtttccag acgttcacgc cgggtcccgt gcgcagcacc acgccggaca ggtcggaacc    7080
gaggatgtgg tacggcaggt cgtggcgcgc ggccagcggc gaggtgcgcc cgtagcgctc    7140
caggaagccg aacgtcggga ggggctcgaa gatggaggac cagaccgtgt tgtagttgac    7200
ggagctggcc atcaccgcga ccagcgcctc cccgggcccc acttcgggca gcggcacctc    7260
gtcgacgtgc agggacttgc gcgggtcctt gtccgcgctc ggcatcccgc ggaacatgtc    7320
ggtgtcctct ttgcggacgg tcacggcgcg gaaggactcg ggcaggggca cgccgcgat    7380 gtcctcgggg gtgcggtccg cggcggtgat cgcggcgagc agcgcgctct gcgcatggct    7440
ttcgggcatg gaacggtctc cgatcgctcg tgtcgtcagg tggcccggtg cagggcggtg    7500
aggcgctcca gggtggggat gatcccggcg ggcgtggggt cggcgagcat ctcctcgctc    7560
agccgccgcg cgcccgccct gatcgcgggg tcgtgcacgg ccgtgtgcac cgcgtcggcc    7620
agaccgcgcg ccgtgagcgt cgccgcgggc aggtcgaacc cggcggacag cgcgctggagt   7680 tgctgcgcct tgagcggcgc gtcccacagg gagggcagca ggatctgcgg cactccgtgg    7740
cgcagggcgg tggaccaggt gcccgctccg ccgtggtgga tgatcgcggc gcagctcggc    7800
agcagcgcgt cgagcggtac gaagtccacg ggcacgacgt tgtcgggag gtgcccagg    7860 cggtcgagct gggaggtgtc cagggtggcc accacctcga tgtccagccg gccgagcgcc    7920
```

```
tccagcagtt cggagtagga daccgcgtcg cggccgtagg tctcgcgggc ggacacgccg   7980
agggtgaggc agacgcgggg gcggtcgggc ttcttgccga gccagggttc gatcacggag   8040
cgcccgttgt agggcacgta gcacatgggc accgtggtct ggcccaggtc gaggcgggtg   8100
ctgcgcgggc ccgggtcgat cacccagtgg ccgagcacgt cgcgttcgtc gaaggcgagc   8160
ccgtaccggt ccagcgtcca gccgagccat tcggcgatgg ggtcctcgcg cagttcctcc   8220
ggcatcccgt cgagggcggc gaggaagcgc aggcgggagc gtccgatggc gtcgggccc    8280
cacaggatgc gcgcgtgggc ggcaccgcag gcgcgggccg cgaccggccc cgcgtaggtc   8340
cagggttccc acacgaccag gtcgggccgc cagccacggg cgaagtcgac gatctcgtcc   8400
atcgtggcgg cgccgttgaa cggggcgaag cacagggcgg ccatcatgct ctgctggccg   8460
agcaggtact cccaggtggt ctcctcctcg ctctccacct caccgaactc gaagccccgc   8520
tggtagggga cgaggtcgct gcccatctcg gcgagcagct ccgcggccgg tcggtcgtcg   8580
cccaccggta cggcggtcag gccggtggag gtgatgacgt cggtgaggga gggcgggctc   8640
gccacccgta cctcgtgccc ggcggcgcgc agcgcccagg cgaggggcac cagactgtag   8700
tagtgggtgt tgtgggcgag ggatgtcagc aggacgcgca cagcggctcc ggtctgggag   8760
ggggcgtacg gacggcgggg tcatcccggg tggacccgga ggcgggcgca ggcgcccagg   8820
accggtgacc gcggccgggt caggggcggt ccctcggccc gcaggccggg caggcggccg   8880
gccgtgacct ggaccgcggt ggtggcggcc aggcggatca gcgggagggc gagcgccagg   8940
tgcggtccgt cggcgccccc gagcggctcc ggcccgggga tctcccgtcc ggcggcggcc   9000
agcaccacga cgtgctcgtc ggcggtgatc cggcggccgc cgagttcgag gccggtgtgc   9060
gcgaccggt tctccagccg ggccgggggg cgctcgcgca gcacctggtc gacggcgttc    9120
gccgcggccg gcgtccggcg ggccctctcc cactccccg gccggccgag cagccggtgg    9180
accgtgtgcg cgacggcggt gacgacgggt tcgggtgcgc cgaccgcgag gagcagcgcg   9240
atgcgctcga cgtcgccggg ggcgacgccg tcgtgcagga ggagggcgag cacgtcgtcg   9300
ggccggggct cggcgttccc gaggcccgg gacttctccg cgacgagctc ggggaccagg    9360
tcggccagtg tgcggacggc gtcggcggac tcccgggcca cggtcagcag ttgcggggcc   9420
atccgggcgt cgagctgggg gccgcaggcg gcgagtgccc gcgcggcggt ggcgcggtcg   9480
cggcccggca ctccgaggag cctgagcatc agctcgacgg cgtagggccg ggcgacctcg   9540
ccgacaaggt cgaacccggc gtcaccggtg ggcagcaggc ggccgagcac tctgcgggcg   9600
gtggtgcgcg ccgcgcaggg cgcctgggcc ggggcgtacc ggctgagcac cggggcggcc   9660
agcgcccgca ggcgtacgag ctccgcgcgt tcgtggtggg ggaacgcctc ggcgaggggc   9720
agcagttcct cgtccgggcg gcgtccgcc cggtccagct gccgaagcg cgggtcggcc     9780
aggacggccg ccgccacctc ggggtccgcg gtcacccagg cgtccagctg ttcgctgcgg   9840
aaccacggtc cgcggcccg gatctcccgt tcgaacggct cggggtcggc gacggcgcgc    9900
aggatcagcg cgtacgggtc gccctggttg ccggcgcacc agtgtgcggc ccgggtcagc   9960
tggagccgac ggccgagcgc acggacgccc gtgctcgtgt ccgcgctcgt gctcgtgctc  10020
gcggggccg tttccgtggc aagggtgggc atggctgccc tgcctttctt ctcgggtcga   10080
tgggggcgct cgcacgatcg ggggaccccgg gtgtgccggg tggtcgggg caaccccgcct 10140
ccgggccgcg gcggtccgcg tcggcaccgg gtcagcggcg ggtgccgatg aacagcccgc  10200
gaccggacgg gccgccttcc tggtagacca cgtcgcagcc ggcgcgctcg aaggccgcct  10260
cgtagtcggc gcgcgggaac agggtgatgg tgtggtcctc ggtcaggtga cggacgccgc  10320
```

-continued

```
cgggtccggc gaggaggtag tgcacctcga tgcgggtggc gttcccctcc cgtacggagt   10380
gcgagacccg gcagacggtg cgctcgcccg cctccgtgat gctggcgccg acgtaaccgg   10440
gggtgaagga ctcggggaac caccagggtt cgacgacgat gacgccggac ggttcgaggt   10500
ggtcggtgaa ggcccgcagc gtgctgtcga gttcgtcggt ggtccgcagg tggcctatgg   10560
agctgaacat gcaggtcacc gcgtcgaacc ggcgtcccag ggagaacgag cgcatgtccc   10620
cttggtggaa ggtgacaccg gggttccggc cggtcgcgag ggccagcatg tcggcggaga   10680
gttccaggcc ctcgacgtgg tcgaagaggc cgtccaggtg gtgcaggtgc tggccggtgc   10740
cgcaggccac gtcgagcagg gtccgggcgc ccggccggtg gacgcgcacg agtgcggcga   10800
tctcctcggc ctcctgccgg tagtccttcc ccttcccctc gtggaccagg tcgtagacgg   10860
ccgcgatgtc gtcggcgtac atcagtgttt ccctccggtg agcggggcgg gaccgggctg   10920
gtgcgggagg ctgtccagcc attcgtgcac cagggacgcg gtgtgccggg cgtgttcggt   10980
gagcatggtg aagtggttgc cgggcacgtc ggcgacggtc cgtgcgaacg ggacctggga   11040
ccgccagtcg ccccgcgccc cgcccgcggg cggccacgcg cacaggggtt cggacgcccg   11100
ggccagcagg acggggcttt cgagggcggt gagccgggtt ccgagcacca gccgctgata   11160
gccggccatg g                                                       11171
```

<210> SEQ ID NO 3
<211> LENGTH: 711
<212> TYPE: DNA
<213> ORGANISM: Streptomyces ambofaciens
<220> FEATURE:
<221> NAME/KEY: CDS
<222> LOCATION: (1)..(711)

<400> SEQUENCE: 3

```
atg tac gcc gac gac atc gcg gcc gtc tac gac ctg gtc cac gag ggg        48
Met Tyr Ala Asp Asp Ile Ala Ala Val Tyr Asp Leu Val His Glu Gly
1               5                   10                  15 aag ggg aag gac tac cgg cag gag gcc gag gag atc gcc gca ctc gtg        96
Lys Gly Lys Asp Tyr Arg Gln Glu Ala Glu Glu Ile Ala Ala Leu Val
            20                  25                  30 cgc gtc cac cgg ccg ggc gcc cgg acc ctg ctc gac gtg gcc tgc ggc       144
Arg Val His Arg Pro Gly Ala Arg Thr Leu Leu Asp Val Ala Cys Gly
        35                  40                  45 acc ggc cag cac ctg cac cac ctg gac ggc ctc ttc gac cac gtc gag       192
Thr Gly Gln His Leu His His Leu Asp Gly Leu Phe Asp His Val Glu
    50                  55                  60 ggc ctg gaa ctc tcc gcc gac atg ctg gcc ctc gcg acc ggc cgg aac       240
Gly Leu Glu Leu Ser Ala Asp Met Leu Ala Leu Ala Thr Gly Arg Asn
65                  70                  75                  80 ccc ggt gtc acc ttc cac caa ggg gac atg cgc tcg ttc tcc ctg gga       288
Pro Gly Val Thr Phe His Gln Gly Asp Met Arg Ser Phe Ser Leu Gly
                85                  90                  95 cgc cgg ttc gac gcg gtg acc tgc atg ttc agc tcc ata ggc cac ctg       336
Arg Arg Phe Asp Ala Val Thr Cys Met Phe Ser Ser Ile Gly His Leu
            100                 105                 110 cgg acc acc gac gaa ctc gac agc acg ctg cgg gcc ttc acc gac cac       384
Arg Thr Thr Asp Glu Leu Asp Ser Thr Leu Arg Ala Phe Thr Asp His
        115                 120                 125 ctc gaa ccg tcc ggc gtc atc gtc gtc gaa ccc tgg tgg ttc ccc gag       432
Leu Glu Pro Ser Gly Val Ile Val Val Glu Pro Trp Trp Phe Pro Glu
    130                 135                 140 tcc ttc acc ccc ggt tac gtc ggc gcc agc atc acg gag gcg ggc gag       480
```

```
Ser Phe Thr Pro Gly Tyr Val Gly Ala Ser Ile Thr Glu Ala Gly Glu
145                 150                 155                 160 cgc acc gtc tgc cgg gtc tcg cac tcc gta cgg gag ggg aac gcc acc     528
Arg Thr Val Cys Arg Val Ser His Ser Val Arg Glu Gly Asn Ala Thr
                    165                 170                 175 cgc atc gag gtg cac tac ctc ctc gcc gga ccc ggc ggc gtc cgt cac     576
Arg Ile Glu Val His Tyr Leu Leu Ala Gly Pro Gly Gly Val Arg His
                180                 185                 190 ctg acc gag gac cac acc atc acc ctg ttc ccg cgc gcc gac tac gag     624
Leu Thr Glu Asp His Thr Ile Thr Leu Phe Pro Arg Ala Asp Tyr Glu
        195                 200                 205 gcg gcc ttc gag cgc gcc ggc tgc gac gtg gtc tac cag gaa ggc ggc     672
Ala Ala Phe Glu Arg Ala Gly Cys Asp Val Val Tyr Gln Glu Gly Gly
    210                 215                 220 ccg tcc ggt cgc ggg ctg ttc atc ggc acc cgc cgc tga                 711
Pro Ser Gly Arg Gly Leu Phe Ile Gly Thr Arg Arg
225                 230                 235
```

<210> SEQ ID NO 4
<211> LENGTH: 236
<212> TYPE: PRT
<213> ORGANISM: Streptomyces ambofaciens

<400> SEQUENCE: 4

```
Met Tyr Ala Asp Asp Ile Ala Ala Val Tyr Asp Leu Val His Glu Gly
1               5                   10                  15

Lys Gly Lys Asp Tyr Arg Gln Glu Ala Glu Glu Ile Ala Ala Leu Val
                20                  25                  30

Arg Val His Arg Pro Gly Ala Arg Thr Leu Leu Asp Val Ala Cys Gly
            35                  40                  45

Thr Gly Gln His Leu His His Leu Asp Gly Leu Phe Asp His Val Glu
        50                  55                  60

Gly Leu Glu Leu Ser Ala Asp Met Leu Ala Leu Ala Thr Gly Arg Asn
65                  70                  75                  80

Pro Gly Val Thr Phe His Gln Gly Asp Met Arg Ser Phe Ser Leu Gly
                85                  90                  95

Arg Arg Phe Asp Ala Val Thr Cys Met Phe Ser Ile Gly His Leu
                100                 105                 110

Arg Thr Thr Asp Glu Leu Asp Ser Thr Leu Arg Ala Phe Thr Asp His
            115                 120                 125

Leu Glu Pro Ser Gly Val Ile Val Val Glu Pro Trp Trp Phe Pro Glu
        130                 135                 140

Ser Phe Thr Pro Gly Tyr Val Gly Ala Ser Ile Thr Glu Ala Gly Glu
145                 150                 155                 160

Arg Thr Val Cys Arg Val Ser His Ser Val Arg Glu Gly Asn Ala Thr
                165                 170                 175

Arg Ile Glu Val His Tyr Leu Leu Ala Gly Pro Gly Gly Val Arg His
            180                 185                 190

Leu Thr Glu Asp His Thr Ile Thr Leu Phe Pro Arg Ala Asp Tyr Glu
        195                 200                 205

Ala Ala Phe Glu Arg Ala Gly Cys Asp Val Val Tyr Gln Glu Gly Gly
    210                 215                 220

Pro Ser Gly Arg Gly Leu Phe Ile Gly Thr Arg Arg
225                 230                 235
```

<210> SEQ ID NO 5
<211> LENGTH: 1272

```
<212> TYPE: DNA
<213> ORGANISM: Streptomyces ambofaciens
<220> FEATURE:
<221> NAME/KEY: CDS
<222> LOCATION: (1)..(1272)

<400> SEQUENCE: 5 atg ccc acc ctt gcc acg gaa acg gcc ccc gcg agc acg agc acg agc      48
Met Pro Thr Leu Ala Thr Glu Thr Ala Pro Ala Ser Thr Ser Thr Ser
1               5                   10                  15 gcg gac acg agc acg ggc gtc cgt gcg ctc ggc cgt cgg ctc cag ctg      96
Ala Asp Thr Ser Thr Gly Val Arg Ala Leu Gly Arg Arg Leu Gln Leu
                20                  25                  30 acc cgg gcc gca cac tgg tgc gcc ggc aac cag ggc gac ccg tac gcg     144
Thr Arg Ala Ala His Trp Cys Ala Gly Asn Gln Gly Asp Pro Tyr Ala
            35                  40                  45 ctg atc ctg cgc gcc gtc gcc gac ccc gag ccg ttc gaa cgg gag atc     192
Leu Ile Leu Arg Ala Val Ala Asp Pro Glu Pro Phe Glu Arg Glu Ile
        50                  55                  60 cgg gcc cgc gga ccg tgg ttc cgc agc gaa cag ctg gac gcc tgg gtg     240
Arg Ala Arg Gly Pro Trp Phe Arg Ser Glu Gln Leu Asp Ala Trp Val
65                  70                  75                  80 acc gcg gac ccc gag gtg gcg gcg gcc gtc ctg gcc gac ccg cgc ttc     288
Thr Ala Asp Pro Glu Val Ala Ala Ala Val Leu Ala Asp Pro Arg Phe
                85                  90                  95 ggc acg ctg gac cgg gcc gga cgc cgc ccg gac gag gaa ctg ctg ccc     336
Gly Thr Leu Asp Arg Ala Gly Arg Arg Pro Asp Glu Glu Leu Leu Pro
                100                 105                 110 ctc gcc gag gcg ttc ccc cac cac gaa cgc gcg gag ctc gta cgc ctg     384
Leu Ala Glu Ala Phe Pro His His Glu Arg Ala Glu Leu Val Arg Leu
            115                 120                 125 cgg gcg ctg gcc gcc ccg gtg ctc agc cgg tac gcc ccg gcc cag gcg     432
Arg Ala Leu Ala Ala Pro Val Leu Ser Arg Tyr Ala Pro Ala Gln Ala
        130                 135                 140 ccc tgc gcg gcg cgc acc acc gcc cgc aga gtg ctc ggc cgc ctg ctg     480
Pro Cys Ala Ala Arg Thr Thr Ala Arg Arg Val Leu Gly Arg Leu Leu
145                 150                 155                 160 ccc acc ggt gac gcc ggg ttc gac ctt gtc ggc gag gtc gcc cgg ccc     528
Pro Thr Gly Asp Ala Gly Phe Asp Leu Val Gly Glu Val Ala Arg Pro
                165                 170                 175 tac gcc gtc gag ctg atg ctc agg ctc ctc gga gtg ccg ggc cgc gac     576
Tyr Ala Val Glu Leu Met Leu Arg Leu Leu Gly Val Pro Gly Arg Asp
                180                 185                 190 cgc gcc acc gcc gcg cgg gca ctc gcc gcc tgc ggc ccc cag ctc gac     624
Arg Ala Thr Ala Ala Arg Ala Leu Ala Ala Cys Gly Pro Gln Leu Asp
            195                 200                 205 gcc cgg atg gcc ccg caa ctg ctg acc gtg gcc cgg gag tcc gcc gac     672
Ala Arg Met Ala Pro Gln Leu Leu Thr Val Ala Arg Glu Ser Ala Asp
210                 215                 220 gcc gtc cgc aca ctg gcc gac ctg gtc ccc gag ctc gtc gcg gag aag     720
Ala Val Arg Thr Leu Ala Asp Leu Val Pro Glu Leu Val Ala Glu Lys
225                 230                 235                 240 tcc cgg ggc ctc ggg aac gcc gag ccc cgg ccc gac gac gtg ctc gcc     768
Ser Arg Gly Leu Gly Asn Ala Glu Pro Arg Pro Asp Asp Val Leu Ala
                245                 250                 255 ctc ctc ctg cac gac ggc gtc gcc ccc ggc gac gtc gag cgc atc gcg     816
Leu Leu Leu His Asp Gly Val Ala Pro Gly Asp Val Glu Arg Ile Ala
                260                 265                 270 ctg ctc ctc gcg gtc ggc gca ccc gaa ccc gtc gtc acc gcc gtc gcg     864
Leu Leu Leu Ala Val Gly Ala Pro Glu Pro Val Val Thr Ala Val Ala
            275                 280                 285
```

```
cac acg gtc cac cgg ctg ctc ggc cgg ccg ggg gag tgg gag agg gcc       912
His Thr Val His Arg Leu Leu Gly Arg Pro Gly Glu Trp Glu Arg Ala
    290                 295                 300 cgc cgg acg ccg gcc gcg gcg aac gcc gtc gac cag gtg ctg cgc gag       960
Arg Arg Thr Pro Ala Ala Ala Asn Ala Val Asp Gln Val Leu Arg Glu
305                 310                 315                 320 cgc ccc ccg gcc cgg ctg gag aac cgg gtc gcg cac acc ggc ctc gaa      1008
Arg Pro Pro Ala Arg Leu Glu Asn Arg Val Ala His Thr Gly Leu Glu
                325                 330                 335 ctc ggc ggc cgc cgg atc acc gcc gac gag cac gtc gtg gtg ctg gcc      1056
Leu Gly Gly Arg Arg Ile Thr Ala Asp Glu His Val Val Val Leu Ala
            340                 345                 350 gcc gcc gga cgg gag atc ccc ggg ccg gag ccg ctc ggg ggc gcc gac      1104
Ala Ala Gly Arg Glu Ile Pro Gly Pro Glu Pro Leu Gly Gly Ala Asp
        355                 360                 365 gga ccg cac ctg gcg ctc gcc ctc ccg ctg atc cgc ctg gcc gcc acc      1152
Gly Pro His Leu Ala Leu Ala Leu Pro Leu Ile Arg Leu Ala Ala Thr
    370                 375                 380 acc gcg gtc cag gtc acg gcc ggc cgc ctg ccc ggc ctg cgg gcc gag      1200
Thr Ala Val Gln Val Thr Ala Gly Arg Leu Pro Gly Leu Arg Ala Glu
385                 390                 395                 400 gga ccg ccc ctg acc cgg ccg cgg tca ccg gtc ctg ggc gcc tgc gcc      1248
Gly Pro Pro Leu Thr Arg Pro Arg Ser Pro Val Leu Gly Ala Cys Ala
                405                 410                 415 cgc ctc cgg gtc cac ccg gga tga                                      1272
Arg Leu Arg Val His Pro Gly
                420
```

<210> SEQ ID NO 6
<211> LENGTH: 423
<212> TYPE: PRT
<213> ORGANISM: Streptomyces ambofaciens

<400> SEQUENCE: 6

```
Met Pro Thr Leu Ala Thr Glu Thr Ala Pro Ala Ser Thr Ser Thr Ser
1               5                   10                  15

Ala Asp Thr Ser Thr Gly Val Arg Ala Leu Gly Arg Arg Leu Gln Leu
            20                  25                  30

Thr Arg Ala Ala His Trp Cys Ala Gly Asn Gln Gly Asp Pro Tyr Ala
        35                  40                  45

Leu Ile Leu Arg Ala Val Ala Asp Pro Glu Pro Phe Glu Arg Glu Ile
    50                  55                  60

Arg Ala Arg Gly Pro Trp Phe Arg Ser Glu Gln Leu Asp Ala Trp Val
65                  70                  75                  80

Thr Ala Asp Pro Glu Val Ala Ala Val Leu Ala Asp Pro Arg Phe
                85                  90                  95

Gly Thr Leu Asp Arg Ala Gly Arg Arg Pro Asp Glu Glu Leu Leu Pro
            100                 105                 110

Leu Ala Glu Ala Phe Pro His His Glu Arg Ala Glu Leu Val Arg Leu
        115                 120                 125

Arg Ala Leu Ala Ala Pro Val Leu Ser Arg Tyr Ala Pro Ala Gln Ala
    130                 135                 140

Pro Cys Ala Ala Arg Thr Thr Ala Arg Arg Val Leu Gly Arg Leu Leu
145                 150                 155                 160

Pro Thr Gly Asp Ala Gly Phe Asp Leu Val Gly Glu Val Ala Arg Pro
                165                 170                 175

Tyr Ala Val Glu Leu Met Leu Arg Leu Leu Gly Val Pro Gly Arg Asp
```

```
              180                 185                 190
Arg Ala Thr Ala Ala Arg Ala Leu Ala Ala Cys Gly Pro Gln Leu Asp
        195                 200                 205

Ala Arg Met Ala Pro Gln Leu Leu Thr Val Ala Arg Glu Ser Ala Asp
    210                 215                 220

Ala Val Arg Thr Leu Ala Asp Leu Val Pro Glu Leu Ala Glu Lys
225                 230                 235                 240

Ser Arg Gly Leu Gly Asn Ala Glu Pro Arg Pro Asp Asp Val Leu Ala
                245                 250                 255

Leu Leu Leu His Asp Gly Val Ala Pro Gly Asp Val Glu Arg Ile Ala
            260                 265                 270

Leu Leu Leu Ala Val Gly Ala Pro Glu Pro Val Val Thr Ala Val Ala
            275                 280                 285

His Thr Val His Arg Leu Leu Gly Arg Pro Gly Glu Trp Glu Arg Ala
            290                 295                 300

Arg Arg Thr Pro Ala Ala Ala Asn Ala Val Asp Gln Val Leu Arg Glu
305                 310                 315                 320

Arg Pro Pro Ala Arg Leu Glu Asn Arg Val Ala His Thr Gly Leu Glu
                325                 330                 335

Leu Gly Gly Arg Arg Ile Thr Ala Asp Glu His Val Val Leu Ala
            340                 345                 350

Ala Ala Gly Arg Glu Ile Pro Gly Pro Glu Pro Leu Gly Gly Ala Asp
            355                 360                 365

Gly Pro His Leu Ala Leu Ala Leu Pro Leu Ile Arg Leu Ala Ala Thr
        370                 375                 380

Thr Ala Val Gln Val Thr Ala Gly Arg Leu Pro Gly Leu Arg Ala Glu
385                 390                 395                 400

Gly Pro Pro Leu Thr Arg Pro Arg Ser Pro Val Leu Gly Ala Cys Ala
                405                 410                 415

Arg Leu Arg Val His Pro Gly
            420

<210> SEQ ID NO 7
<211> LENGTH: 1266
<212> TYPE: DNA
<213> ORGANISM: Streptomyces ambofaciens
<220> FEATURE:
<221> NAME/KEY: CDS
<222> LOCATION: (1)..(1266)

<400> SEQUENCE: 7 gtg cgc gtc ctg ctg aca tcc ctc gcc cac aac acc cac tac tac agt      48
Val Arg Val Leu Leu Thr Ser Leu Ala His Asn Thr His Tyr Tyr Ser
1               5                   10                  15 ctg gtg ccc ctc gcc tgg gcg ctg cgc gcc gcc ggg cac gag gta cgg      96
Leu Val Pro Leu Ala Trp Ala Leu Arg Ala Ala Gly His Glu Val Arg
            20                  25                  30 gtg gcg agc ccg ccc tcc ctc acc gac gtc atc acc tcc acc ggc ctg     144
Val Ala Ser Pro Pro Ser Leu Thr Asp Val Ile Thr Ser Thr Gly Leu
        35                  40                  45 acc gcc gta ccg gtg ggc gac gac cga ccg gcc gcg gag ctg ctc gcc     192
Thr Ala Val Pro Val Gly Asp Asp Arg Pro Ala Ala Glu Leu Leu Ala
    50                  55                  60 gag atg ggc agc gac ctc gtc ccc tac cag cgg ggc ttc gag ttc ggt     240
Glu Met Gly Ser Asp Leu Val Pro Tyr Gln Arg Gly Phe Glu Phe Gly
65                  70                  75                  80 gag gtg gag agc gag gag gag acc acc tgg gag tac ctg ctc ggc cag     288
```

```
                Glu Val Glu Ser Glu Glu Thr Thr Trp Glu Tyr Leu Leu Gly Gln
                            85                  90                  95 cag agc atg atg gcc gcc ctg tgc ttc gcc ccg ttc aac ggc gcc gcc       336
Gln Ser Met Met Ala Ala Leu Cys Phe Ala Pro Phe Asn Gly Ala Ala
            100                 105                 110 acg atg gac gag atc gtc gac ttc gcc cgt ggc tgg cgg ccc gac ctg       384
Thr Met Asp Glu Ile Val Asp Phe Ala Arg Gly Trp Arg Pro Asp Leu
        115                 120                 125 gtc gtg tgg gaa ccc tgg acc tac gcg ggg ccg gtc gcg gcc cgc gcc       432
Val Val Trp Glu Pro Trp Thr Tyr Ala Gly Pro Val Ala Ala Arg Ala
    130                 135                 140 tgc ggt gcc gcc cac gcg cgc atc ctg tgg ggc ccc gac gcc atc gga       480
Cys Gly Ala Ala His Ala Arg Ile Leu Trp Gly Pro Asp Ala Ile Gly
145                 150                 155                 160 cgc tcc cgc ctg cgc ttc ctc gcc gcc ctc gac ggg atg ccg gag gaa       528
Arg Ser Arg Leu Arg Phe Leu Ala Ala Leu Asp Gly Met Pro Glu Glu
                165                 170                 175 ctg cgc gag gac ccc atc gcc gaa tgg ctc ggc tgg acg ctg gac cgg       576
Leu Arg Glu Asp Pro Ile Ala Glu Trp Leu Gly Trp Thr Leu Asp Arg
            180                 185                 190 tac ggg ctc gcc ttc gac gaa cgc gac gtg ctc ggc cac tgg gtg atc       624
Tyr Gly Leu Ala Phe Asp Glu Arg Asp Val Leu Gly His Trp Val Ile
        195                 200                 205 gac ccg ggc ccg cgc agc acc cgc ctc gac ctg ggc cag acc acg gtg       672
Asp Pro Gly Pro Arg Ser Thr Arg Leu Asp Leu Gly Gln Thr Thr Val
    210                 215                 220 ccc atg tgc tac gtg ccc tac aac ggg cgc tcc gtg atc gaa ccc tgg       720
Pro Met Cys Tyr Val Pro Tyr Asn Gly Arg Ser Val Ile Glu Pro Trp
225                 230                 235                 240 ctc ggc aag aag ccc gac cgc ccc cgc gtc tgc ctc acc ctc ggc gtg       768
Leu Gly Lys Lys Pro Asp Arg Pro Arg Val Cys Leu Thr Leu Gly Val
                245                 250                 255 tcc gcc cgc gag acc tac ggc cgc gac gcg gtc tcc tac tcc gaa ctg       816
Ser Ala Arg Glu Thr Tyr Gly Arg Asp Ala Val Ser Tyr Ser Glu Leu
            260                 265                 270 ctg gag gcg ctc ggc cgg ctg gac atc gag gtg gtg gcc acc ctg gac       864
Leu Glu Ala Leu Gly Arg Leu Asp Ile Glu Val Val Ala Thr Leu Asp
        275                 280                 285 acc tcc cag ctc gac cgc ctg ggc acc ctc ccc gac aac gtc gtg ccc       912
Thr Ser Gln Leu Asp Arg Leu Gly Thr Leu Pro Asp Asn Val Val Pro
    290                 295                 300 gtg gac ttc gta ccg ctc gac gcg ctg ctg ccg agc tgc gcc gcg atc       960
Val Asp Phe Val Pro Leu Asp Ala Leu Leu Pro Ser Cys Ala Ala Ile
305                 310                 315                 320 atc cac cac ggc gga gcg ggc acc tgg tcc acc gcc ctg cgc cac gga      1008
Ile His His Gly Gly Ala Gly Thr Trp Ser Thr Ala Leu Arg His Gly
                325                 330                 335 gtg ccg cag atc ctg ctg ccc tcc ctg tgg gac gcg ccg ctc aag gcg      1056
Val Pro Gln Ile Leu Leu Pro Ser Leu Trp Asp Ala Pro Leu Lys Ala
            340                 345                 350 cag caa ctc cag cgc ctg tcc gcc ggg ttc gac ctg ccc gcg gcg acg      1104
Gln Gln Leu Gln Arg Leu Ser Ala Gly Phe Asp Leu Pro Ala Ala Thr
        355                 360                 365 ctc acg gcg cgc ggt ctg gcc gac gcg gtg cac acg gcc gtg cac gac      1152
Leu Thr Ala Arg Gly Leu Ala Asp Ala Val His Thr Ala Val His Asp
    370                 375                 380 ccc gcg atc agg gcg ggc gcg cgg cgg ctg agc gag gag atg ctc gcc      1200
Pro Ala Ile Arg Ala Gly Ala Arg Arg Leu Ser Glu Glu Met Leu Ala
385                 390                 395                 400
```

```
gac ccc acg ccc gcc ggg atc atc ccc acc ctg gag cgc ctc acc gcc    1248
Asp Pro Thr Pro Ala Gly Ile Ile Pro Thr Leu Glu Arg Leu Thr Ala
                405                 410                 415 ctg cac cgg gcc acc tga                                             1266
Leu His Arg Ala Thr
            420
```

<210> SEQ ID NO 8
<211> LENGTH: 421
<212> TYPE: PRT
<213> ORGANISM: Streptomyces ambofaciens

<400> SEQUENCE: 8

```
Val Arg Val Leu Leu Thr Ser Leu Ala His Asn Thr His Tyr Tyr Ser
1               5                   10                  15

Leu Val Pro Leu Ala Trp Ala Leu Arg Ala Ala Gly His Glu Val Arg
            20                  25                  30

Val Ala Ser Pro Pro Ser Leu Thr Asp Val Ile Thr Ser Thr Gly Leu
        35                  40                  45

Thr Ala Val Pro Val Gly Asp Asp Arg Pro Ala Ala Glu Leu Leu Ala
    50                  55                  60

Glu Met Gly Ser Asp Leu Val Pro Tyr Gln Arg Gly Phe Glu Phe Gly
65                  70                  75                  80

Glu Val Glu Ser Glu Glu Thr Thr Trp Glu Tyr Leu Leu Gly Gln
                85                  90                  95

Gln Ser Met Met Ala Ala Leu Cys Phe Ala Pro Phe Asn Gly Ala Ala
            100                 105                 110

Thr Met Asp Glu Ile Val Asp Phe Ala Arg Gly Trp Arg Pro Asp Leu
        115                 120                 125

Val Val Trp Glu Pro Trp Thr Tyr Ala Gly Pro Val Ala Ala Arg Ala
    130                 135                 140

Cys Gly Ala Ala His Ala Arg Ile Leu Trp Gly Pro Asp Ala Ile Gly
145                 150                 155                 160

Arg Ser Arg Leu Arg Phe Leu Ala Ala Leu Asp Gly Met Pro Glu Glu
                165                 170                 175

Leu Arg Glu Asp Pro Ile Ala Glu Trp Leu Gly Trp Thr Leu Asp Arg
            180                 185                 190

Tyr Gly Leu Ala Phe Asp Glu Arg Asp Val Leu Gly His Trp Val Ile
        195                 200                 205

Asp Pro Gly Pro Arg Ser Thr Arg Leu Asp Leu Gly Gln Thr Thr Val
    210                 215                 220

Pro Met Cys Tyr Val Pro Tyr Asn Gly Arg Ser Val Ile Glu Pro Trp
225                 230                 235                 240

Leu Gly Lys Lys Pro Asp Arg Pro Arg Val Cys Leu Thr Leu Gly Val
                245                 250                 255

Ser Ala Arg Glu Thr Tyr Gly Arg Asp Ala Val Ser Tyr Ser Glu Leu
            260                 265                 270

Leu Glu Ala Leu Gly Arg Leu Asp Ile Glu Val Val Ala Thr Leu Asp
        275                 280                 285

Thr Ser Gln Leu Asp Arg Leu Gly Thr Leu Pro Asp Asn Val Val Pro
    290                 295                 300

Val Asp Phe Val Pro Leu Asp Ala Leu Leu Pro Ser Cys Ala Ala Ile
305                 310                 315                 320

Ile His His Gly Gly Ala Gly Thr Trp Ser Thr Ala Leu Arg His Gly
                325                 330                 335
```

-continued

```
Val Pro Gln Ile Leu Leu Pro Ser Leu Trp Asp Ala Pro Leu Lys Ala
            340                 345                 350

Gln Gln Leu Gln Arg Leu Ser Ala Gly Phe Asp Leu Pro Ala Ala Thr
        355                 360                 365

Leu Thr Ala Arg Gly Leu Ala Asp Ala Val His Thr Ala Val His Asp
    370                 375                 380

Pro Ala Ile Arg Ala Gly Ala Arg Arg Leu Ser Glu Glu Met Leu Ala
385                 390                 395                 400

Asp Pro Thr Pro Ala Gly Ile Ile Pro Thr Leu Glu Arg Leu Thr Ala
                405                 410                 415

Leu His Arg Ala Thr
            420

<210> SEQ ID NO 9
<211> LENGTH: 1350
<212> TYPE: DNA
<213> ORGANISM: Streptomyces ambofaciens
<220> FEATURE:
<221> NAME/KEY: CDS
<222> LOCATION: (1)..(1350)

<400> SEQUENCE: 9 atg ccc gaa agc cat gcg cag agc gcg ctg ctc gcc gcg atc acc gcc    48
Met Pro Glu Ser His Ala Gln Ser Ala Leu Leu Ala Ala Ile Thr Ala
1               5                   10                  15 gcg gac cgc acc ccc gag gac atc gcg gcg ctg ccc ctg ccc gag tcc    96
Ala Asp Arg Thr Pro Glu Asp Ile Ala Ala Leu Pro Leu Pro Glu Ser
            20                  25                  30 ttc cgc gcc gtg acc gtc cgc aaa gag gac acc gac atg ttc cgc ggg   144
Phe Arg Ala Val Thr Val Arg Lys Glu Asp Thr Asp Met Phe Arg Gly
        35                  40                  45 atg ccg agc gcg gac aag gac ccg cgc aag tcc ctg cac gtc gac gag   192
Met Pro Ser Ala Asp Lys Asp Pro Arg Lys Ser Leu His Val Asp Glu
    50                  55                  60 gtg ccg ctg ccc gaa gtg ggg ccc ggg gag gcg ctg gtc gcg gtg atg   240
Val Pro Leu Pro Glu Val Gly Pro Gly Glu Ala Leu Val Ala Val Met
65                  70                  75                  80 gcc agc tcc gtc aac tac aac acg gtc tgg tcc tcc atc ttc gag ccc   288
Ala Ser Ser Val Asn Tyr Asn Thr Val Trp Ser Ser Ile Phe Glu Pro
                85                  90                  95 ctc ccg acg ttc ggc ttc ctg gag cgc tac ggg cgc acc tcg ccg ctg   336
Leu Pro Thr Phe Gly Phe Leu Glu Arg Tyr Gly Arg Thr Ser Pro Leu
            100                 105                 110 gcc gcg cgc cac gac ctg ccg tac cac atc ctc ggt tcc gac ctg tcc   384
Ala Ala Arg His Asp Leu Pro Tyr His Ile Leu Gly Ser Asp Leu Ser
        115                 120                 125 ggc gtg gtg ctg cgc acg gga ccc ggc gtg aac gtc tgg aaa ccc ggt   432
Gly Val Val Leu Arg Thr Gly Pro Gly Val Asn Val Trp Lys Pro Gly
    130                 135                 140 gac gag gtc gtc gcg cac tgt ctg tcg gtg gag ctg gag agc ccc gac   480
Asp Glu Val Val Ala His Cys Leu Ser Val Glu Leu Glu Ser Pro Asp
145                 150                 155                 160 ggg cac gac gac acc atg ctc gac ccg gcc cag cgc atc tgg ggc ttc   528
Gly His Asp Asp Thr Met Leu Asp Pro Ala Gln Arg Ile Trp Gly Phe
                165                 170                 175 gag acc aac ttc ggg ggc ctg gcc gag gtg gcc ctc gtc aag tcc aac   576
Glu Thr Asn Phe Gly Gly Leu Ala Glu Val Ala Leu Val Lys Ser Asn
            180                 185                 190 cag ctg atg ccc aag gcg gcc cat ctg acc tgg gag gag gcc gcc gcg   624
Gln Leu Met Pro Lys Ala Ala His Leu Thr Trp Glu Glu Ala Ala Ala
```

```
                195                 200                 205
ccc ggt ctg gtc aac tcc acc gcc tac cgc cag ctg gtc tcc cgc aac      672
Pro Gly Leu Val Asn Ser Thr Ala Tyr Arg Gln Leu Val Ser Arg Asn
    210                 215                 220 ggc gcc ggc atg aag cag ggc gac aac gtg ctg atc tgg ggc gcc agc      720
Gly Ala Gly Met Lys Gln Gly Asp Asn Val Leu Ile Trp Gly Ala Ser
225                 230                 235                 240 ggc ggc ctg ggc tcg tac gcc acc cag ctg gcc ctc gcc ggc ggg gcc      768
Gly Gly Leu Gly Ser Tyr Ala Thr Gln Leu Ala Leu Ala Gly Gly Ala
                245                 250                 255 cac ccc gtc tgc gtg gtc tcc agc gcg cgc aag gcc gag gtg tgc cgg      816
His Pro Val Cys Val Val Ser Ser Ala Arg Lys Ala Glu Val Cys Arg
            260                 265                 270 gcc atg ggc gcg gag gcc atc atc gac cgc tcc gcc gag gac tac cgc      864
Ala Met Gly Ala Glu Ala Ile Ile Asp Arg Ser Ala Glu Asp Tyr Arg
        275                 280                 285 ttc tgg agc gac gag gac acc cag gac ccg cgg gag tgg aag cgc ttc      912
Phe Trp Ser Asp Glu Asp Thr Gln Asp Pro Arg Glu Trp Lys Arg Phe
    290                 295                 300 ggc aag cgc atc cgc gag gtc acc ggg ggc gag gac gtc gac atc gtc      960
Gly Lys Arg Ile Arg Glu Val Thr Gly Gly Glu Asp Val Asp Ile Val
305                 310                 315                 320 ttc gag cac ccc ggc cgg gag acc ttc ggg gcg tcc gtc tac gtc acc     1008
Phe Glu His Pro Gly Arg Glu Thr Phe Gly Ala Ser Val Tyr Val Thr
                325                 330                 335 cgc agg ggc ggc acg atc gtc acc tgc gcc tcc acc tcg ggc ttc cgc     1056
Arg Arg Gly Gly Thr Ile Val Thr Cys Ala Ser Thr Ser Gly Phe Arg
            340                 345                 350 cac gag ttc gac aac cgc tac ctc tgg atg cac ctc aag cgt atc gtc     1104
His Glu Phe Asp Asn Arg Tyr Leu Trp Met His Leu Lys Arg Ile Val
        355                 360                 365 ggc acc cac ttc gcc aac tac cgc gag gcg tgg gag gcg aac cgg ctc     1152
Gly Thr His Phe Ala Asn Tyr Arg Glu Ala Trp Glu Ala Asn Arg Leu
    370                 375                 380 gtc gcc aag ggg agg atc cac ccc acc ctc tcg cgc acc tac ccg ctg     1200
Val Ala Lys Gly Arg Ile His Pro Thr Leu Ser Arg Thr Tyr Pro Leu
385                 390                 395                 400 gcc gac acg gcg gtt gcc gtg cac gac gtg cac ggc aac cag cac cag     1248
Ala Asp Thr Ala Val Ala Val His Asp Val His Gly Asn Gln His Gln
                405                 410                 415 ggc aag gtc ggc gtg ctc tgc ctg gcg ccc acg gag ggg ctg ggc gtg     1296
Gly Lys Val Gly Val Leu Cys Leu Ala Pro Thr Glu Gly Leu Gly Val
            420                 425                 430 cgc gac gag gag aag cgg gcg cgg cac atc gac gcg atc aac cgg ttc     1344
Arg Asp Glu Glu Lys Arg Ala Arg His Ile Asp Ala Ile Asn Arg Phe
        435                 440                 445 cgc tga                                                             1350
Arg

<210> SEQ ID NO 10
<211> LENGTH: 449
<212> TYPE: PRT
<213> ORGANISM: Streptomyces ambofaciens

<400> SEQUENCE: 10

Met Pro Glu Ser His Ala Gln Ser Ala Leu Leu Ala Ala Ile Thr Ala
1               5                   10                  15

Ala Asp Arg Thr Pro Glu Asp Ile Ala Ala Leu Pro Leu Pro Glu Ser
            20                  25                  30
```

```
Phe Arg Ala Val Thr Val Arg Lys Glu Asp Thr Asp Met Phe Arg Gly
            35                  40                  45

Met Pro Ser Ala Asp Lys Asp Pro Arg Lys Ser Leu His Val Asp Glu
 50                  55                  60

Val Pro Leu Pro Glu Val Gly Pro Gly Glu Ala Leu Val Ala Val Met
 65                  70                  75                  80

Ala Ser Ser Val Asn Tyr Asn Thr Val Trp Ser Ser Ile Phe Glu Pro
                 85                  90                  95

Leu Pro Thr Phe Gly Phe Leu Glu Arg Tyr Gly Arg Thr Ser Pro Leu
            100                 105                 110

Ala Ala Arg His Asp Leu Pro Tyr His Ile Leu Gly Ser Asp Leu Ser
            115                 120                 125

Gly Val Val Leu Arg Thr Gly Pro Gly Val Asn Val Trp Lys Pro Gly
130                 135                 140

Asp Glu Val Val Ala His Cys Leu Ser Val Glu Leu Glu Ser Pro Asp
145                 150                 155                 160

Gly His Asp Asp Thr Met Leu Asp Pro Ala Gln Arg Ile Trp Gly Phe
                165                 170                 175

Glu Thr Asn Phe Gly Gly Leu Ala Glu Val Ala Leu Val Lys Ser Asn
            180                 185                 190

Gln Leu Met Pro Lys Ala Ala His Leu Thr Trp Glu Glu Ala Ala Ala
            195                 200                 205

Pro Gly Leu Val Asn Ser Thr Ala Tyr Arg Gln Leu Val Ser Arg Asn
            210                 215                 220

Gly Ala Gly Met Lys Gln Gly Asp Asn Val Leu Ile Trp Gly Ala Ser
225                 230                 235                 240

Gly Gly Leu Gly Ser Tyr Ala Thr Gln Leu Ala Leu Ala Gly Gly Ala
                245                 250                 255

His Pro Val Cys Val Val Ser Ser Ala Arg Lys Ala Glu Val Cys Arg
            260                 265                 270

Ala Met Gly Ala Glu Ala Ile Ile Asp Arg Ser Ala Glu Asp Tyr Arg
            275                 280                 285

Phe Trp Ser Asp Glu Asp Thr Gln Asp Pro Arg Glu Trp Lys Arg Phe
            290                 295                 300

Gly Lys Arg Ile Arg Glu Val Thr Gly Gly Glu Asp Val Asp Ile Val
305                 310                 315                 320

Phe Glu His Pro Gly Arg Glu Thr Phe Gly Ala Ser Val Tyr Val Thr
                325                 330                 335

Arg Arg Gly Gly Thr Ile Val Thr Cys Ala Ser Thr Ser Gly Phe Arg
            340                 345                 350

His Glu Phe Asp Asn Arg Tyr Leu Trp Met His Leu Lys Arg Ile Val
            355                 360                 365

Gly Thr His Phe Ala Asn Tyr Arg Glu Ala Trp Glu Ala Asn Arg Leu
            370                 375                 380

Val Ala Lys Gly Arg Ile His Pro Thr Leu Ser Arg Thr Tyr Pro Leu
385                 390                 395                 400

Ala Asp Thr Ala Val Ala Val His Asp Val His Gly Asn Gln His Gln
                405                 410                 415

Gly Lys Val Gly Val Leu Cys Leu Ala Pro Thr Glu Gly Leu Gly Val
            420                 425                 430

Arg Asp Glu Glu Lys Arg Ala Arg His Ile Asp Ala Ile Asn Arg Phe
            435                 440                 445

Arg
```

<210> SEQ ID NO 11
<211> LENGTH: 675
<212> TYPE: DNA
<213> ORGANISM: Streptomyces ambofaciens
<220> FEATURE:
<221> NAME/KEY: CDS
<222> LOCATION: (1)..(675)

<400> SEQUENCE: 11

```
atg atg agc gtg gca gac cag acg gct ctc agc ccc gcg ctg ctg gag      48
Met Met Ser Val Ala Asp Gln Thr Ala Leu Ser Pro Ala Leu Leu Glu
1               5                  10                  15 tac gcc cgg agc gtc gcg ctg cgg gac gac ggc ctg ctg cgc gaa ctg      96
Tyr Ala Arg Ser Val Ala Leu Arg Asp Asp Gly Leu Leu Arg Glu Leu
            20                  25                  30 cac gag gtg acc gcc ggg ctc ccc ggc ggc cgg gcc atg cag atc atg     144
His Glu Val Thr Ala Gly Leu Pro Gly Gly Arg Ala Met Gln Ile Met
        35                  40                  45 ccc gag gag gcg cag ttc ctc gcc ctg ctg atc cgg ctc gtc ggt gcc     192
Pro Glu Glu Ala Gln Phe Leu Ala Leu Leu Ile Arg Leu Val Gly Ala
    50                  55                  60 cgg cgg gtg ctg gag atc ggc acc ttc acg ggg tac agc acg ctg tgc     240
Arg Arg Val Leu Glu Ile Gly Thr Phe Thr Gly Tyr Ser Thr Leu Cys
65                  70                  75                  80 atg gcg cgg gca ctg ccc gcc gac ggc acc gtc gtc acc tgc gac atc     288
Met Ala Arg Ala Leu Pro Ala Asp Gly Thr Val Val Thr Cys Asp Ile
                85                  90                  95 agc gac agg tgg ccc ggc gtc ggc gca ccg tac tgg cgc cgg gcc ggg     336
Ser Asp Arg Trp Pro Gly Val Gly Ala Pro Tyr Trp Arg Arg Ala Gly
            100                 105                 110 gtg gag tcc cgg atc gac ctg cgc gtc ggc gac gcc gtc cgg acc ctc     384
Val Glu Ser Arg Ile Asp Leu Arg Val Gly Asp Ala Val Arg Thr Leu
        115                 120                 125 gcc gag ctc cgc gag cac gag ggg gac ggc tcg ttc gac ctg gtc ttc     432
Ala Glu Leu Arg Glu His Glu Gly Asp Gly Ser Phe Asp Leu Val Phe
    130                 135                 140 gtc gac gcc gac aag acc ggg tac ccg cac tac tac gag cag gcg ctg     480
Val Asp Ala Asp Lys Thr Gly Tyr Pro His Tyr Tyr Glu Gln Ala Leu
145                 150                 155                 160 gcc ctg gta cgc ccc ggc gga ctg gtg gcg gtc gac aac acc ctg ttc     528
Ala Leu Val Arg Pro Gly Gly Leu Val Ala Val Asp Asn Thr Leu Phe
                165                 170                 175 ttc ggc cgg gtg gcc gac ccg gcc gtc gag gac gcc gac acc gtc gcc     576
Phe Gly Arg Val Ala Asp Pro Ala Val Glu Asp Ala Asp Thr Val Ala
            180                 185                 190 gtg cgc gcg ctc aac gag ctg ctg cgc gac gac gaa cgc gtg gac atc     624
Val Arg Ala Leu Asn Glu Leu Leu Arg Asp Asp Glu Arg Val Asp Ile
        195                 200                 205 gcc ctg ctg acg gtc gcc gac ggg atc act ctg gcc cgc cgg cgg gag     672
Ala Leu Leu Thr Val Ala Asp Gly Ile Thr Leu Ala Arg Arg Arg Glu
    210                 215                 220 tga                                                                  675
```

<210> SEQ ID NO 12
<211> LENGTH: 224
<212> TYPE: PRT
<213> ORGANISM: Streptomyces ambofaciens

<400> SEQUENCE: 12

Met Met Ser Val Ala Asp Gln Thr Ala Leu Ser Pro Ala Leu Leu Glu

```
            1               5                  10                 15
Tyr Ala Arg Ser Val Ala Leu Arg Asp Asp Gly Leu Leu Arg Glu Leu
                20                  25                  30

His Glu Val Thr Ala Gly Leu Pro Gly Arg Ala Met Gln Ile Met
                35                  40                  45

Pro Glu Glu Ala Gln Phe Leu Ala Leu Leu Ile Arg Leu Val Gly Ala
 50                  55                  60

Arg Arg Val Leu Glu Ile Gly Thr Phe Thr Gly Tyr Ser Thr Leu Cys
 65                  70                  75                  80

Met Ala Arg Ala Leu Pro Ala Asp Gly Thr Val Thr Cys Asp Ile
                85                  90                  95

Ser Asp Arg Trp Pro Gly Val Gly Ala Pro Tyr Trp Arg Arg Ala Gly
                100                 105                 110

Val Glu Ser Arg Ile Asp Leu Arg Val Gly Asp Ala Val Arg Thr Leu
                115                 120                 125

Ala Glu Leu Arg Glu His Glu Gly Asp Gly Ser Phe Asp Leu Val Phe
                130                 135                 140

Val Asp Ala Asp Lys Thr Gly Tyr Pro His Tyr Tyr Glu Gln Ala Leu
145                 150                 155                 160

Ala Leu Val Arg Pro Gly Gly Leu Val Ala Val Asp Asn Thr Leu Phe
                165                 170                 175

Phe Gly Arg Val Ala Asp Pro Ala Val Glu Asp Ala Asp Thr Val Ala
                180                 185                 190

Val Arg Ala Leu Asn Glu Leu Leu Arg Asp Asp Glu Arg Val Asp Ile
                195                 200                 205

Ala Leu Leu Thr Val Ala Asp Gly Ile Thr Leu Ala Arg Arg Glu
 210                 215                 220

<210> SEQ ID NO 13
<211> LENGTH: 1245
<212> TYPE: DNA
<213> ORGANISM: Streptomyces ambofaciens
<220> FEATURE:
<221> NAME/KEY: CDS
<222> LOCATION: (1)..(1245)

<400> SEQUENCE: 13 gtg ctc cag cgc gtc gat ctg tcg tca ctc acc ggc ctc cgc tgg tat      48
Val Leu Gln Arg Val Asp Leu Ser Ser Leu Thr Gly Leu Arg Trp Tyr
 1               5                  10                  15 gcg gcg ctg acg gta ttc gcc tgt cac atc gcc cag cag ggc ttc ttc      96
Ala Ala Leu Thr Val Phe Ala Cys His Ile Ala Gln Gln Gly Phe Phe
                20                  25                  30 gcc gac cag cag gtg ggc agc gca ctg ctg cac atc acc ccg ctc ggt     144
Ala Asp Gln Gln Val Gly Ser Ala Leu Leu His Ile Thr Pro Leu Gly
                35                  40                  45 tcc atg gcg gtc tcg atc ttc ttc ata ctg agt gga ttc gtc ctc gcc     192
Ser Met Ala Val Ser Ile Phe Phe Ile Leu Ser Gly Phe Val Leu Ala
 50                  55                  60 tgg tcg gcc cgc gac gag gac tcc gtg ccg act ttc tgg cgg cgc cgc     240
Trp Ser Ala Arg Asp Glu Asp Ser Val Pro Thr Phe Trp Arg Arg Arg
 65                  70                  75                  80 atc gcg aag atc tat ccg ctg cat ctc gcg acg ttc ggc atc gcg gct     288
Ile Ala Lys Ile Tyr Pro Leu His Leu Ala Thr Phe Gly Ile Ala Ala
                85                  90                  95 ctc atc att ttc tcc ctg tcg gag ccg gta ctt ccc ggc ggt tcc gta     336
Leu Ile Ile Phe Ser Leu Ser Glu Pro Val Leu Pro Gly Gly Ser Val
                100                 105                 110
```

```
tgg gac ggg ctg gtg ccc aat gtt ctg ctc gtg cag tcc tgg ctt ccc       384
Trp Asp Gly Leu Val Pro Asn Val Leu Leu Val Gln Ser Trp Leu Pro
        115                 120                 125 gac gcg acc ctc acg gcc agt ttc aac acg ccc agc tgg tcg ctc tcc       432
Asp Ala Thr Leu Thr Ala Ser Phe Asn Thr Pro Ser Trp Ser Leu Ser
130                 135                 140 tgt gag atc gcc ttc tat ctg tcg ttc ccg ctg tgg tac cgg ctg gtg       480
Cys Glu Ile Ala Phe Tyr Leu Ser Phe Pro Leu Trp Tyr Arg Leu Val
145                 150                 155                 160 cgc agg att ccc gca cgg cgg ctg tgg tgc gcc gcg ggg atc gcc           528
Arg Arg Ile Pro Ala Arg Arg Leu Trp Trp Cys Ala Ala Gly Ile Ala
            165                 170                 175 gtg gcc gtg acg tgt gtg ccc ctg ctg gcg ggc ctc ctc ccg gcg agc       576
Val Ala Val Thr Cys Val Pro Leu Leu Ala Gly Leu Leu Pro Ala Ser
        180                 185                 190 gag gag gtg gcc ccc ggg atg tcg ctc aac gag gtc tgg ttc gcg tac       624
Glu Glu Val Ala Pro Gly Met Ser Leu Asn Glu Val Trp Phe Ala Tyr
    195                 200                 205 tgg ctt ccg ccg gtg cgc atg ctg gag ttc gtc ctc ggc atc gtg atg       672
Trp Leu Pro Pro Val Arg Met Leu Glu Phe Val Leu Gly Ile Val Met
210                 215                 220 gcg ctg atc ctg cgc gcg ggg atc tgg aag ggc ccc ggt ccg gcg gtc       720
Ala Leu Ile Leu Arg Ala Gly Ile Trp Lys Gly Pro Gly Pro Ala Val
225                 230                 235                 240 tgc acg gcg ctc ctc gcc gcg agt tac ggc ctc acc cag atg gtg ccc       768
Cys Thr Ala Leu Leu Ala Ala Ser Tyr Gly Leu Thr Gln Met Val Pro
            245                 250                 255 ccg atc ttc acc ctc gtc gcc tgc tcc gtc gta ccg gcg gcg ctg ctg       816
Pro Ile Phe Thr Leu Val Ala Cys Ser Val Val Pro Ala Ala Leu Leu
        260                 265                 270 atc acg gcg ctg gcc gac gcc gac gtg cac ggc cgg cgc acg ggg ctg       864
Ile Thr Ala Leu Ala Asp Ala Asp Val His Gly Arg Arg Thr Gly Leu
    275                 280                 285 cgt tcg gcg acg ctg gtg cgg ctg ggc cag tgg tcc ttc gcc ttc tac       912
Arg Ser Ala Thr Leu Val Arg Leu Gly Gln Trp Ser Phe Ala Phe Tyr
290                 295                 300 ctg gtc cac ttc ctg atc atc cgc tac gga cac cgg ctg atg ggc ggc       960
Leu Val His Phe Leu Ile Ile Arg Tyr Gly His Arg Leu Met Gly Gly
305                 310                 315                 320 gat ctg ggc tac gag cgg cag tgg agc acc ccg gcc gcg atc gcg ctg      1008
Asp Leu Gly Tyr Glu Arg Gln Trp Ser Thr Pro Ala Ala Ile Ala Leu
            325                 330                 335 tcc ctg ggg atg ctg ggg gtg gcg gtc ctg gcc ggc ggt ctg ctg cac      1056
Ser Leu Gly Met Leu Gly Val Ala Val Leu Ala Gly Gly Leu Leu His
        340                 345                 350 acc gtc gtc gaa cag ccc tgc atg cgc ctg ttc ggc agc cgc agg tcc      1104
Thr Val Val Glu Gln Pro Cys Met Arg Leu Phe Gly Ser Arg Arg Ser
    355                 360                 365 gcc tcc cgt ccg aag ccc ggc gcc acc gcg gct ccc cgg aac tca ccc      1152
Ala Ser Arg Pro Lys Pro Gly Ala Thr Ala Ala Pro Arg Asn Ser Pro
370                 375                 380 gcg gcc gac gcg gcc ggc gtg ccc ctg ctc ccg ggc gta ccc ggg ccc      1200
Ala Ala Asp Ala Ala Gly Val Pro Leu Leu Pro Gly Val Pro Gly Pro
385                 390                 395                 400 gcg cac acc ccc gca gcg acg aac gaa ccc acc ccg aga gga tga         1245
Ala His Thr Pro Ala Ala Thr Asn Glu Pro Thr Pro Arg Gly
            405                 410
```

<210> SEQ ID NO 14

```
<211> LENGTH: 414
<212> TYPE: PRT
<213> ORGANISM: Streptomyces ambofaciens

<400> SEQUENCE: 14
```

| | | | | | | | | | | | | | | |
|---|---|---|---|---|---|---|---|---|---|---|---|---|---|---|
|Val|Leu|Gln|Arg|Val|Asp|Leu|Ser|Ser|Leu|Thr|Gly|Leu|Arg|Trp|Tyr
|1| | | |5| | | | |10| | | | |15|
|Ala|Ala|Leu|Thr|Val|Phe|Ala|Cys|His|Ile|Ala|Gln|Gln|Gly|Phe|Phe
| | | |20| | | | |25| | | | |30| | |
|Ala|Asp|Gln|Gln|Val|Gly|Ser|Ala|Leu|Leu|His|Ile|Thr|Pro|Leu|Gly
| | | | |35| | | | |40| | | | |45| |
|Ser|Met|Ala|Val|Ser|Ile|Phe|Phe|Ile|Leu|Ser|Gly|Phe|Val|Leu|Ala
| |50| | | | |55| | | | |60| | | | |
|Trp|Ser|Ala|Arg|Asp|Glu|Asp|Ser|Val|Pro|Thr|Phe|Trp|Arg|Arg|Arg
|65| | | | |70| | | | |75| | | | |80|
|Ile|Ala|Lys|Ile|Tyr|Pro|Leu|His|Leu|Ala|Thr|Phe|Gly|Ile|Ala|Ala
| | | | |85| | | | |90| | | | |95| |
|Leu|Ile|Ile|Phe|Ser|Leu|Ser|Glu|Pro|Val|Leu|Pro|Gly|Gly|Ser|Val
| | | | |100| | | | |105| | | | |110| |
|Trp|Asp|Gly|Leu|Val|Pro|Asn|Val|Leu|Val|Gln|Ser|Trp|Leu|Pro|
| | | | |115| | | | |120| | | | |125| |
|Asp|Ala|Thr|Leu|Thr|Ala|Ser|Phe|Asn|Thr|Pro|Ser|Trp|Ser|Leu|Ser
| |130| | | | |135| | | | |140| | | | |
|Cys|Glu|Ile|Ala|Phe|Tyr|Leu|Ser|Phe|Pro|Leu|Trp|Tyr|Arg|Leu|Val
|145| | | | |150| | | | |155| | | | |160|
|Arg|Arg|Ile|Pro|Ala|Arg|Arg|Leu|Trp|Trp|Cys|Ala|Ala|Gly|Ile|Ala
| | | | |165| | | | |170| | | | |175| |
|Val|Ala|Val|Thr|Cys|Val|Pro|Leu|Leu|Ala|Gly|Leu|Leu|Pro|Ala|Ser
| | | |180| | | | |185| | | | |190| | |
|Glu|Glu|Val|Ala|Pro|Gly|Met|Ser|Leu|Asn|Glu|Val|Trp|Phe|Ala|Tyr
| | | | |195| | | | |200| | | | |205| |
|Trp|Leu|Pro|Pro|Val|Arg|Met|Leu|Glu|Phe|Val|Leu|Gly|Ile|Val|Met
| |210| | | | |215| | | | |220| | | | |
|Ala|Leu|Ile|Leu|Arg|Ala|Gly|Ile|Trp|Lys|Gly|Pro|Gly|Pro|Ala|Val
|225| | | | |230| | | | |235| | | | |240|
|Cys|Thr|Ala|Leu|Leu|Ala|Ala|Ser|Tyr|Gly|Leu|Thr|Gln|Met|Val|Pro
| | | | |245| | | | |250| | | | |255| |
|Pro|Ile|Phe|Thr|Leu|Val|Ala|Cys|Ser|Val|Val|Pro|Ala|Ala|Leu|Leu
| | | |260| | | | |265| | | | |270| | |
|Ile|Thr|Ala|Leu|Ala|Asp|Ala|Asp|Val|His|Gly|Arg|Arg|Thr|Gly|Leu
| | |275| | | | |280| | | | |285| | | |
|Arg|Ser|Ala|Thr|Leu|Val|Arg|Leu|Gly|Gln|Trp|Ser|Phe|Ala|Phe|Tyr
| |290| | | | |295| | | | |300| | | | |
|Leu|Val|His|Phe|Leu|Ile|Ile|Arg|Tyr|Gly|His|Arg|Leu|Met|Gly|Gly
|305| | | | |310| | | | |315| | | | |320|
|Asp|Leu|Gly|Tyr|Glu|Arg|Gln|Trp|Ser|Thr|Pro|Ala|Ala|Ile|Ala|Leu
| | | | |325| | | | |330| | | | |335| |
|Ser|Leu|Gly|Met|Leu|Gly|Val|Ala|Val|Leu|Ala|Gly|Gly|Leu|Leu|His
| | | |340| | | | |345| | | | |350| | |
|Thr|Val|Val|Glu|Gln|Pro|Cys|Met|Arg|Leu|Phe|Gly|Ser|Arg|Arg|Ser
| | | |355| | | | |360| | | | |365| | |
|Ala|Ser|Arg|Pro|Lys|Pro|Gly|Ala|Thr|Ala|Ala|Pro|Arg|Asn|Ser|Pro
| |370| | | | |375| | | | |380| | | | |
|Ala|Ala|Asp|Ala|Ala|Gly|Val|Pro|Leu|Leu|Pro|Gly|Val|Pro|Gly|Pro

```
                385                 390                 395                 400
Ala His Thr Pro Ala Ala Thr Asn Glu Pro Thr Pro Arg Gly
                        405                 410

<210> SEQ ID NO 15
<211> LENGTH: 849
<212> TYPE: DNA
<213> ORGANISM: Streptomyces ambofaciens
<220> FEATURE:
<221> NAME/KEY: CDS
<222> LOCATION: (1)..(849)

<400> SEQUENCE: 15 gtg aca ttg aaa tcc cca ctg cca ccg caa tcc gtc tcc gca ccc gct      48
Val Thr Leu Lys Ser Pro Leu Pro Pro Gln Ser Val Ser Ala Pro Ala
1               5                   10                  15 gat tca cgc agc acc gcg cgg aga gaa tgg ggt cag aac ttc ttt cgt      96
Asp Ser Arg Ser Thr Ala Arg Arg Glu Trp Gly Gln Asn Phe Phe Arg
            20                  25                  30 aca gcc gcc gcg gcc tgt cgt ttc tcc gct cag ctg gac ggt tcg gac     144
Thr Ala Ala Ala Ala Cys Arg Phe Ser Ala Gln Leu Asp Gly Ser Asp
        35                  40                  45 acc att ccg ccc gat tct ccg aat gac ctg atg acc gtc gaa ata ggc     192
Thr Ile Pro Pro Asp Ser Pro Asn Asp Leu Met Thr Val Glu Ile Gly
    50                  55                  60 gcg gga tca ggg cgg gtg acc aaa gtg ctc gcc tca ccc ggg acg cct     240
Ala Gly Ser Gly Arg Val Thr Lys Val Leu Ala Ser Pro Gly Thr Pro
65                  70                  75                  80 tta ctc gcg gtg gaa ata gat ccc cgc tgg gct cgg cgg ctg gcc gcc     288
Leu Leu Ala Val Glu Ile Asp Pro Arg Trp Ala Arg Arg Leu Ala Ala
                85                  90                  95 gaa tcg ctg ccg gac gtc acg gtg gtg aac gag gat ttc ctg acc ctg     336
Glu Ser Leu Pro Asp Val Thr Val Val Asn Glu Asp Phe Leu Thr Leu
            100                 105                 110 caa ctg ccc ggg cag ccg gtc aga ctc atc ggg aat ctt ccc ttc gtc     384
Gln Leu Pro Gly Gln Pro Val Arg Leu Ile Gly Asn Leu Pro Phe Val
        115                 120                 125 acc ggc acc aga atg ctg agg cgc tgc ctc gac atg ggt ccg gcg cgc     432
Thr Gly Thr Arg Met Leu Arg Arg Cys Leu Asp Met Gly Pro Ala Arg
    130                 135                 140 atg cgg cag ggc gtg ttc ctg ttg cag cgg gag tac gtg gga aag cgg     480
Met Arg Gln Gly Val Phe Leu Leu Gln Arg Glu Tyr Val Gly Lys Arg
145                 150                 155                 160 acc gga gcc tgg ggc gga aac ctc ttc aac gcc cag tgg gag ccg tgg     528
Thr Gly Ala Trp Gly Gly Asn Leu Phe Asn Ala Gln Trp Glu Pro Trp
                165                 170                 175 tac tcg ttc gac cgg ggc ctg gcc ttc tca cgc cag gac ttc acc ccc     576
Tyr Ser Phe Asp Arg Gly Leu Ala Phe Ser Arg Gln Asp Phe Thr Pro
            180                 185                 190 gta ccg cgc gcg gac acc cag acc ctg atg gtc gcc ccg cac cgc agg     624
Val Pro Arg Ala Asp Thr Gln Thr Leu Met Val Ala Pro His Arg Arg
        195                 200                 205 ccg tcc gtg ccc tgg cgt gag aag gcc gcc tac cag cgg ttc gtc caa     672
Pro Ser Val Pro Trp Arg Glu Lys Ala Ala Tyr Gln Arg Phe Val Gln
    210                 215                 220 cgg gtc ttc gac acc ggc cag atg acg gtg ggc gac gcc gcg cgg aag     720
Arg Val Phe Asp Thr Gly Gln Met Thr Val Gly Asp Ala Ala Arg Lys
225                 230                 235                 240 gtg ctg cgc cgc gga cac gcc cag ttc gtg cgc ggg gcg ggc gtg agg     768
Val Leu Arg Arg Gly His Ala Gln Phe Val Arg Gly Ala Gly Val Arg
                245                 250                 255
```

```
ccg gcc gac cgg gtc aag gac ctc acg gtc ccg gag tgg acc gca ctc        816
Pro Ala Asp Arg Val Lys Asp Leu Thr Val Pro Glu Trp Thr Ala Leu
        260                 265                 270 ttc cgc gcc tac ggg cgg acg gcc gac cgc tga                            849
Phe Arg Ala Tyr Gly Arg Thr Ala Asp Arg
        275                 280

<210> SEQ ID NO 16
<211> LENGTH: 282
<212> TYPE: PRT
<213> ORGANISM: Streptomyces ambofaciens

<400> SEQUENCE: 16

Val Thr Leu Lys Ser Pro Leu Pro Pro Gln Ser Val Ser Ala Pro Ala
1               5                   10                  15

Asp Ser Arg Ser Thr Ala Arg Arg Glu Trp Gly Gln Asn Phe Phe Arg
            20                  25                  30

Thr Ala Ala Ala Cys Arg Phe Ser Ala Gln Leu Asp Gly Ser Asp
        35                  40                  45

Thr Ile Pro Pro Asp Ser Pro Asn Asp Leu Met Thr Val Glu Ile Gly
    50                  55                  60

Ala Gly Ser Gly Arg Val Thr Lys Val Leu Ala Ser Pro Gly Thr Pro
65                  70                  75                  80

Leu Leu Ala Val Glu Ile Asp Pro Arg Trp Ala Arg Arg Leu Ala Ala
                85                  90                  95

Glu Ser Leu Pro Asp Val Thr Val Val Asn Glu Asp Phe Leu Thr Leu
            100                 105                 110

Gln Leu Pro Gly Gln Pro Val Arg Leu Ile Gly Asn Leu Pro Phe Val
        115                 120                 125

Thr Gly Thr Arg Met Leu Arg Arg Cys Leu Asp Met Gly Pro Ala Arg
    130                 135                 140

Met Arg Gln Gly Val Phe Leu Leu Gln Arg Glu Tyr Val Gly Lys Arg
145                 150                 155                 160

Thr Gly Ala Trp Gly Gly Asn Leu Phe Asn Ala Gln Trp Glu Pro Trp
                165                 170                 175

Tyr Ser Phe Asp Arg Gly Leu Ala Phe Ser Arg Gln Asp Phe Thr Pro
            180                 185                 190

Val Pro Arg Ala Asp Thr Gln Thr Leu Met Val Ala Pro His Arg Arg
        195                 200                 205

Pro Ser Val Pro Trp Arg Glu Lys Ala Ala Tyr Gln Arg Phe Val Gln
    210                 215                 220

Arg Val Phe Asp Thr Gly Gln Met Thr Val Gly Asp Ala Ala Arg Lys
225                 230                 235                 240

Val Leu Arg Arg Gly His Ala Gln Phe Val Arg Gly Ala Gly Val Arg
                245                 250                 255

Pro Ala Asp Arg Val Lys Asp Leu Thr Val Pro Glu Trp Thr Ala Leu
            260                 265                 270

Phe Arg Ala Tyr Gly Arg Thr Ala Asp Arg
        275                 280

<210> SEQ ID NO 17
<211> LENGTH: 831
<212> TYPE: DNA
<213> ORGANISM: Streptomyces ambofaciens
<220> FEATURE:
<221> NAME/KEY: CDS
<222> LOCATION: (1)..(831)
```

<400> SEQUENCE: 17

```
gtg aag gag gtg gcg gtc gac acc ggt acc ccg gcc ggc ccc gtg tgg      48
Val Lys Glu Val Ala Val Asp Thr Gly Thr Pro Ala Gly Pro Val Trp
1               5                   10                  15 cgt ggt gcc ggc ctc ggc acc cag ctg tgg gta ctg acc gcg cgg cag      96
Arg Gly Ala Gly Leu Gly Thr Gln Leu Trp Val Leu Thr Ala Arg Gln
            20                  25                  30 atc cgt tcc atg tac ggc gac cgc cgc ctg gcg ctg ttc agc ctg atg     144
Ile Arg Ser Met Tyr Gly Asp Arg Arg Leu Ala Leu Phe Ser Leu Met
        35                  40                  45 caa ccg gtg atc atg ctg ttg ctg ctg agc gag atc ttc ggc agc atg     192
Gln Pro Val Ile Met Leu Leu Leu Leu Ser Glu Ile Phe Gly Ser Met
    50                  55                  60 gcc gac ccg gac gac ttc ccg cag ggc gtg cgc tac atc gac tac gtg     240
Ala Asp Pro Asp Asp Phe Pro Gln Gly Val Arg Tyr Ile Asp Tyr Val
65                  70                  75                  80 gtg ccc gcg ctg ctg gtc acc acc ggc atc ggc tcg gcc cag ggc gcg     288
Val Pro Ala Leu Leu Val Thr Thr Gly Ile Gly Ser Ala Gln Gly Ala
                85                  90                  95 ggg gtg ggc ctg gtc agg gac atg gac aac ggg atg gtg gcg cgc ttc     336
Gly Val Gly Leu Val Arg Asp Met Asp Asn Gly Met Val Ala Arg Phe
            100                 105                 110 cgc gtc ctg ccg gcc cgg ctg ttc ctg gtg ctg gtc gcc cgg tcg ctg     384
Arg Val Leu Pro Ala Arg Leu Phe Leu Val Leu Val Ala Arg Ser Leu
        115                 120                 125 gcc gat ctg gtc cgt gtg ttc acc gag ttg gtc gtc ctc gtg gcc gtc     432
Ala Asp Leu Val Arg Val Phe Thr Glu Leu Val Val Leu Val Ala Val
    130                 135                 140 ggt gtg atc ctg ctg ggc ttc cgt ccg gcc ggg ggt ttg tgg ggc acg     480
Gly Val Ile Leu Leu Gly Phe Arg Pro Ala Gly Gly Leu Trp Gly Thr
145                 150                 155                 160 tcc gcc gcc ctg ttg ctc acc ctg ttc gtc atc tgg tcg ctg atc tgg     528
Ser Ala Ala Leu Leu Leu Thr Leu Phe Val Ile Trp Ser Leu Ile Trp
                165                 170                 175 ggg ttc atc gcc ctc gcg gcg tgg ctg cgc agc gtg gag gtg atg tcc     576
Gly Phe Ile Ala Leu Ala Ala Trp Leu Arg Ser Val Glu Val Met Ser
            180                 185                 190 agc ctc gcg gtt ctg gtg atg ttc ccg ctc atg ttc gcc tcc agt gcg     624
Ser Leu Ala Val Leu Val Met Phe Pro Leu Met Phe Ala Ser Ser Ala
        195                 200                 205 ttc gtc ccg ctg gac gcc ctc ccg gag tgg ctg cgc tcg gtg gcg cac     672
Phe Val Pro Leu Asp Ala Leu Pro Glu Trp Leu Arg Ser Val Ala His
    210                 215                 220 ctc aac ccc gtg acg tac gcg gtc gac agc gcc cgc cgc ctg gcg ctg     720
Leu Asn Pro Val Thr Tyr Ala Val Asp Ser Ala Arg Arg Leu Ala Leu
225                 230                 235                 240 gac tgg gac ccg ggg tgg agc gtg ccc ggc gcg ctg ctg acc agc acc     768
Asp Trp Asp Pro Gly Trp Ser Val Pro Gly Ala Leu Leu Thr Ser Thr
                245                 250                 255 gcg ctc atg gcg gtg ggg atg tac gtc gcc ggg cgt tcc ttc aag agg     816
Ala Leu Met Ala Val Gly Met Tyr Val Ala Gly Arg Ser Phe Lys Arg
            260                 265                 270 ccc ccg aac gaa tga                                                  831
Pro Pro Asn Glu
        275
```

<210> SEQ ID NO 18
<211> LENGTH: 276
<212> TYPE: PRT

<213> ORGANISM: Streptomyces ambofaciens

<400> SEQUENCE: 18

```
Val Lys Glu Val Ala Val Asp Thr Gly Thr Pro Ala Gly Pro Val Trp
1               5                   10                  15

Arg Gly Ala Gly Leu Gly Thr Gln Leu Trp Val Leu Thr Ala Arg Gln
            20                  25                  30

Ile Arg Ser Met Tyr Gly Asp Arg Arg Leu Ala Leu Phe Ser Leu Met
        35                  40                  45

Gln Pro Val Ile Met Leu Leu Leu Ser Glu Ile Phe Gly Ser Met
    50                  55                  60

Ala Asp Pro Asp Asp Phe Pro Gln Gly Val Arg Tyr Ile Asp Tyr Val
65                  70                  75                  80

Val Pro Ala Leu Leu Val Thr Thr Gly Ile Gly Ser Ala Gln Gly Ala
                85                  90                  95

Gly Val Gly Leu Val Arg Asp Met Asp Asn Gly Met Val Ala Arg Phe
            100                 105                 110

Arg Val Leu Pro Ala Arg Leu Phe Leu Val Leu Val Ala Arg Ser Leu
        115                 120                 125

Ala Asp Leu Val Arg Val Phe Thr Glu Leu Val Val Leu Val Ala Val
    130                 135                 140

Gly Val Ile Leu Leu Gly Phe Arg Pro Ala Gly Gly Leu Trp Gly Thr
145                 150                 155                 160

Ser Ala Ala Leu Leu Leu Thr Leu Phe Val Ile Trp Ser Leu Ile Trp
                165                 170                 175

Gly Phe Ile Ala Leu Ala Ala Trp Leu Arg Ser Val Glu Val Met Ser
            180                 185                 190

Ser Leu Ala Val Leu Val Met Phe Pro Leu Met Phe Ala Ser Ser Ala
        195                 200                 205

Phe Val Pro Leu Asp Ala Leu Pro Glu Trp Leu Arg Ser Val Ala His
    210                 215                 220

Leu Asn Pro Val Thr Tyr Ala Val Asp Ser Ala Arg Arg Leu Ala Leu
225                 230                 235                 240

Asp Trp Asp Pro Gly Trp Ser Val Pro Gly Ala Leu Leu Thr Ser Thr
                245                 250                 255

Ala Leu Met Ala Val Gly Met Tyr Val Ala Gly Arg Ser Phe Lys Arg
            260                 265                 270

Pro Pro Asn Glu
        275
```

<210> SEQ ID NO 19
<211> LENGTH: 882
<212> TYPE: DNA
<213> ORGANISM: Streptomyces ambofaciens
<220> FEATURE:
<221> NAME/KEY: CDS
<222> LOCATION: (1)..(882)

<400> SEQUENCE: 19

```
gtg gac atc gag gtc gaa cgg ggc cgg gtg ctc ggg ctg ctg ggt cac      48
Val Asp Ile Glu Val Glu Arg Gly Arg Val Leu Gly Leu Leu Gly His
1               5                   10                  15 aac ggg gcc ggc aag acg acc ttg gtg aac atc ctt gcc acg gtc tcc      96
Asn Gly Ala Gly Lys Thr Thr Leu Val Asn Ile Leu Ala Thr Val Ser
            20                  25                  30 ccg gcg tcc gcg ggc acg gtg acc gtc gcc ggt ttc gac gtc gcg acg     144
Pro Ala Ser Ala Gly Thr Val Thr Val Ala Gly Phe Asp Val Ala Thr
```

```
                    35                  40                  45
cag ggc gcc gag atc cgc gcg cgc atc ggg gtg acc ggc cag ttc gcg    192
Gln Gly Ala Glu Ile Arg Ala Arg Ile Gly Val Thr Gly Gln Phe Ala
 50                  55                  60 tcg gtg gac gag tac ctg agc gga ttc cgc aac ctc gtc ctg atc ggc    240
Ser Val Asp Glu Tyr Leu Ser Gly Phe Arg Asn Leu Val Leu Ile Gly
 65                  70                  75                  80 cgc ctc ctc ggg gcg gga cgg cgt gag gcg gcg gcc cgg gcc acc gag    288
Arg Leu Leu Gly Ala Gly Arg Arg Glu Ala Ala Ala Arg Ala Thr Glu
                 85                  90                  95 ctc ctg gag ctg ttc gag ctg acc ggg gcg gcc cac cag ccc tcc cgc    336
Leu Leu Glu Leu Phe Glu Leu Thr Gly Ala Ala His Gln Pro Ser Arg
            100                 105                 110 acc tac tcg ggc ggg atg cgc cga cgg ctc gac ctc gcc gcc agc ctg    384
Thr Tyr Ser Gly Gly Met Arg Arg Arg Leu Asp Leu Ala Ala Ser Leu
        115                 120                 125 gtc ggc cgg ccg gac gtg ctg ttc ctc gac gag ccg acg acc ggg ctg    432
Val Gly Arg Pro Asp Val Leu Phe Leu Asp Glu Pro Thr Thr Gly Leu
    130                 135                 140 gac ccg gcg acc cgg atc gcc ctg tgg gag acg gtg gag aag ctg gtg    480
Asp Pro Ala Thr Arg Ile Ala Leu Trp Glu Thr Val Glu Lys Leu Val
145                 150                 155                 160 gcg ggc ggc acg acc gtc ctg ctg acc acc cag tac ctg gac gag gcg    528
Ala Gly Gly Thr Thr Val Leu Leu Thr Thr Gln Tyr Leu Asp Glu Ala
                165                 170                 175 gac cgg ctg gcc gac tgg atc acc gtc ctg tcg aag ggc cgg gtg gtg    576
Asp Arg Leu Ala Asp Trp Ile Thr Val Leu Ser Lys Gly Arg Val Val
            180                 185                 190 gcc tcg gac acc acc gac cgg ctc aag gcc gac ctg ggc cac cgg tcg    624
Ala Ser Asp Thr Thr Asp Arg Leu Lys Ala Asp Leu Gly His Arg Ser
        195                 200                 205 gtg cgg gtg gtc ctt ccg ccc gcc gcc gac ctg acg gcc gcc gcc gcc    672
Val Arg Val Val Leu Pro Pro Ala Ala Asp Leu Thr Ala Ala Ala Ala
    210                 215                 220 gcg ctc acc gcc ggc ggg ttc cgt ccg cgg tcc gac gcc ggg gag cac    720
Ala Leu Thr Ala Gly Gly Phe Arg Pro Arg Ser Asp Ala Gly Glu His
225                 230                 235                 240 gcg ctg acc acg ccc gtg gac acc tcg gcc ggt atc gcg ggc gtc atc    768
Ala Leu Thr Thr Pro Val Asp Thr Ser Ala Gly Ile Ala Gly Val Ile
                245                 250                 255 cgc gcg ctg gac acc gtc gga acg cag gcc gtc gag ctg acc gtc aag    816
Arg Ala Leu Asp Thr Val Gly Thr Gln Ala Val Glu Leu Thr Val Lys
            260                 265                 270 gag ccg tcc ctg gac gac gtc tac ctg gcg ctc acc cat ccc tca ccc    864
Glu Pro Ser Leu Asp Asp Val Tyr Leu Ala Leu Thr His Pro Ser Pro
        275                 280                 285 gcc gcc gac gcg gcc tga                                            882
Ala Ala Asp Ala Ala
    290

<210> SEQ ID NO 20
<211> LENGTH: 293
<212> TYPE: PRT
<213> ORGANISM: Streptomyces ambofaciens

<400> SEQUENCE: 20

Val Asp Ile Glu Val Glu Arg Gly Arg Val Leu Gly Leu Leu Gly His
 1               5                  10                  15

Asn Gly Ala Gly Lys Thr Thr Leu Val Asn Ile Leu Ala Thr Val Ser
             20                  25                  30
```

-continued

Pro Ala Ser Ala Gly Thr Val Thr Val Ala Gly Phe Asp Val Ala Thr
         35                  40                  45

Gln Gly Ala Glu Ile Arg Ala Arg Ile Gly Val Thr Gly Gln Phe Ala
 50                  55                  60

Ser Val Asp Glu Tyr Leu Ser Gly Phe Arg Asn Leu Val Leu Ile Gly
 65                  70                  75                  80

Arg Leu Leu Gly Ala Gly Arg Arg Glu Ala Ala Arg Ala Thr Glu
                 85                  90                  95

Leu Leu Glu Leu Phe Glu Leu Thr Gly Ala Ala His Gln Pro Ser Arg
             100                 105                 110

Thr Tyr Ser Gly Gly Met Arg Arg Leu Asp Leu Ala Ala Ser Leu
             115                 120                 125

Val Gly Arg Pro Asp Val Leu Phe Leu Asp Glu Pro Thr Thr Gly Leu
         130                 135                 140

Asp Pro Ala Thr Arg Ile Ala Leu Trp Glu Thr Val Glu Lys Leu Val
145                 150                 155                 160

Ala Gly Gly Thr Thr Val Leu Leu Thr Thr Gln Tyr Leu Asp Glu Ala
                 165                 170                 175

Asp Arg Leu Ala Asp Trp Ile Thr Val Leu Ser Lys Gly Arg Val Val
             180                 185                 190

Ala Ser Asp Thr Thr Asp Arg Leu Lys Ala Asp Leu Gly His Arg Ser
         195                 200                 205

Val Arg Val Val Leu Pro Pro Ala Ala Asp Leu Thr Ala Ala Ala Ala
210                 215                 220

Ala Leu Thr Ala Gly Gly Phe Arg Pro Arg Ser Asp Ala Gly Glu His
225                 230                 235                 240

Ala Leu Thr Thr Pro Val Asp Thr Ser Ala Gly Ile Ala Gly Val Ile
                 245                 250                 255

Arg Ala Leu Asp Thr Val Gly Thr Gln Ala Val Glu Leu Thr Val Lys
             260                 265                 270

Glu Pro Ser Leu Asp Asp Val Tyr Leu Ala Leu Thr His Pro Ser Pro
         275                 280                 285

Ala Ala Asp Ala Ala
    290

<210> SEQ ID NO 21
<211> LENGTH: 228
<212> TYPE: DNA
<213> ORGANISM: Streptomyces ambofaciens
<220> FEATURE:
<221> NAME/KEY: CDS
<222> LOCATION: (1)..(228)

<400> SEQUENCE: 21 atg agc aac ccg ttc gag gac acg gaa gcc acc tac gtc gtg ctg gtc    48
Met Ser Asn Pro Phe Glu Asp Thr Glu Ala Thr Tyr Val Val Leu Val
 1               5                  10                  15 aac gac gag ggg cag cac tcg ctg tgg ccg tcg ttc gcg gag gtc ccg    96
Asn Asp Glu Gly Gln His Ser Leu Trp Pro Ser Phe Ala Glu Val Pro
             20                  25                  30 gcg ggc tgg tcc gtc gtg gtg ccg gag acg gac cgg cag tcg tgc ctg    144
Ala Gly Trp Ser Val Val Val Pro Glu Thr Asp Arg Gln Ser Cys Leu
         35                  40                  45 gac tac atc aac gag aac tgg acc gac atg cgc ccc aag agc ctc gtc    192
Asp Tyr Ile Asn Glu Asn Trp Thr Asp Met Arg Pro Lys Ser Leu Val
 50                  55                  60

```
gag gcg atg gcg acg gcc ggg cag gac gcc cct tga                      228
Glu Ala Met Ala Thr Ala Gly Gln Asp Ala Pro
65                  70                  75

<210> SEQ ID NO 22
<211> LENGTH: 75
<212> TYPE: PRT
<213> ORGANISM: Streptomyces ambofaciens

<400> SEQUENCE: 22

Met Ser Asn Pro Phe Glu Asp Thr Glu Ala Thr Tyr Val Val Leu Val
1               5                   10                  15

Asn Asp Glu Gly Gln His Ser Leu Trp Pro Ser Phe Ala Glu Val Pro
            20                  25                  30

Ala Gly Trp Ser Val Val Val Pro Glu Thr Asp Arg Gln Ser Cys Leu
        35                  40                  45

Asp Tyr Ile Asn Glu Asn Trp Thr Asp Met Arg Pro Lys Ser Leu Val
    50                  55                  60

Glu Ala Met Ala Thr Ala Gly Gln Asp Ala Pro
65                  70                  75

<210> SEQ ID NO 23
<211> LENGTH: 1212
<212> TYPE: DNA
<213> ORGANISM: Streptomyces ambofaciens
<220> FEATURE:
<221> NAME/KEY: CDS
<222> LOCATION: (1)..(1212)

<400> SEQUENCE: 23 atg ggt gag gcc gtg acg gga ccg atg gag ctg agc aag gac gcg gac      48
Met Gly Glu Ala Val Thr Gly Pro Met Glu Leu Ser Lys Asp Ala Asp
1               5                   10                  15 gcc cgg ggg ctg ctt gag tgg ttc gcg tac aac agg acg cgt cat ccg      96
Ala Arg Gly Leu Leu Glu Trp Phe Ala Tyr Asn Arg Thr Arg His Pro
            20                  25                  30 gtg ttc tgg gac gag acc cga cag gcg tgg cag gtc ttc ggc tac gac     144
Val Phe Trp Asp Glu Thr Arg Gln Ala Trp Gln Val Phe Gly Tyr Asp
        35                  40                  45 gac tac gtg acg gtg tcg aac aac ccg cag ttc ttc tcc tcg gac ttc     192
Asp Tyr Val Thr Val Ser Asn Asn Pro Gln Phe Phe Ser Ser Asp Phe
    50                  55                  60 aac atg gtg atg ccg acg ccg ccc gaa ctg gag atg atc atc ggt ccg     240
Asn Met Val Met Pro Thr Pro Pro Glu Leu Glu Met Ile Ile Gly Pro
65                  70                  75                  80 ggc acg atc ggc gcg ctg gac ccg ccc gcg cac gga ccg atg cgc aag     288
Gly Thr Ile Gly Ala Leu Asp Pro Pro Ala His Gly Pro Met Arg Lys
                85                  90                  95 ctg gtg agc cag gcg ttc acc ccc cga cgg atc gcc cgg ctg gag ccc     336
Leu Val Ser Gln Ala Phe Thr Pro Arg Arg Ile Ala Arg Leu Glu Pro
            100                 105                 110 agg gtg cgc gcg atc acc gag gag ctc ctg gac aag gtg ggg cag cag     384
Arg Val Arg Ala Ile Thr Glu Glu Leu Leu Asp Lys Val Gly Gln Gln
        115                 120                 125 gac gtc gtc gac gcc gtg ggt gac ctg tcc tac gcg ctg ccg gtc atc     432
Asp Val Val Asp Ala Val Gly Asp Leu Ser Tyr Ala Leu Pro Val Ile
    130                 135                 140 gtg atc gcc gaa ctg ctg ggc ata ccc gcc ggc gac cgt gac ctg ttc     480
Val Ile Ala Glu Leu Leu Gly Ile Pro Ala Gly Asp Arg Asp Leu Phe
145                 150                 155                 160 cgg gag tgg gtc gac acc ctg ctg acg aac gag ggc ctg gag tac ccg     528
```

```
Arg Glu Trp Val Asp Thr Leu Leu Thr Asn Glu Gly Leu Glu Tyr Pro
            165                 170                 175 aac ctc ccg gac aac ttc acc gag acg atc gcg ccc gcg ctc aag gag     576
Asn Leu Pro Asp Asn Phe Thr Glu Thr Ile Ala Pro Ala Leu Lys Glu
        180                 185                 190 atg acc gac tac ctc ctg aag cag atc cac gcc aag cgg gac gcg ccc     624
Met Thr Asp Tyr Leu Leu Lys Gln Ile His Ala Lys Arg Asp Ala Pro
            195                 200                 205 gcc gac gac ctg gtc agc ggg ctg gtc cag gcg gag cag gac ggc cgc     672
Ala Asp Asp Leu Val Ser Gly Leu Val Gln Ala Glu Gln Asp Gly Arg
        210                 215                 220 cgg ctg acc gac gtc gag atc gtc aac atc gtc gcg ctg ctc ctg acg     720
Arg Leu Thr Asp Val Glu Ile Val Asn Ile Val Ala Leu Leu Leu Thr
225                 230                 235                 240 gcg ggg cac gtc tcc tcc agc acc ctg ctc agc aac ctg ttc ctg gtc     768
Ala Gly His Val Ser Ser Ser Thr Leu Leu Ser Asn Leu Phe Leu Val
                245                 250                 255 ctg gag gag aac ccg cag gcg ctg gag gac ctg cgg gcc gat cgc tcc     816
Leu Glu Glu Asn Pro Gln Ala Leu Glu Asp Leu Arg Ala Asp Arg Ser
            260                 265                 270 ctg gtg ccc ggc gcg atc gag gag acg ctg cgc tac cgc agc ccc ttc     864
Leu Val Pro Gly Ala Ile Glu Glu Thr Leu Arg Tyr Arg Ser Pro Phe
        275                 280                 285 aac aac atc ttc cgg ttc gtc aag gag gac acc acc gtc ctc ggt ccg     912
Asn Asn Ile Phe Arg Phe Val Lys Glu Asp Thr Thr Val Leu Gly Pro
    290                 295                 300 ctc atg gag aag ggc cag atg gtg atc gcc tgg agc cag tcc gcc aac     960
Leu Met Glu Lys Gly Gln Met Val Ile Ala Trp Ser Gln Ser Ala Asn
305                 310                 315                 320 cgg gac ccc cgg cac ttc ccg gac ccg gac acc ttc gac atc cgc cgc    1008
Arg Asp Pro Arg His Phe Pro Asp Pro Asp Thr Phe Asp Ile Arg Arg
                325                 330                 335 tcg gac ggc acc cgg cac atg gcc ttc ggg cac ggc atc cac cac tgc    1056
Ser Asp Gly Thr Arg His Met Ala Phe Gly His Gly Ile His His Cys
            340                 345                 350 ctg ggt gcc gcc ctc gcc cgc ctg gag ggc aag gtc atg ctc gaa ctc    1104
Leu Gly Ala Ala Leu Ala Arg Leu Glu Gly Lys Val Met Leu Glu Leu
        355                 360                 365 ctc ctg gac cgg gtc caa ggc ttc cgc atc gac cac gag cac acc gtg    1152
Leu Leu Asp Arg Val Gln Gly Phe Arg Ile Asp His Glu His Thr Val
    370                 375                 380 ttc tac gag gcc gac cag ctc act ccg aag tac ctg ccc gtc cgg gtc    1200
Phe Tyr Glu Ala Asp Gln Leu Thr Pro Lys Tyr Leu Pro Val Arg Val
385                 390                 395                 400 gac tgg aac tga                                                    1212
Asp Trp Asn <210> SEQ ID NO 24
<211> LENGTH: 403
<212> TYPE: PRT
<213> ORGANISM: Streptomyces ambofaciens

<400> SEQUENCE: 24

Met Gly Glu Ala Val Thr Gly Pro Met Glu Leu Ser Lys Asp Ala Asp
1               5                   10                  15

Ala Arg Gly Leu Leu Glu Trp Phe Ala Tyr Asn Arg Thr Arg His Pro
            20                  25                  30

Val Phe Trp Asp Glu Thr Arg Gln Ala Trp Gln Val Phe Gly Tyr Asp
        35                  40                  45
```

-continued

```
Asp Tyr Val Thr Val Ser Asn Pro Gln Phe Phe Ser Asp Phe
 50                  55                  60

Asn Met Val Met Pro Thr Pro Pro Glu Leu Glu Met Ile Ile Gly Pro
 65                  70                  75                  80

Gly Thr Ile Gly Ala Leu Asp Pro Pro Ala His Gly Pro Met Arg Lys
                 85                  90                  95

Leu Val Ser Gln Ala Phe Thr Pro Arg Arg Ile Ala Arg Leu Glu Pro
                100                 105                 110

Arg Val Arg Ala Ile Thr Glu Glu Leu Leu Asp Lys Val Gly Gln Gln
            115                 120                 125

Asp Val Val Asp Ala Val Gly Asp Leu Ser Tyr Ala Leu Pro Val Ile
130                 135                 140

Val Ile Ala Glu Leu Leu Gly Ile Pro Ala Gly Asp Arg Asp Leu Phe
145                 150                 155                 160

Arg Glu Trp Val Asp Thr Leu Leu Thr Asn Glu Gly Leu Glu Tyr Pro
                165                 170                 175

Asn Leu Pro Asp Asn Phe Thr Glu Thr Ile Ala Pro Ala Leu Lys Glu
            180                 185                 190

Met Thr Asp Tyr Leu Leu Lys Gln Ile His Ala Lys Arg Asp Ala Pro
        195                 200                 205

Ala Asp Asp Leu Val Ser Gly Leu Val Gln Ala Glu Gln Asp Gly Arg
210                 215                 220

Arg Leu Thr Asp Val Glu Ile Val Asn Ile Val Ala Leu Leu Leu Thr
225                 230                 235                 240

Ala Gly His Val Ser Ser Ser Thr Leu Leu Ser Asn Leu Phe Leu Val
                245                 250                 255

Leu Glu Glu Asn Pro Gln Ala Leu Glu Asp Leu Arg Ala Asp Arg Ser
            260                 265                 270

Leu Val Pro Gly Ala Ile Glu Glu Thr Leu Arg Tyr Arg Ser Pro Phe
        275                 280                 285

Asn Asn Ile Phe Arg Phe Val Lys Glu Asp Thr Thr Val Leu Gly Pro
290                 295                 300

Leu Met Glu Lys Gly Gln Met Val Ile Ala Trp Ser Gln Ser Ala Asn
305                 310                 315                 320

Arg Asp Pro Arg His Phe Pro Asp Pro Asp Thr Phe Asp Ile Arg Arg
                325                 330                 335

Ser Asp Gly Thr Arg His Met Ala Phe Gly His Gly Ile His His Cys
            340                 345                 350

Leu Gly Ala Ala Leu Ala Arg Leu Gly Leu Lys Val Met Leu Glu Leu
        355                 360                 365

Leu Leu Asp Arg Val Gln Gly Phe Arg Ile Asp His Glu His Thr Val
370                 375                 380

Phe Tyr Glu Ala Asp Gln Leu Thr Pro Lys Tyr Leu Pro Val Arg Val
385                 390                 395                 400

Asp Trp Asn

<210> SEQ ID NO 25
<211> LENGTH: 540
<212> TYPE: DNA
<213> ORGANISM: Streptomyces ambofaciens
<220> FEATURE:
<221> NAME/KEY: CDS
<222> LOCATION: (1)..(540)
<220> FEATURE:
<221> NAME/KEY: CDS
<222> LOCATION: (190)..(540)
```

```
<400> SEQUENCE: 25 ctg aac ccg agg gtc tcg tcc cgg agt cca ggg ccg tcc cga gcc ggc    48
Leu Asn Pro Arg Val Ser Ser Arg Ser Pro Gly Pro Ser Arg Ala Gly
1               5                   10                  15 cct gga cct cac gac cgc ccg ata agg agc gcc gcc atc gcc gag aac    96
Pro Gly Pro His Asp Arg Pro Ile Arg Ser Ala Ala Ile Ala Glu Asn
            20                  25                  30 aca gcc gag ctc cct gcc cgg cgg gtc ggc agg atc aag ccg tgc cgg   144
Thr Ala Glu Leu Pro Ala Arg Arg Val Gly Arg Ile Lys Pro Cys Arg
        35                  40                  45 ctg atc agg ctc gag cag cac atc gac ccg cgc ggc agc ctc tcc gtg   192
Leu Ile Arg Leu Glu Gln His Ile Asp Pro Arg Gly Ser Leu Ser Val
50                  55                  60 atc gag tcc ggc gtg acc gtg gac ttc ccc gtc cga cgc gtc tac tac   240
Ile Glu Ser Gly Val Thr Val Asp Phe Pro Val Arg Arg Val Tyr Tyr
65                  70                  75                  80 atg cat ggc cag acc cag tcc tct ccc ccg cgc ggc ctg cac gcg cac   288
Met His Gly Gln Thr Gln Ser Ser Pro Pro Arg Gly Leu His Ala His
                85                  90                  95 cgc acc ctg gaa caa ctc gtc atc gcc gtc cac ggc gcc ttc tcc atc   336
Arg Thr Leu Glu Gln Leu Val Ile Ala Val His Gly Ala Phe Ser Ile
            100                 105                 110 acc ctc gac gac ggc ttc cag cac gcc acc tac cgt ctg gac gaa ccc   384
Thr Leu Asp Asp Gly Phe Gln His Ala Thr Tyr Arg Leu Asp Glu Pro
        115                 120                 125 gga gcc gga ctc tgc atc ggc ccc atg gtc tgg cgc gtc ctg aag gac   432
Gly Ala Gly Leu Cys Ile Gly Pro Met Val Trp Arg Val Leu Lys Asp
    130                 135                 140 ttc gac ccc gac acc gtg gcc ctg gtc ctc gcc tcg cag cac tac gag   480
Phe Asp Pro Asp Thr Val Ala Leu Val Leu Ala Ser Gln His Tyr Glu
145                 150                 155                 160 gag tcc gac tac tac cgc gac tac gac acc ttc ctg cat gac gca cgg   528
Glu Ser Asp Tyr Tyr Arg Asp Tyr Asp Thr Phe Leu His Asp Ala Arg
                165                 170                 175 agc ctc aca tga                                                    540
Ser Leu Thr <210> SEQ ID NO 26
<211> LENGTH: 179
<212> TYPE: PRT
<213> ORGANISM: Streptomyces ambofaciens

<400> SEQUENCE: 26

Leu Asn Pro Arg Val Ser Ser Arg Ser Pro Gly Pro Ser Arg Ala Gly
1               5                   10                  15

Pro Gly Pro His Asp Arg Pro Ile Arg Ser Ala Ala Ile Ala Glu Asn
            20                  25                  30

Thr Ala Glu Leu Pro Ala Arg Arg Val Gly Arg Ile Lys Pro Cys Arg
        35                  40                  45

Leu Ile Arg Leu Glu Gln His Ile Asp Pro Arg Gly Ser Leu Ser Val
    50                  55                  60

Ile Glu Ser Gly Val Thr Val Asp Phe Pro Val Arg Arg Val Tyr Tyr
65                  70                  75                  80

Met His Gly Gln Thr Gln Ser Ser Pro Pro Arg Gly Leu His Ala His
                85                  90                  95

Arg Thr Leu Glu Gln Leu Val Ile Ala Val His Gly Ala Phe Ser Ile
            100                 105                 110
```

```
Thr Leu Asp Asp Gly Phe Gln His Ala Thr Tyr Arg Leu Asp Glu Pro
        115                 120                 125

Gly Ala Gly Leu Cys Ile Gly Pro Met Val Trp Arg Val Leu Lys Asp
    130                 135                 140

Phe Asp Pro Asp Thr Val Ala Leu Val Leu Ala Ser Gln His Tyr Glu
145                 150                 155                 160

Glu Ser Asp Tyr Tyr Arg Asp Tyr Asp Thr Phe Leu His Asp Ala Arg
                165                 170                 175

Ser Leu Thr

<210> SEQ ID NO 27
<211> LENGTH: 116
<212> TYPE: PRT
<213> ORGANISM: Streptomyces ambofaciens

<400> SEQUENCE: 27

Val Ile Glu Ser Gly Val Thr Val Asp Phe Pro Val Arg Arg Val Tyr
1               5                   10                  15

Tyr Met His Gly Gln Thr Gln Ser Ser Pro Pro Arg Gly Leu His Ala
            20                  25                  30

His Arg Thr Leu Glu Gln Leu Val Ile Ala Val His Gly Ala Phe Ser
        35                  40                  45

Ile Thr Leu Asp Asp Gly Phe Gln His Ala Thr Tyr Arg Leu Asp Glu
    50                  55                  60

Pro Gly Ala Gly Leu Cys Ile Gly Pro Met Val Trp Arg Val Leu Lys
65                  70                  75                  80

Asp Phe Asp Pro Asp Thr Val Ala Leu Val Leu Ala Ser Gln His Tyr
                85                  90                  95

Glu Glu Ser Asp Tyr Tyr Arg Asp Tyr Asp Thr Phe Leu His Asp Ala
                100                 105                 110

Arg Ser Leu Thr
        115

<210> SEQ ID NO 28
<211> LENGTH: 1167
<212> TYPE: DNA
<213> ORGANISM: Streptomyces ambofaciens
<220> FEATURE:
<221> NAME/KEY: CDS
<222> LOCATION: (1)..(1167)

<400> SEQUENCE: 28 atg acc atc ccc ttc ctc gac gcg ggc gcc ggc tac cgg gag ttg cga      48
Met Thr Ile Pro Phe Leu Asp Ala Gly Ala Gly Tyr Arg Glu Leu Arg
1               5                   10                  15 gcc gag atc gac gcg gcc ctg cag cgg gtg tcc gcc tcc ggc cgc tat      96
Ala Glu Ile Asp Ala Ala Leu Gln Arg Val Ser Ala Ser Gly Arg Tyr
            20                  25                  30 ctg ctc gac gcg gaa ctc gcg gcc ttc gag gag gag ttc gcc gcg tac     144
Leu Leu Asp Ala Glu Leu Ala Ala Phe Glu Glu Glu Phe Ala Ala Tyr
        35                  40                  45 tgc gac aac gac cac tgt gtg gcg gtg ggc agt ggc tgc gac gcg ctg     192
Cys Asp Asn Asp His Cys Val Ala Val Gly Ser Gly Cys Asp Ala Leu
    50                  55                  60 gag ctg tcc ctg cgg gcg ctg gac atc ggt ccc ggg gac gag gtg gtg     240
Glu Leu Ser Leu Arg Ala Leu Asp Ile Gly Pro Gly Asp Glu Val Val
65                  70                  75                  80 gtg ccc gcg cac acc ttc atc ggg acc tgg ctg gcc gtg tcc gct acc     288
Val Pro Ala His Thr Phe Ile Gly Thr Trp Leu Ala Val Ser Ala Thr
```

-continued

|     |     |     | 85  |     |     |     | 90  |     |     |     | 95  |     |     |     |     |      |
|-----|-----|-----|-----|-----|-----|-----|-----|-----|-----|-----|-----|-----|-----|-----|-----|------|
| ggg | gca | cgg | ccg | gtg | gcc | gtc | gac | ccg | acg | ccg | gac | ggg | ctc | tcc | ctc | 336  |
| Gly | Ala | Arg | Pro | Val | Ala | Val | Asp | Pro | Thr | Pro | Asp | Gly | Leu | Ser | Leu |      |
|     |     | 100 |     |     |     |     | 105 |     |     |     |     | 110 |     |     |     |      |

| gac | ccg | gcg | ctg | gtg | gag | gcg | gcg | ctc | acc | cct | cgg | acc | aga | gcc | ctg | 384  |
|-----|-----|-----|-----|-----|-----|-----|-----|-----|-----|-----|-----|-----|-----|-----|-----|------|
| Asp | Pro | Ala | Leu | Val | Glu | Ala | Ala | Leu | Thr | Pro | Arg | Thr | Arg | Ala | Leu |      |
|     | 115 |     |     |     |     | 120 |     |     |     |     | 125 |     |     |     |     |      |

| atg | ccg | gtg | cac | ctg | cac | ggg | cac | ccg | gcc | gac | ctc | gac | ccg | cta | ctg | 432  |
|-----|-----|-----|-----|-----|-----|-----|-----|-----|-----|-----|-----|-----|-----|-----|-----|------|
| Met | Pro | Val | His | Leu | His | Gly | His | Pro | Ala | Asp | Leu | Asp | Pro | Leu | Leu |      |
| 130 |     |     |     |     | 135 |     |     |     |     | 140 |     |     |     |     |     |      |

| gcg | atc | gcc | gga | cgg | cac | ggc | ctg | gcc | gtg | gtc | gag | gac | gcc | gcg | cag | 480  |
|-----|-----|-----|-----|-----|-----|-----|-----|-----|-----|-----|-----|-----|-----|-----|-----|------|
| Ala | Ile | Ala | Gly | Arg | His | Gly | Leu | Ala | Val | Val | Glu | Asp | Ala | Ala | Gln |      |
| 145 |     |     |     |     | 150 |     |     |     |     | 155 |     |     |     |     | 160 |      |

| gcc | cac | ggc | gcc | cgt | tac | cgg | ggc | cgc | agg | atc | ggc | tcg | ggc | cac | gtg | 528  |
|-----|-----|-----|-----|-----|-----|-----|-----|-----|-----|-----|-----|-----|-----|-----|-----|------|
| Ala | His | Gly | Ala | Arg | Tyr | Arg | Gly | Arg | Arg | Ile | Gly | Ser | Gly | His | Val |      |
|     |     |     |     | 165 |     |     |     |     | 170 |     |     |     |     | 175 |     |      |

| gtc | gcg | ttc | agc | ttc | tac | ccc | ggc | aag | aac | ctc | ggc | gcc | atg | ggg | gac | 576  |
|-----|-----|-----|-----|-----|-----|-----|-----|-----|-----|-----|-----|-----|-----|-----|-----|------|
| Val | Ala | Phe | Ser | Phe | Tyr | Pro | Gly | Lys | Asn | Leu | Gly | Ala | Met | Gly | Asp |      |
|     |     |     | 180 |     |     |     |     | 185 |     |     |     |     | 190 |     |     |      |

| ggc | ggc | gcg | gtg | gtc | acg | ggt | gac | tcc | ggt | gtg | gcc | gag | cgg | atc | cgg | 624  |
|-----|-----|-----|-----|-----|-----|-----|-----|-----|-----|-----|-----|-----|-----|-----|-----|------|
| Gly | Gly | Ala | Val | Val | Thr | Gly | Asp | Ser | Gly | Val | Ala | Glu | Arg | Ile | Arg |      |
|     |     | 195 |     |     |     |     | 200 |     |     |     |     | 205 |     |     |     |      |

| ttg | ctg | cgc | aac | tgc | ggc | tcg | cgg | gag | aag | tac | cgg | cac | gag | gtg | cgc | 672  |
|-----|-----|-----|-----|-----|-----|-----|-----|-----|-----|-----|-----|-----|-----|-----|-----|------|
| Leu | Leu | Arg | Asn | Cys | Gly | Ser | Arg | Glu | Lys | Tyr | Arg | His | Glu | Val | Arg |      |
| 210 |     |     |     |     | 215 |     |     |     |     | 220 |     |     |     |     |     |      |

| tcg | acc | cac | tcc | cgg | ctc | gac | gag | ttc | cag | gcg | gcc | gtg | ctg | cgg | gcc | 720  |
|-----|-----|-----|-----|-----|-----|-----|-----|-----|-----|-----|-----|-----|-----|-----|-----|------|
| Ser | Thr | His | Ser | Arg | Leu | Asp | Glu | Phe | Gln | Ala | Ala | Val | Leu | Arg | Ala |      |
| 225 |     |     |     |     | 230 |     |     |     |     | 235 |     |     |     |     | 240 |      |

| aaa | ctg | ccg | cgg | ctc | gac | gcg | tgg | aac | gcc | cgc | cgg | gcc | ggc | acg | gcc | 768  |
|-----|-----|-----|-----|-----|-----|-----|-----|-----|-----|-----|-----|-----|-----|-----|-----|------|
| Lys | Leu | Pro | Arg | Leu | Asp | Ala | Trp | Asn | Ala | Arg | Arg | Ala | Gly | Thr | Ala |      |
|     |     |     |     | 245 |     |     |     |     | 250 |     |     |     |     | 255 |     |      |

| gaa | cgg | tac | ggg | cgg | gcc | ctg | ggt | ccg | gta | ccg | cag | atc | gcc | gtc | ccg | 816  |
|-----|-----|-----|-----|-----|-----|-----|-----|-----|-----|-----|-----|-----|-----|-----|-----|------|
| Glu | Arg | Tyr | Gly | Arg | Ala | Leu | Gly | Pro | Val | Pro | Gln | Ile | Ala | Val | Pro |      |
|     |     . | 260 |     |     |     |     | 265 |     |     |     |     | 270 |     |     |     |      |

| gtc | acc | gct | ccc | tgg | gcc | gac | ccg | gtg | tgg | cac | ctg | tac | gtg | atc | cgc | 864  |
|-----|-----|-----|-----|-----|-----|-----|-----|-----|-----|-----|-----|-----|-----|-----|-----|------|
| Val | Thr | Ala | Pro | Trp | Ala | Asp | Pro | Val | Trp | His | Leu | Tyr | Val | Ile | Arg |      |
|     |     | 275 |     |     |     |     | 280 |     |     |     |     | 285 |     |     |     |      |

| tgc | gcg | gag | cgc | gac | gag | ctg | cgc | cgc | cgg | ctg | gaa | cga | gcc | ggg | gtc | 912  |
|-----|-----|-----|-----|-----|-----|-----|-----|-----|-----|-----|-----|-----|-----|-----|-----|------|
| Cys | Ala | Glu | Arg | Asp | Glu | Leu | Arg | Arg | Arg | Leu | Glu | Arg | Ala | Gly | Val |      |
|     | 290 |     |     |     |     | 295 |     |     |     |     | 300 |     |     |     |     |      |

| cag | acc | ctg | atc | cac | tac | ccc | gtg | ccc | ccg | cac | cgg | tcc | ccg | gcc | tac | 960  |
|-----|-----|-----|-----|-----|-----|-----|-----|-----|-----|-----|-----|-----|-----|-----|-----|------|
| Gln | Thr | Leu | Ile | His | Tyr | Pro | Val | Pro | Pro | His | Arg | Ser | Pro | Ala | Tyr |      |
| 305 |     |     |     |     | 310 |     |     |     |     | 315 |     |     |     |     | 320 |      |

| gcc | gac | gac | ccg | gcc | ggc | gca | ccg | gcg | ggg | acc | cac | ccg | ctc | agt | gag | 1008 |
|-----|-----|-----|-----|-----|-----|-----|-----|-----|-----|-----|-----|-----|-----|-----|-----|------|
| Ala | Asp | Asp | Pro | Ala | Gly | Ala | Pro | Ala | Gly | Thr | His | Pro | Leu | Ser | Glu |      |
|     |     |     |     | 325 |     |     |     |     | 330 |     |     |     |     | 335 |     |      |

| cgc | ctg | gcg | gcg | cag | agc | ctc | agc | ctt | ccc | ctg | gga | ccg | cac | ctc | ggg | 1056 |
|-----|-----|-----|-----|-----|-----|-----|-----|-----|-----|-----|-----|-----|-----|-----|-----|------|
| Arg | Leu | Ala | Ala | Gln | Ser | Leu | Ser | Leu | Pro | Leu | Gly | Pro | His | Leu | Gly |      |
|     |     |     | 340 |     |     |     |     | 345 |     |     |     |     | 350 |     |     |      |

| gag | gac | gag | gcc | cgc | gcc | gtc | gtg | gcg | gcg | gtc | cgg | gcg | gcg | tcc | gca | 1104 |
|-----|-----|-----|-----|-----|-----|-----|-----|-----|-----|-----|-----|-----|-----|-----|-----|------|
| Glu | Asp | Glu | Ala | Arg | Ala | Val | Val | Ala | Ala | Val | Arg | Ala | Ala | Ser | Ala |      |
|     |     | 355 |     |     |     |     | 360 |     |     |     |     | 365 |     |     |     |      |

| ggg | ctg | gcg | gcg | tac | ccg | acg | ccg | gac | ggc | cag | cgt | ttt | cct | cta | gtg | 1152 |
|-----|-----|-----|-----|-----|-----|-----|-----|-----|-----|-----|-----|-----|-----|-----|-----|------|
| Gly | Leu | Ala | Ala | Tyr | Pro | Thr | Pro | Asp | Gly | Gln | Arg | Phe | Pro | Leu | Val |      |
| 370 |     |     |     |     | 375 |     |     |     |     | 380 |     |     |     |     |     |      |

| acg | gag | aaa | cga | tga |     |     |     |     |     |     |     |     |     |     |     | 1167 |
|-----|-----|-----|-----|-----|-----|-----|-----|-----|-----|-----|-----|-----|-----|-----|-----|------|
| Thr | Glu | Lys | Arg |     |     |     |     |     |     |     |     |     |     |     |     |      |
| 385 |     |     |     |     |     |     |     |     |     |     |     |     |     |     |     |      |

<210> SEQ ID NO 29
<211> LENGTH: 388
<212> TYPE: PRT
<213> ORGANISM: Streptomyces ambofaciens

<400> SEQUENCE: 29

```
Met Thr Ile Pro Phe Leu Asp Ala Gly Ala Gly Tyr Arg Glu Leu Arg
1               5                   10                  15

Ala Glu Ile Asp Ala Ala Leu Gln Arg Val Ser Ala Ser Gly Arg Tyr
            20                  25                  30

Leu Leu Asp Ala Glu Leu Ala Ala Phe Glu Glu Glu Phe Ala Ala Tyr
        35                  40                  45

Cys Asp Asn Asp His Cys Val Ala Val Gly Ser Gly Cys Asp Ala Leu
    50                  55                  60

Glu Leu Ser Leu Arg Ala Leu Asp Ile Gly Pro Gly Asp Glu Val Val
65                  70                  75                  80

Val Pro Ala His Thr Phe Ile Gly Thr Trp Leu Ala Val Ser Ala Thr
                85                  90                  95

Gly Ala Arg Pro Val Ala Val Asp Pro Thr Pro Asp Gly Leu Ser Leu
            100                 105                 110

Asp Pro Ala Leu Val Glu Ala Ala Leu Thr Pro Arg Thr Arg Ala Leu
        115                 120                 125

Met Pro Val His Leu His Gly His Pro Ala Asp Leu Asp Pro Leu Leu
    130                 135                 140

Ala Ile Ala Gly Arg His Gly Leu Ala Val Val Glu Asp Ala Ala Gln
145                 150                 155                 160

Ala His Gly Ala Arg Tyr Arg Gly Arg Arg Ile Gly Ser Gly His Val
                165                 170                 175

Val Ala Phe Ser Phe Tyr Pro Gly Lys Asn Leu Gly Ala Met Gly Asp
            180                 185                 190

Gly Gly Ala Val Val Thr Gly Asp Ser Gly Val Ala Glu Arg Ile Arg
        195                 200                 205

Leu Leu Arg Asn Cys Gly Ser Arg Glu Lys Tyr Arg His Glu Val Arg
    210                 215                 220

Ser Thr His Ser Arg Leu Asp Glu Phe Gln Ala Ala Val Leu Arg Ala
225                 230                 235                 240

Lys Leu Pro Arg Leu Asp Ala Trp Asn Ala Arg Arg Ala Gly Thr Ala
                245                 250                 255

Glu Arg Tyr Gly Arg Ala Leu Gly Pro Val Pro Gln Ile Ala Val Pro
            260                 265                 270

Val Thr Ala Pro Trp Ala Asp Pro Val Trp His Leu Tyr Val Ile Arg
        275                 280                 285

Cys Ala Glu Arg Asp Glu Leu Arg Arg Arg Leu Glu Arg Ala Gly Val
    290                 295                 300

Gln Thr Leu Ile His Tyr Pro Val Pro Pro His Arg Ser Pro Ala Tyr
305                 310                 315                 320

Ala Asp Asp Pro Ala Gly Ala Pro Ala Gly Thr His Pro Leu Ser Glu
                325                 330                 335

Arg Leu Ala Ala Gln Ser Leu Ser Leu Pro Leu Gly Pro His Leu Gly
            340                 345                 350

Glu Asp Glu Ala Arg Ala Val Val Ala Ala Val Arg Ala Ala Ser Ala
        355                 360                 365

Gly Leu Ala Ala Tyr Pro Thr Pro Asp Gly Gln Arg Phe Pro Leu Val
    370                 375                 380
```

Thr Glu Lys Arg
385

<210> SEQ ID NO 30
<211> LENGTH: 909
<212> TYPE: DNA
<213> ORGANISM: Streptomyces ambofaciens
<220> FEATURE:
<221> NAME/KEY: CDS
<222> LOCATION: (1)..(909)
<220> FEATURE:
<221> NAME/KEY: CDS
<222> LOCATION: (10)..(909)
<220> FEATURE:
<221> NAME/KEY: CDS
<222> LOCATION: (28)..(909)

<400> SEQUENCE: 30

| | | | | | | | | | | | | | | | | |
|---|---|---|---|---|---|---|---|---|---|---|---|---|---|---|---|---|
| atg | acc | gag | gtc | atg | tca | ggg | cgt | ccc | gga | atg | aaa | ggg | atc | atc | ctc | 48 |
| Met | Thr | Glu | Val | Met | Ser | Gly | Arg | Pro | Gly | Met | Lys | Gly | Ile | Ile | Leu | |
| 1 | | | | 5 | | | | | 10 | | | | | 15 | | |

| gca | ggc | ggc | gga | ggg | acc | cgc | cta | cgc | ccc | ttg | acc | ggc | acg | ctg | tcc | 96 |
|---|---|---|---|---|---|---|---|---|---|---|---|---|---|---|---|---|
| Ala | Gly | Gly | Gly | Gly | Thr | Arg | Leu | Arg | Pro | Leu | Thr | Gly | Thr | Leu | Ser | |
| | | | 20 | | | | | 25 | | | | | 30 | | | |

| aag | caa | ctg | ctg | ccc | gtc | tac | gac | aag | ccg | atg | atc | tac | tac | ccg | ctg | 144 |
|---|---|---|---|---|---|---|---|---|---|---|---|---|---|---|---|---|
| Lys | Gln | Leu | Leu | Pro | Val | Tyr | Asp | Lys | Pro | Met | Ile | Tyr | Tyr | Pro | Leu | |
| | | 35 | | | | | 40 | | | | | 45 | | | | |

| tcc | gtc | ctg | atg | ctg | ggc | ggc | atc | cgc | gag | atc | ctc | gtc | gtc | tcc | tcc | 192 |
|---|---|---|---|---|---|---|---|---|---|---|---|---|---|---|---|---|
| Ser | Val | Leu | Met | Leu | Gly | Gly | Ile | Arg | Glu | Ile | Leu | Val | Val | Ser | Ser | |
| 50 | | | | | 55 | | | | | 60 | | | | | | |

| acc | cag | cac | atc | gag | ctg | ttc | cag | cgg | ctg | ctg | ggc | gac | ggc | tcc | cgc | 240 |
|---|---|---|---|---|---|---|---|---|---|---|---|---|---|---|---|---|
| Thr | Gln | His | Ile | Glu | Leu | Phe | Gln | Arg | Leu | Leu | Gly | Asp | Gly | Ser | Arg | |
| 65 | | | | | 70 | | | | | 75 | | | | | 80 | |

| ctc | ggc | ctc | gac | atc | acc | tac | gcc | gaa | cag | gcc | gag | ccc | gag | ggc | ata | 288 |
|---|---|---|---|---|---|---|---|---|---|---|---|---|---|---|---|---|
| Leu | Gly | Leu | Asp | Ile | Thr | Tyr | Ala | Glu | Gln | Ala | Glu | Pro | Glu | Gly | Ile | |
| | | | | 85 | | | | | 90 | | | | | 95 | | |

| gcg | cag | gcc | atc | acc | atc | ggc | acc | gac | cac | atc | ggc | gac | tca | ccg | gtc | 336 |
|---|---|---|---|---|---|---|---|---|---|---|---|---|---|---|---|---|
| Ala | Gln | Ala | Ile | Thr | Ile | Gly | Thr | Asp | His | Ile | Gly | Asp | Ser | Pro | Val | |
| | | | 100 | | | | | 105 | | | | | 110 | | | |

| gcg | ctc | atc | ctg | ggc | gac | aac | atc | ttc | cac | ggc | ccc | ggc | ttc | tcg | gcc | 384 |
|---|---|---|---|---|---|---|---|---|---|---|---|---|---|---|---|---|
| Ala | Leu | Ile | Leu | Gly | Asp | Asn | Ile | Phe | His | Gly | Pro | Gly | Phe | Ser | Ala | |
| | | 115 | | | | | 120 | | | | | 125 | | | | |

| gtg | ctc | cag | ggc | agc | atc | cgc | cac | ctc | gac | ggc | tgt | gtg | ctg | ttc | ggc | 432 |
|---|---|---|---|---|---|---|---|---|---|---|---|---|---|---|---|---|
| Val | Leu | Gln | Gly | Ser | Ile | Arg | His | Leu | Asp | Gly | Cys | Val | Leu | Phe | Gly | |
| | 130 | | | | | 135 | | | | | 140 | | | | | |

| tac | ccg | gtc | agc | gac | ccg | aag | cgc | tac | ggc | gtc | ggc | gag | atc | gac | gac | 480 |
|---|---|---|---|---|---|---|---|---|---|---|---|---|---|---|---|---|
| Tyr | Pro | Val | Ser | Asp | Pro | Lys | Arg | Tyr | Gly | Val | Gly | Glu | Ile | Asp | Asp | |
| 145 | | | | | 150 | | | | | 155 | | | | | 160 | |

| cag | ggc | gta | ctg | ctg | tcc | ctg | gag | gag | aaa | ccg | gcc | cgg | ccc | cgc | tcc | 528 |
|---|---|---|---|---|---|---|---|---|---|---|---|---|---|---|---|---|
| Gln | Gly | Val | Leu | Leu | Ser | Leu | Glu | Glu | Lys | Pro | Ala | Arg | Pro | Arg | Ser | |
| | | | | 165 | | | | | 170 | | | | | 175 | | |

| aac | ctc | gcc | gtc | acc | ggc | ctc | tac | ctc | tac | gac | aac | gac | gtg | gtc | gac | 576 |
|---|---|---|---|---|---|---|---|---|---|---|---|---|---|---|---|---|
| Asn | Leu | Ala | Val | Thr | Gly | Leu | Tyr | Leu | Tyr | Asp | Asn | Asp | Val | Val | Asp | |
| | | | 180 | | | | | 185 | | | | | 190 | | | |

| atc | gcc | aag | aac | atc | cgg | ccc | tcg | gcg | cgc | ggc | gaa | ctc | gag | atc | acg | 624 |
|---|---|---|---|---|---|---|---|---|---|---|---|---|---|---|---|---|
| Ile | Ala | Lys | Asn | Ile | Arg | Pro | Ser | Ala | Arg | Gly | Glu | Leu | Glu | Ile | Thr | |
| | | 195 | | | | | 200 | | | | | 205 | | | | |

| gac | gtc | aac | agg | acc | tac | ctg | gag | cag | aaa | cgc | gcc | cgg | ctc | atc | gaa | 672 |
|---|---|---|---|---|---|---|---|---|---|---|---|---|---|---|---|---|
| Asp | Val | Asn | Arg | Thr | Tyr | Leu | Glu | Gln | Lys | Arg | Ala | Arg | Leu | Ile | Glu | |
| | 210 | | | | | 215 | | | | | 220 | | | | | |

| ctg | ggc | cac | ggc | ttc | gcc | tgg | ctc | gac | atg | ggc | acc | cac | gac | tcc | ctg | 720 |
|---|---|---|---|---|---|---|---|---|---|---|---|---|---|---|---|---|
| Leu | Gly | His | Gly | Phe | Ala | Trp | Leu | Asp | Met | Gly | Thr | His | Asp | Ser | Leu | |
| 225 | | | | | 230 | | | | | 235 | | | | | 240 | |

```
ctc cag ggc ggc cag tac gtc cag ctc atc gag cag cgc cag gga gtg      768
Leu Gln Gly Gly Gln Tyr Val Gln Leu Ile Glu Gln Arg Gln Gly Val
                245                 250                 255 cgg atc gcc tgc atc gag gag atc gcc ctg cgc atg ggc ttc atc gac      816
Arg Ile Ala Cys Ile Glu Glu Ile Ala Leu Arg Met Gly Phe Ile Asp
            260                 265                 270 gcc gac acc ctc cac cgg ctc ggc cgc gaa ctg ggc acc tcc gga tac      864
Ala Asp Thr Leu His Arg Leu Gly Arg Glu Leu Gly Thr Ser Gly Tyr
        275                 280                 285 ggc gcg tac ctg atg gag gtg gcc acc cgt gca ggc acc gaa tga          909
Gly Ala Tyr Leu Met Glu Val Ala Thr Arg Ala Gly Thr Glu
    290                 295                 300
```

<210> SEQ ID NO 31
<211> LENGTH: 302
<212> TYPE: PRT
<213> ORGANISM: Streptomyces ambofaciens

<400> SEQUENCE: 31

```
Met Thr Glu Val Met Ser Gly Arg Pro Gly Met Lys Gly Ile Ile Leu
1               5                   10                  15

Ala Gly Gly Gly Gly Thr Arg Leu Arg Pro Leu Thr Gly Thr Leu Ser
                20                  25                  30

Lys Gln Leu Leu Pro Val Tyr Asp Lys Pro Met Ile Tyr Tyr Pro Leu
            35                  40                  45

Ser Val Leu Met Leu Gly Gly Ile Arg Glu Ile Leu Val Val Ser Ser
        50                  55                  60

Thr Gln His Ile Glu Leu Phe Gln Arg Leu Leu Gly Asp Gly Ser Arg
65              70                  75                  80

Leu Gly Leu Asp Ile Thr Tyr Ala Glu Gln Ala Glu Pro Glu Gly Ile
                85                  90                  95

Ala Gln Ala Ile Thr Ile Gly Thr Asp His Ile Gly Asp Ser Pro Val
            100                 105                 110

Ala Leu Ile Leu Gly Asp Asn Ile Phe His Gly Pro Gly Phe Ser Ala
        115                 120                 125

Val Leu Gln Gly Ser Ile Arg His Leu Asp Gly Cys Val Leu Phe Gly
    130                 135                 140

Tyr Pro Val Ser Asp Pro Lys Arg Tyr Gly Val Gly Glu Ile Asp Asp
145                 150                 155                 160

Gln Gly Val Leu Leu Ser Leu Glu Glu Lys Pro Ala Arg Pro Arg Ser
                165                 170                 175

Asn Leu Ala Val Thr Gly Leu Tyr Leu Tyr Asp Asn Asp Val Val Asp
            180                 185                 190

Ile Ala Lys Asn Ile Arg Pro Ser Ala Arg Gly Glu Leu Glu Ile Thr
        195                 200                 205

Asp Val Asn Arg Thr Tyr Leu Glu Gln Lys Arg Ala Arg Leu Ile Glu
    210                 215                 220

Leu Gly His Gly Phe Ala Trp Leu Asp Met Gly Thr His Asp Ser Leu
225                 230                 235                 240

Leu Gln Gly Gly Gln Tyr Val Gln Leu Ile Glu Gln Arg Gln Gly Val
                245                 250                 255

Arg Ile Ala Cys Ile Glu Glu Ile Ala Leu Arg Met Gly Phe Ile Asp
            260                 265                 270

Ala Asp Thr Leu His Arg Leu Gly Arg Glu Leu Gly Thr Ser Gly Tyr
        275                 280                 285
```

```
Gly Ala Tyr Leu Met Glu Val Ala Thr Arg Ala Gly Thr Glu
    290                 295                 300
```

<210> SEQ ID NO 32
<211> LENGTH: 299
<212> TYPE: PRT
<213> ORGANISM: Streptomyces ambofaciens

<400> SEQUENCE: 32

```
Val Met Ser Gly Arg Pro Gly Met Lys Gly Ile Ile Leu Ala Gly Gly
1               5                   10                  15

Gly Gly Thr Arg Leu Arg Pro Leu Thr Gly Thr Leu Ser Lys Gln Leu
            20                  25                  30

Leu Pro Val Tyr Asp Lys Pro Met Ile Tyr Tyr Pro Leu Ser Val Leu
        35                  40                  45

Met Leu Gly Gly Ile Arg Glu Ile Leu Val Val Ser Ser Thr Gln His
    50                  55                  60

Ile Glu Leu Phe Gln Arg Leu Leu Gly Asp Gly Ser Arg Leu Gly Leu
65                  70                  75                  80

Asp Ile Thr Tyr Ala Glu Gln Ala Glu Pro Glu Gly Ile Ala Gln Ala
                85                  90                  95

Ile Thr Ile Gly Thr Asp His Ile Gly Asp Ser Pro Val Ala Leu Ile
            100                 105                 110

Leu Gly Asp Asn Ile Phe His Gly Pro Gly Phe Ser Ala Val Leu Gln
        115                 120                 125

Gly Ser Ile Arg His Leu Asp Gly Cys Val Leu Phe Gly Tyr Pro Val
    130                 135                 140

Ser Asp Pro Lys Arg Tyr Gly Val Gly Glu Ile Asp Asp Gln Gly Val
145                 150                 155                 160

Leu Leu Ser Leu Glu Glu Lys Pro Ala Arg Pro Arg Ser Asn Leu Ala
                165                 170                 175

Val Thr Gly Leu Tyr Leu Tyr Asp Asn Asp Val Val Asp Ile Ala Lys
            180                 185                 190

Asn Ile Arg Pro Ser Ala Arg Gly Glu Leu Glu Ile Thr Asp Val Asn
        195                 200                 205

Arg Thr Tyr Leu Glu Gln Lys Arg Ala Arg Leu Ile Glu Leu Gly His
    210                 215                 220

Gly Phe Ala Trp Leu Asp Met Gly Thr His Asp Ser Leu Leu Gln Gly
225                 230                 235                 240

Gly Gln Tyr Val Gln Leu Ile Gln Arg Gln Gly Val Arg Ile Ala
                245                 250                 255

Cys Ile Glu Glu Ile Ala Leu Arg Met Gly Phe Ile Asp Ala Asp Thr
            260                 265                 270

Leu His Arg Leu Gly Arg Glu Leu Gly Thr Ser Gly Tyr Gly Ala Tyr
        275                 280                 285

Leu Met Glu Val Ala Thr Arg Ala Gly Thr Glu
    290                 295
```

<210> SEQ ID NO 33
<211> LENGTH: 293
<212> TYPE: PRT
<213> ORGANISM: Streptomyces ambofaciens

<400> SEQUENCE: 33

```
Gly Met Lys Gly Ile Ile Leu Ala Gly Gly Gly Thr Arg Leu Arg
1               5                   10                  15
```

```
Pro Leu Thr Gly Thr Leu Ser Lys Gln Leu Leu Pro Val Tyr Asp Lys
         20                  25                  30

Pro Met Ile Tyr Tyr Pro Leu Ser Val Leu Met Leu Gly Gly Ile Arg
         35                  40                  45

Glu Ile Leu Val Val Ser Ser Thr Gln His Ile Glu Leu Phe Gln Arg
 50                  55                  60

Leu Leu Gly Asp Gly Ser Arg Leu Gly Leu Asp Ile Thr Tyr Ala Glu
 65                  70                  75                  80

Gln Ala Glu Pro Glu Gly Ile Ala Gln Ala Ile Thr Ile Gly Thr Asp
                 85                  90                  95

His Ile Gly Asp Ser Pro Val Ala Leu Ile Leu Gly Asp Asn Ile Phe
            100                 105                 110

His Gly Pro Gly Phe Ser Ala Val Leu Gln Gly Ser Ile Arg His Leu
            115                 120                 125

Asp Gly Cys Val Leu Phe Gly Tyr Pro Val Ser Asp Pro Lys Arg Tyr
130                 135                 140

Gly Val Gly Glu Ile Asp Asp Gln Gly Val Leu Leu Ser Leu Glu Glu
145                 150                 155                 160

Lys Pro Ala Arg Pro Arg Ser Asn Leu Ala Val Thr Gly Leu Tyr Leu
                165                 170                 175

Tyr Asp Asn Asp Val Val Asp Ile Ala Lys Asn Ile Arg Pro Ser Ala
            180                 185                 190

Arg Gly Glu Leu Glu Ile Thr Asp Val Asn Arg Thr Tyr Leu Glu Gln
            195                 200                 205

Lys Arg Ala Arg Leu Ile Glu Leu Gly His Gly Phe Ala Trp Leu Asp
210                 215                 220

Met Gly Thr His Asp Ser Leu Leu Gln Gly Gln Tyr Val Gln Leu
225                 230                 235                 240

Ile Glu Gln Arg Gln Gly Val Arg Ile Ala Cys Ile Glu Glu Ile Ala
                245                 250                 255

Leu Arg Met Gly Phe Ile Asp Ala Asp Thr Leu His Arg Leu Gly Arg
            260                 265                 270

Glu Leu Gly Thr Ser Gly Tyr Gly Ala Tyr Leu Met Glu Val Ala Thr
            275                 280                 285

Arg Ala Gly Thr Glu
        290
```

<210> SEQ ID NO 34
<211> LENGTH: 1038
<212> TYPE: DNA
<213> ORGANISM: Streptomyces ambofaciens
<220> FEATURE:
<221> NAME/KEY: CDS
<222> LOCATION: (1)..(1038)

<400> SEQUENCE: 34

```
gtg cag gca ccg aat gag acg ccg cgc cgg ccc gcc cgc tcc gcc ggc      48
Val Gln Ala Pro Asn Glu Thr Pro Arg Arg Pro Ala Arg Ser Ala Gly
 1               5                  10                  15 cga cgg ccg ccg gcc cgg atc ctc gtc acc ggg ggc gcc ggc ttc atc      96
Arg Arg Pro Pro Ala Arg Ile Leu Val Thr Gly Gly Ala Gly Phe Ile
                 20                  25                  30 ggc tcg cgc ttc gtg aac gcg ctg ctg gac ggc tcc ctg ccg gag ttc     144
Gly Ser Arg Phe Val Asn Ala Leu Leu Asp Gly Ser Leu Pro Glu Phe
            35                  40                  45 ggc aaa ccc gag gtg agg gtg ctc gac gcg ctc acc tac gcg ggc aac     192
Gly Lys Pro Glu Val Arg Val Leu Asp Ala Leu Thr Tyr Ala Gly Asn
```

```
                50                  55                  60
ctg gcc aat ctg gcc ccg gtg ggc gac tgt ccc cgg ctg cgg atc ttc        240
Leu Ala Asn Leu Ala Pro Val Gly Asp Cys Pro Arg Leu Arg Ile Phe
 65                  70                  75                  80 ccg ggg gac atc cgc gac cgc ggc gcg gtc acc cag gcg atg gcg ggg        288
Pro Gly Asp Ile Arg Asp Arg Gly Ala Val Thr Gln Ala Met Ala Gly
                     85                  90                  95 gtc gac ctg gtg gtg cac ttc gcg gcc gag tcg cac gtg gac cgc tcg        336
Val Asp Leu Val Val His Phe Ala Ala Glu Ser His Val Asp Arg Ser
                100                 105                 110 atc gac gac gcc gac gcc ttc gtg cgc acc aac gtg ctg ggc acc cag        384
Ile Asp Asp Ala Asp Ala Phe Val Arg Thr Asn Val Leu Gly Thr Gln
            115                 120                 125 gtc ctc ctc cag gag gca ctg gcc gta cgc ccc ggg ctg ttc gtg cac        432
Val Leu Leu Gln Glu Ala Leu Ala Val Arg Pro Gly Leu Phe Val His
        130                 135                 140 gtc tcg acg gac gag gtg tac ggc tcc atc gag gag ggg tcc tgg ccc        480
Val Ser Thr Asp Glu Val Tyr Gly Ser Ile Glu Glu Gly Ser Trp Pro
145                 150                 155                 160 gag gag cac ccg ctg aac ccc aac tcg ccc tac gcc gcc tcg aag gcg        528
Glu Glu His Pro Leu Asn Pro Asn Ser Pro Tyr Ala Ala Ser Lys Ala
                165                 170                 175 tcc tcc gac ctg ctg gcg ctg gcc cac cac cgc acg cac gga ctg ccg        576
Ser Ser Asp Leu Leu Ala Leu Ala His His Arg Thr His Gly Leu Pro
            180                 185                 190 gtg tgc gtc acc cgc tgc tcc aac aac tac ggg ccc tac cag tac ccg        624
Val Cys Val Thr Arg Cys Ser Asn Asn Tyr Gly Pro Tyr Gln Tyr Pro
        195                 200                 205 gag aag atc atc ccg ctg ttc acc agc agc ctc ctc gac ggc ggg acc        672
Glu Lys Ile Ile Pro Leu Phe Thr Ser Ser Leu Leu Asp Gly Gly Thr
210                 215                 220 gtc ccg ctc tac ggg gac ggc ggc aac cgg cgc gac tgg ctg cac gtg        720
Val Pro Leu Tyr Gly Asp Gly Gly Asn Arg Arg Asp Trp Leu His Val
225                 230                 235                 240 gac gac cac tgc cgg ggc atc gcc ctg gtg gcc cgg ggc ggc cgg ccc        768
Asp Asp His Cys Arg Gly Ile Ala Leu Val Ala Arg Gly Gly Arg Pro
                245                 250                 255 ggc gag gtc tac aac atc ggc ggc ggc acc gag ctg agc aac gtc gag        816
Gly Glu Val Tyr Asn Ile Gly Gly Gly Thr Glu Leu Ser Asn Val Glu
            260                 265                 270 ctc acg gag cgt ctg ctg aaa ctg tgc gga gcc gac tgg tcg gcg gtg        864
Leu Thr Glu Arg Leu Leu Lys Leu Cys Gly Ala Asp Trp Ser Ala Val
        275                 280                 285 cgg cgg gtg ccc gac cgc aag ggc cac gac cgg cgc tac tcc gtc gac        912
Arg Arg Val Pro Asp Arg Lys Gly His Asp Arg Arg Tyr Ser Val Asp
290                 295                 300 tac acc aag atc gcg gac gag ctg ggt tac gcg ccg cgg atc acc atc        960
Tyr Thr Lys Ile Ala Asp Glu Leu Gly Tyr Ala Pro Arg Ile Thr Ile
305                 310                 315                 320 gac gaa ggg ctg gag cgg acc gtg cac tgg tac cgg gag aac cgc gcg       1008
Asp Glu Gly Leu Glu Arg Thr Val His Trp Tyr Arg Glu Asn Arg Ala
                325                 330                 335 tgg tgg gcg ccc gcg aag agg ggg cga tga                               1038
Trp Trp Ala Pro Ala Lys Arg Gly Arg
                340                 345
```

<210> SEQ ID NO 35
<211> LENGTH: 345
<212> TYPE: PRT
<213> ORGANISM: Streptomyces ambofaciens

```
<400> SEQUENCE: 35

Val Gln Ala Pro Asn Glu Thr Pro Arg Arg Pro Ala Arg Ser Ala Gly
1               5                   10                  15

Arg Arg Pro Pro Ala Arg Ile Leu Val Thr Gly Gly Ala Gly Phe Ile
            20                  25                  30

Gly Ser Arg Phe Val Asn Ala Leu Leu Asp Gly Ser Leu Pro Glu Phe
        35                  40                  45

Gly Lys Pro Glu Val Arg Val Leu Asp Ala Leu Thr Tyr Ala Gly Asn
    50                  55                  60

Leu Ala Asn Leu Ala Pro Val Gly Asp Cys Pro Arg Leu Arg Ile Phe
65                  70                  75                  80

Pro Gly Asp Ile Arg Asp Arg Gly Ala Val Thr Gln Ala Met Ala Gly
                85                  90                  95

Val Asp Leu Val Val His Phe Ala Ala Glu Ser His Val Asp Arg Ser
            100                 105                 110

Ile Asp Asp Ala Asp Ala Phe Val Arg Thr Asn Val Leu Gly Thr Gln
        115                 120                 125

Val Leu Leu Gln Glu Ala Leu Ala Val Arg Pro Gly Leu Phe Val His
    130                 135                 140

Val Ser Thr Asp Glu Val Tyr Gly Ser Ile Glu Glu Gly Ser Trp Pro
145                 150                 155                 160

Glu Glu His Pro Leu Asn Pro Asn Ser Pro Tyr Ala Ala Ser Lys Ala
                165                 170                 175

Ser Ser Asp Leu Leu Ala Leu Ala His His Arg Thr His Gly Leu Pro
            180                 185                 190

Val Cys Val Thr Arg Cys Ser Asn Asn Tyr Gly Pro Tyr Gln Tyr Pro
        195                 200                 205

Glu Lys Ile Ile Pro Leu Phe Thr Ser Ser Leu Leu Asp Gly Gly Thr
    210                 215                 220

Val Pro Leu Tyr Gly Asp Gly Gly Asn Arg Arg Asp Trp Leu His Val
225                 230                 235                 240

Asp Asp His Cys Arg Gly Ile Ala Leu Val Ala Arg Gly Gly Arg Pro
                245                 250                 255

Gly Glu Val Tyr Asn Ile Gly Gly Gly Thr Glu Leu Ser Asn Val Glu
            260                 265                 270

Leu Thr Glu Arg Leu Leu Lys Leu Cys Gly Ala Asp Trp Ser Ala Val
        275                 280                 285

Arg Arg Val Pro Asp Arg Lys Gly His Asp Arg Arg Tyr Ser Val Asp
    290                 295                 300

Tyr Thr Lys Ile Ala Asp Glu Leu Gly Tyr Ala Pro Arg Ile Thr Ile
305                 310                 315                 320

Asp Glu Gly Leu Glu Arg Thr Val His Trp Tyr Arg Glu Asn Arg Ala
                325                 330                 335

Trp Trp Ala Pro Ala Lys Arg Gly Arg
                340                 345

<210> SEQ ID NO 36
<211> LENGTH: 804
<212> TYPE: DNA
<213> ORGANISM: Streptomyces ambofaciens
<220> FEATURE:
<221> NAME/KEY: CDS
<222> LOCATION: (1)..(804)
<220> FEATURE:
<221> NAME/KEY: CDS
```

<222> LOCATION: (7)..(804)
<220> FEATURE:
<221> NAME/KEY: CDS
<222> LOCATION: (22)..(804)

<400> SEQUENCE: 36

```
atg acg gtg acg acc gca tcc gtg gac ccg ctc gac ctg tgg ctc cgc      48
Met Thr Val Thr Thr Ala Ser Val Asp Pro Leu Asp Leu Trp Leu Arg
1               5                   10                  15 cgg tac cag ccg tcc gcg tca ccc gcc gtc cgg ctg gtg tgc ttc ccg      96
Arg Tyr Gln Pro Ser Ala Ser Pro Ala Val Arg Leu Val Cys Phe Pro
                20                  25                  30 cac gcg ggc ggc tcg gcg agt tcg ttc ctg ccg ttc acc cgg cag ctg     144
His Ala Gly Gly Ser Ala Ser Ser Phe Leu Pro Phe Thr Arg Gln Leu
            35                  40                  45 ccg gac cgg atc gag gtc gtg gcc gtc cag tac ccc ggg cgc cag gac     192
Pro Asp Arg Ile Glu Val Val Ala Val Gln Tyr Pro Gly Arg Gln Asp
        50                  55                  60 cgc agg agc gaa ccg ctg gtc gac acc atc gag gga ctg gcc gag ccc     240
Arg Arg Ser Glu Pro Leu Val Asp Thr Ile Glu Gly Leu Ala Glu Pro
65                  70                  75                  80 ctg gcc ggc ctg ctg gag gcg cag gcc ggc ccc ccg gtg gtg ctg ttc     288
Leu Ala Gly Leu Leu Glu Ala Gln Ala Gly Pro Pro Val Val Leu Phe
                85                  90                  95 ggg cac agc atg ggc gcg ctg gtg gcc tac gag gtc gcc cgc gcg ctc     336
Gly His Ser Met Gly Ala Leu Val Ala Tyr Glu Val Ala Arg Ala Leu
                100                 105                 110 cag cgg cgg gga gcg gct ccg gtg cgc ctg gtg gtc tcc ggg cgc cgg     384
Gln Arg Arg Gly Ala Ala Pro Val Arg Leu Val Val Ser Gly Arg Arg
            115                 120                 125 gcc ccc gcc gtc gac cgg ccg atg acc gtg cac ctc tac gac gac gac     432
Ala Pro Ala Val Asp Arg Pro Met Thr Val His Leu Tyr Asp Asp Asp
        130                 135                 140 cgg ctg gtc gag gaa ctc cgc aag ctc gac ggc acc gac agc cag gtg     480
Arg Leu Val Glu Glu Leu Arg Lys Leu Asp Gly Thr Asp Ser Gln Val
145                 150                 155                 160 ttc gcc gat ccg gag ctg ctc cgg ctg gtg ctg ccc gtg atc cgc aac     528
Phe Ala Asp Pro Glu Leu Leu Arg Leu Val Leu Pro Val Ile Arg Asn
                165                 170                 175 gac tac cgg gcc gtg gcg gcc tac gcc cac cgc ccg ggg gcg ccg ctg     576
Asp Tyr Arg Ala Val Ala Ala Tyr Ala His Arg Pro Gly Ala Pro Leu
                180                 185                 190 gac tgc ccc ctc acc gtg ttc acc ggc gcc gac gac ccc acc gtg acc     624
Asp Cys Pro Leu Thr Val Phe Thr Gly Ala Asp Asp Pro Thr Val Thr
            195                 200                 205 gcg gcc gag gcg gcg gcc tgg cac gag gcg gcg gcg tcc gac gtc gag     672
Ala Ala Glu Ala Ala Ala Trp His Glu Ala Ala Ala Ser Asp Val Glu
        210                 215                 220 acg cgc acc ttc ccc ggt ggc cac ttc ttc ccg tac cag cgg acc gcg     720
Thr Arg Thr Phe Pro Gly Gly His Phe Phe Pro Tyr Gln Arg Thr Ala
225                 230                 235                 240 gag gtg tgc ggg gcc ctg gtc gac acg ctc gag ccg ctg ctg tcg gcc     768
Glu Val Cys Gly Ala Leu Val Asp Thr Leu Glu Pro Leu Leu Ser Ala
                245                 250                 255 ggg acg cgc ggt gtc cgg cgg gtc cgc ccg ggg tga                     804
Gly Thr Arg Gly Val Arg Arg Val Arg Pro Gly
                260                 265
```

<210> SEQ ID NO 37
<211> LENGTH: 267
<212> TYPE: PRT

<213> ORGANISM: Streptomyces ambofaciens

<400> SEQUENCE: 37

Met Thr Val Thr Thr Ala Ser Val Asp Pro Leu Asp Leu Trp Leu Arg
1               5                   10                  15

Arg Tyr Gln Pro Ser Ala Ser Pro Ala Val Arg Leu Val Cys Phe Pro
                20                  25                  30

His Ala Gly Gly Ser Ala Ser Ser Phe Leu Pro Phe Thr Arg Gln Leu
            35                  40                  45

Pro Asp Arg Ile Glu Val Val Ala Val Gln Tyr Pro Gly Arg Gln Asp
        50                  55                  60

Arg Arg Ser Glu Pro Leu Val Asp Thr Ile Glu Gly Leu Ala Glu Pro
65                  70                  75                  80

Leu Ala Gly Leu Leu Glu Ala Gln Ala Gly Pro Pro Val Val Leu Phe
                85                  90                  95

Gly His Ser Met Gly Ala Leu Val Ala Tyr Glu Val Ala Arg Ala Leu
            100                 105                 110

Gln Arg Arg Gly Ala Ala Pro Val Arg Leu Val Val Ser Gly Arg Arg
        115                 120                 125

Ala Pro Ala Val Asp Arg Pro Met Thr Val His Leu Tyr Asp Asp Asp
130                 135                 140

Arg Leu Val Glu Glu Leu Arg Lys Leu Asp Gly Thr Asp Ser Gln Val
145                 150                 155                 160

Phe Ala Asp Pro Glu Leu Leu Arg Leu Val Leu Pro Val Ile Arg Asn
                165                 170                 175

Asp Tyr Arg Ala Val Ala Ala Tyr Ala His Arg Pro Gly Ala Pro Leu
            180                 185                 190

Asp Cys Pro Leu Thr Val Phe Thr Gly Ala Asp Asp Pro Thr Val Thr
        195                 200                 205

Ala Ala Glu Ala Ala Ala Trp His Glu Ala Ala Ser Asp Val Glu
210                 215                 220

Thr Arg Thr Phe Pro Gly Gly His Phe Phe Pro Tyr Gln Arg Thr Ala
225                 230                 235                 240

Glu Val Cys Gly Ala Leu Val Asp Thr Leu Glu Pro Leu Leu Ser Ala
                245                 250                 255

Gly Thr Arg Gly Val Arg Arg Val Arg Pro Gly
            260                 265

<210> SEQ ID NO 38
<211> LENGTH: 265
<212> TYPE: PRT
<213> ORGANISM: Streptomyces ambofaciens

<400> SEQUENCE: 38

Val Thr Thr Ala Ser Val Asp Pro Leu Asp Leu Trp Leu Arg Arg Tyr
1               5                   10                  15

Gln Pro Ser Ala Ser Pro Ala Val Arg Leu Val Cys Phe Pro His Ala
                20                  25                  30

Gly Gly Ser Ala Ser Ser Phe Leu Pro Phe Thr Arg Gln Leu Pro Asp
            35                  40                  45

Arg Ile Glu Val Val Ala Val Gln Tyr Pro Gly Arg Gln Asp Arg Arg
        50                  55                  60

Ser Glu Pro Leu Val Asp Thr Ile Glu Gly Leu Ala Glu Pro Leu Ala
65                  70                  75                  80

Gly Leu Leu Glu Ala Gln Ala Gly Pro Pro Val Val Leu Phe Gly His

```
                    85                  90                  95
Ser Met Gly Ala Leu Val Ala Tyr Glu Val Ala Arg Ala Leu Gln Arg
                100                 105                 110
Arg Gly Ala Ala Pro Val Arg Leu Val Val Ser Gly Arg Arg Ala Pro
                115                 120                 125
Ala Val Asp Arg Pro Met Thr Val His Leu Tyr Asp Asp Arg Leu
        130                 135                 140
Val Glu Glu Leu Arg Lys Leu Asp Gly Thr Asp Ser Gln Val Phe Ala
145                 150                 155                 160
Asp Pro Glu Leu Leu Arg Leu Val Leu Pro Val Ile Arg Asn Asp Tyr
                165                 170                 175
Arg Ala Val Ala Ala Tyr Ala His Arg Pro Gly Ala Pro Leu Asp Cys
                180                 185                 190
Pro Leu Thr Val Phe Thr Gly Ala Asp Asp Pro Thr Val Thr Ala Ala
                195                 200                 205
Glu Ala Ala Ala Trp His Glu Ala Ala Ser Asp Val Glu Thr Arg
        210                 215                 220
Thr Phe Pro Gly Gly His Phe Phe Pro Tyr Gln Arg Thr Ala Glu Val
225                 230                 235                 240
Cys Gly Ala Leu Val Asp Thr Leu Glu Pro Leu Leu Ser Ala Gly Thr
                245                 250                 255
Arg Gly Val Arg Arg Val Arg Pro Gly
                260                 265

<210> SEQ ID NO 39
<211> LENGTH: 260
<212> TYPE: PRT
<213> ORGANISM: Streptomyces ambofaciens

<400> SEQUENCE: 39

Val Asp Pro Leu Asp Leu Trp Leu Arg Arg Tyr Gln Pro Ser Ala Ser
1               5                   10                  15
Pro Ala Val Arg Leu Val Cys Phe Pro His Ala Gly Gly Ser Ala Ser
                20                  25                  30
Ser Phe Leu Pro Phe Thr Arg Gln Leu Pro Asp Arg Ile Glu Val Val
        35                  40                  45
Ala Val Gln Tyr Pro Gly Arg Gln Asp Arg Arg Ser Glu Pro Leu Val
        50                  55                  60
Asp Thr Ile Glu Gly Leu Ala Glu Pro Leu Ala Gly Leu Leu Glu Ala
65                  70                  75                  80
Gln Ala Gly Pro Pro Val Val Leu Phe Gly His Ser Met Gly Ala Leu
                85                  90                  95
Val Ala Tyr Glu Val Ala Arg Ala Leu Gln Arg Arg Gly Ala Ala Pro
                100                 105                 110
Val Arg Leu Val Val Ser Gly Arg Arg Ala Pro Ala Val Asp Arg Pro
                115                 120                 125
Met Thr Val His Leu Tyr Asp Asp Arg Leu Val Glu Glu Leu Arg
        130                 135                 140
Lys Leu Asp Gly Thr Asp Ser Gln Val Phe Ala Asp Pro Glu Leu Leu
145                 150                 155                 160
Arg Leu Val Leu Pro Val Ile Arg Asn Asp Tyr Arg Ala Val Ala Ala
                165                 170                 175
Tyr Ala His Arg Pro Gly Ala Pro Leu Asp Cys Pro Leu Thr Val Phe
                180                 185                 190
```

-continued

```
Thr Gly Ala Asp Asp Pro Thr Val Thr Ala Ala Glu Ala Ala Ala Trp
        195                 200                 205

His Glu Ala Ala Ala Ser Asp Val Glu Thr Arg Thr Phe Pro Gly Gly
        210                 215                 220

His Phe Phe Pro Tyr Gln Arg Thr Ala Glu Val Cys Gly Ala Leu Val
225                 230                 235                 240

Asp Thr Leu Glu Pro Leu Leu Ser Ala Gly Thr Arg Gly Val Arg Arg
                245                 250                 255

Val Arg Pro Gly
            260

<210> SEQ ID NO 40
<211> LENGTH: 1410
<212> TYPE: DNA
<213> ORGANISM: Streptomyces ambofaciens
<220> FEATURE:
<221> NAME/KEY: CDS
<222> LOCATION: (1)..(1410)
<220> FEATURE:
<221> NAME/KEY: CDS
<222> LOCATION: (46)..(1410)

<400> SEQUENCE: 40
```

| | | | | | | | | | | | | | | | | |
|---|---|---|---|---|---|---|---|---|---|---|---|---|---|---|---|---|
| gtg | ggc | acg | gtc | gag | tac | gcc | gtc | cac | cgg | cgt | acc | gcg | gaa | cgg | gtg | 48 |
| Val | Gly | Thr | Val | Glu | Tyr | Ala | Val | His | Arg | Arg | Thr | Ala | Glu | Arg | Val | |
| 1 | | | | 5 | | | | | 10 | | | | | 15 | | |

| agg | gtc | tcc | gcc | gac | acc | ctg | gac | agc | ccg | gtc | acc | gcg | ctg | gcg | gag | 96 |
|---|---|---|---|---|---|---|---|---|---|---|---|---|---|---|---|---|
| Arg | Val | Ser | Ala | Asp | Thr | Leu | Asp | Ser | Pro | Val | Thr | Ala | Leu | Ala | Glu | |
| | | | 20 | | | | | 25 | | | | | 30 | | | |

| gtg | ccc | cgc | tgg | ctg | gag | gaa | tac | cac | cgg | gcg | cac | cgc | ttc | cac | gtc | 144 |
|---|---|---|---|---|---|---|---|---|---|---|---|---|---|---|---|---|
| Val | Pro | Arg | Trp | Leu | Glu | Glu | Tyr | His | Arg | Ala | His | Arg | Phe | His | Val | |
| | | 35 | | | | | 40 | | | | | 45 | | | | |

| gag | ccg | atc | ccc | ttc | gac | cgg | ctc | cgg | cgg | tgg | tcc | ttc | gag | ccg | ggc | 192 |
|---|---|---|---|---|---|---|---|---|---|---|---|---|---|---|---|---|
| Glu | Pro | Ile | Pro | Phe | Asp | Arg | Leu | Arg | Arg | Trp | Ser | Phe | Glu | Pro | Gly | |
| | 50 | | | | | 55 | | | | | 60 | | | | | |

| acc | ggc | gac | ctg | cgg | cac | gag | acg | ggc | cgc | ttc | ttc | tcc | gtg | gag | ggg | 240 |
|---|---|---|---|---|---|---|---|---|---|---|---|---|---|---|---|---|
| Thr | Gly | Asp | Leu | Arg | His | Glu | Thr | Gly | Arg | Phe | Phe | Ser | Val | Glu | Gly | |
| 65 | | | | | 70 | | | | | 75 | | | | | 80 | |

| ctg | cgc | acc | agc | tcg | gac | gcc | gat | ccg | gtc | gcc | cgt | gtc | cag | ccg | atc | 288 |
|---|---|---|---|---|---|---|---|---|---|---|---|---|---|---|---|---|
| Leu | Arg | Thr | Ser | Ser | Asp | Ala | Asp | Pro | Val | Ala | Arg | Val | Gln | Pro | Ile | |
| | | | | 85 | | | | | 90 | | | | | 95 | | |

| atc | gtg | cag | ccc | gag | gtg | ggg | ctg | ctc | ggc | atc | ctg | gcc | cgg | gag | ttc | 336 |
|---|---|---|---|---|---|---|---|---|---|---|---|---|---|---|---|---|
| Ile | Val | Gln | Pro | Glu | Val | Gly | Leu | Leu | Gly | Ile | Leu | Ala | Arg | Glu | Phe | |
| | | | 100 | | | | | 105 | | | | | 110 | | | |

| gac | ggg | gtg | ctg | cac | ttc | ctg | atg | cag | gcc | aaa | ccc | gag | ccc | ggc | aac | 384 |
|---|---|---|---|---|---|---|---|---|---|---|---|---|---|---|---|---|
| Asp | Gly | Val | Leu | His | Phe | Leu | Met | Gln | Ala | Lys | Pro | Glu | Pro | Gly | Asn | |
| | | 115 | | | | | 120 | | | | | 125 | | | | |

| gtc | aac | ggg | ctg | cag | atc | tcc | ccc | acg | gtg | cag | gcc | acg | cgc | agc | aac | 432 |
|---|---|---|---|---|---|---|---|---|---|---|---|---|---|---|---|---|
| Val | Asn | Gly | Leu | Gln | Ile | Ser | Pro | Thr | Val | Gln | Ala | Thr | Arg | Ser | Asn | |
| | 130 | | | | | 135 | | | | | 140 | | | | | |

| ttc | gac | gag | gtg | cac | cac | ggc | cgg | tcc | acc | ccg | ttc | ctc | gac | cac | ttc | 480 |
|---|---|---|---|---|---|---|---|---|---|---|---|---|---|---|---|---|
| Phe | Asp | Glu | Val | His | His | Gly | Arg | Ser | Thr | Pro | Phe | Leu | Asp | His | Phe | |
| 145 | | | | | 150 | | | | | 155 | | | | | 160 | |

| atc | cac | cgc | ccc | ggc | cgc | cgg | gtc | ctg | atc | gac | agc | atc | cag | tcc | gaa | 528 |
|---|---|---|---|---|---|---|---|---|---|---|---|---|---|---|---|---|
| Ile | His | Arg | Pro | Gly | Arg | Arg | Val | Leu | Ile | Asp | Ser | Ile | Gln | Ser | Glu | |
| | | | | 165 | | | | | 170 | | | | | 175 | | |

| cag | ggc | gac | tgg | ttc | ctg | cac | aag | cgc | aac | cgc | aac | atg | gtc | gtc | gag | 576 |
|---|---|---|---|---|---|---|---|---|---|---|---|---|---|---|---|---|
| Gln | Gly | Asp | Trp | Phe | Leu | His | Lys | Arg | Asn | Arg | Asn | Met | Val | Val | Glu | |
| | | | 180 | | | | | 185 | | | | | 190 | | | |

| atc | gac | acc | gac | atc | gag | gcc | gac | gcc | gcg | ttc | cgc | tgg | ctg | acc | ctc | 624 |
|---|---|---|---|---|---|---|---|---|---|---|---|---|---|---|---|---|
| Ile | Asp | Thr | Asp | Ile | Glu | Ala | Asp | Ala | Ala | Phe | Arg | Trp | Leu | Thr | Leu | |

```
                195                 200                 205
ggg cag atc cgc cgg ctg atg ctc cag gac gac ctc gtc aac atg gac    672
Gly Gln Ile Arg Arg Leu Met Leu Gln Asp Asp Leu Val Asn Met Asp
210                 215                 220 acc cgc agt gtg ctg gcc tgt ctg ccc acc gcg cac ggc acg ccc gac    720
Thr Arg Ser Val Leu Ala Cys Leu Pro Thr Ala His Gly Thr Pro Asp
225                 230                 235                 240 gac ggt gac gac tcc ttc ccg gcg gcg ctg cgc cgc tcc ctc tac ggg    768
Asp Gly Asp Asp Ser Phe Pro Ala Ala Leu Arg Arg Ser Leu Tyr Gly
                    245                 250                 255 gag acc gcg ccg ttg cac gat ctg cac gcc atc acc agc tgc ctc acc    816
Glu Thr Ala Pro Leu His Asp Leu His Ala Ile Thr Ser Cys Leu Thr
                260                 265                 270 gac gtc cgg gcg ctg cgg gtg ctg cgc cag cag agc gtg ccg ctc gac    864
Asp Val Arg Ala Leu Arg Val Leu Arg Gln Gln Ser Val Pro Leu Asp
            275                 280                 285 gac gcc cgg cgg gac ggc tgg gag cgg acc ggg agc gcg atc cgg cat    912
Asp Ala Arg Arg Asp Gly Trp Glu Arg Thr Gly Ser Ala Ile Arg His
        290                 295                 300 cgc agc ggc agg cat ttc gag atc atg gcg gtg gag gtg acc gcg gag    960
Arg Ser Gly Arg His Phe Glu Ile Met Ala Val Glu Val Thr Ala Glu
305                 310                 315                 320 cgc cgt gaa gtg gcc tcg tgg acc cag ccg ttg ctg cgc ccg tgc tcg   1008
Arg Arg Glu Val Ala Ser Trp Thr Gln Pro Leu Leu Arg Pro Cys Ser
                    325                 330                 335 cag gga ctg gcg gcc ctg atc acc cgg cgg atc aac ggg gtg ctg cac   1056
Gln Gly Leu Ala Ala Leu Ile Thr Arg Arg Ile Asn Gly Val Leu His
                340                 345                 350 gcc ctg gtg gcg gcg cgg tcg gag gtc ggc acg ctc aac gtc gcc gag   1104
Ala Leu Val Ala Ala Arg Ser Glu Val Gly Thr Leu Asn Val Ala Glu
            355                 360                 365 ttc gga ccg acc gtc cag tgc cgg ccc gac gag gcg gac ggc cag tcg   1152
Phe Gly Pro Thr Val Gln Cys Arg Pro Asp Glu Ala Asp Gly Gln Ser
        370                 375                 380 ccc ccg tac ctg gac cgg gtg ctg acg gcc gga gcc gac cgc gtc cgc   1200
Pro Pro Tyr Leu Asp Arg Val Leu Thr Ala Gly Ala Asp Arg Val Arg
385                 390                 395                 400 tac gac gtg gtg cag tcg gag gag ggc ggg cgc ttc tac cac gcg cgc   1248
Tyr Asp Val Val Gln Ser Glu Glu Gly Gly Arg Phe Tyr His Ala Arg
                    405                 410                 415 aac cgc tat ctg gtg gtc gag gcg ggg ccg gag ctc gac acg ggc tgc   1296
Asn Arg Tyr Leu Val Val Glu Ala Gly Pro Glu Leu Asp Thr Gly Cys
                420                 425                 430 ccg ccc ggc ttc tgc tgg gct acc ttc ggc cag ctc acc gaa ctg ctc   1344
Pro Pro Gly Phe Cys Trp Ala Thr Phe Gly Gln Leu Thr Glu Leu Leu
            435                 440                 445 gcg cac ggc aac tat ctc aac gtc gaa ctc cgc acc ctc atg gcg tgc   1392
Ala His Gly Asn Tyr Leu Asn Val Glu Leu Arg Thr Leu Met Ala Cys
        450                 455                 460 gca cac gcc tcc tac tga                                            1410
Ala His Ala Ser Tyr
465

<210> SEQ ID NO 41
<211> LENGTH: 469
<212> TYPE: PRT
<213> ORGANISM: Streptomyces ambofaciens

<400> SEQUENCE: 41

Val Gly Thr Val Glu Tyr Ala Val His Arg Arg Thr Ala Glu Arg Val
```

```
1               5                   10                  15
Arg Val Ser Ala Asp Thr Leu Asp Ser Pro Val Thr Ala Leu Ala Glu
                20                  25                  30

Val Pro Arg Trp Leu Glu Glu Tyr His Arg Ala His Arg Phe His Val
                35                  40                  45

Glu Pro Ile Pro Phe Asp Arg Leu Arg Arg Trp Ser Phe Glu Pro Gly
        50                  55                  60

Thr Gly Asp Leu Arg His Glu Thr Gly Arg Phe Phe Ser Val Glu Gly
65                  70                  75                  80

Leu Arg Thr Ser Ser Asp Ala Asp Pro Val Ala Arg Val Gln Pro Ile
                85                  90                  95

Ile Val Gln Pro Glu Val Gly Leu Leu Gly Ile Leu Ala Arg Glu Phe
                100                 105                 110

Asp Gly Val Leu His Phe Leu Met Gln Ala Lys Pro Glu Pro Gly Asn
                115                 120                 125

Val Asn Gly Leu Gln Ile Ser Pro Thr Val Gln Ala Thr Arg Ser Asn
                130                 135                 140

Phe Asp Glu Val His His Gly Arg Ser Thr Pro Phe Leu Asp His Phe
145                 150                 155                 160

Ile His Arg Pro Gly Arg Arg Val Leu Ile Asp Ser Ile Gln Ser Glu
                165                 170                 175

Gln Gly Asp Trp Phe Leu His Lys Arg Asn Arg Asn Met Val Val Glu
                180                 185                 190

Ile Asp Thr Asp Ile Glu Ala Asp Ala Ala Phe Arg Trp Leu Thr Leu
                195                 200                 205

Gly Gln Ile Arg Arg Leu Met Leu Gln Asp Asp Leu Val Asn Met Asp
                210                 215                 220

Thr Arg Ser Val Leu Ala Cys Leu Pro Thr Ala His Gly Thr Pro Asp
225                 230                 235                 240

Asp Gly Asp Asp Ser Phe Pro Ala Ala Leu Arg Arg Ser Leu Tyr Gly
                245                 250                 255

Glu Thr Ala Pro Leu His Asp Leu His Ala Ile Thr Ser Cys Leu Thr
                260                 265                 270

Asp Val Arg Ala Leu Arg Val Leu Arg Gln Gln Ser Val Pro Leu Asp
                275                 280                 285

Asp Ala Arg Arg Asp Gly Trp Glu Arg Thr Gly Ser Ala Ile Arg His
                290                 295                 300

Arg Ser Gly Arg His Phe Glu Ile Met Ala Val Glu Val Thr Ala Glu
305                 310                 315                 320

Arg Arg Glu Val Ala Ser Trp Thr Gln Pro Leu Leu Arg Pro Cys Ser
                325                 330                 335

Gln Gly Leu Ala Ala Leu Ile Thr Arg Arg Ile Asn Gly Val Leu His
                340                 345                 350

Ala Leu Val Ala Ala Arg Ser Glu Val Gly Thr Leu Asn Val Ala Glu
                355                 360                 365

Phe Gly Pro Thr Val Gln Cys Arg Pro Asp Glu Ala Asp Gly Gln Ser
                370                 375                 380

Pro Pro Tyr Leu Asp Arg Val Leu Thr Ala Gly Ala Asp Arg Val Arg
385                 390                 395                 400

Tyr Asp Val Val Gln Ser Glu Glu Gly Gly Arg Phe Tyr His Ala Arg
                405                 410                 415

Asn Arg Tyr Leu Val Val Glu Ala Gly Pro Glu Leu Asp Thr Gly Cys
                420                 425                 430
```

```
Pro Pro Gly Phe Cys Trp Ala Thr Phe Gly Gln Leu Thr Glu Leu Leu
        435                 440                 445

Ala His Gly Asn Tyr Leu Asn Val Glu Leu Arg Thr Leu Met Ala Cys
    450                 455                 460

Ala His Ala Ser Tyr
465

<210> SEQ ID NO 42
<211> LENGTH: 454
<212> TYPE: PRT
<213> ORGANISM: Streptomyces ambofaciens

<400> SEQUENCE: 42

Val Arg Val Ser Ala Asp Thr Leu Asp Ser Pro Val Thr Ala Leu Ala
1               5                   10                  15

Glu Val Pro Arg Trp Leu Glu Glu Tyr His Arg Ala His Arg Phe His
            20                  25                  30

Val Glu Pro Ile Pro Phe Asp Arg Leu Arg Arg Trp Ser Phe Glu Pro
        35                  40                  45

Gly Thr Gly Asp Leu Arg His Glu Thr Gly Arg Phe Phe Ser Val Glu
    50                  55                  60

Gly Leu Arg Thr Ser Ser Asp Ala Asp Pro Val Ala Arg Val Gln Pro
65                  70                  75                  80

Ile Ile Val Gln Pro Glu Val Gly Leu Leu Gly Ile Leu Ala Arg Glu
                85                  90                  95

Phe Asp Gly Val Leu His Phe Leu Met Gln Ala Lys Pro Glu Pro Gly
            100                 105                 110

Asn Val Asn Gly Leu Gln Ile Ser Pro Thr Val Gln Ala Thr Arg Ser
        115                 120                 125

Asn Phe Asp Glu Val His His Gly Arg Ser Thr Pro Phe Leu Asp His
    130                 135                 140

Phe Ile His Arg Pro Gly Arg Arg Val Leu Ile Asp Ser Ile Gln Ser
145                 150                 155                 160

Glu Gln Gly Asp Trp Phe Leu His Lys Arg Asn Arg Asn Met Val Val
                165                 170                 175

Glu Ile Asp Thr Asp Ile Glu Ala Asp Ala Ala Phe Arg Trp Leu Thr
            180                 185                 190

Leu Gly Gln Ile Arg Arg Leu Met Leu Gln Asp Asp Leu Val Asn Met
        195                 200                 205

Asp Thr Arg Ser Val Leu Ala Cys Leu Pro Thr Ala His Gly Thr Pro
    210                 215                 220

Asp Asp Gly Asp Ser Phe Pro Ala Ala Leu Arg Arg Ser Leu Tyr
225                 230                 235                 240

Gly Glu Thr Ala Pro Leu His Asp Leu His Ala Ile Thr Ser Cys Leu
                245                 250                 255

Thr Asp Val Arg Ala Leu Arg Val Leu Arg Gln Gln Ser Val Pro Leu
            260                 265                 270

Asp Asp Ala Arg Arg Asp Gly Trp Glu Arg Thr Gly Ser Ala Ile Arg
        275                 280                 285

His Arg Ser Gly Arg His Phe Glu Ile Met Ala Val Glu Val Thr Ala
    290                 295                 300

Glu Arg Arg Glu Val Ala Ser Trp Thr Gln Pro Leu Leu Arg Pro Cys
305                 310                 315                 320

Ser Gln Gly Leu Ala Ala Leu Ile Thr Arg Arg Ile Asn Gly Val Leu
```

```
                    325                 330                 335
His Ala Leu Val Ala Ala Arg Ser Glu Val Gly Thr Leu Asn Val Ala
            340                 345                 350

Glu Phe Gly Pro Thr Val Gln Cys Arg Pro Asp Glu Ala Asp Gly Gln
            355                 360                 365

Ser Pro Pro Tyr Leu Asp Arg Val Leu Thr Ala Gly Ala Asp Arg Val
            370                 375                 380

Arg Tyr Asp Val Val Gln Ser Glu Glu Gly Gly Arg Phe Tyr His Ala
385                 390                 395                 400

Arg Asn Arg Tyr Leu Val Val Glu Ala Gly Pro Glu Leu Asp Thr Gly
                405                 410                 415

Cys Pro Pro Gly Phe Cys Trp Ala Thr Phe Gly Gln Leu Thr Glu Leu
            420                 425                 430

Leu Ala His Gly Asn Tyr Leu Asn Val Glu Leu Arg Thr Leu Met Ala
            435                 440                 445

Cys Ala His Ala Ser Tyr
            450

<210> SEQ ID NO 43
<211> LENGTH: 1248
<212> TYPE: DNA
<213> ORGANISM: Streptomyces ambofaciens
<220> FEATURE:
<221> NAME/KEY: CDS
<222> LOCATION: (1)..(1248)

<400> SEQUENCE: 43 atg ccg ggc ggg acg gac ggc gac tgc gcg cgg acg gcg gcc cgg cgt      48
Met Pro Gly Gly Thr Asp Gly Asp Cys Ala Arg Thr Ala Ala Arg Arg
1               5                   10                  15 cga acg cac ctg ccc gag tcc gga cga gac agc gcg acg cga gag gcg      96
Arg Thr His Leu Pro Glu Ser Gly Arg Asp Ser Ala Thr Arg Glu Ala
                20                  25                  30 aaa atg atc aat ctc ttc cag ccc cag atg ggg gcc gag gaa ctg gcg     144
Lys Met Ile Asn Leu Phe Gln Pro Gln Met Gly Ala Glu Glu Leu Ala
            35                  40                  45 gcg gtg tcc gag gtc ttc gac gac caa tgg ctc ggt cac gga ccc cgg     192
Ala Val Ser Glu Val Phe Asp Asp Gln Trp Leu Gly His Gly Pro Arg
        50                  55                  60 acc gcg gcg ttc gag tcc gcg ttc gcc gag cac ctc ggg gtc ggc ccc     240
Thr Ala Ala Phe Glu Ser Ala Phe Ala Glu His Leu Gly Val Gly Pro
65                  70                  75                  80 gag cac gtc gtc ttc ctc aac tcg ggc acc gcc ggc ctc ttc ctg gcc     288
Glu His Val Val Phe Leu Asn Ser Gly Thr Ala Gly Leu Phe Leu Ala
                85                  90                  95 ctg gag tcg ctc ggc ctg cgg ccc ggc gac gag gtc gtg ctc ccc tcg     336
Leu Glu Ser Leu Gly Leu Arg Pro Gly Asp Glu Val Val Leu Pro Ser
            100                 105                 110 ccc agc ttc ctc gcc gcg gcg aac gcc gta cag ctc tcg gga gcg cgc     384
Pro Ser Phe Leu Ala Ala Ala Asn Ala Val Gln Leu Ser Gly Ala Arg
        115                 120                 125 ccg gtg ttc tgc gac acc gac ccg cgg acg ctg aac ccc gcc ctg gag     432
Pro Val Phe Cys Asp Thr Asp Pro Arg Thr Leu Asn Pro Ala Leu Glu
    130                 135                 140 cac atc gag gcg gcc gtc acc ccg cgc acc agg gcc gtc atc gcg ctc     480
His Ile Glu Ala Ala Val Thr Pro Arg Thr Arg Ala Val Ile Ala Leu
145                 150                 155                 160 cac tac ggc ggc cac ccc ggc gac atc gtg cgc atc gcc gag cgc tgc     528
His Tyr Gly Gly His Pro Gly Asp Ile Val Arg Ile Ala Glu Arg Cys
```

-continued

|  | 165 | | | | 170 | | | | 175 | | | | |
|---|---|---|---|---|---|---|---|---|---|---|---|---|---|
| cgg | gag | cgg | ggc | atc | acc | ctg | atc | gag | gac | gcc | gcg | tgc tcc gtg gcc | 576 |
| Arg | Glu | Arg | Gly | Ile | Thr | Leu | Ile | Glu | Asp | Ala | Ala | Cys Ser Val Ala | |
|  |  | 180 | | | | | 185 | | | | 190 | | | tcc cgc gtc gac ggc cga ccg gtc ggc acc ttc ggc gac ctc gcc atg    624
Ser Arg Val Asp Gly Arg Pro Val Gly Thr Phe Gly Asp Leu Ala Met
        195                 200                 205 tgg agc ttc gac gcc atg aag gtc ctg gtc acc ggc gac gga ggg atg    672
Trp Ser Phe Asp Ala Met Lys Val Leu Val Thr Gly Asp Gly Gly Met
    210                 215                 220 atc tac gtc aag gac ccc ggg gcg gcc gcc cgg atc cgg cgc ctc gcc    720
Ile Tyr Val Lys Asp Pro Gly Ala Ala Ala Arg Ile Arg Arg Leu Ala
225                 230                 235                 240 tac cac ggc ctc acg cgg tcc agc ggc ctg gga tac gcc agg gtc tcg    768
Tyr His Gly Leu Thr Arg Ser Ser Gly Leu Gly Tyr Ala Arg Val Ser
                245                 250                 255 gcg cgc tgg tgg gag atg gac gtc ccc gaa ccg ggc cgc cgc gtc atc    816
Ala Arg Trp Trp Glu Met Asp Val Pro Glu Pro Gly Arg Arg Val Ile
            260                 265                 270 ggg aac gac ctc acc gcg gcc atc ggc gcg gtc cag ttg cgc cgg ctt    864
Gly Asn Asp Leu Thr Ala Ala Ile Gly Ala Val Gln Leu Arg Arg Leu
        275                 280                 285 ccc ggc ttc gtg gcc cgc cgc agg gag atc gtc gcc ctg tac gac agc    912
Pro Gly Phe Val Ala Arg Arg Arg Glu Ile Val Ala Leu Tyr Asp Ser
    290                 295                 300 gaa ctg agc tcg ctg gag ggc gtg ctg aca ccg ccc gcg cca ccc gcg    960
Glu Leu Ser Ser Leu Glu Gly Val Leu Thr Pro Pro Ala Pro Pro Ala
305                 310                 315                 320 ggg cac gag tcc acg cac tac ttc tac tgg atc cag ctg gcc ccc ggc    1008
Gly His Glu Ser Thr His Tyr Phe Tyr Trp Ile Gln Leu Ala Pro Gly
                325                 330                 335 gtc cgg gac cgg gtg gca cgc gac ctc ctc acc gac ggc atc tac acc    1056
Val Arg Asp Arg Val Ala Arg Asp Leu Leu Thr Asp Gly Ile Tyr Thr
            340                 345                 350 acc ttc cgc tac gca cct ctg cac aag gtg ccc gcc tac ggc cac acc    1104
Thr Phe Arg Tyr Ala Pro Leu His Lys Val Pro Ala Tyr Gly His Thr
        355                 360                 365 gga ggc gaa ctg ccc ggc gtg gag cgg gcg tcc gaa cgg acc ctg tgc    1152
Gly Gly Glu Leu Pro Gly Val Glu Arg Ala Ser Glu Arg Thr Leu Cys
    370                 375                 380 ctg ccc ctg cac ccc ggc ctg tcg gac gcc gac gtc cgc acc gtc gtg    1200
Leu Pro Leu His Pro Gly Leu Ser Asp Ala Asp Val Arg Thr Val Val
385                 390                 395                 400 tcc tcc ctg cgc aga gcc ctg agc gcc gcg gat ccg gcc ccc gcc tga    1248
Ser Ser Leu Arg Arg Ala Leu Ser Ala Ala Asp Pro Ala Pro Ala
                405                 410                 415

<210> SEQ ID NO 44
<211> LENGTH: 415
<212> TYPE: PRT
<213> ORGANISM: Streptomyces ambofaciens

<400> SEQUENCE: 44

Met Pro Gly Gly Thr Asp Gly Asp Cys Ala Arg Thr Ala Ala Arg Arg
1               5                   10                  15

Arg Thr His Leu Pro Glu Ser Gly Arg Asp Ser Ala Thr Arg Glu Ala
            20                  25                  30

Lys Met Ile Asn Leu Phe Gln Pro Gln Met Gly Ala Glu Glu Leu Ala
        35                  40                  45

```
Ala Val Ser Glu Val Phe Asp Asp Gln Trp Leu Gly His Gly Pro Arg
 50                  55                  60

Thr Ala Ala Phe Glu Ser Ala Phe Ala Glu His Leu Gly Val Gly Pro
 65                  70                  75                  80

Glu His Val Val Phe Leu Asn Ser Gly Thr Ala Gly Leu Phe Leu Ala
                 85                  90                  95

Leu Glu Ser Leu Gly Leu Arg Pro Gly Asp Glu Val Val Leu Pro Ser
            100                 105                 110

Pro Ser Phe Leu Ala Ala Asn Ala Val Gln Leu Ser Gly Ala Arg
            115                 120                 125

Pro Val Phe Cys Asp Thr Asp Pro Arg Thr Leu Asn Pro Ala Leu Glu
            130                 135                 140

His Ile Glu Ala Ala Val Thr Pro Arg Thr Arg Ala Val Ile Ala Leu
145                 150                 155                 160

His Tyr Gly Gly His Pro Gly Asp Ile Val Arg Ile Ala Glu Arg Cys
                165                 170                 175

Arg Glu Arg Gly Ile Thr Leu Ile Glu Asp Ala Ala Cys Ser Val Ala
            180                 185                 190

Ser Arg Val Asp Gly Arg Pro Val Gly Thr Phe Gly Asp Leu Ala Met
            195                 200                 205

Trp Ser Phe Asp Ala Met Lys Val Leu Val Thr Gly Asp Gly Gly Met
210                 215                 220

Ile Tyr Val Lys Asp Pro Gly Ala Ala Arg Ile Arg Arg Leu Ala
225                 230                 235                 240

Tyr His Gly Leu Thr Arg Ser Ser Gly Leu Gly Tyr Ala Arg Val Ser
                245                 250                 255

Ala Arg Trp Trp Glu Met Asp Val Pro Glu Pro Gly Arg Arg Val Ile
            260                 265                 270

Gly Asn Asp Leu Thr Ala Ala Ile Gly Ala Val Gln Leu Arg Arg Leu
            275                 280                 285

Pro Gly Phe Val Ala Arg Arg Glu Ile Val Ala Leu Tyr Asp Ser
            290                 295                 300

Glu Leu Ser Ser Leu Glu Gly Val Leu Thr Pro Ala Pro Ala
305                 310                 315                 320

Gly His Glu Ser Thr His Tyr Phe Tyr Trp Ile Gln Leu Ala Pro Gly
                325                 330                 335

Val Arg Asp Arg Val Ala Arg Asp Leu Leu Thr Asp Gly Ile Tyr Thr
            340                 345                 350

Thr Phe Arg Tyr Ala Pro Leu His Lys Val Pro Ala Tyr Gly His Thr
            355                 360                 365

Gly Gly Glu Leu Pro Gly Val Glu Arg Ala Ser Glu Arg Thr Leu Cys
            370                 375                 380

Leu Pro Leu His Pro Gly Leu Ser Asp Ala Asp Val Arg Thr Val Val
385                 390                 395                 400

Ser Ser Leu Arg Arg Ala Leu Ser Ala Ala Asp Pro Ala Pro Ala
                405                 410                 415

<210> SEQ ID NO 45
<211> LENGTH: 720
<212> TYPE: DNA
<213> ORGANISM: Streptomyces ambofaciens
<220> FEATURE:
<221> NAME/KEY: CDS
<222> LOCATION: (1)..(720)

<400> SEQUENCE: 45
```

```
atg tac gag aac gac agt gcc gcc gag gtc tac gac ctg ctc tac cag      48
Met Tyr Glu Asn Asp Ser Ala Ala Glu Val Tyr Asp Leu Leu Tyr Gln
1               5                   10                  15 gac cgc aag gac tac gcg ggt gag gcc gcc cgg gtc acc gac ctg atc      96
Asp Arg Lys Asp Tyr Ala Gly Glu Ala Ala Arg Val Thr Asp Leu Ile
            20                  25                  30 cgg gaa cgt acg ccg gac gcg gcc agc ctg ctc gac atc gcg tgc ggc     144
Arg Glu Arg Thr Pro Asp Ala Ala Ser Leu Leu Asp Ile Ala Cys Gly
        35                  40                  45 acc ggt acc cac ctg gag gcc ttc gcc aag ctc tac gac cgc gtg agc     192
Thr Gly Thr His Leu Glu Ala Phe Ala Lys Leu Tyr Asp Arg Val Ser
50                  55                  60 ggc ctg gag ctg tcc gag tgg atg gcg gcc cgc gcc gag gag cgg ctc     240
Gly Leu Glu Leu Ser Glu Trp Met Ala Ala Arg Ala Glu Glu Arg Leu
65                  70                  75                  80 ccc ggc gtc acc ctc cac cgc ggt gac atg cgg gcg ttc gac ctc ggc     288
Pro Gly Val Thr Leu His Arg Gly Asp Met Arg Ala Phe Asp Leu Gly
                85                  90                  95 gag acg ttc gac gcc gtg gtc tgc atg ttc agc tcg atc ggg tac ctg     336
Glu Thr Phe Asp Ala Val Val Cys Met Phe Ser Ser Ile Gly Tyr Leu
            100                 105                 110 gag acc acg gcc gac ctg gag gac gcc gtc gcc gcc atg gcg cgg cac     384
Glu Thr Thr Ala Asp Leu Glu Asp Ala Val Ala Ala Met Ala Arg His
        115                 120                 125 ctg acc gcg gac ggt gtc ctg gcc gtc gaa ccg tgg tac ttc ccc gac     432
Leu Thr Ala Asp Gly Val Leu Ala Val Glu Pro Trp Tyr Phe Pro Asp
130                 135                 140 acc ttc ctg gac ggc cac gtc tcc acc cac gcc ctg cgg acg gca ccg     480
Thr Phe Leu Asp Gly His Val Ser Thr His Ala Leu Arg Thr Ala Pro
145                 150                 155                 160 ggc gac cag ggc gtc gcc cgt gtc tcc cac tcg acc cgg gag ggc ggg     528
Gly Asp Gln Gly Val Ala Arg Val Ser His Ser Thr Arg Glu Gly Gly
                165                 170                 175 cgg acc cgg atg gag atc cac tac ctg atc gcg cac acc gcg gag ggc     576
Arg Thr Arg Met Glu Ile His Tyr Leu Ile Ala His Thr Ala Glu Gly
            180                 185                 190 atc cgg cac cgc agc gag gtg gac tac ctc acg ctg ttc tcg cgt gcg     624
Ile Arg His Arg Ser Glu Val Asp Tyr Leu Thr Leu Phe Ser Arg Ala
        195                 200                 205 gag tac gag gcc gcg tac cgc aag gcc ggc ctg gac gtc gag tac gtc     672
Glu Tyr Glu Ala Ala Tyr Arg Lys Ala Gly Leu Asp Val Glu Tyr Val
210                 215                 220 gtg acg ggc gag ggc tca ccg ggc ttc ttc ctc ggc acg cgt cgc tga     720
Val Thr Gly Glu Gly Ser Pro Gly Phe Phe Leu Gly Thr Arg Arg
225                 230                 235
```

<210> SEQ ID NO 46
<211> LENGTH: 239
<212> TYPE: PRT
<213> ORGANISM: Streptomyces ambofaciens

<400> SEQUENCE: 46

```
Met Tyr Glu Asn Asp Ser Ala Ala Glu Val Tyr Asp Leu Leu Tyr Gln
1               5                   10                  15

Asp Arg Lys Asp Tyr Ala Gly Glu Ala Ala Arg Val Thr Asp Leu Ile
            20                  25                  30

Arg Glu Arg Thr Pro Asp Ala Ala Ser Leu Leu Asp Ile Ala Cys Gly
        35                  40                  45

Thr Gly Thr His Leu Glu Ala Phe Ala Lys Leu Tyr Asp Arg Val Ser
```

```
                    50                  55                  60
Gly Leu Glu Leu Ser Glu Trp Met Ala Ala Arg Ala Glu Glu Arg Leu
 65                  70                  75                  80

Pro Gly Val Thr Leu His Arg Gly Asp Met Arg Ala Phe Asp Leu Gly
                 85                  90                  95

Glu Thr Phe Asp Ala Val Val Cys Met Phe Ser Ser Ile Gly Tyr Leu
            100                 105                 110

Glu Thr Thr Ala Asp Leu Glu Asp Ala Val Ala Met Ala Arg His
        115                 120                 125

Leu Thr Ala Asp Gly Val Leu Ala Val Glu Pro Trp Tyr Phe Pro Asp
130                 135                 140

Thr Phe Leu Asp Gly His Val Ser Thr His Ala Leu Arg Thr Ala Pro
145                 150                 155                 160

Gly Asp Gln Gly Val Ala Arg Val Ser His Ser Thr Arg Glu Gly Gly
                165                 170                 175

Arg Thr Arg Met Glu Ile His Tyr Leu Ile Ala His Thr Ala Glu Gly
            180                 185                 190

Ile Arg His Arg Ser Glu Val Asp Tyr Leu Thr Leu Phe Ser Arg Ala
        195                 200                 205

Glu Tyr Glu Ala Ala Tyr Arg Lys Ala Gly Leu Asp Val Glu Tyr Val
    210                 215                 220

Val Thr Gly Glu Gly Ser Pro Gly Phe Phe Leu Gly Thr Arg Arg
225                 230                 235

<210> SEQ ID NO 47
<211> LENGTH: 1968
<212> TYPE: DNA
<213> ORGANISM: Streptomyces ambofaciens
<220> FEATURE:
<221> NAME/KEY: CDS
<222> LOCATION: (1)..(1968)

<400> SEQUENCE: 47 atg agt gac ctg ggt tct ggt gaa gaa ggg tcc gaa gaa gac gag tcg      48
Met Ser Asp Leu Gly Ser Gly Glu Glu Gly Ser Glu Glu Asp Glu Ser
  1               5                  10                  15 gac gac gca ctc gcc ttc ctc gag ttc atc gcc cgg tcg gca cca cgg      96
Asp Asp Ala Leu Ala Phe Leu Glu Phe Ile Ala Arg Ser Ala Pro Arg
                 20                  25                  30 agc gaa tac gac cgg ctc atg gcc cgc gcc gaa cgc tcg ggc gcc gac     144
Ser Glu Tyr Asp Arg Leu Met Ala Arg Ala Glu Arg Ser Gly Ala Asp
             35                  40                  45 gag gac cgg atg cgc cga ctg gag cgc ttc aac cgg ctc gcc ctc acc     192
Glu Asp Arg Met Arg Arg Leu Glu Arg Phe Asn Arg Leu Ala Leu Thr
         50                  55                  60 gcg cag tcg atg atc gag tac cgc cgc gac cgg gag gcg gag ctc gcg     240
Ala Gln Ser Met Ile Glu Tyr Arg Arg Asp Arg Glu Ala Glu Leu Ala
 65                  70                  75                  80 gcc ctg gtc gac gcc gcg cac gag ttc gtc gcc gcc cgg cgg ggc aag     288
Ala Leu Val Asp Ala Ala His Glu Phe Val Ala Ala Arg Arg Gly Lys
                 85                  90                  95 gac ctg ctg gag tcc atc gcc cgc aga gca cgg ctg ctg ctg aag ctg     336
Asp Leu Leu Glu Ser Ile Ala Arg Arg Ala Arg Leu Leu Leu Lys Leu
            100                 105                 110 gac gtc tcc tac gtc ggc ctg cac gag gag gac cgg ccc ggc acg gtg     384
Asp Val Ser Tyr Val Gly Leu His Glu Glu Asp Arg Pro Gly Thr Val
        115                 120                 125 gtg ctg agc gcc gac ggc aac gcg gtc aag gtc gcc gag agc tac cgg     432
```

```
                Val Leu Ser Ala Asp Gly Asn Ala Val Lys Val Ala Glu Ser Tyr Arg
                    130                 135                 140 ctg ccg gcc gac ggc gga ctg ggc gcc atg gtg cgc acc tgc cgc gct          480
Leu Pro Ala Asp Gly Gly Leu Gly Ala Met Val Arg Thr Cys Arg Ala
145                 150                 155                 160 ccc ttc tgg acc ccg gac tac ctc ggg gac aac agc ttc acg cac gtc          528
Pro Phe Trp Thr Pro Asp Tyr Leu Gly Asp Asn Ser Phe Thr His Val
                    165                 170                 175 gag gcc gtc gac gac atc gtc cgc gcc gaa ggc ctg cgc gcg gtc ctg          576
Glu Ala Val Asp Asp Ile Val Arg Ala Glu Gly Leu Arg Ala Val Leu
                180                 185                 190 gcc gtc ccg ctg tgc gcc ggg ggc gaa ccg atg ggg gtc ctc tac gtc          624
Ala Val Pro Leu Cys Ala Gly Gly Glu Pro Met Gly Val Leu Tyr Val
            195                 200                 205 gcc gac cgt cag gtg cgg cat ctg acc ccc aac gag gtc acc ctg ctg          672
Ala Asp Arg Gln Val Arg His Leu Thr Pro Asn Glu Val Thr Leu Leu
        210                 215                 220 tgc tcg ctc gcc gat ctg gcc gcg gtg gcg atc gag cgc aac cgg ctg          720
Cys Ser Leu Ala Asp Leu Ala Ala Val Ala Ile Glu Arg Asn Arg Leu
225                 230                 235                 240 gtc gag gag ctc cac gac acc atc ggg caa ctg cgc cag gac atc ggc          768
Val Glu Glu Leu His Asp Thr Ile Gly Gln Leu Arg Gln Asp Ile Gly
                    245                 250                 255 gag gcc cgc acc gcc ctc gcg cgc acc cgc agg tcc gcc gac ctc cag          816
Glu Ala Arg Thr Ala Leu Ala Arg Thr Arg Arg Ser Ala Asp Leu Gln
                260                 265                 270 tcg cac ctg gtc acg cag gtg atg gac agg cgc ggc gcc gac tcg tta          864
Ser His Leu Val Thr Gln Val Met Asp Arg Arg Gly Ala Asp Ser Leu
            275                 280                 285 ctc gcg acg gcc gcc gag gcg ctc ggc ggc gga gcc ggc ctg tgc agc          912
Leu Ala Thr Ala Ala Glu Ala Leu Gly Gly Gly Ala Gly Leu Cys Ser
        290                 295                 300 ccg ctc ggg cgc ccg ctc gcc gag tac ggg acc ctg cgc ccc gtc gcc          960
Pro Leu Gly Arg Pro Leu Ala Glu Tyr Gly Thr Leu Arg Pro Val Ala
305                 310                 315                 320 ccc acg gaa ctg cgc gcg gcg tgc cgc cgg gcc gcc gag acc ggc cgg         1008
Pro Thr Glu Leu Arg Ala Ala Cys Arg Arg Ala Ala Glu Thr Gly Arg
                    325                 330                 335 ccc acc tcc gtg gcc ccg ggg gtc tgg acg gtg ccc ctg ctt ccc ggg         1056
Pro Thr Ser Val Ala Pro Gly Val Trp Thr Val Pro Leu Leu Pro Gly
                340                 345                 350 ggc aac gcc ggc ttc ctg ctg acc gac ctc ggt ccg gac gcg gac cac         1104
Gly Asn Ala Gly Phe Leu Leu Thr Asp Leu Gly Pro Asp Ala Asp His
            355                 360                 365 acc gcc gtc ccc ctg ctc ccg atg gtc gcc cgc acc ctc gcg ctg cac         1152
Thr Ala Val Pro Leu Leu Pro Met Val Ala Arg Thr Leu Ala Leu His
        370                 375                 380 ctg cgc gtc cag cac gac gac tcc ccc aag gcg cag agc cac cag gag         1200
Leu Arg Val Gln His Asp Asp Ser Pro Lys Ala Gln Ser His Gln Glu
385                 390                 395                 400 ttc ttc gac gac ctg atc ggg gcg ccc cgc tca ccc acg ctc ctc agg         1248
Phe Phe Asp Asp Leu Ile Gly Ala Pro Arg Ser Pro Thr Leu Leu Arg
                    405                 410                 415 gaa cgc gcc ctg atg ttc tcc ctc agc ttc cgc cgc ccg cac gtg gtg         1296
Glu Arg Ala Leu Met Phe Ser Leu Ser Phe Arg Arg Pro His Val Val
                420                 425                 430 ctg gtg gcg gac gga ccc cgc ggg acc tcg ccg cgg ctg gag gcc tcc         1344
Leu Val Ala Asp Gly Pro Arg Gly Thr Ser Pro Arg Leu Glu Ala Ser
            435                 440                 445
```

```
ggc gcc gac tac gcg aag gag ctc ggc ggg ctg tgc agc gtg cgg gac      1392
Gly Ala Asp Tyr Ala Lys Glu Leu Gly Gly Leu Cys Ser Val Arg Asp
    450                 455                 460 ggc gcc gtc gtc ctg ctg ctc ccc ggc gac gac ccc gtc gcc gtg gcg      1440
Gly Ala Val Val Leu Leu Leu Pro Gly Asp Asp Pro Val Ala Val Ala
465                 470                 475                 480 cag acc gcc gcc ccg gag ctg acc gac cgc gcc ggg cac ccc gtc acc      1488
Gln Thr Ala Ala Pro Glu Leu Thr Asp Arg Ala Gly His Pro Val Thr
                485                 490                 495 gtg ggg gtc gcg ggc ccc gcc tcg acc gtc gac ggc atc gcc gac gcg      1536
Val Gly Val Ala Gly Pro Ala Ser Thr Val Asp Gly Ile Ala Asp Ala
            500                 505                 510 cac cgt gag gcc gcg aag tgt ctg gag acc ctc cgc gcg ctc ggc ggc      1584
His Arg Glu Ala Ala Lys Cys Leu Glu Thr Leu Arg Ala Leu Gly Gly
        515                 520                 525 gac ggc ggc acc gcg tgc gcc tcc gac ctg ggt ttc ctc ggc atg ctc      1632
Asp Gly Gly Thr Ala Cys Ala Ser Asp Leu Gly Phe Leu Gly Met Leu
    530                 535                 540 ctc gcc gag gag aac gac gtc ccc ggt tac atc agg acg acg atc ggc      1680
Leu Ala Glu Glu Asn Asp Val Pro Gly Tyr Ile Arg Thr Thr Ile Gly
545                 550                 555                 560 ccc gtg gtc gac tac gac acc cac cgc ttc acg gat ctg gtt ccc act      1728
Pro Val Val Asp Tyr Asp Thr His Arg Phe Thr Asp Leu Val Pro Thr
                565                 570                 575 ctg agg gtg tac ctg gag tcg ggc agg agc ccc acg cgt gcc gca gag      1776
Leu Arg Val Tyr Leu Glu Ser Gly Arg Ser Pro Thr Arg Ala Ala Glu
            580                 585                 590 aca ctg cgc gtg cac ccg aac acc gtc tca cgg cgg ctg gag cgc atc      1824
Thr Leu Arg Val His Pro Asn Thr Val Ser Arg Arg Leu Glu Arg Ile
        595                 600                 605 ggc gta ctg ctg gga gag gac tgg cag tca ccg gag cgg gtg ctg gac      1872
Gly Val Leu Leu Gly Glu Asp Trp Gln Ser Pro Glu Arg Val Leu Asp
    610                 615                 620 ata caa ctg gcc ctg cgg ctc tat cag gtg cgc tcg gcg ctc tcc tcg      1920
Ile Gln Leu Ala Leu Arg Leu Tyr Gln Val Arg Ser Ala Leu Ser Ser
625                 630                 635                 640 caa ccg gcg tcc gag acc cgg gcc gtg ctc gga tcg ctg cgc gag tga      1968
Gln Pro Ala Ser Glu Thr Arg Ala Val Leu Gly Ser Leu Arg Glu
                645                 650                 655
```

<210> SEQ ID NO 48
<211> LENGTH: 655
<212> TYPE: PRT
<213> ORGANISM: Streptomyces ambofaciens

<400> SEQUENCE: 48

```
Met Ser Asp Leu Gly Ser Gly Glu Glu Gly Ser Glu Glu Asp Glu Ser
1               5                   10                  15

Asp Asp Ala Leu Ala Phe Leu Glu Phe Ile Ala Arg Ser Ala Pro Arg
            20                  25                  30

Ser Glu Tyr Asp Arg Leu Met Ala Arg Ala Glu Arg Ser Gly Ala Asp
        35                  40                  45

Glu Asp Arg Met Arg Arg Leu Glu Arg Phe Asn Arg Leu Ala Leu Thr
    50                  55                  60

Ala Gln Ser Met Ile Glu Tyr Arg Arg Asp Arg Glu Ala Glu Leu Ala
65                  70                  75                  80

Ala Leu Val Asp Ala Ala His Glu Phe Val Ala Ala Arg Arg Gly Lys
                85                  90                  95

Asp Leu Leu Glu Ser Ile Ala Arg Arg Ala Arg Leu Leu Leu Lys Leu
```

-continued

```
            100                 105                 110
Asp Val Ser Tyr Val Gly Leu His Glu Glu Asp Arg Pro Gly Thr Val
        115                 120                 125
Val Leu Ser Ala Asp Gly Asn Ala Val Lys Val Ala Glu Ser Tyr Arg
    130                 135                 140
Leu Pro Ala Asp Gly Gly Leu Gly Ala Met Val Arg Thr Cys Arg Ala
145                 150                 155                 160
Pro Phe Trp Thr Pro Asp Tyr Leu Gly Asp Asn Ser Phe Thr His Val
                165                 170                 175
Glu Ala Val Asp Asp Ile Val Arg Ala Glu Gly Leu Arg Ala Val Leu
            180                 185                 190
Ala Val Pro Leu Cys Ala Gly Gly Glu Pro Met Gly Val Leu Tyr Val
        195                 200                 205
Ala Asp Arg Gln Val Arg His Leu Thr Pro Asn Glu Val Thr Leu Leu
    210                 215                 220
Cys Ser Leu Ala Asp Leu Ala Ala Val Ala Ile Glu Arg Asn Arg Leu
225                 230                 235                 240
Val Glu Glu Leu His Asp Thr Ile Gly Gln Leu Arg Gln Asp Ile Gly
                245                 250                 255
Glu Ala Arg Thr Ala Leu Ala Arg Thr Arg Arg Ser Ala Asp Leu Gln
            260                 265                 270
Ser His Leu Val Thr Gln Val Met Asp Arg Arg Gly Ala Asp Ser Leu
        275                 280                 285
Leu Ala Thr Ala Ala Glu Ala Leu Gly Gly Ala Gly Leu Cys Ser
    290                 295                 300
Pro Leu Gly Arg Pro Leu Ala Glu Tyr Gly Thr Leu Arg Pro Val Ala
305                 310                 315                 320
Pro Thr Glu Leu Arg Ala Ala Cys Arg Arg Ala Glu Thr Gly Arg
                325                 330                 335
Pro Thr Ser Val Ala Pro Gly Val Trp Thr Val Pro Leu Leu Pro Gly
            340                 345                 350
Gly Asn Ala Gly Phe Leu Leu Thr Asp Leu Gly Pro Asp Ala Asp His
        355                 360                 365
Thr Ala Val Pro Leu Leu Pro Met Val Ala Arg Thr Leu Ala Leu His
    370                 375                 380
Leu Arg Val Gln His Asp Asp Ser Pro Lys Ala Gln Ser His Gln Glu
385                 390                 395                 400
Phe Phe Asp Asp Leu Ile Gly Ala Pro Arg Ser Pro Thr Leu Leu Arg
                405                 410                 415
Glu Arg Ala Leu Met Phe Ser Leu Ser Phe Arg Arg Pro His Val Val
            420                 425                 430
Leu Val Ala Asp Gly Pro Arg Gly Thr Ser Pro Arg Leu Glu Ala Ser
        435                 440                 445
Gly Ala Asp Tyr Ala Lys Glu Leu Gly Gly Leu Cys Ser Val Arg Asp
    450                 455                 460
Gly Ala Val Val Leu Leu Pro Gly Asp Pro Val Ala Val Ala
465                 470                 475                 480
Gln Thr Ala Ala Pro Glu Leu Thr Asp Arg Ala Gly His Pro Val Thr
                485                 490                 495
Val Gly Val Ala Gly Pro Ala Ser Thr Val Asp Gly Ile Ala Asp Ala
            500                 505                 510
His Arg Glu Ala Ala Lys Cys Leu Glu Thr Leu Arg Ala Leu Gly Gly
        515                 520                 525
```

```
Asp Gly Gly Thr Ala Cys Ala Ser Asp Leu Gly Phe Leu Gly Met Leu
    530                 535                 540

Leu Ala Glu Glu Asn Asp Val Pro Gly Tyr Ile Arg Thr Thr Ile Gly
545                 550                 555                 560

Pro Val Val Asp Tyr Asp Thr His Arg Phe Thr Asp Leu Val Pro Thr
                565                 570                 575

Leu Arg Val Tyr Leu Glu Ser Gly Arg Ser Pro Thr Arg Ala Ala Glu
            580                 585                 590

Thr Leu Arg Val His Pro Asn Thr Val Ser Arg Arg Leu Glu Arg Ile
        595                 600                 605

Gly Val Leu Leu Gly Glu Asp Trp Gln Ser Pro Glu Arg Val Leu Asp
610                 615                 620

Ile Gln Leu Ala Leu Arg Leu Tyr Gln Val Arg Ser Ala Leu Ser Ser
625                 630                 635                 640

Gln Pro Ala Ser Glu Thr Arg Ala Val Leu Gly Ser Leu Arg Glu
                645                 650                 655

<210> SEQ ID NO 49
<211> LENGTH: 1749
<212> TYPE: DNA
<213> ORGANISM: Streptomyces ambofaciens
<220> FEATURE:
<221> NAME/KEY: CDS
<222> LOCATION: (1)..(1749)
<220> FEATURE:
<221> NAME/KEY: CDS
<222> LOCATION: (76)..(1749)
<220> FEATURE:
<221> NAME/KEY: CDS
<222> LOCATION: (97)..(1749)

<400> SEQUENCE: 49 atg tcc gca gtg gtg gcg tcc ctt ctg ctt tcc gtt ctt tct gcg agc          48
Met Ser Ala Val Val Ala Ser Leu Leu Leu Ser Val Leu Ser Ala Ser
1               5                   10                  15 gcg ctc acg cat cca ctc atc ctc atc gtg gaa aca gga gac tta cgc         96
Ala Leu Thr His Pro Leu Ile Leu Ile Val Glu Thr Gly Asp Leu Arg
                20                  25                  30 gtg tcg att gcg caa tac gcc cta cac gac atc acg aag cgc tac cac        144
Val Ser Ile Ala Gln Tyr Ala Leu His Asp Ile Thr Lys Arg Tyr His
            35                  40                  45 gac tgt gtc gtg ctc gac cgg gtc ggt ttc agc atc aag ccg ggc gag        192
Asp Cys Val Val Leu Asp Arg Val Gly Phe Ser Ile Lys Pro Gly Glu
    50                  55                  60 aag gtc ggc gtg atc ggc gac aac ggt tcc ggc aag tcc acg ctg ctc        240
Lys Val Gly Val Ile Gly Asp Asn Gly Ser Gly Lys Ser Thr Leu Leu
65                  70                  75                  80 aag atc ctc gcc ggc cgc gtg gag ccc gac aac ggc gcg ctc acc gtg        288
Lys Ile Leu Ala Gly Arg Val Glu Pro Asp Asn Gly Ala Leu Thr Val
                85                  90                  95 gtc gct ccc ggc ggc gtc ggc tac ctg gcg cag aca ctg gaa ctg ccc        336
Val Ala Pro Gly Gly Val Gly Tyr Leu Ala Gln Thr Leu Glu Leu Pro
                100                 105                 110 ctc gac gcc acc gtc cag gac gcc gtc gac ctg gcc ctg tcc gac ctg        384
Leu Asp Ala Thr Val Gln Asp Ala Val Asp Leu Ala Leu Ser Asp Leu
            115                 120                 125 cgc gag ctc gaa gcg gcg atg cgc gag gcc gag gcg gag ctg ggc gag        432
Arg Glu Leu Glu Ala Ala Met Arg Glu Ala Glu Ala Glu Leu Gly Glu
        130                 135                 140 agc gac gag aac ggc tcc gag cgc gag ctg tcc gcc ggc ctc cag cgc        480
```

```
Ser Asp Glu Asn Gly Ser Glu Arg Glu Leu Ser Ala Gly Leu Gln Arg
145                 150                 155                 160 tac gcc gct ctg gtc gag cag tac cag gcg cgt ggc ggc tac gag gcc      528
Tyr Ala Ala Leu Val Glu Gln Tyr Gln Ala Arg Gly Gly Tyr Glu Ala
                165                 170                 175 gac gtg cgc gtg gag gtc gcg ctg cac ggc ctc gga ctg ccg agc ctg      576
Asp Val Arg Val Glu Val Ala Leu His Gly Leu Gly Leu Pro Ser Leu
            180                 185                 190 gac cgc gac cgc aag ctc gga acc ctc tcc ggt ggc gaa cgc tcc cgc      624
Asp Arg Asp Arg Lys Leu Gly Thr Leu Ser Gly Gly Glu Arg Ser Arg
        195                 200                 205 ctc gcg ctc gcc gcg acc ctc gcc tcg tcg ccg gag ctg ctg ctc ctg      672
Leu Ala Leu Ala Ala Thr Leu Ala Ser Ser Pro Glu Leu Leu Leu Leu
    210                 215                 220 gac gaa ccg acc aac gac ctc gac gac cgg gcg atg gaa tgg ctg gag      720
Asp Glu Pro Thr Asn Asp Leu Asp Asp Arg Ala Met Glu Trp Leu Glu
225                 230                 235                 240 gac cac ctg gcc ggc cac cgc ggc acg gtg atc gcg gtc acc cac gac      768
Asp His Leu Ala Gly His Arg Gly Thr Val Ile Ala Val Thr His Asp
                245                 250                 255 cgg gtc ttc ctc gac cgg ctc acc acc acg atc ctg gag gtc gac tcc      816
Arg Val Phe Leu Asp Arg Leu Thr Thr Thr Ile Leu Glu Val Asp Ser
            260                 265                 270 ggc agc gtc acc cgc tac ggc aac ggc tac gag ggc tac ctg acg gcc      864
Gly Ser Val Thr Arg Tyr Gly Asn Gly Tyr Glu Gly Tyr Leu Thr Ala
        275                 280                 285 aag gcc gtg gaa cgc gag cgg cgg ctg cgg gag tac gag gag tgg cgt      912
Lys Ala Val Glu Arg Glu Arg Arg Leu Arg Glu Tyr Glu Glu Trp Arg
    290                 295                 300 gcc gaa ctc gac cgc aac cgc ggg ctg atc acc tcc aac gtg gcg cgg      960
Ala Glu Leu Asp Arg Asn Arg Gly Leu Ile Thr Ser Asn Val Ala Arg
305                 310                 315                 320 atg gac ggc atc ccg cgc aag atg tcc ctc tcc gtg ttc ggc cac ggc     1008
Met Asp Gly Ile Pro Arg Lys Met Ser Leu Ser Val Phe Gly His Gly
                325                 330                 335 gcc tac cgc agg cga ggg cgc gac cac ggc gcg atg gtg cgg atc cgc     1056
Ala Tyr Arg Arg Arg Gly Arg Asp His Gly Ala Met Val Arg Ile Arg
            340                 345                 350 aac gcg aag caa cgc gtg gcg cag ctg acc gag aac ccg gtc cac gct     1104
Asn Ala Lys Gln Arg Val Ala Gln Leu Thr Glu Asn Pro Val His Ala
        355                 360                 365 ccc gcc gac ccg ttg tcc ttc gcc gcc cgc atc gac acc gcg ggc ccg     1152
Pro Ala Asp Pro Leu Ser Phe Ala Ala Arg Ile Asp Thr Ala Gly Pro
    370                 375                 380 gag gcg gag gag gcg gtg gcc gaa ctc acc gac gtg cgc gtc gcg ggt     1200
Glu Ala Glu Glu Ala Val Ala Glu Leu Thr Asp Val Arg Val Ala Gly
385                 390                 395                 400 cgg ctc gcc gtg gac tcc ctg acg atc cgg ccc ggc gaa cgg ctg ctc     1248
Arg Leu Ala Val Asp Ser Leu Thr Ile Arg Pro Gly Glu Arg Leu Leu
                405                 410                 415 gtc aca ggt ccc aac ggt gcg ggc aag tcc acc ttg ttg cgg gtg ctg     1296
Val Thr Gly Pro Asn Gly Ala Gly Lys Ser Thr Leu Leu Arg Val Leu
            420                 425                 430 tcc ggg gaa ctg gag ccg gac ggc ggc tcg gtg cgc gtc ggc tgc cgg     1344
Ser Gly Glu Leu Glu Pro Asp Gly Gly Ser Val Arg Val Gly Cys Arg
        435                 440                 445 gtc ggt cat ctg cgg cag gac gag acg ccc tgg gcg ccc gga ctg acc     1392
Val Gly His Leu Arg Gln Asp Glu Thr Pro Trp Ala Pro Gly Leu Thr
    450                 455                 460
```

```
gtg ctg cgg gcc ttc gcc cag ggc cgg gag ggc tac ctg gag gac cac    1440
Val Leu Arg Ala Phe Ala Gln Gly Arg Glu Gly Tyr Leu Glu Asp His
465                 470                 475                 480 gcg gag aaa ctg ctg tcg ctc ggc ctg ttc agc ccg tcc gac ctg cgg    1488
Ala Glu Lys Leu Leu Ser Leu Gly Leu Phe Ser Pro Ser Asp Leu Arg
                485                 490                 495 cga cgc gtg aag gat ctg tcc tac ggg cag cgc cgg atc gag atc        1536
Arg Arg Val Lys Asp Leu Ser Tyr Gly Gln Arg Arg Ile Glu Ile
            500                 505                 510 gcc cgg ctg gtg agc gac ccg atg gac ctg ctg ctg gac gag ccc        1584
Ala Arg Leu Val Ser Asp Pro Met Asp Leu Leu Leu Asp Glu Pro
            515                 520                 525 acc aac cac ctc acc ccg gtg ctg gtg gag gag ttg gag cag gca ctc    1632
Thr Asn His Leu Thr Pro Val Leu Val Glu Glu Leu Glu Gln Ala Leu
530                 535                 540 gcg gac tac cgc ggc gcc gtc gtg gtc gtc acc cac gac cgt cgg atg    1680
Ala Asp Tyr Arg Gly Ala Val Val Val Val Thr His Asp Arg Arg Met
545                 550                 555                 560 cgg tcc cgg ttc acc ggc gcc cgg ctg acc atg gga gac ggg cgc atc    1728
Arg Ser Arg Phe Thr Gly Ala Arg Leu Thr Met Gly Asp Gly Arg Ile
                565                 570                 575 gcc gag ttc agc gcc ggc tga                                        1749
Ala Glu Phe Ser Ala Gly
                580

<210> SEQ ID NO 50
<211> LENGTH: 582
<212> TYPE: PRT
<213> ORGANISM: Streptomyces ambofaciens

<400> SEQUENCE: 50

Met Ser Ala Val Val Ala Ser Leu Leu Leu Ser Val Leu Ser Ala Ser
1               5                   10                  15

Ala Leu Thr His Pro Leu Ile Leu Ile Val Glu Thr Gly Asp Leu Arg
                20                  25                  30

Val Ser Ile Ala Gln Tyr Ala Leu His Asp Ile Thr Lys Arg Tyr His
            35                  40                  45

Asp Cys Val Val Leu Asp Arg Val Gly Phe Ser Ile Lys Pro Gly Glu
        50                  55                  60

Lys Val Gly Val Ile Gly Asp Asn Gly Ser Gly Lys Ser Thr Leu Leu
65                  70                  75                  80

Lys Ile Leu Ala Gly Arg Val Glu Pro Asp Asn Gly Ala Leu Thr Val
                85                  90                  95

Val Ala Pro Gly Gly Val Gly Tyr Leu Ala Gln Thr Leu Glu Leu Pro
            100                 105                 110

Leu Asp Ala Thr Val Gln Asp Ala Val Asp Leu Ala Leu Ser Asp Leu
        115                 120                 125

Arg Glu Leu Glu Ala Ala Met Arg Glu Ala Glu Ala Leu Gly Glu
    130                 135                 140

Ser Asp Glu Asn Gly Ser Glu Arg Glu Leu Ser Ala Gly Leu Gln Arg
145                 150                 155                 160

Tyr Ala Ala Leu Val Glu Gln Tyr Gln Ala Arg Gly Gly Tyr Glu Ala
                165                 170                 175

Asp Val Arg Val Glu Val Ala Leu His Gly Leu Gly Leu Pro Ser Leu
            180                 185                 190

Asp Arg Asp Arg Lys Leu Gly Thr Leu Ser Gly Gly Glu Arg Ser Arg
        195                 200                 205
```

```
Leu Ala Leu Ala Ala Thr Leu Ala Ser Ser Pro Glu Leu Leu Leu
    210                 215                 220

Asp Glu Pro Thr Asn Asp Leu Asp Asp Arg Ala Met Glu Trp Leu Glu
225                 230                 235                 240

Asp His Leu Ala Gly His Arg Gly Thr Val Ile Ala Val Thr His Asp
                245                 250                 255

Arg Val Phe Leu Asp Arg Leu Thr Thr Thr Ile Leu Glu Val Asp Ser
            260                 265                 270

Gly Ser Val Thr Arg Tyr Gly Asn Gly Tyr Glu Gly Tyr Leu Thr Ala
        275                 280                 285

Lys Ala Val Glu Arg Glu Arg Arg Leu Arg Glu Tyr Glu Glu Trp Arg
    290                 295                 300

Ala Glu Leu Asp Arg Asn Arg Gly Leu Ile Thr Ser Asn Val Ala Arg
305                 310                 315                 320

Met Asp Gly Ile Pro Arg Lys Met Ser Leu Ser Val Phe Gly His Gly
                325                 330                 335

Ala Tyr Arg Arg Gly Arg Asp His Gly Ala Met Val Arg Ile Arg
            340                 345                 350

Asn Ala Lys Gln Arg Val Ala Gln Leu Thr Glu Asn Pro Val His Ala
        355                 360                 365

Pro Ala Asp Pro Leu Ser Phe Ala Ala Arg Ile Asp Thr Ala Gly Pro
    370                 375                 380

Glu Ala Glu Glu Ala Val Ala Glu Leu Thr Asp Val Arg Val Ala Gly
385                 390                 395                 400

Arg Leu Ala Val Asp Ser Leu Thr Ile Arg Pro Gly Glu Arg Leu Leu
                405                 410                 415

Val Thr Gly Pro Asn Gly Ala Gly Lys Ser Thr Leu Leu Arg Val Leu
            420                 425                 430

Ser Gly Glu Leu Glu Pro Asp Gly Gly Ser Val Arg Val Gly Cys Arg
        435                 440                 445

Val Gly His Leu Arg Gln Asp Glu Thr Pro Trp Ala Pro Gly Leu Thr
    450                 455                 460

Val Leu Arg Ala Phe Ala Gln Gly Arg Glu Gly Tyr Leu Glu Asp His
465                 470                 475                 480

Ala Glu Lys Leu Leu Ser Leu Gly Leu Phe Ser Pro Ser Asp Leu Arg
                485                 490                 495

Arg Arg Val Lys Asp Leu Ser Tyr Gly Gln Arg Arg Ile Glu Ile
            500                 505                 510

Ala Arg Leu Val Ser Asp Pro Met Asp Leu Leu Leu Asp Glu Pro
        515                 520                 525

Thr Asn His Leu Thr Pro Val Leu Val Glu Glu Leu Glu Gln Ala Leu
    530                 535                 540

Ala Asp Tyr Arg Gly Ala Val Val Val Thr His Asp Arg Arg Met
545                 550                 555                 560

Arg Ser Arg Phe Thr Gly Ala Arg Leu Thr Met Gly Asp Gly Arg Ile
                565                 570                 575

Ala Glu Phe Ser Ala Gly
            580

<210> SEQ ID NO 51
<211> LENGTH: 557
<212> TYPE: PRT
<213> ORGANISM: Streptomyces ambofaciens

<400> SEQUENCE: 51
```

-continued

```
Val Glu Thr Gly Asp Leu Arg Val Ser Ile Ala Gln Tyr Ala Leu His
1               5                   10                  15

Asp Ile Thr Lys Arg Tyr His Asp Cys Val Val Leu Asp Arg Val Gly
            20                  25                  30

Phe Ser Ile Lys Pro Gly Glu Lys Val Gly Val Ile Gly Asp Asn Gly
        35                  40                  45

Ser Gly Lys Ser Thr Leu Leu Lys Ile Leu Ala Gly Arg Val Glu Pro
50                  55                  60

Asp Asn Gly Ala Leu Thr Val Ala Pro Gly Val Gly Tyr Leu
65              70                  75              80

Ala Gln Thr Leu Glu Leu Pro Leu Asp Ala Thr Val Gln Asp Ala Val
                85                  90                  95

Asp Leu Ala Leu Ser Asp Leu Arg Leu Glu Ala Ala Met Arg Glu
            100                 105                 110

Ala Glu Ala Glu Leu Gly Glu Ser Asp Glu Asn Gly Ser Glu Arg Glu
            115                 120                 125

Leu Ser Ala Gly Leu Gln Arg Tyr Ala Ala Leu Val Glu Gln Tyr Gln
130                 135                 140

Ala Arg Gly Gly Tyr Glu Ala Asp Val Arg Val Glu Val Ala Leu His
145                 150                 155                 160

Gly Leu Gly Leu Pro Ser Leu Asp Arg Asp Arg Lys Leu Gly Thr Leu
                165                 170                 175

Ser Gly Gly Glu Arg Ser Arg Leu Ala Leu Ala Ala Thr Leu Ala Ser
            180                 185                 190

Ser Pro Glu Leu Leu Leu Leu Asp Glu Pro Thr Asn Asp Leu Asp Asp
        195                 200                 205

Arg Ala Met Glu Trp Leu Glu Asp His Leu Ala Gly His Arg Gly Thr
210                 215                 220

Val Ile Ala Val Thr His Asp Arg Val Phe Leu Asp Arg Leu Thr Thr
225                 230                 235                 240

Thr Ile Leu Glu Val Asp Ser Gly Ser Val Thr Arg Tyr Gly Asn Gly
            245                 250                 255

Tyr Glu Gly Tyr Leu Thr Ala Lys Ala Val Glu Arg Glu Arg Arg Leu
            260                 265                 270

Arg Glu Tyr Glu Glu Trp Arg Ala Glu Leu Asp Arg Asn Arg Gly Leu
            275                 280                 285

Ile Thr Ser Asn Val Ala Arg Met Asp Gly Ile Pro Arg Lys Met Ser
        290                 295                 300

Leu Ser Val Phe Gly His Gly Ala Tyr Arg Arg Arg Gly Arg Asp His
305                 310                 315                 320

Gly Ala Met Val Arg Ile Arg Asn Ala Lys Gln Arg Val Ala Gln Leu
                325                 330                 335

Thr Glu Asn Pro Val His Ala Pro Ala Asp Pro Leu Ser Phe Ala Ala
            340                 345                 350

Arg Ile Asp Thr Ala Gly Pro Glu Ala Glu Ala Val Ala Glu Leu
            355                 360                 365

Thr Asp Val Arg Val Ala Gly Arg Leu Ala Val Asp Ser Leu Thr Ile
        370                 375                 380

Arg Pro Gly Glu Arg Leu Leu Val Thr Gly Pro Asn Gly Ala Gly Lys
385                 390                 395                 400

Ser Thr Leu Leu Arg Val Leu Ser Gly Glu Leu Glu Pro Asp Gly Gly
                405                 410                 415
```

-continued

```
Ser Val Arg Val Gly Cys Arg Val Gly His Leu Arg Gln Asp Glu Thr
                420                 425                 430

Pro Trp Ala Pro Gly Leu Thr Val Leu Arg Ala Phe Ala Gln Gly Arg
            435                 440                 445

Glu Gly Tyr Leu Glu Asp His Ala Glu Lys Leu Ser Leu Gly Leu
        450                 455                 460

Phe Ser Pro Ser Asp Leu Arg Arg Val Lys Asp Leu Ser Tyr Gly
465                 470                 475                 480

Gln Arg Arg Ile Glu Ile Ala Arg Leu Val Ser Asp Pro Met Asp
                485                 490                 495

Leu Leu Leu Leu Asp Glu Pro Thr Asn His Leu Thr Pro Val Leu Val
            500                 505                 510

Glu Glu Leu Glu Gln Ala Leu Ala Asp Tyr Arg Gly Ala Val Val Val
        515                 520                 525

Val Thr His Asp Arg Arg Met Arg Ser Arg Phe Thr Gly Ala Arg Leu
    530                 535                 540

Thr Met Gly Asp Gly Arg Ile Ala Glu Phe Ser Ala Gly
545                 550                 555

<210> SEQ ID NO 52
<211> LENGTH: 550
<212> TYPE: PRT
<213> ORGANISM: Streptomyces ambofaciens

<400> SEQUENCE: 52

Val Ser Ile Ala Gln Tyr Ala Leu His Asp Ile Thr Lys Arg Tyr His
1               5                   10                  15

Asp Cys Val Val Leu Asp Arg Val Gly Phe Ser Ile Lys Pro Gly Glu
                20                  25                  30

Lys Val Gly Val Ile Gly Asp Asn Gly Ser Gly Lys Ser Thr Leu Leu
            35                  40                  45

Lys Ile Leu Ala Gly Arg Val Glu Pro Asp Asn Gly Ala Leu Thr Val
        50                  55                  60

Val Ala Pro Gly Gly Val Gly Tyr Leu Ala Gln Thr Leu Glu Leu Pro
65                  70                  75                  80

Leu Asp Ala Thr Val Gln Asp Ala Val Asp Leu Ala Leu Ser Asp Leu
                85                  90                  95

Arg Glu Leu Glu Ala Ala Met Arg Glu Ala Glu Ala Glu Leu Gly Glu
                100                 105                 110

Ser Asp Glu Asn Gly Ser Glu Arg Glu Leu Ser Ala Gly Leu Gln Arg
            115                 120                 125

Tyr Ala Ala Leu Val Glu Gln Tyr Gln Ala Arg Gly Gly Tyr Glu Ala
        130                 135                 140

Asp Val Arg Val Glu Val Ala Leu His Gly Leu Gly Leu Pro Ser Leu
145                 150                 155                 160

Asp Arg Asp Arg Lys Leu Gly Thr Leu Ser Gly Gly Glu Arg Ser Arg
                165                 170                 175

Leu Ala Leu Ala Ala Thr Leu Ala Ser Ser Pro Glu Leu Leu Leu Leu
            180                 185                 190

Asp Glu Pro Thr Asn Asp Leu Asp Asp Arg Ala Met Glu Trp Leu Glu
        195                 200                 205

Asp His Leu Ala Gly His Arg Gly Thr Val Ile Ala Val Thr His Asp
    210                 215                 220

Arg Val Phe Leu Asp Arg Leu Thr Thr Thr Ile Leu Glu Val Asp Ser
225                 230                 235                 240
```

-continued

```
Gly Ser Val Thr Arg Tyr Gly Asn Gly Tyr Glu Gly Tyr Leu Thr Ala
            245                 250                 255
Lys Ala Val Glu Arg Glu Arg Leu Arg Glu Tyr Glu Glu Trp Arg
        260                 265                 270
Ala Glu Leu Asp Arg Asn Arg Gly Leu Ile Thr Ser Asn Val Ala Arg
            275                 280                 285
Met Asp Gly Ile Pro Arg Lys Met Ser Leu Ser Val Phe Gly His Gly
        290                 295                 300
Ala Tyr Arg Arg Arg Gly Arg Asp His Gly Ala Met Val Arg Ile Arg
305                 310                 315                 320
Asn Ala Lys Gln Arg Val Ala Gln Leu Thr Glu Asn Pro Val His Ala
                325                 330                 335
Pro Ala Asp Pro Leu Ser Phe Ala Ala Arg Ile Asp Thr Ala Gly Pro
            340                 345                 350
Glu Ala Glu Glu Ala Val Ala Glu Leu Thr Asp Val Arg Val Ala Gly
        355                 360                 365
Arg Leu Ala Val Asp Ser Leu Thr Ile Arg Pro Gly Glu Arg Leu Leu
    370                 375                 380
Val Thr Gly Pro Asn Gly Ala Gly Lys Ser Thr Leu Leu Arg Val Leu
385                 390                 395                 400
Ser Gly Glu Leu Glu Pro Asp Gly Gly Ser Val Arg Val Gly Cys Arg
                405                 410                 415
Val Gly His Leu Arg Gln Asp Glu Thr Pro Trp Ala Pro Gly Leu Thr
            420                 425                 430
Val Leu Arg Ala Phe Ala Gln Gly Arg Glu Gly Tyr Leu Glu Asp His
        435                 440                 445
Ala Glu Lys Leu Leu Ser Leu Gly Leu Phe Ser Pro Ser Asp Leu Arg
    450                 455                 460
Arg Arg Val Lys Asp Leu Ser Tyr Gly Gln Arg Arg Ile Glu Ile
465                 470                 475                 480
Ala Arg Leu Val Ser Asp Pro Met Asp Leu Leu Leu Asp Glu Pro
                485                 490                 495
Thr Asn His Leu Thr Pro Val Leu Val Glu Glu Leu Glu Gln Ala Leu
            500                 505                 510
Ala Asp Tyr Arg Gly Ala Val Val Val Thr His Asp Arg Arg Met
        515                 520                 525
Arg Ser Arg Phe Thr Gly Ala Arg Leu Thr Met Gly Asp Gly Arg Ile
    530                 535                 540
Ala Glu Phe Ser Ala Gly
545                 550

<210> SEQ ID NO 53
<211> LENGTH: 1431
<212> TYPE: DNA
<213> ORGANISM: Streptomyces ambofaciens
<220> FEATURE:
<221> NAME/KEY: CDS
<222> LOCATION: (1)..(1431)
<220> FEATURE:
<221> NAME/KEY: CDS
<222> LOCATION: (16)..(1431)
<220> FEATURE:
<221> NAME/KEY: CDS
<222> LOCATION: (37)..(1431)
<220> FEATURE:
<221> NAME/KEY: CDS
<222> LOCATION: (40)..(1431)
<220> FEATURE:
```

```
<221> NAME/KEY: CDS
<222> LOCATION: (79)..(1431)
<220> FEATURE:
<221> NAME/KEY: CDS
<222> LOCATION: (130)..(1431)

<400> SEQUENCE: 53 gtg ccg cgc aac ggt atg cgt gtc gca ccg gcc gac gtg atg cag tcg     48
Val Pro Arg Asn Gly Met Arg Val Ala Pro Ala Asp Val Met Gln Ser
1               5                   10                  15 gac cgg gat gat cgc ttg tcc ggc ggc cgg atg cct agc ctc ggg agc     96
Asp Arg Asp Asp Arg Leu Ser Gly Gly Arg Met Pro Ser Leu Gly Ser
            20                  25                  30 aac cac agc ggt ctt tca cga gag ggg tcg acc atg ggc gat ctc agg    144
Asn His Ser Gly Leu Ser Arg Glu Gly Ser Thr Met Gly Asp Leu Arg
        35                  40                  45 aac cgc atc acc gag ctg gtc cgc gcg tac cac cgg gaa cag gcg ccc    192
Asn Arg Ile Thr Glu Leu Val Arg Ala Tyr His Arg Glu Gln Ala Pro
    50                  55                  60 ggg ggc ttc gtt ccc ggg acg acg cac gta ccg gtc tcc ggc gcg gtg    240
Gly Gly Phe Val Pro Gly Thr Thr His Val Pro Val Ser Gly Ala Val
65                  70                  75                  80 ctg agc gag gag gac cgg ctg gcg ctg gtg gag acg gcg ctg gag atg    288
Leu Ser Glu Glu Asp Arg Leu Ala Leu Val Glu Thr Ala Leu Glu Met
                85                  90                  95 cgg atc gcg gcc ggc ccg gcc tcc cgg ggc ttc gag cgg cag ttc gcc    336
Arg Ile Ala Ala Gly Pro Ala Ser Arg Gly Phe Glu Arg Gln Phe Ala
            100                 105                 110 cgg tac ctc ggg ctc cgg aag gcg cac ctg acc aac tcc ggt tcc tcc    384
Arg Tyr Leu Gly Leu Arg Lys Ala His Leu Thr Asn Ser Gly Ser Ser
        115                 120                 125 gcc aac ctc ctc gcc ctc ggc gcg ctc acc tcg ccg cag ctg gag gag    432
Ala Asn Leu Leu Ala Leu Gly Ala Leu Thr Ser Pro Gln Leu Glu Glu
    130                 135                 140 aga cgg ctg cgt ccg ggg gac gag gtc gtc acg gtc gcc gcc ggg ttc    480
Arg Arg Leu Arg Pro Gly Asp Glu Val Val Thr Val Ala Ala Gly Phe
145                 150                 155                 160 ccc acg acg gtc aac ccg atc ttc cac aac ggg ctg gtg ccc gtc ttc    528
Pro Thr Thr Val Asn Pro Ile Phe His Asn Gly Leu Val Pro Val Phe
                165                 170                 175 gtg gac gtc gag ctc ggc acg tac aac acg acg ccc gag cgc atc gag    576
Val Asp Val Glu Leu Gly Thr Tyr Asn Thr Thr Pro Glu Arg Ile Glu
            180                 185                 190 cgg gcc atc ggc ccc cgg acc agg gcg atc atg atc gcg cac gcc ctg    624
Arg Ala Ile Gly Pro Arg Thr Arg Ala Ile Met Ile Ala His Ala Leu
        195                 200                 205 ggc aac ccc ttc gag gcc gaa gag gtg gcc cgc ctc gcg gac gag cgg    672
Gly Asn Pro Phe Glu Ala Glu Glu Val Ala Arg Leu Ala Asp Glu Arg
    210                 215                 220 gag ctg ttc ctc atc gag gac aac tgc gac gcg gtg ggg tcc cgc tac    720
Glu Leu Phe Leu Ile Glu Asp Asn Cys Asp Ala Val Gly Ser Arg Tyr
225                 230                 235                 240 cgg ggc agg ctc acc ggc tcc ttc ggc gac ctg tcg acc gtc agc ttc    768
Arg Gly Arg Leu Thr Gly Ser Phe Gly Asp Leu Ser Thr Val Ser Phe
                245                 250                 255 tat ccc gcg cac cac atc gcg atg ggt gag ggg ggc tgc gtg ctc acc    816
Tyr Pro Ala His His Ile Ala Met Gly Glu Gly Gly Cys Val Leu Thr
            260                 265                 270 gac aac ctg gcc ctg gcg cgg atc gtg gaa tca ctg cgc gac tgg ggg    864
Asp Asn Leu Ala Leu Ala Arg Ile Val Glu Ser Leu Arg Asp Trp Gly
        275                 280                 285
```

```
cgc gac tgc tgg tgc gag ccg ggt gag gac aac cgc tgc ctc aag cgg      912
Arg Asp Cys Trp Cys Glu Pro Gly Glu Asp Asn Arg Cys Leu Lys Arg
    290                 295                 300 ttc gac cag aag atg ggt gac ctg ccg ccc ggg tac gac cac aag tac      960
Phe Asp Gln Lys Met Gly Asp Leu Pro Pro Gly Tyr Asp His Lys Tyr
305                 310                 315                 320 atc ttc tcg cac gtc ggt tac aac ctg aag tcg acc gac ctg cag gcg     1008
Ile Phe Ser His Val Gly Tyr Asn Leu Lys Ser Thr Asp Leu Gln Ala
                325                 330                 335 gcc ctc ggg ctg tcc cag ctg acc cgg atc gag gag ttc acc gag gcc     1056
Ala Leu Gly Leu Ser Gln Leu Thr Arg Ile Glu Glu Phe Thr Glu Ala
            340                 345                 350 agg cgc gcc aac tgg cgg cat ctg cgc gcc gcg ttg gac ggg ctg ccc     1104
Arg Arg Ala Asn Trp Arg His Leu Arg Ala Ala Leu Asp Gly Leu Pro
        355                 360                 365 ggt ctg ctg ctg cct cat gcc aca ccg ggc agc gat ccg agc tgg ttc     1152
Gly Leu Leu Leu Pro His Ala Thr Pro Gly Ser Asp Pro Ser Trp Phe
    370                 375                 380 ggg ttc ctc atc acc gtg gac ccg gac gcc gcg tac agc agg gcg gcc     1200
Gly Phe Leu Ile Thr Val Asp Pro Asp Ala Ala Tyr Ser Arg Ala Ala
385                 390                 395                 400 ctg gtc gac cac ctg gaa tcg cgc cgg atc agc acc cgc cgc ctg ttc     1248
Leu Val Asp His Leu Glu Ser Arg Arg Ile Ser Thr Arg Arg Leu Phe
                405                 410                 415 ggg ggc aac ctc gtg cgg cac ccc gcc tac acc gac cgt cgg tac cgg     1296
Gly Gly Asn Leu Val Arg His Pro Ala Tyr Thr Asp Arg Arg Tyr Arg
            420                 425                 430 gtg tcc ggc tcc ctg gag aac agc gac ctg atc acc gac cag acg ttc     1344
Val Ser Gly Ser Leu Glu Asn Ser Asp Leu Ile Thr Asp Gln Thr Phe
        435                 440                 445 tgg atc ggg gtc ttc ccc ggc atc acc ccg gag atg atc gcc tac gtc     1392
Trp Ile Gly Val Phe Pro Gly Ile Thr Pro Glu Met Ile Ala Tyr Val
    450                 455                 460 ggc gac acg atc cgg gag ttc gtg ctc aag cac tcc tga                 1431
Gly Asp Thr Ile Arg Glu Phe Val Leu Lys His Ser
465                 470                 475

<210> SEQ ID NO 54
<211> LENGTH: 476
<212> TYPE: PRT
<213> ORGANISM: Streptomyces ambofaciens

<400> SEQUENCE: 54

Val Pro Arg Asn Gly Met Arg Val Ala Pro Ala Asp Val Met Gln Ser
1               5                   10                  15

Asp Arg Asp Asp Arg Leu Ser Gly Gly Arg Met Pro Ser Leu Gly Ser
                20                  25                  30

Asn His Ser Gly Leu Ser Arg Glu Gly Ser Thr Met Gly Asp Leu Arg
            35                  40                  45

Asn Arg Ile Thr Glu Leu Val Arg Ala Tyr His Arg Glu Gln Ala Pro
        50                  55                  60

Gly Gly Phe Val Pro Gly Thr Thr His Val Pro Val Ser Gly Ala Val
65                  70                  75                  80

Leu Ser Glu Glu Asp Arg Leu Ala Leu Val Glu Thr Ala Leu Glu Met
                85                  90                  95

Arg Ile Ala Ala Gly Pro Ala Ser Arg Gly Phe Glu Arg Gln Phe Ala
                100                 105                 110

Arg Tyr Leu Gly Leu Arg Lys Ala His Leu Thr Asn Ser Gly Ser Ser
```

```
                115                 120                 125
Ala Asn Leu Leu Ala Leu Gly Ala Leu Thr Ser Pro Gln Leu Glu Glu
            130                 135                 140
Arg Arg Leu Arg Pro Gly Asp Glu Val Val Thr Val Ala Ala Gly Phe
145                 150                 155                 160
Pro Thr Thr Val Asn Pro Ile Phe His Asn Gly Leu Val Pro Val Phe
                165                 170                 175
Val Asp Val Glu Leu Gly Thr Tyr Asn Thr Thr Pro Glu Arg Ile Glu
            180                 185                 190
Arg Ala Ile Gly Pro Arg Thr Arg Ala Ile Met Ile Ala His Ala Leu
            195                 200                 205
Gly Asn Pro Phe Glu Ala Glu Glu Val Ala Arg Leu Ala Asp Glu Arg
            210                 215                 220
Glu Leu Phe Leu Ile Glu Asp Asn Cys Asp Ala Val Gly Ser Arg Tyr
225                 230                 235                 240
Arg Gly Arg Leu Thr Gly Ser Phe Gly Asp Leu Ser Thr Val Ser Phe
                245                 250                 255
Tyr Pro Ala His His Ile Ala Met Gly Glu Gly Gly Cys Val Leu Thr
                260                 265                 270
Asp Asn Leu Ala Leu Ala Arg Ile Val Glu Ser Leu Arg Asp Trp Gly
            275                 280                 285
Arg Asp Cys Trp Cys Glu Pro Gly Glu Asp Asn Arg Cys Leu Lys Arg
            290                 295                 300
Phe Asp Gln Lys Met Gly Asp Leu Pro Pro Gly Tyr Asp His Lys Tyr
305                 310                 315                 320
Ile Phe Ser His Val Gly Tyr Asn Leu Lys Ser Thr Asp Leu Gln Ala
                325                 330                 335
Ala Leu Gly Leu Ser Gln Leu Thr Arg Ile Glu Glu Phe Thr Glu Ala
            340                 345                 350
Arg Arg Ala Asn Trp Arg His Leu Arg Ala Ala Leu Asp Gly Leu Pro
            355                 360                 365
Gly Leu Leu Leu Pro His Ala Thr Pro Gly Ser Asp Pro Ser Trp Phe
            370                 375                 380
Gly Phe Leu Ile Thr Val Asp Pro Asp Ala Ala Tyr Ser Arg Ala Ala
385                 390                 395                 400
Leu Val Asp His Leu Glu Ser Arg Arg Ile Ser Thr Arg Arg Leu Phe
                405                 410                 415
Gly Gly Asn Leu Val Arg His Pro Ala Tyr Thr Asp Arg Arg Tyr Arg
            420                 425                 430
Val Ser Gly Ser Leu Glu Asn Ser Asp Leu Ile Thr Asp Gln Thr Phe
            435                 440                 445
Trp Ile Gly Val Phe Pro Gly Ile Thr Pro Glu Met Ile Ala Tyr Val
450                 455                 460
Gly Asp Thr Ile Arg Glu Phe Val Leu Lys His Ser
465                 470                 475

<210> SEQ ID NO 55
<211> LENGTH: 471
<212> TYPE: PRT
<213> ORGANISM: Streptomyces ambofaciens

<400> SEQUENCE: 55

Met Arg Val Ala Pro Ala Asp Val Met Gln Ser Asp Arg Asp Arg
1               5                   10                  15
```

```
Leu Ser Gly Gly Arg Met Pro Ser Leu Gly Ser Asn His Ser Gly Leu
            20                  25                  30

Ser Arg Glu Gly Ser Thr Met Gly Asp Leu Arg Asn Arg Ile Thr Glu
            35                  40                  45

Leu Val Arg Ala Tyr His Arg Glu Gln Ala Pro Gly Gly Phe Val Pro
 50                  55                  60

Gly Thr Thr His Val Pro Val Ser Gly Ala Val Leu Ser Glu Glu Asp
 65                  70                  75                  80

Arg Leu Ala Leu Val Glu Thr Ala Leu Glu Met Arg Ile Ala Ala Gly
                85                  90                  95

Pro Ala Ser Arg Gly Phe Glu Arg Gln Phe Ala Arg Tyr Leu Gly Leu
            100                 105                 110

Arg Lys Ala His Leu Thr Asn Ser Gly Ser Ser Ala Asn Leu Leu Ala
            115                 120                 125

Leu Gly Ala Leu Thr Ser Pro Gln Leu Glu Glu Arg Arg Leu Arg Pro
130                 135                 140

Gly Asp Glu Val Val Thr Val Ala Ala Gly Phe Pro Thr Thr Val Asn
145                 150                 155                 160

Pro Ile Phe His Asn Gly Leu Val Pro Val Phe Val Asp Val Glu Leu
                165                 170                 175

Gly Thr Tyr Asn Thr Thr Pro Glu Arg Ile Glu Arg Ala Ile Gly Pro
                180                 185                 190

Arg Thr Arg Ala Ile Met Ile Ala His Ala Leu Gly Asn Pro Phe Glu
            195                 200                 205

Ala Glu Glu Val Ala Arg Leu Ala Asp Glu Arg Glu Leu Phe Leu Ile
210                 215                 220

Glu Asp Asn Cys Asp Ala Val Gly Ser Arg Tyr Arg Gly Arg Leu Thr
225                 230                 235                 240

Gly Ser Phe Gly Asp Leu Ser Thr Val Ser Phe Tyr Pro Ala His His
                245                 250                 255

Ile Ala Met Gly Glu Gly Gly Cys Val Leu Thr Asp Asn Leu Ala Leu
            260                 265                 270

Ala Arg Ile Val Glu Ser Leu Arg Asp Trp Gly Arg Asp Cys Trp Cys
            275                 280                 285

Glu Pro Gly Glu Asp Asn Arg Cys Leu Lys Arg Phe Asp Gln Lys Met
290                 295                 300

Gly Asp Leu Pro Pro Gly Tyr Asp His Lys Tyr Ile Phe Ser His Val
305                 310                 315                 320

Gly Tyr Asn Leu Lys Ser Thr Asp Leu Gln Ala Ala Leu Gly Leu Ser
                325                 330                 335

Gln Leu Thr Arg Ile Glu Glu Phe Thr Glu Ala Arg Arg Ala Asn Trp
            340                 345                 350

Arg His Leu Arg Ala Ala Leu Asp Gly Leu Pro Gly Leu Leu Leu Pro
            355                 360                 365

His Ala Thr Pro Gly Ser Asp Pro Ser Trp Phe Gly Phe Leu Ile Thr
            370                 375                 380

Val Asp Pro Asp Ala Ala Tyr Ser Arg Ala Ala Leu Val Asp His Leu
385                 390                 395                 400

Glu Ser Arg Arg Ile Ser Thr Arg Arg Leu Phe Gly Gly Asn Leu Val
            405                 410                 415

Arg His Pro Ala Tyr Thr Asp Arg Arg Tyr Arg Val Ser Gly Ser Leu
            420                 425                 430

Glu Asn Ser Asp Leu Ile Thr Asp Gln Thr Phe Trp Ile Gly Val Phe
```

-continued

```
                435                 440                 445
Pro Gly Ile Thr Pro Glu Met Ile Ala Tyr Val Gly Asp Thr Ile Arg
    450                 455                 460
Glu Phe Val Leu Lys His Ser
465                 470

<210> SEQ ID NO 56
<211> LENGTH: 464
<212> TYPE: PRT
<213> ORGANISM: Streptomyces ambofaciens

<400> SEQUENCE: 56

Val Met Gln Ser Asp Arg Asp Arg Leu Ser Gly Gly Arg Met Pro
1               5                   10                  15

Ser Leu Gly Ser Asn His Ser Gly Leu Ser Arg Glu Gly Ser Thr Met
                20                  25                  30

Gly Asp Leu Arg Asn Arg Ile Thr Glu Leu Val Arg Ala Tyr His Arg
            35                  40                  45

Glu Gln Ala Pro Gly Gly Phe Val Pro Gly Thr Thr His Val Pro Val
        50                  55                  60

Ser Gly Ala Val Leu Ser Glu Glu Asp Arg Leu Ala Leu Val Glu Thr
65                  70                  75                  80

Ala Leu Glu Met Arg Ile Ala Ala Gly Pro Ala Ser Arg Gly Phe Glu
                85                  90                  95

Arg Gln Phe Ala Arg Tyr Leu Gly Leu Arg Lys Ala His Leu Thr Asn
            100                 105                 110

Ser Gly Ser Ser Ala Asn Leu Leu Ala Leu Gly Ala Leu Thr Ser Pro
        115                 120                 125

Gln Leu Glu Glu Arg Arg Leu Arg Pro Gly Asp Glu Val Val Thr Val
    130                 135                 140

Ala Ala Gly Phe Pro Thr Thr Val Asn Pro Ile Phe His Asn Gly Leu
145                 150                 155                 160

Val Pro Val Phe Val Asp Val Glu Leu Gly Thr Tyr Asn Thr Thr Pro
                165                 170                 175

Glu Arg Ile Glu Arg Ala Ile Gly Pro Arg Thr Arg Ala Ile Met Ile
            180                 185                 190

Ala His Ala Leu Gly Asn Pro Phe Glu Ala Glu Val Ala Arg Leu
        195                 200                 205

Ala Asp Glu Arg Glu Leu Phe Leu Ile Glu Asp Asn Cys Asp Ala Val
    210                 215                 220

Gly Ser Arg Tyr Arg Gly Arg Leu Thr Gly Ser Phe Gly Asp Leu Ser
225                 230                 235                 240

Thr Val Ser Phe Tyr Pro Ala His His Ile Ala Met Gly Glu Gly Gly
                245                 250                 255

Cys Val Leu Thr Asp Asn Leu Ala Leu Ala Arg Ile Val Glu Ser Leu
            260                 265                 270

Arg Asp Trp Gly Arg Asp Cys Trp Cys Glu Pro Gly Glu Asp Asn Arg
        275                 280                 285

Cys Leu Lys Arg Phe Asp Gln Lys Met Gly Asp Leu Pro Pro Gly Tyr
    290                 295                 300

Asp His Lys Tyr Ile Phe Ser His Val Gly Tyr Asn Leu Lys Ser Thr
305                 310                 315                 320

Asp Leu Gln Ala Ala Leu Gly Leu Ser Gln Leu Thr Arg Ile Glu Glu
                325                 330                 335
```

```
Phe Thr Glu Ala Arg Arg Ala Asn Trp Arg His Leu Arg Ala Ala Leu
            340                 345                 350

Asp Gly Leu Pro Gly Leu Leu Pro His Ala Thr Pro Gly Ser Asp
            355                 360                 365

Pro Ser Trp Phe Gly Phe Leu Ile Thr Val Asp Pro Asp Ala Ala Tyr
            370                 375                 380

Ser Arg Ala Ala Leu Val Asp His Leu Glu Ser Arg Arg Ile Ser Thr
385                 390                 395                 400

Arg Arg Leu Phe Gly Gly Asn Leu Val Arg His Pro Ala Tyr Thr Asp
            405                 410                 415

Arg Arg Tyr Arg Val Ser Gly Ser Leu Glu Asn Ser Asp Leu Ile Thr
            420                 425                 430

Asp Gln Thr Phe Trp Ile Gly Val Phe Pro Gly Ile Thr Pro Glu Met
            435                 440                 445

Ile Ala Tyr Val Gly Asp Thr Ile Arg Glu Phe Val Leu Lys His Ser
            450                 455                 460

<210> SEQ ID NO 57
<211> LENGTH: 463
<212> TYPE: PRT
<213> ORGANISM: Streptomyces ambofaciens

<400> SEQUENCE: 57

Met Gln Ser Asp Arg Asp Asp Arg Leu Ser Gly Gly Arg Met Pro Ser
1               5                   10                  15

Leu Gly Ser Asn His Ser Gly Leu Ser Arg Glu Gly Ser Thr Met Gly
            20                  25                  30

Asp Leu Arg Asn Arg Ile Thr Glu Leu Val Arg Ala Tyr His Arg Glu
        35                  40                  45

Gln Ala Pro Gly Gly Phe Val Pro Gly Thr Thr His Val Pro Val Ser
    50                  55                  60

Gly Ala Val Leu Ser Glu Asp Arg Leu Ala Leu Val Glu Thr Ala
65                  70                  75                  80

Leu Glu Met Arg Ile Ala Ala Gly Pro Ala Ser Arg Gly Phe Glu Arg
                85                  90                  95

Gln Phe Ala Arg Tyr Leu Gly Leu Arg Lys Ala His Leu Thr Asn Ser
            100                 105                 110

Gly Ser Ser Ala Asn Leu Leu Ala Leu Gly Ala Leu Thr Ser Pro Gln
        115                 120                 125

Leu Glu Glu Arg Arg Leu Arg Pro Gly Asp Glu Val Val Thr Val Ala
    130                 135                 140

Ala Gly Phe Pro Thr Thr Val Asn Pro Ile Phe His Asn Gly Leu Val
145                 150                 155                 160

Pro Val Phe Val Asp Val Glu Leu Gly Thr Tyr Asn Thr Thr Pro Glu
                165                 170                 175

Arg Ile Glu Arg Ala Ile Gly Pro Arg Thr Arg Ala Ile Met Ile Ala
            180                 185                 190

His Ala Leu Gly Asn Pro Phe Glu Ala Glu Val Ala Arg Leu Ala
        195                 200                 205

Asp Glu Arg Glu Leu Phe Leu Ile Glu Asp Asn Cys Asp Ala Val Gly
    210                 215                 220

Ser Arg Tyr Arg Gly Arg Leu Thr Gly Ser Phe Gly Asp Leu Ser Thr
225                 230                 235                 240

Val Ser Phe Tyr Pro Ala His His Ile Ala Met Gly Glu Gly Gly Cys
                245                 250                 255
```

Val Leu Thr Asp Asn Leu Ala Leu Ala Arg Ile Val Glu Ser Leu Arg
        260                 265                 270

Asp Trp Gly Arg Asp Cys Trp Cys Glu Pro Gly Glu Asp Asn Arg Cys
        275                 280                 285

Leu Lys Arg Phe Asp Gln Lys Met Gly Asp Leu Pro Pro Gly Tyr Asp
        290                 295                 300

His Lys Tyr Ile Phe Ser His Val Gly Tyr Asn Leu Lys Ser Thr Asp
305                 310                 315                 320

Leu Gln Ala Ala Leu Gly Leu Ser Gln Leu Thr Arg Ile Glu Glu Phe
                325                 330                 335

Thr Glu Ala Arg Arg Ala Asn Trp Arg His Leu Arg Ala Ala Leu Asp
            340                 345                 350

Gly Leu Pro Gly Leu Leu Pro His Ala Thr Pro Gly Ser Asp Pro
        355                 360                 365

Ser Trp Phe Gly Phe Leu Ile Thr Val Asp Pro Asp Ala Ala Tyr Ser
    370                 375                 380

Arg Ala Ala Leu Val Asp His Leu Glu Ser Arg Ile Ser Thr Arg
385                 390                 395                 400

Arg Leu Phe Gly Gly Asn Leu Val Arg His Pro Ala Tyr Thr Asp Arg
                405                 410                 415

Arg Tyr Arg Val Ser Gly Ser Leu Glu Asn Ser Asp Leu Ile Thr Asp
            420                 425                 430

Gln Thr Phe Trp Ile Gly Val Phe Pro Gly Ile Thr Pro Glu Met Ile
        435                 440                 445

Ala Tyr Val Gly Asp Thr Ile Arg Glu Phe Val Leu Lys His Ser
    450                 455                 460

<210> SEQ ID NO 58
<211> LENGTH: 450
<212> TYPE: PRT
<213> ORGANISM: Streptomyces ambofaciens

<400> SEQUENCE: 58

Met Pro Ser Leu Gly Ser Asn His Ser Gly Leu Ser Arg Glu Gly Ser
1               5                   10                  15

Thr Met Gly Asp Leu Arg Asn Arg Ile Thr Glu Leu Val Arg Ala Tyr
            20                  25                  30

His Arg Glu Gln Ala Pro Gly Gly Phe Val Pro Gly Thr Thr His Val
        35                  40                  45

Pro Val Ser Gly Ala Val Leu Ser Glu Glu Asp Arg Leu Ala Leu Val
    50                  55                  60

Glu Thr Ala Leu Glu Met Arg Ile Ala Ala Gly Pro Ala Ser Arg Gly
65                  70                  75                  80

Phe Glu Arg Gln Phe Ala Arg Tyr Leu Gly Leu Arg Lys Ala His Leu
                85                  90                  95

Thr Asn Ser Gly Ser Ser Ala Asn Leu Leu Ala Leu Gly Ala Leu Thr
            100                 105                 110

Ser Pro Gln Leu Glu Glu Arg Leu Arg Pro Gly Asp Glu Val Val
        115                 120                 125

Thr Val Ala Ala Gly Phe Pro Thr Thr Val Asn Pro Ile Phe His Asn
    130                 135                 140

Gly Leu Val Pro Val Phe Val Asp Val Glu Leu Gly Thr Tyr Asn Thr
145                 150                 155                 160

Thr Pro Glu Arg Ile Glu Arg Ala Ile Gly Pro Arg Thr Arg Ala Ile

```
                    165                 170                 175
Met Ile Ala His Ala Leu Gly Asn Pro Phe Glu Ala Glu Val Ala
                180                 185                 190

Arg Leu Ala Asp Glu Arg Glu Leu Phe Leu Ile Glu Asp Asn Cys Asp
            195                 200                 205

Ala Val Gly Ser Arg Tyr Arg Gly Arg Leu Thr Gly Ser Phe Gly Asp
        210                 215                 220

Leu Ser Thr Val Ser Phe Tyr Pro Ala His His Ile Ala Met Gly Glu
225                 230                 235                 240

Gly Gly Cys Val Leu Thr Asp Asn Leu Ala Leu Ala Arg Ile Val Glu
                245                 250                 255

Ser Leu Arg Asp Trp Gly Arg Asp Cys Trp Cys Glu Pro Gly Glu Asp
            260                 265                 270

Asn Arg Cys Leu Lys Arg Phe Asp Gln Lys Met Gly Asp Leu Pro Pro
        275                 280                 285

Gly Tyr Asp His Lys Tyr Ile Phe Ser His Val Gly Tyr Asn Leu Lys
        290                 295                 300

Ser Thr Asp Leu Gln Ala Ala Leu Gly Leu Ser Gln Leu Thr Arg Ile
305                 310                 315                 320

Glu Glu Phe Thr Glu Ala Arg Arg Ala Asn Trp Arg His Leu Arg Ala
                325                 330                 335

Ala Leu Asp Gly Leu Pro Gly Leu Leu Leu Pro His Ala Thr Pro Gly
            340                 345                 350

Ser Asp Pro Ser Trp Phe Gly Phe Leu Ile Thr Val Asp Pro Asp Ala
        355                 360                 365

Ala Tyr Ser Arg Ala Ala Leu Val Asp His Leu Glu Ser Arg Arg Ile
        370                 375                 380

Ser Thr Arg Arg Leu Phe Gly Gly Asn Leu Val Arg His Pro Ala Tyr
385                 390                 395                 400

Thr Asp Arg Arg Tyr Arg Val Ser Gly Ser Leu Glu Asn Ser Asp Leu
                405                 410                 415

Ile Thr Asp Gln Thr Phe Trp Ile Gly Val Phe Pro Gly Ile Thr Pro
            420                 425                 430

Glu Met Ile Ala Tyr Val Gly Asp Thr Ile Arg Glu Phe Val Leu Lys
        435                 440                 445

His Ser
    450

<210> SEQ ID NO 59
<211> LENGTH: 433
<212> TYPE: PRT
<213> ORGANISM: Streptomyces ambofaciens

<400> SEQUENCE: 59

Met Gly Asp Leu Arg Asn Arg Ile Thr Glu Leu Val Arg Ala Tyr His
1               5                   10                  15

Arg Glu Gln Ala Pro Gly Gly Phe Val Pro Gly Thr Thr His Val Pro
            20                  25                  30

Val Ser Gly Ala Val Leu Ser Glu Glu Asp Arg Leu Ala Leu Val Glu
        35                  40                  45

Thr Ala Leu Glu Met Arg Ile Ala Ala Gly Pro Ala Ser Arg Gly Phe
    50                  55                  60

Glu Arg Gln Phe Ala Arg Tyr Leu Gly Leu Arg Lys Ala His Leu Thr
65                  70                  75                  80
```

```
Asn Ser Gly Ser Ser Ala Asn Leu Leu Ala Leu Gly Ala Leu Thr Ser
                85                  90                  95

Pro Gln Leu Glu Glu Arg Arg Leu Arg Pro Gly Asp Glu Val Val Thr
            100                 105                 110

Val Ala Ala Gly Phe Pro Thr Thr Val Asn Pro Ile Phe His Asn Gly
        115                 120                 125

Leu Val Pro Val Phe Val Asp Val Glu Leu Gly Thr Tyr Asn Thr Thr
    130                 135                 140

Pro Glu Arg Ile Glu Arg Ala Ile Gly Pro Arg Thr Arg Ala Ile Met
145                 150                 155                 160

Ile Ala His Ala Leu Gly Asn Pro Phe Glu Ala Glu Val Ala Arg
                165                 170                 175

Leu Ala Asp Glu Arg Glu Leu Phe Leu Ile Glu Asp Asn Cys Asp Ala
            180                 185                 190

Val Gly Ser Arg Tyr Arg Gly Arg Leu Thr Gly Ser Phe Gly Asp Leu
        195                 200                 205

Ser Thr Val Ser Phe Tyr Pro Ala His His Ile Ala Met Gly Glu Gly
    210                 215                 220

Gly Cys Val Leu Thr Asp Asn Leu Ala Leu Ala Arg Ile Val Glu Ser
225                 230                 235                 240

Leu Arg Asp Trp Gly Arg Asp Cys Trp Cys Glu Pro Gly Glu Asp Asn
                245                 250                 255

Arg Cys Leu Lys Arg Phe Asp Gln Lys Met Gly Asp Leu Pro Pro Gly
            260                 265                 270

Tyr Asp His Lys Tyr Ile Phe Ser His Val Gly Tyr Asn Leu Lys Ser
        275                 280                 285

Thr Asp Leu Gln Ala Ala Leu Gly Leu Ser Gln Leu Thr Arg Ile Glu
    290                 295                 300

Glu Phe Thr Glu Ala Arg Arg Ala Asn Trp Arg His Leu Arg Ala Ala
305                 310                 315                 320

Leu Asp Gly Leu Pro Gly Leu Leu Pro His Ala Thr Pro Gly Ser
                325                 330                 335

Asp Pro Ser Trp Phe Gly Phe Leu Ile Thr Val Asp Pro Asp Ala Ala
            340                 345                 350

Tyr Ser Arg Ala Ala Leu Val Asp His Leu Glu Ser Arg Arg Ile Ser
        355                 360                 365

Thr Arg Arg Leu Phe Gly Gly Asn Leu Val Arg His Pro Ala Tyr Thr
    370                 375                 380

Asp Arg Arg Tyr Arg Val Ser Gly Ser Leu Glu Asn Ser Asp Leu Ile
385                 390                 395                 400

Thr Asp Gln Thr Phe Trp Ile Gly Val Phe Pro Gly Ile Thr Pro Glu
                405                 410                 415

Met Ile Ala Tyr Val Gly Asp Thr Ile Arg Glu Phe Val Leu Lys His
            420                 425                 430

Ser

<210> SEQ ID NO 60
<211> LENGTH: 1398
<212> TYPE: DNA
<213> ORGANISM: Streptomyces ambofaciens
<220> FEATURE:
<221> NAME/KEY: CDS
<222> LOCATION: (1)..(1398)

<400> SEQUENCE: 60
```

-continued

| | |
|---|---|
| atg gac gac acg atg gcc ggc gcc gac gcc gag gaa tgg gac ggc gat<br>Met Asp Asp Thr Met Ala Gly Ala Asp Ala Glu Glu Trp Asp Gly Asp<br>1                         5                        10                     15 | 48 |
| cag tta gac cgc gag gac cgg gcc tcc ctc cgc cgt gtc gcg ggg ctc<br>Gln Leu Asp Arg Glu Asp Arg Ala Ser Leu Arg Arg Val Ala Gly Leu<br>                  20                        25                        30 | 96 |
| tcc acc gaa ctg acc gac gtc tcc gag gtc gag tac cgc cag ctg cga<br>Ser Thr Glu Leu Thr Asp Val Ser Glu Val Glu Tyr Arg Gln Leu Arg<br>             35                        40                        45 | 144 |
| ctc gag cgg gtg gtg ctc gtc ggc atc tgg acc tcg gga acg gcc gcg<br>Leu Glu Arg Val Val Leu Val Gly Ile Trp Thr Ser Gly Thr Ala Ala<br>     50                        55                        60 | 192 |
| gag gcc gac agt tcg ctc gcc gag ctg gcg gcg ctc gcc gag acc gcg<br>Glu Ala Asp Ser Ser Leu Ala Glu Leu Ala Ala Leu Ala Glu Thr Ala<br>65                        70                        75                        80 | 240 |
| ggc gcc ctc gtg ctg gac ggc gtc gtg cag cgc cgg cag aag ccg gac<br>Gly Ala Leu Val Leu Asp Gly Val Val Gln Arg Arg Gln Lys Pro Asp<br>                            85                        90                        95 | 288 |
| ccg gcg acg tac atc ggc tcg ggc aag gcg tcg cag ctg cgc gac atc<br>Pro Ala Thr Tyr Ile Gly Ser Gly Lys Ala Ser Gln Leu Arg Asp Ile<br>                  100                       105                      110 | 336 |
| gtc gag gag acc ggc gcc gac acc gtg gtg tgc gac ggg gaa ctg agc<br>Val Glu Glu Thr Gly Ala Asp Thr Val Val Cys Asp Gly Glu Leu Ser<br>        115                       120                       125 | 384 |
| ccc agt cag ctg atg cac ctg gag gag gtc gtc ggg gtc aag gtc gtg<br>Pro Ser Gln Leu Met His Leu Glu Glu Val Val Gly Val Lys Val Val<br>130                        135                       140 | 432 |
| gac cgc acg gcc ctg atc ctg gac atc ttc gcg cag cac gcc cag tcc<br>Asp Arg Thr Ala Leu Ile Leu Asp Ile Phe Ala Gln His Ala Gln Ser<br>145                        150                       155                  160 | 480 |
| cgg gag ggc aag gcg cag gtg gcg ctg gcg cag atg cag tac atg ctg<br>Arg Glu Gly Lys Ala Gln Val Ala Leu Ala Gln Met Gln Tyr Met Leu<br>                  165                       170                      175 | 528 |
| ccg cgg ctg cgc ggc tgg ggc cag tcg ctg tcc cgg cag atg ggc ggc<br>Pro Arg Leu Arg Gly Trp Gly Gln Ser Leu Ser Arg Gln Met Gly Gly<br>        180                       185                       190 | 576 |
| ggt ggc ggc ggt ggc atg gcc acg cgc ggt ccc ggt gag acg aag atc<br>Gly Gly Gly Gly Gly Met Ala Thr Arg Gly Pro Gly Glu Thr Lys Ile<br>195                        200                       205 | 624 |
| gag acg gac cgg cgg cgg atc aac gac aag atg gcc agg ctc cgc cgg<br>Glu Thr Asp Arg Arg Arg Ile Asn Asp Lys Met Ala Arg Leu Arg Arg<br>210                        215                       220 | 672 |
| gag ctg gag cag ctg aag acc ggc cgg gac gtg aac cgg gag gag cga<br>Glu Leu Glu Gln Leu Lys Thr Gly Arg Asp Val Asn Arg Glu Glu Arg<br>225                        230                       235                      240 | 720 |
| cgg cgc aac aag gtg ctg tcg gtc gcc ctc gcc ggc tac acc aac gcc<br>Arg Arg Asn Lys Val Leu Ser Val Ala Leu Ala Gly Tyr Thr Asn Ala<br>                      245                       250                      255 | 768 |
| ggc aag tca tcg ctg ctc aac cgc ctc acc gga gcc ggc gtg ctg gtg<br>Gly Lys Ser Ser Leu Leu Asn Arg Leu Thr Gly Ala Gly Val Leu Val<br>                260                       265                      270 | 816 |
| gag aac gcc ctg ttc gcc acc ctg gac acg acc gtg cgg cgg gcg acg<br>Glu Asn Ala Leu Phe Ala Thr Leu Asp Thr Thr Val Arg Arg Ala Thr<br>        275                       280                       285 | 864 |
| acg ccg agc ggg cgc ccc tac acc atc gcc gac acc gtg ggc ttc gta<br>Thr Pro Ser Gly Arg Pro Tyr Thr Ile Ala Asp Thr Val Gly Phe Val<br>290                        295                       300 | 912 |
| cgc cac ctc ccg cac cac ctg gtg gag gcg ttc cgt tcc acg atc gaa<br>Arg His Leu Pro His His Leu Val Glu Ala Phe Arg Ser Thr Ile Glu<br>305                        310                       315                  320 | 960 |

```
gag gtc gcg gac gcg cat ctg gtg ctg cac gtg gtc gac ggt tcg cac        1008
Glu Val Ala Asp Ala His Leu Val Leu His Val Val Asp Gly Ser His
                325                 330                 335 ccg gac ccc ggc gcg cag ctg gcc tcg gtg cgc gag gtg ctg cgg gac        1056
Pro Asp Pro Gly Ala Gln Leu Ala Ser Val Arg Glu Val Leu Arg Asp
            340                 345                 350 gtg ggc gcc ggc gag tcc acc gag gtc gtg gtc gtc aac aag gcc gat        1104
Val Gly Ala Gly Glu Ser Thr Glu Val Val Val Val Asn Lys Ala Asp
        355                 360                 365 gtc gcg gac ccg gac gtc ctc gcc cgt ctg ctg gag cag gag ccg gac        1152
Val Ala Asp Pro Asp Val Leu Ala Arg Leu Leu Glu Gln Glu Pro Asp
    370                 375                 380 gcg atc gtc gtg tcc gcc cgt tcg ggt cgg ggc atc gac gag ctg cgg        1200
Ala Ile Val Val Ser Ala Arg Ser Gly Arg Gly Ile Asp Glu Leu Arg
385                 390                 395                 400 gaa ctg atc gac cgc ctg ctg ccg cac ccc gag gtg gag gtg gag gtc        1248
Glu Leu Ile Asp Arg Leu Leu Pro His Pro Glu Val Glu Val Glu Val
                405                 410                 415 gtg atc ccc tac gac gag ggg agc ctg gtg gcg cgg gtg cac gac gag        1296
Val Ile Pro Tyr Asp Glu Gly Ser Leu Val Ala Arg Val His Asp Glu
            420                 425                 430 ggc gag gtg ctc agc acc gag cac acg ccg gag ggc acc ctg ctc acc        1344
Gly Glu Val Leu Ser Thr Glu His Thr Pro Glu Gly Thr Leu Leu Thr
        435                 440                 445 gcg cgg gtc cac ccc gac ctc gcc tcg gag ctt cgg acg ctt ccg cgg        1392
Ala Arg Val His Pro Asp Leu Ala Ser Glu Leu Arg Thr Leu Pro Arg
    450                 455                 460 ccg tga                                                                 1398
Pro
465

<210> SEQ ID NO 61
<211> LENGTH: 465
<212> TYPE: PRT
<213> ORGANISM: Streptomyces ambofaciens

<400> SEQUENCE: 61

Met Asp Asp Thr Met Ala Gly Ala Asp Ala Glu Glu Trp Asp Gly Asp
1               5                   10                  15

Gln Leu Asp Arg Glu Asp Arg Ala Ser Leu Arg Arg Val Ala Gly Leu
            20                  25                  30

Ser Thr Glu Leu Thr Asp Val Ser Glu Val Glu Tyr Arg Gln Leu Arg
        35                  40                  45

Leu Glu Arg Val Val Leu Val Gly Ile Trp Thr Ser Gly Thr Ala Ala
    50                  55                  60

Glu Ala Asp Ser Ser Leu Ala Glu Leu Ala Ala Leu Ala Glu Thr Ala
65                  70                  75                  80

Gly Ala Leu Val Leu Asp Gly Val Val Gln Arg Gln Lys Pro Asp
                85                  90                  95

Pro Ala Thr Tyr Ile Gly Ser Gly Lys Ala Ser Gln Leu Arg Asp Ile
            100                 105                 110

Val Glu Glu Thr Gly Ala Asp Thr Val Val Cys Asp Gly Glu Leu Ser
        115                 120                 125

Pro Ser Gln Leu Met His Leu Glu Glu Val Val Gly Val Lys Val Val
    130                 135                 140

Asp Arg Thr Ala Leu Ile Leu Asp Ile Phe Ala Gln His Ala Gln Ser
145                 150                 155                 160
```

```
Arg Glu Gly Lys Ala Gln Val Ala Leu Ala Gln Met Gln Tyr Met Leu
            165                 170                 175

Pro Arg Leu Arg Gly Trp Gly Gln Ser Leu Ser Arg Gln Met Gly Gly
        180                 185                 190

Gly Gly Gly Gly Met Ala Thr Arg Gly Pro Gly Glu Thr Lys Ile
        195                 200                 205

Glu Thr Asp Arg Arg Ile Asn Asp Lys Met Ala Arg Leu Arg Arg
    210                 215                 220

Glu Leu Glu Gln Leu Lys Thr Gly Arg Asp Val Asn Arg Glu Glu Arg
225                 230                 235                 240

Arg Arg Asn Lys Val Leu Ser Val Ala Leu Ala Gly Tyr Thr Asn Ala
                245                 250                 255

Gly Lys Ser Ser Leu Leu Asn Arg Leu Thr Gly Ala Gly Val Leu Val
                260                 265                 270

Glu Asn Ala Leu Phe Ala Thr Leu Asp Thr Thr Val Arg Arg Ala Thr
            275                 280                 285

Thr Pro Ser Gly Arg Pro Tyr Thr Ile Ala Asp Thr Val Gly Phe Val
        290                 295                 300

Arg His Leu Pro His His Leu Val Glu Ala Phe Arg Ser Thr Ile Glu
305                 310                 315                 320

Glu Val Ala Asp Ala His Leu Val Leu His Val Val Asp Gly Ser His
                325                 330                 335

Pro Asp Pro Gly Ala Gln Leu Ala Ser Val Arg Glu Val Leu Arg Asp
                340                 345                 350

Val Gly Ala Gly Glu Ser Thr Glu Val Val Val Asn Lys Ala Asp
            355                 360                 365

Val Ala Asp Pro Asp Val Leu Ala Arg Leu Leu Glu Gln Glu Pro Asp
        370                 375                 380

Ala Ile Val Val Ser Ala Arg Ser Gly Arg Gly Ile Asp Glu Leu Arg
385                 390                 395                 400

Glu Leu Ile Asp Arg Leu Leu Pro His Pro Glu Val Glu Val Glu Val
                405                 410                 415

Val Ile Pro Tyr Asp Glu Gly Ser Leu Val Ala Arg Val His Asp Glu
                420                 425                 430

Gly Glu Val Leu Ser Thr Glu His Thr Pro Glu Gly Thr Leu Leu Thr
            435                 440                 445

Ala Arg Val His Pro Asp Leu Ala Ser Glu Leu Arg Thr Leu Pro Arg
        450                 455                 460

Pro
465

<210> SEQ ID NO 62
<211> LENGTH: 1044
<212> TYPE: DNA
<213> ORGANISM: Streptomyces ambofaciens
<220> FEATURE:
<221> NAME/KEY: CDS
<222> LOCATION: (1)..(1044)

<400> SEQUENCE: 62 atg cga gta ctc att atc ggg ggt tca cag ttc gtg ggc cgg gcc ttc      48
Met Arg Val Leu Ile Ile Gly Gly Ser Gln Phe Val Gly Arg Ala Phe
1               5                   10                  15 gcc gcc gag gca ctg gcc gcg ggg cac cgg gtc acc acg ttc aac cgg      96
Ala Ala Glu Ala Leu Ala Ala Gly His Arg Val Thr Thr Phe Asn Arg
            20                  25                  30
```

-continued

| | | |
|---|---|---|
| ggt gtc agc ggc acc gac ctg ccc ggc gtc gag gcg gtc agg ggc gac<br>Gly Val Ser Gly Thr Asp Leu Pro Gly Val Glu Ala Val Arg Gly Asp<br>35                     40                    45 | 144 | |
| cgc gag gtg gcc ggc gac ctg gag cgg ctg gtg tcc gga agg cac tgg<br>Arg Glu Val Ala Gly Asp Leu Glu Arg Leu Val Ser Gly Arg His Trp<br>50                     55                    60 | 192 | |
| gac gcg gtc gtg gac acc tgc ggt tac gtg ccc cgc acg gtg ggg gcc<br>Asp Ala Val Val Asp Thr Cys Gly Tyr Val Pro Arg Thr Val Gly Ala<br>65                  70                    75                    80 | 240 | |
| tcg gcc gcg gcg ctg tcc ggg cac gcg gac acc tac ctc tac gtc tcc<br>Ser Ala Ala Ala Leu Ser Gly His Ala Asp Thr Tyr Leu Tyr Val Ser<br>                    85                    90                    95 | 288 | |
| agc atc gcc tgc ctg ccc gac tgg gcg cag gcg gtc cgt ccg gtg gac<br>Ser Ile Ala Cys Leu Pro Asp Trp Ala Gln Ala Val Arg Pro Val Asp<br>                  100                  105                 110 | 336 | |
| gac gac tca cct gcc cac gac tgc ccg ccg gac gcc gga ccg gac cac<br>Asp Asp Ser Pro Ala His Asp Cys Pro Pro Asp Ala Gly Pro Asp His<br>                  115                  120                 125 | 384 | |
| gcc gac ggt gac tac ggc gtc ctg aag gcc ggc tgc gag cgc gcc gtg<br>Ala Asp Gly Asp Tyr Gly Val Leu Lys Ala Gly Cys Glu Arg Ala Val<br>130                     135                  140 | 432 | |
| gac cgg cac ttc gcg ggc cgg acc ctg cac ctg cgg gcc ggt gtc atc<br>Asp Arg His Phe Ala Gly Arg Thr Leu His Leu Arg Ala Gly Val Ile<br>145                     150                  155                 160 | 480 | |
| ctc ggg ccg cac gac acc atg cgc atg ctc gac gcc tgg ctg tgg cgc<br>Leu Gly Pro His Asp Thr Met Arg Met Leu Asp Ala Trp Leu Trp Arg<br>                  165                  170                 175 | 528 | |
| atg cgc gtc gcc gag ggg gag cac cgc cgg gtg ctc gcc ccg ggc aac<br>Met Arg Val Ala Glu Gly Glu His Arg Arg Val Leu Ala Pro Gly Asn<br>                    180                  185                 190 | 576 | |
| ccc gag gtg ggc atg cgc ctg atc gac gta cgc gat gtc gcc gtc ttc<br>Pro Glu Val Gly Met Arg Leu Ile Asp Val Arg Asp Val Ala Val Phe<br>                  195                  200                 205 | 624 | |
| ggc ctc gac tgc ctc gcg gac ggc cgt acc ggc gcc ttc atc gtc aac<br>Gly Leu Asp Cys Leu Ala Asp Gly Arg Thr Gly Ala Phe Ile Val Asn<br>210                     215                  220 | 672 | |
| ccg ccg gag aag aac acc acc ttc ggg gag ttg ctc acg gag tgc gtc<br>Pro Pro Glu Lys Asn Thr Thr Phe Gly Glu Leu Leu Thr Glu Cys Val<br>225                     230                  235                 240 | 720 | |
| aag gcc acc ggt tcg gcc gcg gag ccg gtg tgg gtc gac gag ggg ttc<br>Lys Ala Thr Gly Ser Ala Ala Glu Pro Val Trp Val Asp Glu Gly Phe<br>                    245                  250                 255 | 768 | |
| ctc gcc gag cac ggc gtg agt ccg tgg acg gac ctg ccg atg tgg gtg<br>Leu Ala Glu His Gly Val Ser Pro Trp Thr Asp Leu Pro Met Trp Val<br>                  260                  265                 270 | 816 | |
| ccc gac acc gcg cgg gac acc ctc gtg tgg gcg gcc gga gca ccg cgc<br>Pro Asp Thr Ala Arg Asp Thr Leu Val Trp Ala Ala Gly Ala Pro Arg<br>275                     280                  285 | 864 | |
| gcc cgg gcc gcg ggt ctg gcc tgc cgg ccc ttc tcc gac acc gtg cgg<br>Ala Arg Ala Ala Gly Leu Ala Cys Arg Pro Phe Ser Asp Thr Val Arg<br>290                     295                  300 | 912 | |
| gac gcc tgg gag gtc gtc cgg gac cgg ccc gtc ccg gaa ctg ccg ctc<br>Asp Ala Trp Glu Val Val Arg Asp Arg Pro Val Pro Glu Leu Pro Leu<br>305                     310                  315                 320 | 960 | |
| gcg gcc ggc tgc ggc ctg tcc ctg agc cgg gag aag gag ctg ctc gcc<br>Ala Ala Gly Cys Gly Leu Ser Leu Ser Arg Glu Lys Glu Leu Leu Ala<br>                    325                  330                 335 | 1008 | |
| gcc tgg gac gct cgc ggc ggt gcg gcg gcg ggc tga<br>Ala Trp Asp Ala Arg Gly Gly Ala Ala Ala Gly<br>                    340                  345 | 1044 | |

<210> SEQ ID NO 63
<211> LENGTH: 347
<212> TYPE: PRT
<213> ORGANISM: Streptomyces ambofaciens

<400> SEQUENCE: 63

Met Arg Val Leu Ile Ile Gly Gly Ser Gln Phe Val Gly Arg Ala Phe
1               5                   10                  15

Ala Ala Glu Ala Leu Ala Ala Gly His Arg Val Thr Thr Phe Asn Arg
            20                  25                  30

Gly Val Ser Gly Thr Asp Leu Pro Gly Val Glu Ala Val Arg Gly Asp
        35                  40                  45

Arg Glu Val Ala Gly Asp Leu Glu Arg Leu Val Ser Gly Arg His Trp
    50                  55                  60

Asp Ala Val Val Asp Thr Cys Gly Tyr Val Pro Arg Thr Val Gly Ala
65                  70                  75                  80

Ser Ala Ala Leu Ser Gly His Ala Asp Thr Tyr Leu Tyr Val Ser
                85                  90                  95

Ser Ile Ala Cys Leu Pro Asp Trp Ala Gln Ala Val Arg Pro Val Asp
            100                 105                 110

Asp Asp Ser Pro Ala His Asp Cys Pro Pro Asp Ala Gly Pro Asp His
        115                 120                 125

Ala Asp Gly Asp Tyr Gly Val Leu Lys Ala Gly Cys Glu Arg Ala Val
    130                 135                 140

Asp Arg His Phe Ala Gly Arg Thr Leu His Leu Arg Ala Gly Val Ile
145                 150                 155                 160

Leu Gly Pro His Asp Thr Met Arg Met Leu Asp Ala Trp Leu Trp Arg
                165                 170                 175

Met Arg Val Ala Glu Gly Glu His Arg Arg Val Leu Ala Pro Gly Asn
            180                 185                 190

Pro Glu Val Gly Met Arg Leu Ile Asp Val Arg Asp Val Ala Val Phe
        195                 200                 205

Gly Leu Asp Cys Leu Ala Asp Gly Arg Thr Gly Ala Phe Ile Val Asn
    210                 215                 220

Pro Pro Glu Lys Asn Thr Thr Phe Gly Glu Leu Leu Thr Glu Cys Val
225                 230                 235                 240

Lys Ala Thr Gly Ser Ala Ala Glu Pro Val Trp Val Asp Glu Gly Phe
                245                 250                 255

Leu Ala Glu His Gly Val Ser Pro Trp Thr Asp Leu Pro Met Trp Val
            260                 265                 270

Pro Asp Thr Ala Arg Asp Thr Leu Val Trp Ala Ala Gly Ala Pro Arg
        275                 280                 285

Ala Arg Ala Ala Gly Leu Ala Cys Arg Pro Phe Ser Asp Thr Val Arg
    290                 295                 300

Asp Ala Trp Glu Val Val Arg Asp Arg Pro Val Pro Glu Leu Pro Leu
305                 310                 315                 320

Ala Ala Gly Cys Gly Leu Ser Leu Ser Arg Glu Lys Glu Leu Leu Ala
                325                 330                 335

Ala Trp Asp Ala Arg Gly Gly Ala Ala Gly
            340                 345

<210> SEQ ID NO 64
<211> LENGTH: 1041
<212> TYPE: DNA

```
<213> ORGANISM: Streptomyces ambofaciens
<220> FEATURE:
<221> NAME/KEY: CDS
<222> LOCATION: (1)..(1041)

<400> SEQUENCE: 64 atg acc gcc ctg ggt act tct gct gaa ccg ttc gcc gca ccc ggc ccg        48
Met Thr Ala Leu Gly Thr Ser Ala Glu Pro Phe Ala Ala Pro Gly Pro
 1               5                  10                  15 ccg cgg ccg gaa gcg tcc ccg gtg ctg cgc ttc gga gcg atc ggc tgc        96
Pro Arg Pro Glu Ala Ser Pro Val Leu Arg Phe Gly Ala Ile Gly Cys
             20                  25                  30 ggc gac atc gcg ggc cgt cgc acc ctg ccc gcc ctg ctc tcc acc ccc       144
Gly Asp Ile Ala Gly Arg Arg Thr Leu Pro Ala Leu Leu Ser Thr Pro
         35                  40                  45 ggc acc gtg ctg acc tgc gtc ggc agc cgc gac gcg gac cgg gcc aag       192
Gly Thr Val Leu Thr Cys Val Gly Ser Arg Asp Ala Asp Arg Ala Lys
 50                  55                  60 gcc ctg ggc agg cac ttc gac tgc gag gcg gtc gcg ccc tac gag gcc       240
Ala Leu Gly Arg His Phe Asp Cys Glu Ala Val Ala Pro Tyr Glu Ala
 65                  70                  75                  80 ctg ctg gaa cgc ccc gac gtg gac gcc gtc tac atc gcg gtg ccc agc       288
Leu Leu Glu Arg Pro Asp Val Asp Ala Val Tyr Ile Ala Val Pro Ser
                 85                  90                  95 atg ctg cac gcc gaa tgg gcc gcg gcg gcg ctg cgg gcg ggc aaa cac       336
Met Leu His Ala Glu Trp Ala Ala Ala Ala Leu Arg Ala Gly Lys His
            100                 105                 110 gtc ctc gtg gag aag ccc gcc gcc gcc aac cac gcc gac gcg gcc cgc       384
Val Leu Val Glu Lys Pro Ala Ala Ala Asn His Ala Asp Ala Ala Arg
        115                 120                 125 ctg ttc gcc atg gcc cgg gag cgc gga ctg gta ctg atg gag aac ttc       432
Leu Phe Ala Met Ala Arg Glu Arg Gly Leu Val Leu Met Glu Asn Phe
    130                 135                 140 atg ttc ctc cac cac tct caa cac gcc acc gtc aaa gcc ctg ttg gag       480
Met Phe Leu His His Ser Gln His Ala Thr Val Lys Ala Leu Leu Glu
145                 150                 155                 160 gcc ggt gcc atc gga gag ctg cgc acc ttc tcc gcc gcc ttc acc atc       528
Ala Gly Ala Ile Gly Glu Leu Arg Thr Phe Ser Ala Ala Phe Thr Ile
                165                 170                 175 ccg ccg cgc gcc gac gac gac atg cgc tac cga ccc gac atc ggc ggc       576
Pro Pro Arg Ala Asp Asp Asp Met Arg Tyr Arg Pro Asp Ile Gly Gly
            180                 185                 190 ggc gca ctg ctc gac aac ggc gtc tac ccg ctg cgg gcc gcg ctg cac       624
Gly Ala Leu Leu Asp Asn Gly Val Tyr Pro Leu Arg Ala Ala Leu His
        195                 200                 205 ttc ctc gga ccc gaa ctg cgc ctg acc ggc gcc gtg ctg cgc cgt gac       672
Phe Leu Gly Pro Glu Leu Arg Leu Thr Gly Ala Val Leu Arg Arg Asp
    210                 215                 220 cgc cgc cgg ggc gtc gtg gtc tcc ggc agc gtc ctg ctc gcc gcc ccc       720
Arg Arg Arg Gly Val Val Val Ser Gly Ser Val Leu Leu Ala Ala Pro
225                 230                 235                 240 cag ggc gtg gcc gcc cac ctc gcc ttc ggc atg gaa cac ggc tac cgc       768
Gln Gly Val Ala Ala His Leu Ala Phe Gly Met Glu His Gly Tyr Arg
                245                 250                 255 tcg gcg tac gag ctg cac ggc agc acc ggc tcg ctc gcc ctg agc cac       816
Ser Ala Tyr Glu Leu His Gly Ser Thr Gly Ser Leu Ala Leu Ser His
            260                 265                 270 gtc ttc acg acc ccg gac agc cac cac ccc gta ctg cgg ctg tcc cgc       864
Val Phe Thr Thr Pro Asp Ser His His Pro Val Leu Arg Leu Ser Arg
        275                 280                 285
```

| | | | | | | | | | | | | | | | | |
|---|---|---|---|---|---|---|---|---|---|---|---|---|---|---|---|---|
| cag | gac | cac | cgg | gag | gag | cgc | gtc | ctg | ccc | gtg | gac | cgg | cac | ttc | gtg | 912 |
| Gln | Asp | His | Arg | Glu | Glu | Arg | Val | Leu | Pro | Val | Asp | Arg | His | Phe | Val | |
| | 290 | | | | 295 | | | | | 300 | | | | | | |
| aac | atc | ctg | tcg | gtc | ttc | cgc | cgt | gcg | gtg | atc | cgg | gcc | gag | gac | gtc | 960 |
| Asn | Ile | Leu | Ser | Val | Phe | Arg | Arg | Ala | Val | Ile | Arg | Ala | Glu | Asp | Val | |
| 305 | | | | | 310 | | | | | 315 | | | | | 320 | |
| tcc | gcc | gag | tcg | tac | gcc | gcg | ctg | cgc | cag | gcg | ggg | ctg | gtc | gac | gag | 1008 |
| Ser | Ala | Glu | Ser | Tyr | Ala | Ala | Leu | Arg | Gln | Ala | Gly | Leu | Val | Asp | Glu | |
| | | | | 325 | | | | | 330 | | | | | 335 | | |
| atc | gtg | gcc | cgc | gcc | gag | acc | ttc | acc | gtg | tag | | | | | | 1041 |
| Ile | Val | Ala | Arg | Ala | Glu | Thr | Phe | Thr | Val | | | | | | | |
| | | | 340 | | | | | 345 | | | | | | | | |

<210> SEQ ID NO 65
<211> LENGTH: 346
<212> TYPE: PRT
<213> ORGANISM: Streptomyces ambofaciens

<400> SEQUENCE: 65

Met Thr Ala Leu Gly Thr Ser Ala Glu Pro Phe Ala Ala Pro Gly Pro
1               5                   10                  15

Pro Arg Pro Glu Ala Ser Pro Val Leu Arg Phe Gly Ala Ile Gly Cys
            20                  25                  30

Gly Asp Ile Ala Gly Arg Arg Thr Leu Pro Ala Leu Leu Ser Thr Pro
        35                  40                  45

Gly Thr Val Leu Thr Cys Val Gly Ser Arg Asp Ala Asp Arg Ala Lys
    50                  55                  60

Ala Leu Gly Arg His Phe Asp Cys Glu Ala Val Ala Pro Tyr Glu Ala
65                  70                  75                  80

Leu Leu Glu Arg Pro Asp Val Asp Ala Val Tyr Ile Ala Val Pro Ser
                85                  90                  95

Met Leu His Ala Glu Trp Ala Ala Ala Leu Arg Ala Gly Lys His
            100                 105                 110

Val Leu Val Glu Lys Pro Ala Ala Ala Asn His Ala Asp Ala Ala Arg
        115                 120                 125

Leu Phe Ala Met Ala Arg Glu Arg Gly Leu Val Leu Met Glu Asn Phe
    130                 135                 140

Met Phe Leu His His Ser Gln His Ala Thr Val Lys Ala Leu Leu Glu
145                 150                 155                 160

Ala Gly Ala Ile Gly Glu Leu Arg Thr Phe Ser Ala Ala Phe Thr Ile
                165                 170                 175

Pro Pro Arg Ala Asp Asp Met Arg Tyr Arg Pro Asp Ile Gly Gly
            180                 185                 190

Gly Ala Leu Leu Asp Asn Gly Val Tyr Pro Leu Arg Ala Ala Leu His
        195                 200                 205

Phe Leu Gly Pro Glu Leu Arg Leu Thr Gly Ala Val Leu Arg Arg Asp
    210                 215                 220

Arg Arg Arg Gly Val Val Val Ser Gly Ser Val Leu Leu Ala Ala Pro
225                 230                 235                 240

Gln Gly Val Ala Ala His Leu Ala Phe Gly Met Glu His Gly Tyr Arg
                245                 250                 255

Ser Ala Tyr Glu Leu His Gly Ser Thr Gly Ser Leu Ala Leu Ser His
            260                 265                 270

Val Phe Thr Thr Pro Asp Ser His Pro Val Leu Arg Leu Ser Arg
        275                 280                 285

Gln Asp His Arg Glu Glu Arg Val Leu Pro Val Asp Arg His Phe Val

```
                       290                 295                 300
Asn Ile Leu Ser Val Phe Arg Arg Ala Val Ile Arg Ala Glu Asp Val
305                 310                 315                 320

Ser Ala Glu Ser Tyr Ala Ala Leu Arg Gln Ala Gly Leu Val Asp Glu
                325                 330                 335

Ile Val Ala Arg Ala Glu Thr Phe Thr Val
                340                 345

<210> SEQ ID NO 66
<211> LENGTH: 1239
<212> TYPE: DNA
<213> ORGANISM: Streptomyces ambofaciens
<220> FEATURE:
<221> NAME/KEY: CDS
<222> LOCATION: (1)..(1239)

<400> SEQUENCE: 66 gtg acg gac gcg atc acg acc gag ctg gcc gac cgc gaa ctg ggg cgc      48
Val Thr Asp Ala Ile Thr Thr Glu Leu Ala Asp Arg Glu Leu Gly Arg
1               5                  10                  15 aga ctg cac cgg ata cgc ggc gtc cac tgg tat ttc ggc aac cac ggt      96
Arg Leu His Arg Ile Arg Gly Val His Trp Tyr Phe Gly Asn His Gly
            20                  25                  30 gac ccg tac gcc ctc atc ctg cgc ggt cag acc gac gac ccg tcg gtg     144
Asp Pro Tyr Ala Leu Ile Leu Arg Gly Gln Thr Asp Asp Pro Ser Val
        35                  40                  45 tac gag gag cgg gtc cgc gag ggc ggg ccg ctg ttc cgc agc cgt acc     192
Tyr Glu Glu Arg Val Arg Glu Gly Gly Pro Leu Phe Arg Ser Arg Thr
    50                  55                  60 ggg acc tgg gtg acc gcg gac ccg gag gtg gcc gcg gcc gtg ctg ggc     240
Gly Thr Trp Val Thr Ala Asp Pro Glu Val Ala Ala Ala Val Leu Gly
65                  70                  75                  80 gac tcg cgc ttc ggt gcg ctg gac cgc gcc gga cgg cgc ccg gag gag     288
Asp Ser Arg Phe Gly Ala Leu Asp Arg Ala Gly Arg Arg Pro Glu Glu
                85                  90                  95 tac ctc cag ccg tcg ccc gcc acg tac ctg ggg ctg gac cgc gcc gcg     336
Tyr Leu Gln Pro Ser Pro Ala Thr Tyr Leu Gly Leu Asp Arg Ala Ala
            100                 105                 110 tac gcg cgt ctg cgg cgg gtg gcc gag ccc gtg ctg ggc gcg gac gcc     384
Tyr Ala Arg Leu Arg Arg Val Ala Glu Pro Val Leu Gly Ala Asp Ala
        115                 120                 125 gcc gcc gcg tgg cgc cgg ctc ggc gag gac gtc ggg cgc cgg ctg ctc     432
Ala Ala Ala Trp Arg Arg Leu Gly Glu Asp Val Gly Arg Arg Leu Leu
    130                 135                 140 gcc ggc cgc ggt tcc ggc ctc gac ctg acg gcg gac ttc gcc cgc cgg     480
Ala Gly Arg Gly Ser Gly Leu Asp Leu Thr Ala Asp Phe Ala Arg Arg
145                 150                 155                 160 ctg ccg gca ttg gtc ctg gcc gcg tgg ctc ggg gtg ccg ggc gaa cgg     528
Leu Pro Ala Leu Val Leu Ala Ala Trp Leu Gly Val Pro Gly Glu Arg
                165                 170                 175 tgc gac gag tgg gag gag tcg ctg cgg gcg gcg ggg ccg ctg ctg gac     576
Cys Asp Glu Trp Glu Glu Ser Leu Arg Ala Ala Gly Pro Leu Leu Asp
            180                 185                 190 ggt ctg ctg tgt ccg cag acg ctg gcg gcc acc cgt gcg gcg gac tcg     624
Gly Leu Leu Cys Pro Gln Thr Leu Ala Ala Thr Arg Ala Ala Asp Ser
        195                 200                 205 gcc gcc gag ggg ctg cgc gcg ctg ttg gac gag gtg gtc gcc gcg cgt     672
Ala Ala Glu Gly Leu Arg Ala Leu Leu Asp Glu Val Val Ala Ala Arg
    210                 215                 220 ccc ggc ggg tcc ggc gag ggt gcg gtg gcc cgc atg gtc ggc gcc gga     720
```

```
                                                                                    -continued Pro Gly Gly Ser Gly Glu Gly Ala Val Ala Arg Met Val Gly Ala Gly
225                 230                 235                 240 gcc gcc ccc gac gac gcg gtg gcc gcc gcc gtg tgc ctg gcg ctc tcg         768
Ala Ala Pro Asp Asp Ala Val Ala Ala Ala Val Cys Leu Ala Leu Ser
                245                 250                 255 gcc gtc gaa ccg acg acg acc ctg gtg tgc gaa gcg gtc cgg ctg ctg         816
Ala Val Glu Pro Thr Thr Thr Leu Val Cys Glu Ala Val Arg Leu Leu
                260                 265                 270 ctc gac cga ccc gag tgg tgg cgg cgg ttg tgc gac tcc ccc gct ctg         864
Leu Asp Arg Pro Glu Trp Trp Arg Arg Leu Cys Asp Ser Pro Ala Leu
            275                 280                 285 gcg ccg gcc gcg gtc cgg cac acc ctg cgg cac gcg ccc ccg gtg cgg         912
Ala Pro Ala Ala Val Arg His Thr Leu Arg His Ala Pro Pro Val Arg
        290                 295                 300 ctg gag agc cgg gtg gcc cac gag gac gtg acg gtg gcg gat cgt ccg         960
Leu Glu Ser Arg Val Ala His Glu Asp Val Thr Val Ala Asp Arg Pro
305                 310                 315                 320 ctg ccc gcc ggg agc cac gtg gtg gtg ctc gtg ggc gcg gca cgg cgc        1008
Leu Pro Ala Gly Ser His Val Val Val Leu Val Gly Ala Ala Arg Arg
                325                 330                 335 gcg ggc gcc ccg gcc gcg gag ccg gcg gac ctg gcg ggc gca ccg gcg        1056
Ala Gly Ala Pro Ala Ala Glu Pro Ala Asp Leu Ala Gly Ala Pro Ala
                340                 345                 350 gcg gag ctg ccg gac gac ctg tgg ttc gcg ctg tcc ggg gag ttc gtc        1104
Ala Glu Leu Pro Asp Asp Leu Trp Phe Ala Leu Ser Gly Glu Phe Val
            355                 360                 365 ggc cgt gcc gcc gag acc gcg ctg ggc gtg ctg gcc gag gcc gcc ccg        1152
Gly Arg Ala Ala Glu Thr Ala Leu Gly Val Leu Ala Glu Ala Ala Pro
        370                 375                 380 gga ctg cgg cgg gac ggc gac atc gtc cgg cgg cgc cgt tcc ccg gtc        1200
Gly Leu Arg Arg Asp Gly Asp Ile Val Arg Arg Arg Ser Pro Val
385                 390                 395                 400 ctc ggc agg tac gcg cgg ttc ccc gtc gcg tac tcc tga                    1239
Leu Gly Arg Tyr Ala Arg Phe Pro Val Ala Tyr Ser
                405                 410

<210> SEQ ID NO 67
<211> LENGTH: 412
<212> TYPE: PRT
<213> ORGANISM: Streptomyces ambofaciens

<400> SEQUENCE: 67

Val Thr Asp Ala Ile Thr Thr Glu Leu Ala Asp Arg Glu Leu Gly Arg
1               5                   10                  15

Arg Leu His Arg Ile Arg Gly Val His Trp Tyr Phe Gly Asn His Gly
                20                  25                  30

Asp Pro Tyr Ala Leu Ile Leu Arg Gly Gln Thr Asp Pro Ser Val
            35                  40                  45

Tyr Glu Glu Arg Val Arg Glu Gly Gly Pro Leu Phe Arg Ser Arg Thr
        50                  55                  60

Gly Thr Trp Val Thr Ala Asp Pro Glu Val Ala Ala Val Leu Gly
65                  70                  75                  80

Asp Ser Arg Phe Gly Ala Leu Asp Arg Ala Gly Arg Pro Glu Glu
                85                  90                  95

Tyr Leu Gln Pro Ser Pro Ala Thr Tyr Leu Gly Leu Asp Arg Ala Ala
            100                 105                 110

Tyr Ala Arg Leu Arg Arg Val Ala Glu Pro Val Leu Gly Ala Asp Ala
        115                 120                 125
```

```
Ala Ala Ala Trp Arg Arg Leu Gly Glu Asp Val Gly Arg Arg Leu Leu
    130                 135                 140

Ala Gly Arg Gly Ser Gly Leu Asp Leu Thr Ala Asp Phe Ala Arg Arg
145                 150                 155                 160

Leu Pro Ala Leu Val Leu Ala Ala Trp Leu Gly Val Pro Gly Glu Arg
                165                 170                 175

Cys Asp Glu Trp Glu Glu Ser Leu Arg Ala Ala Gly Pro Leu Leu Asp
                180                 185                 190

Gly Leu Leu Cys Pro Gln Thr Leu Ala Ala Thr Arg Ala Ala Asp Ser
            195                 200                 205

Ala Ala Glu Gly Leu Arg Ala Leu Leu Asp Glu Val Val Ala Ala Arg
    210                 215                 220

Pro Gly Gly Ser Gly Glu Gly Ala Val Ala Arg Met Val Gly Ala Gly
225                 230                 235                 240

Ala Ala Pro Asp Asp Ala Val Ala Ala Val Cys Leu Ala Leu Ser
                245                 250                 255

Ala Val Glu Pro Thr Thr Thr Leu Val Cys Glu Ala Val Arg Leu Leu
                260                 265                 270

Leu Asp Arg Pro Glu Trp Trp Arg Arg Leu Cys Asp Ser Pro Ala Leu
            275                 280                 285

Ala Pro Ala Ala Val Arg His Thr Leu Arg His Ala Pro Pro Val Arg
    290                 295                 300

Leu Glu Ser Arg Val Ala His Glu Asp Val Thr Val Ala Asp Arg Pro
305                 310                 315                 320

Leu Pro Ala Gly Ser His Val Val Val Leu Val Gly Ala Ala Arg Arg
                325                 330                 335

Ala Gly Ala Pro Ala Ala Glu Pro Ala Asp Leu Ala Gly Ala Pro Ala
            340                 345                 350

Ala Glu Leu Pro Asp Asp Leu Trp Phe Ala Leu Ser Gly Glu Phe Val
    355                 360                 365

Gly Arg Ala Ala Glu Thr Ala Leu Gly Val Leu Ala Glu Ala Pro
370                 375                 380

Gly Leu Arg Arg Asp Gly Asp Ile Val Arg Arg Arg Ser Pro Val
385                 390                 395                 400

Leu Gly Arg Tyr Ala Arg Phe Pro Val Ala Tyr Ser
                405                 410

<210> SEQ ID NO 68
<211> LENGTH: 1272
<212> TYPE: DNA
<213> ORGANISM: Streptomyces ambofaciens
<220> FEATURE:
<221> NAME/KEY: CDS
<222> LOCATION: (1)..(1272)

<400> SEQUENCE: 68 gtg cgc gtc ctg gtg acc tcc atc ccg cac cac acg cac tac tac cac      48
Val Arg Val Leu Val Thr Ser Ile Pro His His Thr His Tyr Tyr His
1               5                   10                  15 ctg gta ccg ctg atc tgg gct ctg cgt gcc tcg ggg cac gag gtg gtg      96
Leu Val Pro Leu Ile Trp Ala Leu Arg Ala Ser Gly His Glu Val Val
                20                  25                  30 gcg gcc ggc cag ccg tcg ctg gtc gac gcc atc acc gcc agc ggc atc      144
Ala Ala Gly Gln Pro Ser Leu Val Asp Ala Ile Thr Ala Ser Gly Ile
            35                  40                  45 ccg gcg ttc gcc ctg gcc gag gag gag tcg ctg gcg cag atc ttc gag      192
Pro Ala Phe Ala Leu Ala Glu Glu Glu Ser Leu Ala Gln Ile Phe Glu
```

```
            50                  55                  60
gag gtc gag ggc gat ctc cag ccg tat cag cac ggc atc gac gag ttc      240
Glu Val Glu Gly Asp Leu Gln Pro Tyr Gln His Gly Ile Asp Glu Phe
 65              70                  75                  80 gac ttc ttc ggc acc ctg aag gac gag ctg gac tgg gag aag ctg ctc      288
Asp Phe Phe Gly Thr Leu Lys Asp Glu Leu Asp Trp Glu Lys Leu Leu
                 85                  90                  95 gcc cag cag gtg atc ctg tcc ggc ctg tgg ctg gaa ccg ctc aac ggc      336
Ala Gln Gln Val Ile Leu Ser Gly Leu Trp Leu Glu Pro Leu Asn Gly
                    100                 105                 110 gcc acg acc ctc gac agc atc gtc gac ttc gcc cgg gcc tgg aag ccc      384
Ala Thr Thr Leu Asp Ser Ile Val Asp Phe Ala Arg Ala Trp Lys Pro
                115                 120                 125 gac ctg gtg ctg tgg gag ccg ttc acc tat gcg ggg ccg gtg gcg gcc      432
Asp Leu Val Leu Trp Glu Pro Phe Thr Tyr Ala Gly Pro Val Ala Ala
            130                 135                 140 cgg gcg tgc ggg gcc gcg cac gcc cgc gtc ctg tgg ggg ccg gac acg      480
Arg Ala Cys Gly Ala Ala His Ala Arg Val Leu Trp Gly Pro Asp Thr
145                 150                 155                 160 atc ggg ctg ctg cgg acg aag ttc ctt cag gcc cag gcg cgt cag ccc      528
Ile Gly Leu Leu Arg Thr Lys Phe Leu Gln Ala Gln Ala Arg Gln Pro
                165                 170                 175 gag gag cac cgg gac gac ccg gtc gcg gag tgg atg acc tgg gcc ctg      576
Glu Glu His Arg Asp Asp Pro Val Ala Glu Trp Met Thr Trp Ala Leu
            180                 185                 190 gcg cgc tac ggg tgc gac ttc cgg gag gag gac gtg ctc ggt cag tgg      624
Ala Arg Tyr Gly Cys Asp Phe Arg Glu Glu Asp Val Leu Gly Gln Trp
        195                 200                 205 agc gtg gac ccg atg gcg gag ggc gtc agt ctg ggc ctc gac ctg ccg      672
Ser Val Asp Pro Met Ala Glu Gly Val Ser Leu Gly Leu Asp Leu Pro
    210                 215                 220 acc gtc ccg atg cgc tac acc ccg tac aac ggg tcg gcg gtg atc ccc      720
Thr Val Pro Met Arg Tyr Thr Pro Tyr Asn Gly Ser Ala Val Ile Pro
225                 230                 235                 240 gac tgg ctg acc gag gaa ccg aaa cgg cct cgg gtc tgc ctg acc ctg      768
Asp Trp Leu Thr Glu Glu Pro Lys Arg Pro Arg Val Cys Leu Thr Leu
                245                 250                 255 ggg gtg tcc tcg cgg gag cac agt gag gac gag gtc ccg gtg cag agg      816
Gly Val Ser Ser Arg Glu His Ser Glu Asp Glu Val Pro Val Gln Arg
            260                 265                 270 ttt atc gag gcg ctg gcc gat ctc gac atc gag ctg gtg gcg acc ctg      864
Phe Ile Glu Ala Leu Ala Asp Leu Asp Ile Glu Leu Val Ala Thr Leu
        275                 280                 285 gac gac gcc cag cgg gac ctg ctg ccg agg atc ccg gac aac acg cgc      912
Asp Asp Ala Gln Arg Asp Leu Leu Pro Arg Ile Pro Asp Asn Thr Arg
    290                 295                 300 atc gtc gac ttc gtg ccc atg gac gcg ttg ctg ccg acg tgc tcg gcg      960
Ile Val Asp Phe Val Pro Met Asp Ala Leu Leu Pro Thr Cys Ser Ala
305                 310                 315                 320 atc atc aac cac agc ggt tcg ggc acg tgc aac acc gcc gcg ctg cac      1008
Ile Ile Asn His Ser Gly Ser Gly Thr Cys Asn Thr Ala Ala Leu His
                325                 330                 335 ggg gtg ccg cag atc atc ctc ggc ggc atc ctg gac gcc gcc gta cgg      1056
Gly Val Pro Gln Ile Ile Leu Gly Gly Ile Leu Asp Ala Ala Val Arg
            340                 345                 350 cag cac atg ttc gcg cag aac tcc gcc gcc ctc acc ttc gct ccg gag      1104
Gln His Met Phe Ala Gln Asn Ser Ala Ala Leu Thr Phe Ala Pro Glu
        355                 360                 365 gag gtg acc ggc gcg tcg ctg agg agc gcg ctg gtg cgc ctg ctc gag      1152
```

-continued

```
Glu Val Thr Gly Ala Ser Leu Arg Ser Ala Leu Val Arg Leu Leu Glu
    370                 375                 380 gag ccg cgg ttc cgc gac ggc gcg cgg cgg ctg aag gag cgg atg cgg      1200
Glu Pro Arg Phe Arg Asp Gly Ala Arg Arg Leu Lys Glu Arg Met Arg
385                 390                 395                 400 gcc atg ccc agc ccg gcc ggg atc gtg ccg acc ctg gag cgc ctc acg      1248
Ala Met Pro Ser Pro Ala Gly Ile Val Pro Thr Leu Glu Arg Leu Thr
                405                 410                 415 gcc cag cac cgc cgg gcg tgt tga                                      1272
Ala Gln His Arg Arg Ala Cys
            420
```

<210> SEQ ID NO 69
<211> LENGTH: 423
<212> TYPE: PRT
<213> ORGANISM: Streptomyces ambofaciens

<400> SEQUENCE: 69

```
Val Arg Val Leu Val Thr Ser Ile Pro His His Thr His Tyr Tyr His
1               5                   10                  15

Leu Val Pro Leu Ile Trp Ala Leu Arg Ala Ser Gly His Glu Val Val
            20                  25                  30

Ala Ala Gly Gln Pro Ser Leu Val Asp Ala Ile Thr Ala Ser Gly Ile
        35                  40                  45

Pro Ala Phe Ala Leu Ala Glu Glu Ser Leu Ala Gln Ile Phe Glu
    50                  55                  60

Glu Val Glu Gly Asp Leu Gln Pro Tyr Gln His Gly Ile Asp Glu Phe
65                  70                  75                  80

Asp Phe Phe Gly Thr Leu Lys Asp Glu Leu Asp Trp Glu Lys Leu Leu
                85                  90                  95

Ala Gln Gln Val Ile Leu Ser Gly Leu Trp Leu Glu Pro Leu Asn Gly
            100                 105                 110

Ala Thr Thr Leu Asp Ser Ile Val Asp Phe Ala Arg Ala Trp Lys Pro
        115                 120                 125

Asp Leu Val Leu Trp Glu Pro Phe Thr Tyr Ala Gly Pro Val Ala Ala
    130                 135                 140

Arg Ala Cys Gly Ala Ala His Ala Arg Val Leu Trp Gly Pro Asp Thr
145                 150                 155                 160

Ile Gly Leu Leu Arg Thr Lys Phe Leu Gln Ala Gln Ala Arg Gln Pro
                165                 170                 175

Glu Glu His Arg Asp Asp Pro Val Ala Glu Trp Met Thr Trp Ala Leu
            180                 185                 190

Ala Arg Tyr Gly Cys Asp Phe Arg Glu Glu Asp Val Leu Gly Gln Trp
        195                 200                 205

Ser Val Asp Pro Met Ala Glu Gly Val Ser Leu Gly Leu Asp Leu Pro
    210                 215                 220

Thr Val Pro Met Arg Tyr Thr Pro Tyr Asn Gly Ser Ala Val Ile Pro
225                 230                 235                 240

Asp Trp Leu Thr Glu Glu Pro Lys Arg Pro Arg Val Cys Leu Thr Leu
                245                 250                 255

Gly Val Ser Ser Arg Glu His Ser Glu Asp Glu Val Pro Val Gln Arg
            260                 265                 270

Phe Ile Glu Ala Leu Ala Asp Leu Asp Ile Glu Leu Val Ala Thr Leu
        275                 280                 285

Asp Asp Ala Gln Arg Asp Leu Leu Pro Arg Ile Pro Asp Asn Thr Arg
    290                 295                 300
```

```
Ile Val Asp Phe Val Pro Met Asp Ala Leu Leu Pro Thr Cys Ser Ala
305                 310                 315                 320

Ile Ile Asn His Ser Gly Ser Gly Thr Cys Asn Thr Ala Ala Leu His
            325                 330                 335

Gly Val Pro Gln Ile Ile Leu Gly Gly Ile Leu Asp Ala Ala Val Arg
            340                 345                 350

Gln His Met Phe Ala Gln Asn Ser Ala Ala Leu Thr Phe Ala Pro Glu
            355                 360                 365

Glu Val Thr Gly Ala Ser Leu Arg Ser Ala Leu Val Arg Leu Leu Glu
            370                 375                 380

Glu Pro Arg Phe Arg Asp Gly Ala Arg Arg Leu Lys Glu Arg Met Arg
385                 390                 395                 400

Ala Met Pro Ser Pro Ala Gly Ile Val Pro Thr Leu Glu Arg Leu Thr
            405                 410                 415

Ala Gln His Arg Arg Ala Cys
            420

<210> SEQ ID NO 70
<211> LENGTH: 1179
<212> TYPE: DNA
<213> ORGANISM: Streptomyces ambofaciens
<220> FEATURE:
<221> NAME/KEY: CDS
<222> LOCATION: (1)..(1179)

<400> SEQUENCE: 70 atg cgg gcc ctc ttc acg acc gcg ccg ctc gcg ggc cac ctg ctt ccg      48
Met Arg Ala Leu Phe Thr Thr Ala Pro Leu Ala Gly His Leu Leu Pro
1               5                   10                  15 ctg gtg ccc atc gcg tgg gcc ctg cgg gcg gcc ggc cac gag gta ctg      96
Leu Val Pro Ile Ala Trp Ala Leu Arg Ala Ala Gly His Glu Val Leu
            20                  25                  30 gtg gcg acc cgg gag gac ttc gtg ccg gtc gcc ctg cgg tcg ggg ctg     144
Val Ala Thr Arg Glu Asp Phe Val Pro Val Ala Leu Arg Ser Gly Leu
        35                  40                  45 ccg tcc gcc tcg tgc ggg ccg ccc gcg gcg gac ctg gcg ggc gcg gcc     192
Pro Ser Ala Ser Cys Gly Pro Pro Ala Ala Asp Leu Ala Gly Ala Ala
    50                  55                  60 gag gcg ggg gcg ctc gcg cgg ccc cgc gga gcg gcg gag gct cgg ggg     240
Glu Ala Gly Ala Leu Ala Arg Pro Arg Gly Ala Ala Glu Ala Arg Gly
65                  70                  75                  80 gtc ctg agc ggg gcg ctg gcg cgc gtc gcc cgg ggc agt ctg gcg ggg     288
Val Leu Ser Gly Ala Leu Ala Arg Val Ala Arg Gly Ser Leu Ala Gly
                85                  90                  95 gtg cgg cgg ctg gcg gac gcc tgg cgg ccg gat ctg atc gtc agc gaa     336
Val Arg Arg Leu Ala Asp Ala Trp Arg Pro Asp Leu Ile Val Ser Glu
            100                 105                 110 cgg gcc gag ttc gcc ggg ccg ctg gtc gcg gcg gcc ctc ggg gtc ccg     384
Arg Ala Glu Phe Ala Gly Pro Leu Val Ala Ala Ala Leu Gly Val Pro
        115                 120                 125 tgg gtc cgc tac cac tgg tcg gtc tcg tcc ctg gag gag tac cgg cga     432
Trp Val Arg Tyr His Trp Ser Val Ser Ser Leu Glu Glu Tyr Arg Arg
    130                 135                 140 gcg gcc gag gcc gag ttc gcg ccc gag ctg gcg gcg ctc ggc ctc gac     480
Ala Ala Glu Ala Glu Phe Ala Pro Glu Leu Ala Ala Leu Gly Leu Asp
145                 150                 155                 160 cgg ttc ccg gag gcg gcg cgc gtg ctc gat ccg tgg ccg gtg tcg ctg     528
Arg Phe Pro Glu Ala Ala Arg Val Leu Asp Pro Trp Pro Val Ser Leu
                165                 170                 175
```

```
cgc cgg ccg gac gcg gtc gcc cac gac ggg gtc cgg cac gta ccg gcc    576
Arg Arg Pro Asp Ala Val Ala His Asp Gly Val Arg His Val Pro Ala
        180                 185                 190 cac ggg gac gcc ccc gtc ccc gac tgg gcg ttc acg cgc ggt cgc ggg    624
His Gly Asp Ala Pro Val Pro Asp Trp Ala Phe Thr Arg Gly Arg Gly
        195                 200                 205 ccg cgg atc tgc gtg acg ctc ggc acc atg ctg ccc cgg tac ggc gcc    672
Pro Arg Ile Cys Val Thr Leu Gly Thr Met Leu Pro Arg Tyr Gly Ala
        210                 215                 220 gcc ggg atg gcc gac ttc ctg acg gag ctg gtg gcg gag acc cgc gga    720
Ala Gly Met Ala Asp Phe Leu Thr Glu Leu Val Ala Glu Thr Arg Gly
225                 230                 235                 240 ggg gac tgc gaa ctg ctc gtg gcg gtc gac gac gac gtc gtc gcg cgg    768
Gly Asp Cys Glu Leu Leu Val Ala Val Asp Asp Asp Val Val Ala Arg
                245                 250                 255 tgg ccg tcg ctg ccc tcc gcg gtg cgg tac gcc ggc cgg ctg ccg ctg    816
Trp Pro Ser Leu Pro Ser Ala Val Arg Tyr Ala Gly Arg Leu Pro Leu
                260                 265                 270 gcg gag gtg ctg ccc gcg tgc gac gcg gtg gtg cac cac ggc ggg cag    864
Ala Glu Val Leu Pro Ala Cys Asp Ala Val Val His His Gly Gly Gln
            275                 280                 285 ggc acg tcc ctg acc gcg ctg gcc gcg ggt cgg ccg cag gtc gtc atg    912
Gly Thr Ser Leu Thr Ala Leu Ala Ala Gly Arg Pro Gln Val Val Met
        290                 295                 300 gcg cgg ctc gac gac cag ttc gac aac gcg cgg gca ctg gcg gcg gcg    960
Ala Arg Leu Asp Asp Gln Phe Asp Asn Ala Arg Ala Leu Ala Ala Ala
305                 310                 315                 320 ggg gcg gcc ctg ctc gta ccg ccg tcc cgg gcc act ccc gcg gcc gtg   1008
Gly Ala Ala Leu Leu Val Pro Pro Ser Arg Ala Thr Pro Ala Ala Val
                325                 330                 335 gcc gcg ggg tgc gcc gaa gtg ctg gag aac gcc ctg tat gcc aag gcg   1056
Ala Ala Gly Cys Ala Glu Val Leu Glu Asn Ala Leu Tyr Ala Lys Ala
                340                 345                 350 gca gcc ggg ctc gcc gag gag atg gcg ctg ctg ccg tcg ccg tcg gcg   1104
Ala Ala Gly Leu Ala Glu Glu Met Ala Leu Leu Pro Ser Pro Ser Ala
            355                 360                 365 gcg gtc gga ctc ctg gaa cac ccg ggg ccc ggg ccg gac atg ccg cgg   1152
Ala Val Gly Leu Leu Glu His Pro Gly Pro Gly Pro Asp Met Pro Arg
        370                 375                 380 agt tac ccg aac gag gat gcg gtg tga                               1179
Ser Tyr Pro Asn Glu Asp Ala Val
385                 390

<210> SEQ ID NO 71
<211> LENGTH: 392
<212> TYPE: PRT
<213> ORGANISM: Streptomyces ambofaciens

<400> SEQUENCE: 71

Met Arg Ala Leu Phe Thr Thr Ala Pro Leu Ala Gly His Leu Leu Pro
1               5                   10                  15

Leu Val Pro Ile Ala Trp Ala Leu Arg Ala Ala Gly His Glu Val Leu
            20                  25                  30

Val Ala Thr Arg Glu Asp Phe Val Pro Val Ala Leu Arg Ser Gly Leu
        35                  40                  45

Pro Ser Ala Ser Cys Gly Pro Pro Ala Ala Asp Leu Ala Gly Ala Ala
    50                  55                  60

Glu Ala Gly Ala Leu Ala Arg Pro Arg Gly Ala Ala Glu Ala Arg Gly
65                  70                  75                  80
```

```
Val Leu Ser Gly Ala Leu Ala Arg Val Ala Arg Gly Ser Leu Ala Gly
                85                  90                  95

Val Arg Arg Leu Ala Asp Ala Trp Arg Pro Asp Leu Ile Val Ser Glu
            100                 105                 110

Arg Ala Glu Phe Ala Gly Pro Leu Val Ala Ala Leu Gly Val Pro
        115                 120                 125

Trp Val Arg Tyr His Trp Ser Val Ser Leu Glu Glu Tyr Arg Arg
    130                 135                 140

Ala Ala Glu Ala Glu Phe Ala Pro Glu Leu Ala Leu Gly Leu Asp
145                 150                 155                 160

Arg Phe Pro Glu Ala Ala Arg Val Leu Asp Pro Trp Pro Val Ser Leu
                165                 170                 175

Arg Arg Pro Asp Ala Val Ala His Asp Gly Val Arg His Val Pro Ala
            180                 185                 190

His Gly Asp Ala Pro Val Pro Asp Trp Ala Phe Thr Arg Gly Arg Gly
        195                 200                 205

Pro Arg Ile Cys Val Thr Leu Gly Thr Met Leu Pro Arg Tyr Gly Ala
    210                 215                 220

Ala Gly Met Ala Asp Phe Leu Thr Glu Leu Val Ala Glu Thr Arg Gly
225                 230                 235                 240

Gly Asp Cys Glu Leu Leu Val Ala Val Asp Asp Val Val Ala Arg
                245                 250                 255

Trp Pro Ser Leu Pro Ser Ala Val Arg Tyr Ala Gly Arg Leu Pro Leu
            260                 265                 270

Ala Glu Val Leu Pro Ala Cys Asp Ala Val Val His His Gly Gly Gln
        275                 280                 285

Gly Thr Ser Leu Thr Ala Leu Ala Ala Gly Arg Pro Gln Val Val Met
    290                 295                 300

Ala Arg Leu Asp Asp Gln Phe Asp Asn Ala Arg Ala Leu Ala Ala Ala
305                 310                 315                 320

Gly Ala Ala Leu Leu Val Pro Pro Ser Arg Ala Thr Pro Ala Ala Val
                325                 330                 335

Ala Ala Gly Cys Ala Glu Val Leu Glu Asn Ala Leu Tyr Ala Lys Ala
            340                 345                 350

Ala Ala Gly Leu Ala Glu Glu Met Ala Leu Leu Pro Ser Pro Ser Ala
        355                 360                 365

Ala Val Gly Leu Leu Glu His Pro Gly Pro Gly Pro Asp Met Pro Arg
    370                 375                 380

Ser Tyr Pro Asn Glu Asp Ala Val
385                 390

<210> SEQ ID NO 72
<211> LENGTH: 993
<212> TYPE: DNA
<213> ORGANISM: Streptomyces ambofaciens
<220> FEATURE:
<221> NAME/KEY: CDS
<222> LOCATION: (1)..(993)

<400> SEQUENCE: 72 gtg aat ctg gaa gta ctc aac cgt tcg aac gat ccg cgc ggg ccg gtg     48
Val Asn Leu Glu Val Leu Asn Arg Ser Asn Asp Pro Arg Gly Pro Val
1               5                   10                  15 atc acg gtg gtc ggc gcg tcc ggc ttc atc ggg tcc gcc ctg gtc gcc     96
Ile Thr Val Val Gly Ala Ser Gly Phe Ile Gly Ser Ala Leu Val Ala
            20                  25                  30
```

-continued

```
gag ctg gcg cgc atg ccg gtg cgg ctg cgg gcg gtg gcc cgg cgc gag      144
Glu Leu Ala Arg Met Pro Val Arg Leu Arg Ala Val Ala Arg Arg Glu
         35                  40                  45 acc ccc gtt ccc gcg ggg gca cgg gcc gcc gtc gag gtc cgc cgg gcg      192
Thr Pro Val Pro Ala Gly Ala Arg Ala Ala Val Glu Val Arg Arg Ala
 50                  55                  60 gac ctc gcc cgg ccg gac gag gtc ggg gcc gcc gtc gag ggg gcg gac      240
Asp Leu Ala Arg Pro Asp Glu Val Gly Ala Ala Val Glu Gly Ala Asp
 65                  70                  75                  80 gcc gtc gtg cac ctc gcc gcc cac atc ggc ggc gcg cgg tcg tgg cgc      288
Ala Val Val His Leu Ala Ala His Ile Gly Gly Ala Arg Ser Trp Arg
                 85                  90                  95 gcg gcc gac gag cgg tcg ctg cgg gtg aac gtc ggt ctg ctg cgc gac      336
Ala Ala Asp Glu Arg Ser Leu Arg Val Asn Val Gly Leu Leu Arg Asp
            100                 105                 110 gtg gcc gac gcg ttc cgg gac cgc tcg ggg ccc gcc ccg gcc gtg gtc      384
Val Ala Asp Ala Phe Arg Asp Arg Ser Gly Pro Ala Pro Ala Val Val
        115                 120                 125 ctg gcc agt acc ctc cag gcc ggc gtc gag ctg tcc cgg cag ggc ccg      432
Leu Ala Ser Thr Leu Gln Ala Gly Val Glu Leu Ser Arg Gln Gly Pro
130                 135                 140 tac gcc cgg cag aag tcg gcc gcc gag gag gtc ctg ctg cgg gcc gcc      480
Tyr Ala Arg Gln Lys Ser Ala Ala Glu Glu Val Leu Leu Arg Ala Ala
145                 150                 155                 160 tcc gag gag gtg gtc cgc ggc gtc gtg ctg cgg ctg ccg acc gtc tac      528
Ser Glu Glu Val Val Arg Gly Val Val Leu Arg Leu Pro Thr Val Tyr
                165                 170                 175 ggg cgc agc ccg ctg acc ggg tgg acg ggc cgc ggg gtg gtc gcg tcg      576
Gly Arg Ser Pro Leu Thr Gly Trp Thr Gly Arg Gly Val Val Ala Ser
            180                 185                 190 gtg gca cgg cag gcc gtc tcg ggc gag ccg gtc acg atg tgg cac gac      624
Val Ala Arg Gln Ala Val Ser Gly Glu Pro Val Thr Met Trp His Asp
        195                 200                 205 ggc acg gtc ggg cgc gat ctg ctc cac gtg gag gac gcg gcc cgc gcc      672
Gly Thr Val Gly Arg Asp Leu Leu His Val Glu Asp Ala Ala Arg Ala
210                 215                 220 ttc gcg gcg gcg ctc ggt cac gtg gag cgg ctg gac ggc ggc acg tgg      720
Phe Ala Ala Ala Leu Gly His Val Glu Arg Leu Asp Gly Gly Thr Trp
225                 230                 235                 240 tcc gtc ggt acg ggc cgg ctg gag ccc ttg gga gag gtg ttc tcg gcc      768
Ser Val Gly Thr Gly Arg Leu Glu Pro Leu Gly Glu Val Phe Ser Ala
                245                 250                 255 ctc gcc ggg ctg gtg gcc gag cgg acg ggg agg ccc ccc gta ccg gtg      816
Leu Ala Gly Leu Val Ala Glu Arg Thr Gly Arg Pro Pro Val Pro Val
            260                 265                 270 gtc tcc acg gag ccg ccc gac cat gcc gag gcg ggc gac ttc gag agc      864
Val Ser Thr Glu Pro Pro Asp His Ala Glu Ala Gly Asp Phe Glu Ser
        275                 280                 285 gcg gtc tgt gac ccc tcc gcg ttc cgc gcg gtg acc ggg tgg tct ccc      912
Ala Val Cys Asp Pro Ser Ala Phe Arg Ala Val Thr Gly Trp Ser Pro
290                 295                 300 ctc gtt ccg ttg cgg gcg ggg ctc ggc gcc gtg gtg gag acg atg gtg      960
Leu Val Pro Leu Arg Ala Gly Leu Gly Ala Val Val Glu Thr Met Val
305                 310                 315                 320 gcc gac gga gcg agg ggt ggg atc cga acg tga                          993
Ala Asp Gly Ala Arg Gly Gly Ile Arg Thr
                325                 330
```

<210> SEQ ID NO 73

-continued

```
<211> LENGTH: 330
<212> TYPE: PRT
<213> ORGANISM: Streptomyces ambofaciens

<400> SEQUENCE: 73

Val Asn Leu Glu Val Leu Asn Arg Ser Asn Asp Pro Arg Gly Pro Val
 1               5                  10                  15

Ile Thr Val Val Gly Ala Ser Gly Phe Ile Gly Ser Ala Leu Val Ala
            20                  25                  30

Glu Leu Ala Arg Met Pro Val Arg Leu Arg Ala Val Ala Arg Arg Glu
        35                  40                  45

Thr Pro Val Pro Ala Gly Ala Arg Ala Ala Val Glu Val Arg Arg Ala
    50                  55                  60

Asp Leu Ala Arg Pro Asp Glu Val Gly Ala Ala Val Glu Gly Ala Asp
65                  70                  75                  80

Ala Val Val His Leu Ala Ala His Ile Gly Gly Ala Arg Ser Trp Arg
                85                  90                  95

Ala Ala Asp Glu Arg Ser Leu Arg Val Asn Val Gly Leu Leu Arg Asp
            100                 105                 110

Val Ala Asp Ala Phe Arg Asp Arg Ser Gly Pro Ala Pro Ala Val Val
        115                 120                 125

Leu Ala Ser Thr Leu Gln Ala Gly Val Glu Leu Ser Arg Gln Gly Pro
    130                 135                 140

Tyr Ala Arg Gln Lys Ser Ala Ala Glu Glu Val Leu Leu Arg Ala Ala
145                 150                 155                 160

Ser Glu Glu Val Val Arg Gly Val Val Leu Arg Leu Pro Thr Val Tyr
                165                 170                 175

Gly Arg Ser Pro Leu Thr Gly Trp Thr Gly Arg Gly Val Val Ala Ser
            180                 185                 190

Val Ala Arg Gln Ala Val Ser Gly Glu Pro Val Thr Met Trp His Asp
        195                 200                 205

Gly Thr Val Gly Arg Asp Leu Leu His Val Glu Asp Ala Ala Arg Ala
    210                 215                 220

Phe Ala Ala Leu Gly His Val Glu Arg Leu Asp Gly Gly Thr Trp
225                 230                 235                 240

Ser Val Gly Thr Gly Arg Leu Glu Pro Leu Gly Glu Val Phe Ser Ala
                245                 250                 255

Leu Ala Gly Leu Val Ala Glu Arg Thr Gly Arg Pro Val Pro Val
            260                 265                 270

Val Ser Thr Glu Pro Pro Asp His Ala Glu Ala Gly Asp Phe Glu Ser
    275                 280                 285

Ala Val Cys Asp Pro Ser Ala Phe Arg Ala Val Thr Gly Trp Ser Pro
290                 295                 300

Leu Val Pro Leu Arg Ala Gly Leu Gly Ala Val Val Glu Thr Met Val
                310                 315                 320

Ala Asp Gly Ala Arg Gly Gly Ile Arg Thr
            325                 330

<210> SEQ ID NO 74
<211> LENGTH: 1008
<212> TYPE: DNA
<213> ORGANISM: Streptomyces ambofaciens
<220> FEATURE:
<221> NAME/KEY: CDS
<222> LOCATION: (1)..(1008)

<400> SEQUENCE: 74
```

```
gtg agc acg gac cgg gag cag gcc gcg cac acg cgg ctc ggt cgc agc        48
Val Ser Thr Asp Arg Glu Gln Ala Ala His Thr Arg Leu Gly Arg Ser
1               5                   10                  15 gcg acc ctg gtg agc cgg ctc tgg ctg ggc acc gtg aac ttc agc ggc        96
Ala Thr Leu Val Ser Arg Leu Trp Leu Gly Thr Val Asn Phe Ser Gly
            20                  25                  30 cgg gtc gag gac ggt gac gcg atg cag ctg atg gag gcg gcg gtc gac       144
Arg Val Glu Asp Gly Asp Ala Met Gln Leu Met Glu Ala Ala Val Asp
        35                  40                  45 cgc ggc atc aac tgc atc gac acc gcg gac atc tac ggc tgg cgg atc       192
Arg Gly Ile Asn Cys Ile Asp Thr Ala Asp Ile Tyr Gly Trp Arg Ile
    50                  55                  60 cac aag ggc cac acc gag gaa ctg gtg ggc cgg tgg ctg gcc aag agc       240
His Lys Gly His Thr Glu Glu Leu Val Gly Arg Trp Leu Ala Lys Ser
65                  70                  75                  80 gcc gcg cgg cgg gag gac gtc ctg ctg gcc acc aag gtc ggc ggg gac       288
Ala Ala Arg Arg Glu Asp Val Leu Leu Ala Thr Lys Val Gly Gly Asp
                85                  90                  95 atg agc gaa cgg ctc aac gac ggc ggc ctg tcg gcg cgg cac atc gtc       336
Met Ser Glu Arg Leu Asn Asp Gly Gly Leu Ser Ala Arg His Ile Val
            100                 105                 110 acg gcc tgc gag cag tcg ctg cgg cgc ctg ggc gtg gac cac atc gac       384
Thr Ala Cys Glu Gln Ser Leu Arg Arg Leu Gly Val Asp His Ile Asp
        115                 120                 125 ctg tac cag atg cac cgc gtc gac cac gcc gcg ccg tgg gac gag atc       432
Leu Tyr Gln Met His Arg Val Asp His Ala Ala Pro Trp Asp Glu Ile
    130                 135                 140 tgg cag gcg atg gac cgt ctg gtg gcg agc ggc aag gtg acc tac gtg       480
Trp Gln Ala Met Asp Arg Leu Val Ala Ser Gly Lys Val Thr Tyr Val
145                 150                 155                 160 ggg tcg tcg aac ttc gcc ggc tgg aac gtc gcc gcg cag gac gcg            528
Gly Ser Ser Asn Phe Ala Gly Trp Asn Val Ala Ala Gln Asp Ala
                165                 170                 175 gcc cgg cgg cgc cag tcc ctc ggt ctg gtg tcc gag cag tgc ctg tac       576
Ala Arg Arg Arg Gln Ser Leu Gly Leu Val Ser Glu Gln Cys Leu Tyr
            180                 185                 190 aac ctg gcg gtg cgc cac gcc gag ctg gaa ctg ctg ccg gcc gcc cag       624
Asn Leu Ala Val Arg His Ala Glu Leu Glu Leu Leu Pro Ala Ala Gln
        195                 200                 205 gcg tac gga ctg ggc gtg ttc gcc tgg tcg ccg ctg cac ggc ggg ctg       672
Ala Tyr Gly Leu Gly Val Phe Ala Trp Ser Pro Leu His Gly Gly Leu
    210                 215                 220 ctc agc ggg gtg ctg cgc aag ctc gcg gcg ggc gtc gcg gtg aag tcg       720
Leu Ser Gly Val Leu Arg Lys Leu Ala Ala Gly Val Ala Val Lys Ser
225                 230                 235                 240 gca cag ggg cgg gcc cag ctg ctg ctg ccc gag ctg cgc gcg acg atc       768
Ala Gln Gly Arg Ala Gln Leu Leu Leu Pro Glu Leu Arg Ala Thr Ile
                245                 250                 255 gag gcg tac gag ggg ttc tgc ggc cgg atc ggc gcg gat ccg gcc gag       816
Glu Ala Tyr Glu Gly Phe Cys Gly Arg Ile Gly Ala Asp Pro Ala Glu
            260                 265                 270 gtc ggt ctg gcc tgg gtg ctg tcc cgg ccg ggg atc agc ggc gcg gtg       864
Val Gly Leu Ala Trp Val Leu Ser Arg Pro Gly Ile Ser Gly Ala Val
        275                 280                 285 atc ggt ccg cgc acg gtg gac cag ctg gac tcg gcg ctg cgg tcc ctg       912
Ile Gly Pro Arg Thr Val Asp Gln Leu Asp Ser Ala Leu Arg Ser Leu
    290                 295                 300 gac ctg gtc ctc ggg gag gcc gaa ctg gcc gag ctg gac gcc atc ttc       960
Asp Leu Val Leu Gly Glu Ala Glu Leu Ala Glu Leu Asp Ala Ile Phe
```

```
                          305                 310                 315                 320
     ccg ccc ctg ggc aag ggc ggc cgg gcg ccg gac gcg tgg atc agc tga          1008
     Pro Pro Leu Gly Lys Gly Gly Arg Ala Pro Asp Ala Trp Ile Ser
                      325                 330                 335

<210> SEQ ID NO 75
<211> LENGTH: 335
<212> TYPE: PRT
<213> ORGANISM: Streptomyces ambofaciens

<400> SEQUENCE: 75

Val Ser Thr Asp Arg Glu Gln Ala Ala His Thr Arg Leu Gly Arg Ser
1               5                   10                  15

Ala Thr Leu Val Ser Arg Leu Trp Leu Gly Thr Val Asn Phe Ser Gly
            20                  25                  30

Arg Val Glu Asp Gly Asp Ala Met Gln Leu Met Glu Ala Ala Val Asp
        35                  40                  45

Arg Gly Ile Asn Cys Ile Asp Thr Ala Asp Ile Tyr Gly Trp Arg Ile
    50                  55                  60

His Lys Gly His Thr Glu Glu Leu Val Gly Arg Trp Leu Ala Lys Ser
65                  70                  75                  80

Ala Ala Arg Arg Glu Asp Val Leu Leu Ala Thr Lys Val Gly Gly Asp
                85                  90                  95

Met Ser Glu Arg Leu Asn Asp Gly Gly Leu Ser Ala Arg His Ile Val
            100                 105                 110

Thr Ala Cys Glu Gln Ser Leu Arg Arg Leu Gly Val Asp His Ile Asp
        115                 120                 125

Leu Tyr Gln Met His Arg Val Asp His Ala Ala Pro Trp Asp Glu Ile
    130                 135                 140

Trp Gln Ala Met Asp Arg Leu Val Ala Ser Gly Lys Val Thr Tyr Val
145                 150                 155                 160

Gly Ser Ser Asn Phe Ala Gly Trp Asn Val Ala Ala Gln Asp Ala
                165                 170                 175

Ala Arg Arg Arg Gln Ser Leu Gly Leu Val Ser Glu Gln Cys Leu Tyr
            180                 185                 190

Asn Leu Ala Val Arg His Ala Glu Leu Glu Leu Pro Ala Ala Gln
        195                 200                 205

Ala Tyr Gly Leu Gly Val Phe Ala Trp Ser Pro Leu His Gly Gly Leu
    210                 215                 220

Leu Ser Gly Val Leu Arg Lys Leu Ala Ala Gly Val Ala Val Lys Ser
225                 230                 235                 240

Ala Gln Gly Arg Ala Gln Leu Leu Pro Glu Leu Arg Ala Thr Ile
                245                 250                 255

Glu Ala Tyr Glu Gly Phe Cys Gly Arg Ile Gly Ala Asp Pro Ala Glu
            260                 265                 270

Val Gly Leu Ala Trp Val Leu Ser Arg Pro Gly Ile Ser Gly Ala Val
        275                 280                 285

Ile Gly Pro Arg Thr Val Asp Gln Leu Asp Ser Ala Leu Arg Ser Leu
    290                 295                 300

Asp Leu Val Leu Gly Glu Ala Glu Leu Ala Glu Leu Asp Ala Ile Phe
305                 310                 315                 320

Pro Pro Leu Gly Lys Gly Gly Arg Ala Pro Asp Ala Trp Ile Ser
                325                 330                 335

<210> SEQ ID NO 76
```

<211> LENGTH: 1233
<212> TYPE: DNA
<213> ORGANISM: Streptomyces ambofaciens
<220> FEATURE:
<221> NAME/KEY: CDS
<222> LOCATION: (1)..(1233)

<400> SEQUENCE: 76

| | | | | | | | | | | | | | | | | |
|---|---|---|---|---|---|---|---|---|---|---|---|---|---|---|---|---|
| atg | att | gcc | acc | gcg | tgc | cgc | gtc | tgc | ggc | aac | aag | gag | ctg | ctc | tcc | 48 |
| Met | Ile | Ala | Thr | Ala | Cys | Arg | Val | Cys | Gly | Asn | Lys | Glu | Leu | Leu | Ser | |
| 1 | | | | 5 | | | | | 10 | | | | | 15 | | |
| gta | ctc | gac | ctg | ggc | gaa | cag | gcg | ctc | acc | ggg | gtg | ttc | ccg | gcc | gac | 96 |
| Val | Leu | Asp | Leu | Gly | Glu | Gln | Ala | Leu | Thr | Gly | Val | Phe | Pro | Ala | Asp | |
| | | | 20 | | | | | 25 | | | | | 30 | | | |
| cgc | gac | gag | gtc | gtg | ccg | tcg | gtc | ccg | ctg | gaa | ctc | gtc | gcg | tgt | tcc | 144 |
| Arg | Asp | Glu | Val | Val | Pro | Ser | Val | Pro | Leu | Glu | Leu | Val | Ala | Cys | Ser | |
| | | 35 | | | | | 40 | | | | | 45 | | | | |
| ccg | gcc | gga | tgc | ggc | ctc | gtg | caa | ctg | cgc | cac | acc | ccc | gac | ccg | gac | 192 |
| Pro | Ala | Gly | Cys | Gly | Leu | Val | Gln | Leu | Arg | His | Thr | Pro | Asp | Pro | Asp | |
| | 50 | | | | | 55 | | | | | 60 | | | | | |
| ctc | atg | tac | ggc | gag | ggc | tac | ggc | tac | cgc | tcg | ggc | atc | cgg | ccc | ttc | 240 |
| Leu | Met | Tyr | Gly | Glu | Gly | Tyr | Gly | Tyr | Arg | Ser | Gly | Ile | Arg | Pro | Phe | |
| 65 | | | | | 70 | | | | | 75 | | | | | 80 | |
| atg | gtc | gac | cac | ctg | cat | ggc | aag | gtc | gcc | gcc | gtc | cgc | cgg | ctg | gtg | 288 |
| Met | Val | Asp | His | Leu | His | Gly | Lys | Val | Ala | Ala | Val | Arg | Arg | Leu | Val | |
| | | | | 85 | | | | | 90 | | | | | 95 | | |
| gac | ctc | ggc | ccg | gac | gac | ctg | gtc | ctc | gac | atc | ggc | agc | aac | gac | gcc | 336 |
| Asp | Leu | Gly | Pro | Asp | Asp | Leu | Val | Leu | Asp | Ile | Gly | Ser | Asn | Asp | Ala | |
| | | | 100 | | | | | 105 | | | | | 110 | | | |
| acg | ctc | ctc | aag | ggc | tac | ccc | gcc | gac | ggc | ccg | cga | ctg | gtc | ggc | atc | 384 |
| Thr | Leu | Leu | Lys | Gly | Tyr | Pro | Ala | Asp | Gly | Pro | Arg | Leu | Val | Gly | Ile | |
| | | 115 | | | | | 120 | | | | | 125 | | | | |
| gac | ccg | acc | ggc | ggc | aag | ttc | cgc | gac | ctg | tac | ccg | ccg | aac | gcc | gag | 432 |
| Asp | Pro | Thr | Gly | Gly | Lys | Phe | Arg | Asp | Leu | Tyr | Pro | Pro | Asn | Ala | Glu | |
| | 130 | | | | | 135 | | | | | 140 | | | | | |
| ttg | gtc | gtg | gac | tac | ttc | acc | cgc | gcg | acc | ttc | gag | aac | cgc | ttc | ggg | 480 |
| Leu | Val | Val | Asp | Tyr | Phe | Thr | Arg | Ala | Thr | Phe | Glu | Asn | Arg | Phe | Gly | |
| 145 | | | | | 150 | | | | | 155 | | | | | 160 | |
| gcg | cgg | cgg | gcg | aag | gcc | gtc | acc | tcc | atc | gcg | atg | ttc | tac | gac | ctg | 528 |
| Ala | Arg | Arg | Ala | Lys | Ala | Val | Thr | Ser | Ile | Ala | Met | Phe | Tyr | Asp | Leu | |
| | | | | 165 | | | | | 170 | | | | | 175 | | |
| ccg | gac | ccg | ctg | cgc | ttc | atg | agc | gac | gtc | cgc | gac | gtc | ctc | gcc | gag | 576 |
| Pro | Asp | Pro | Leu | Arg | Phe | Met | Ser | Asp | Val | Arg | Asp | Val | Leu | Ala | Glu | |
| | | | 180 | | | | | 185 | | | | | 190 | | | |
| gac | ggc | gtc | tgg | atg | atg | gag | cag | agc | tac | ctg | ccc | gcc | atg | ctc | gaa | 624 |
| Asp | Gly | Val | Trp | Met | Met | Glu | Gln | Ser | Tyr | Leu | Pro | Ala | Met | Leu | Glu | |
| | | 195 | | | | | 200 | | | | | 205 | | | | |
| gcc | gac | gcg | tac | gac | atc | gtc | tgc | cac | gag | cac | ctg | gag | tac | tac | gcg | 672 |
| Ala | Asp | Ala | Tyr | Asp | Ile | Val | Cys | His | Glu | His | Leu | Glu | Tyr | Tyr | Ala | |
| | 210 | | | | | 215 | | | | | 220 | | | | | |
| ctg | cgc | cag | atc | gag | tgg | atg | gcg | gaa | cgc | gtc | ggc | ctc | acc | gtc | atc | 720 |
| Leu | Arg | Gln | Ile | Glu | Trp | Met | Ala | Glu | Arg | Val | Gly | Leu | Thr | Val | Ile | |
| 225 | | | | | 230 | | | | | 235 | | | | | 240 | |
| cgg | gcc | gag | ctc | acc | gag | gtg | tac | ggc | ggc | agc | ctg | tgc | gtc | acg | ctc | 768 |
| Arg | Ala | Glu | Leu | Thr | Glu | Val | Tyr | Gly | Gly | Ser | Leu | Cys | Val | Thr | Leu | |
| | | | | 245 | | | | | 250 | | | | | 255 | | |
| gcc | agg | acc | ggt | tcc | cgg | cac | ccg | agg | gac | gag | gcg | ggc | ctg | gcc | cgc | 816 |
| Ala | Arg | Thr | Gly | Ser | Arg | His | Pro | Arg | Asp | Glu | Ala | Gly | Leu | Ala | Arg | |
| | | | 260 | | | | | 265 | | | | | 270 | | | |
| atc | cgg | gcc | gcc | gag | gcc | gcc | gcg | gga | ctg | gac | ggc | atg | gca | ccg | ttc | 864 |
| Ile | Arg | Ala | Ala | Glu | Ala | Ala | Ala | Gly | Leu | Asp | Gly | Met | Ala | Pro | Phe | |

-continued

```
                275                 280                 285
gag gcc ttc gcc cgc cgc gtc gcc gac cag cgg gac gcc ctg cgc ggc      912
Glu Ala Phe Ala Arg Arg Val Ala Asp Gln Arg Asp Ala Leu Arg Gly
    290                 295                 300 ttc ctg gac cgc tcc cgc caa gag ggc ctg ctg acc ctc ggg tac ggc      960
Phe Leu Asp Arg Ser Arg Gln Glu Gly Leu Leu Thr Leu Gly Tyr Gly
305                 310                 315                 320 gcc tcc acc aag ggc aac gtc atc ctc cag tac tgc ggg atc acc gaa     1008
Ala Ser Thr Lys Gly Asn Val Ile Leu Gln Tyr Cys Gly Ile Thr Glu
                325                 330                 335 cgg gac ctg ccg tgc atc ggc gag gtg agc gag gag aag gcg ggg cgt     1056
Arg Asp Leu Pro Cys Ile Gly Glu Val Ser Glu Glu Lys Ala Gly Arg
            340                 345                 350 ttc acc ccc ggg acg ggc atc ccc atc gtg tcc gag gag gac gcg aag     1104
Phe Thr Pro Gly Thr Gly Ile Pro Ile Val Ser Glu Glu Asp Ala Lys
        355                 360                 365 gcg cag aag ccg gac cag ttg ctg gtc ctg ccc tgg atc tac cgg gac     1152
Ala Gln Lys Pro Asp Gln Leu Leu Val Leu Pro Trp Ile Tyr Arg Asp
    370                 375                 380 ggg ttc gtc gaa cgg gag cgg gag ttc ctc gac ggc ggc gga cga ctg     1200
Gly Phe Val Glu Arg Glu Arg Glu Phe Leu Asp Gly Gly Gly Arg Leu
385                 390                 395                 400 gtc ttc ccg ctg ccc gcg ctc gac gtc gtg tga                         1233
Val Phe Pro Leu Pro Ala Leu Asp Val Val
                405                 410
```

<210> SEQ ID NO 77
<211> LENGTH: 410
<212> TYPE: PRT
<213> ORGANISM: Streptomyces ambofaciens

<400> SEQUENCE: 77

Met Ile Ala Thr Ala Cys Arg Val Cys Gly Asn Lys Glu Leu Leu Ser
1               5                   10                  15

Val Leu Asp Leu Gly Glu Gln Ala Leu Thr Gly Val Phe Pro Ala Asp
            20                  25                  30

Arg Asp Glu Val Val Pro Ser Pro Leu Glu Leu Val Ala Cys Ser
        35                  40                  45

Pro Ala Gly Cys Gly Leu Val Gln Leu Arg His Thr Pro Asp Pro Asp
    50                  55                  60

Leu Met Tyr Gly Glu Gly Tyr Gly Tyr Arg Ser Gly Ile Arg Pro Phe
65                  70                  75                  80

Met Val Asp His Leu His Gly Lys Val Ala Ala Val Arg Arg Leu Val
                85                  90                  95

Asp Leu Gly Pro Asp Asp Leu Val Leu Asp Ile Gly Ser Asn Asp Ala
            100                 105                 110

Thr Leu Leu Lys Gly Tyr Pro Ala Asp Gly Pro Arg Leu Val Gly Ile
        115                 120                 125

Asp Pro Thr Gly Gly Lys Phe Arg Asp Leu Tyr Pro Pro Asn Ala Glu
    130                 135                 140

Leu Val Val Asp Tyr Phe Thr Arg Ala Thr Phe Glu Asn Arg Phe Gly
145                 150                 155                 160

Ala Arg Arg Ala Lys Ala Val Thr Ser Ile Ala Met Phe Tyr Asp Leu
                165                 170                 175

Pro Asp Pro Leu Arg Phe Met Ser Asp Val Arg Asp Val Leu Ala Glu
            180                 185                 190

Asp Gly Val Trp Met Met Glu Gln Ser Tyr Leu Pro Ala Met Leu Glu

-continued

```
                195                 200                 205
Ala Asp Ala Tyr Asp Ile Val Cys His Glu His Leu Glu Tyr Tyr Ala
    210                 215                 220

Leu Arg Gln Ile Glu Trp Met Ala Glu Arg Val Gly Leu Thr Val Ile
225                 230                 235                 240

Arg Ala Glu Leu Thr Glu Val Tyr Gly Gly Ser Leu Cys Val Thr Leu
                245                 250                 255

Ala Arg Thr Gly Ser Arg His Pro Arg Asp Glu Ala Gly Leu Ala Arg
            260                 265                 270

Ile Arg Ala Ala Glu Ala Ala Gly Leu Asp Gly Met Ala Pro Phe
        275                 280                 285

Glu Ala Phe Ala Arg Arg Val Ala Asp Gln Arg Asp Ala Leu Arg Gly
    290                 295                 300

Phe Leu Asp Arg Ser Arg Gln Glu Gly Leu Leu Thr Leu Gly Tyr Gly
305                 310                 315                 320

Ala Ser Thr Lys Gly Asn Val Ile Leu Gln Tyr Cys Gly Ile Thr Glu
                325                 330                 335

Arg Asp Leu Pro Cys Ile Gly Glu Val Ser Glu Lys Ala Gly Arg
            340                 345                 350

Phe Thr Pro Gly Thr Gly Ile Pro Ile Val Ser Glu Glu Asp Ala Lys
        355                 360                 365

Ala Gln Lys Pro Asp Gln Leu Leu Val Leu Pro Trp Ile Tyr Arg Asp
    370                 375                 380

Gly Phe Val Glu Arg Glu Arg Glu Phe Leu Asp Gly Gly Gly Arg Leu
385                 390                 395                 400

Val Phe Pro Leu Pro Ala Leu Asp Val Val
                405                 410

<210> SEQ ID NO 78
<211> LENGTH: 1116
<212> TYPE: DNA
<213> ORGANISM: Streptomyces ambofaciens
<220> FEATURE:
<221> NAME/KEY: CDS
<222> LOCATION: (1)..(1116)

<400> SEQUENCE: 78 gtg cac cgg gac aac gcc gcc gag ccg ttg gtc aaa tgc ctg gtc tgg     48
Val His Arg Asp Asn Ala Ala Glu Pro Leu Val Lys Cys Leu Val Trp
 1               5                  10                  15 gac ctg gac aac acc ctc tgg cag ggc acc ctc ctc gag gag gac gag     96
Asp Leu Asp Asn Thr Leu Trp Gln Gly Thr Leu Leu Glu Glu Asp Glu
                20                  25                  30 gtc cgg ctc gcc ccg gac gtc ctg cgg acc atc acc gag ctg gac gcg    144
Val Arg Leu Ala Pro Asp Val Leu Arg Thr Ile Thr Glu Leu Asp Ala
            35                  40                  45 cgc ggc atc ctg cag gcg gtg gcc agc aag aac gac cac gat cac gcc    192
Arg Gly Ile Leu Gln Ala Val Ala Ser Lys Asn Asp His Asp His Ala
        50                  55                  60 tgg gcg aag ctc gaa cag ctc ggc gtc gcc gag tac ttc gtg ctc ccg    240
Trp Ala Lys Leu Glu Gln Leu Gly Val Ala Glu Tyr Phe Val Leu Pro
 65                  70                  75                  80 agg atc ggc tgg ggc ccg aag tcg aag tcg gtc cgc gag atc gcc gac    288
Arg Ile Gly Trp Gly Pro Lys Ser Lys Ser Val Arg Glu Ile Ala Asp
                85                  90                  95 cgg ctg aac ttc gcg ccg agc acc ctc gcc ttc atc gac gac cag ccc    336
Arg Leu Asn Phe Ala Pro Ser Thr Leu Ala Phe Ile Asp Asp Gln Pro
            100                 105                 110
```

-continued

```
ttc gaa cgg gcc gag gtc acc cac gaa ctg ccg gag gtc cgc acc tac        384
Phe Glu Arg Ala Glu Val Thr His Glu Leu Pro Glu Val Arg Thr Tyr
        115                 120                 125 gcc gcc gag cag gcg acc cgg ctg acc ggc ctc ccg gag ttc agc ccg        432
Ala Ala Glu Gln Ala Thr Arg Leu Thr Gly Leu Pro Glu Phe Ser Pro
130                 135                 140 ggc acc gtc acc gtc gac tcg acc cgc cgc cgc tcc atg tac cag gcg        480
Gly Thr Val Thr Val Asp Ser Thr Arg Arg Arg Ser Met Tyr Gln Ala
145                 150                 155                 160 tcc ttc cgc cgg gac gcc gag cgg tcc gac ttc acc gga ccc gac gcg        528
Ser Phe Arg Arg Asp Ala Glu Arg Ser Asp Phe Thr Gly Pro Asp Ala
        165                 170                 175 gac ttc ctg cgc tcg ctg gac atc cgg atg cgg atc agc cgc gcc acg        576
Asp Phe Leu Arg Ser Leu Asp Ile Arg Met Arg Ile Ser Arg Ala Thr
        180                 185                 190 ccc ctg gag ctg tcg cgg gtc gag gaa ctg acc ctg cgc acc agc cag        624
Pro Leu Glu Leu Ser Arg Val Glu Glu Leu Thr Leu Arg Thr Ser Gln
        195                 200                 205 atg aac gcc acc gga gtg cac tac tcc gag gac gag ctg cgc gcc ctc        672
Met Asn Ala Thr Gly Val His Tyr Ser Glu Asp Glu Leu Arg Ala Leu
210                 215                 220 atc gac gac ccc gac cac gag gtg ctg gtc acc acc gtc acc gat cgc        720
Ile Asp Asp Pro Asp His Glu Val Leu Val Thr Thr Val Thr Asp Arg
225                 230                 235                 240 ttc ggt ccc tac ggc gcg gtc ggc gtc gtg ctg ctg cgg cgc ggc ccc        768
Phe Gly Pro Tyr Gly Ala Val Gly Val Val Leu Leu Arg Arg Gly Pro
        245                 250                 255 gag gcc tgg cgg atc aag ctg ctg gcc acc tcg tgc cgg gtg gtg tcg        816
Glu Ala Trp Arg Ile Lys Leu Leu Ala Thr Ser Cys Arg Val Val Ser
        260                 265                 270 ctg ggg gcc ggc acg gtg atc ctg cgc tgg ctg acg gac cag gcg cac        864
Leu Gly Ala Gly Thr Val Ile Leu Arg Trp Leu Thr Asp Gln Ala His
        275                 280                 285 cgg gcc ggg gtg cac ctc gga gcc gac ttc cgg gcc acc gaa cgc aac        912
Arg Ala Gly Val His Leu Gly Ala Asp Phe Arg Ala Thr Glu Arg Asn
290                 295                 300 cgg atg atg gaa gtg gcc tac cgc ttc gcc gga ttc acc gac gat ccc        960
Arg Met Met Glu Val Ala Tyr Arg Phe Ala Gly Phe Thr Asp Asp Pro
305                 310                 315                 320 tgc ccg tgc cag gac gcc tcc gcc gcc acc ggc gcg atc ggc cgc ctg       1008
Cys Pro Cys Gln Asp Ala Ser Ala Ala Thr Gly Ala Ile Gly Arg Leu
        325                 330                 335 cac ctg gtg ccg tcc ccc cgg ccc gcc ccc gac acc ctc cgt ctg gaa       1056
His Leu Val Pro Ser Pro Arg Pro Ala Pro Asp Thr Leu Arg Leu Glu
        340                 345                 350 gct ccc gac ctg gcc acg ggc cgg cgg cgc ccc ggc cag gat ccc gaa       1104
Ala Pro Asp Leu Ala Thr Gly Arg Arg Arg Pro Gly Gln Asp Pro Glu
        355                 360                 365 agg acc cca tga                                                       1116
Arg Thr Pro
        370
```

<210> SEQ ID NO 79
<211> LENGTH: 371
<212> TYPE: PRT
<213> ORGANISM: Streptomyces ambofaciens

<400> SEQUENCE: 79

```
Val His Arg Asp Asn Ala Ala Glu Pro Leu Val Lys Cys Leu Val Trp
1               5                   10                  15
```

Asp Leu Asp Asn Thr Leu Trp Gln Gly Thr Leu Leu Glu Glu Asp Glu
            20                  25                  30

Val Arg Leu Ala Pro Asp Val Leu Arg Thr Ile Thr Glu Leu Asp Ala
        35                  40                  45

Arg Gly Ile Leu Gln Ala Val Ala Ser Lys Asn Asp His Asp His Ala
    50                  55                  60

Trp Ala Lys Leu Glu Gln Leu Gly Val Ala Glu Tyr Phe Val Leu Pro
65                  70                  75                  80

Arg Ile Gly Trp Gly Pro Lys Ser Lys Ser Val Arg Glu Ile Ala Asp
                85                  90                  95

Arg Leu Asn Phe Ala Pro Ser Thr Leu Ala Phe Ile Asp Asp Gln Pro
            100                 105                 110

Phe Glu Arg Ala Glu Val Thr His Glu Leu Pro Glu Val Arg Thr Tyr
        115                 120                 125

Ala Ala Glu Gln Ala Thr Arg Leu Thr Gly Leu Pro Glu Phe Ser Pro
    130                 135                 140

Gly Thr Val Thr Val Asp Ser Thr Arg Arg Ser Met Tyr Gln Ala
145                 150                 155                 160

Ser Phe Arg Arg Asp Ala Glu Arg Ser Asp Phe Thr Gly Pro Asp Ala
                165                 170                 175

Asp Phe Leu Arg Ser Leu Asp Ile Arg Met Arg Ile Ser Arg Ala Thr
            180                 185                 190

Pro Leu Glu Leu Ser Arg Val Glu Glu Leu Thr Leu Arg Thr Ser Gln
        195                 200                 205

Met Asn Ala Thr Gly Val His Tyr Ser Glu Asp Glu Leu Arg Ala Leu
    210                 215                 220

Ile Asp Asp Pro Asp His Glu Val Leu Val Thr Val Thr Asp Arg
225                 230                 235                 240

Phe Gly Pro Tyr Gly Ala Val Gly Val Val Leu Leu Arg Arg Gly Pro
                245                 250                 255

Glu Ala Trp Arg Ile Lys Leu Leu Ala Thr Ser Cys Arg Val Val Ser
            260                 265                 270

Leu Gly Ala Gly Thr Val Ile Leu Arg Trp Leu Thr Asp Gln Ala His
        275                 280                 285

Arg Ala Gly Val His Leu Gly Ala Asp Phe Arg Ala Thr Glu Arg Asn
    290                 295                 300

Arg Met Met Glu Val Ala Tyr Arg Phe Ala Gly Phe Thr Asp Asp Pro
305                 310                 315                 320

Cys Pro Cys Gln Asp Ala Ser Ala Ala Thr Gly Ala Ile Gly Arg Leu
                325                 330                 335

His Leu Val Pro Ser Pro Arg Pro Ala Pro Asp Thr Leu Arg Leu Glu
            340                 345                 350

Ala Pro Asp Leu Ala Thr Gly Arg Arg Pro Gly Gln Asp Pro Glu
        355                 360                 365

Arg Thr Pro
    370

<210> SEQ ID NO 80
<211> LENGTH: 1122
<212> TYPE: DNA
<213> ORGANISM: Streptomyces ambofaciens
<220> FEATURE:
<221> NAME/KEY: CDS
<222> LOCATION: (1)..(1122)

-continued

```
<400> SEQUENCE: 80 gtg gct gac acc tcc cac gcc gac ggc acc gag gcc gag gag ctg ttc      48
Val Ala Asp Thr Ser His Ala Asp Gly Thr Glu Ala Glu Glu Leu Phe
 1               5                  10                  15 acc gcg ctg gtc ggc gac cgg gcg gcc gag tgg gac cgg acg ggc gag      96
Thr Ala Leu Val Gly Asp Arg Ala Ala Glu Trp Asp Arg Thr Gly Glu
             20                  25                  30 ctg ccc ctc ggc ctg ctg cac gac ctc ggc tcc cgg ggc ctg ctg tgc     144
Leu Pro Leu Gly Leu Leu His Asp Leu Gly Ser Arg Gly Leu Leu Cys
         35                  40                  45 gca cag gcg ccc gcg gtc cac ggc ggc ctc ggc tgg acc agc cgg cgc     192
Ala Gln Ala Pro Ala Val His Gly Gly Leu Gly Trp Thr Ser Arg Arg
     50                  55                  60 aac ggc gaa ctc acc gcg cac gtc ggc gcc ctc tgc agc tcg ttg cgg     240
Asn Gly Glu Leu Thr Ala His Val Gly Ala Leu Cys Ser Ser Leu Arg
 65                  70                  75                  80 agc gtc atg acc tcg cag ggc atg gcc gcc tgg acg ctg cgc cgg ctc     288
Ser Val Met Thr Ser Gln Gly Met Ala Ala Trp Thr Leu Arg Arg Leu
                 85                  90                  95 gcc gga gcg gac cag cag gcc tcc ctg gtg ccc cgg ttg acc ggc ggc     336
Ala Gly Ala Asp Gln Gln Ala Ser Leu Val Pro Arg Leu Thr Gly Gly
            100                 105                 110 gaa ctg gcc gcc gtg gcg ttc acc gag gcc ggc gcc ggc agc gac ctg     384
Glu Leu Ala Ala Val Ala Phe Thr Glu Ala Gly Ala Gly Ser Asp Leu
        115                 120                 125 tcc gcc ctg cgc acc cgc atc acc tcc gac ggc gac gaa gtc gtc gtc     432
Ser Ala Leu Arg Thr Arg Ile Thr Ser Asp Gly Asp Glu Val Val Val
    130                 135                 140 gac ggc gtc aag gtg tgg gcg acc aac gcc gcg tac gcg gac ctg ctg     480
Asp Gly Val Lys Val Trp Ala Thr Asn Ala Ala Tyr Ala Asp Leu Leu
145                 150                 155                 160 gtg gtc ttc ggc cgc acg gag cag ggc gcg ggc gcc gtc gtg gtg ccc     528
Val Val Phe Gly Arg Thr Glu Gln Gly Ala Gly Ala Val Val Val Pro
                165                 170                 175 gcc tcg gcc ccc ggc gta cgc gtc gag cgc atc acc gac gcg cac ggc     576
Ala Ser Ala Pro Gly Val Arg Val Glu Arg Ile Thr Asp Ala His Gly
            180                 185                 190 tgc cgc gcg gcc gga cac gcc gac atc cac ctg gac ggg gtc cgg ctg     624
Cys Arg Ala Ala Gly His Ala Asp Ile His Leu Asp Gly Val Arg Leu
        195                 200                 205 ccg gca gac gcc ctg ctc cag ggc cac gac cgc acc ccc gcc ctg ctg     672
Pro Ala Asp Ala Leu Leu Gln Gly His Asp Arg Thr Pro Ala Leu Leu
    210                 215                 220 gtc acc acc gcg ctg agc tac ggc cgg atg tcg gtg gcc tgg ggc tcc     720
Val Thr Thr Ala Leu Ser Tyr Gly Arg Met Ser Val Ala Trp Gly Ser
225                 230                 235                 240 ctg ggc atc ctg cgc gcc tgc ctg gcc gcc gca cgt cac gcc ggc         768
Leu Gly Ile Leu Arg Ala Cys Leu Ala Ala Ala Arg His Ala Gly
                245                 250                 255 gga cgg gag cag ttc ggc acg cgg ctc tcg gac cac cag ctc gtc gcc     816
Gly Arg Glu Gln Phe Gly Thr Arg Leu Ser Asp His Gln Leu Val Ala
            260                 265                 270 cgg cac ctc gcc gaa ctg ttc gtc gcc gaa cag cac gcc gcc cgg gcg     864
Arg His Leu Ala Glu Leu Phe Val Ala Glu Gln His Ala Ala Arg Ala
        275                 280                 285 tgc gag cac gcc agc gcc cag tgg gac gag ggc agc ccc gac atg gtg     912
Cys Glu His Ala Ser Ala Gln Trp Asp Glu Gly Ser Pro Asp Met Val
    290                 295                 300 gtc gcc gcc gtc ctg gcc aag cac gtc gcg gcc acc ggc gcc gca cgc     960
```

```
Val Ala Ala Val Leu Ala Lys His Val Ala Ala Thr Gly Ala Ala Arg
305                 310                 315                 320 ggg gcc gaa cgg gcc gtg cag gtg ctg gcg tcg gcc ggg gcg cgg gag      1008
Gly Ala Glu Arg Ala Val Gln Val Leu Ala Ser Ala Gly Ala Arg Glu
                325                 330                 335 gga cac gtc gtc gca cgg gcg cac cgc gac gcc aag ctc atg gag atc      1056
Gly His Val Val Ala Arg Ala His Arg Asp Ala Lys Leu Met Glu Ile
                340                 345                 350 atc gag ggc agc aac gag atc tgc gaa ctg gtc ctg gcc cgg cac gtg      1104
Ile Glu Gly Ser Asn Glu Ile Cys Glu Leu Val Leu Ala Arg His Val
                355                 360                 365 atg tcc gcg gcc ggg tga                                              1122
Met Ser Ala Ala Gly
370

<210> SEQ ID NO 81
<211> LENGTH: 373
<212> TYPE: PRT
<213> ORGANISM: Streptomyces ambofaciens

<400> SEQUENCE: 81

Val Ala Asp Thr Ser His Ala Asp Gly Thr Glu Ala Glu Glu Leu Phe
1               5                   10                  15

Thr Ala Leu Val Gly Asp Arg Ala Ala Glu Trp Asp Arg Thr Gly Glu
                20                  25                  30

Leu Pro Leu Gly Leu Leu His Asp Leu Gly Ser Arg Gly Leu Leu Cys
            35                  40                  45

Ala Gln Ala Pro Ala Val His Gly Gly Leu Gly Trp Thr Ser Arg Arg
        50                  55                  60

Asn Gly Glu Leu Thr Ala His Val Gly Ala Leu Cys Ser Ser Leu Arg
65                  70                  75                  80

Ser Val Met Thr Ser Gln Gly Met Ala Ala Trp Thr Leu Arg Arg Leu
                85                  90                  95

Ala Gly Ala Asp Gln Gln Ala Ser Leu Val Pro Arg Leu Thr Gly Gly
                100                 105                 110

Glu Leu Ala Ala Val Ala Phe Thr Glu Ala Gly Ala Gly Ser Asp Leu
            115                 120                 125

Ser Ala Leu Arg Thr Arg Ile Thr Ser Asp Gly Asp Glu Val Val Val
        130                 135                 140

Asp Gly Val Lys Val Trp Ala Thr Asn Ala Ala Tyr Ala Asp Leu Leu
145                 150                 155                 160

Val Val Phe Gly Arg Thr Glu Gln Gly Ala Gly Val Val Val Pro
                165                 170                 175

Ala Ser Ala Pro Gly Val Arg Val Glu Arg Ile Thr Asp Ala His Gly
                180                 185                 190

Cys Arg Ala Ala Gly His Ala Asp Ile His Leu Asp Gly Val Arg Leu
            195                 200                 205

Pro Ala Asp Ala Leu Leu Gln Gly His Asp Arg Thr Pro Ala Leu Leu
        210                 215                 220

Val Thr Thr Ala Leu Ser Tyr Gly Arg Met Ser Val Ala Trp Gly Ser
225                 230                 235                 240

Leu Gly Ile Leu Arg Ala Cys Leu Ala Ala Ala Arg His Ala Gly
                245                 250                 255

Gly Arg Glu Gln Phe Gly Thr Arg Leu Ser Asp His Gln Leu Val Ala
                260                 265                 270

Arg His Leu Ala Glu Leu Phe Val Ala Glu Gln His Ala Ala Arg Ala
```

```
                275                 280                 285
Cys Glu His Ala Ser Ala Gln Trp Asp Glu Gly Ser Pro Asp Met Val
    290                 295                 300

Val Ala Ala Val Leu Ala Lys His Val Ala Ala Thr Gly Ala Ala Arg
305                 310                 315                 320

Gly Ala Glu Arg Ala Val Gln Val Leu Ala Ser Ala Gly Ala Arg Glu
                325                 330                 335

Gly His Val Val Ala Arg Ala His Arg Asp Ala Lys Leu Met Glu Ile
            340                 345                 350

Ile Glu Gly Ser Asn Glu Ile Cys Glu Leu Val Leu Ala Arg His Val
        355                 360                 365

Met Ser Ala Ala Gly
    370

<210> SEQ ID NO 82
<211> LENGTH: 312
<212> TYPE: DNA
<213> ORGANISM: Streptomyces ambofaciens
<220> FEATURE:
<221> NAME/KEY: CDS
<222> LOCATION: (1)..(312)

<400> SEQUENCE: 82 atg acc acg acg tcc ggt cgg ccc gac ccc acc ggc acg acc ccc acc      48
Met Thr Thr Thr Ser Gly Arg Pro Asp Pro Thr Gly Thr Thr Pro Thr
1               5                   10                  15 gcc gac gag gtc gcc ggg gaa ctg ctc ggg ttc ctc gag gac cgc acc      96
Ala Asp Glu Val Ala Gly Glu Leu Leu Gly Phe Leu Glu Asp Arg Thr
                20                  25                  30 aag acc acc tgg gag cgc gac cag gac ctg ttc gcc gtc ggc ggg atg     144
Lys Thr Thr Trp Glu Arg Asp Gln Asp Leu Phe Ala Val Gly Gly Met
            35                  40                  45 tcc tcg ctg ttc gcc atg cag ctc gtc gtg cac ctg gag aag acc tac     192
Ser Ser Leu Phe Ala Met Gln Leu Val Val His Leu Glu Lys Thr Tyr
        50                  55                  60 ggc atc gtc atc agc ggc gcc gac ctg atg ctc gac aac ttc cgc acc     240
Gly Ile Val Ile Ser Gly Ala Asp Leu Met Leu Asp Asn Phe Arg Thr
65                  70                  75                  80 gtc gac gcg atg gtc cgg ctg gtc gga cgg ctg gcc gcg ccc ggc gag     288
Val Asp Ala Met Val Arg Leu Val Gly Arg Leu Ala Ala Pro Gly Glu
                85                  90                  95 gcg acc ggg cac gca ggt ggc tga                                     312
Ala Thr Gly His Ala Gly Gly
                100

<210> SEQ ID NO 83
<211> LENGTH: 103
<212> TYPE: PRT
<213> ORGANISM: Streptomyces ambofaciens

<400> SEQUENCE: 83

Met Thr Thr Thr Ser Gly Arg Pro Asp Pro Thr Gly Thr Thr Pro Thr
1               5                   10                  15

Ala Asp Glu Val Ala Gly Glu Leu Leu Gly Phe Leu Glu Asp Arg Thr
                20                  25                  30

Lys Thr Thr Trp Glu Arg Asp Gln Asp Leu Phe Ala Val Gly Gly Met
            35                  40                  45

Ser Ser Leu Phe Ala Met Gln Leu Val Val His Leu Glu Lys Thr Tyr
        50                  55                  60
```

```
Gly Ile Val Ile Ser Gly Ala Asp Leu Met Leu Asp Asn Phe Arg Thr
 65                  70                  75                  80

Val Asp Ala Met Val Arg Leu Val Gly Arg Leu Ala Ala Pro Gly Glu
                 85                  90                  95

Ala Thr Gly His Ala Gly Gly
            100

<210> SEQ ID NO 84
<211> LENGTH: 867
<212> TYPE: DNA
<213> ORGANISM: Streptomyces ambofaciens
<220> FEATURE:
<221> NAME/KEY: CDS
<222> LOCATION: (1)..(867)

<400> SEQUENCE: 84 gtg ccc gat tcc aag gaa aat tct ccg ctc gtc gtg ctc ggc gcg ggc    48
Val Pro Asp Ser Lys Glu Asn Ser Pro Leu Val Val Leu Gly Ala Gly
  1               5                  10                  15 gtc atg ggc acg gcc atc gcg gca ctc gcc gtc gga cac ggg cac ccg    96
Val Met Gly Thr Ala Ile Ala Ala Leu Ala Val Gly His Gly His Pro
                 20                  25                  30 gtc aca ctg gtc gac acc tcc gcc ggg gcg cgc gcg gcc gcc ccc gac   144
Val Thr Leu Val Asp Thr Ser Ala Gly Ala Arg Ala Ala Ala Pro Asp
             35                  40                  45 gcg gtc gcg ctg cat ctg cgg acg gcc cgg ctg atg ggc gcg ctg ccc   192
Ala Val Ala Leu His Leu Arg Thr Ala Arg Leu Met Gly Ala Leu Pro
         50                  55                  60 cac gac cgc ccg ccc ggg gag ctg acc gtc gag gag gcg ccg gcc gcc   240
His Asp Arg Pro Pro Gly Glu Leu Thr Val Glu Glu Ala Pro Ala Ala
 65                  70                  75                  80 gtc gcc acc gcg acc gcc gtg atc gag gcc gtc acc gag gac ccc gag   288
Val Ala Thr Ala Thr Ala Val Ile Glu Ala Val Thr Glu Asp Pro Glu
                 85                  90                  95 cgg aag gcc gag gtg ctg gcg gac ctg gcg tcc gtg gcg cgc ccg ggg   336
Arg Lys Ala Glu Val Leu Ala Asp Leu Ala Ser Val Ala Arg Pro Gly
            100                 105                 110 acg ctg ctc gtc agc aac acc tcg ggc gtc ccc atc gac gag ctg gcc   384
Thr Leu Leu Val Ser Asn Thr Ser Gly Val Pro Ile Asp Glu Leu Ala
        115                 120                 125 gac gcc gtc ccc cgc ccc gag gac ctc gtc ggc gtg cac ttc atg aac   432
Asp Ala Val Pro Arg Pro Glu Asp Leu Val Gly Val His Phe Met Asn
130                 135                 140 ccc gcg tac gtg atc ccc acg gtc gag gtg gtc ctc gga ccg cgc agc   480
Pro Ala Tyr Val Ile Pro Thr Val Glu Val Val Leu Gly Pro Arg Ser
145                 150                 155                 160 gga gag gcg gcc gcc cgg gcc acc cgg gac ctg ctg tcc ggc ctg ggc   528
Gly Glu Ala Ala Ala Arg Ala Thr Arg Asp Leu Leu Ser Gly Leu Gly
                165                 170                 175 cgc cgg ggc atc gtc gtc ggc gac ggc gcc ggc ttc gtg acc agc cgc   576
Arg Arg Gly Ile Val Val Gly Asp Gly Ala Gly Phe Val Thr Ser Arg
            180                 185                 190 ctg ctg cac cgg atg ctg aac gac gcc atc gcg gtg gtg cac gag ggc   624
Leu Leu His Arg Met Leu Asn Asp Ala Ile Ala Val Val His Glu Gly
        195                 200                 205 cgg gcc acc ccg gag acc gtg gac gcg ctg atg cgc gac tgc atc ggc   672
Arg Ala Thr Pro Glu Thr Val Asp Ala Leu Met Arg Asp Cys Ile Gly
    210                 215                 220 cac cgc acc gga ccc ctg gcc acg gcc gac ctg atc gga ctg gac aac   720
His Arg Thr Gly Pro Leu Ala Thr Ala Asp Leu Ile Gly Leu Asp Asn
225                 230                 235                 240
```

```
ctg gcc gac tcg ctg cgg gtg atg cac gaa cgg acc ggc gat ccg gcg      768
Leu Ala Asp Ser Leu Arg Val Met His Glu Arg Thr Gly Asp Pro Ala
            245                 250                 255 ctc cgc ccg agc gag ctg ctg ctg gac aag gtc cgc cag ggc ctg ctc      816
Leu Arg Pro Ser Glu Leu Leu Leu Asp Lys Val Arg Gln Gly Leu Leu
        260                 265                 270 ggc cgc aag agc ggc cgg gga ttc tac gac tac cag gag gcc acg cga      864
Gly Arg Lys Ser Gly Arg Gly Phe Tyr Asp Tyr Gln Glu Ala Thr Arg
            275                 280                 285 tga                                                                   867
```

<210> SEQ ID NO 85
<211> LENGTH: 288
<212> TYPE: PRT
<213> ORGANISM: Streptomyces ambofaciens

<400> SEQUENCE: 85

```
Val Pro Asp Ser Lys Glu Asn Ser Pro Leu Val Val Leu Gly Ala Gly
1               5                   10                  15

Val Met Gly Thr Ala Ile Ala Ala Leu Ala Val Gly His Gly His Pro
            20                  25                  30

Val Thr Leu Val Asp Thr Ser Ala Gly Ala Arg Ala Ala Ala Pro Asp
        35                  40                  45

Ala Val Ala Leu His Leu Arg Thr Ala Arg Leu Met Gly Ala Leu Pro
    50                  55                  60

His Asp Arg Pro Pro Gly Glu Leu Thr Val Glu Glu Ala Pro Ala Ala
65                  70                  75                  80

Val Ala Thr Ala Thr Ala Val Ile Glu Ala Val Thr Glu Asp Pro Glu
                85                  90                  95

Arg Lys Ala Glu Val Leu Ala Asp Leu Ala Ser Val Ala Arg Pro Gly
            100                 105                 110

Thr Leu Leu Val Ser Asn Thr Ser Gly Val Pro Ile Asp Glu Leu Ala
        115                 120                 125

Asp Ala Val Pro Arg Pro Glu Asp Leu Val Gly Val His Phe Met Asn
    130                 135                 140

Pro Ala Tyr Val Ile Pro Thr Val Glu Val Val Leu Gly Pro Arg Ser
145                 150                 155                 160

Gly Glu Ala Ala Ala Arg Ala Thr Arg Asp Leu Leu Ser Gly Leu Gly
                165                 170                 175

Arg Arg Gly Ile Val Val Gly Asp Gly Ala Gly Phe Val Thr Ser Arg
            180                 185                 190

Leu Leu His Arg Met Leu Asn Asp Ala Ile Ala Val Val His Glu Gly
        195                 200                 205

Arg Ala Thr Pro Glu Thr Val Asp Ala Leu Met Arg Asp Cys Ile Gly
    210                 215                 220

His Arg Thr Gly Pro Leu Ala Thr Ala Asp Leu Ile Gly Leu Asp Asn
225                 230                 235                 240

Leu Ala Asp Ser Leu Arg Val Met His Glu Arg Thr Gly Asp Pro Ala
                245                 250                 255

Leu Arg Pro Ser Glu Leu Leu Leu Asp Lys Val Arg Gln Gly Leu Leu
            260                 265                 270

Gly Arg Lys Ser Gly Arg Gly Phe Tyr Asp Tyr Gln Glu Ala Thr Arg
        275                 280                 285
```

<210> SEQ ID NO 86

<211> LENGTH: 1040
<212> TYPE: DNA
<213> ORGANISM: Streptomyces fradiae

<400> SEQUENCE: 86

```
ggcaggagcc acccgtgaca gggctgccgc ggcccgccgt ccgggtgccg ttccacgatc      60
tgcgggacgt gcacgcggcc acggggtgg agtcggagat cggcggcgcg ctgctgcgcg      120
tcgccgcgcg cgggcgctat ctgctgggtg ccgaactcgc cgcgttcgag gagcggttcg      180
ccgagtactg cggcaacgcc cactgtgtcg ccgtgggcag cgggctcgac gacgctcgtc      240
tggcgctgtg ggcgctcggg gtgggcgagg gcgacgagg gatcgtgccc tcgcacacgt      300
tcatcgcgtc ctggctcgcg gtgtcggcga cgggtgccac cccggtgccg gtcgagcccg      360
gtgatcccgg cgagccgggg cccgggcgt tcctgctcga cccggaccgg ctggaggccg      420
cgctgacccc gcgaccagg gccgtgatgc ccgtgcatct ctacgggcac cggtggatc      480
tggacccggt cggggcgttc gcggagccgc acgggctggc cgtcgtggag gacgcggcgc      540
aggccacggc ccgttaccgc gggaggcgga tcggcagcgg ccaccgcacg cgttcagct      600
tctacccggg gaagaacctg ggcgcgctcg gcgacggcgg tgccgtggtc acctcggacc      660
cggaactcgc ggaccggctg cggctgttgc gcaactacgg cgcccgggag aagtaccggc      720
acgaggagcg gggcaccaac tcccgcctgg acgagctgca ggcggccgtg ctgtcggtca      780
agctgccgta cctggacgcc tggaacaccc gccgcggga atcgccgcc cgctacggcg      840
aggcgctggc cggtctgccg ggcgtcaccg tgccggaggg ccgcgtggcg gagccggtct      900
ggcatcagta cgtgctgcgc agcccgtacc gcgaccggtt cggcggcgg ctggccgagg      960
cgggggtgga daccctggtc cactatccgg tggccgtgca cgcgtcgggc gcgtacgcgg      1020
gcgcggggcc gtgtcccgcc                                                 1040
```

<210> SEQ ID NO 87
<211> LENGTH: 388
<212> TYPE: PRT
<213> ORGANISM: Streptomyces fradiae

<400> SEQUENCE: 87

```
Met Thr Gly Leu Pro Arg Pro Ala Val Arg Val Pro Phe His Asp Leu
1               5                   10                  15

Arg Asp Val His Ala Ala Thr Gly Val Glu Ser Glu Ile Gly Gly Ala
                20                  25                  30

Leu Leu Arg Val Ala Ala Arg Gly Arg Tyr Leu Leu Gly Ala Glu Leu
        35                  40                  45

Ala Ala Phe Glu Glu Arg Phe Ala Glu Tyr Cys Gly Asn Ala His Cys
    50                  55                  60

Val Ala Val Gly Ser Gly Leu Asp Asp Ala Arg Leu Ala Leu Trp Ala
65                  70                  75                  80

Leu Gly Val Gly Glu Gly Asp Glu Val Ile Val Pro Ser His Thr Phe
                85                  90                  95

Ile Ala Ser Trp Leu Ala Val Ser Ala Thr Gly Ala Thr Pro Val Pro
                100                 105                 110

Val Glu Pro Gly Asp Pro Gly Glu Pro Gly Pro Gly Ala Phe Leu Leu
            115                 120                 125

Asp Pro Asp Arg Leu Glu Ala Ala Leu Thr Pro Arg Thr Arg Ala Val
        130                 135                 140

Met Pro Val His Leu Tyr Gly His Pro Val Asp Leu Asp Pro Val Gly
145                 150                 155                 160
```

```
Ala Phe Ala Glu Pro His Gly Leu Ala Val Val Glu Asp Ala Ala Gln
            165                 170                 175

Ala Thr Ala Arg Tyr Arg Gly Arg Ile Gly Ser Gly His Arg Thr
        180                 185                 190

Ala Phe Ser Phe Tyr Pro Gly Lys Asn Leu Gly Ala Leu Gly Asp Gly
            195                 200                 205

Gly Ala Val Val Thr Ser Asp Pro Glu Leu Ala Asp Arg Leu Arg Leu
        210                 215                 220

Leu Arg Asn Tyr Gly Ala Arg Glu Lys Tyr Arg His Glu Glu Arg Gly
225                 230                 235                 240

Thr Asn Ser Arg Leu Asp Glu Leu Gln Ala Ala Val Leu Ser Val Lys
                245                 250                 255

Leu Pro Tyr Leu Asp Ala Trp Asn Thr Arg Arg Glu Ile Ala Ala
        260                 265                 270

Arg Tyr Gly Glu Ala Leu Ala Gly Leu Pro Gly Val Thr Val Pro Glu
        275                 280                 285

Gly Arg Val Ala Glu Pro Val Trp His Gln Tyr Val Leu Arg Ser Pro
    290                 295                 300

Tyr Arg Asp Arg Leu Arg Arg Leu Ala Glu Ala Gly Val Glu Thr
305                 310                 315                 320

Leu Val His Tyr Pro Val Ala Val His Ala Ser Gly Ala Tyr Ala Gly
                325                 330                 335

Ala Gly Pro Cys Pro Ala Gly Gly Leu Pro Arg Ala Glu Arg Leu Ala
            340                 345                 350

Gly Glu Val Leu Ser Leu Pro Ile Gly Pro His Leu Pro Asp Glu Ala
            355                 360                 365

Val Glu Val Val Ile Ala Ala Val Gln Ser Ala Ala Leu Asp Ser Trp
        370                 375                 380

Glu Glu Gly Pro
385

<210> SEQ ID NO 88
<211> LENGTH: 271
<212> TYPE: PRT
<213> ORGANISM: Streptomyces mycarofaciens

<400> SEQUENCE: 88

Met Ser Pro Ile Ser Ala Ser Ala Pro Ala Ala Ser Arg Ser Thr Ala
1               5                   10                  15

Arg Arg Glu Leu Gly Gln Asn Phe Phe Arg Ser Ala Ala Ala Ala Cys
            20                  25                  30

Arg Phe Ser Asp Gln Leu Asp Ala Phe Cys Ala Asp Leu Pro Gly Ser
        35                  40                  45

Leu Ala Asp Val Leu Thr Val Glu Ile Gly Ala Gly Ser Gly Arg Val
    50                  55                  60

Thr Lys Ala Leu Ala Ser Ala Gly Arg Ser Leu Leu Ala Val Glu Ile
65                  70                  75                  80

Asp Ala Tyr Trp Ala Arg Arg Leu Thr Ala Glu Ser Leu Pro Asp Val
                85                  90                  95

Thr Val Val Asn Glu Asp Phe Leu Asn Leu Gln Leu Pro Arg Gln Pro
            100                 105                 110

Ile Arg Leu Ile Gly Asn Leu Pro Phe Val Ser Gly Thr Lys Ile Leu
        115                 120                 125

Arg Arg Cys Leu Glu Leu Gly Pro Asn Arg Met Cys Gln Ala Val Phe
```

-continued

```
           130                 135                 140
Leu Leu Gln Arg Glu Tyr Val Gly Lys Arg Thr Gly Ala Trp Gly Gly
145                 150                 155                 160

Asn Leu Phe Asn Ala Gln Trp Glu Pro Trp Tyr Thr Phe Glu Gly Gly
                165                 170                 175

Leu Ala Phe Ser Arg Asn Glu Phe Ser Pro Val Pro Arg Ala Asp Thr
            180                 185                 190

Gln Thr Leu Val Val Met Pro Arg Arg Pro Ser Val Pro Trp Arg
        195                 200                 205

Glu Arg Thr Asp Tyr Gln Arg Phe Thr Gln Gln Ile Phe Asp Thr Gly
210                 215                 220

Gln Met Thr Ile Gly Glu Ala Ala Arg Lys Val Leu Arg Arg Gly His
225                 230                 235                 240

Ala Gln Phe Val Arg Ser Ala Gly Val Arg Pro Ala Asp Arg Val Lys
                245                 250                 255

Asp Leu Thr Val Arg Asp Trp Ala Ala Leu Phe Arg Ala Asn Pro
            260                 265                 270

<210> SEQ ID NO 89
<211> LENGTH: 25
<212> TYPE: DNA
<213> ORGANISM: Artificial
<220> FEATURE:
<223> OTHER INFORMATION: Oligonucleotide SRMR1

<400> SEQUENCE: 89
ctgccagtcc tctcccagca gtacg                                              25

<210> SEQ ID NO 90
<211> LENGTH: 25
<212> TYPE: DNA
<213> ORGANISM: Artificial Sequence
<220> FEATURE:
<223> OTHER INFORMATION: Oligonucleotide SRMR2

<400> SEQUENCE: 90
tgaagctgga cgtctcctac gtcgg                                              25

<210> SEQ ID NO 91
<211> LENGTH: 2755
<212> TYPE: DNA
<213> ORGANISM: Artificial Sequence
<220> FEATURE:
<223> OTHER INFORMATION: Cassette excisable

<400> SEQUENCE: 91
gatatctacc tcttcgtccc gaagcaactt gggtgggcgc tcgaccttgg gccagtgtgc        60
ttctcacctg cggcgccagt ccatgggtgc tcgcggttgt ccgccgctgt gcgctggcgt       120
tgtcacgcag ttagacactc accttcccac gggcggtgtc gtagggctcg gctaagttgc       180
ccgcatgact gacagggatc cctcgagaag ctttatgctt gtaaaccgtt ttgtgaaaaa       240
atttttaaaa taaaaagggg gacctctagg gtccccaatt aattagtaat ataatctatt      300
aaaggtcatt caaaaggtca tccaccggat caattcccct gctcgcgcag ctgggtgcc       360 aagctctcgg gtaacatcaa ggcccgatcc ttggagcccc tgccctcccg cacgatgatc      420
gtgccgtgat cgaaatccag atccttgacc cgcagttgca aaccctcact gatccgtaat      480
gtgagttagc tcactcatta ggcacccag gctttacact ttatgcttcc ggctcgtatg      540
ttgtgtggaa ttgtgagcgg ataacaattt cacacaggaa acagctatga ccatgattac      600
```

```
gccaagctgc ggtggcgtac accgtcgcct cggtcggccc gtagagattg gcgatcccga    660
ccgcagcacc accgagaacg tccccgacgt ggccgaccag cccgtcatcg tcaacgcctg    720
accgcggtgc ggacaggccg tgtcgcgacc ggccgtgcgg aattaagccg gcccgtaccc    780
tgtgaataga ggtccgctgt gacacaagaa tccctgttac ttctcgaccg tattgattcg    840
gatgattcct acgcgagcct gcggaacgac caggaattct gggagccgct ggcccgccga    900
gccctggagg agctcgggct gccggtgccg ccggtgctgc gggtgcccgg cgagagcacc    960
aaccccgtac tggtcggcga gcccgacccg gtgatcaagc tgttcggcga gcactggtgc   1020
ggtccggaga gcctcgcgtc ggagtcggag gcgtacgcgg tcctggcgga cgccccggtg   1080
ccggtgcccc gcctcctcgg ccgcggcgag ctgcggcccg gcaccggagc ctggccgtgg   1140
ccctacctgg tgatgagccg gatgaccggc accacctggc ggtccgcgat ggacggcacg   1200
accgaccgga acgcgctgct cgccctggcc cgcgaactcg gccgggtgct cggccggctg   1260
cacagggtgc cgctgaccgg gaacaccgtg ctcacccccc attccgaggt cttcccggaa   1320
ctgctgcggg aacgccgcgc ggcgaccgtc gaggaccacc gcgggtgggg ctacctctcg   1380
ccccggctgc tggaccgcct ggaggactgg ctgccggacg tggacacgct gctggccggc   1440
cgcgaacccc ggttcgtcca cggcgacctg cacgggacca acatcttcgt ggacctggcc   1500
gcgaccgagg tcaccgggat cgtcgacttc accgacgtct atgcgggaga ctcccgctac   1560
agcctggtgc aactgcatct caacgccttc cggggcgacc gcgagatcct ggccgcgctg   1620
ctcgacgggg cgcagtggaa gcggaccgag gacttcgccc gcgaactgct cgccttcacc   1680
ttcctgcacg acttcgaggt gttcgaggag accccgctgg atctctccgg cttcaccgat   1740
ccggaggaac tggcgcagtt cctctggggg ccgccggaca ccgcccccgg cgcctgacgc   1800
cccgggccgc ccggcgccgc ccccggcccc cggcggccgc ccggagcccc gcccgcgctc   1860
gggagccccg gccccgcgcc gaagcccgct gctgcgagcc cggagcgggc cggccgacgg   1920
cggtgcgggc ccggcggcgg acgctcagca gcggcgggcg tgaaaggccc tggcatcctc   1980
gatcatctcc tccagggtgg tcggccgagc ttccatccca gctcggcaag gatcgatccg   2040
cgcagatcag ttggaagaat tgtccactca cgtgaaaggc gagatcacca aggtagtcgg   2100
caaataatgt ctaacaattc gttcaagccg acgccgcttc gcggcgcggc ttaactcaag   2160
cgttagatgc actaagcaca taattgctca cagccaaact atcaggtcaa gtctgctttt   2220
attatttta agcgtgcata ataagcccta cacaaattgg gagatatatc atgaaaggct   2280
ggctttttct tgttatcgca atagttggcg aagtaatcgc aacatccgca ttaaaatcta   2340
gcgagggctt tactaagctg atccggtgga tgacctttg aatgacctt aatagattat   2400
attactaatt aattggggac cctagaggtc ccctttttta ttttaaaaat tttttcacaa   2460
aacggtttac aagcataaag cttgttaaca gatctcccgg ctcgtcggac actccggtac   2520
ggccgtgact gaggaggtct accggaagca gatccggccc gtcatccaga ccggcgctgt   2580
ggtcatggac ggcatcttca gcggggtcc ggcgcgatag tcacgcagat agacacgcac   2640
agaaaacagg tgaggcagac cgtaacgtta cggtctgcct cacctggtgt ttctctgtcg   2700
gggtggcggg atttgaaccc acgacctctt cgtcccgaac gaagcgcgcg atatc         2755
```

<210> SEQ ID NO 92
<211> LENGTH: 2208
<212> TYPE: DNA
<213> ORGANISM: Artificial Sequence
<220> FEATURE:

<223> OTHER INFORMATION: Cassette excisable

<400> SEQUENCE: 92

```
gatatcgcgc gcgcttcgtt cgggacgaag aggtcgtggg ttcaaatccc gccaccccga        60
cagagaaaca ccaggtgagg cagaccgtaa cgttacggtc tgcctcacct gttttctgtg       120
cgtgtctatc tgcgtgacta tcgcgccgga ccccgcttga agatgccgtc catgaccaca       180
gcgccggtct ggatgacggg ccggatctgc ttccggtaga cctcctcagt cacggccgta       240
ccggagtgtc cgacgagccg ggagatctgt taacaagctt tatgcttgta aaccgttttg       300
tgaaaaaatt tttaaaataa aaagggggac tctcagggtc cccaattaat tagtaatata       360
atctattaaa ggtcattcaa aaggtcatcc accggatcaa ttcccctgct cgcgcaggct       420
gggtgccaag ctctcgggta acatcaaggc ccgatccttg gagcccttgc cctcccgcac       480
gatgatcgtg ccgtgatcga aatccagatc cttgacccgc agttgcaaac cctcactgat       540
ccggctcacg gtaactgatg ccgtatttgc agtaccagcg tacggcccac agaatgatgt       600
cacgctgaaa atgccggcct ttgaatgggt tcatgtgcag ctccatcagc aaaaggggat       660
gataagttta tcaccaccga ctatttgcaa cagtgccgtt gatcgtgcta tgatcgactg       720
atgtcatcag cggtggagtg caatgtcgtg caatacgaat ggcgaaaagc cgagctcatc       780
ggtcagcttc tcaaccttgg ggttaccccc ggcggtgtgc tgctggtcca cagctccttc       840
cgtagcgtcc ggcccctcga agatgggcca cttggactga tcgaggccct gcgtgctgcg       900
ctgggtccgg gagggacgct cgtcatgccc tcgtggtcag gtctggacga cgagccgttc       960
gatcctgcca cgtcgcccgt tacaccggac cttggagttg tctctgacac attctggcgc      1020
ctgccaaatg taaagcgcag cgcccatcca tttgcctttg cggcagcggg gccacaggca      1080
gagcagatca tctctgatcc attgcccctg ccacctcact cgcctgcaag cccggtcgcc      1140
cgtgtccatg aactcgatgg gcaggtactt ctcctcggcg tgggacacga tgccaacacg      1200
acgctgcatc ttgccgagtt gatggcaaag gttccctatg gggtgccgag acactgcacc      1260
attcttcagg atggcaagtt ggtacgcgtc gattatctcg agaatgacca ctgctgtgag      1320
cgctttgcct tggcggacag gtggctcaag gagaagagcc ttcagaagga aggtccagtc      1380
ggtcatgcct ttgctcggtt gatccgctcc cgcgacattg tggcgacagc cctgggtcaa      1440
ctgggccgag atccgttgat cttcctgcat ccgccagagg gcgggatgcg aagaatgcga      1500
tgccgctcgc cagtcgattg gctgagctca tgagcggaga acgagatgac gttggagggg      1560
caaggtcgcg ctgattgctg ggcaacacg tgaaaggcga gatcaccaag gtagtcggca       1620
aataatgtct aacaattcgt tcaagccgac gccgcttcgc ggcgcggctt aactcaagcg      1680
ttagatgcac taagcacata attgctcaca gccaaactat caggtcaagt ctgcttttat      1740
tatttttaag cgtgcataat aagccctaca caaattggga gatatatcat gaaaggctgg      1800
cttttcttg ttatcgcaat agttggcgaa gtaatcgcaa catccgcatt aaaatctagc       1860
gagggcttta ctaagctgat ccggtggatg acctttttgaa tgacctttaa tagattatat      1920
tactaattaa ttggggaccc tagaggtccc cttttttatt ttaaaattt tttcacaaaa       1980
cggtttacaa gcataaagct tctcgaggga tccctgtcag tcatgcgggc aacttagccg      2040
agccctacga caccgcccgt gggaaggtga gtgtctaact gcgtgacaac gccagcgcac      2100
agcggcggac aaccgcgagc acccatggac tggcgccgca ggtgagaagc acactggccc      2160
aaggtcgagc gcccacccaa gttgcttcgg gacgaagagg cagatatc                   2208
```

<210> SEQ ID NO 93
<211> LENGTH: 60
<212> TYPE: DNA
<213> ORGANISM: Artificial Sequence
<220> FEATURE:
<223> OTHER INFORMATION: Oligonucleotide ORF2A

<400> SEQUENCE: 93
cccgcgcggc agcctctccg tgatcgagtc cggcgtgacc atcgcgcgcg cttcgttcgg    60

<210> SEQ ID NO 94
<211> LENGTH: 60
<212> TYPE: DNA
<213> ORGANISM: Artificial Sequence
<220> FEATURE:
<223> OTHER INFORMATION: Oligonucleotide ORF2B

<400> SEQUENCE: 94
gctccgtgcg tcatgcagga aggtgtcgta gtcgcggtag atctgcctct tcgtcccgaa    60

<210> SEQ ID NO 95
<211> LENGTH: 35
<212> TYPE: DNA
<213> ORGANISM: Artificial Sequence
<220> FEATURE:
<223> OTHER INFORMATION: Cicatrice att3

<400> SEQUENCE: 95
atcgcgcgcg cttcgttcgg gacgaagagg tagat                               35

<210> SEQ ID NO 96
<211> LENGTH: 59
<212> TYPE: DNA
<213> ORGANISM: Artificial Sequence
<220> FEATURE:
<223> OTHER INFORMATION: Oligonucleotide EDR8

<400> SEQUENCE: 96
cgggatgatc gcttgtccgg cggccggatg cctagcctca tcgcgcgcgc ttcgttcgg     59

<210> SEQ ID NO 97
<211> LENGTH: 60
<212> TYPE: DNA
<213> ORGANISM: Artificial Sequence
<220> FEATURE:
<223> OTHER INFORMATION: Oligonucleotide EDR9

<400> SEQUENCE: 97
cccgatccag aacgtctggt cggtgatcag gtcgctgttc atctgcctct tcgtcccgaa    60

<210> SEQ ID NO 98
<211> LENGTH: 60
<212> TYPE: DNA
<213> ORGANISM: Artificial Sequence
<220> FEATURE:
<223> OTHER INFORMATION: Oligonucleotide EDR3

<400> SEQUENCE: 98
accggggcgg tcctcccctc cggggcgtca cggccgcgga atctgcctct tcgtcccgaa    60

<210> SEQ ID NO 99
<211> LENGTH: 60
<212> TYPE: DNA
<213> ORGANISM: Artificial Sequence
<220> FEATURE:
<223> OTHER INFORMATION: Oligonucleotide EDR4

```
<400> SEQUENCE: 99
cacgcagcga gccgacgcac tgatggacga cacgatggcc atcgcgcgcg cttcgttcgg    60

<210> SEQ ID NO 100
<211> LENGTH: 60
<212> TYPE: DNA
<213> ORGANISM: Artificial Sequence
<220> FEATURE:
<223> OTHER INFORMATION: Oligonucleotide EDR5

<400> SEQUENCE: 100
gggcgtgaag cgggcgagtg tggatgtcat gcgagtactc atcgcgcgcg cttcgttcgg    60

<210> SEQ ID NO 101
<211> LENGTH: 60
<212> TYPE: DNA
<213> ORGANISM: Artificial Sequence
<220> FEATURE:
<223> OTHER INFORMATION: Oligonucleotide EDR6

<400> SEQUENCE: 101
cgggaaacgg cgtcgcactc ctcggggggcc gcgtcagccc atctgcctct tcgtcccgaa    60

<210> SEQ ID NO 102
<211> LENGTH: 26
<212> TYPE: DNA
<213> ORGANISM: Artificial Sequence
<220> FEATURE:
<223> OTHER INFORMATION: Oligonucleotide C9583

<400> SEQUENCE: 102
ctgcaggtgc tccagcgcgt cgatct                                          26

<210> SEQ ID NO 103
<211> LENGTH: 26
<212> TYPE: DNA
<213> ORGANISM: Artificial Sequence
<220> FEATURE:
<223> OTHER INFORMATION: Oligonucleotide C9584

<400> SEQUENCE: 103
ctgcagacgg aggcggacct gcggct                                          26

<210> SEQ ID NO 104
<211> LENGTH: 33
<212> TYPE: DNA
<213> ORGANISM: Artificial Sequence
<220> FEATURE:
<223> OTHER INFORMATION: Cicatrice att1

<400> SEQUENCE: 104
atcgcgcgct tcgttcggga cgaagaggta gat                                  33

<210> SEQ ID NO 105
<211> LENGTH: 34
<212> TYPE: DNA
<213> ORGANISM: Artificial Sequence
<220> FEATURE:
<223> OTHER INFORMATION: Cicatrice att2

<400> SEQUENCE: 105
atcggcgcgc ttcgttcggg acgaagaggt agat                                 34

<210> SEQ ID NO 106
<211> LENGTH: 10325
```

```
<212> TYPE: DNA
<213> ORGANISM: Streptomyces ambofaciens
<220> FEATURE:
<221> NAME/KEY: misc_feature
<222> LOCATION: (3620)..(4069)
<223> OTHER INFORMATION: n is a, c, g, or t

<400> SEQUENCE: 106
```

| | | | | | |
|---|---|---|---|---|---|
| ctgcagaggg | cgccgacgtg | cgcggtgagt | tcgccgttgc | gccggctggt | ccagccgagg | 60 |
| ccgccgtgga | ccgcgggcgc | ctgtgcgcac | agcaggcccc | gggagccgag | gtcgtgcagc | 120 |
| aggccgaggg | gcagctcgcc | cgtccggtcc | cactcggccg | cccggtcgcc | gaccagcgcg | 180 |
| gtgaacagct | cctcggcctc | ggtgccgtcg | gcgtgggagg | tgtcagccac | ctgcgtgccc | 240 |
| ggtcgcctcg | ccgggcgcgg | ccagccgtcc | gaccagccgg | accatcgcgt | cgacggtgcg | 300 |
| gaagttgtcg | agcatcaggt | cggcgccgct | gatgacgatg | ccgtaggtct | tctccaggtg | 360 |
| cacgacgagc | tgcatggcga | acagcgagga | catcccgccg | acggcgaaca | ggtcctggtc | 420 |
| gcgctcccag | gtggtcttgg | tgcggtcctc | gaggaacccg | agcagttccc | cggcgacctc | 480 |
| gtcggcggtg | ggggtcgtgc | cggtggggtc | gggccgaccg | gacgtcgtgg | tcatcgcgtg | 540 |
| gcctcctggt | agtcgtagaa | tccccggccg | ctcttgcggc | cgagcaggcc | ctggcggacc | 600 |
| ttgtccagca | gcagctcgct | cgggcggagc | gccggatcgc | cggtccgttc | gtgcatcacc | 660 |
| cgcagcgagt | cggccaggtt | gtccagtccg | atcaggtcgg | ccgtggccag | gggtccggtg | 720 |
| cggtggccga | tgcagtcgcg | catcagcgcg | tccacggtct | ccggggtggc | ccggccctcg | 780 |
| tgcaccaccg | cgatggcgtc | gttcagcatc | cggtgcagca | ggcggctggt | cacgaagccg | 840 |
| gcgccgtcgc | cgacgacgat | gccccggcgg | ccaggccgg | acagcaggtc | ccgggtggcc | 900 |
| cgggcggcca | cctctccgct | gcgcggtccg | aggaccacct | cgaccgtggg | gatcacgtac | 960 |
| gcggggttca | tgaagtgcac | gccgacgagg | tcctcggggc | ggggacggc | gtcggccagc | 1020 |
| tcgtcgatgg | ggacgcccga | ggtgttgctg | acgagcagcg | tccccgggcg | cgccacggac | 1080 |
| gccaggtccg | ccagcacctc | ggccttccgc | tcggggtcct | cggtgacggc | ctcgatcacg | 1140 |
| gcggtcgcg | tggcgacggc | ggccggcgcc | tcctcgacgg | tcagctcccc | gggcgggcgg | 1200 |
| tcgtggggca | gcgcgcccat | cagccgggcc | gtccgcagat | gcagcgcgac | cgcgtcgggg | 1260 |
| gcggccgcgc | gcgccccggc | ggaggtgtcg | accagtgtga | ccgggtgccc | gtgtccgacg | 1320 |
| gcgagtgccg | cgatggccgt | gcccatgacg | cccgcgccga | gcacgacgag | cggagaattt | 1380 |
| tccttggaat | cgggcacgga | tcctccagaa | tcccggggc | ggcggctgtg | cgaaatgctg | 1440 |
| tcccgaatcg | cttccgcgct | ccatcacccg | ggcgtgactt | tgtcacctag | caagcggtgg | 1500 |
| gaggccgggc | ggaggctatg | tcatctcggc | cttgtccgct | tacgagttcc | gtccttaaag | 1560 |
| tgcgcccggc | gaacgcacgg | cggaattgac | tcgccgtccg | tcaaggaccc | gcggttcgaa | 1620 |
| ggacctcgac | gcatgaaggg | tttcacatgg | ctcatatcgc | attcttcatc | cttccgttg | 1680 |
| ccgggcatgt | gaatccgacc | ctgggagtcg | ccgaggaact | ggtcgcgcgc | ggccaccggg | 1740 |
| tgacgttcgc | gctgtccgag | gacctcgccg | agcgggcccg | gctgatcggc | gccgaggtgg | 1800 |
| tcacctatcc | ggtggacagg | caacggttcc | tggaccagat | ggtgccgcgg | caggacgcgg | 1860 |
| acgagtacac | ggacgaggac | gagttcgtcc | gggtcctgga | gtggctgctg | gacatgacgg | 1920 |
| tgcagaccat | ggaaccgctg | gagaggcact | tcgccgggga | ccgcccgac | gtcgtcgtca | 1980 |
| acgatccgtc | gtcgctgtgg | acgggacggc | tgctggcgga | ccggtggggc | atcccggtca | 2040 |
| tccgcagcac | tccgacctat | gccgccaacg | aacactggtc | gctgcatccg | ccggtcgact | 2100 |

```
cggccgagcc gccggacgac cccgagctgc acaagctgct cgcgcggatc gagcggctgc    2160
tggaggagca gggcgtcgag cacgacctgg ccggcttcac cggggtcctg cacggcggtc    2220
cggccctgct gtacatgccc cgctcgttcc agtacgcggg cgagaccttc gacgcacagc    2280
accacttcgt cggccctgc ccgccccgca ccgcgttcca cggcgagtgg aggccggggg    2340
acgacgacgg ccggcccctg gtgctggtga gtctcggaac cctgtacaac gaccggccgg    2400
acttcttccg cacctgcctg gaggcgttcg gcgacgagcc ctggaacgtg cttctggtgc    2460
tgggcggcgg ggtgcccgcg gccgacctgg gcccgcttcc cggcaatgtc cgggtgaccg    2520
acttcgtgtc gctgcgcgac gtcctgccgc acacggcggt ggtggtgaac cacggtggga    2580
tgagcaccgc catggaggtg ttctcgcacg gtgtgccggt ggtggcgatc ccggtgatgc    2640
cggagccccg ggccaccgcg cggcggatcg tcgaactggg cctgggcgac agctgctga    2700
actcggagct gacggccgag tccctgcgtg ccacggtacg gcgggtgctg gcggactccg    2760
cgatcccggg gaacatgcgc gggttccggg agcagatcag gcggccggc ggggcgcccg    2820
cggcggccga cgcgatcgag ggactgctgc cccgggtggg ctgagacgtc cgcgcccgac    2880
acgcgttcac cttccgaacg gcgggatcgc cccatgctca tcaccgaaac agcagtgccc    2940
gacgtgttcc gcatcgatcc ggaaccgctg ccggaccacc ggggccggtt ctacgaagcg    3000
gtgcgccgcg ggccgctgga ggccgccgtc gggcactcgg tcgaggtccg caggtccac    3060
tgcaccgtct ccgggcgcaa cgtactgcgc ggcctgcacg ccaccaccct gccgccgggc    3120
caggccaaga tcctcacctg tgtgcggggt gcggcgctga ctatggtggt cgacatgagg    3180
gtcgggtcac cgggcttcgg acggtacgag gcggtgcggc aggatgcccc gtcgggcacc    3240
gcgctctacc tgccggacgg catccggctg ggctacgtgg ccctcgcgga cgacacatgc    3300
atgaactacc tgtgcaccga ggagtacgtc ccgggcatgg tcatcgacgt ggacgccctg    3360
gaccccgaac tcggcctgcc gtggggactg accggggatc ccgtccgctc cgcccggac    3420
gcggcggcgc cgtccctgcg gcggccgcg gcggcgggaa ttctgcccac gtacgaggac    3480
tgcttacggg tgcgcacgtc cgtgcccgcc cctcccgacc ggactcggct ctgacgcgac    3540
ggacacgacc gccgcgcatc cgacgcgaat ccgacgcgaa tccgaactcg atttcccgaa    3600
ccgtggacgg agcgcgtccn nnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnnnnnnnnn nnnnnnnnnn nnnnnnnnnn nnnnnnnnnn nnnnnnnnnn nnnnnnnnnn    3840
nnnnnnnnnn nnnnnnnnnn nnnnnnnnnn nnnnnnnnnn nnnnnnnnnn nnnnnnnnnn    3900
nnnnnnnnnn nnnnnnnnnn nnnnnnnnnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
nnnnnnnnnn nnnnnnnnnn nnnnnnnnnn nnnnnnnnnn nnnnnnnnnc cgccacaccc    4080
cccagcagcg tcagcgtccg cctcgggacc acacccggca ggacgacggg gtgcggggcg    4140
acgaggctga gggagccccg caactccacg gggcggctca accgcttgag ctgctccatc    4200
aactgctggg ccgaggtggt cccgtgtgg tggtccaccg ggccgcggcc gctcgccgag    4260
gccagccgga ggttcccgcc cacccgcacc atgaagggca ggcccgcgag accgagccct    4320
cgcaccagtc gtggcagcac ggccgcgcgt cgtccatca ccacggggcg ggccaaggag    4380
cggttggcct gagcggcttc ggccaccagg cggacgatgt tctcctcctc accgggtgcg    4440
ccggggtgcc ggggtgtgcc ctccccgctc cggccgccgc ccagcgtcag gcgccagctg    4500
```

```
accggggcgg ccgtcgtgcc cgaggccagc cacagcccgt gactctgctg gcagctcacc    4560
acccggccca ggtcggagac gaagcgccgg ctcaccccga cggagcgcac ccccgccttg    4620
gagaccacca tcggccagat cacccaggcg tcggggtca gcctgtcgtc cacgtagcgg    4680
gccagcgcgg cccgcacctc gccccagtcc caggtcgacc cggcgacgaa gtggtgcagg    4740
ctctgttccg ccgcgccctc tccgacgaag gcggcgaggt tccgggcggt cttgcgtccc    4800
tgtgccgtga gcagcccgcg tatgtactgc tcacctcttc tgcgctggtc cgcccggcgg    4860
agcgaaccga gtaactccgc acatgcgtcg gagacgagcg agtcgaagtc gtgccgcgcg    4920
gcgggaccca cgggggcgc cgcgccggcg ggtcgaagcg tgcgtaaggt cataggagtc    4980
ctcgtggggg cctcgtcatc actgcgagtg gactgcgacc agcatcgcca attcacccgt    5040
tgctccccag gtacaccggg cacactcgtt ccgcttcgct ccccggcgg cacggcccgc    5100 gtgtggagca ctccccgctc tccggacggt gggggggaag cccaccgcac gcgcgccggt    5160
agcggtgccg gggcccaca acccctcacc gacgggtcc gttcgaccac atgccgtgat    5220
gatgccttcg ccgcacggcc tccttgaatg acggaccgtc agaaagacgt cactccgcgc    5280
gcgcccgctc ccgccccgac cccgcccggc cgccgtcccg ccccgcgac cctgtgggcc    5340 gacgccctct tgacggaccc ggaatcccgg gccgcgggac gggacggcga ggaactcgat    5400
gccgcaaagg ttccgcgtcc tcaccggcac ctccgagatc cagcgcaacg gcatcgccaa    5460
gctcctggct ttccaccact gagccgcacc ccctggcgag cagatccggg acaagacgcc    5520
accttcgcga cagtgtttag gaaaagttaa gtaaagaatt ccgcgagcgg attgccaggg    5580
agaacaaccc attgacgcgc accggtgcag cggccacatt gacggcacct gtcaagttca    5640
cccccaggag cttggaatcc catgcaggca attcggcatc acgtcatgct cgtcatggcc    5700
ttcgtgaccg tcgccacgac tttccttctc tggccgtcga cgcaatccgc gcaagcgttt    5760
cccccgaccc cgaagcagac ggtactgaac cacctccgcg ccatttccgg gaatcacatc    5820
gtctccggac agcacaacaa ggagcccgcc tccgccccgg gccagtacac ccagcaggtc    5880
aaggacgtca ccgggcagta cccccggcctg tggggcggtg acctgatgtt cgccgcggcg    5940
gacgtggccg gccgccagcg cgtcgtcgac caggccagga ccgagtgggc gaacggatcg    6000
ctggtctcgc tcacctggca cgtctgcccg ccgaccggcg gcagcacctg tgcgttcgag    6060
ggcggcgtca gtccacgct gacgaacgcg cagttctcgc aggtcctcac ggagggcagt    6120
gccctgaaca gcgcatggaa gcggcgcctg gacgaggtcg tccgtacct gcagcagctg    6180 gagaacgcgg gcgtccccgt cctcttccgg ccgctgcacg agatgaacga atcctggaac    6240
tggtggggaa accggcccgg agcgaacggc agcgcacgcc tctaccagat cacccgcgat    6300
cacctcgccg ggacgaaagg gctggacaat ctgatctggg tctggaacgt ccaggacaat    6360
ccggcgggaa actggaacag ctactatccg ggagatcagt acgtggacgt cgtttcgctg    6420
gacgtctggt acaagagcca cccgagttcc gccgactacc agcagatgcg gagcatcgcg    6480
ggaacaaaac ccatggccct cgcggagctg ggcaaaatgc cgaccgccgc gctgctggac    6540
agccagacgc ggtggacatg gttcatgatg tggtccgagc atctgcgcgg gaacaattcc    6600
aacgccgaaa tacagacggc gtatttccac ccccgtgtac tgaaccaggg ggaggtcgca    6660
ctgccctgac gctcggcgct gcccggctct ctcacgcgcg ttctgacagg acgtcgcgga    6720
gagtgcgggg caagcggccg gtgagctggg cgcagtcgtc gcggacccga tcccagcgct    6780
gttcgcgtac cgaggcgaac agggaggaga aggcgtagag ccaccaggga tccaggccgg    6840
```

```
tcgccgctgt tcggcagag tacgtgtcgg ccgggatgtc cacgtaggcg accggtgtcc    6900
gccacacctc cgccgccgtg gaggcgatgc ctgccaggtc cgtcgactcg ggtcccgtga    6960
tgtcgtggtg acggccggtc ggcccgccca ccgcgagggc ggcgagggcg cgggccacgt    7020
cgtcgcgcgc caccagggac acccggccat cggctgccgg cagcctcagc agcccggtcg    7080
agcgcgcctg ggtgagccag cctaggaaga actcgatgta cagcgaggcc ctggcgaacg    7140
agcacggcac gccggaggcg agcagcagat cctcggtgag ccggttgacg acggcgtagc    7200
agaacgggga ggccgagtcg gcgtcgacgc tgctcagtgc cgcgacatgg ccgacgcgct    7260
cggccaccac ggcggcgacg acgttgcggt ggtgcagcag cacccgtgcg tcgggcccgt    7320
cgctggagac gaggaccaga gtgtccacgc ccttcagcgc cgcacgcaga gcgggcgggt    7380
cggcgtagtc ggcgacggcg cactccaccc cggcggtag tgcctcggca ggcagcttcc    7440
gcctggtcat cgccacgacg tccacgtcgg cccggtccgc gagcagctgc accacccgcc    7500
tgcccagact gcccgccgcc cctgtcaccg cgatacgcat cgtcgccccc gtcgccttgt    7560
cgtcggtcgt accaccgtag ggggccaacc gcgaccaggg cttggaacga gccggcccgc    7620
cagggcacag acgcgcgatc ggtccggttt cccgtgctc ttttggaccg ggacgccgga    7680
ccgcttcctt tctacggtgg agccgttccc gcccgagccc gcacgtcatc gacgtgcggg    7740
gaagacagag gtgataccga tgctccgacg ccgtctcgga gggccgtcag gccccctcgt    7800
cagtgccctg tgcctgggcg cgatgcccttt cggcaccacc gtcgacgaga agacgtcctt    7860
cgccatcctc gaccggttcg tcgaggccgg cggcagtctc gtcgacaccg ccgacaacta    7920
cgcgttctgg gctcccggcg ggaccgggga cgagagcgag aacaccgtcg ggcgctggct    7980
ggcgagccgc cgccgccgcg acgaggtggt gatctccacc aaggtgggtg cccgccccac    8040
cgtccccggc agcggcctgg agaccgccga agggctgtcg gctcccgtca tacgaaggc    8100
cgccgaggac agcctgcgac gcctgggcac cgatcgcatc gatctgtact ggacccacat    8160
cgaggaccgg accgtccctc tggaggagac gctcggagct ctcgacgagc tggtcggcgg    8220
cggcaaggtg gcggtgctgg gctgctccaa ccacgcgggc tggcgcatcg aacgggcccg    8280
cgcgctcgcc cggaccaacg gctggacggc gtacacctgc gtccagcagc gctactccta    8340
ccttcagccg cgcttcgacg tcggactgcc ggagagcgga cacgtccacg cgacctccga    8400
actcctcgac cacgtacgca gcgagcccga cctgacgctg ctggcctact cgtccctgct    8460
ctcgggcgcg tacacccggc cggacaagac cctgtccgcc gcctacgacc acccgggcac    8520
cgggcagcgg ctgaccgtgc tgcggaggt ggccgccgag ctcggtgcca ccgccaacca    8580
ggtggtgctg tcctggttgc tcggaggtga tccgccggtg atcccgatcg tgggggtgag    8640
ttccgtcgag cagctggacg aggtgctggc cgccgtcgag ctggagctgc cccggggagac    8700
gagggcacgg ctggacctcg ccgggcgggg ctgacgggcc acacaccgcc cctcgcccgg    8760
gacgggctga ccgccgcac accgtccctc agcggggacg ggctgacggc cacacacccg    8820
cccctcagcc cggctgggct gggctgacgg ccacacaccc gctcctcagc ccggctgggc    8880
tgggctgacg ccacacacc cgcccctcag cccggctggg ctgggctgac ggccacacgc    8940
cgtccctcgc ccgggtcggg ctgaccagcc acacgccgtc cctcagtcgg cccgctcccc    9000
ggcccgcccg gcgtcgacgt gccgccggtc gtggcgccgg gccgcgtcga tggcctgtgc    9060
caggcgccgc acggctccgg gcacggcgtg gtccgccaga ttgccgtagc cgaggaccag    9120
cgcggggccg gcggcggcca cggcccgcgc ccgccggag tcgccggccc gggccgtcgg    9180
gtggtgctcg gcccgcgcca tccggtaggc gtcgagatcc gccagcctca cgtcacgccg    9240
```

-continued

```
cgccgcctcc ctgacgacgg tgggcgccga gcagtccgtc agggacagca gcaggtggaa    9300
gccggccgcc gcaccggaca cctggaaccc cggcagcgac gccgcgagtt ctcccatgag    9360
gtgatcgcgg cgccgtttgt agcgcagccg tgccgcccgc aggtaccggt cgtaggaccc    9420
gcgggccagg aaccgggcga acgcctcctg gtcgatgacg ggcggtggta cgcccccgac    9480
gtgctccgcg cccagggcct cggtccagcg cggcggggtc accgcccagc cgatccgcag    9540
ggccggcgag agcgtcttgc tgaccgaccc cagcagcgcg acgtgctccg gtgccatgcc    9600
ctgcagggcg cccacggggt ggcggtcgta tcggaactcg gcgtcgtagt cgtcctccag    9660
caccaggccg tcgacctcgc gggcccaggc gaccagctcg ccgcgacggg ccggggcgag    9720
gaccacaccg gtcgggaact ggtgggcggg agcgacgatc accgaccgga cctgaggcgc    9780
gcgccgcagc aggtcgaccc gcaggccgtc gccgtccacg ggaacgggga cgggcaccag    9840
cccctccgcc ccgaccgtgg cgctcagccg cgaccagcca gggtcctcca gggccatgtg    9900
ggtgtggccc tcggtccgca ggacccggca cagcctgcgc accgcgtcca gcgtgcccgc    9960
gcagacgacg agctgccggg cttccagcga cgcgccgcgt cccgcacga ggtaggccgc    10020
gagccgctgc cggagccggg cgagaccggc cggatcgggg tagccgagct cgccccaggt    10080
cagtgcgccg gtggcctccc gcaccgcgtc cgcccaccgt ccgcggggaa aggcccgcag    10140
gtcgggtatg ccgggcagca tgtcgaactc cggctccac cgcgtaccga cgtccgcctc    10200
gggcgtcacc ggagcgggga cggcctgcgc cctgacccgg gtggccgagc cgctgcgcgc    10260
ctccaggtac ccctccgcga cgagctgctc gtagggggga tcctctagag tcgacctgca    10320
ggcct                                                                10325

<210> SEQ ID NO 107
<211> LENGTH: 1218
<212> TYPE: DNA
<213> ORGANISM: Streptomyces ambofaciens
<220> FEATURE:
<221> NAME/KEY: CDS
<222> LOCATION: (1)..(1218)

<400> SEQUENCE: 107 atg gct cat atc gca ttc ttc atc ctt ccg gtt gcc ggg cat gtg aat    48
Met Ala His Ile Ala Phe Phe Ile Leu Pro Val Ala Gly His Val Asn
1               5                   10                  15 ccg acc ctg gga gtc gcc gag gaa ctg gtc gcg cgc ggc cac cgg gtg    96
Pro Thr Leu Gly Val Ala Glu Glu Leu Val Ala Arg Gly His Arg Val
            20                  25                  30 acg ttc gcg ctg tcc gag gac ctc gcc gag cgg gcc cgg ctg atc ggc    144
Thr Phe Ala Leu Ser Glu Asp Leu Ala Glu Arg Ala Arg Leu Ile Gly
        35                  40                  45 gcc gag gtg gtc acc tat ccg gtg gac agg caa cgg ttc ctg gac cag    192
Ala Glu Val Val Thr Tyr Pro Val Asp Arg Gln Arg Phe Leu Asp Gln
    50                  55                  60 atg gtg ccg cgg cag gac gcg gac gag tac acg gac gag gac gag ttc    240
Met Val Pro Arg Gln Asp Ala Asp Glu Tyr Thr Asp Glu Asp Glu Phe
65                  70                  75                  80 gtc cgg gtc ctg gag tgg ctg ctg gac atg acg gtg cag acc atg gaa    288
Val Arg Val Leu Glu Trp Leu Leu Asp Met Thr Val Gln Thr Met Glu
                85                  90                  95 ccg ctg gag agg cac ttc gcc ggg gac cgg ccc gac gtc gtc gtc aac    336
Pro Leu Glu Arg His Phe Ala Gly Asp Arg Pro Asp Val Val Val Asn
            100                 105                 110 gat ccg tcg tcg ctg tgg acg gga cgg ctg ctg gcg gac cgg tgg ggc    384
```

```
Asp Pro Ser Ser Leu Trp Thr Gly Arg Leu Leu Ala Asp Arg Trp Gly
        115                 120                 125 atc ccg gtc atc cgc agc act ccg acc tat gcc gcc aac gaa cac tgg      432
Ile Pro Val Ile Arg Ser Thr Pro Thr Tyr Ala Ala Asn Glu His Trp
    130                 135                 140 tcg ctg cat ccg ccg gtc gac tcg gcc gag ccg ccg gac gac ccc gag      480
Ser Leu His Pro Pro Val Asp Ser Ala Glu Pro Pro Asp Asp Pro Glu
145                 150                 155                 160 ctg cac aag ctg ctc gcg cgg atc gag cgg ctg ctg gag gag cag ggc      528
Leu His Lys Leu Leu Ala Arg Ile Glu Arg Leu Leu Glu Glu Gln Gly
                165                 170                 175 gtc gag cac gac ctg gcc ggc ttc acc ggg gtc ctg cac ggc ggt ccg      576
Val Glu His Asp Leu Ala Gly Phe Thr Gly Val Leu His Gly Gly Pro
            180                 185                 190 gcc ctg ctg tac atg ccc cgc tcg ttc cag tac gcg ggc gag acc ttc      624
Ala Leu Leu Tyr Met Pro Arg Ser Phe Gln Tyr Ala Gly Glu Thr Phe
        195                 200                 205 gac gca cag cac cac ttc gtc ggc ccc tgc ccg ccc cgc acc gcg ttc      672
Asp Ala Gln His His Phe Val Gly Pro Cys Pro Pro Arg Thr Ala Phe
    210                 215                 220 cac ggc gag tgg agg ccg ggg gac gac gac ggc cgg ccc ctg gtg ctg      720
His Gly Glu Trp Arg Pro Gly Asp Asp Asp Gly Arg Pro Leu Val Leu
225                 230                 235                 240 gtg agt ctc gga acc ctg tac aac gac cgg ccg gac ttc ttc cgc acc      768
Val Ser Leu Gly Thr Leu Tyr Asn Asp Arg Pro Asp Phe Phe Arg Thr
                245                 250                 255 tgc ctg gag gcg ttc ggc gac gag ccc tgg aac gtg ctt ctg gtg ctg      816
Cys Leu Glu Ala Phe Gly Asp Glu Pro Trp Asn Val Leu Leu Val Leu
            260                 265                 270 ggc ggg ggg gtg ccc gcg gcc gac ctg ggc ccg ctt ccc ggc aat gtc      864
Gly Gly Gly Val Pro Ala Ala Asp Leu Gly Pro Leu Pro Gly Asn Val
        275                 280                 285 cgg gtg acc gac ttc gtg tcg ctg cgc gac gtc ctg ccg cac acg gcg      912
Arg Val Thr Asp Phe Val Ser Leu Arg Asp Val Leu Pro His Thr Ala
    290                 295                 300 gtg gtg gtg aac cac ggt ggg atg agc acc gcc atg gag gtg ttc tcg      960
Val Val Val Asn His Gly Gly Met Ser Thr Ala Met Glu Val Phe Ser
305                 310                 315                 320 cac ggt gtg ccg gtg gtg gcg atc ccg gtg atg ccg gag ccc cgg gcc     1008
His Gly Val Pro Val Val Ala Ile Pro Val Met Pro Glu Pro Arg Ala
                325                 330                 335 acc gcg cgg cgg atc gtc gaa ctg ggc ctg ggc gac cag ctg ctg aac     1056
Thr Ala Arg Arg Ile Val Glu Leu Gly Leu Gly Asp Gln Leu Leu Asn
            340                 345                 350 tcg gag ctg acg gcc gag tcc ctg cgt gcc acg gta cgg cgg gtg ctg     1104
Ser Glu Leu Thr Ala Glu Ser Leu Arg Ala Thr Val Arg Arg Val Leu
        355                 360                 365 gcg gac tcc gcg atc ccg ggg aac atg cgc ggg ttc cgg gag cag atc     1152
Ala Asp Ser Ala Ile Pro Gly Asn Met Arg Gly Phe Arg Glu Gln Ile
    370                 375                 380 agg gcg gcc ggc ggg gcg ccc gcg gcc gac gcg atc gag gga ctg         1200
Arg Ala Ala Gly Gly Ala Pro Ala Ala Asp Ala Ile Glu Gly Leu
385                 390                 395                 400 ctg ccc cgg gtg ggc tga                                              1218
Leu Pro Arg Val Gly
            405

<210> SEQ ID NO 108
<211> LENGTH: 405
<212> TYPE: PRT
```

-continued

<213> ORGANISM: Streptomyces ambofaciens

<400> SEQUENCE: 108

```
Met Ala His Ile Ala Phe Phe Ile Leu Pro Val Ala Gly His Val Asn
1               5                   10                  15

Pro Thr Leu Gly Val Ala Glu Glu Leu Val Ala Arg Gly His Arg Val
                20                  25                  30

Thr Phe Ala Leu Ser Glu Asp Leu Ala Glu Arg Ala Arg Leu Ile Gly
            35                  40                  45

Ala Glu Val Val Thr Tyr Pro Val Asp Arg Gln Arg Phe Leu Asp Gln
        50                  55                  60

Met Val Pro Arg Gln Asp Ala Asp Glu Tyr Thr Asp Glu Asp Glu Phe
65                  70                  75                  80

Val Arg Val Leu Glu Trp Leu Leu Asp Met Thr Val Gln Thr Met Glu
                85                  90                  95

Pro Leu Glu Arg His Phe Ala Gly Asp Arg Pro Asp Val Val Val Asn
                100                 105                 110

Asp Pro Ser Ser Leu Trp Thr Gly Arg Leu Leu Ala Asp Arg Trp Gly
            115                 120                 125

Ile Pro Val Ile Arg Ser Thr Pro Thr Tyr Ala Ala Asn Glu His Trp
        130                 135                 140

Ser Leu His Pro Pro Val Asp Ser Ala Glu Pro Pro Asp Asp Pro Glu
145                 150                 155                 160

Leu His Lys Leu Leu Ala Arg Ile Glu Arg Leu Leu Glu Glu Gln Gly
                165                 170                 175

Val Glu His Asp Leu Ala Gly Phe Thr Gly Val Leu His Gly Gly Pro
                180                 185                 190

Ala Leu Leu Tyr Met Pro Arg Ser Phe Gln Tyr Ala Gly Glu Thr Phe
            195                 200                 205

Asp Ala Gln His His Phe Val Gly Pro Cys Pro Pro Arg Thr Ala Phe
        210                 215                 220

His Gly Glu Trp Arg Pro Gly Asp Asp Gly Arg Pro Leu Val Leu
225                 230                 235                 240

Val Ser Leu Gly Thr Leu Tyr Asn Asp Arg Pro Asp Phe Phe Arg Thr
                245                 250                 255

Cys Leu Glu Ala Phe Gly Asp Glu Pro Trp Asn Val Leu Leu Val Leu
            260                 265                 270

Gly Gly Gly Val Pro Ala Ala Asp Leu Gly Pro Leu Pro Gly Asn Val
        275                 280                 285

Arg Val Thr Asp Phe Val Ser Leu Arg Asp Val Leu Pro His Thr Ala
290                 295                 300

Val Val Val Asn His Gly Gly Met Ser Thr Ala Met Glu Val Phe Ser
305                 310                 315                 320

His Gly Val Pro Val Val Ala Ile Pro Val Met Pro Glu Pro Arg Ala
                325                 330                 335

Thr Ala Arg Arg Ile Val Glu Leu Gly Leu Gly Asp Gln Leu Leu Asn
            340                 345                 350

Ser Glu Leu Thr Ala Glu Ser Leu Arg Ala Thr Val Arg Arg Val Leu
        355                 360                 365

Ala Asp Ser Ala Ile Pro Gly Asn Met Arg Gly Phe Arg Glu Gln Ile
    370                 375                 380

Arg Ala Ala Gly Gly Ala Pro Ala Ala Ala Asp Ala Ile Glu Gly Leu
385                 390                 395                 400
```

Leu Pro Arg Val Gly
            405

<210> SEQ ID NO 109
<211> LENGTH: 621
<212> TYPE: DNA
<213> ORGANISM: Streptomyces ambofaciens
<220> FEATURE:
<221> NAME/KEY: CDS
<222> LOCATION: (1)..(621)

<400> SEQUENCE: 109

```
atg ctc atc acc gaa aca gca gtg ccc gac gtg ttc cgc atc gat ccg      48
Met Leu Ile Thr Glu Thr Ala Val Pro Asp Val Phe Arg Ile Asp Pro
1               5                   10                  15 gaa ccg ctg ccg gac cac cgg ggc cgg ttc tac gaa gcg gtg cgc cgc      96
Glu Pro Leu Pro Asp His Arg Gly Arg Phe Tyr Glu Ala Val Arg Arg
                20                  25                  30 ggg ccg ctg gag gcc gcc gtc ggg cac tcg gtc gag gtc cgg cag gtc     144
Gly Pro Leu Glu Ala Ala Val Gly His Ser Val Glu Val Arg Gln Val
            35                  40                  45 cac tgc acc gtc tcc ggg cgc aac gta ctg cgc ggc ctg cac gcc acc     192
His Cys Thr Val Ser Gly Arg Asn Val Leu Arg Gly Leu His Ala Thr
        50                  55                  60 acc ctg ccg ccg ggc cag gcc aag atc ctc acc tgt gtg cgg ggt gcg     240
Thr Leu Pro Pro Gly Gln Ala Lys Ile Leu Thr Cys Val Arg Gly Ala
65                  70                  75                  80 gcg ctg act atg gtg gtc gac atg agg gtc ggg tca ccg ggc ttc gga     288
Ala Leu Thr Met Val Val Asp Met Arg Val Gly Ser Pro Gly Phe Gly
                85                  90                  95 cgg tac gag gcg gtg cgg cag gat gcc ccg tcg ggc acc gcg ctc tac     336
Arg Tyr Glu Ala Val Arg Gln Asp Ala Pro Ser Gly Thr Ala Leu Tyr
                100                 105                 110 ctg ccg gac ggc atc ggc ctg ggc tac gtg gcc ctc gcg gac gac aca     384
Leu Pro Asp Gly Ile Gly Leu Gly Tyr Val Ala Leu Ala Asp Asp Thr
            115                 120                 125 tgc atg aac tac ctg tgc acc gag gag tac gtc ccg ggc atg gtc atc     432
Cys Met Asn Tyr Leu Cys Thr Glu Glu Tyr Val Pro Gly Met Val Ile
        130                 135                 140 gac gtg gac gcc ctg gac ccc gaa ctc ggc ctg ccg tgg gga ctg acc     480
Asp Val Asp Ala Leu Asp Pro Glu Leu Gly Leu Pro Trp Gly Leu Thr
145                 150                 155                 160 ggg gat ccc gtc cgc tcc gcc cgg gac gcg gcg gcg ccg tcc ctg cgg     528
Gly Asp Pro Val Arg Ser Ala Arg Asp Ala Ala Ala Pro Ser Leu Arg
                165                 170                 175 gcg gcc gcg gcg gcg gga att ctg ccc acg tac gag gac tgc tta cgg     576
Ala Ala Ala Ala Ala Gly Ile Leu Pro Thr Tyr Glu Asp Cys Leu Arg
                180                 185                 190 gtg cgc acg tcc gtg ccc gcc cct ccc gac cgg act cgg ctc tga         621
Val Arg Thr Ser Val Pro Ala Pro Pro Asp Arg Thr Arg Leu
            195                 200                 205
```

<210> SEQ ID NO 110
<211> LENGTH: 206
<212> TYPE: PRT
<213> ORGANISM: Streptomyces ambofaciens

<400> SEQUENCE: 110

```
Met Leu Ile Thr Glu Thr Ala Val Pro Asp Val Phe Arg Ile Asp Pro
1               5                   10                  15

Glu Pro Leu Pro Asp His Arg Gly Arg Phe Tyr Glu Ala Val Arg Arg
                20                  25                  30
```

```
Gly Pro Leu Glu Ala Ala Val Gly His Ser Val Glu Val Arg Gln Val
        35                  40                  45

His Cys Thr Val Ser Gly Arg Asn Val Leu Arg Gly Leu His Ala Thr
 50                  55                  60

Thr Leu Pro Pro Gly Gln Ala Lys Ile Leu Thr Cys Val Arg Gly Ala
 65                  70                  75                  80

Ala Leu Thr Met Val Val Asp Met Arg Val Gly Ser Pro Gly Phe Gly
                 85                  90                  95

Arg Tyr Glu Ala Val Arg Gln Asp Ala Pro Ser Gly Thr Ala Leu Tyr
            100                 105                 110

Leu Pro Asp Gly Ile Gly Leu Gly Tyr Val Ala Leu Ala Asp Asp Thr
            115                 120                 125

Cys Met Asn Tyr Leu Cys Thr Glu Glu Tyr Val Pro Gly Met Val Ile
130                 135                 140

Asp Val Asp Ala Leu Asp Pro Glu Leu Gly Leu Pro Trp Gly Leu Thr
145                 150                 155                 160

Gly Asp Pro Val Arg Ser Ala Arg Asp Ala Ala Pro Ser Leu Arg
                165                 170                 175

Ala Ala Ala Ala Ala Gly Ile Leu Pro Thr Tyr Glu Asp Cys Leu Arg
            180                 185                 190

Val Arg Thr Ser Val Pro Ala Pro Pro Asp Arg Thr Arg Leu
            195                 200                 205

<210> SEQ ID NO 111
<211> LENGTH: 960
<212> TYPE: DNA
<213> ORGANISM: Streptomyces ambofaciens
<220> FEATURE:
<221> NAME/KEY: CDS
<222> LOCATION: (1)..(903)
<220> FEATURE:
<221> NAME/KEY: misc_feature
<222> LOCATION: (905)..(960)
<223> OTHER INFORMATION: n is a, c, g, or t

<400> SEQUENCE: 111 atg acc tta cgc acg ctt cga ccc gcc ggc gcg gcg ccc ccc gtg ggt     48
Met Thr Leu Arg Thr Leu Arg Pro Ala Gly Ala Ala Pro Pro Val Gly
 1               5                  10                  15 ccc gcc gcg cgg cac gac ttc gac tcg ctc gtc tcc gac gca tgt gcg     96
Pro Ala Ala Arg His Asp Phe Asp Ser Leu Val Ser Asp Ala Cys Ala
                20                  25                  30 gag tta ctc ggt tcg ctc cgc cgg gcg gac cag cgc aga aga ggt gag    144
Glu Leu Leu Gly Ser Leu Arg Arg Ala Asp Gln Arg Arg Arg Gly Glu
            35                  40                  45 cag tac ata cgc ggg ctg ctc acg gca cag gga cgc aag acc gcc cgg    192
Gln Tyr Ile Arg Gly Leu Leu Thr Ala Gln Gly Arg Lys Thr Ala Arg
 50                  55                  60 aac ctc gcc gcc ttc gtc gga gag ggc gcg gcg gaa cag agc ctg cac    240
Asn Leu Ala Ala Phe Val Gly Glu Gly Ala Ala Glu Gln Ser Leu His
 65                  70                  75                  80 cac ttc gtc gcc ggg tcg acc tgg gac tgg ggc gag gtg cgg gcc gcg    288
His Phe Val Ala Gly Ser Thr Trp Asp Trp Gly Glu Val Arg Ala Ala
                 85                  90                  95 ctg gcc cgc tac gtg gac gac agg ctg acc ccc gac gcc tgg gtg atc    336
Leu Ala Arg Tyr Val Asp Asp Arg Leu Thr Pro Asp Ala Trp Val Ile
            100                 105                 110 tgg ccg atg gtg gtc tcc aag gcg ggg gtg cgc tcc gtc ggg gtg agc    384
Trp Pro Met Val Val Ser Lys Ala Gly Val Arg Ser Val Gly Val Ser
```

-continued

```
            115                 120                 125
cgg cgc ttc gtc tcc gac ctg ggc cgg gtg gtg agc tgc cag cag agt       432
Arg Arg Phe Val Ser Asp Leu Gly Arg Val Val Ser Cys Gln Gln Ser
    130                 135                 140 cac ggg ctg tgg ctg gcc tcg ggc acg acg gcc gcc ccg gtc agc tgg       480
His Gly Leu Trp Leu Ala Ser Gly Thr Thr Ala Ala Pro Val Ser Trp
145                 150                 155                 160 cgc ctg acg ctg ggc ggc ggc cgg agc ggg gag ggc aca ccc cgg cac       528
Arg Leu Thr Leu Gly Gly Gly Arg Ser Gly Glu Gly Thr Pro Arg His
                165                 170                 175 ccc ggc gca ccc ggt gag gag gag aac atc gtc cgc ctg gtg gcc gaa       576
Pro Gly Ala Pro Gly Glu Glu Glu Asn Ile Val Arg Leu Val Ala Glu
            180                 185                 190 gcc gct cag gcc aac cgc tcc ttg gcc cgc ccc gtg gtg atg gac gca       624
Ala Ala Gln Ala Asn Arg Ser Leu Ala Arg Pro Val Val Met Asp Ala
        195                 200                 205 cgc gcg gcc gtg ctg cca cga ctg gtg cga ggg ctc ggt ctc gcg ggc       672
Arg Ala Ala Val Leu Pro Arg Leu Val Arg Gly Leu Gly Leu Ala Gly
    210                 215                 220 ctg ccc ttc atg gtg cgg gtg ggc ggg aac ctc cgg ctg gcc tcg gcg       720
Leu Pro Phe Met Val Arg Val Gly Gly Asn Leu Arg Leu Ala Ser Ala
225                 230                 235                 240 agc ggc cgc ggc ccg gtg gac cac cac acg ggg acc acc tcg gcc cag       768
Ser Gly Arg Gly Pro Val Asp His His Thr Gly Thr Thr Ser Ala Gln
                245                 250                 255 cag ttg atg gag cag ctc aag cgg ttg agc cgc ccc gtg gag ttg cgg       816
Gln Leu Met Glu Gln Leu Lys Arg Leu Ser Arg Pro Val Glu Leu Arg
            260                 265                 270 ggc tcc ctc agc ctc gtc gcc ccg cac ccc gtc gtc ctg ccg ggt gtg       864
Gly Ser Leu Ser Leu Val Ala Pro His Pro Val Val Leu Pro Gly Val
        275                 280                 285 gtc ccg agg cgg acg ctg acg ctg ctg ggg ggt gtg gcg gnnnnnnnnn       913
Val Pro Arg Arg Thr Leu Thr Leu Leu Gly Gly Val Ala
    290                 295                 300 nnnnnnnnnn nnnnnnnnnn nnnnnnnnnn nnnnnnnnnn nnnnnn              960
```

<210> SEQ ID NO 112
<211> LENGTH: 301
<212> TYPE: PRT
<213> ORGANISM: Streptomyces ambofaciens

<400> SEQUENCE: 112

```
Met Thr Leu Arg Thr Leu Arg Pro Ala Gly Ala Ala Pro Pro Val Gly
1               5                   10                  15

Pro Ala Ala Arg His Asp Phe Asp Ser Leu Val Ser Asp Ala Cys Ala
            20                  25                  30

Glu Leu Leu Gly Ser Leu Arg Arg Ala Asp Gln Arg Arg Gly Glu
        35                  40                  45

Gln Tyr Ile Arg Gly Leu Leu Thr Ala Gln Gly Arg Lys Thr Ala Arg
    50                  55                  60

Asn Leu Ala Ala Phe Val Gly Glu Gly Ala Ala Glu Gln Ser Leu His
65                  70                  75                  80

His Phe Val Ala Gly Ser Thr Trp Asp Trp Gly Glu Val Arg Ala Ala
                85                  90                  95

Leu Ala Arg Tyr Val Asp Asp Arg Leu Thr Pro Asp Ala Trp Val Ile
            100                 105                 110

Trp Pro Met Val Val Ser Lys Ala Gly Val Arg Ser Val Gly Val Ser
        115                 120                 125
```

```
Arg Arg Phe Val Ser Asp Leu Gly Arg Val Val Ser Cys Gln Gln Ser
            130                 135                 140

His Gly Leu Trp Leu Ala Ser Gly Thr Thr Ala Ala Pro Val Ser Trp
145                 150                 155                 160

Arg Leu Thr Leu Gly Gly Gly Arg Ser Gly Glu Gly Thr Pro Arg His
                165                 170                 175

Pro Gly Ala Pro Gly Glu Glu Asn Ile Val Arg Leu Val Ala Glu
                180                 185                 190

Ala Ala Gln Ala Asn Arg Ser Leu Ala Arg Pro Val Val Met Asp Ala
                195                 200                 205

Arg Ala Ala Val Leu Pro Arg Leu Val Arg Gly Leu Gly Leu Ala Gly
            210                 215                 220

Leu Pro Phe Met Val Arg Val Gly Gly Asn Leu Arg Leu Ala Ser Ala
225                 230                 235                 240

Ser Gly Arg Gly Pro Val Asp His His Thr Gly Thr Thr Ser Ala Gln
                245                 250                 255

Gln Leu Met Glu Gln Leu Lys Arg Leu Ser Arg Pro Val Glu Leu Arg
                260                 265                 270

Gly Ser Leu Ser Leu Val Ala Pro His Pro Val Val Leu Pro Gly Val
            275                 280                 285

Val Pro Arg Arg Thr Leu Thr Leu Leu Gly Gly Val Ala
            290                 295                 300

<210> SEQ ID NO 113
<211> LENGTH: 1008
<212> TYPE: DNA
<213> ORGANISM: Streptomyces ambofaciens
<220> FEATURE:
<221> NAME/KEY: CDS
<222> LOCATION: (1)..(1008)

<400> SEQUENCE: 113 atg cag gca att cgg cat cac gtc atg ctc gtc atg gcc ttc gtg acc      48
Met Gln Ala Ile Arg His His Val Met Leu Val Met Ala Phe Val Thr
1               5                   10                  15 gtc gcc acg act ttc ctt ctc tgg ccg tcg acg caa tcc gcg caa gcg      96
Val Ala Thr Thr Phe Leu Leu Trp Pro Ser Thr Gln Ser Ala Gln Ala
                20                  25                  30 ttt ccc ccg acc ccg aag cag acg gta ctg aac cac ctc cgc gcc att     144
Phe Pro Pro Thr Pro Lys Gln Thr Val Leu Asn His Leu Arg Ala Ile
            35                  40                  45 tcc ggg aat cac atc gtc tcc gga cag cac aac aag gag ccc gcc tcc     192
Ser Gly Asn His Ile Val Ser Gly Gln His Asn Lys Glu Pro Ala Ser
50                  55                  60 gcc ccg ggc cag tac acc cag cag gtc aag gac gtc acc ggg cag tac     240
Ala Pro Gly Gln Tyr Thr Gln Gln Val Lys Asp Val Thr Gly Gln Tyr
65                  70                  75                  80 ccc ggc ctg tgg ggc ggt gac ctg atg ttc gcc gcg gcg gac gtg gcc     288
Pro Gly Leu Trp Gly Gly Asp Leu Met Phe Ala Ala Ala Asp Val Ala
                85                  90                  95 ggc cgc cag cgc gtc gtc gac cag gcc agg acc gag tgg gcg aac gga     336
Gly Arg Gln Arg Val Val Asp Gln Ala Arg Thr Glu Trp Ala Asn Gly
            100                 105                 110 tcg ctg gtc tcg ctc acc tgg cac gtc tgc ccg ccg acc ggc ggc agc     384
Ser Leu Val Ser Leu Thr Trp His Val Cys Pro Pro Thr Gly Gly Ser
        115                 120                 125 acc tgt gcg ttc gag ggc ggc gtc aag tcc acg ctg acg aac gcg cag     432
Thr Cys Ala Phe Glu Gly Gly Val Lys Ser Thr Leu Thr Asn Ala Gln
```

```
         130                 135                 140
ttc tcg cag gtc ctc acg gag ggc agt gcc ctg aac agc gca tgg aag      480
Phe Ser Gln Val Leu Thr Glu Gly Ser Ala Leu Asn Ser Ala Trp Lys
145                 150                 155                 160 cgg cgc ctg gac gag gtc gtc ccg tac ctg cag cag ctg gag aac gcg      528
Arg Arg Leu Asp Glu Val Val Pro Tyr Leu Gln Gln Leu Glu Asn Ala
                165                 170                 175 ggc gtc ccc gtc ctc ttc cgg ccg ctg cac gag atg aac gaa tcc tgg      576
Gly Val Pro Val Leu Phe Arg Pro Leu His Glu Met Asn Glu Ser Trp
            180                 185                 190 aac tgg tgg gga aac cgg ccc gga gcg aac ggc agc gca cgc ctc tac      624
Asn Trp Trp Gly Asn Arg Pro Gly Ala Asn Gly Ser Ala Arg Leu Tyr
        195                 200                 205 cag atc acc cgc gat cac ctc gcc ggg acg aaa ggg ctg gac aat ctg      672
Gln Ile Thr Arg Asp His Leu Ala Gly Thr Lys Gly Leu Asp Asn Leu
    210                 215                 220 atc tgg gtc tgg aac gtc cag gac aat ccg gcg gga aac tgg aac agc      720
Ile Trp Val Trp Asn Val Gln Asp Asn Pro Ala Gly Asn Trp Asn Ser
225                 230                 235                 240 tac tat ccg gga gat cag tac gtg gac gtc gtt tcg ctg gac gtc tgg      768
Tyr Tyr Pro Gly Asp Gln Tyr Val Asp Val Val Ser Leu Asp Val Trp
                245                 250                 255 tac aag agc cac ccg agt tcc gcc gac tac cag cag atg cgg agc atc      816
Tyr Lys Ser His Pro Ser Ser Ala Asp Tyr Gln Gln Met Arg Ser Ile
            260                 265                 270 gcg gga aca aaa ccc atg gcc ctc gcg gag ctg ggc aaa atg ccg acc      864
Ala Gly Thr Lys Pro Met Ala Leu Ala Glu Leu Gly Lys Met Pro Thr
        275                 280                 285 gcc gcg ctg ctg gac agc cag acg cgg tgg aca tgg ttc atg atg tgg      912
Ala Ala Leu Leu Asp Ser Gln Thr Arg Trp Thr Trp Phe Met Met Trp
    290                 295                 300 tcc gag cat ctg cgc ggg aac aat tcc aac gcc gaa ata cag acg gcg      960
Ser Glu His Leu Arg Gly Asn Asn Ser Asn Ala Glu Ile Gln Thr Ala
305                 310                 315                 320 tat ttc cac ccc cgt gta ctg aac cag ggg gag gtc gca ctg ccc tga     1008
Tyr Phe His Pro Arg Val Leu Asn Gln Gly Glu Val Ala Leu Pro
                325                 330                 335

<210> SEQ ID NO 114
<211> LENGTH: 335
<212> TYPE: PRT
<213> ORGANISM: Streptomyces ambofaciens

<400> SEQUENCE: 114

Met Gln Ala Ile Arg His His Val Met Leu Val Met Ala Phe Val Thr
1               5                   10                  15

Val Ala Thr Thr Phe Leu Leu Trp Pro Ser Thr Gln Ser Ala Gln Ala
                20                  25                  30

Phe Pro Pro Thr Pro Lys Gln Thr Val Leu Asn His Leu Arg Ala Ile
            35                  40                  45

Ser Gly Asn His Ile Val Ser Gly Gln His Asn Lys Glu Pro Ala Ser
        50                  55                  60

Ala Pro Gly Gln Tyr Thr Gln Val Lys Asp Val Thr Gly Gln Tyr
65                  70                  75                  80

Pro Gly Leu Trp Gly Gly Asp Leu Met Phe Ala Ala Asp Val Ala
                85                  90                  95

Gly Arg Gln Arg Val Val Asp Gln Ala Arg Thr Glu Trp Ala Asn Gly
            100                 105                 110
```

-continued

```
Ser Leu Val Ser Leu Thr Trp His Val Cys Pro Pro Thr Gly Gly Ser
            115                 120                 125

Thr Cys Ala Phe Glu Gly Gly Val Lys Ser Thr Leu Thr Asn Ala Gln
        130                 135                 140

Phe Ser Gln Val Leu Thr Glu Gly Ser Ala Leu Asn Ser Ala Trp Lys
145                 150                 155                 160

Arg Arg Leu Asp Glu Val Val Pro Tyr Leu Gln Gln Leu Glu Asn Ala
                165                 170                 175

Gly Val Pro Val Leu Phe Arg Pro Leu His Glu Met Asn Glu Ser Trp
            180                 185                 190

Asn Trp Trp Gly Asn Arg Pro Gly Ala Asn Gly Ser Ala Arg Leu Tyr
        195                 200                 205

Gln Ile Thr Arg Asp His Leu Ala Gly Thr Lys Gly Leu Asp Asn Leu
    210                 215                 220

Ile Trp Val Trp Asn Val Gln Asp Asn Pro Ala Gly Asn Trp Asn Ser
225                 230                 235                 240

Tyr Tyr Pro Gly Asp Gln Tyr Val Asp Val Val Ser Leu Asp Val Trp
                245                 250                 255

Tyr Lys Ser His Pro Ser Ser Ala Asp Tyr Gln Gln Met Arg Ser Ile
            260                 265                 270

Ala Gly Thr Lys Pro Met Ala Leu Ala Glu Leu Gly Lys Met Pro Thr
        275                 280                 285

Ala Ala Leu Leu Asp Ser Gln Thr Arg Trp Thr Trp Phe Met Met Trp
290                 295                 300

Ser Glu His Leu Arg Gly Asn Asn Ser Asn Ala Glu Ile Gln Thr Ala
305                 310                 315                 320

Tyr Phe His Pro Arg Val Leu Asn Gln Gly Glu Val Ala Leu Pro
                325                 330                 335

<210> SEQ ID NO 115
<211> LENGTH: 1038
<212> TYPE: DNA
<213> ORGANISM: Streptomyces ambofaciens
<220> FEATURE:
<221> NAME/KEY: CDS
<222> LOCATION: (1)..(1038)
<220> FEATURE:
<221> NAME/KEY: CDS2
<222> LOCATION: (190)..(1038)

<400> SEQUENCE: 115 atg acg tgc ggg ctc ggg cgg gaa cgg ctc cac cgt aga aag gaa gcg     48
Met Thr Cys Gly Leu Gly Arg Glu Arg Leu His Arg Arg Lys Glu Ala
1               5                   10                  15 gtc cgg cgt ccc ggt cca aaa gag cac ggg aaa acc gga ccg atc gcg     96
Val Arg Arg Pro Gly Pro Lys Glu His Gly Lys Thr Gly Pro Ile Ala
            20                  25                  30 cgt ctg tgc cct ggc ggg ccg gct cgt tcc aag ccc tgg tcg cgg ttg    144
Arg Leu Cys Pro Gly Gly Pro Ala Arg Ser Lys Pro Trp Ser Arg Leu
        35                  40                  45 gcc ccc tac ggt ggt acg acc gac gac aag gcg acg ggg gcg acg atg    192
Ala Pro Tyr Gly Gly Thr Thr Asp Asp Lys Ala Thr Gly Ala Thr Met
    50                  55                  60 cgt atc gcg gtg aca ggg gcg gcg ggc agt ctg ggc agg cgg gtg gtg    240
Arg Ile Ala Val Thr Gly Ala Ala Gly Ser Leu Gly Arg Arg Val Val
65                  70                  75                  80 cag ctg ctc gcg gac cgg gcc gac gtg gac gtc gtg gcg atg acc agg    288
Gln Leu Leu Ala Asp Arg Ala Asp Val Asp Val Val Ala Met Thr Arg
                85                  90                  95
```

```
cgg aag ctg cct gcc gag gca cta ccg ccg ggg gtg gag tgc gcc gtc       336
Arg Lys Leu Pro Ala Glu Ala Leu Pro Pro Gly Val Glu Cys Ala Val
        100                 105                 110 gcc gac tac gcc gac ccg ccc gct ctg cgt gcg gcg ctg aag ggc gtg       384
Ala Asp Tyr Ala Asp Pro Pro Ala Leu Arg Ala Ala Leu Lys Gly Val
            115                 120                 125 gac act ctg gtc ctc gtc tcc agc gac ggg ccc gac gca cgg gtg ctg       432
Asp Thr Leu Val Leu Val Ser Ser Asp Gly Pro Asp Ala Arg Val Leu
    130                 135                 140 ctg cac cac cgc aac gtc gtc gcc gcc gtg gtg gcc gag cgt gtc ggc       480
Leu His His Arg Asn Val Val Ala Ala Val Val Ala Glu Arg Val Gly
145                 150                 155                 160 cat gtc gcg gca ctg agc agc gtc gac gcc gac tcg gcc tcc ccg ttc       528
His Val Ala Ala Leu Ser Ser Val Asp Ala Asp Ser Ala Ser Pro Phe
                165                 170                 175 tgc tac gcc gtc gtc aac cgg ctc acc gag gat ctg ctg ctc gcc tcc       576
Cys Tyr Ala Val Val Asn Arg Leu Thr Glu Asp Leu Leu Leu Ala Ser
            180                 185                 190 ggc gtg ccg tgc tcg ttc gcc agg gcc tcg ctg tac atc gag ttc ttc       624
Gly Val Pro Cys Ser Phe Ala Arg Ala Ser Leu Tyr Ile Glu Phe Phe
        195                 200                 205 cta ggc tgg ctc acc cag gcg cgc tcg acc ggg ctg ctg agg ctg ccg       672
Leu Gly Trp Leu Thr Gln Ala Arg Ser Thr Gly Leu Leu Arg Leu Pro
    210                 215                 220 gca gcc gat ggc cgg gtg tcc ctg gtg gcg cgc gac gac gtg gcc cgc       720
Ala Ala Asp Gly Arg Val Ser Leu Val Ala Arg Asp Asp Val Ala Arg
225                 230                 235                 240 gcc ctc gcc gcc ctc gcg gtg ggc ggg ccg acc ggc cgt cac cac gac       768
Ala Leu Ala Ala Leu Ala Val Gly Gly Pro Thr Gly Arg His His Asp
                245                 250                 255 atc acg gga ccc gag tcg acg gac ctg gca ggc atc gcc tcc acg gcg       816
Ile Thr Gly Pro Glu Ser Thr Asp Leu Ala Gly Ile Ala Ser Thr Ala
            260                 265                 270 gcg gag gtg tgg cgg aca ccg gtc gcc tac gtg gac atc ccg gcc gac       864
Ala Glu Val Trp Arg Thr Pro Val Ala Tyr Val Asp Ile Pro Ala Asp
        275                 280                 285 acg tac tct gcc gaa aca gcg gcg acc ggc ctg gat ccc tgg tgg ctc       912
Thr Tyr Ser Ala Glu Thr Ala Ala Thr Gly Leu Asp Pro Trp Trp Leu
    290                 295                 300 tac gcc ttc tcc tcc ctg ttc gcc tcg gta cgc gaa cag cgc tgg gat       960
Tyr Ala Phe Ser Ser Leu Phe Ala Ser Val Arg Glu Gln Arg Trp Asp
305                 310                 315                 320 cgg gtc cgc gac gac tgc gcc cag ctc acc ggc cgc ttg ccc cgc act      1008
Arg Val Arg Asp Asp Cys Ala Gln Leu Thr Gly Arg Leu Pro Arg Thr
                325                 330                 335 ctc cgc gac gtc ctg tca gaa cgc gcg tga                              1038
Leu Arg Asp Val Leu Ser Glu Arg Ala
            340                 345

<210> SEQ ID NO 116
<211> LENGTH: 345
<212> TYPE: PRT
<213> ORGANISM: Streptomyces ambofaciens

<400> SEQUENCE: 116

Met Thr Cys Gly Leu Gly Arg Glu Arg Leu His Arg Arg Lys Glu Ala
1               5                   10                  15

Val Arg Arg Pro Gly Pro Lys Glu His Gly Lys Thr Gly Pro Ile Ala
            20                  25                  30
```

-continued

```
Arg Leu Cys Pro Gly Gly Pro Ala Arg Ser Lys Pro Trp Ser Arg Leu
         35                  40                  45

Ala Pro Tyr Gly Gly Thr Thr Asp Asp Lys Ala Thr Gly Ala Thr Met
 50                  55                  60

Arg Ile Ala Val Thr Gly Ala Ala Gly Ser Leu Gly Arg Arg Val Val
65                  70                  75                  80

Gln Leu Leu Ala Asp Arg Ala Asp Val Asp Val Val Ala Met Thr Arg
                 85                  90                  95

Arg Lys Leu Pro Ala Glu Ala Leu Pro Pro Gly Val Glu Cys Ala Val
            100                 105                 110

Ala Asp Tyr Ala Asp Pro Pro Ala Leu Arg Ala Ala Leu Lys Gly Val
            115                 120                 125

Asp Thr Leu Val Leu Val Ser Ser Asp Gly Pro Asp Ala Arg Val Leu
        130                 135                 140

Leu His His Arg Asn Val Val Ala Ala Val Ala Glu Arg Val Gly
145                 150                 155                 160

His Val Ala Ala Leu Ser Ser Val Asp Ala Asp Ser Ala Ser Pro Phe
                165                 170                 175

Cys Tyr Ala Val Val Asn Arg Leu Thr Glu Asp Leu Leu Leu Ala Ser
            180                 185                 190

Gly Val Pro Cys Ser Phe Ala Arg Ala Ser Leu Tyr Ile Glu Phe Phe
            195                 200                 205

Leu Gly Trp Leu Thr Gln Ala Arg Ser Thr Gly Leu Leu Arg Leu Pro
        210                 215                 220

Ala Ala Asp Gly Arg Val Ser Leu Val Ala Arg Asp Asp Val Ala Arg
225                 230                 235                 240

Ala Leu Ala Ala Leu Ala Val Gly Gly Pro Thr Gly Arg His His Asp
                245                 250                 255

Ile Thr Gly Pro Glu Ser Thr Asp Leu Ala Gly Ile Ala Ser Thr Ala
            260                 265                 270

Ala Glu Val Trp Arg Thr Pro Val Ala Tyr Val Asp Ile Pro Ala Asp
            275                 280                 285

Thr Tyr Ser Ala Glu Thr Ala Ala Thr Gly Leu Asp Pro Trp Trp Leu
        290                 295                 300

Tyr Ala Phe Ser Ser Leu Phe Ala Ser Val Arg Glu Gln Arg Trp Asp
305                 310                 315                 320

Arg Val Arg Asp Asp Cys Ala Gln Leu Thr Gly Arg Leu Pro Arg Thr
                325                 330                 335

Leu Arg Asp Val Leu Ser Glu Arg Ala
            340                 345
```

<210> SEQ ID NO 117
<211> LENGTH: 282
<212> TYPE: PRT
<213> ORGANISM: Streptomyces ambofaciens

<400> SEQUENCE: 117

```
Met Arg Ile Ala Val Thr Gly Ala Ala Gly Ser Leu Gly Arg Arg Val
1               5                   10                  15

Val Gln Leu Leu Ala Asp Arg Ala Asp Val Asp Val Val Ala Met Thr
                20                  25                  30

Arg Arg Lys Leu Pro Ala Glu Ala Leu Pro Pro Gly Val Glu Cys Ala
            35                  40                  45

Val Ala Asp Tyr Ala Asp Pro Pro Ala Leu Arg Ala Ala Leu Lys Gly
        50                  55                  60
```

```
Val Asp Thr Leu Val Leu Val Ser Ser Asp Gly Pro Asp Ala Arg Val
 65                  70                  75                  80

Leu Leu His His Arg Asn Val Ala Ala Val Val Ala Glu Arg Val
             85                  90                  95

Gly His Val Ala Ala Leu Ser Ser Val Asp Ala Asp Ser Ala Ser Pro
            100                 105                 110

Phe Cys Tyr Ala Val Val Asn Arg Leu Thr Glu Asp Leu Leu Leu Ala
            115                 120                 125

Ser Gly Val Pro Cys Ser Phe Ala Arg Ala Ser Leu Tyr Ile Glu Phe
130                 135                 140

Phe Leu Gly Trp Leu Thr Gln Ala Arg Ser Thr Gly Leu Leu Arg Leu
145                 150                 155                 160

Pro Ala Ala Asp Gly Arg Val Ser Leu Val Ala Arg Asp Asp Val Ala
                165                 170                 175

Arg Ala Leu Ala Ala Leu Ala Val Gly Gly Pro Thr Gly Arg His His
            180                 185                 190

Asp Ile Thr Gly Pro Glu Ser Thr Asp Leu Ala Gly Ile Ala Ser Thr
            195                 200                 205

Ala Ala Glu Val Trp Arg Thr Pro Val Ala Tyr Val Asp Ile Pro Ala
210                 215                 220

Asp Thr Tyr Ser Ala Glu Thr Ala Ala Thr Gly Leu Asp Pro Trp Trp
225                 230                 235                 240

Leu Tyr Ala Phe Ser Ser Leu Phe Ala Ser Val Arg Glu Gln Arg Trp
                245                 250                 255

Asp Arg Val Arg Asp Asp Cys Ala Gln Leu Thr Gly Arg Leu Pro Arg
            260                 265                 270

Thr Leu Arg Asp Val Leu Ser Glu Arg Ala
            275                 280

<210> SEQ ID NO 118
<211> LENGTH: 975
<212> TYPE: DNA
<213> ORGANISM: Streptomyces ambofaciens
<220> FEATURE:
<221> NAME/KEY: CDS
<222> LOCATION: (1)..(975)

<400> SEQUENCE: 118 atg ctc cga cgc cgt ctc gga ggg ccg tca ggc ccc ctc gtc agt gcc      48
Met Leu Arg Arg Arg Leu Gly Gly Pro Ser Gly Pro Leu Val Ser Ala
1               5                  10                  15 ctg tgc ctg ggc gcg atg ccc ttc ggc acc acc gtc gac gag aag acg      96
Leu Cys Leu Gly Ala Met Pro Phe Gly Thr Thr Val Asp Glu Lys Thr
            20                  25                  30 tcc ttc gcc atc ctc gac cgg ttc gtc gag gcc ggc ggc agt ctc gtc     144
Ser Phe Ala Ile Leu Asp Arg Phe Val Glu Ala Gly Gly Ser Leu Val
        35                  40                  45 gac acc gcc gac aac tac gcg ttc tgg gct ccc ggc ggg acc ggg gac     192
Asp Thr Ala Asp Asn Tyr Ala Phe Trp Ala Pro Gly Gly Thr Gly Asp
    50                  55                  60 gag agc gag aac acc gtc ggg cgc tgg ctg gcg agc cgc cgc cgc cgc     240
Glu Ser Glu Asn Thr Val Gly Arg Trp Leu Ala Ser Arg Arg Arg Arg
65                  70                  75                  80 gac gag gtg gtg atc tcc acc aag gtg ggt gcc cgc ccc acc gtc ccc     288
Asp Glu Val Val Ile Ser Thr Lys Val Gly Ala Arg Pro Thr Val Pro
                85                  90                  95 ggc agc ggc ctg gag acc gcc gaa ggg ctg tcg gct ccc gtc ata cgg     336
```

```
Gly Ser Gly Leu Glu Thr Ala Glu Gly Leu Ser Ala Pro Val Ile Arg
            100                 105                 110 aag gcc gcg gag gac agc ctg cga cgc ctg ggc acc gat cgc atc gat      384
Lys Ala Ala Glu Asp Ser Leu Arg Arg Leu Gly Thr Asp Arg Ile Asp
            115                 120                 125 ctg tac tgg acc cac atc gag gac cgg acc gtc cct ctg gag gag acg      432
Leu Tyr Trp Thr His Ile Glu Asp Arg Thr Val Pro Leu Glu Glu Thr
130                 135                 140 ctc gga gct ctc gac gag ctg gtc ggc ggc ggc aag gtg gcg gtg ctg      480
Leu Gly Ala Leu Asp Glu Leu Val Gly Gly Gly Lys Val Ala Val Leu
145                 150                 155                 160 ggc tgc tcc aac cac gcg ggc tgg cgc atc gaa cgg gcc cgc gcg ctc      528
Gly Cys Ser Asn His Ala Gly Trp Arg Ile Glu Arg Ala Arg Ala Leu
                165                 170                 175 gcc cgg acc aac ggc tgg acg gcg tac acc tgc gtc cag cag cgc tac      576
Ala Arg Thr Asn Gly Trp Thr Ala Tyr Thr Cys Val Gln Gln Arg Tyr
                180                 185                 190 tcc tac ctt cag ccg cgc ttc gac gtc gga ctg ccg gag agc gga cac      624
Ser Tyr Leu Gln Pro Arg Phe Asp Val Gly Leu Pro Glu Ser Gly His
                195                 200                 205 gtc cac gcg acc tcc gaa ctc ctc gac cac gta cgc agc gag ccc gac      672
Val His Ala Thr Ser Glu Leu Leu Asp His Val Arg Ser Glu Pro Asp
210                 215                 220 ctg acg ctg ctg gcc tac tcg tcc ctg ctc tcg ggc gcg tac acc cgg      720
Leu Thr Leu Leu Ala Tyr Ser Ser Leu Leu Ser Gly Ala Tyr Thr Arg
225                 230                 235                 240 ccg gac aag acc ctg tcc gcc gcc tac gac cac ccg ggc acc ggg cag      768
Pro Asp Lys Thr Leu Ser Ala Ala Tyr Asp His Pro Gly Thr Gly Gln
                245                 250                 255 cgg ctg acc gtg ctg cgg gag gtg gcc gcc gag ctc ggt gcc acc gcc      816
Arg Leu Thr Val Leu Arg Glu Val Ala Ala Glu Leu Gly Ala Thr Ala
                260                 265                 270 aac cag gtg gtg ctg tcc tgg ttg ctc gga ggt gat ccg ccg gtg atc      864
Asn Gln Val Val Leu Ser Trp Leu Leu Gly Gly Asp Pro Pro Val Ile
                275                 280                 285 ccg atc gtg ggg gtg agt tcc gtc gag cag ctg gac gag gtg ctg gcc      912
Pro Ile Val Gly Val Ser Ser Val Glu Gln Leu Asp Glu Val Leu Ala
                290                 295                 300 gcc gtc gag ctg gag ctg ccc cgg gag acg agg gca cgg ctg gac ctc      960
Ala Val Glu Leu Glu Leu Pro Arg Glu Thr Arg Ala Arg Leu Asp Leu
305                 310                 315                 320 gcc ggg cgg ggc tga                                                   975
Ala Gly Arg Gly <210> SEQ ID NO 119
<211> LENGTH: 324
<212> TYPE: PRT
<213> ORGANISM: Streptomyces ambofaciens

<400> SEQUENCE: 119

Met Leu Arg Arg Leu Gly Gly Pro Ser Gly Pro Leu Val Ser Ala
1               5                   10                  15

Leu Cys Leu Gly Ala Met Pro Phe Gly Thr Thr Val Asp Glu Lys Thr
            20                  25                  30

Ser Phe Ala Ile Leu Asp Arg Phe Val Glu Ala Gly Gly Ser Leu Val
        35                  40                  45

Asp Thr Ala Asp Asn Tyr Ala Phe Trp Ala Pro Gly Thr Gly Asp
    50                  55                  60

Glu Ser Glu Asn Thr Val Gly Arg Trp Leu Ala Ser Arg Arg Arg Arg
```

```
                 65                  70                  75                  80
Asp Glu Val Val Ile Ser Thr Lys Val Gly Ala Arg Pro Thr Val Pro
                     85                  90                  95

Gly Ser Gly Leu Glu Thr Ala Glu Gly Leu Ser Ala Pro Val Ile Arg
                100                 105                 110

Lys Ala Ala Glu Asp Ser Leu Arg Arg Leu Gly Thr Asp Arg Ile Asp
                115                 120                 125

Leu Tyr Trp Thr His Ile Glu Asp Arg Thr Val Pro Leu Glu Glu Thr
        130                 135                 140

Leu Gly Ala Leu Asp Glu Leu Val Gly Gly Lys Val Ala Val Leu
145                 150                 155                 160

Gly Cys Ser Asn His Ala Gly Trp Arg Ile Glu Arg Ala Arg Ala Leu
                165                 170                 175

Ala Arg Thr Asn Gly Trp Thr Ala Tyr Thr Cys Val Gln Gln Arg Tyr
                180                 185                 190

Ser Tyr Leu Gln Pro Arg Phe Asp Val Gly Leu Pro Glu Ser Gly His
                195                 200                 205

Val His Ala Thr Ser Glu Leu Leu Asp His Val Arg Ser Glu Pro Asp
        210                 215                 220

Leu Thr Leu Leu Ala Tyr Ser Ser Leu Leu Ser Gly Ala Tyr Thr Arg
225                 230                 235                 240

Pro Asp Lys Thr Leu Ser Ala Ala Tyr Asp His Pro Gly Thr Gly Gln
                245                 250                 255

Arg Leu Thr Val Leu Arg Glu Val Ala Ala Glu Leu Gly Ala Thr Ala
                260                 265                 270

Asn Gln Val Val Leu Ser Trp Leu Leu Gly Gly Asp Pro Pro Val Ile
                275                 280                 285

Pro Ile Val Gly Val Ser Ser Val Glu Gln Leu Asp Glu Val Leu Ala
            290                 295                 300

Ala Val Glu Leu Glu Leu Pro Arg Glu Thr Arg Ala Arg Leu Asp Leu
305                 310                 315                 320

Ala Gly Arg Gly

<210> SEQ ID NO 120
<211> LENGTH: 1227
<212> TYPE: DNA
<213> ORGANISM: Streptomyces ambofaciens
<220> FEATURE:
<221> NAME/KEY: CDS
<222> LOCATION: (1)..(1227)

<400> SEQUENCE: 120 gtg acg ccc gag gcg gac gtc ggt acg cgg tgg gag ccg gag ttc gac      48
Val Thr Pro Glu Ala Asp Val Gly Thr Arg Trp Glu Pro Glu Phe Asp
 1               5                  10                  15 atg ctg ccc ggc ata ccc gac ctg cgg gcc ttt ccc cgc gga cgg tgg      96
Met Leu Pro Gly Ile Pro Asp Leu Arg Ala Phe Pro Arg Gly Arg Trp
                20                  25                  30 gcg gac gcg gtg cgg gag gcc acc ggc gca ctg acc tgg ggc gag ctc     144
Ala Asp Ala Val Arg Glu Ala Thr Gly Ala Leu Thr Trp Gly Glu Leu
            35                  40                  45 ggc tac ccc gat ccg gcc ggt ctc gcc cgg ctc cgg cag cgg ctc gcg     192
Gly Tyr Pro Asp Pro Ala Gly Leu Ala Arg Leu Arg Gln Arg Leu Ala
        50                  55                  60 gcc tac ctc gtg cgg gga cgc ggc gcg tcg ctg gaa gcc cgg cag ctc     240
Ala Tyr Leu Val Arg Gly Arg Gly Ala Ser Leu Glu Ala Arg Gln Leu
65                  70                  75                  80
```

-continued

| | |
|---|---|
| gtc gtc tgc gcg ggc acg ctg gac gcg gtg cgc agg ctg tgc cgg gtc<br>Val Val Cys Ala Gly Thr Leu Asp Ala Val Arg Arg Leu Cys Arg Val<br>                   85                          90                    95 | 288 |
| ctg cgg acc gag ggc cac acc cac atg gcc ctg gag gac cct ggc tgg<br>Leu Arg Thr Glu Gly His Thr His Met Ala Leu Glu Asp Pro Gly Trp<br>                100                     105                     110 | 336 |
| tcg cgg ctg agc gcc acg gtc ggg gcg gag ggg ctg gtg ccc gtc ccg<br>Ser Arg Leu Ser Ala Thr Val Gly Ala Glu Gly Leu Val Pro Val Pro<br>               115                     120                   125 | 384 |
| gtt ccc gtg gac ggc gac ggc ctg cgg gtc gac ctg ctg cgg cgc gcg<br>Val Pro Val Asp Gly Asp Gly Leu Arg Val Asp Leu Leu Arg Arg Ala<br> 130                         135                     140 | 432 |
| cct cag gtc cgg tcg gtg atc gtc gct ccc gcc cac cag ttc ccg acc<br>Pro Gln Val Arg Ser Val Ile Val Ala Pro Ala His Gln Phe Pro Thr<br>145                      150                     155                     160 | 480 |
| ggt gtg gtc ctc gcc ccg gcc cgt cgc ggc gag ctg gtc gcc tgg gcc<br>Gly Val Val Leu Ala Pro Ala Arg Arg Gly Glu Leu Val Ala Trp Ala<br>                   165                     170                   175 | 528 |
| cgc gag gtc gac ggc ctg gtg ctg gag gac gac tac gac gcc gag ttc<br>Arg Glu Val Asp Gly Leu Val Leu Glu Asp Asp Tyr Asp Ala Glu Phe<br>               180                     185                   190 | 576 |
| cga tac gac cgc cac ccc gtg ggc gcc ctg cag ggc atg gca ccg gag<br>Arg Tyr Asp Arg His Pro Val Gly Ala Leu Gln Gly Met Ala Pro Glu<br>             195                     200                   205 | 624 |
| cac gtc gcg ctg ctg ggg tcg gtc agc aag acg ctc tcg ccg gcc ctg<br>His Val Ala Leu Leu Gly Ser Val Ser Lys Thr Leu Ser Pro Ala Leu<br>       210                     215                     220 | 672 |
| cgg atc ggc tgg gcg gtg acc ccg ccg cgc tgg acc gag gcc ctg ggc<br>Arg Ile Gly Trp Ala Val Thr Pro Pro Arg Trp Thr Glu Ala Leu Gly<br>225                      230                     235                   240 | 720 |
| gcg gag cac gtc ggg ggc gta cca ccg ccc gtc atc gac cag gag gcg<br>Ala Glu His Val Gly Gly Val Pro Pro Pro Val Ile Asp Gln Glu Ala<br>                   245                     250                   255 | 768 |
| ttc gcc cgg ttc ctg gcc cgc ggg tcc tac gac cgg tac ctg cgg gcg<br>Phe Ala Arg Phe Leu Ala Arg Gly Ser Tyr Asp Arg Tyr Leu Arg Ala<br>                 260                     265                   270 | 816 |
| gca cgg ctg cgc tac aaa cgg cgc cgc gat cac ctc atg gga gaa ctc<br>Ala Arg Leu Arg Tyr Lys Arg Arg Arg Asp His Leu Met Gly Glu Leu<br>        275                     280                     285 | 864 |
| gcg gcg tcg ctg ccg ggg ttc cag gtg tcc ggt gcg gcg gcc ggc ttc<br>Ala Ala Ser Leu Pro Gly Phe Gln Val Ser Gly Ala Ala Ala Gly Phe<br>290                      295                     300 | 912 |
| cac ctg ctg ctg tcc ctg acg gac tgc tcg gcg ccc acc gtc gtc agg<br>His Leu Leu Leu Ser Leu Thr Asp Cys Ser Ala Pro Thr Val Val Arg<br>305                      310                     315                   320 | 960 |
| gag gcg gcg cgg cgt gac gtg agg ctg gcg gat ctc gac gcc tac cgg<br>Glu Ala Ala Arg Arg Asp Val Arg Leu Ala Asp Leu Asp Ala Tyr Arg<br>                   325                     330                   335 | 1008 |
| atg gcg cgg gcc gag cac cac ccg acg gcc cgg gcc ggc gac tcc ggc<br>Met Ala Arg Ala Glu His His Pro Thr Ala Arg Ala Gly Asp Ser Gly<br>               340                     345                   350 | 1056 |
| ggg gcg cgg gcc gtg gcc gcc gcc ggc ccc gcg ctg gtc ctc ggc tac<br>Gly Ala Arg Ala Val Ala Ala Ala Gly Pro Ala Leu Val Leu Gly Tyr<br>         355                     360                     365 | 1104 |
| ggc aat ctg gcg gac cac gcc gtg ccc gga gcc gtg cgg cgc ctg gca<br>Gly Asn Leu Ala Asp His Ala Val Pro Gly Ala Val Arg Arg Leu Ala<br>   370                         375                     380 | 1152 |
| cag gcc atc gac gcg gcc cgg cgc cac gac cgg cgg cac gtc gac gcc<br>Gln Ala Ile Asp Ala Ala Arg Arg His Asp Arg Arg His Val Asp Ala | 1200 |

-continued

```
                385                 390                 395                 400
ggg cgg gcc ggg gag cgg gcc gac tga                                              1227
Gly Arg Ala Gly Glu Arg Ala Asp
                405
```

<210> SEQ ID NO 121
<211> LENGTH: 408
<212> TYPE: PRT
<213> ORGANISM: Streptomyces ambofaciens

<400> SEQUENCE: 121

```
Val Thr Pro Glu Ala Asp Val Gly Thr Arg Trp Glu Pro Glu Phe Asp
1               5                   10                  15

Met Leu Pro Gly Ile Pro Asp Leu Arg Ala Phe Pro Arg Gly Arg Trp
            20                  25                  30

Ala Asp Ala Val Arg Glu Ala Thr Gly Ala Leu Thr Trp Gly Glu Leu
        35                  40                  45

Gly Tyr Pro Asp Pro Ala Gly Leu Ala Arg Leu Arg Gln Arg Leu Ala
    50                  55                  60

Ala Tyr Leu Val Arg Gly Arg Gly Ala Ser Leu Glu Ala Arg Gln Leu
65                  70                  75                  80

Val Val Cys Ala Gly Thr Leu Asp Ala Val Arg Arg Leu Cys Arg Val
                85                  90                  95

Leu Arg Thr Glu Gly His Thr His Met Ala Leu Glu Asp Pro Gly Trp
            100                 105                 110

Ser Arg Leu Ser Ala Thr Val Gly Ala Glu Gly Leu Val Pro Val Pro
        115                 120                 125

Val Pro Val Asp Gly Asp Gly Leu Arg Val Asp Leu Leu Arg Arg Ala
    130                 135                 140

Pro Gln Val Arg Ser Val Ile Val Ala Pro Ala His Gln Phe Pro Thr
145                 150                 155                 160

Gly Val Val Leu Ala Pro Ala Arg Arg Gly Glu Leu Val Ala Trp Ala
                165                 170                 175

Arg Glu Val Asp Gly Leu Val Leu Glu Asp Asp Tyr Asp Ala Glu Phe
            180                 185                 190

Arg Tyr Asp Arg His Pro Val Gly Ala Leu Gln Gly Met Ala Pro Glu
        195                 200                 205

His Val Ala Leu Leu Gly Ser Val Ser Lys Thr Leu Ser Pro Ala Leu
    210                 215                 220

Arg Ile Gly Trp Ala Val Thr Pro Pro Arg Trp Thr Glu Ala Leu Gly
225                 230                 235                 240

Ala Glu His Val Gly Gly Val Pro Pro Val Ile Asp Gln Glu Ala
                245                 250                 255

Phe Ala Arg Phe Leu Ala Arg Gly Ser Tyr Asp Arg Tyr Leu Arg Ala
            260                 265                 270

Ala Arg Leu Arg Tyr Lys Arg Arg Asp His Leu Met Gly Glu Leu
        275                 280                 285

Ala Ala Ser Leu Pro Gly Phe Gln Val Ser Gly Ala Ala Ala Gly Phe
    290                 295                 300

His Leu Leu Ser Leu Thr Asp Cys Ser Ala Pro Thr Val Val Arg
305                 310                 315                 320

Glu Ala Ala Arg Arg Asp Val Arg Leu Ala Asp Leu Asp Ala Tyr Arg
                325                 330                 335

Met Ala Arg Ala Glu His His Pro Thr Ala Arg Ala Gly Asp Ser Gly
            340                 345                 350
```

Gly Ala Arg Ala Val Ala Ala Gly Pro Ala Leu Val Leu Gly Tyr
        355                 360                 365

Gly Asn Leu Ala Asp His Ala Val Pro Gly Ala Val Arg Arg Leu Ala
    370                 375                 380

Gln Ala Ile Asp Ala Ala Arg Arg His Asp Arg Arg His Val Asp Ala
385                 390                 395                 400

Gly Arg Ala Gly Glu Arg Ala Asp
            405

<210> SEQ ID NO 122
<211> LENGTH: 46
<212> TYPE: DNA
<213> ORGANISM: Artificial Sequence
<220> FEATURE:
<223> OTHER INFORMATION: Oligonucleotide EDR39

<400> SEQUENCE: 122
cccaagcttg agaagggagc ggacattcat ggcccgcgcc gaacgc         46

<210> SEQ ID NO 123
<211> LENGTH: 46
<212> TYPE: DNA
<213> ORGANISM: Artificial Sequence
<220> FEATURE:
<223> OTHER INFORMATION: Oligonucleotide EDR42

<400> SEQUENCE: 123
cgggatccgg ctgaccatgg gagacgggcg catcgccgag ttcagc         46

<210> SEQ ID NO 124
<211> LENGTH: 46
<212> TYPE: DNA
<213> ORGANISM: Artificial Sequence
<220> FEATURE:
<223> OTHER INFORMATION: Oligonucleotide EDR40

<400> SEQUENCE: 124
cccaagcttg agaagggagc ggacattcaa tgctttggta aagcac         46

<210> SEQ ID NO 125
<211> LENGTH: 38
<212> TYPE: DNA
<213> ORGANISM: Artificial Sequence
<220> FEATURE:
<223> OTHER INFORMATION: Oligonucleotide EDR41

<400> SEQUENCE: 125
cccaagcttt caaggaacga cggggtggtc agtcaagt                  38

<210> SEQ ID NO 126
<211> LENGTH: 32
<212> TYPE: DNA
<213> ORGANISM: Artificial Sequence
<220> FEATURE:
<223> OTHER INFORMATION: Oligonucleotide A

<400> SEQUENCE: 126
ccagtagata tcccgccaac ccggagctgc ac                        32

<210> SEQ ID NO 127
<211> LENGTH: 32
<212> TYPE: DNA
<213> ORGANISM: Artificial Sequence
<220> FEATURE:

```
<223> OTHER INFORMATION: Oligonucleotide B

<400> SEQUENCE: 127
gaaaagatcc gtcatggggt cgtgcgctcc tt                          32

<210> SEQ ID NO 128
<211> LENGTH: 32
<212> TYPE: DNA
<213> ORGANISM: Artificial Sequence
<220> FEATURE:
<223> OTHER INFORMATION: Oligonucleotide C

<400> SEQUENCE: 128
cacgacccca tgacggatct tttccgctgc at                          32

<210> SEQ ID NO 129
<211> LENGTH: 32
<212> TYPE: DNA
<213> ORGANISM: Artificial Sequence
<220> FEATURE:
<223> OTHER INFORMATION: Oligonucleotide D

<400> SEQUENCE: 129
gagccggata tcatcggtct tgccttgctc gt                          32

<210> SEQ ID NO 130
<211> LENGTH: 25
<212> TYPE: DNA
<213> ORGANISM: Artificial Sequence
<220> FEATURE:
<223> OTHER INFORMATION: Oligonucleotide ORF23c

<400> SEQUENCE: 130
acgtgcgcgg tgagttcgcc gttgc                                  25

<210> SEQ ID NO 131
<211> LENGTH: 25
<212> TYPE: DNA
<213> ORGANISM: Artificial Sequence
<220> FEATURE:
<223> OTHER INFORMATION: Oligonucleotide ORF25c

<400> SEQUENCE: 131
ctgaacgacg ccatcgcggt ggtgc                                  25

<210> SEQ ID NO 132
<211> LENGTH: 25
<212> TYPE: DNA
<213> ORGANISM: Artificial Sequence
<220> FEATURE:
<223> OTHER INFORMATION: Oligonucleotide ORF1*c

<400> SEQUENCE: 132
gaccacctcg aaccgtccgg cgtca                                  25

<210> SEQ ID NO 133
<211> LENGTH: 23
<212> TYPE: DNA
<213> ORGANISM: Artificial Sequence
<220> FEATURE:
<223> OTHER INFORMATION: Oligonucleotide ORF2*c

<400> SEQUENCE: 133
ggcccggtcc agcgtgccga agc                                    23
```

<210> SEQ ID NO 134
<211> LENGTH: 6174
<212> TYPE: DNA
<213> ORGANISM: Streptomyces ambofaciens
<220> FEATURE:
<221> NAME/KEY: misc_feature
<222> LOCATION: (3620)..(4069)
<223> OTHER INFORMATION: n is a, c, g, or t

<400> SEQUENCE: 134

```
ctgcagaggg cgccgacgtg cgcggtgagt tcgccgttgc gccggctggt ccagccgagg      60
ccgccgtgga ccgcgggcgc ctgtgcgcac agcaggcccc gggagccgag gtcgtgcagc     120
aggccgaggg gcagctcgcc cgtccggtcc cactcggccg cccggtcgcc gaccagcgcg     180
gtgaacagct cctcggcctc ggtgccgtcg gcgtgggagg tgtcagccac ctgcgtgccc     240
ggtcgcctcg ccgggcgcgg ccagccgtcc gaccagccgg accatcgcgt cgacggtgcg     300
gaagttgtcg agcatcaggt cggcgccgct gatgacgatg ccgtaggtct tctccaggtg     360
cacgacgagc tgcatggcga acagcgagga catcccgccg acggcgaaca ggtcctggtc     420
gcgctcccag gtggtcttgg tgcggtcctc gaggaacccg agcagttccc cggcgacctc     480
gtcgcggtg ggggtcgtgc cggtggggtc gggccgaccg gacgtcgtgg tcatcgcgtg     540
gcctcctggt agtcgtagaa tccccggccg ctcttgcggc cgagcaggcc ctggcggacc     600
ttgtccagca gcagctcgct cgggcggagc gccggatcgc cggtccgttc gtgcatcacc     660
cgcagcgagt cggccaggtt gtccagtccg atcaggtcgg ccgtggccag gggtccggtg     720
cggtggccga tgcagtcgcg catcagcgcg tccacggtct ccggggtggc ccggccctcg     780
tgcaccaccg cgatggcgtc gttcagcatc cggtgcagca ggcggctggt cacgaagccg     840
gcgccgtcgc cgacgacgat gccccggcgg cccaggccgg acagcaggtc ccgggtggcc     900
cgggcggccg cctctccgct gcgcggtccg aggaccacct cgaccgtggg gatcacgtac     960
gcggggttca tgaagtgcac gccgacgagg tcctcggggc ggggacggc gtcggccagc    1020
tcgtcgatgg ggacgcccga ggtgttgctg acgagcagcg tccccgggcg cgccacggac    1080
gccaggtccg ccagcacctc ggccttccgc tcggggtcct cggtgacggc ctcgatcacg    1140
gcggtcgcgg tggcgacggc ggccggcgcc tcctcgacgg tcagctcccc gggcgggcgg    1200
tcgtggggca gcgcgcccat cagccggcc gtccgcagat gcagcgcgac cgcgtcgggg    1260
gcggccgcgc gcgccccggc ggaggtgtcg accagtgtga ccgggtgccc gtgtccgacg    1320
gcgagtgccg cgatggccgt gcccatgacg cccgcgccga gcacgacgag cggagaattt    1380
tccttggaat cgggcacgga tcctccagaa tcccggggc ggcggctgtg cgaaatgctg    1440
tcccgaatcg cttccgcgct ccatcacccg ggcgtgactt tgtcacctag caagcggtgg    1500
gaggccgggc ggaggctatg tcatctcggc cttgtccgct tacgagttcc gtccttaaag    1560
tgcgcccggc gaacgcacgg cggaattgac tcgccgtccg tcaaggaccc gcggttcgaa    1620
ggacctcgac gcatgaaggg tttcacatgg ctcatatcgc attcttcatc cttccggttg    1680
ccgggcatgt gaatccgacc ctgggagtcg ccgaggaact ggtcgcgcgc ggccaccggg    1740
tgacgttcgc gctgtccgag gacctcgccg agcgggcccg gctgatcggc gccgaggtgg    1800
tcacctatcc ggtggacagg caacggttcc tggaccagat ggtgccgcgg caggacgcgg    1860
acgagtacac ggacgaggac gagttcgtcc gggtcctgga gtggctgctg acatgacgg    1920
tgcagaccat ggaaccgctg gagaggcact tcgccgggga ccggcccgac gtcgtcgtca    1980
acgatccgtc gtcgctgtgg acgggacggc tgctggcgga ccggtggggc atcccggtca    2040
```

-continued

| | |
|---|---|
| tccgcagcac tccgacctat gccgccaacg aacactggtc gctgcatccg ccggtcgact | 2100 |
| cggccgagcc gccggacgac cccgagctgc acaagctgct cgcgcggatc gagcggctgc | 2160 |
| tggaggagca gggcgtcgag cacgacctgg ccggcttcac cggggtcctg cacggcggtc | 2220 |
| cggccctgct gtacatgccc cgctcgttcc agtacgcggg cgagaccttc gacgcacagc | 2280 |
| accacttcgt cggcccctgc ccgccccgca ccgcgttcca cggcgagtgg aggccggggg | 2340 |
| acgacgacgg ccggcccctg gtgctggtga gtctcggaac cctgtacaac gaccggccgg | 2400 |
| acttcttccg cacctgcctg gaggcgttcg gcgacgagcc ctggaacgtg cttctggtgc | 2460 |
| tgggcggcgg ggtgcccgcg gccgacctgg gcccgcttcc cggcaatgtc cgggtgaccg | 2520 |
| acttcgtgtc gctgcgcgac gtcctgccgc acacggcggt ggtggtgaac acggtggga | 2580 |
| tgagcaccgc catggaggtg ttctcgcacg gtgtgccggt ggtggcgatc ccggtgatgc | 2640 |
| cggagccccg ggccaccgcg cggcggatcg tcgaactggg cctgggcgac cagctgctga | 2700 |
| actcggagct gacggccgag tccctgcgtg ccacggtacg gcgggtgctg gcggactccg | 2760 |
| cgatcccggg gaacatgcgc gggttccggg agcagatcag ggcggccggc ggggcgcccg | 2820 |
| cggcggccga cgcgatcgag ggactgctgc cccgggtggg ctgagacgtc cgcgcccgac | 2880 |
| acgcgttcac cttccgaacg gcgggatcgc cccatgctca tcaccgaaac agcagtgccc | 2940 |
| gacgtgttcc gcatcgatcc ggaaccgctg ccggaccacc ggggccggtt ctacgaagcg | 3000 |
| gtgcgccgcg ggccgctgga ggccgccgtc gggcactcgg tcgaggtccg gcaggtccac | 3060 |
| tgcaccgtct ccgggcgcaa cgtactgcgc ggcctgcacg ccaccaccct gccgccgggc | 3120 |
| caggccaaga tcctcacctg tgtgcggggt gcggcgctga ctatggtggt cgacatgagg | 3180 |
| gtcgggtcac cgggcttcgg acggtacgag gcggtgcggc aggatgcccc gtcgggcacc | 3240 |
| gcgctctacc tgccggacgg catcggcctg ggctacgtgg ccctcgcgga cgacacatgc | 3300 |
| atgaactacc tgtgcaccga ggagtacgtc ccgggcatgg tcatcgacgt ggacgccctg | 3360 |
| gaccccgaac tcggcctgcc gtggggactg accggggatc ccgtccgctc cgcccgggac | 3420 |
| gcggcggcgc cgtccctgcg gcggccgcg cggcgggaa ttctgcccac gtacgaggac | 3480 |
| tgcttacggg tgcgcacgtc cgtgcccgcc cctcccgacc ggactcggct ctgacgcgac | 3540 |
| ggacacgacc gccgcgcatc cgacgcgaat ccgacgcgaa tccgaactcg atttcccgaa | 3600 |
| ccgtggacgg agcgcgtccn nnnnnnnnn nnnnnnnnnn nnnnnnnnnn nnnnnnnnnn | 3660 |
| nnnnnnnnnn nnnnnnnnnn nnnnnnnnnn nnnnnnnnnn nnnnnnnnnn nnnnnnnnnn | 3720 |
| nnnnnnnnnn nnnnnnnnnn nnnnnnnnnn nnnnnnnnnn nnnnnnnnnn nnnnnnnnnn | 3780 |
| nnnnnnnnnn nnnnnnnnnn nnnnnnnnnn nnnnnnnnnn nnnnnnnnnn nnnnnnnnnn | 3840 |
| nnnnnnnnnn nnnnnnnnnn nnnnnnnnnn nnnnnnnnnn nnnnnnnnnn nnnnnnnnnn | 3900 |
| nnnnnnnnnn nnnnnnnnnn nnnnnnnnnn nnnnnnnnnn nnnnnnnnnn nnnnnnnnnn | 3960 |
| nnnnnnnnnn nnnnnnnnnn nnnnnnnnnn nnnnnnnnnn nnnnnnnnnn nnnnnnnnnn | 4020 |
| nnnnnnnnnn nnnnnnnnnn nnnnnnnnnn nnnnnnnnnn nnnnnnnnnc cgccacaccc | 4080 |
| cccagcagcg tcagcgtccg cctcgggacc acacccggca ggacgacggg gtgcggggcg | 4140 |
| acgaggctga gggagccccg caactccacg gggcggctca accgcttgag ctgctccatc | 4200 |
| aactgctggg ccgaggtggt ccccgtgtgg tggtccaccg ggccgcggcc gctcgccgag | 4260 |
| gccagccgga ggttcccgcc caccccgcacc atgaagggca ggcccgcgag accgagccct | 4320 |
| cgcaccagtc gtggcagcac ggccgcgcgt cgtccatca ccacggggcg ggccaaggag | 4380 |
| cggttggcct gagcggcttc ggccaccagg cggacgatgt tctcctcctc accgggtgcg | 4440 |

```
ccggggtgcc ggggtgtgcc ctccccgctc cggccgccgc ccagcgtcag gcgccagctg    4500
accggggcgg ccgtcgtgcc cgaggccagc cacagcccgt gactctgctg gcagctcacc    4560
acccggccca ggtcggagac gaagcgccgg ctcaccccga cggagcgcac cccgccttg     4620 gagaccacca tcggccagat cacccaggcg tcggggtca gcctgtcgtc cacgtagcgg     4680
gccagcgcgg cccgcacctc gccccagtcc caggtcgacc cggcgacgaa gtggtgcagg    4740
ctctgttccg ccgcgccctc tccgacgaag gcggcgaggt tccgggcggt cttgcgtccc    4800
tgtgccgtga gcagcccgcg tatgtactgc tcacctcttc tgcgctggtc cgcccggcgg    4860
agcgaaccga gtaactccgc acatgcgtcg gagacgagcg agtcgaagtc gtgccgcgcg    4920
gcggacccca cggggggcgc cgcgccggcg ggtcgaagcg tgcgtaaggt cataggagtc    4980 ctcgtgggg cctcgtcatc actgcgagtg gactgcgacc agcatcgcca attcacccgt     5040
tgctccccag gtacaccggg cacactcgtt ccgcttcgct ccccggcgg cacggcccgc     5100 gtgtggagca ctccccgctc tccggacggt ggggggaag cccaccgcac gcgcgccggt     5160
agcggtgccg ggcccccaca acccctcacc gacggggtcc gttcgaccac atgccgtgat    5220
gatgccttcg ccgcacggcc tccttgaatg acggaccgtc agaaagacgt cactccgcgc    5280
gcgcccgctc ccgccccgac cccgccggcc cgccgtcccg ccccccgcgac cctgtgggcc   5340 gacgccctct tgacggaccc ggaatcccgg gccgcgggac gggacggcga ggaactcgat    5400
gccgcaaagg ttccgcgtcc tcaccggcac ctccgagatc cagcgcaacg gcatcgccaa    5460
gctcctggct ttccaccact gagccgcacc ccctggcgag cagatccggg acaagacgcc    5520
accttcgcga cagtgtttag gaaaagttaa gtaaagaatt ccgcgagcgg attgccaggg    5580
agaacaaccc attgacgcgc accggtgcag cggccacatt gacggcacct gtcaagttca    5640
cccccaggag cttggaatcc catgcaggca attcggcatc acgtcatgct cgtcatggcc    5700
ttcgtgaccg tcgccacgac tttccttctc tggccgtcga cgcaatccgc gcaagcgttt    5760
ccccgacccc gaagcagac ggtactgaac cacctccgcg ccatttccgg gaatcacatc     5820
gtctccggac agcacaacaa ggagcccgcc tccgccccgg ccagtacac ccagcaggtc     5880 aaggacgtca ccgggcagta cccggcctg tggggcggtg acctgatgtt cgccgcggcg     5940
gacgtggccg gccgccagcg cgtcgtcgac caggccagga ccgagtgggc gaacggatcg    6000
ctggtctcgc tcacctggca cgtctgcccg ccgaccggcg gcagcacctg tgcgttcgag    6060
ggcggcgtca gtccacgct gacgaacgcg cagttctcgc aggtcctcac ggagggcagt     6120
gccctgaaca gcgcatggaa gcggcgcctg gacgaggtcg tcccgtacct gcag           6174
```

<210> SEQ ID NO 135
<211> LENGTH: 4770
<212> TYPE: DNA
<213> ORGANISM: Streptomyces ambofaciens

<400> SEQUENCE: 135

```
gaattccgcg agcggattgc cagggagaac aacccattga cgcgcaccgg tgcagcggcc      60
acattgacgg cacctgtcaa gttcaccccc aggagcttgg aatcccatgc aggcaattcg     120
gcatcacgtc atgctcgtca tggccttcgt gaccgtcgcc acgactttcc ttctctggcc     180
gtcgacgcaa tccgcgcaag cgtttccccc gaccccgaag cagacggtac tgaaccacct    240
ccgcgccatt tccgggaatc acatcgtctc cggacagcac aacaaggagc ccgcctccgc    300
cccgggccag tacacccagc aggtcaagga cgtcaccggg cagtacccg gcctgtgggg    360
```

-continued

```
cggtgacctg atgttcgccg cggcggacgt ggccggccgc cagcgcgtcg tcgaccaggc      420
caggaccgag tgggcgaacg gatcgctggt ctcgctcacc tggcacgtct gcccgccgac      480
cggcggcagc acctgtgcgt tcgagggcgg cgtcaagtcc acgctgacga acgcgcagtt      540
ctcgcaggtc ctcacggagg gcagtgccct gaacagcgca tggaagcggc gcctggacga      600
ggtcgtcccg tacctgcagc agctggagaa cgcgggcgtc cccgtcctct tccggccgct      660
gcacgagatg aacgaatcct ggaactggtg gggaaaccgg cccggagcga acggcagcgc      720
acgcctctac cagatcaccc gcgatcacct cgccgggacg aaagggctgg acaatctgat      780
ctgggtctgg aacgtccagg acaatccggc gggaaactgg aacagctact atccgggaga      840
tcagtacgtg gacgtcgttt cgctggacgt ctggtacaag agccacccga gttccgccga      900
ctaccagcag atgcgcagca tcgcgggaac aaaacccatg gccctcgcgg agctgggcaa      960
aatgccgacc gccgcgctgc tggacagcca gacgcggtgg acatggttca tgatgtggtc     1020
cgagcatctg cgcgggaaca attccaacgc cgaaatacag acggcgtatt tccacccccg     1080
tgtactgaac caggggggagg tcgcactgcc ctgacgctcg gcgctgcccg gctctctcac     1140
gcgcgttctg acaggacgtc gcggagagtg cggggcaagc ggccggtgag ctgggcgcag     1200
tcgtcgcgga cccgatccca gcgctgttcg cgtaccgagg cgaacaggga ggagaaggcg     1260
tagagccacc agggatccag gccggtcgcc gctgtttcgg cagagtacgt gtcggccggg     1320
atgtccacgt aggcgaccgg tgtccgccac acctccgccg ccgtggaggc gatgcctgcc     1380
aggtccgtcg actcgggtcc cgtgatgtcg tggtgacggc cggtcggccc gcccaccgcg     1440
agggcggcga gggcgcgggc cacgtcgtcg cgcgccacca gggacacccg gccatcggct     1500
gccggcagcc tcagcagccc ggtcgagcgc gcctgggtga ccagcctag gaagaactcg     1560 atgtacagcg aggccctggc gaacgagcac ggcacgccgg aggcgagcag cagatcctcg     1620
gtgagccggt tgacgacggc gtagcagaac ggggaggccg agtcggcgtc gacgctgctc     1680
agtgccgcga catggccgac gcgctcggcc accacggcgg cgacgacgtt gcggtggtgc     1740
agcagcaccc gtgcgtcggg cccgtcgctg gagacgagga ccagagtgtc cacgcccttc     1800
agcgccgcac gcagagcggg cgggtcggcg tagtcggcga cggcgcactc cacccccggc     1860
ggtagtgcct cggcaggcag cttccgcctg gtcatcgcca cgacgtccac gtcggcccgg     1920
tccgcgagca gctgcaccac ccgcctgccc agactgcccg ccgcccctgt caccgcgata     1980
cgcatcgtcg cccccgtcgc cttgtcgtcg gtcgtaccac cgtaggggc caaccgcgac     2040 cagggcttgg aacgagccgg cccgccaggg cacagacgcg cgatcggtcc ggttttcccg     2100
tgctcttttg gaccgggacg ccggaccgct tcctttctac ggtggagccg ttccgcccg      2160 agcccgcacg tcatcgacgt gcggggaaga cagaggtgat accgatgctc cgacgccgtc     2220
tcggagggcc gtcaggcccc ctcgtcagtg ccctgtgcct gggcgcgatg cccttcggca     2280
ccaccgtcga cgagaagacg tccttcgcca tcctcgaccg gttcgtcgag gccggcggca     2340
gtctcgtcga caccgccgac aactacgcgt tctgggctcc cggcgggacc ggggacgaga     2400
gcgagaacac cgtcgggcgc tggctggcga ccgccgccg ccgcgacgag gtggtgatct      2460
ccaccaaggt gggtgcccgc cccaccgtcc ccggcagcgg cctggagacc gccgaagggc     2520
tgtcggctcc cgtcatacgg aaggccgcgg aggacagcct gcgacgcctg gcaccgatc      2580 gcatcgatct gtactggacc cacatcgagg accggaccgt ccctctggag gagacgctcg     2640
gagctctcga cgagctggtc ggcggcggca aggtggcggt gctgggctgc tccaaccacg     2700
cgggctggcg catcgaacgg gcccgcgcgc tcgcccggac caacggctgg acggcgtaca     2760
```

```
cctgcgtcca gcagcgctac tcctaccttc agccgcgctt cgacgtcgga ctgccggaga    2820
gcggacacgt ccacgcgacc tccgaactcc tcgaccacgt acgcagcgag cccgacctga    2880
cgctgctggc ctactcgtcc ctgctctcgg gcgcgtacac ccggccggac aagaccctgt    2940
ccgccgccta cgaccacccg ggcaccgggc agcggctgac cgtgctgcgg gaggtggccg    3000
ccgagctcgt tgccaccgcc aaccaggtgg tgctgtcctg gttgctcgga ggtgatccgc    3060
cggtgatccc gatcgtgggg gtgagttccg tcgagcagct ggacgaggtg ctggccgccg    3120
tcgagctgga gctgccccgg gagacgaggg cacggctgga cctcgccggg cggggctgac    3180
gggccacaca ccgcccctcg cccgggacgg gctgaccggc cgcacaccgt ccctcagccg    3240
ggacgggctg acgccacac acccgcccct cagcccggct gggctgggct gacgccaca    3300 cacccgctcc tcagcccggc tgggctgggc tgacggccac acacccgccc ctcagcccgg    3360
ctgggctggg ctgacggcca cacgccgtcc ctcgcccggg tcgggctgac cagccacacg    3420
ccgtccctca gtcggcccgc tccccggccc gccggcgtc gacgtgccgc cggtcgtggc    3480
gccgggccgc gtcgatggcc tgtgccaggc gccgcacggc tccgggcacg gcgtggtccg    3540
ccagattgcc gtagccgagg accagcgcgg ggccggcgg ggccacggcc cgcgcccgc    3600 cggagtcgcc ggcccgggcc gtcgggtggt gctcggcccg cgccatccgg taggcgtcga    3660
gatccgccag cctcacgtca cgccgcgcg cctccctgac gacggtgggc gccgagcagt    3720
ccgtcaggga cagcagcagg tggaagccgg ccgccgcacc ggacacctgg aaccccggca    3780
gcgacgccgc gagttctccc atgaggtgat cgcggcgccg tttgtagcgc agccgtgccg    3840
cccgcaggta ccgtcgtag gaccgcggg ccaggaaccg ggcgaacgcc tcctggtcga    3900
tgacgggcgg tggtacgccc ccgacgtgct ccgcgcccag ggcctcggtc cagcgcggcg    3960
gggtcaccgc ccagccgatc cgcagggccg gcgagagcgt cttgctgacc gaccccagca    4020
gcgcgacgtg ctccggtgcc atgccctgca gggcgcccac ggggtggcgg tcgtatcgga    4080
actcggcgtc gtagtcgtcc tccagcacca ggccgtcgac ctcgcgggcc caggcgacca    4140
gctcgccgcg acgggccggg gcgaggacca caccggtcgg gaactggtgg gcgggagcga    4200
cgatcaccga ccggacctga ggcgcgcgcc gcagcaggtc gacccgcagg ccgtcgccgt    4260
ccacgggaac cgggacgggc accagcccct ccgcccgac cgtggcgctc agccgcgacc    4320
agccagggtc ctccagggcc atgtgggtgt ggccctcggt ccgcaggacc cggcacagcc    4380
tgcgcaccgc gtccagcgtg cccgcgcaga cgacagcctg ccgggcttcc agcgacgcgc    4440
cgcgtccccg cacgaggtag gccgcgagcc gctgccggag ccgggcgaga ccggccggat    4500
cggggtagcc gagctcgccc caggtcagtg cgccggtggc ctcccgcacc gcgtccgccc    4560
accgtccgcg gggaaaggcc cgcaggtcgg gtatgccggg cagcatgtcg aactccggct    4620
cccaccgcgt accgacgtcc gcctcgggcg tcaccggagc ggggacggcc tgcgccctga    4680
cccgggtggc cgagccgctg cgcgcctcca ggtacccctc cgcgacgagc tgctcgtagg    4740
ggggatcctc tagagtcgac ctgcaggcct                                     4770
```

<210> SEQ ID NO 136
<211> LENGTH: 28
<212> TYPE: DNA
<213> ORGANISM: Artificial Sequence
<220> FEATURE:
<223> OTHER INFORMATION: Oligonucleotide EDR31

<400> SEQUENCE: 136
cccaagcttc tgcgcccgcg ggcgtgaa                                         28

<210> SEQ ID NO 137
<211> LENGTH: 28
<212> TYPE: DNA
<213> ORGANISM: Artificial Sequence
<220> FEATURE:
<223> OTHER INFORMATION: Oligonucleotide EDR37

<400> SEQUENCE: 137
gctctagaac cgtgtagccg cgccccgg                                         28

<210> SEQ ID NO 138
<211> LENGTH: 30
<212> TYPE: DNA
<213> ORGANISM: Artificial Sequence
<220> FEATURE:
<223> OTHER INFORMATION: Oligonucleotide KF30

<400> SEQUENCE: 138
aagcttgtgt gcccggtgta cctggggagc                                       30

<210> SEQ ID NO 139
<211> LENGTH: 30
<212> TYPE: DNA
<213> ORGANISM: Artificial Sequence
<220> FEATURE:
<223> OTHER INFORMATION: Oligonucleotide KF31

<400> SEQUENCE: 139
ggatcccgcg acggacacga ccgccgcgca                                       30

<210> SEQ ID NO 140
<211> LENGTH: 12134
<212> TYPE: DNA
<213> ORGANISM: Streptomyces ambofaciens

<400> SEQUENCE: 140
ctgcagaggg cgccgacgtg cgcggtgagt tcgccgttgc gccggctggt ccagccgagg      60
ccgccgtgga ccgcgggcgc ctgtgcgcac agcaggcccc gggagccgag gtcgtgcagc     120
aggccgaggg gcagctcgcc cgtccggtcc cactcggccg cccggtcgcc gaccagcgcg     180
gtgaacagct cctcggcctc ggtgccgtcg gcgtgggagg tgtcagccac ctgcgtgccc     240
ggtcgcctcg ccgggcgcgg ccagccgtcc gaccagccgg accatcgcgt cgacggtgcg     300
gaagttgtcg agcatcaggt cggcgccgct gatgacgatg ccgtaggtct tctccaggtg     360
cacgacgagc tgcatggcga acagcgagga catcccgccg acggcgaaca ggtcctggtc     420
gcgctcccag gtggtcttgg tgcggtcctc gaggaacccg agcagttccc cggcgacctc     480
gtcggcggtg ggggtcgtgc cggtggggtc gggccgaccg gacgtcgtgg tcatcgcgtg     540
gcctcctggt agtcgtagaa tccccggccg ctcttgcggc cgagcaggcc ctggcggacc     600
ttgtccagca gcagctcgct cgggcggagc gccggatcgc cggtccgttc gtgcatcacc     660
cgcagcgagt cggccaggtt gtccagtccg atcaggtcgg ccgtggccag gggtccggtg     720
cggtggccga tgcagtcgcg catcagcgcg tccacggtct ccggggtggc ccggccctcg     780
tgcaccaccg cgatggcgtc gttcagcatc cggtgcagca ggcggctggt cacgaagccg     840
gcgccgtcgc cgacgacgat gcccgcccgg ccaggccgcc acagcaggtc ccgggtggcc     900
cgggcggccg cctctccgct gcgcggtccg aggaccacct cgaccgtggg gatcacgtac     960
gcggggttca tgaagtgcac gccgacgagg tcctcggggc ggggacggc gtcggccagc      1020

```
tcgtcgatgg ggacgcccga ggtgttgctg acgagcagcg tccccgggcg cgccacggac   1080
gccaggtccg ccagcacctc ggccttccgc tcggggtcct cggtgacggc ctcgatcacg   1140
gcggtcgcgg tggcgacggc ggccggcgcc tcctcgacgg tcagctcccc gggcgggcgg   1200
tcgtggggca gcgcgcccat cagccgggcc gtccgcagat gcagcgcgac cgcgtcgggg   1260
gcggccgcgc gcgccccggc ggaggtgtcg accagtgtga ccgggtgccc gtgtccgacg   1320
gcgagtgccg cgatggccgt gcccatgacg cccgcgccga gcacgacgag cggagaattt   1380
tccttggaat cgggcacgga tcctccagaa tcccgggggc ggcggctgtg cgaaatgctg   1440
tcccgaatcg cttccgcgct ccatcacccg ggcgtgactt tgtcacctag caagcggtgg   1500
gaggccgggc ggaggctatg tcatctcggc cttgtccgct tacgagttcc gtccttaaag   1560
tgcgcccggc gaacgcacgg cggaattgac tcgccgtccg tcaaggaccc gcggttcgaa   1620
ggacctcgac gcatgaaggg tttcacatgg ctcatatcgc attcttcatc cttccggttg   1680
ccgggcatgt gaatccgacc ctgggagtcg ccgaggaact ggtcgcgcgc ggccaccggg   1740
tgacgttcgc gctgtccgag gacctcgccg agcgggcccg gctgatcggc gccgaggtgg   1800
tcacctatcc ggtggacagg caacggttcc tggaccagat ggtgccgcgg caggacgcgg   1860
acgagtacac ggacgaggac gagttcgtcc gggtcctgga gtggctgctg acatgacgg    1920
tgcagaccat ggaaccgctg agaggcact  tcgccgggga ccggcccgac gtcgtcgtca   1980
acgatccgtc gtcgctgtgg acgggacggc tgctggcgga ccggtggggc atcccggtca   2040
tccgcagcac tccgacctat gccgccaacg aacactggtc gctgcatccg ccggtcgact   2100
cggccgagcc gccggacgac cccgagctgc acaagctgct cgcgcggatc gagcggctgc   2160
tggaggagca gggcgtcgag cacgacctgg ccggcttcac cggggtcctg cacggcggtc   2220
cggccctgct gtacatgccc cgctcgttcc agtacgcggg cgagaccttc gacgcacagc   2280
accacttcgt cggcccctgc ccgccccgca ccgcgttcca cggcgagtgg aggccggggg   2340
acgacgacgg ccggcccctg gtgctggtga gtctcggaac cctgtacaac gaccggccgg   2400
acttcttccg cacctgcctg gaggcgttcg gcgacgagcc ctggaacgtg cttctggtgc   2460
tgggcggcgg ggtgcccgcg gccgacctgg gcccgcttcc cggcaatgtc cgggtgaccg   2520
acttcgtgtc gctgcgcgac gtcctgccgc acacggcggt ggtggtgaac cacgtgggga   2580
tgagcaccgc catggaggtg ttctcgcacg tgtgccggt ggtggcgatc ccggtgatgc    2640
cggagccccg ggccaccgcg cggcggatcg tcgaactggg cctgggcgac cagctgctga   2700
actcggagct gacggccgag tccctgcgtg ccacggtacg gcgggtgctg gcggactccg   2760
cgatcccggg gaacatgcgc gggttccggg agcagatcag gcggccggc ggggcgcccg    2820
cggcggccga cgcgatcgag ggactgctgc cccgggtggg ctgagacgtc cgcgcccgac   2880
acgcgttcac cttccgaacg gcgggatcgc cccatgctca tcaccgaaac agcagtgccc   2940
gacgtgttcc gcatcgatcc ggaaccgctg ccggaccacc ggggccggtt ctacgaagcg   3000
gtgcgccgcg gccgctgga ggccgccgtc gggcactcgg tcgaggtccg gcaggtccac    3060
tgcaccgtct ccgggcgcaa cgtactgcgc ggcctgcacg ccaccaccct gccgccgggc   3120
caggccaaga tcctcacctg tgtgcggggt gcggcgctga ctatggtggt cgacatgagg   3180
gtcgggtcac cgggcttcgg acggtacgag gcggtgcggc aggatgcccc gtcgggcacc   3240
gcgctctacc tgccggacgg catcggcctg ggctacgtgg ccctcgcgga cgacacatgc   3300
atgaactacc tgtgcaccga ggagtacgtc ccgggcatgg tcatcgacgt ggacgccctg   3360
```

```
gaccccgaac tcggcctgcc gtggggactg accgggatcc ccgtccgctc cgcccgggac    3420
gcggcggcgc cgtccctgcg ggcggccgcg gcggcgggaa ttctgccgac gtacgaggac    3480
tgcttacggg tgcgcacgtc cgtgcccgcc cctcccgacc ggactcggct ctgacgcgac    3540
ggacacgacc gccgcgcatc cgacgcgaat ccgacgcgaa tccgaactcg atttcccgaa    3600
ccgtggacgg agcgcgccga ggagcggaaa ggtctgccgc agaaacaggc tgcggccctt    3660
tctttccgct ttttccggta ccgggacggc cgttccgatg aaagcgaacg tccgcatgcg    3720
acggccgtcc ctcccgtacg ctcctccccc gtcgcggccg gcgggcggg cgggccggcc     3780 gaccgcgacg gggcggggcg gggtcacacc gccgtcgccc caccgaggtc gccgcgcgcg    3840
gagggctgcg ccagccgcag cgtgtgggcg atggacgcca gggtcacgtg ccggtgccag    3900
ccctggaacg accgtccttc gaagtcgcgc atgcccacgc ccacgctcac ccggtcgaag    3960
tcggcgtcga cctgttcggt gagcatcgcc agccgcagca gggcgccgcg gtcccaggac    4020
gtgaggtcgg tcagccacag gtcggcgggg cgccggcggt tgccccgcca cacccccagc    4080
agcgtcagcg tccgcctcgg gaccacaccc ggcaggacga cggggtgcgg ggcgacgagg    4140
ctgagggagc cccgcaactc cacggggcgg ctcaaccgct tgagctgctc catcaactgc    4200
tgggccgagg tggtccccgt gtggtggtcc accgggccgc ggccgctcgc cgaggccagc    4260
cggaggttcc cgcccacccg caccatgaag ggcaggcccg cgagaccgag ccctcgcacc    4320
agtcgtggca gcacggccgc gcgtgcgtcc atcaccacgg ggcgggccaa ggagcggttg    4380
gcctgagcgg cttcggccac caggcggacg atgttctcct cctcaccggg tgcgccgggg    4440
tgccggggtg tgccctcccc gctccggccg ccgcccagcg tcaggcgcca gctgaccggg    4500
gcggccgtcg tgcccgaggc cagccacagc ccgtgactct gctggcagct caccacccgg    4560
cccaggtcgg agacgaagcg ccggctcacc ccgacggagc gcaccccccgc cttggagacc    4620 accatcggcc agatcaccca ggcgtcgggg gtcagcctgt cgtccacgta gcgggccagc    4680
gcggcccgca cctcgcccca gtcccaggtc gacccggcga cgaagtggtg caggctctgt    4740
tccgccgcgc cctctccgac gaaggcgcg aggttccggg cggtcttgcg tccctgtgcc     4800
gtgagcagcc cgcgtatgta ctgctcacct cttctgcgct ggtccgcccg gcggagcgaa    4860
ccgagtaact ccgcacatgc gtcggagacg agcgagtcga agtcgtgccg cgcggcggga    4920
cccacggggg gcgccgcgcc ggcgggtcga agcgtgcgta aggtcatagg agtcctcgtg    4980
ggggcctcgt catcactgcg agtggactgc gaccagcatc gccaattcac ccgttgctcc    5040
ccaggtacac cgggcacact cgttccgctt cgctcccccg gcggcacggc ccgcgtgtgg    5100
agcactcccc gctctccgga cggtgggggg gaagcccacc gcacgcgcgc cggtagcggt    5160
gccgggcccc acaacccct caccgacggg gtccgttcga ccacatgccg tgatgatgcc     5220
ttcgccgcac ggcctccttg aatgacggac cgtcagaaag acgtcactcc gcgcgcgccc    5280
gctccccgcc cgacccgcc cggccgccgt cccgccccg cgaccctgtg ggccgacgcc      5340
ctcttgacgg acccggaatc ccgggccgcg ggacgggacg gcgaggaact cgatgccgca    5400
aaggttccgc gtcctcaccg gcacctccga gatccagcgc aacggcatcg ccaagctcct    5460
ggctttccac cactgagccg caccccctgg cgagcagatc cgggacaaga cgccaccttc    5520
gcgacagtgt ttaggaaaag ttaagtaaag aattccgcga gcggattgcc agggagaaca    5580
acccattgac gcgcaccggt gcagcggcca cattgacggc acctgtcaag ttcaccccca    5640
ggagcttgga atcccatgca ggcaattcgg catcacgtca tgctcgtcat ggccttcgtg    5700
accgtcgcca cgactttcct tctctggccg tcgacgcaat ccgcgcaagc gtttcccccg    5760
```

```
accccgaagc agacggtact gaaccacctc cgcgccattt ccgggaatca catcgtctcc   5820
ggacagcaca acaaggagcc cgcctccgcc ccgggccagt acacccagca ggtcaaggac   5880
gtcaccgggc agtaccccgg cctgtggggc ggtgacctga tgttcgccgc ggcggacgtg   5940
gccggccgcc agcgcgtcgt cgaccaggcc aggaccgagt gggcgaacgg atcgctggtc   6000
tcgctcacct ggcacgtctg cccgccgacc ggcggcagca cctgtgcgtt cgagggcggc   6060
gtcaagtcca cgctgacgaa cgcgcagttc tcgcaggtcc tcacggaggg cagtgccctg   6120
aacagcgcat ggaagcggcg cctggacgag gtcgtcccgt acctgcagca gctggagaac   6180
gcgggcgtcc ccgtcctctt ccggccgctg cacgagatga acgaatcctg gaactggtgg   6240
ggaaaccggc ccgagcgaa cggcagcgca cgcctctacc agatcacccg cgatcacctc   6300
gccgggacga aagggctgga caatctgatc tgggtctgga acgtccagga caatccggcg   6360
ggaaactgga acagctacta tccgggagat cagtacgtgg acgtcgtttc gctggacgtc   6420
tggtacaaga gccacccgag ttccgccgac taccagcaga tgcggagcat cgcgggaaca   6480
aaacccatgg ccctcgcgga gctgggcaaa atgccgaccg ccgcgctgct ggacagccag   6540
acgcggtgga catggttcat gatgtggtcc gagcatctgc gcgggaacaa ttccaacgcc   6600
gaaatacaga cggcgtattt ccaccccgt gtactgaacc agggggaggt cgcactgccc   6660
tgacgctcgg cgctgcccgg ctctctcacg cgcgttctga caggacgtcg cggagagtgc   6720
ggggcaagcg gccggtgagc tgggcgcagt cgtcgcggac ccgatcccag cgctgttcgc   6780
gtaccgaggc gaacagggag gagaaggcgt agagccacca gggatccagg ccggtcgccg   6840
ctgtttcggc agagtacgtg tcggccggga tgtccacgta ggcgaccggt gtccgccaca   6900
cctccgccgc cgtggaggcg atgcctgcca ggtccgtcga ctcgggtccc gtgatgtcgt   6960
ggtgacggcc ggtcggcccg cccaccgcga gggcggcgag ggcgcgggcc acgtcgtcgc   7020
gcgccaccag ggacacccgg ccatcggctg ccggcagcct cagcagcccg gtcgagcgcg   7080
cctgggtgag ccagcctagg aagaactcga tgtacagcga ggccctggcg aacgagcacg   7140
gcacgccgga ggcgagcagc agatcctcgg tgagccggtt gacgacggcg tagcagaacg   7200
gggaggccga gtcggcgtcg acgctgctca gtgccgcgac atggccgacg cgctcggcca   7260
ccacggcggc gacgacgttg cggtggtgca gcagcacccg tgcgtcgggc ccgtcgctgg   7320
agacgaggac cagagtgtcc acgcccttca gcgccgcacg cagagcgggc gggtcggcgt   7380
agtcggcgac ggcgcactcc accccgcg gtagtgcctc ggcaggcagc ttccgcctgg   7440
tcatcgccac gacgtccacg tcggcccggt ccgcgagcag ctgcaccacc gcctgccca   7500
gactgccgcg cgcccctgtc accgcgatac gcatcgtcgc cccgtcgcc ttgtcgtcgg   7560
tcgtaccacc gtagggggcc aaccgcgacc agggcttgga acgagccggc ccgccagggc   7620
acagacgcgc gatcggtccg gttttcccgt gctcttttgg accgggacgc cggaccgctt   7680
cctttctacg gtggagccgt tcccgcccga gcccgcacgt catcgacgtg cggggaagac   7740
agaggtgata ccgatgctcc gacgccgtct cggagggccg tcaggccccc tcgtcagtgc   7800
cctgtgcctg ggcgcgatgc ccttcggcac caccgtcgac gagaagacgt ccttcgccat   7860
cctcgaccgg ttcgtcgagg ccggcggcag tctcgtcgac accgccgaca actacgcgtt   7920
ctgggctccc ggcgggaccg gggacgagag cgagaacacc gtcgggcgct ggctggcgag   7980
ccgccgccgc cgcgacgagg tggtgatctc caccaaggtg ggtgcccgcc ccaccgtccc   8040
cggcagcggc ctggagaccg ccgaagggct gtcggctccc gtcatacgga aggccgcgga   8100
```

```
ggacagcctg cgacgcctgg gcaccgatcg catcgatctg tactggaccc acatcgagga   8160
ccggaccgtc cctctggagg agacgctcgg agctctcgac gagctggtcg gcggcggcaa   8220
ggtggcggtg ctgggctgct ccaaccacgc gggctggcgc atcgaacggg cccgcgcgct   8280
cgcccggacc aacggctgga cggcgtacac ctgcgtccag cagcgctact cctaccttca   8340
gccgcgcttc gacgtcggac tgccggagag cggacgcgtc cacgcgacct ccgaactcct   8400
cgaccacgta cgcagcgagc ccgacctgac gctgctggcc tactcgtccc tgctctcggg   8460
cgcgtacacc cggccggaca agaccctgtc cgccgcctac gaccacccgg gcaccgggca   8520
gcggctgacc gtgctgcggg aggtggccgc cgagctcggt gccaccgcca accaggtggt   8580
gctgtcctgg ttgctcggag gtgatccgcc ggtgatcccg atcgtggggg tgagttccgt   8640
cgagcagctg gacgaggtgc tggccgccgt cgagctggac ctgccccggg agacgagggc   8700
acggctggac ctcgccgggc ggggctgacg ggccacacac cgcccctcgc ccgggacggg   8760
ctgaccggcc gcacaccgtc cctcagccgg gacgggctga cggccacaca cccgcccctc   8820
agcccggctg ggctgggctg acggccacac acccgctcct cagcccggct gggctgggct   8880
gacgccacac acccgccccc tcagcccggc tgggctgggc tgacggccac acgccgtccc   8940
tcgcccgggt cgggctgacc agccacacgc cgtccctcag tcggcccgct ccccggcccg   9000
cccggcgtcg acgtgccgcc ggtcgtggcg ccgggccgcg tcgatggcct gtgccaggcg   9060
ccgcacggct ccgggcacgg cgtggtccgc cagattgccg tagccgagga ccagcgcggg   9120
gccggcggcg gccacggccc gcgccccgcc ggagtcgccg gcccgggccg tcgggtggtg   9180
ctcggcccgc gccatccggt aggcgtcgag atccgccagc tcacgtcac gccgcgccgc   9240
ctccctgacg acgtgtgggcg ccgagcagtc cgtcagggac agcagcaggt ggaagccggc   9300
cgccgcaccg gacacctgga accccggcag cgacgccgcg agttctccca tgaggtgatc   9360
gcggcgccgt ttgtagcgca gccgtgccgc ccgcaggtac cggtcgtagg acccgcgggc   9420
caggaaccgg gcgaacgcct cctggtcgat gacgggcggt ggtacgcccc cgacgtgctc   9480
cgcgcccagg gcctcggtcc agcgcggcgg ggtcaccgcc cagccgatcc gcagggccgg   9540
cgagagcgtc ttgctgaccg accccagcag cgcgacgtgc tccggtgcca tgccctgcag   9600
ggcgcccacg gggtggcggt cgtatcggaa ctcggcgtcg tagtcgtcct ccagcaccag   9660
gccgtcgacc tcgcgggccc aggcgaccag ctcgccgcga cgggccgggg cgaggaccac   9720
accggtcggg aactggtggg cgggagcgac gatcaccgac cggacctgag gcgcgcgccg   9780
cagcaggtcg acccgcaggc cgtcgccgtc cacgggaacc gggacgggca ccagcccctc   9840
cgccccgacc gtggcgctca gccgcgacca gccagggtcc tccagggcca tgtgggtgtg   9900
gccctcggtc cgcaggaccc ggcacagcct gcgcaccgcg tccagcgtgc ccgcgcagac   9960
gacgagctgc cgggcttcca gcgacgcgcc gcgtccccgc acgaggtagg ccgcgagccg  10020
ctgccggagc cgggcgagac cggccggatc ggggtagccg agctcgcccc aggtcagtgc  10080
gccggtggcc tcccgcaccg cgtccgccca ccgtccgcgg ggaaaggccc gcaggtcggg  10140
tatgccgggc agcatgtcga actccggctc ccaccgcgta ccgacgtccg cctcgggcgt  10200
caccggagcg gggacggcct gcgccctgac ccggtggcc agccgctgc gcgcctccag  10260
gtaccctcc gcgacgagct gcgcgtaggc ctccgtcacc acccaccgcg agcagccag  10320
gtccgccgcc agcgccctgc tcggcggcag cgcgctgccg gaggcgatcc gcccaccggt  10380
caccgccgcc cgcagggcac ggctcagccg gacgtcagc gggccgtccg ccggcccgcc  10440
cagttcgaga aaggttcccc atgccgggtc ggtccggtcg tcgcccacgg cagccgatgc  10500
```

```
tacccaccgc cccgcgacgg ccgggcggcg gcgtccacgg gcccggtgca cactggatgg    10560
cgtggcggag acggaccggc atctcgacca gcggctggag caggccatca tggacctgct    10620
ggagcgacgg gcggccactg cctcgatctg tccgtccgac gccgcgcgtc gggtccacga    10680
gggtgacgac gagggctggc gagccctgct ggaacccgcg cgccgagcgg cctggcgtct    10740
ggtggggtcc ggcgaggtcg aggtgaccca ggccggccgg cccgtcacgc aggccgaggc    10800
ccgcgggccc gtccgcattc gtcgggcggg ttcctgacgg ctcgatccga aggcggaact    10860
cccgtgcccc ggcggcacgg gagctcgacg ccgggaggtc agcgccgcag ggtgagcaca    10920
cccggccgcc acggcagctg gtcgtagggg ccgcccgcgg tgggtgactt gccctggtag    10980
aggaaccgca ggttgcaggg gtcgacggtc atggtctggt cggggttgtc gcggaccagg    11040
tcaccgtggc tgatgtcgtt ggtccaggtg gccccgctgt tggccttgcc cgcgaagggg    11100
ttgctctcgc tcgcggcctg cggggtccac gagccgctca ggctggaggc cgtgaaggaa    11160
cggaagtagc gtccgttcgc gcccatcgcc tcgacgatca tcaggtactg gttctggccc    11220
tgaaccttgt agacctgcac gccctcgaac aggttggcct tcgtgtcgct catgatcgtc    11280
gtgtacgacg agccgaagct gcccgggaag ttcccgatcg gcatgctcgc ccggtagatc    11340
ttgccgttgt caccggcgaa gaacaggtac atgttctgtc cgtcggcgat cagggtctgg    11400
tcgatcgggc cggtgtcgga tcctgagatg ctccggtga acaacggctg cggagccgac    11460
cagccgttgg ggttggccgg gtcgctggac gtgcggtaga cgaagggcca cgcgccccac    11520
tggtacgcca gcacccagac gttcttgggc gcgaagtaga cagggtggg cgccaccgcc    11580 gcctgactca tcccggtctg gccggccgac gccatgtccg accagttcgt gaaggggctg    11640
aacatcatcg agccgtagga cgaccccgac acgttcgacg cgtagaccag gtgcttgccg    11700
ttgtgggtca cggtggtgaa gtccttgacc gccgcccacc cgttcgccgg ctgcgccagc    11760 acaccgtcg acgaccaccg gtacgccgac ggaagggcac acgccccgtc cgtcgggggc    11820
gtcccggtca ggccggacca cttctgcccg ctgccaccga cgcacgtccc gatctgcacc    11880
gccgtgccgt tggccgtacc ggcgcccgcg gcctccaggc acagcccgga ctccacgccg    11940
acgaccgtgc cgtcggagtt caccgccac tgctggttcg caccgccgga acagctccag    12000
atctgcaccc gcgtcccggg tgtggtggcg tgacccggaa cgtccaggca cttgttgccg    12060
tacacggtca gccgacggtc gtccgtcaac gtccactgct gattgctccc gccccagcag    12120
tcgtatatct gcag                                                      12134
```

<210> SEQ ID NO 141  
<211> LENGTH: 1164  
<212> TYPE: DNA  
<213> ORGANISM: Streptomyces ambofaciens  
<220> FEATURE:  
<221> NAME/KEY: CDS  
<222> LOCATION: (1)..(1164)

<400> SEQUENCE: 141

```
atg acc tta cgc acg ctt cga ccc gcc ggc gcg gcg ccc ccc gtg ggt     48
Met Thr Leu Arg Thr Leu Arg Pro Ala Gly Ala Ala Pro Pro Val Gly
1               5                   10                  15 ccc gcc gcg cgg cac gac ttc gac tcg ctc gtc tcc gac gca tgt gcg     96
Pro Ala Ala Arg His Asp Phe Asp Ser Leu Val Ser Asp Ala Cys Ala
            20                  25                  30 gag tta ctc ggt tcg ctc cgc cgg gcg gac cag cgc aga aga ggt gag    144
Glu Leu Leu Gly Ser Leu Arg Arg Ala Asp Gln Arg Arg Arg Gly Glu
        35                  40                  45
```

-continued

| | |
|---|---|
| cag tac ata cgc ggg ctg ctc acg gca cag gga cgc aag acc gcc cgg<br>Gln Tyr Ile Arg Gly Leu Leu Thr Ala Gln Gly Arg Lys Thr Ala Arg<br> 50                             55                          60 | 192 |
| aac ctc gcc gcc ttc gtc gga gag ggc gcg gcg gaa cag agc ctg cac<br>Asn Leu Ala Ala Phe Val Gly Glu Gly Ala Ala Glu Gln Ser Leu His<br>65                       70                       75                       80 | 240 |
| cac ttc gtc gcc ggg tcg acc tgg gac tgg ggc gag gtg cgg gcc gcg<br>His Phe Val Ala Gly Ser Thr Trp Asp Trp Gly Glu Val Arg Ala Ala<br>                  85                       90                       95 | 288 |
| ctg gcc cgc tac gtg gac gac agg ctg acc ccc gac gcc tgg gtg atc<br>Leu Ala Arg Tyr Val Asp Asp Arg Leu Thr Pro Asp Ala Trp Val Ile<br>            100                       105                      110 | 336 |
| tgg ccg atg gtg gtc tcc aag gcg ggg gtg cgc tcc gtc ggg gtg agc<br>Trp Pro Met Val Val Ser Lys Ala Gly Val Arg Ser Val Gly Val Ser<br>            115                       120                      125 | 384 |
| cgg cgc ttc gtc tcc gac ctg ggc cgg gtg gtg agc tgc cag cag agt<br>Arg Arg Phe Val Ser Asp Leu Gly Arg Val Val Ser Cys Gln Gln Ser<br>130                       135                      140 | 432 |
| cac ggg ctg tgg ctg gcc tcg ggc acg acg gcc gcc ccg gtc agc tgg<br>His Gly Leu Trp Leu Ala Ser Gly Thr Thr Ala Ala Pro Val Ser Trp<br>145                     150                       155                   160 | 480 |
| cgc ctg acg ctg ggc ggc ggc cgg agc ggg gag ggc aca ccc cgg cac<br>Arg Leu Thr Leu Gly Gly Gly Arg Ser Gly Glu Gly Thr Pro Arg His<br>            165                       170                      175 | 528 |
| ccc ggc gca ccc ggt gag gag gag aac atc gtc cgc ctg gtg gcc gaa<br>Pro Gly Ala Pro Gly Glu Glu Glu Asn Ile Val Arg Leu Val Ala Glu<br>                  180                       185                      190 | 576 |
| gcc gct cag gcc aac cgc tcc ttg gcc cgc ccc gtg gtg atg gac gca<br>Ala Ala Gln Ala Asn Arg Ser Leu Ala Arg Pro Val Val Met Asp Ala<br>                  195                       200                      205 | 624 |
| cgc gcg gcc gtg ctg cca cga ctg gtg cga ggg ctc ggt ctc gcg ggc<br>Arg Ala Ala Val Leu Pro Arg Leu Val Arg Gly Leu Gly Leu Ala Gly<br>210                       215                      220 | 672 |
| ctg ccc ttc atg gtg cgg gtg ggc ggg aac ctc cgg ctg gcc tcg gcg<br>Leu Pro Phe Met Val Arg Val Gly Gly Asn Leu Arg Leu Ala Ser Ala<br>225                     230                      235                   240 | 720 |
| agc ggc cgc ggc ccg gtg gac cac cac acg ggg acc acc tcg gcc cag<br>Ser Gly Arg Gly Pro Val Asp His His Thr Gly Thr Thr Ser Ala Gln<br>            245                       250                      255 | 768 |
| cag ttg atg gag cag ctc aag cgg ttg agc cgc ccc gtg gag ttg cgg<br>Gln Leu Met Glu Gln Leu Lys Arg Leu Ser Arg Pro Val Glu Leu Arg<br>                  260                       265                      270 | 816 |
| ggc tcc ctc agc ctc gtc gcc ccg cac ccc gtc gtc ctg ccg ggt gtg<br>Gly Ser Leu Ser Leu Val Ala Pro His Pro Val Val Leu Pro Gly Val<br>            275                       280                      285 | 864 |
| gtc ccg agg cgg acg ctg acg ctg ctg ggg gtg tgg cgg ggc aac cgc<br>Val Pro Arg Arg Thr Leu Thr Leu Leu Gly Val Trp Arg Gly Asn Arg<br>290                     295                      300 | 912 |
| cgg cgc ccc gcc gac ctg tgg ctg acc gac ctc acg tcc tgg gac cgc<br>Arg Arg Pro Ala Asp Leu Trp Leu Thr Asp Leu Thr Ser Trp Asp Arg<br>305                     310                      315                   320 | 960 |
| ggc gcc ctg ctg cgg ctg gcg atg ctc acc gaa cag gtc gac gcc gac<br>Gly Ala Leu Leu Arg Leu Ala Met Leu Thr Glu Gln Val Asp Ala Asp<br>                  325                       330                      335 | 1008 |
| ttc gac cgg gtg agc gtg ggt ggc atg cgc gac ttc gaa gga cgg<br>Phe Asp Arg Val Ser Val Gly Val Gly Met Arg Asp Phe Glu Gly Arg<br>                  340                       345                      350 | 1056 |
| tcg ttc cag ggc tgg cac cgg cac gtg acc ctg gcg tcc atc gcc cac<br>Ser Phe Gln Gly Trp His Arg His Val Thr Leu Ala Ser Ile Ala His | 1104 |

```
                     355                 360                 365
acg ctg cgg ctg gcg cag ccc tcc gcg cgc ggc gac ctc ggt ggg gcg    1152
Thr Leu Arg Leu Ala Gln Pro Ser Ala Arg Gly Asp Leu Gly Gly Ala
    370                 375                 380 acg gcg gtg tga                                                    1164
Thr Ala Val
385
```

<210> SEQ ID NO 142
<211> LENGTH: 387
<212> TYPE: PRT
<213> ORGANISM: Streptomyces ambofaciens

<400> SEQUENCE: 142

```
Met Thr Leu Arg Thr Leu Arg Pro Ala Gly Ala Pro Pro Val Gly
1               5                   10                  15

Pro Ala Ala Arg His Asp Phe Asp Ser Leu Val Ser Asp Ala Cys Ala
                20                  25                  30

Glu Leu Leu Gly Ser Leu Arg Arg Ala Asp Gln Arg Arg Gly Glu
            35                  40                  45

Gln Tyr Ile Arg Gly Leu Thr Ala Gln Gly Arg Lys Thr Ala Arg
50                  55                  60

Asn Leu Ala Ala Phe Val Gly Glu Gly Ala Ala Glu Gln Ser Leu His
65                  70                  75                  80

His Phe Val Ala Gly Ser Thr Trp Asp Trp Gly Glu Val Arg Ala Ala
                85                  90                  95

Leu Ala Arg Tyr Val Asp Asp Arg Leu Thr Pro Asp Ala Trp Val Ile
                100                 105                 110

Trp Pro Met Val Val Ser Lys Ala Gly Val Arg Ser Val Gly Val Ser
            115                 120                 125

Arg Arg Phe Val Ser Asp Leu Gly Arg Val Val Ser Cys Gln Gln Ser
        130                 135                 140

His Gly Leu Trp Leu Ala Ser Gly Thr Thr Ala Ala Pro Val Ser Trp
145                 150                 155                 160

Arg Leu Thr Leu Gly Gly Gly Arg Ser Gly Glu Gly Thr Pro Arg His
                165                 170                 175

Pro Gly Ala Pro Gly Glu Glu Asn Ile Val Arg Leu Val Ala Glu
            180                 185                 190

Ala Ala Gln Ala Asn Arg Ser Leu Ala Arg Pro Val Val Met Asp Ala
        195                 200                 205

Arg Ala Ala Val Leu Pro Arg Leu Val Arg Gly Leu Gly Leu Ala Gly
    210                 215                 220

Leu Pro Phe Met Val Arg Val Gly Gly Asn Leu Arg Leu Ala Ser Ala
225                 230                 235                 240

Ser Gly Arg Gly Pro Val Asp His His Thr Gly Thr Thr Ser Ala Gln
                245                 250                 255

Gln Leu Met Glu Gln Leu Lys Arg Leu Ser Arg Pro Val Glu Leu Arg
            260                 265                 270

Gly Ser Leu Ser Leu Val Ala Pro His Pro Val Val Leu Pro Gly Val
        275                 280                 285

Val Pro Arg Arg Thr Leu Thr Leu Leu Gly Val Trp Arg Gly Asn Arg
    290                 295                 300

Arg Arg Pro Ala Asp Leu Trp Leu Thr Asp Leu Thr Ser Trp Asp Arg
305                 310                 315                 320

Gly Ala Leu Leu Arg Leu Ala Met Leu Thr Glu Gln Val Asp Ala Asp
```

```
                   325                 330                 335
Phe Asp Arg Val Ser Val Gly Val Gly Met Arg Asp Phe Glu Gly Arg
            340                 345                 350

Ser Phe Gln Gly Trp His Arg His Val Thr Leu Ala Ser Ile Ala His
            355                 360                 365

Thr Leu Arg Leu Ala Gln Pro Ser Ala Arg Gly Asp Leu Gly Gly Ala
            370                 375                 380

Thr Ala Val
385

<210> SEQ ID NO 143
<211> LENGTH: 849
<212> TYPE: DNA
<213> ORGANISM: Streptomyces ambofaciens
<220> FEATURE:
<221> NAME/KEY: CDS
<222> LOCATION: (1)..(849)

<400> SEQUENCE: 143 atg cgt atc gcg gtg aca ggg gcg gcg ggc agt ctg ggc agg cgg gtg        48
Met Arg Ile Ala Val Thr Gly Ala Ala Gly Ser Leu Gly Arg Arg Val
 1               5                  10                  15 gtg cag ctg ctc gcg gac cgg gcc gac gtg gac gtc gtg gcg atg acc        96
Val Gln Leu Leu Ala Asp Arg Ala Asp Val Asp Val Val Ala Met Thr
                20                  25                  30 agg cgg aag ctg cct gcc gag gca cta ccg ccg ggg gtg gag tgc gcc       144
Arg Arg Lys Leu Pro Ala Glu Ala Leu Pro Pro Gly Val Glu Cys Ala
            35                  40                  45 gtc gcc gac tac gcc gac ccg ccc gct ctg cgt gcg gcg ctg aag ggc       192
Val Ala Asp Tyr Ala Asp Pro Pro Ala Leu Arg Ala Ala Leu Lys Gly
        50                  55                  60 gtg gac act ctg gtc ctc gtc tcc agc gac ggg ccc gac gca cgg gtg       240
Val Asp Thr Leu Val Leu Val Ser Ser Asp Gly Pro Asp Ala Arg Val
65                  70                  75                  80 ctg ctg cac cac cgc aac gtc gtc gcc gcc gtg gtg gcc gag cgc gtc       288
Leu Leu His His Arg Asn Val Val Ala Ala Val Val Ala Glu Arg Val
                85                  90                  95 ggc cat gtc gcg gca ctg agc agc gtc gac gcc gac tcg gcc tcc ccg       336
Gly His Val Ala Ala Leu Ser Ser Val Asp Ala Asp Ser Ala Ser Pro
            100                 105                 110 ttc tgc tac gcc gtc gtc aac cgg ctc acc gag gat ctg ctg ctc gcc       384
Phe Cys Tyr Ala Val Val Asn Arg Leu Thr Glu Asp Leu Leu Leu Ala
        115                 120                 125 tcc ggc gtg ccg tgc tcg ttc gcc agg gcc tcg ctg tac atc gag ttc       432
Ser Gly Val Pro Cys Ser Phe Ala Arg Ala Ser Leu Tyr Ile Glu Phe
    130                 135                 140 ttc cta ggc tgg ctc acc cag gcg cgc tcg acc ggg ctg ctg agg ctg       480
Phe Leu Gly Trp Leu Thr Gln Ala Arg Ser Thr Gly Leu Leu Arg Leu
145                 150                 155                 160 ccg gca gcc gat ggc cgg gtg tcc ctg gtg gcg cgc gac gac gtg gcc       528
Pro Ala Ala Asp Gly Arg Val Ser Leu Val Ala Arg Asp Asp Val Ala
                165                 170                 175 cgc gcc ctc gcc gcc ctc gcg gtg ggc ggg ccg acc ggc cgt cac cac       576
Arg Ala Leu Ala Ala Leu Ala Val Gly Gly Pro Thr Gly Arg His His
            180                 185                 190 gac atc acg gga ccc gag tcg acg gac ctg gca ggc atc gcc tcc acg       624
Asp Ile Thr Gly Pro Glu Ser Thr Asp Leu Ala Gly Ile Ala Ser Thr
        195                 200                 205 gcg gcg gag gtg tgg cgg aca ccg gtc gcc tac gtg gac atc ccg gcc       672
Ala Ala Glu Val Trp Arg Thr Pro Val Ala Tyr Val Asp Ile Pro Ala
```

```
               210                 215                 220
gac acg tac tct gcc gaa aca gcg gcg acc ggc ctg gat ccc tgg tgg      720
Asp Thr Tyr Ser Ala Glu Thr Ala Ala Thr Gly Leu Asp Pro Trp Trp
225                 230                 235                 240 ctc tac gcc ttc tcc tcc ctg ttc gcc tcg gta cgc gaa cag cgc tgg      768
Leu Tyr Ala Phe Ser Ser Leu Phe Ala Ser Val Arg Glu Gln Arg Trp
                245                 250                 255 gat cgg gtc cgc gac gac tgc gcc cag ctc acc ggc cgc ttg ccc cgc      816
Asp Arg Val Arg Asp Asp Cys Ala Gln Leu Thr Gly Arg Leu Pro Arg
            260                 265                 270 act ctc cgc gac gtc ctg tca gaa cgc gcg tga                          849
Thr Leu Arg Asp Val Leu Ser Glu Arg Ala
        275                 280

<210> SEQ ID NO 144
<211> LENGTH: 282
<212> TYPE: PRT
<213> ORGANISM: Streptomyces ambofaciens

<400> SEQUENCE: 144

Met Arg Ile Ala Val Thr Gly Ala Ala Gly Ser Leu Gly Arg Arg Val
1               5                   10                  15

Val Gln Leu Leu Ala Asp Arg Ala Asp Val Asp Val Val Ala Met Thr
            20                  25                  30

Arg Arg Lys Leu Pro Ala Glu Ala Leu Pro Pro Gly Val Glu Cys Ala
        35                  40                  45

Val Ala Asp Tyr Ala Asp Pro Pro Ala Leu Arg Ala Ala Leu Lys Gly
    50                  55                  60

Val Asp Thr Leu Val Leu Val Ser Ser Asp Gly Pro Asp Ala Arg Val
65                  70                  75                  80

Leu Leu His His Arg Asn Val Ala Ala Val Val Ala Glu Arg Val
                85                  90                  95

Gly His Val Ala Ala Leu Ser Ser Val Asp Ala Asp Ser Ala Ser Pro
            100                 105                 110

Phe Cys Tyr Ala Val Val Asn Arg Leu Thr Glu Asp Leu Leu Leu Ala
        115                 120                 125

Ser Gly Val Pro Cys Ser Phe Ala Arg Ala Ser Leu Tyr Ile Glu Phe
    130                 135                 140

Phe Leu Gly Trp Leu Thr Gln Ala Arg Ser Thr Gly Leu Leu Arg Leu
145                 150                 155                 160

Pro Ala Ala Asp Gly Arg Val Ser Leu Val Ala Arg Asp Val Ala
                165                 170                 175

Arg Ala Leu Ala Ala Leu Ala Val Gly Gly Pro Thr Gly Arg His His
            180                 185                 190

Asp Ile Thr Gly Pro Glu Ser Thr Asp Leu Ala Gly Ile Ala Ser Thr
        195                 200                 205

Ala Ala Glu Val Trp Arg Thr Pro Val Ala Tyr Val Asp Ile Pro Ala
    210                 215                 220

Asp Thr Tyr Ser Ala Glu Thr Ala Ala Thr Gly Leu Asp Pro Trp Trp
225                 230                 235                 240

Leu Tyr Ala Phe Ser Ser Leu Phe Ala Ser Val Arg Glu Gln Arg Trp
                245                 250                 255

Asp Arg Val Arg Asp Asp Cys Ala Gln Leu Thr Gly Arg Leu Pro Arg
            260                 265                 270

Thr Leu Arg Asp Val Leu Ser Glu Arg Ala
        275                 280
```

```
<210> SEQ ID NO 145
<211> LENGTH: 1512
<212> TYPE: DNA
<213> ORGANISM: Streptomyces ambofaciens
<220> FEATURE:
<221> NAME/KEY: CDS
<222> LOCATION: (1)..(1512)

<400> SEQUENCE: 145
```

| | | | | | | | | | | | | | | | | |
|---|---|---|---|---|---|---|---|---|---|---|---|---|---|---|---|---|
| gtg | ggc | gac | gac | cgg | acc | gac | ccg | gca | tgg | gga | acc | ttt | ctc | gaa | ctg | 48 |
| Val | Gly | Asp | Asp | Arg | Thr | Asp | Pro | Ala | Trp | Gly | Thr | Phe | Leu | Glu | Leu | |
| 1 | | | | 5 | | | | | 10 | | | | | 15 | | |
| ggc | ggg | ccg | gcg | gac | ggc | ccg | ctg | cac | gtc | cgg | ctg | agc | cgt | gcc | ctg | 96 |
| Gly | Gly | Pro | Ala | Asp | Gly | Pro | Leu | His | Val | Arg | Leu | Ser | Arg | Ala | Leu | |
| | | | 20 | | | | | 25 | | | | | 30 | | | |
| cgg | gcg | gcg | gtg | acc | ggt | ggg | cgg | atc | gcc | tcc | ggc | agc | gcg | ctg | ccg | 144 |
| Arg | Ala | Ala | Val | Thr | Gly | Gly | Arg | Ile | Ala | Ser | Gly | Ser | Ala | Leu | Pro | |
| | 35 | | | | | 40 | | | | | 45 | | | | | |
| ccg | agc | agg | gcg | ctg | gcg | gcg | gac | ctg | ggc | tgc | tcg | cgg | tgg | gtg | gtg | 192 |
| Pro | Ser | Arg | Ala | Leu | Ala | Ala | Asp | Leu | Gly | Cys | Ser | Arg | Trp | Val | Val | |
| 50 | | | | | 55 | | | | | 60 | | | | | | |
| acg | gag | gcc | tac | gcg | cag | ctc | gtc | gcg | gag | ggg | tac | ctg | gag | gcg | cgc | 240 |
| Thr | Glu | Ala | Tyr | Ala | Gln | Leu | Val | Ala | Glu | Gly | Tyr | Leu | Glu | Ala | Arg | |
| 65 | | | | | 70 | | | | | 75 | | | | | 80 | |
| agc | ggc | tcg | gcc | acc | cgg | gtc | agg | gcg | cag | gcc | gtc | ccc | gct | ccg | gtg | 288 |
| Ser | Gly | Ser | Ala | Thr | Arg | Val | Arg | Ala | Gln | Ala | Val | Pro | Ala | Pro | Val | |
| | | | | 85 | | | | | 90 | | | | | 95 | | |
| acg | ccc | gag | gcg | gac | gtc | ggt | acg | cgg | tgg | gag | ccg | gag | ttc | gac | atg | 336 |
| Thr | Pro | Glu | Ala | Asp | Val | Gly | Thr | Arg | Trp | Glu | Pro | Glu | Phe | Asp | Met | |
| | | | 100 | | | | | 105 | | | | | 110 | | | |
| ctg | ccc | ggc | ata | ccc | gac | ctg | cgg | gcc | ttt | ccc | cgc | gga | cgg | tgg | gcg | 384 |
| Leu | Pro | Gly | Ile | Pro | Asp | Leu | Arg | Ala | Phe | Pro | Arg | Gly | Arg | Trp | Ala | |
| | | | 115 | | | | | 120 | | | | | 125 | | | |
| gac | gcg | gtg | cgg | gag | gcc | acc | ggc | gca | ctg | acc | tgg | ggc | gag | ctc | ggc | 432 |
| Asp | Ala | Val | Arg | Glu | Ala | Thr | Gly | Ala | Leu | Thr | Trp | Gly | Glu | Leu | Gly | |
| | 130 | | | | | 135 | | | | | 140 | | | | | |
| tac | ccc | gat | ccg | gcc | ggt | ctc | gcc | cgg | ctc | cgg | cag | cgg | ctc | gcg | gcc | 480 |
| Tyr | Pro | Asp | Pro | Ala | Gly | Leu | Ala | Arg | Leu | Arg | Gln | Arg | Leu | Ala | Ala | |
| 145 | | | | | 150 | | | | | 155 | | | | | 160 | |
| tac | ctc | gtg | cgg | gga | cgc | ggc | gcg | tcg | ctg | gaa | gcc | cgg | cag | ctc | gtc | 528 |
| Tyr | Leu | Val | Arg | Gly | Arg | Gly | Ala | Ser | Leu | Glu | Ala | Arg | Gln | Leu | Val | |
| | | | | 165 | | | | | 170 | | | | | 175 | | |
| gtc | tgc | gcg | ggc | acg | ctg | gac | gcg | gtg | cgc | agg | ctg | tgc | cgg | gtc | ctg | 576 |
| Val | Cys | Ala | Gly | Thr | Leu | Asp | Ala | Val | Arg | Arg | Leu | Cys | Arg | Val | Leu | |
| | | | 180 | | | | | 185 | | | | | 190 | | | |
| cgg | acc | gag | ggc | cac | acc | cac | atg | gcc | ctg | gag | gac | cct | ggc | tgg | tcg | 624 |
| Arg | Thr | Glu | Gly | His | Thr | His | Met | Ala | Leu | Glu | Asp | Pro | Gly | Trp | Ser | |
| | | | 195 | | | | | 200 | | | | | 205 | | | |
| cgg | ctg | agc | gcc | acg | gtc | ggg | gcg | gag | ggg | ctg | gtg | ccc | gtc | ccg | gtt | 672 |
| Arg | Leu | Ser | Ala | Thr | Val | Gly | Ala | Glu | Gly | Leu | Val | Pro | Val | Pro | Val | |
| | 210 | | | | | 215 | | | | | 220 | | | | | |
| ccc | gtg | gac | ggc | gac | ggc | ctg | cgg | gtc | gac | ctg | ctg | cgg | cgc | gcg | cct | 720 |
| Pro | Val | Asp | Gly | Asp | Gly | Leu | Arg | Val | Asp | Leu | Leu | Arg | Arg | Ala | Pro | |
| 225 | | | | | 230 | | | | | 235 | | | | | 240 | |
| cag | gtc | cgg | tcg | gtg | atc | gtc | gct | ccc | gcc | cac | cag | ttc | ccg | acc | ggt | 768 |
| Gln | Val | Arg | Ser | Val | Ile | Val | Ala | Pro | Ala | His | Gln | Phe | Pro | Thr | Gly | |
| | | | | 245 | | | | | 250 | | | | | 255 | | |
| gtg | gtc | ctc | gcc | ccg | gcc | cgt | cgc | ggc | gag | ctg | gtc | gcc | tgg | gcc | cgc | 816 |
| Val | Val | Leu | Ala | Pro | Ala | Arg | Arg | Gly | Glu | Leu | Val | Ala | Trp | Ala | Arg | |
| | | | 260 | | | | | 265 | | | | | 270 | | | |

-continued

```
gag gtc gac ggc ctg gtg ctg gag gac gac tac gac gcc gag ttc cga      864
Glu Val Asp Gly Leu Val Leu Glu Asp Asp Tyr Asp Ala Glu Phe Arg
            275                 280                 285 tac gac cgc cac ccc gtg ggc gcc ctg cag ggc atg gca ccg gag cac      912
Tyr Asp Arg His Pro Val Gly Ala Leu Gln Gly Met Ala Pro Glu His
        290                 295                 300 gtc gcg ctg ctg ggg tcg gtc agc aag acg ctc tcg ccg gcc ctg cgg      960
Val Ala Leu Leu Gly Ser Val Ser Lys Thr Leu Ser Pro Ala Leu Arg
305                 310                 315                 320 atc ggc tgg gcg gtg acc ccg cgc tgg acc gag gcc ctg ggc gcg         1008
Ile Gly Trp Ala Val Thr Pro Arg Trp Thr Glu Ala Leu Gly Ala
                325                 330                 335 gag cac gtc ggg ggc gta cca ccg ccc gtc atc gac cag gag gcg ttc     1056
Glu His Val Gly Gly Val Pro Pro Pro Val Ile Asp Gln Glu Ala Phe
            340                 345                 350 gcc cgg ttc ctg gcc cgc ggg tcc tac gac cgg tac ctg cgg gcg gca     1104
Ala Arg Phe Leu Ala Arg Gly Ser Tyr Asp Arg Tyr Leu Arg Ala Ala
        355                 360                 365 cgg ctg cgc tac aaa cgg cgc cgc gat cac ctc atg gga gaa ctc gcg     1152
Arg Leu Arg Tyr Lys Arg Arg Arg Asp His Leu Met Gly Glu Leu Ala
370                 375                 380 gcg tcg ctg ccg ggg ttc cag gtg tcc ggt gcg gcg gcc ggc ttc cac     1200
Ala Ser Leu Pro Gly Phe Gln Val Ser Gly Ala Ala Ala Gly Phe His
            385                 390                 395                 400 ctg ctg ctg tcc ctg acg gac tgc tcg gcg ccc acc gtc gtc agg gag     1248
Leu Leu Leu Ser Leu Thr Asp Cys Ser Ala Pro Thr Val Val Arg Glu
                405                 410                 415 gcg gcg cgg cgt gac gtg agg ctg gcg gat ctc gac gcc tac cgg atg     1296
Ala Ala Arg Arg Asp Val Arg Leu Ala Asp Leu Asp Ala Tyr Arg Met
            420                 425                 430 gcg cgg gcc gag cac cac ccg acg gcc cgg gcc ggc gac tcc ggc ggg     1344
Ala Arg Ala Glu His His Pro Thr Ala Arg Ala Gly Asp Ser Gly Gly
        435                 440                 445 gcg cgg gcc gtg gcc gcc gcc ggc ccc gcg ctg gtc ctc ggc tac ggc     1392
Ala Arg Ala Val Ala Ala Ala Gly Pro Ala Leu Val Leu Gly Tyr Gly
450                 455                 460 aat ctg gcg gac cac gcc gtg ccc gga gcc gtg cgg cgc ctg gca cag     1440
Asn Leu Ala Asp His Ala Val Pro Gly Ala Val Arg Arg Leu Ala Gln
465                 470                 475                 480 gcc atc gac gcg gcc cgg cgc cac gac cgg cgg cac gtc gac gcc ggg     1488
Ala Ile Asp Ala Ala Arg Arg His Asp Arg Arg His Val Asp Ala Gly
                485                 490                 495 cgg gcc ggg gag cgg gcc gac tga                                      1512
Arg Ala Gly Glu Arg Ala Asp
            500
```

<210> SEQ ID NO 146
<211> LENGTH: 503
<212> TYPE: PRT
<213> ORGANISM: Streptomyces ambofaciens

<400> SEQUENCE: 146

```
Val Gly Asp Asp Arg Thr Asp Pro Ala Trp Gly Thr Phe Leu Glu Leu
1               5                   10                  15

Gly Gly Pro Ala Asp Gly Pro Leu His Val Arg Leu Ser Arg Ala Leu
            20                  25                  30

Arg Ala Ala Val Thr Gly Gly Arg Ile Ala Ser Gly Ser Ala Leu Pro
        35                  40                  45

Pro Ser Arg Ala Leu Ala Ala Asp Leu Gly Cys Ser Arg Trp Val Val
```

-continued

```
              50                  55                  60
Thr Glu Ala Tyr Ala Gln Leu Val Ala Glu Gly Tyr Leu Glu Ala Arg
 65                  70                  75                  80

Ser Gly Ser Ala Thr Arg Val Arg Ala Gln Ala Val Pro Ala Pro Val
                 85                  90                  95

Thr Pro Glu Ala Asp Val Gly Thr Arg Trp Glu Pro Glu Phe Asp Met
            100                 105                 110

Leu Pro Gly Ile Pro Asp Leu Arg Ala Phe Pro Arg Gly Arg Trp Ala
            115                 120                 125

Asp Ala Val Arg Glu Ala Thr Gly Ala Leu Thr Trp Gly Glu Leu Gly
130                 135                 140

Tyr Pro Asp Pro Ala Gly Leu Ala Arg Leu Arg Gln Arg Leu Ala Ala
145                 150                 155                 160

Tyr Leu Val Arg Gly Arg Gly Ala Ser Leu Glu Ala Arg Gln Leu Val
                165                 170                 175

Val Cys Ala Gly Thr Leu Asp Ala Val Arg Arg Leu Cys Arg Val Leu
            180                 185                 190

Arg Thr Glu Gly His Thr His Met Ala Leu Glu Asp Pro Gly Trp Ser
            195                 200                 205

Arg Leu Ser Ala Thr Val Gly Ala Glu Gly Leu Val Pro Val Pro Val
            210                 215                 220

Pro Val Asp Gly Asp Gly Leu Arg Val Asp Leu Leu Arg Arg Ala Pro
225                 230                 235                 240

Gln Val Arg Ser Val Ile Val Ala Pro Ala His Gln Phe Pro Thr Gly
                245                 250                 255

Val Val Leu Ala Pro Ala Arg Arg Gly Glu Leu Val Ala Trp Ala Arg
            260                 265                 270

Glu Val Asp Gly Leu Val Leu Glu Asp Asp Tyr Asp Ala Glu Phe Arg
            275                 280                 285

Tyr Asp Arg His Pro Val Gly Ala Leu Gln Gly Met Ala Pro Glu His
            290                 295                 300

Val Ala Leu Leu Gly Ser Val Ser Lys Thr Leu Ser Pro Ala Leu Arg
305                 310                 315                 320

Ile Gly Trp Ala Val Thr Pro Pro Arg Trp Thr Glu Ala Leu Gly Ala
                325                 330                 335

Glu His Val Gly Gly Val Pro Pro Val Ile Asp Gln Glu Ala Phe
            340                 345                 350

Ala Arg Phe Leu Ala Arg Gly Ser Tyr Asp Arg Tyr Leu Arg Ala Ala
            355                 360                 365

Arg Leu Arg Tyr Lys Arg Arg Asp His Leu Met Gly Glu Leu Ala
370                 375                 380

Ala Ser Leu Pro Gly Phe Gln Val Ser Gly Ala Ala Ala Gly Phe His
385                 390                 395                 400

Leu Leu Leu Ser Leu Thr Asp Cys Ser Ala Pro Thr Val Val Arg Glu
                405                 410                 415

Ala Ala Arg Arg Asp Val Arg Leu Ala Asp Leu Asp Ala Tyr Arg Met
            420                 425                 430

Ala Arg Ala Glu His His Pro Thr Ala Arg Ala Gly Asp Ser Gly Gly
            435                 440                 445

Ala Arg Ala Val Ala Ala Gly Pro Ala Leu Val Leu Gly Tyr Gly
            450                 455                 460

Asn Leu Ala Asp His Ala Val Pro Gly Ala Val Arg Arg Leu Ala Gln
465                 470                 475                 480
```

```
<210> SEQ ID NO 147
<211> LENGTH: 276
<212> TYPE: DNA
<213> ORGANISM: Streptomyces ambofaciens
<220> FEATURE:
<221> NAME/KEY: CDS
<222> LOCATION: (1)..(276)

<400> SEQUENCE: 147 gtg gcg gag acg gac cgg cat ctc gac cag cgg ctg gag cag gcc atc      48
Val Ala Glu Thr Asp Arg His Leu Asp Gln Arg Leu Glu Gln Ala Ile
1               5                   10                  15 atg gac ctg ctg gag cga cgg gcg gcc act gcc tcg atc tgt ccg tcc      96
Met Asp Leu Leu Glu Arg Arg Ala Ala Thr Ala Ser Ile Cys Pro Ser
            20                  25                  30 gac gcc gcg cgt cgg gtc cac gag ggt gac gac gag ggc tgg cga gcc     144
Asp Ala Ala Arg Arg Val His Glu Gly Asp Asp Glu Gly Trp Arg Ala
        35                  40                  45 ctg ctg gaa ccc gcg cgc cga gcg gcc tgg cgt ctg gtg ggg tcc ggc     192
Leu Leu Glu Pro Ala Arg Arg Ala Ala Trp Arg Leu Val Gly Ser Gly
    50                  55                  60 gag gtc gag gtg acc cag gcc ggc cgg ccc gtc acg cag gcc gag gcc     240
Glu Val Glu Val Thr Gln Ala Gly Arg Pro Val Thr Gln Ala Glu Ala
65                  70                  75                  80 cgc ggg ccc gtc cgc att cgt cgg gcg ggt tcc tga                     276
Arg Gly Pro Val Arg Ile Arg Arg Ala Gly Ser
                85                  90

<210> SEQ ID NO 148
<211> LENGTH: 91
<212> TYPE: PRT
<213> ORGANISM: Streptomyces ambofaciens

<400> SEQUENCE: 148

Val Ala Glu Thr Asp Arg His Leu Asp Gln Arg Leu Glu Gln Ala Ile
1               5                   10                  15

Met Asp Leu Leu Glu Arg Arg Ala Ala Thr Ala Ser Ile Cys Pro Ser
            20                  25                  30

Asp Ala Ala Arg Arg Val His Glu Gly Asp Asp Glu Gly Trp Arg Ala
        35                  40                  45

Leu Leu Glu Pro Ala Arg Arg Ala Ala Trp Arg Leu Val Gly Ser Gly
    50                  55                  60

Glu Val Glu Val Thr Gln Ala Gly Arg Pro Val Thr Gln Ala Glu Ala
65                  70                  75                  80

Arg Gly Pro Val Arg Ile Arg Arg Ala Gly Ser
                85                  90

<210> SEQ ID NO 149
<211> LENGTH: 1236
<212> TYPE: DNA
<213> ORGANISM: Streptomyces ambofaciens
<220> FEATURE:
<221> NAME/KEY: CDS
<222> LOCATION: (1)..(1236)

<400> SEQUENCE: 149
```

Preceding the SEQ ID NO 147 block:

```
Ala Ile Asp Ala Ala Arg Arg His Asp Arg Arg His Val Asp Ala Gly
            485                 490                 495

Arg Ala Gly Glu Arg Ala Asp
            500
```

-continued

| | |
|---|---|
| ctg cag ata tac gac tgc tgg ggc ggg agc aat cag cag tgg acg ttg<br>Leu Gln Ile Tyr Asp Cys Trp Gly Gly Ser Asn Gln Gln Trp Thr Leu<br>1               5                  10                 15 | 48 |
| acg gac gac cgt cgg ctg acc gtg tac ggc aac aag tgc ctg gac gtt<br>Thr Asp Asp Arg Arg Leu Thr Val Tyr Gly Asn Lys Cys Leu Asp Val<br>            20                 25                 30 | 96 |
| ccg ggt cac gcc acc aca ccc ggg acg cgg gtg cag atc tgg agc tgt<br>Pro Gly His Ala Thr Thr Pro Gly Thr Arg Val Gln Ile Trp Ser Cys<br>        35                 40                 45 | 144 |
| tcc ggt gcg aac cag cag tgg cgg gtg aac tcc gac ggc acg gtc<br>Ser Gly Ala Asn Gln Gln Trp Arg Val Asn Ser Asp Gly Thr Val<br>50                 55                 60 | 192 |
| gtc ggc gtg gag tcc ggg ctg tgc ctg gag gcc gcg ggc gcc ggt acg<br>Val Gly Val Glu Ser Gly Leu Cys Leu Glu Ala Ala Gly Ala Gly Thr<br>65                 70                 75                 80 | 240 |
| gcc aac ggc acg gcg gtg cag atc ggg acg tgc gtc ggt ggc agc ggg<br>Ala Asn Gly Thr Ala Val Gln Ile Gly Thr Cys Val Gly Gly Ser Gly<br>            85                 90                 95 | 288 |
| cag aag tgg tcc ggc ctg acc ggg acg ccc acg gac ggg gcg tgt<br>Gln Lys Trp Ser Gly Leu Thr Gly Thr Pro Thr Asp Gly Ala Cys<br>        100                105                110 | 336 |
| gcc ctt ccg tcg gcg tac cgg tgg tcg tcg acg ggt gtg ctg gcg cag<br>Ala Leu Pro Ser Ala Tyr Arg Trp Ser Ser Thr Gly Val Leu Ala Gln<br>    115                120                125 | 384 |
| ccg gcg aac ggg tgg gcg gcg gtc aag gac ttc acc acc gtg acc cac<br>Pro Ala Asn Gly Trp Ala Ala Val Lys Asp Phe Thr Thr Val Thr His<br>130                135                140 | 432 |
| aac ggc aag cac ctg gtc tac gcg tcg aac gtg tcg ggg tcg tcc tac<br>Asn Gly Lys His Leu Val Tyr Ala Ser Asn Val Ser Gly Ser Ser Tyr<br>145                150                155                160 | 480 |
| ggc tcg atg atg ttc agc ccc ttc acg aac tgg tcg gac atg gcg tcg<br>Gly Ser Met Met Phe Ser Pro Phe Thr Asn Trp Ser Asp Met Ala Ser<br>                165                170                175 | 528 |
| gcc ggc cag acc ggg atg agt cag gcg gcg gtg gcg ccc acc ctg ttc<br>Ala Gly Gln Thr Gly Met Ser Gln Ala Ala Val Ala Pro Thr Leu Phe<br>            180                185                190 | 576 |
| tac ttc gcg ccc aag aac gtc tgg gtg ctg gcg tac cag tgg ggc gcg<br>Tyr Phe Ala Pro Lys Asn Val Trp Val Leu Ala Tyr Gln Trp Gly Ala<br>        195                200                205 | 624 |
| tgg ccc ttc gtc tac cgc acg tcc agc gac ccg gcc aac ccc aac ggc<br>Trp Pro Phe Val Tyr Arg Thr Ser Ser Asp Pro Ala Asn Pro Asn Gly<br>    210                215                220 | 672 |
| tgg tcg gct ccc cag ccg ttg ttc acc ggg agc atc tca gga tcc gac<br>Trp Ser Ala Pro Gln Pro Leu Phe Thr Gly Ser Ile Ser Gly Ser Asp<br>225                230                235                240 | 720 |
| acc ggc ccg atc gac cag acc ctg atc gcc gac gga cag aac atg tac<br>Thr Gly Pro Ile Asp Gln Thr Leu Ile Ala Asp Gly Gln Asn Met Tyr<br>                245                250                255 | 768 |
| ctg ttc ttc gcc ggt gac aac ggc aag atc tac cgg gcg agc atg ccg<br>Leu Phe Phe Ala Gly Asp Asn Gly Lys Ile Tyr Arg Ala Ser Met Pro<br>            260                265                270 | 816 |
| atc ggg aac ttc ccg ggc agc ttc ggc tcg tcg tac acg acg atc atg<br>Ile Gly Asn Phe Pro Gly Ser Phe Gly Ser Ser Tyr Thr Thr Ile Met<br>        275                280                285 | 864 |
| agc gac acg aag gcc aac ctg ttc gag ggc gtg cag gtc tac aag gtt<br>Ser Asp Thr Lys Ala Asn Leu Phe Glu Gly Val Gln Val Tyr Lys Val<br>    290                295                300 | 912 |
| cag ggc cag aac cag tac ctg atg atc gtc gag gcg atg ggc gcg aac<br>Gln Gly Gln Asn Gln Tyr Leu Met Ile Val Glu Ala Met Gly Ala Asn<br>305                310                315                320 | 960 |

```
gga cgc tac ttc cgt tcc ttc acg gcc tcc agc ctg agc ggc tcg tgg       1008
Gly Arg Tyr Phe Arg Ser Phe Thr Ala Ser Ser Leu Ser Gly Ser Trp
            325                 330                 335 acc ccg cag gcc gcg agc gag agc aac ccc ttc gcg ggc aag gcc aac       1056
Thr Pro Gln Ala Ala Ser Glu Ser Asn Pro Phe Ala Gly Lys Ala Asn
        340                 345                 350 agc ggg gcc acc tgg acc aac gac atc agc cac ggt gac ctg gtc cgc       1104
Ser Gly Ala Thr Trp Thr Asn Asp Ile Ser His Gly Asp Leu Val Arg
            355                 360                 365 gac aac ccc gac cag acc atg acc gtc gac ccc tgc aac ctg cgg ttc       1152
Asp Asn Pro Asp Gln Thr Met Thr Val Asp Pro Cys Asn Leu Arg Phe
370                 375                 380 ctc tac cag ggc aag tca ccc acc gcg ggc ggc ccc tac gac cag ctg       1200
Leu Tyr Gln Gly Lys Ser Pro Thr Ala Gly Gly Pro Tyr Asp Gln Leu
385                 390                 395                 400 ccg tgg cgg ccg ggt gtg ctc acc ctg cgg cgc tga                       1236
Pro Trp Arg Pro Gly Val Leu Thr Leu Arg Arg
            405                 410

<210> SEQ ID NO 150
<211> LENGTH: 411
<212> TYPE: PRT
<213> ORGANISM: Streptomyces ambofaciens

<400> SEQUENCE: 150

Leu Gln Ile Tyr Asp Cys Trp Gly Gly Ser Asn Gln Gln Trp Thr Leu
1               5                   10                  15

Thr Asp Asp Arg Arg Leu Thr Val Tyr Gly Asn Lys Cys Leu Asp Val
            20                  25                  30

Pro Gly His Ala Thr Thr Pro Gly Thr Arg Val Gln Ile Trp Ser Cys
        35                  40                  45

Ser Gly Gly Ala Asn Gln Gln Trp Arg Val Asn Ser Asp Gly Thr Val
    50                  55                  60

Val Gly Val Glu Ser Gly Leu Cys Leu Glu Ala Ala Gly Ala Gly Thr
65                  70                  75                  80

Ala Asn Gly Thr Ala Val Gln Ile Gly Thr Cys Val Gly Gly Ser Gly
                85                  90                  95

Gln Lys Trp Ser Gly Leu Thr Gly Thr Pro Pro Thr Asp Gly Ala Cys
            100                 105                 110

Ala Leu Pro Ser Ala Tyr Arg Trp Ser Thr Gly Val Leu Ala Gln
        115                 120                 125

Pro Ala Asn Gly Trp Ala Ala Val Lys Asp Phe Thr Thr Val Thr His
    130                 135                 140

Asn Gly Lys His Leu Val Tyr Ala Ser Asn Val Ser Gly Ser Ser Tyr
145                 150                 155                 160

Gly Ser Met Met Phe Ser Pro Phe Thr Asn Trp Ser Asp Met Ala Ser
                165                 170                 175

Ala Gly Gln Thr Gly Met Ser Gln Ala Ala Val Ala Pro Thr Leu Phe
            180                 185                 190

Tyr Phe Ala Pro Lys Asn Val Trp Val Leu Ala Tyr Gln Trp Gly Ala
        195                 200                 205

Trp Pro Phe Val Tyr Arg Thr Ser Ser Asp Pro Ala Asn Pro Asn Gly
    210                 215                 220

Trp Ser Ala Pro Gln Pro Leu Phe Thr Gly Ser Ile Ser Gly Ser Asp
225                 230                 235                 240

Thr Gly Pro Ile Asp Gln Thr Leu Ile Ala Asp Gly Gln Asn Met Tyr
```

```
                245                 250                 255
Leu Phe Phe Ala Gly Asp Asn Gly Lys Ile Tyr Arg Ala Ser Met Pro
            260                 265                 270

Ile Gly Asn Phe Pro Gly Ser Phe Gly Ser Ser Tyr Thr Thr Ile Met
        275                 280                 285

Ser Asp Thr Lys Ala Asn Leu Phe Glu Gly Val Gln Val Tyr Lys Val
    290                 295                 300

Gln Gly Gln Asn Gln Tyr Leu Met Ile Val Glu Ala Met Gly Ala Asn
305                 310                 315                 320

Gly Arg Tyr Phe Arg Ser Phe Thr Ala Ser Ser Leu Ser Gly Ser Trp
                325                 330                 335

Thr Pro Gln Ala Ala Ser Glu Ser Asn Pro Phe Ala Gly Lys Ala Asn
            340                 345                 350

Ser Gly Ala Thr Trp Thr Asn Asp Ile Ser His Gly Asp Leu Val Arg
        355                 360                 365

Asp Asn Pro Asp Gln Thr Met Thr Val Asp Pro Cys Asn Leu Arg Phe
    370                 375                 380

Leu Tyr Gln Gly Lys Ser Pro Thr Ala Gly Gly Pro Tyr Asp Gln Leu
385                 390                 395                 400

Pro Trp Arg Pro Gly Val Leu Thr Leu Arg Arg
                405                 410
```

<210> SEQ ID NO 151
<211> LENGTH: 22
<212> TYPE: DNA
<213> ORGANISM: Artificial Sequence
<220> FEATURE:
<223> OTHER INFORMATION: Oligonucleotide KF36

<400> SEQUENCE: 151
ttgccgtagc cgaggaccag cg                                    22

<210> SEQ ID NO 152
<211> LENGTH: 22
<212> TYPE: DNA
<213> ORGANISM: Artificial Sequence
<220> FEATURE:
<223> OTHER INFORMATION: Oligonucleotide KF37

<400> SEQUENCE: 152
cacatggccc tggaggaccc tg                                    22

<210> SEQ ID NO 153
<211> LENGTH: 30
<212> TYPE: DNA
<213> ORGANISM: Artificial Sequence
<220> FEATURE:
<223> OTHER INFORMATION: Oligonucleotide KF42

<400> SEQUENCE: 153
aagcttgtac ggcccacaga atgatgtcac                            30

<210> SEQ ID NO 154
<211> LENGTH: 30
<212> TYPE: DNA
<213> ORGANISM: Artificial Sequence
<220> FEATURE:
<223> OTHER INFORMATION: Oligonucleotide KF43

<400> SEQUENCE: 154
aagcttcgac taccttggtg atctcgcctt                            30

<210> SEQ ID NO 155
<211> LENGTH: 65
<212> TYPE: DNA
<213> ORGANISM: Artificial Sequence
<220> FEATURE:
<223> OTHER INFORMATION: Oligonucleotide KF32

<400> SEQUENCE: 155
caaccgcttg agctgctcca tcaactgctg ggccgaggta tcgcgcgcgc ttcgttcggg    60
acgaa    65

<210> SEQ ID NO 156
<211> LENGTH: 65
<212> TYPE: DNA
<213> ORGANISM: Artificial Sequence
<220> FEATURE:
<223> OTHER INFORMATION: Oligonucleotide KF33

<400> SEQUENCE: 156
tgggtcccgc cgcgcggcac gacttcgact cgctcgtcta tctgcctctt cgtcccgaag    60
caact    65

<210> SEQ ID NO 157
<211> LENGTH: 65
<212> TYPE: DNA
<213> ORGANISM: Artificial
<220> FEATURE:
<223> OTHER INFORMATION: Oligonucleotide EDR71

<400> SEQUENCE: 157
cgtcatcgac gtgcggggaa gacagaggtg ataccgatga tcgcgcgcgc ttcgttcggg    60
acgaa    65

<210> SEQ ID NO 158
<211> LENGTH: 65
<212> TYPE: DNA
<213> ORGANISM: Artificial
<220> FEATURE:
<223> OTHER INFORMATION: Oligonucleotide EDR72

<400> SEQUENCE: 158
gccagcacct cgtccagctg ctcgacggaa ctcaccccca tctgcctctt cgtcccgaag    60
caact    65

<210> SEQ ID NO 159
<211> LENGTH: 66
<212> TYPE: DNA
<213> ORGANISM: Artificial
<220> FEATURE:
<223> OTHER INFORMATION: Oligonucleotide KF52

<400> SEQUENCE: 159
gatccgccag cctcacgtca cgccgcgccg cctccctgac atcgcgcgcg cttcgttcgg    60
gacgaa    66

<210> SEQ ID NO 160
<211> LENGTH: 66
<212> TYPE: DNA
<213> ORGANISM: Artificial
<220> FEATURE:
<223> OTHER INFORMATION: Oligonucleotide KF53

<400> SEQUENCE: 160

```
gaggcggacg tcggtacgcg gtgggagccg gagttcgaca atctgcctct tcgtcccgaa      60
gcaact                                                                 66
```

<210> SEQ ID NO 161
<211> LENGTH: 2540
<212> TYPE: DNA
<213> ORGANISM: Streptomyces ambofaciens

<400> SEQUENCE: 161

```
ctgcagggcg cccacggggt ggcggtcgta tcggaactcg gcgtcgtagt cgtcctccag      60
caccaggccg tcgacctcgc gggcccaggc gaccagctcg ccgcgacggg ccggggcgag     120
gaccacaccg gtcgggaact ggtgggcggg agcgacgatc accgaccgga cctgaggcgc     180
gcgccgcagc aggtcgaccc gcaggccgtc gccgtccacg ggaaccggga cgggcaccag     240
cccctccgcc ccgaccgtgg cgctcagccg cgaccagcca gggtcctcca gggccatgtg     300
ggtgtggccc tcggtccgca ggacccggca cagcctgcgc accgcgtcca gcgtgcccgc     360
gcagacgacg agctgccggg cttccagcga cgcgccgcgt ccccgcacga ggtaggccgc     420
gagccgctgc cggagccggg cgagaccggc cggatcgggg tagccgagct cgccccaggt     480
cagtgcgccg gtggcctccc gcaccgcgtc cgcccaccgt ccgcgggaa aggcccgcag     540
gtcgggtatg ccgggcagca tgtcgaactc cggctcccac cgcgtaccga cgtccgcctc     600
gggcgtcacc ggagcgggga cggcctgcgc cctgacccgg gtggccgagc cgctgcgcgc     660
ctccaggtac ccctccgcga cgagctgcgc gtaggcctcc gtcaccaccc accgcgagca     720
gcccaggtcc gccgccagcg ccctgctcgg cggcagcgcg ctgccggagg cgatccgccc     780
accggtcacc gccgcccgca gggcacggct cagccggacg tgcagcgggc cgtccgccgg     840
cccgcccagt tcgagaaagg ttccccatgc cgggtcggtc cggtcgtcgc ccacggcagc     900
cgatgctacc caccgccccg cgacggccgg gcggcggcgt ccacgggccc ggtgcacact     960
ggatggcgtg gcggagacgg accggcatct cgaccagcgg ctggagcagg ccatcatgga    1020
cctgctggag cgacgggcgg ccactgcctc gatctgtccg tccgacgccg cgcgtcgggt    1080
ccacgagggt gacgacgagg gctggcgagc cctgctggaa cccgcgcgcc gagcggcctg    1140
gcgtctggtg gggtccggcg aggtcgaggt gacccaggcc ggccggcccg tcacgcaggc    1200
cgaggcccgc gggcccgtcc gcattcgtcg ggcgggttcc tgacggctcg atccgaaggc    1260
ggaactcccg tgccccggcg gcacgggagc tcgacgccgg gaggtcagcg ccgcagggtg    1320
agcacacccg gccgccacgg cagctggtcg taggggccgc ccgcggtggg tgacttgccc    1380
tggtagagga accgcaggtt gcaggggtcg acggtcatgg tctggtcggg gttgtcgcgg    1440
accaggtcac cgtggctgat gtcgttggtc caggtggccc cgctgttggc cttgcccgcg    1500
aaggggttgc tctcgctcgc ggcctgcggg gtccacgagc cgctcaggct ggaggccgtg    1560
aaggaacgga agtagcgtcc gttcgcgccc atcgcctcga cgatcatcag gtactggttc    1620
tggccctgaa ccttgtagac ctgcacgccc tcgaacaggt tggccttcgt gtcgctcatg    1680
atcgtcgtgt acgacgagcc gaagctgccc gggaagttcc cgatcggcat gctcgcccgg    1740
tagatcttgc cgttgtcacc ggcgaagaac aggtacatgt tctgtccgtc ggcgatcagg    1800
gtctggtcga tcgggccggt gtcggatcct gagatgctcc cggtgaacaa cggctgcgga    1860
gccgaccagc cgttggggtt ggcgggtcg ctggacgtgc ggtagacgaa gggccacgcg    1920
ccccactggt acgccagcac ccagacgttc ttgggcgcga agtagaacag ggtgggcgcc    1980
```

```
accgccgcct gactcatccc ggtctggccg gccgacgcca tgtccgacca gttcgtgaag    2040
gggctgaaca tcatcgagcc gtaggacgac cccgacacgt tcgacgcgta gaccaggtgc    2100
ttgccgttgt gggtcacggt ggtgaagtcc ttgaccgccg cccacccgtt cgccggctgc    2160
gccagcacac ccgtcgacga ccaccggtac gccgacggaa gggcacacgc cccgtccgtc    2220 ggggcgtcc  cggtcaggcc ggaccacttc tgcccgctgc caccgacgca cgtcccgatc    2280
tgcaccgccg tgccgttggc cgtaccggcg cccgcggcct ccaggcacag cccggactcc    2340
acgccgacga ccgtgccgtc ggagttcacc cgccactgct ggttcgcacc gccggaacag    2400
ctccagatct gcacccgcgt cccgggtgtg gtggcgtgac ccggaacgtc caggcacttg    2460
ttgccgtaca cggtcagccg acggtcgtcc gtcaacgtcc actgctgatt gctcccgccc    2520
cagcagtcgt atatctgcag                                                2540
```